United States Patent
Kobayashi et al.

(10) Patent No.: US 10,626,112 B2
(45) Date of Patent: Apr. 21, 2020

(54) HETEROCYCLIC SULFONAMIDE DERIVATIVE AND MEDICINE COMPRISING SAME

(71) Applicant: EA PHARMA CO., LTD., Tokyo (JP)

(72) Inventors: Kaori Kobayashi, Kawasaki (JP);
Tamotsu Suzuki, Kawasaki (JP);
Tomohiro Fujii, Kawasaki (JP);
Tatsuya Okuzumi, Tokyo (JP)

(73) Assignee: EA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/222,178

(22) Filed: Jul. 28, 2016

(65) Prior Publication Data

US 2016/0332999 A1 Nov. 17, 2016

Related U.S. Application Data

(63) Continuation of application No. PCT/JP2015/052415, filed on Jan. 28, 2015.

(30) Foreign Application Priority Data

Jan. 28, 2014 (JP) ................... 2014-013729
Aug. 6, 2014 (JP) ................... 2014-160250

(51) Int. Cl.
| C07D 307/82 | (2006.01) |
| C07D 405/12 | (2006.01) |
| C07D 405/14 | (2006.01) |
| C07D 407/12 | (2006.01) |
| C07D 409/14 | (2006.01) |
| C07D 413/14 | (2006.01) |
| C07D 453/06 | (2006.01) |
| C07D 498/04 | (2006.01) |
| C07D 491/048 | (2006.01) |

(52) U.S. Cl.
CPC ......... *C07D 405/14* (2013.01); *C07D 307/82* (2013.01); *C07D 405/12* (2013.01); *C07D 407/12* (2013.01); *C07D 409/14* (2013.01); *C07D 413/14* (2013.01); *C07D 491/048* (2013.01); *C07D 498/04* (2013.01)

(58) Field of Classification Search
CPC .. C07D 409/14; C07D 405/14; C07D 405/12; C07D 307/82; C07D 407/12; C07D 413/14; C07D 453/06; C07D 491/048; C07D 498/04
USPC .................. 514/178; 544/279, 284, 310, 312
See application file for complete search history.

(56) References Cited

U.S. PATENT DOCUMENTS

| 6,645,939 | B1 | 11/2003 | Durette et al. |
| 8,586,748 | B2 | 11/2013 | Abeywardane et al. |
| 8,614,201 | B2 | 12/2013 | Berthelot et al. |
| 9,533,985 | B2 * | 1/2017 | Ueno .................. C07D 403/12 |
| 9,562,043 | B2 * | 2/2017 | Suzuki ................. C07D 413/14 |
| 2011/0275800 | A1 | 11/2011 | Abeywardane et al. |
| 2012/0083474 | A1 | 4/2012 | Berthelot et al. |
| 2014/0329796 | A1 | 11/2014 | Suzuki et al. |
| 2015/0284375 | A1 * | 10/2015 | Kobayashi ........... A61K 31/397 |
| | | | 514/210.18 |

FOREIGN PATENT DOCUMENTS

| JP | 2011-516563 A | 5/2011 |
| WO | WO 2010/141805 A1 | 12/2010 |
| WO | WO 2013/108857 A1 | 7/2013 |
| WO | WO 2014/098098 A1 | 6/2014 |

OTHER PUBLICATIONS

Estrada et al. (AN 2016:1354759 HCAPLUS. DN 165:298569; abstract of WO 2016128529).*
Estrada et al. (AN 2016:1353750 HCAPLUS, DN 165:298569 abstract of WO 2016128529, US 20160264567-PD Feb. 15, 2015).*
Michael Bandell, et al., "Noxious Cold Ion Channel TRPA1 Is Activated by Pungent Compounds and Bradykinin", Neuron. Mar. 25, 2004, vol. 41, pp. 849-857.
Lindsey J. Macpherson, et al., "Noxious compounds activate TRPA1 ion channels through covalent modification of cysteines", Nature. 05544, 2007, vol. 445, pp. 541-545.
Marcello Trevisani, et al., "4-Hydroxynonenal, an endogenous aldehyde, causes pain and neurogenic inflammation through activation of the irritant receptor TRPA1", Proc Natl Acad Sci U S A, PNAS, Aug. 14, 2007, vol. 104, No. 33, pp. 13519-13524.
Sandra Zurborg, et al., "Direct activation of the ion channel TRPA1 by $Ca^{2+}$", Nature Neuroscience, Mar. 2007, vol. 10, No. 3, pp. 277-279.

(Continued)

*Primary Examiner* — Sabiha N Qazi
(74) *Attorney, Agent, or Firm* — Oblon, McClelland, Maier & Neustadt, L.L.P.

(57) ABSTRACT

The present invention provides a compound represented by the formula (I):

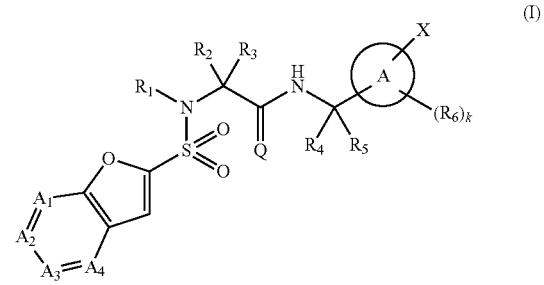

wherein each symbol is as defined in the DESCRIPTION, or a pharmaceutically acceptable salt thereof. The compound has a superior TRPA1 antagonist activity, and can provide a medicament useful for the prophylaxis or treatment of diseases involving TRPA1 antagonist and TRPA1.

10 Claims, No Drawings

Specification includes a Sequence Listing.

(56) References Cited

OTHER PUBLICATIONS

Keiichi Nagata, et al., "Nociceptor and Hair Cell Transducer Properties of TRPA1, a Channel for Pain and Hearing", The Journal of Neuroscience, Apr. 20, 2005, 25(16), pp. 4052-4061.
Gina M. Story, et al., "ANKTM1, a TRP-like Channel Expressed in Nociceptive Neurons, Is Activated by Cold Temperatures", Cell., Mar. 21, 2003, vol. 112, pp. 819-829.
Dian M. Bautista, et al., "Pungent products from garlic activate the sensory ion channel TRPA1", Proc Natl Acad Sci U S A., PNAS, 2005, vol. 102, No. 34, pp. 12248-12252.
Koichi Obata, et al., "TRPA1 induced in sensory neurons contributes to cold hyperalgesia after inflammation and nerve injury" The Journal of Clinical Investigation, 2005, vol. 115, No. 9, pp. 2393-24401.
Colleen R. McNamara, et al.,"TRPA1 mediates formalin-induced pain", Proc Natl Acad Sci U S A., PNAS, 2007, vol. 104, No. 33, pp. 13525-13530.
S. Benemei, et al., "The TRPA1 channel in migraine mechanism and treatment", Brithsi Journal of Pharmacology, 2014, 171, pp. 2552-2567.
Hong Wei, et al., "Attenuation of Mechanical Hypersensitivity by an Antagonist of the TRPA1 Ion Channel in Diabetic Animals", Anesthesiology, 2009, 111, pp. 147-154.
Takashi Kondo, et al., "Role of Transient Receptor Potential A1 in Gastric Nociception", Digestion, 2010, 82, (3), pp. 150-155.
Fiore Cattaruzza, et al., "Transient receptor potential ankyrin-1 has a major role in mediating visceral pain in mice", Am J Physiol Gastrointest Liver Physiol., 2010, 298, pp. G81-G91.
Fiore Cattaruzza, et al., "Transient receptor potential ankyrin 1 mediates chronic pancreatitis pain in mice", Am J Physiol Gastrointest Live Physiol., 2013, 304, G1002-G1012.
Ana I. Caceresa, et al., "A sensory neuronal ion channel essential for airway inflammation and hyperreactivity in asthma", PNAS, Proc Natl Acad Sci U S A., 2009, vol. 106, No. 22, pp. 9099-9104.
Bailong Xiao, et al., "Scratching the surface: a role of pain-sensing TRPA1 in itch", Nat Neuroscience, May 2011, vol. 14, No. 5, pp. 540-542.
Sarah R Wilson, et al., "TRPA1 is required for histamine-independent, Mas-related G protein-coupled receptor-mediated itch", Nature Neuroscience, May 2011, vol. 14, No. 5, pp. 595-602.
Min-Hee Oh, et al., "TRPA1-Dependent Pruritus in IL-13-Induced Chronic Atopic Dermatitis", J lmmunol., Dec. 1, 2013, 191, (11) pp. 5371-5382.
Boyi Liu, et al., "TRPA1 controls inflammation and pruritogen responses in allergic contact dermatitis", FASEB Journal, Oct. 2016, vol. 27, No. 9, pp. 3549-3563.
Steve McGaraughty, et al., "TRPA1 modulation of spontaneous and mechanically evoked firing of spinal neurons in uninjured, osteoarthritic, and inflamed rats", Molecular Pain, 2010, 6:14, 11 pages.
Karl-Erik Andersson, et al., "The role of the transient receptor potential (TRP) superfamily of cation-selective channels in the management of the overactive bladder ",BJU International, 2010, 106, (8), pp. 1114-11127.
Romina Nassini, et al., " Oxaliplatin elicits mechanical and cold allodynia in rodents via TRPA1 receptor stimulation", Pain, 2011, 152, pp. 1621-1631.
Serena Materazzi, et al., "TRPA1 and TRPV4 mediate paclitaxel-induced peripheral neuropathy in mice via a glutathione-sensitive mechanism", Pflugers Arch-Eur J. Physio., Ion channels, Recetor and Transporters, 2012, 463, pp. 561-569.
Gabriela Trevisan, et al., "Novel Therapeutic Strategy to Prevent Chemotherapy-Induced Persistent Sensory Neuropathy by TRPA1 Blockade", Cancer Res., Therapeutics, Targets, and Chemical Biology May 15, 2013, 73(10), pp. 3120-3131.
Extended European Search Report dated Sep. 8, 2017 issued in corresponding European patent application No. 15742861.6.
First Office Action and Search Report dated Mar. 16, 2018 issued in corresponding Chinese patent application No. 201580006396.3 (with English translation).
Second Office Action dated Nov. 12, 2018 issued in corresponding Chinese patent application No. 201580006396.3 (with English translation).

\* cited by examiner

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: synthetic primer 1

<400> SEQUENCE: 1
aactttagta agcttcgatc gccatgaag                                29

<210> SEQ ID NO 2
<211> LENGTH: 34
<212> TYPE: DNA
<213> ORGANISM: Artificial Sequence
<220> FEATURE:
<223> OTHER INFORMATION: synthetic primer 2

<400> SEQUENCE: 2
gtaccgatct agaattcgtt tactaaggct caag                          34
```

HETEROCYCLIC SULFONAMIDE DERIVATIVE AND MEDICINE COMPRISING SAME

CROSS REFERENCES TO RELATED APPLICATIONS

This application is a continuation of International Patent Application No. PCT/JP2015/052415, filed on Jan. 28, 2015, and claims priority to Japanese Patent Application No. 2014-013729, filed on Jan. 28, 2014, and Japanese Patent Application No. 2014-160250, filed on Aug. 6, 2014, all of which are incorporated herein by reference in their entireties.

BACKGROUND OF THE INVENTION

Field of the Invention

The present invention relates to a novel heterocyclic sulfonamide compound having a Transient Receptor Potential Ankyrin 1 (TRPA1) antagonist activity and a pharmaceutical composition containing the compound, as well as a medicament useful for the prophylaxis and/or treatment of a disease involving TRPA1.

Discussion of the Background

Transient Receptor Potential Ankyrin 1 (TRPA1) is a non-selective cation channel belonging to the Transient Receptor Potential (TRP) channel superfamily. Like other TRP channel family, it has 6 transmembrane domains and forms a tetramer consisting of 4 subunits. TRPA1 is a ligand-gated ion channel, which changes structure by the binding of ligand. As a result, the channel opens to allow intracellular flow of cations such as calcium ion, sodium ion and the like, thereby controlling the membrane potential of the cells. As the TRPA1 ligand, irritating natural substances (e.g., allylisothiocyanate (AITC), cinnamaldehyde and the like), environmental irritants (e.g., formalin, acrolein and the like), endogenous substances (e.g., 4-hydroxynonenal and the like) and the like are known (non-patent documents 1-3). It is known that the ligand is also activated by cold stimulation, intracellular $Ca^{2+}$ and the like (non-patent document 1). Many ligands such as AITC, cinnamaldehyde and the like form a covalent bond with the cysteine residue and the lysine residue at the N-terminus in the cytoplasm, and activate the channel (non-patent document 2). In addition, intracellular $Ca^{2+}$ is considered to bind to the N-terminus EF hand domain and opens the channel (non-patent document 4). TRPA1 has been reported to be highly expressed in the sensory nerves such as spinal cord nerve, vagus nerve, trigeminal nerve and the like. Also, TRPA1 has been reported to be co-expressed with TRPV1, perception•pain-related markers such as calcitonin gene related peptide (CGRP), substance P and the like (non-patent documents 5-7). Therefore, it is considered that, once TRPA1 in the sensory nerve is activated by various stimulations, channel opening and depolarization of the cellular membrane occur, neuropeptides (CGRP, substance P) are released from the nerve ending, and perception such as nociception and the like is transmitted.

In fact, it has been reported that TRPA1 gene knockdown by the gene specific antisense method improves hyperalgesia induced by inflammation and nerve damage in pain model (non-patent document 8). Also, it has been reported that a pain behavior induced by formalin is ablated in TRPA1 gene knockout mouse (non-patent document 9). From the above, TRPA1 is considered to play an important role in the nociceptive transmission. Involvement of TRPA1 in migraine and diabetic neuropathy is suggested in reports (non-patent documents 10, 11), and TRPA1 is also expected as a therapeutic target in pain-related diseases such as nociceptive pain, neuropathic pain and the like.

Also, TRPA1 is known to be highly expressed in the afferent sensory nerve projected on the gastrointestinal tract such as esophagus, stomach, large intestine and the like. It has been reported that TRPA1 knockdown decreases pain reaction through stomach extension (non-patent document 12), and colon hyperalgesia induced by AITC and 2,4,6-trinitrobenzenesulfonic acid (TNBS) are normalized in TRPA1 gene knockout mouse (non-patent document 13). From the above, TRPA1 is suggested to play an important role in the transmission of perception and nociception in the gastrointestinal tract, and is expected to be effective for the treatment of digestive tract diseases such as functional dyspepsia, irritable bowel syndrome, reflux esophagitis, inflammatory bowel disease (Crohn's disease, ulcerative colitis), pancreatitis (non-patent document 14) and the like.

Furthermore, TRPA1 plays a key role in the detection of a noxious substance in the trachea. It has been reported that TRPA1 gene knockout suppresses inflammation of the trachea in OVA model (non-patent document 15). Therefore, antagonism of TRPA1 is considered to be also useful for pulmonary diseases such as asthma, chronic coughing, chronic obstructive pulmonary disease (COPD) and the like.

As other diseases involving TRPA1, dermatic diseases such as pruritus, allergic dermatitis including atopic dermatitis, burn and the like (non-patent documents 16, 17, 18, 19), inflammatory diseases such as burn, osteoarthritis and the like (non-patent document 20), bladder diseases such as overactive bladder, abnormal urination, cystitis and the like (non-patent document 21), neurological diseases such as anticancer agent-induced neuropathy and the like (non-patent documents 22-24) and the like are known. Thus, a compound capable of regulating function of TRPA1 is industrially and therapeutically useful in many aspects. In particular, a compound that antagonizes TRPA1 is highly expected as a new therapeutic drug for pain diseases, digestive tract diseases, lung diseases, dermatic diseases, inflammatory diseases, bladder diseases and neurological diseases in human.

As a TRPA1 antagonist, a compound of the following formula has been reported (patent document 1).

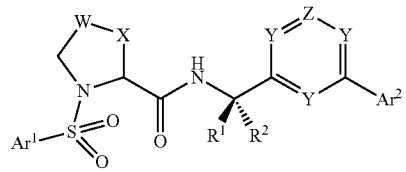

wherein definition of each symbol is as described in patent document 1.

However, these compounds are structurally different from the compound represented by the formula (I) to be mentioned later. While patent document 3 also reports them as TRPA1 antagonists, they are structurally different from the compound represented by the formula (I) of the present invention to be mentioned later.

In addition, a compound having the following structure is known (patent document 2).

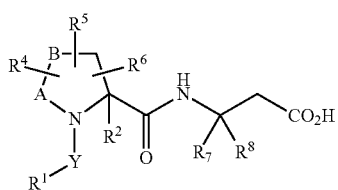

wherein definition of each symbol is as described in patent document 2.

However, these compounds are VLA-4 and α4β7 antagonists and have different action mechanism from that of the compound of the present invention. In addition, they have an alkyl group substituted by carboxylic acid or carboxylic acid as a substituent on the carbon atom adjacent to an amide bond, and are structurally different from the compound of the present invention.

DOCUMENT LIST

Patent Documents patent document 1: WO 2010/141805
patent document 2: U.S. Pat. No. 6,645,939
patent document 3: WO 2013/108857

Non-Patent Documents non-patent document 1: Bandell M, et al., Neuron. 2004 Mar. 25; 41(6):849-57.
non-patent document 2: Macpherson L J, et al., Nature. 2007 445(7127):541-5.
non-patent document 3: Trevisani M, et al., Proc Natl Acad Sci USA. 2007 104(33):13519-24.
non-patent document 4: Zurborg S, et al., Nat Neurosci. 2007 10(3):277-9.
non-patent document 5: Nagata K, et al., J Neurosci. 2005 25(16):4052-61.
non-patent document 6: Story G M, et al., Cell. 2003 112(6):819-29.
non-patent document 7: Bautista D M, et al., Proc Natl Acad Sci USA. 2005 102(34):12248-52.
non-patent document 8: Obata K, et al., J Clin Invest. 2005 115(9):2393-401.
non-patent document 9: McNamara C R, et al., Proc Natl Acad Sci USA. 2007 104(33):13525-30.
non-patent document 10: Benemei S, et al., Br J Pharmacol. 2014 171(10):2552-67.
non-patent document 11: Wei H, et al., Anesthesiology. 2009 111(1):147-54.
non-patent document 12: Kondo T, et al., Digestion. 2010; 82(3):150-5.
non-patent document 13: Cattaruzza F, et al., Am J Physiol Gastrointest Liver Physiol. 2010 298(1):G81-91.
non-patent document 14: Cattaruzza F, et al., Am J Physiol Gastrointest Live Physiol. 2013 Jun. 1; 304(11):G1002-12.
non-patent document 15: Caceres A I, et al., Proc Natl Acad Sci USA. 2009 106(22):9099-104.
non-patent document 16: Xiao B, and Patapoutian A., Nat Neurosci. 2011 May; 14(5):540-2.
non-patent document 17: Wilson S R, et al., Nat Neurosci. 2011 May; 14(5):595-602.
non-patent document 18: Oh M H, et al., J Immunol. 2013 Dec. 1; 191(11):5371-82.
non-patent document 19: Liu B, et al., FASEB J. 2013 September; 27(9):3549-63.
non-patent document 20: McGaraughty S, et al., Mol Pain. 2010 Mar. 5; 6:14.
non-patent document 21: Andersson K E, et al., BJU Int. 2010 October; 106(8):1114-27.
non-patent document 22: Nassini R, et al., Pain. 2011 July; 152(7):1621-31.
non-patent document 23: Materazzi S, et al., Pflugers Arch. 2012 April; 463(4):561-9.
non-patent document 24: Trevisan G, et al., Cancer Res. 2013 May 15; 73(10):3120-31.

SUMMARY OF THE INVENTION

Problems to be Solved by the Invention

The present invention aims to provide a novel compound having a transient receptor potential ankyrin 1 (TRPA1) antagonist activity.

The present invention also aims to provide a TRPA1 antagonist.

The present invention also aims to provide a medicament containing the above-mentioned novel compound.

The present invention also aims to provide a medicament useful for the prophylaxis or treatment of a disease involving TRPA1.

Means of Solving the Problems

In view of the aforementioned situation, the present inventors have conducted various studies and found that a certain particular heterocyclic sulfonamide compound has a strong TRPA1 antagonist activity.

For creation of a novel TRPA1 antagonist, the present inventors first assumed a structure of the below-mentioned formula (I) wherein thiophene is bonded to sulfonamide, and further studied a benzothiophene structure wherein the thiophene structure is fused with an aromatic ring. However, structural conversion of the thiophene structure to the benzothiophene structure caused a decrease in the TRPA1 antagonist activity. On the other hand, they assumed a structure wherein furan is bonded to sulfonamide, and studied the benzofuran structure fused with an aromatic ring. Surprisingly, structural conversion of the furan structure to the benzofuran structure markedly improved the TRPA1 antagonist activity. The present inventors further found that a compound group having a structure analogous to the benzofuran structure also shows a strong TRPA1 antagonist activity. The present inventors have found that the compound of the present invention has a TRPA1 antagonist activity, and is useful for the prophylaxis and/or treatment of diseases involving TRPA1 (e.g., pain associated diseases, digestive tract diseases, lung diseases, bladder diseases, inflammatory diseases, dermatic diseases, and neurological diseases), and completed the present invention.

Accordingly, the present invention provides the following.

[1] A compound represented by the formula (I):

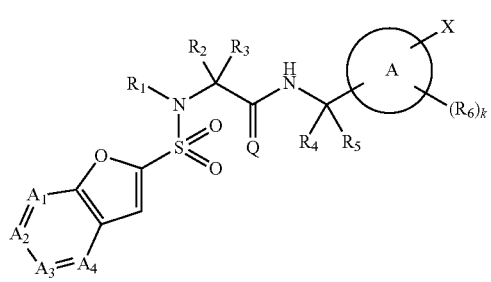

wherein
Q is =O or =S;
ring A is a 6-membered monocyclic aromatic ring or heteroaromatic ring, or a bicyclic aromatic ring or heteroaromatic ring;
$A_1$ is —C(Ra)= or —N=;
$A_2$ is —C(Rb)= or —N=;
$A_3$ is —C(Rc)= or —N=;
$A_4$ is —C(Rd)= or —N=;
Ra, Rb, Rc and Rd are the same or different and each is hydrogen, a halogeno group, a cyano group, a hydroxy group, a $C_{1-6}$ alkyl group, a $C_{1-6}$ alkoxy group, a halogeno$C_{1-6}$ alkyl group or a halogeno$C_1$-6 alkoxy group;
provided at least two of $A_1$-$A_4$ are not —N=;
$R_1$ is hydrogen or a $C_{1-6}$ alkyl group optionally having substituent(s);
$R_2$ is hydrogen, a $C_{1-6}$ alkyl group optionally having substituent(s) or a $C_{2-6}$ alkenyl group optionally having substituent(s);
$R_3$ is hydrogen or a $C_{1-6}$ alkyl group;
$R_4$ is hydrogen or a $C_{1-6}$ alkyl group;
$R_5$ is hydrogen or a $C_{1-6}$ alkyl group;
$R_1$ and $R_2$ are optionally joined to form a nitrogen-containing ring optionally having substituent(s);
$R_4$ and $R_5$ are optionally joined to form cycloalkane;
X is hydrogen,
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—N($R_{x5}$)—N($R_{x6}$)-Cy,
—O—N($R_{x5}$)-Cy,
—N($R_{x5}$)—O-Cy,
—C(O)—N($R_{x5}$)-Cy,
—N($R_{x5}$)—C(O)-Cy,
—S(O)m-N($R_{x5}$)-Cy,
—N($R_{x5}$)—S(O)m-Cy,
—O—S(O)m-Cy, or
—S(O)m-O-Cy;
n is an integer of 0-2;
m is 1 or 2;

Cy is a saturated or unsaturated cyclic group optionally having substituent(s) (optionally containing a hetero atom);
$R_{x1}$, $R_{x2}$, $R_{x3}$, $R_{x4}$, $R_{x5}$ and $R_{x6}$ are the same or different and each is hydrogen, a C-s alkyl group optionally having substituent(s) or a $C_{1-6}$ alkoxycarbonyl group optionally having substituent(s);
$R_6$ is a $C_{1-6}$ alkyl group optionally having substituent(s), a $C_{2-6}$ alkenyl group, a cyclic $C_{3-6}$ alkyl group (optionally containing a hetero atom), a halogeno group, a hydroxy group, a $C_{1-6}$ alkoxy group optionally having substituent(s), a halogeno$C_{1-6}$ alkyl group, a halogeno$C_{1-6}$ alkoxy group, an amino group, an amino group mono- or di-substituted by a $C_{1-6}$ alkyl group optionally having substituent(s), a cyano group, a $C_{1-6}$ alkylthio group, a carboxyl group, a $C_{1-6}$ alkoxycarbonyl group optionally having substituent(s), a carbamoyl group, a carbamoyl group mono- or di-substituted by a $C_{1-6}$ alkyl group optionally having substituent(s), or an amino group substituted by an acyl group optionally having substituent(s);
when $R_6$ is present in plurality, they may be the same or different; and
k is an integer of 0-3, or a pharmaceutically acceptable salt thereof, excluding the following compound:

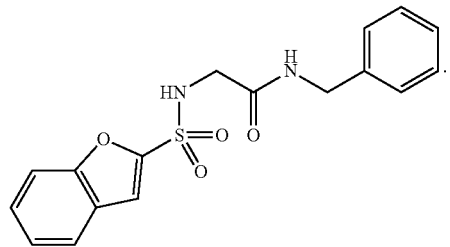 [SMILES: O=C(CNS(=O)(=O)c1cc2ccccc2o1)NCc1ccccc1]

[2] The compound of the above-mentioned [1], wherein, in the formula (I),
Q is =O;
$R_1$ is hydrogen or a $C_{1-6}$ alkyl group;
$R_4$ is hydrogen or a $C_{1-6}$ alkyl group;
$R_5$ is hydrogen or a $C_{1-6}$ alkyl group;
provided that $R_4$ and $R_5$ are not joined to form cycloalkane; and
X is hydrogen,
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—N($R_{x5}$)—N($R_{x6}$)-Cy,
—O—N($R_{x5}$)-Cy,
—N($R_{x5}$)—O-Cy,
—C(O)—N($R_{x5}$)-Cy,
—N($R_{x5}$)—C(O)-Cy,
—S(O)m-N($R_{x5}$)-Cy, or
—N($R_{x5}$)—S(O)m-Cy, or a pharmaceutically acceptable salt thereof.

[3] The compound of the above-mentioned [1], which is represented by the following formula (II):

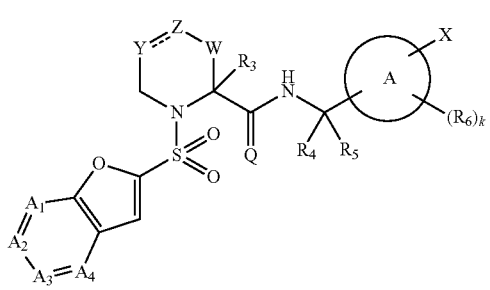

(II)

wherein

------ is a single bond or double bond;
Y is —CR$_{y1}$R$_{y2}$— or —CR$_{y3}$=;
Z is a bond, —O—, —CR$_{z1}$R$_{z2}$— or —CR$_{z3}$=;
W is a bond or —CR$_{w1}$R$_{w2}$—;
R$_{y1}$, R$_{y2}$, R$_{y3}$, R$_{z1}$, R$_{z2}$, R$_{z3}$, R$_{w1}$ and R$_{w2}$ are the same or different and each is hydrogen, a halogeno group, a hydroxy group or a C$_{1-6}$ alkyl group optionally having substituent(s); and other symbols are as defined in the above-mentioned [1], or a pharmaceutically acceptable salt thereof.
[4] The compound of the above-mentioned [3], wherein, in the formula (II),
Q is =O;
R$_4$ is hydrogen or a C$_{1-6}$ alkyl group;
R$_5$ is hydrogen or a C$_{1-6}$ alkyl group;
provided that R$_4$ and R$_5$ are not joined to form cycloalkane; and
X is hydrogen,
-Cy,
—C(R$_{x1}$R$_{x2}$)-Cy,
—C(R$_{x1}$R$_{x2}$)—C(R$_{x3}$R$_{x4}$)-Cy,
—C(R$_{x1}$)=C(R$_{x2}$)-Cy,
—O-Cy,
—O—C(R$_{x1}$R$_{x2}$)-Cy,
—C(R$_{x1}$R$_{x2}$)—O-Cy,
—S(O)n-Cy,
—S(O)n-C(R$_{x1}$R$_{x2}$)-Cy,
—C(R$_{x1}$R$_{x2}$)—S(O)n-Cy,
—N(R$_{x5}$)-Cy,
—N(R$_{x5}$)—C(R$_{x1}$R$_{x2}$)-Cy,
—C(R$_{x1}$R$_{x2}$)—N(R$_{x5}$)-Cy,
—N(R$_{x5}$)—N(R$_{x6}$)-Cy,
—O—N(R$_{x5}$)-Cy,
—N(R$_{x5}$)—O-Cy,
—C(O)—N(R$_{x5}$)-Cy,
—N(R$_{x5}$)—C(O)-Cy,
—S(O)m-N(R$_{x5}$)-Cy, or
—N(R$_{x5}$)—S(O)m-Cy,
or a pharmaceutically acceptable salt thereof.
[5] The compound of the above-mentioned [2], wherein R$_1$ is hydrogen, R$_2$ is a C$_{1-6}$ alkyl group, and R$_3$ is hydrogen, or a pharmaceutically acceptable salt thereof.
[6] The compound of the above-mentioned [4], wherein Y is —CH$_2$—, Z is —CH$_2$—, W is a bond, R$_3$ is hydrogen, or a pharmaceutically acceptable salt thereof.
[7] The compound of the above-mentioned [4], wherein Y is —CH$_2$—, Z is a bond, W is a bond, R$_3$ is hydrogen, or a pharmaceutically acceptable salt thereof.

[8] The compound of the above-mentioned [2], wherein partial structure (a)

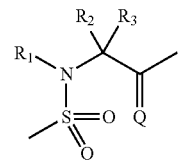

(a)

is any of the groups of the following formulas

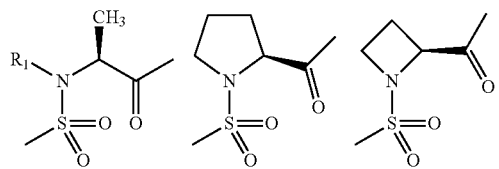

wherein R$_1$ is hydrogen or a C$_{1-6}$ alkyl group optionally having substituent(s), or a pharmaceutically acceptable salt thereof.
[9] The compound of the above-mentioned [8], wherein R$_1$ is hydrogen, or a pharmaceutically acceptable salt thereof.
[10] The compound of the above-mentioned [9], wherein R$_4$ and R$_5$ are each hydrogen, or a pharmaceutically acceptable salt thereof.
[11] The compound of the above-mentioned [9], wherein ring A is a 6-membered monocyclic aromatic ring or a heteroaromatic ring, or a pharmaceutically acceptable salt thereof.
[12] The compound of the above-mentioned [9], wherein ring A is benzene, pyridine or pyrimidine, or a pharmaceutically acceptable salt thereof.
[13] The compound of the above-mentioned [1], [2], [4], [8] or [9], wherein partial structure (b) containing ring A

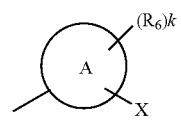

(b)

is any of the groups of the following formulas

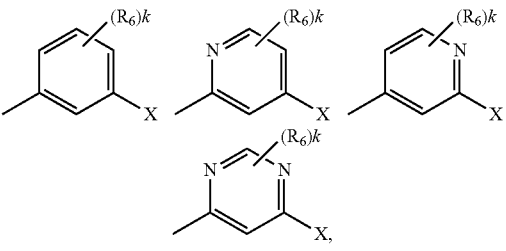

or a pharmaceutically acceptable salt thereof.
[14] The compound of the above-mentioned [9], wherein k is an integer of 0 to 2, R$_6$ is a C$_{1-6}$ alkyl group, a cyclic C$_{3-6}$ alkyl group (optionally containing a hetero atom), a halogeno group, a hydroxy group, a C$_{1-6}$ alkoxy group optionally having substituent(s), an amino group, a $C_{1-6}$ alkoxycarbonyl group or an amino group mono- or di-substituted by a $C_{1-6}$ alkyl group, or a pharmaceutically acceptable salt thereof.

[15] The compound of the above-mentioned [9], wherein k is 0, or a pharmaceutically acceptable salt thereof.

[16] The compound of the above-mentioned [9], wherein partial structure (b) containing ring A

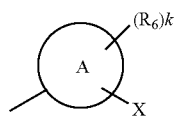
(b)

is any of the groups of the following formulas;

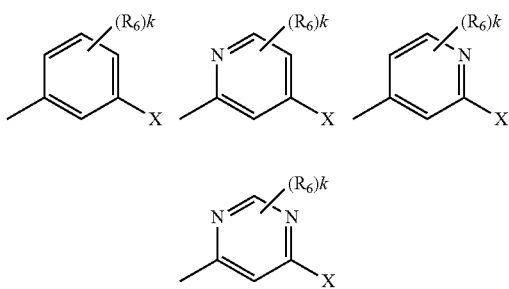

k is 0 or 1, $R_6$ is a cyclic $C_{3-6}$ alkyl group (optionally containing a hetero atom), a halogeno group, a $C_{1-6}$alkoxycarbonyl group, an amino group, an amino group mono- or di-substituted by a $C_{1-6}$ alkyl group or a hydroxy group, or a pharmaceutically acceptable salt thereof.

[17] The compound of the above-mentioned [9], wherein partial structure (b) containing ring A

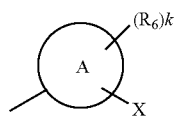
(b)

is any of the groups of the following formulas

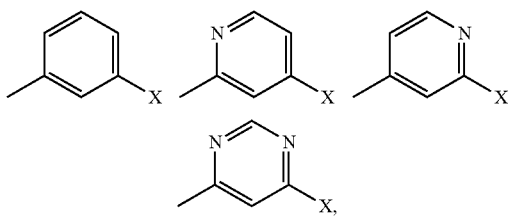

or a pharmaceutically acceptable salt thereof.

[18] The compound of the above-mentioned [9], wherein partial structure (b) containing ring A

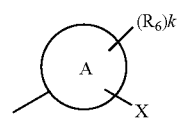
(b)

is a group of the following formula,

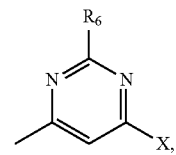

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$ alkyl group, or a pharmaceutically acceptable salt thereof.

[19] The compound of the above-mentioned [9], wherein $A_1$ is —C(Ra)═, $A_2$ is —C(Rb)═, As is —C(Rc)═, $A_4$ is —C(Rd)═, or a pharmaceutically acceptable salt thereof.

[20] The compound of the above-mentioned [9], wherein A is —C(Ra)═, $A_2$ is —C(Rb)═, $A_3$ is —C(Rc)═, $A_4$ is —C(Rd)═;

Ra, Rb, Rc and Rd are all hydrogens, or any one of them is a halogeno group, or a pharmaceutically acceptable salt thereof.

[21] The compound of the above-mentioned [1], [2], [4], [8] or [9], wherein partial structure (c)

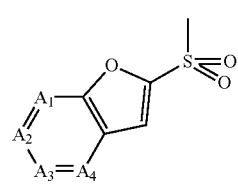
(c)

is any of the groups of the following formulas

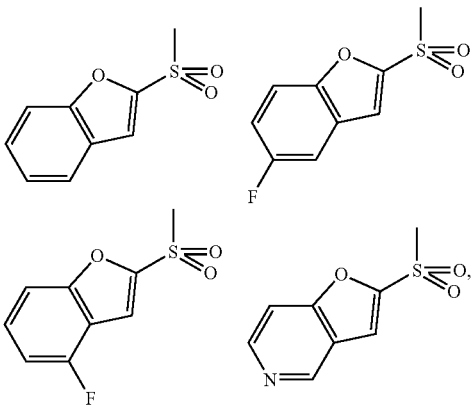

or a pharmaceutically acceptable salt thereof.

[22] The compound of the above-mentioned [1], [2], [4], [8] or [9], wherein X is hydrogen, -Cy, —O-Cy or —O—CH$_2$-Cy, or a pharmaceutically acceptable salt thereof.

[23] The compound of the above-mentioned [9], wherein X is -Cy, or a pharmaceutically acceptable salt thereof.
[24] The compound of the above-mentioned [9], wherein Cy is benzene optionally having substituent(s), pyridine optionally having substituent(s), pyrimidine optionally having substituent(s), pyridazine optionally having substituent(s), or pyrazine optionally having substituent (s), or a pharmaceutically acceptable salt thereof.
[25] The compound of the above-mentioned [9], wherein Cy is any of the groups of the following formulas

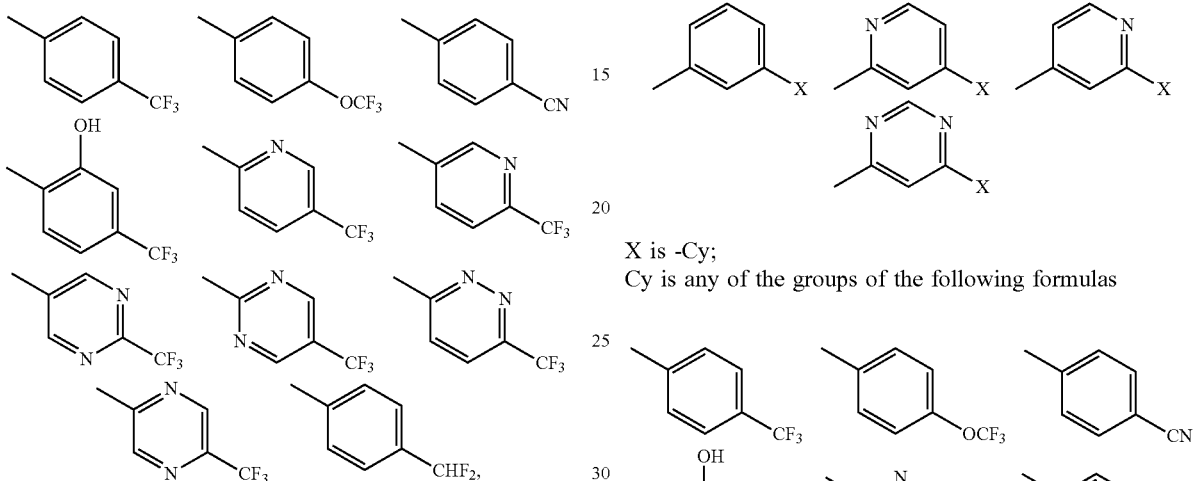

or a pharmaceutically acceptable salt thereof.
[26] The compound of the above-mentioned [9], wherein X is -Cy; Cy is benzene optionally having substituent(s), pyridine optionally having substituent(s), pyrimidine optionally having substituent(s), pyridazine optionally having substituent(s), or pyrazine optionally having substituent(s), or a pharmaceutically acceptable salt thereof.
[27] The compound of the above-mentioned [1], [2], [4], [8] or [9], wherein X is -Cy;
Cy is any of the groups of the following formulas

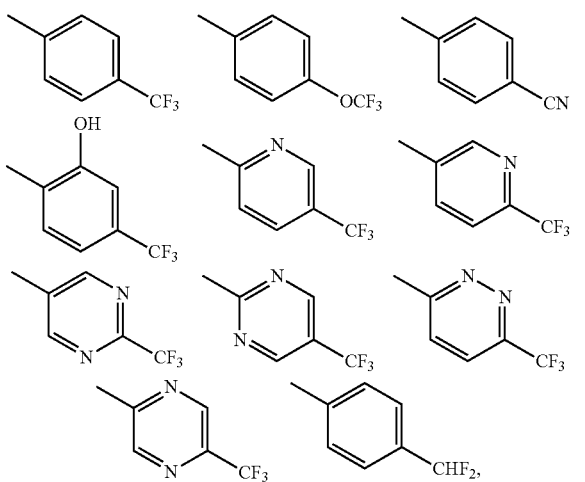

or a pharmaceutically acceptable salt thereof.
[28] The compound of the above-mentioned [9], wherein $R_4$ and $R_5$ are each hydrogen;
partial structure (b) containing ring A

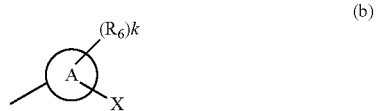

is any of the groups of the following formulas;

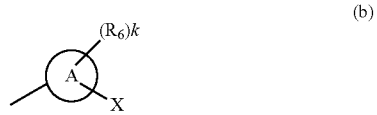

X is -Cy;
Cy is any of the groups of the following formulas

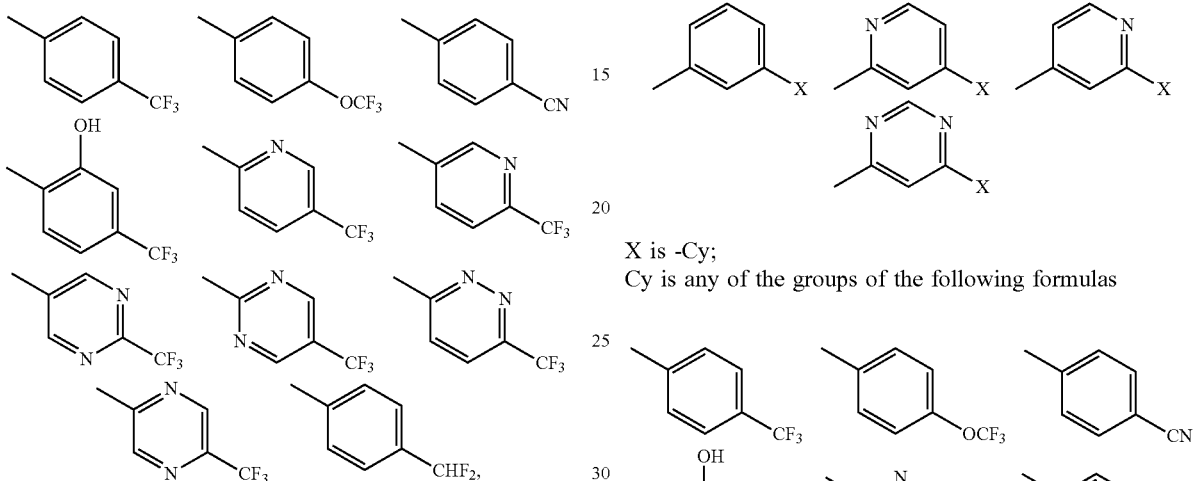

or a pharmaceutically acceptable salt thereof.
[29] The compound the above-mentioned [1], [2], [4], [8] or [9], wherein $R_4$ and $R_5$ are each hydrogen;
partial structure (b) containing ring A

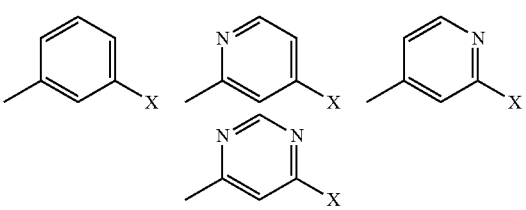

is any of the groups of the following formulas;

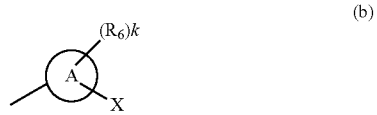

X is -Cy;

Cy is any of the groups of the following formulas;

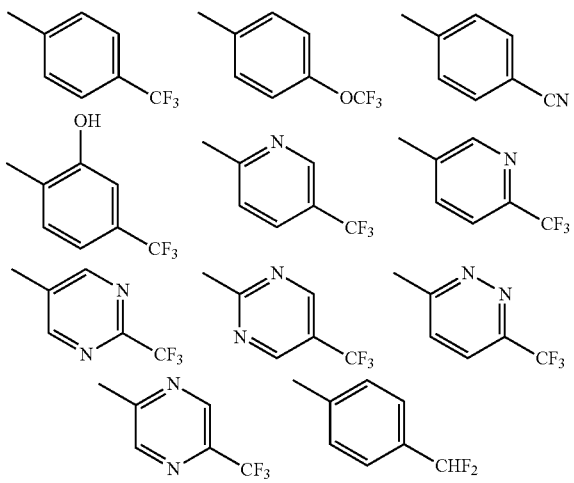

partial structure (c)

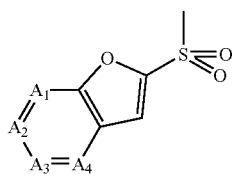

is any of the groups of the following formulas

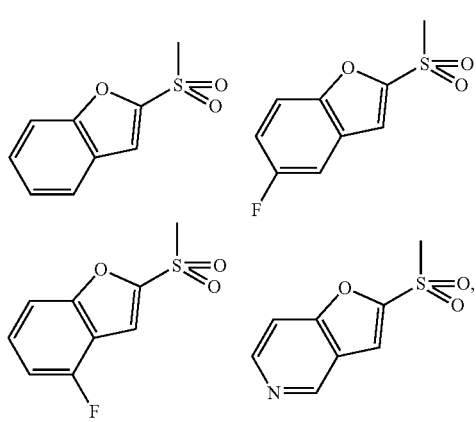

or a pharmaceutically acceptable salt thereof.
[30] The compound of the above-mentioned [1], [2], [4], [8] or [9], wherein $R_4$ and $R_5$ are each hydrogen;
partial structure (b) containing ring A

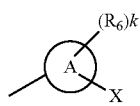

is a group of the following formula,

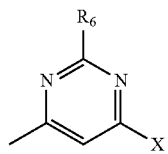

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$ alkyl group,
X is -Cy;
Cy is any of the groups of the following formulas;

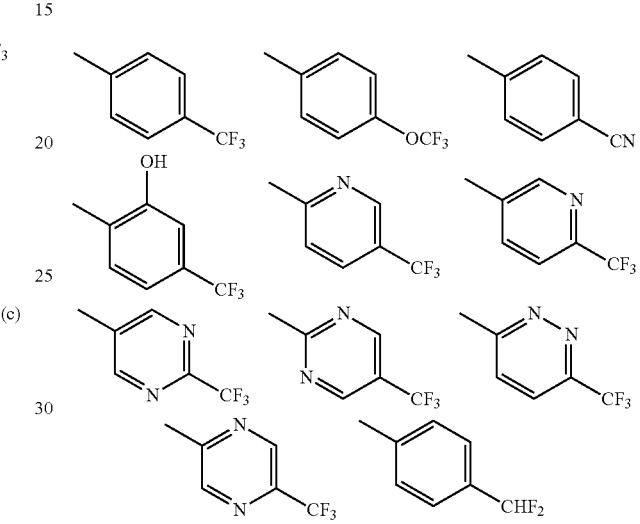

partial structure (c)

is any of the groups of the following formulas

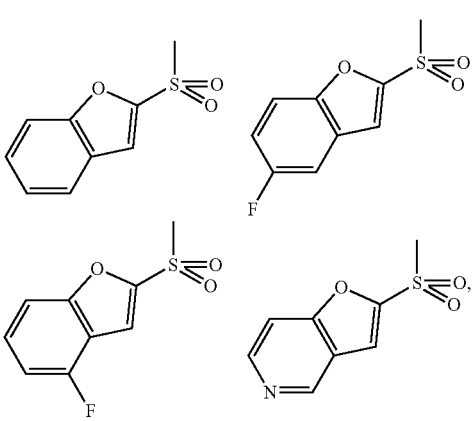

or a pharmaceutically acceptable salt thereof.
[31] The compound of the above-mentioned [2], which is represented by any of the following structural formulas, or a pharmaceutically acceptable salt thereof:
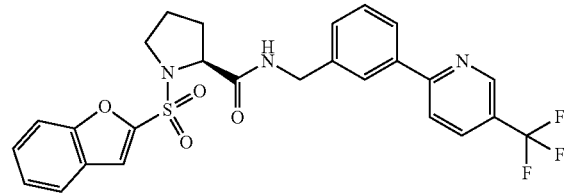
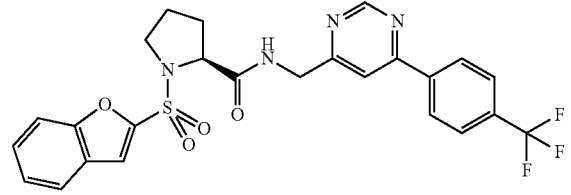
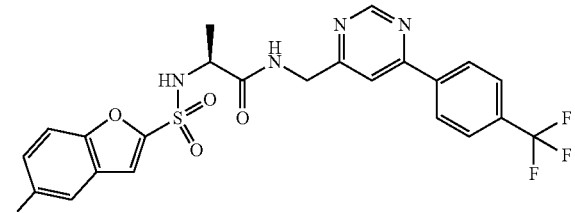
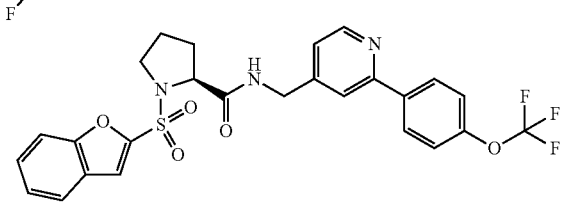
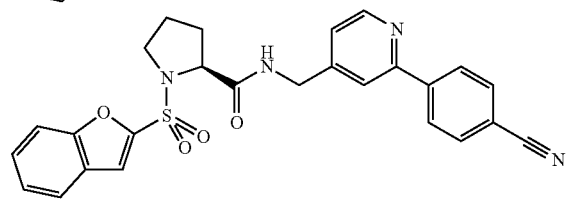
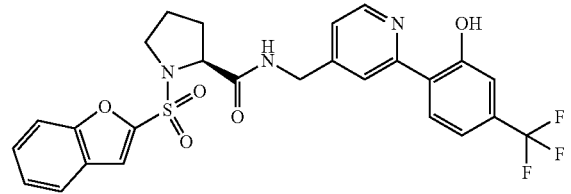
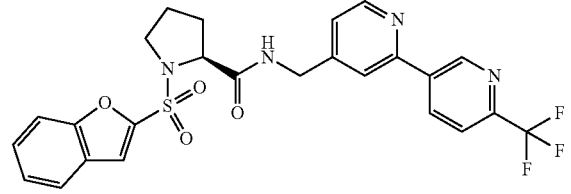
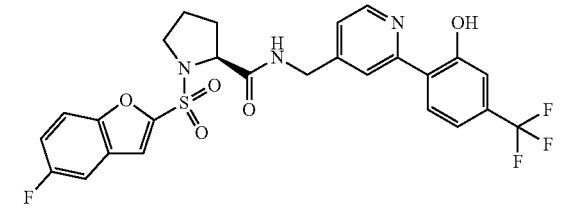
-continued
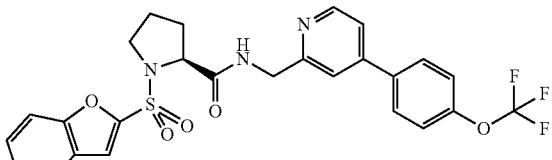
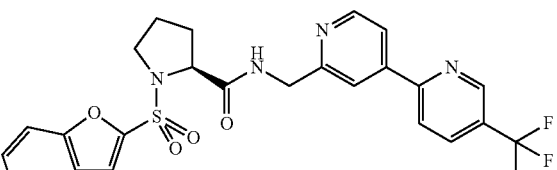
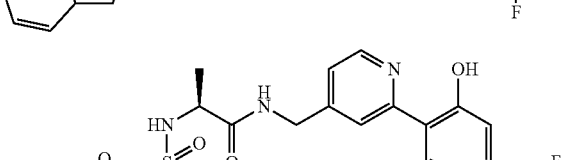
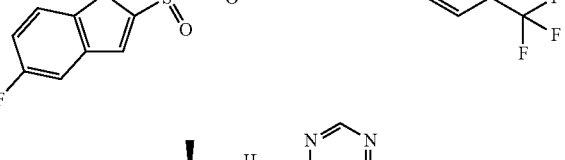
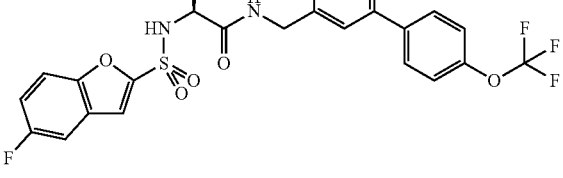
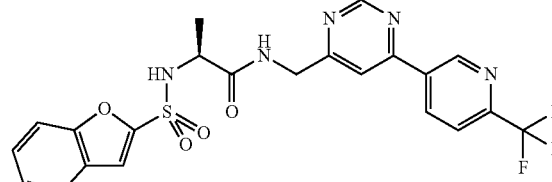
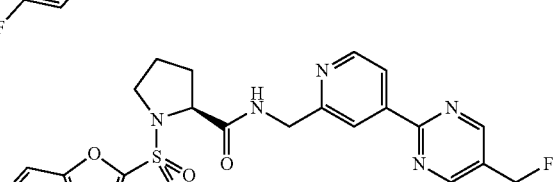
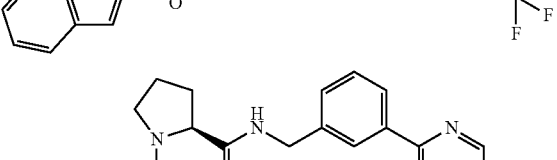
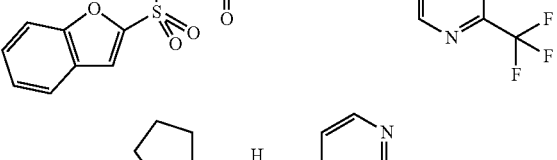
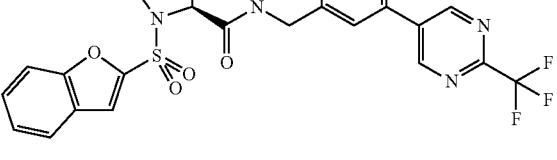

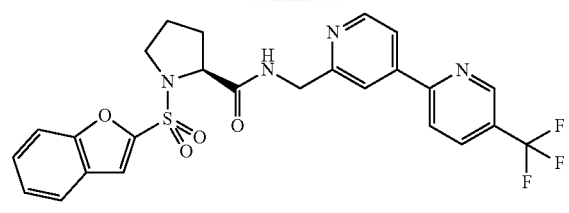
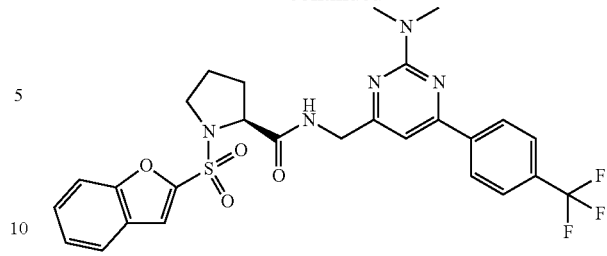
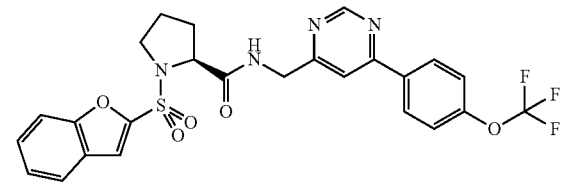
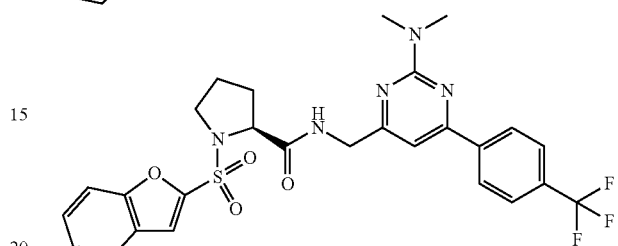
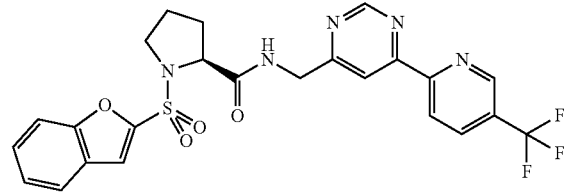
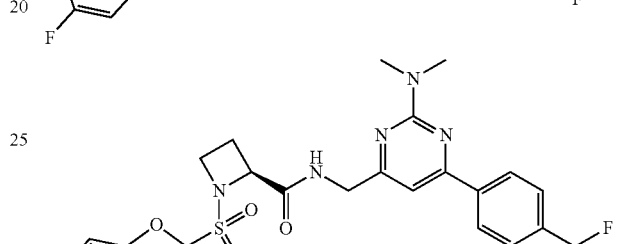
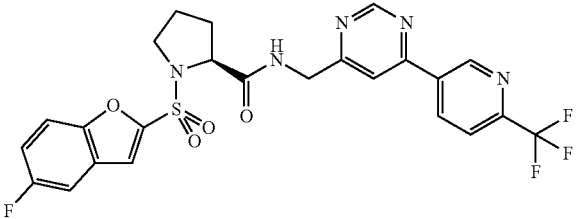
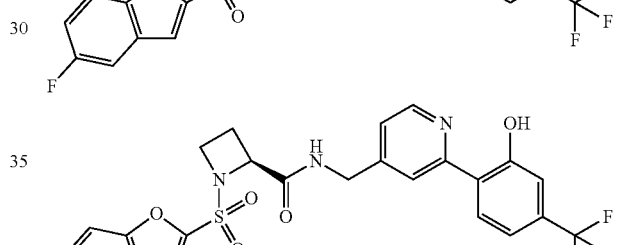
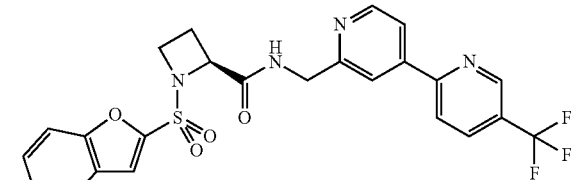
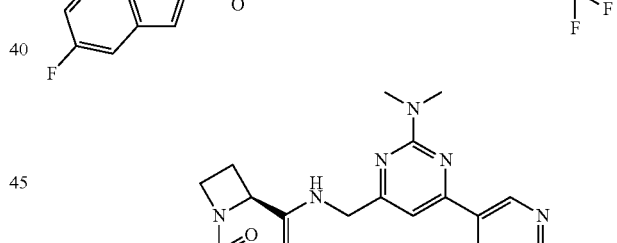
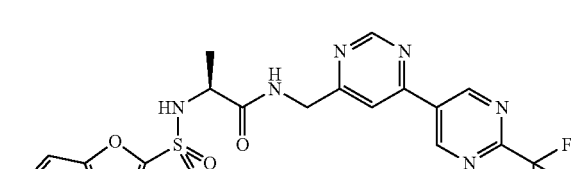
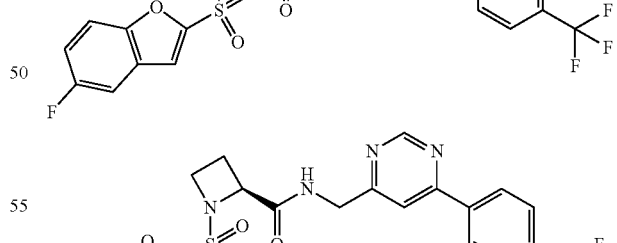
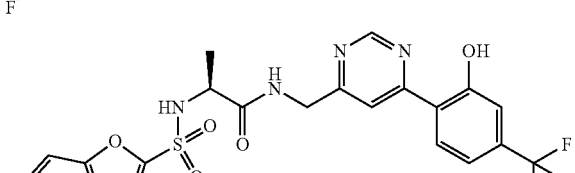
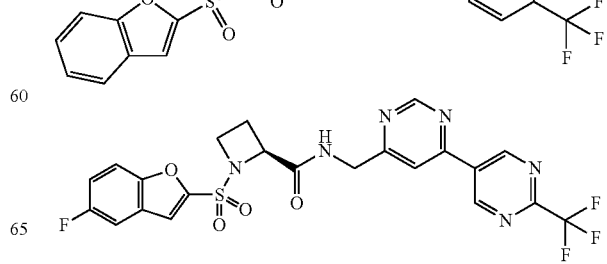

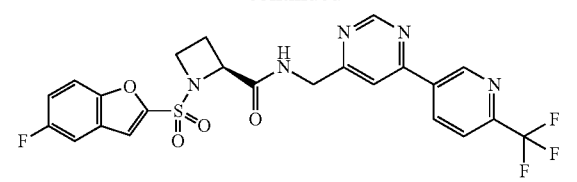
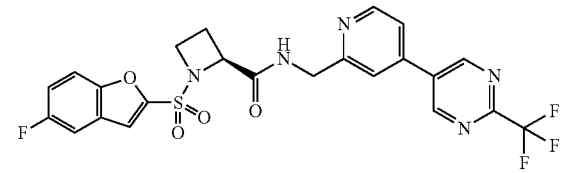
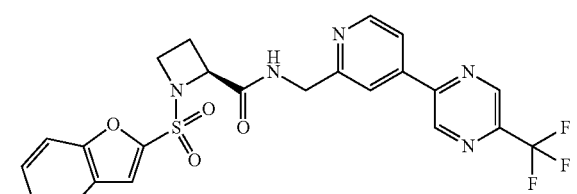
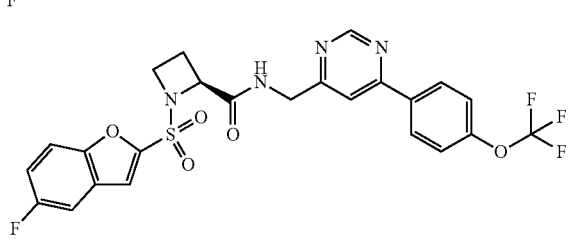
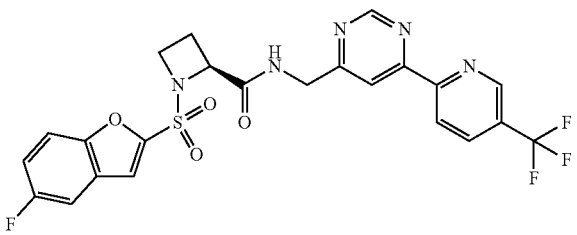
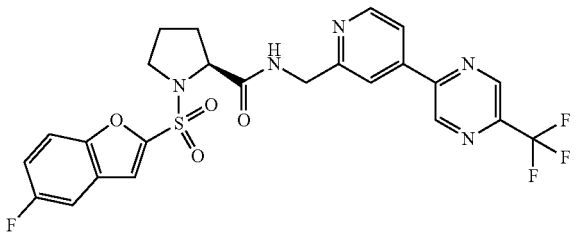
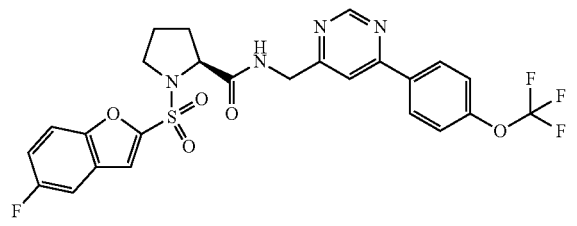
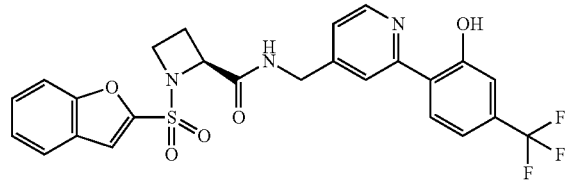
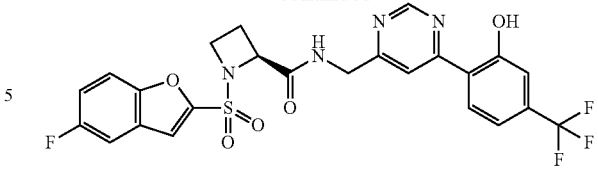

[32] A TRPA1 antagonist comprising the compound of any of the above-mentioned [1]-[31] or a pharmaceutically acceptable salt thereof.

[33] A medicament comprising the compound of any of the above mentioned [1]-[31] or a pharmaceutically acceptable salt thereof.

[34] The medicament of the above-mentioned [33], which is for the prophylaxis and/or treatment of a disease involving TRPA1.

[35] The medicament of the above-mentioned [34], wherein the disease involving TRPA1 is selected from the group consisting of chronic pain, acute pain, diabetic neuropathy, osteoarthritis, asthma, chronic coughing, chronic obstructive pulmonary diseases, functional gastrointestinal disorder, reflux esophagitis, irritable bowel syndrome, inflammatory bowel disease, pancreatitis, anticancer agent-induced neuropathy, pruritus and allergic dermatitis.

[36] The medicament of the above-mentioned [34], wherein the disease involving TRPA1 is selected from the group consisting of chronic pain, acute pain, asthma, chronic obstructive pulmonary diseases, functional gastrointestinal disorder, reflux esophagitis, inflammatory bowel disease, anticancer agent-induced neuropathy and pruritus.

[37] A method for the prophylaxis and/or treatment of a disease involving TRPA1, comprising administering an effective amount of the compound of any of the above-mentioned [1]-[31] to a subject in need thereof.

[38] The method of the above-mentioned [37], wherein the disease involving TRPA1 is selected from the group consisting of chronic pain, acute pain, diabetic neuropathy, osteoarthritis, asthma, chronic coughing, chronic obstructive pulmonary diseases, functional gastrointestinal disorder, reflux esophagitis, irritable bowel syndrome, inflammatory bowel disease, pancreatitis, anticancer agent-induced neuropathy, pruritus and allergic dermatitis.

[39] The method of the above-mentioned [37], wherein the disease involving TRPA1 is selected from the group consisting of chronic pain, acute pain, asthma, chronic obstructive pulmonary diseases, functional gastrointestinal disorder, reflux esophagitis, inflammatory bowel disease, anticancer agent-induced neuropathy and pruritus.

[40] The compound of any of the above-mentioned [1]-[31], or a pharmaceutically acceptable salt thereof for use in the prophylaxis and/or treatment of a disease involving TRPA1.

[41] The compound of the above-mentioned [40] or a pharmaceutically acceptable salt thereof, wherein the disease involving TRPA1 is selected from the group consisting of chronic pain, acute pain, diabetic neuropathy, osteoarthritis, asthma, chronic coughing, chronic obstructive pulmonary diseases, functional gastrointestinal disorder, reflux esophagitis, irritable bowel syndrome, inflammatory bowel disease, pancreatitis, anticancer agent-induced neuropathy, pruritus and allergic dermatitis.

[42] The compound of the above-mentioned [40] or a pharmaceutically acceptable salt thereof, the disease involving TRPA1 is selected from the group consisting of chronic pain, acute pain, asthma, chronic obstructive pulmonary diseases, functional gastrointestinal disorder, reflux esoph- As still another embodiment of compound (I), a compound represented by the following (I')

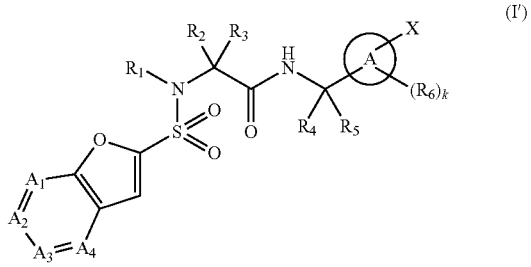

wherein
ring A is a 6-membered monocyclic aromatic ring or heteroaromatic ring, or a bicyclic aromatic ring or heteroaromatic ring;
$A_1$ is —C(Ra)= or —N=;
$A_2$ is —C(Rb)= or —N=;
$A_3$ is —C(Rc)= or —N=;
$A_4$ is —C(Rd)= or —N=;
Ra, Rb, Rc and Rd are the same or different and each is hydrogen, a halogeno group, a cyano group, a hydroxy group, a $C_{1-6}$ alkyl group, a $C_{1-6}$ alkoxy group, a halogeno$C_{1-6}$ alkyl group or a halogeno$C_{1-6}$ alkoxy group;
provided at least two of $A_1$-$A_4$ are not —N=;
$R_1$ is hydrogen or a $C_{1-6}$ alkyl group;
$R_2$ is hydrogen, a $C_{1-6}$ alkyl group optionally having substituent(s) or a $C_{2-6}$ alkenyl group optionally having substituent(s);
$R_3$ is hydrogen or a $C_{1-6}$ alkyl group;
$R_4$ is hydrogen or a $C_{1-6}$ alkyl group;
$R_5$ is hydrogen or a $C_{1-6}$ alkyl group;
$R_1$ and $R_2$ are optionally joined to form a nitrogen-containing ring optionally having substituent(s);
X is hydrogen,
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—N($R_{x5}$)—N($R_{x6}$)-Cy,
—O—N($R_{x5}$)-Cy,
—N($R_{x5}$)—O-Cy,
—C(O)—N($R_{x5}$)-Cy,
—N($R_{x5}$)—C(O)-Cy,
—S(O)m-N($R_{x5}$)-Cy, or
—N($R_{x5}$)—S(O) m-Cy;
n is an integer of 0-2;
m is 1 or 2;
Cy is a saturated or unsaturated cyclic group optionally having substituent(s) (optionally containing a hetero atom);

$R_{x1}$, $R_{x2}$, $R_{x3}$, $R_{x4}$, $R_{x5}$ and $R_{x6}$ are the same or different and each is hydrogen, a $C_{1-6}$ alkyl group optionally having substituent(s) or a $C_{1-6}$ alkoxycarbonyl group optionally having substituent(s);
$R_6$ is a $C_{1-6}$ alkyl group optionally having substituent(s), a $C_{2-6}$ alkenyl group, a cyclic $C_{3-6}$ alkyl group (optionally containing a hetero atom), a halogeno group, a hydroxy group, a $C_{1-6}$ alkoxy group optionally having substituent(s), a halogeno$C_{1-6}$ alkyl group, a halogeno$C_{1-6}$ alkoxy group, an amino group, an amino group mono- or di-substituted by a $C_{1-6}$ alkyl group optionally having substituent(s), a cyano group, a $C_{1-6}$ alkylthio group, a carboxyl group, a $C_{1-6}$ alkoxycarbonyl group optionally having substituent(s), a carbamoyl group, a carbamoyl group mono- or di-substituted by a $C_{1-6}$ alkyl group optionally having substituent(s) or an amino group substituted by an acyl group optionally having substituent(s);
when $R_6$ is present in plurality, they may be the same or different; and
k is an integer of 0-3, or a pharmaceutically acceptable salt thereof can be mentioned, excluding the following compound:

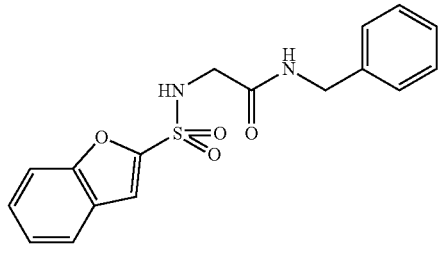

As still another embodiment of compound (II), a compound represented by the following formula (II')

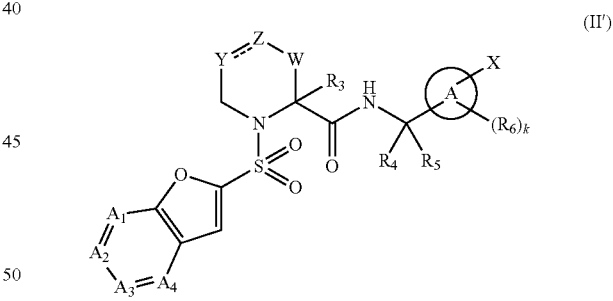

wherein
------ is a single bond or double bond;
Y is —C$R_{y1}R_{y2}$— or —C$R_{y3}$=;
Z is a bond, —O—, —C$R_{z1}R_{z2}$— or —C$R_{z3}$=;
W is a bond or —C$R_{w1}R_{w2}$—;
$R_{y1}$, $R_{y2}$, $R_{y3}$, $R_{z1}$, $R_{z2}$, $R_{z3}$, $R_{w1}$ and $R_{w2}$ are the same or different and each is hydrogen, a halogeno group, a hydroxy group or a $C_{1-6}$ alkyl group optionally having substituent(s); and other symbols are as defined in the formula (I'), or a pharmaceutically acceptable salt thereof
can be mentioned.
As other preferable embodiment of compound (I), the compounds described in the below-mentioned Examples or pharmaceutically acceptable salts thereof can be mentioned.

More preferred are the compounds described in Examples 1, 2, 4, 5, 6, 7, 8, 9, 10, 11, 12, 13, 14, 16, 17, 18, 19, 20, 25, 26, 27, 30, 31, 34, 35, 36, 37, 38, 41, 42, 43, 44, 47, 48, 49, 51, 53, 54, 56, 57, 65, 66, 67, 69, 70, 71, 77, 79, 80, 84, 86, 87, 88, 89, 90, 92, 93, 94, 95, 97, 98, 99, 100, 101, 102, 104, 106, 107, 108, 109, 110, 115, 116, 117, 119, 123, 124, 127, 128, 129, 130, 132, 133, 135, 136, 137, 138, 139, 140, 141, 142, 145, 148, 149, 150, 151, 153, 155, 156, 157, 158, 159, 160, 161, 164, 172, 173, 174, 175, 179, 181, 190, 191, 192, 193, 194, 195, 196, 197, 198, 199, 200, 201, 202, 203, 205, 206, 207, 210, 212, 214, 215, 216, 221, 222, 223, 224, 225, 226, 229, 230, 231, 233, 235, 239, 240, 248, 252, 255, 258, 259, 262, 263, 264, 265, 267, 268, 269, 270, 271, 272, 273, 274, 275, 278, 279, 281, 285, 287, 288, 289, 290, 291, 293, 296, 297, 298, 299, 309, 310, 311, 312, 315, 318, 326, 327, 328, 329, 330, 332, 333, 336, 337, 338, 339, 341, 344, 348, 349, 357, 359, 360, 362, 364, 368, 369, 371, 372, 374, 375, 376, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 417, 418, 419, 420, 421, 422, 423, 424, 426 and in the following Tables (Table 1), and pharmaceutically acceptable salts thereof.
TABLE 1
| Example No. | Structural formula |
| --- | --- |
| 1 | 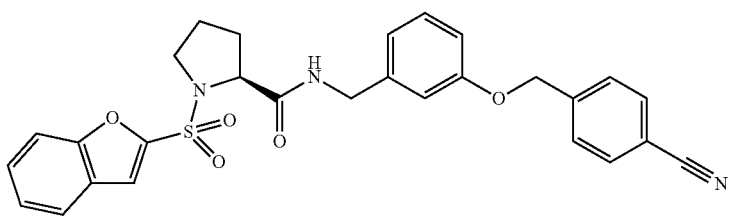 [SMILES: N#Cc1ccc(COc2cccc(CNC(=O)[C@@H]3CCCN3S(=O)(=O)c3cc4ccccc4o3)c2)cc1] |
| 2 | 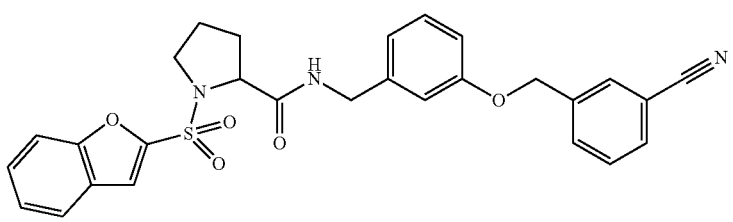 [SMILES: N#Cc1cccc(COc2cccc(CNC(=O)C3CCCN3S(=O)(=O)c3cc4ccccc4o3)c2)c1] |
| 4 | 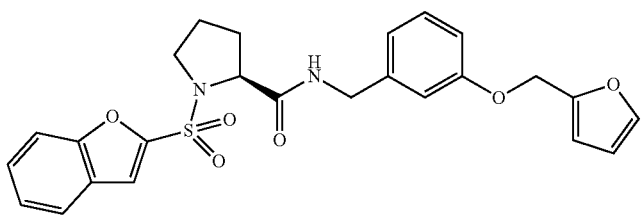 [SMILES: O=C(NCc1cccc(OCc2cccs2)c1)[C@@H]1CCCN1S(=O)(=O)c1cc2ccccc2o1] |
| 5 | 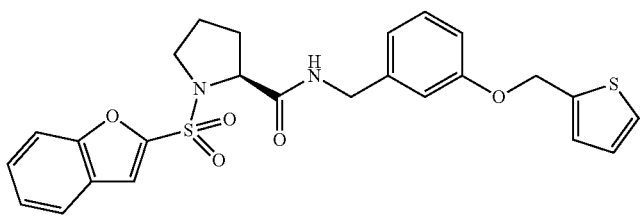 |
| 6 | 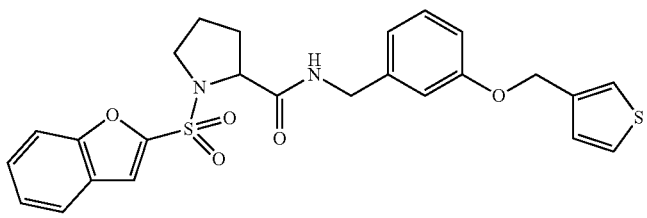 [SMILES: O=C(NCc1cccc(OCc2ccsc2)c1)C1CCCN1S(=O)(=O)c1cc2ccccc2o1] |

TABLE 1-continued
| Example No. | Structural formula |
|---|---|
| 7 | 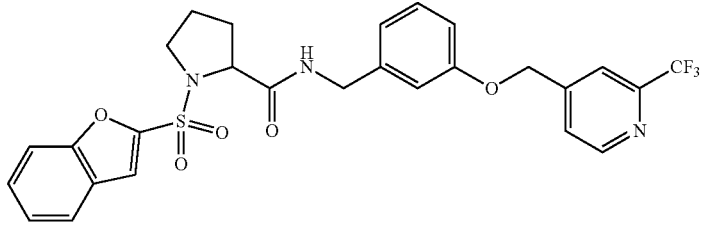 [SMILES: O=C(NCc1cccc(OCc2ccnc(C(F)(F)F)c2)c1)C1CCCN1S(=O)(=O)c1cc2ccccc2o1] |
| 8 | 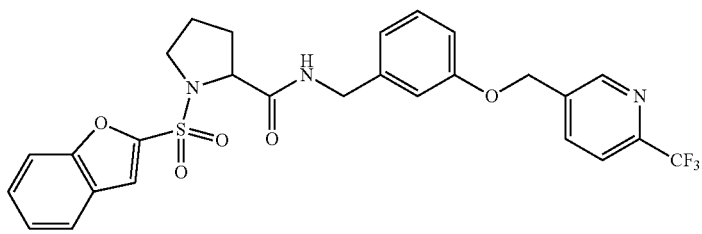 [SMILES: O=C(NCc1cccc(OCc2ccc(C(F)(F)F)nc2)c1)C1CCCN1S(=O)(=O)c1cc2ccccc2o1] |
| 9 | 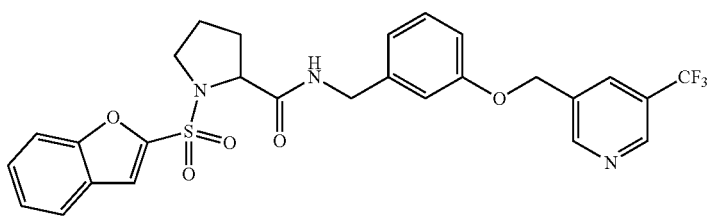 [SMILES: O=C(NCc1cccc(OCc2cncc(C(F)(F)F)c2)c1)C1CCCN1S(=O)(=O)c1cc2ccccc2o1] |
| 10 | 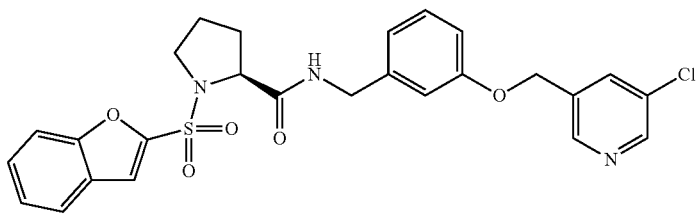 [SMILES: O=C(NCc1cccc(OCc2cncc(Cl)c2)c1)[C@@H]1CCCN1S(=O)(=O)c1cc2ccccc2o1] |
| 11 | 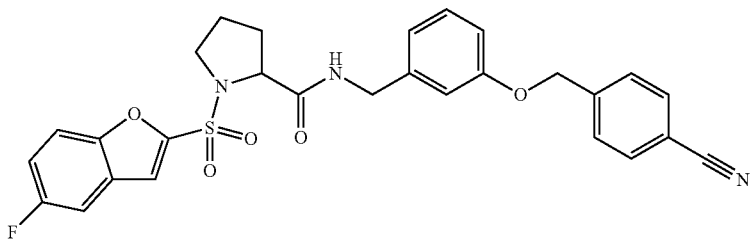 [SMILES: N#Cc1ccc(COc2cccc(CNC(=O)C3CCCN3S(=O)(=O)c3cc4cc(F)ccc4o3)c2)cc1] |
| 12 | 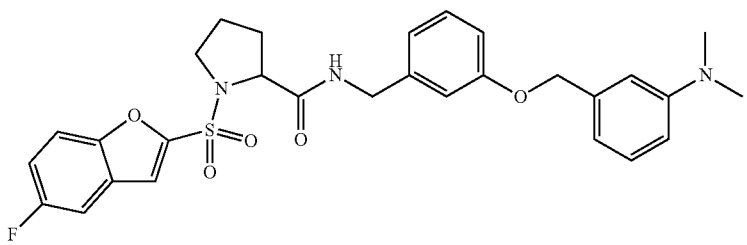 [SMILES: CN(C)c1cccc(COc2cccc(CNC(=O)C3CCCN3S(=O)(=O)c3cc4cc(F)ccc4o3)c2)c1] |

TABLE 1-continued
| Example No. | Structural formula |
|---|---|
| 13 | 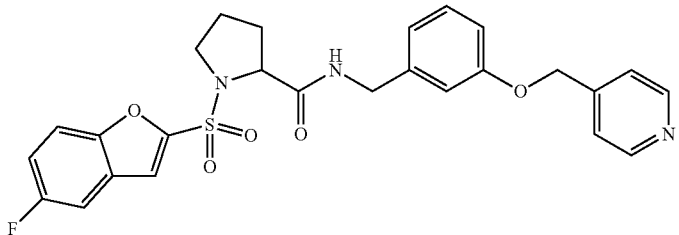 [SMILES: O=C(NCc1cccc(OCc2ccncc2)c1)C1CCCN1S(=O)(=O)c1cc2cc(F)ccc2o1] |
| 14 | 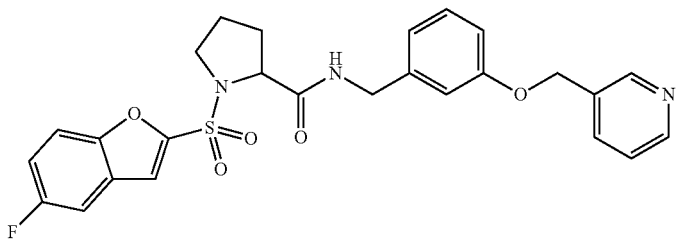 [SMILES: O=C(NCc1cccc(OCc2cccnc2)c1)C1CCCN1S(=O)(=O)c1cc2cc(F)ccc2o1] |
| 16 | 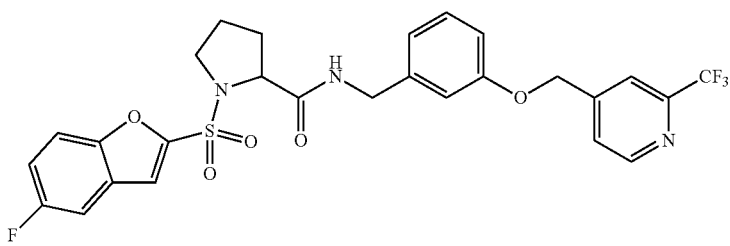 [SMILES: O=C(NCc1cccc(OCc2ccnc(C(F)(F)F)c2)c1)C1CCCN1S(=O)(=O)c1cc2cc(F)ccc2o1] |
| 17 | 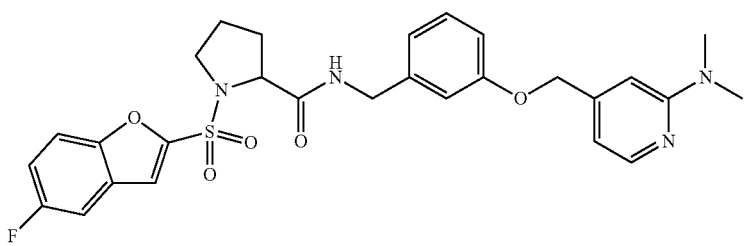 [SMILES: CN(C)c1cc(COc2cccc(CNC(=O)C3CCCN3S(=O)(=O)c3cc4cc(F)ccc4o3)c2)ccn1] |
| 18 | 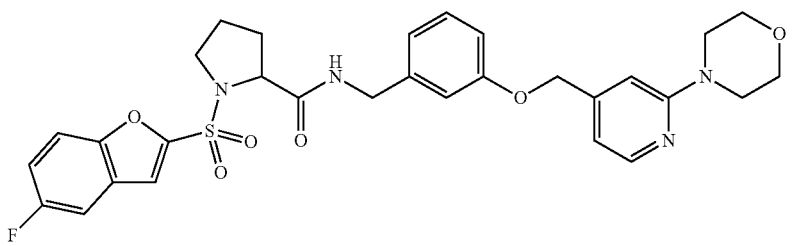 [SMILES: O=C(NCc1cccc(OCc2ccnc(N3CCOCC3)c2)c1)C1CCCN1S(=O)(=O)c1cc2cc(F)ccc2o1] |
| 19 | 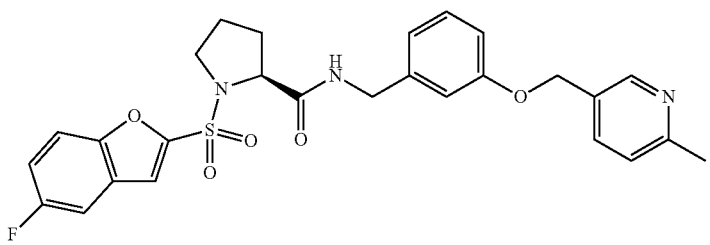 [SMILES: Cc1ccc(COc2cccc(CNC(=O)[C@@H]3CCCN3S(=O)(=O)c3cc4cc(F)ccc4o3)c2)cn1] |

TABLE 1-continued
| Example No. | Structural formula |
|---|---|
| 20 | 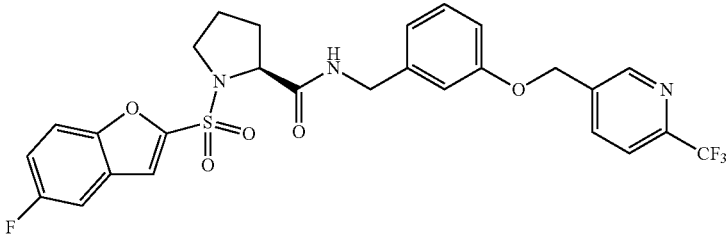 [SMILES: O=C(NCc1cccc(OCc2ccc(C(F)(F)F)nc2)c1)[C@@H]1CCCN1S(=O)(=O)c1cc2cc(F)ccc2o1] |
| 25 | 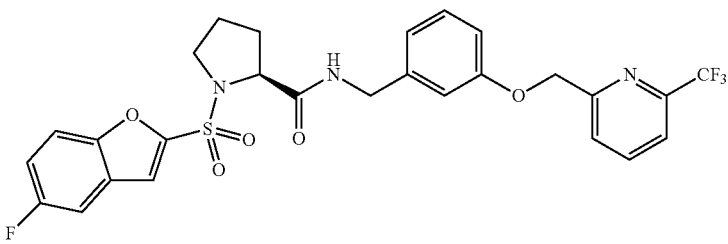 [SMILES: O=C(NCc1cccc(OCc2cccc(C(F)(F)F)n2)c1)[C@@H]1CCCN1S(=O)(=O)c1cc2cc(F)ccc2o1] |
| 26 | 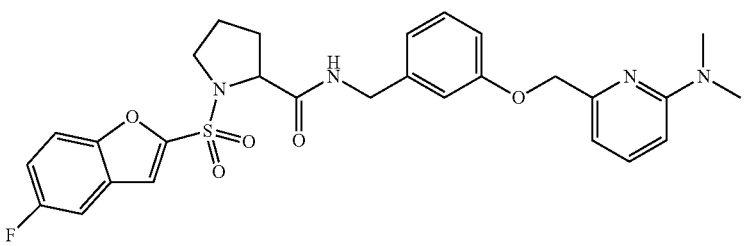 [SMILES: CN(C)c1cccc(COc2cccc(CNC(=O)C3CCCN3S(=O)(=O)c3cc4cc(F)ccc4o3)c2)n1] |
| 27 | 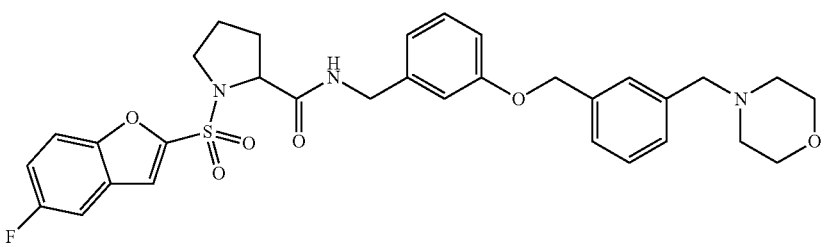 [SMILES: O=C(NCc1cccc(OCc2cccc(CN3CCOCC3)c2)c1)C1CCCN1S(=O)(=O)c1cc2cc(F)ccc2o1] |
| 30 | 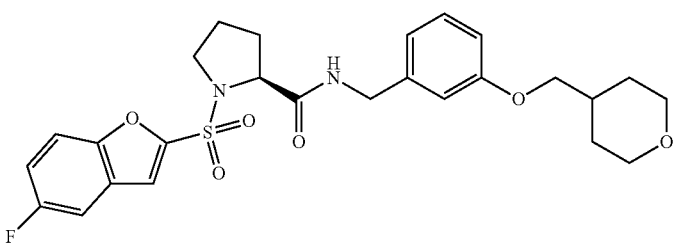 |
| 31 | 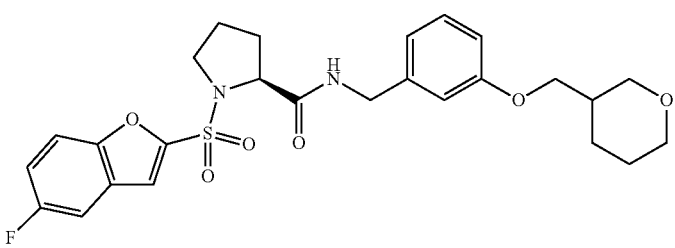 [SMILES: O=C(NCc1cccc(OCC2CCCOC2)c1)[C@@H]1CCCN1S(=O)(=O)c1cc2cc(F)ccc2o1] |

TABLE 1-continued
| Example No. | Structural formula |
|---|---|
| 34 | 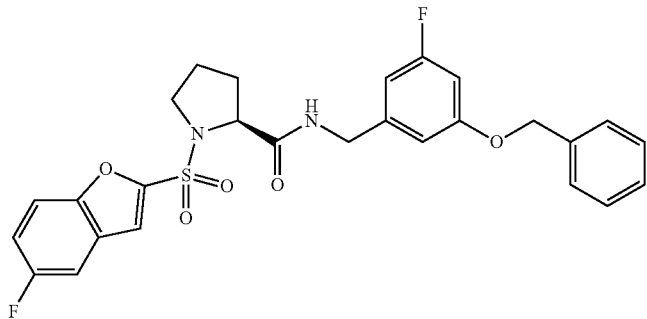 [SMILES: O=C(NCc1cc(F)cc(OCc2ccccc2)c1)[C@@H]1CCCN1S(=O)(=O)c1cc2cc(F)ccc2o1] |
| 35 | 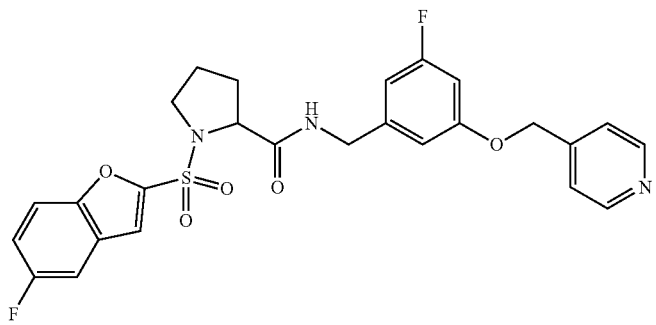 [SMILES: O=C(NCc1cc(F)cc(OCc2ccncc2)c1)C1CCCN1S(=O)(=O)c1cc2cc(F)ccc2o1] |
| 36 | 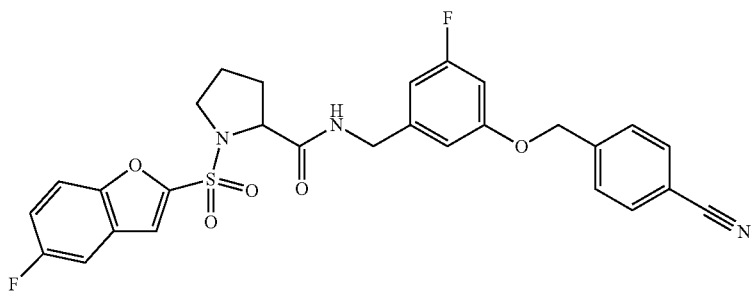 [SMILES: N#Cc1ccc(COc2cc(F)cc(CNC(=O)C3CCCN3S(=O)(=O)c3cc4cc(F)ccc4o3)c2)cc1] |
| 37 | 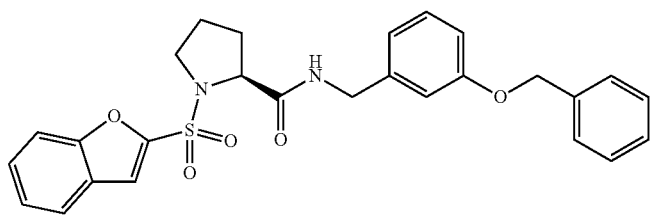 [SMILES: O=C(NCc1cccc(OCc2ccccc2)c1)[C@@H]1CCCN1S(=O)(=O)c1cc2ccccc2o1] |
| 38 | 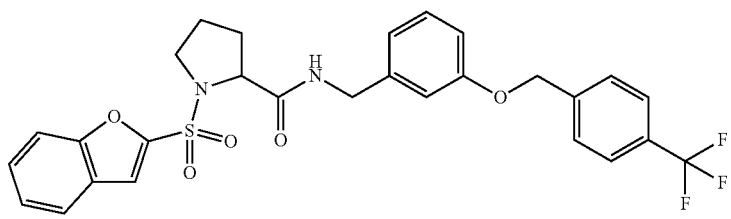 [SMILES: O=C(NCc1cccc(OCc2ccc(C(F)(F)F)cc2)c1)C1CCCN1S(=O)(=O)c1cc2ccccc2o1] |

TABLE 1-continued
| Example No. | Structural formula |
|---|---|
| 41 | 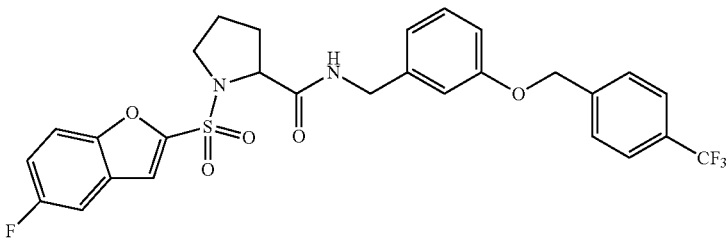 [SMILES: O=C(NCc1cccc(OCc2ccc(C(F)(F)F)cc2)c1)C1CCCN1S(=O)(=O)c1cc2cc(F)ccc2o1] |
| 42 | 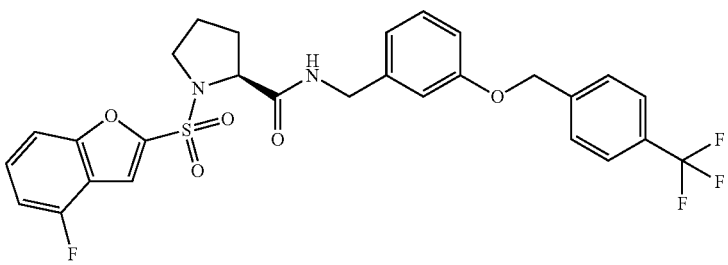 [SMILES: O=C(NCc1cccc(OCc2ccc(C(F)(F)F)cc2)c1)[C@@H]1CCCN1S(=O)(=O)c1cc2c(F)cccc2o1] |
| 43 | 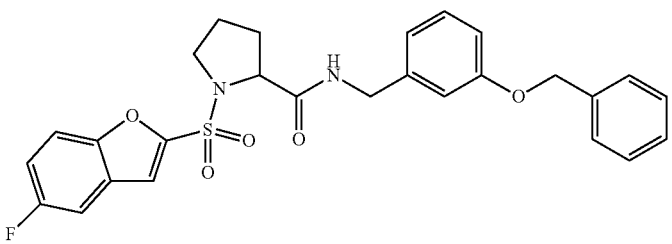 [SMILES: O=C(NCc1cccc(OCc2ccccc2)c1)C1CCCN1S(=O)(=O)c1cc2cc(F)ccc2o1] |
| 44 | 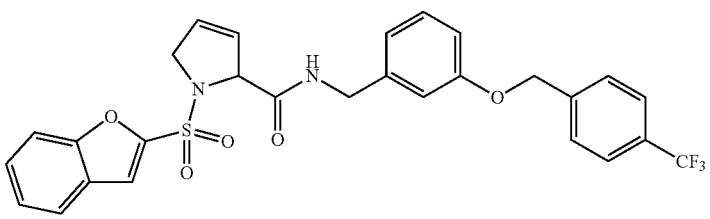 [SMILES: O=C(NCc1cccc(OCc2ccc(C(F)(F)F)cc2)c1)C1C=CCN1S(=O)(=O)c1cc2ccccc2o1] |
| 47 | 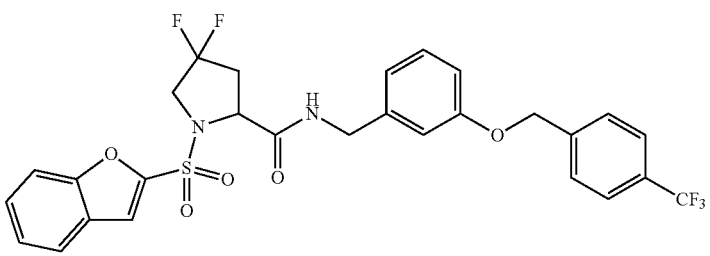 [SMILES: O=C(NCc1cccc(OCc2ccc(C(F)(F)F)cc2)c1)C1CC(F)(F)CN1S(=O)(=O)c1cc2ccccc2o1] |
| 48 | 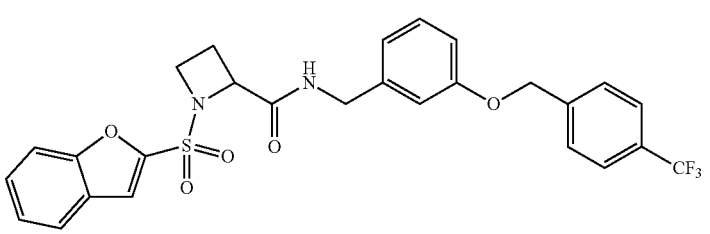 [SMILES: O=C(NCc1cccc(OCc2ccc(C(F)(F)F)cc2)c1)C1CCN1S(=O)(=O)c1cc2ccccc2o1] |

TABLE 1-continued
| Example No. | Structural formula |
|---|---|
| 49 | 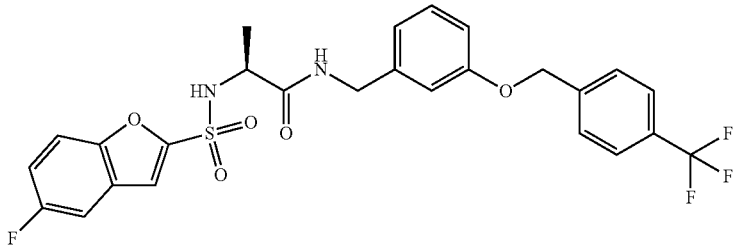 [SMILES: C[C@H](NS(=O)(=O)c1cc2cc(F)ccc2o1)C(=O)NCc1cccc(OCc2ccc(C(F)(F)F)cc2)c1] |
| 51 | 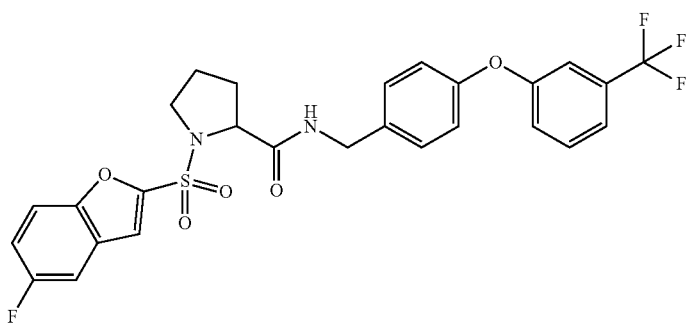 [SMILES: O=C(NCc1ccc(Oc2cccc(C(F)(F)F)c2)cc1)C1CCCN1S(=O)(=O)c1cc2cc(F)ccc2o1] |
| 53 | 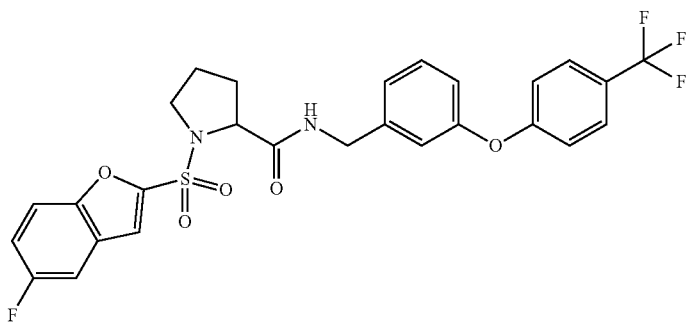 [SMILES: O=C(NCc1cccc(Oc2ccc(C(F)(F)F)cc2)c1)C1CCCN1S(=O)(=O)c1cc2cc(F)ccc2o1] |
| 54 | 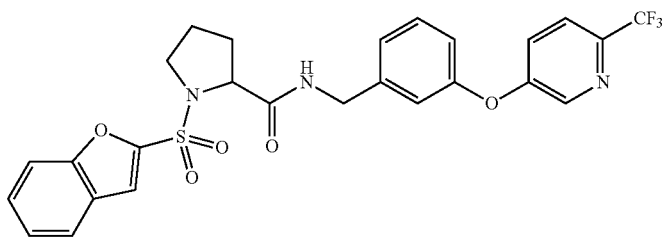 [SMILES: O=C(NCc1cccc(Oc2ccc(C(F)(F)F)nc2)c1)C1CCCN1S(=O)(=O)c1cc2ccccc2o1] |
| 56 | 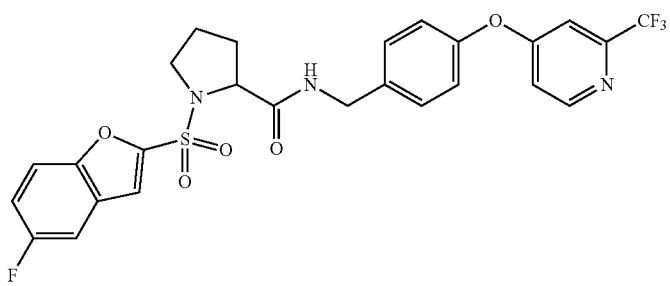 [SMILES: O=C(NCc1ccc(Oc2ccnc(C(F)(F)F)c2)cc1)C1CCCN1S(=O)(=O)c1cc2cc(F)ccc2o1] |

TABLE 1-continued
| Example No. | Structural formula |
|---|---|
| 57 | 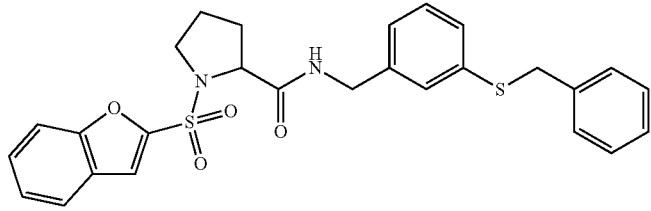 [SMILES: O=C(NCc1cccc(SCc2ccccc2)c1)C1CCCN1S(=O)(=O)c1cc2ccccc2o1] |
| 65 | 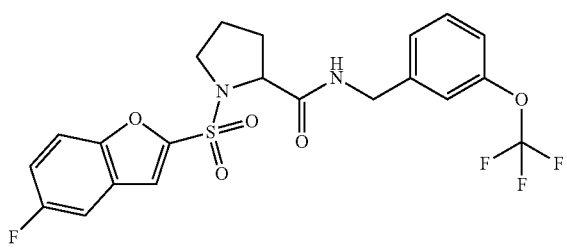 [SMILES: O=C(NCc1cccc(OC(F)(F)F)c1)C1CCCN1S(=O)(=O)c1cc2cc(F)ccc2o1] |
| 66 | 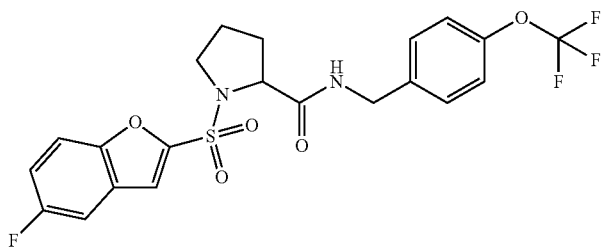 [SMILES: O=C(NCc1ccc(OC(F)(F)F)cc1)C1CCCN1S(=O)(=O)c1cc2cc(F)ccc2o1] |
| 67 | 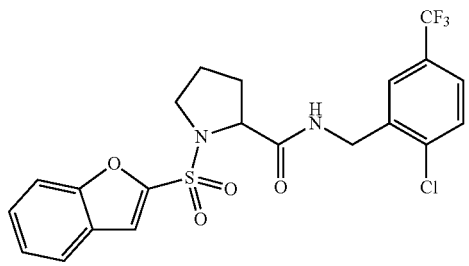 [SMILES: O=C(NCc1cc(C(F)(F)F)ccc1Cl)C1CCCN1S(=O)(=O)c1cc2ccccc2o1] |
| 69 | 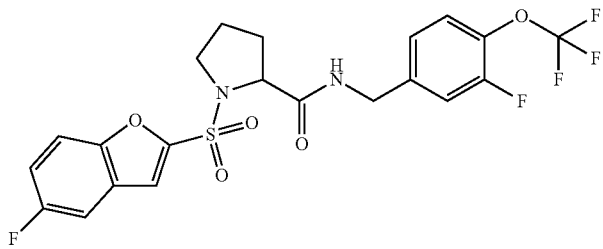 [SMILES: O=C(NCc1ccc(OC(F)(F)F)c(F)c1)C1CCCN1S(=O)(=O)c1cc2cc(F)ccc2o1] |
| 70 | 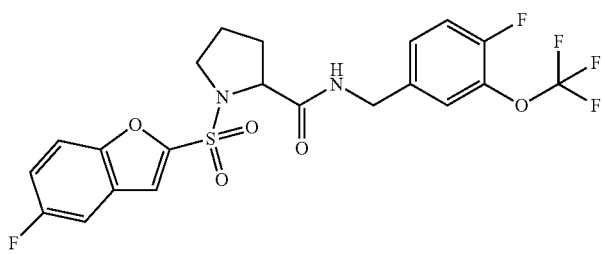 [SMILES: O=C(NCc1ccc(F)c(OC(F)(F)F)c1)C1CCCN1S(=O)(=O)c1cc2cc(F)ccc2o1] |

US 10,626,112 B2
TABLE 1-continued
| Example No. | Structural formula |
|---|---|
| 71 | 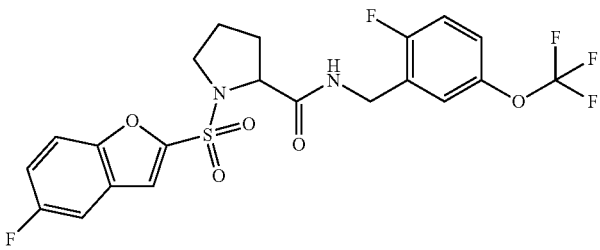 [SMILES: O=C(NCc1cc(OC(F)(F)F)ccc1F)C1CCCN1S(=O)(=O)c1cc2cc(F)ccc2o1] |
| 77 | 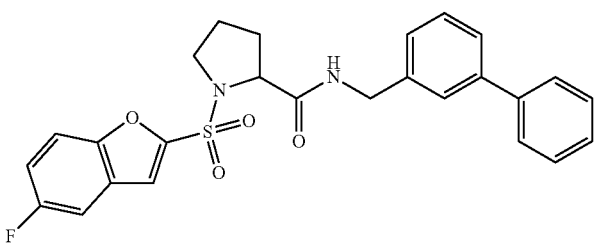 [SMILES: O=C(NCc1cccc(-c2ccccc2)c1)C1CCCN1S(=O)(=O)c1cc2cc(F)ccc2o1] |
| 79 | 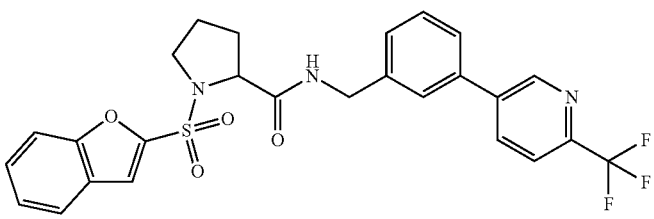 [SMILES: O=C(NCc1cccc(-c2ccc(C(F)(F)F)nc2)c1)C1CCCN1S(=O)(=O)c1cc2ccccc2o1] |
| 80 | 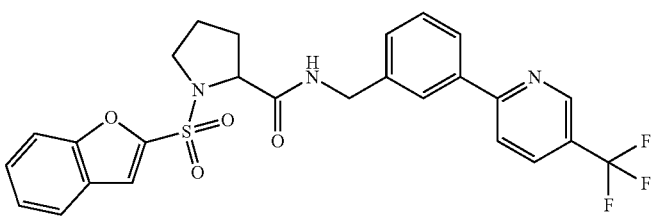 [SMILES: O=C(NCc1cccc(-c2ccc(C(F)(F)F)cn2)c1)C1CCCN1S(=O)(=O)c1cc2ccccc2o1] |
| 84 | 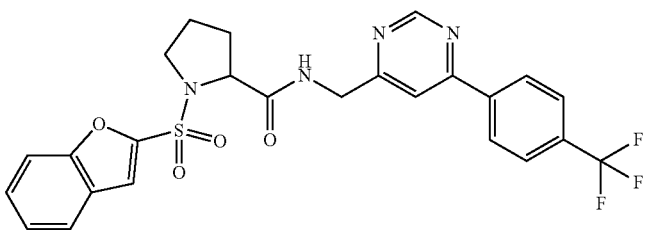 [SMILES: O=C(NCc1cc(-c2ccc(C(F)(F)F)cc2)ncn1)C1CCCN1S(=O)(=O)c1cc2ccccc2o1] |
| 86 | 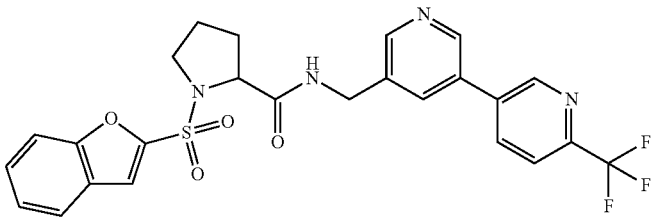 [SMILES: O=C(NCc1cncc(-c2ccc(C(F)(F)F)nc2)c1)C1CCCN1S(=O)(=O)c1cc2ccccc2o1] |

TABLE 1-continued
| Example No. | Structural formula |
|---|---|
| 87 | 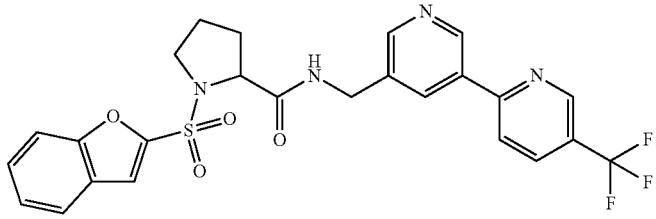 |
| 88 | 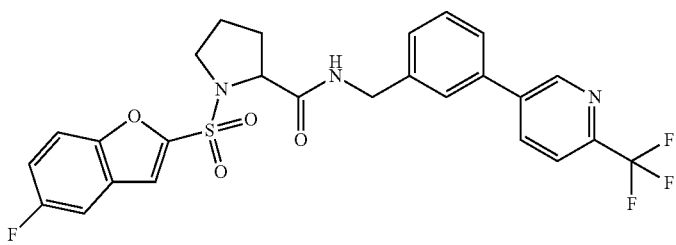 [SMILES: O=C(NCc1cccc(-c2ccc(C(F)(F)F)nc2)c1)C1CCCN1S(=O)(=O)c1cc2cc(F)ccc2o1] |
| 89 | 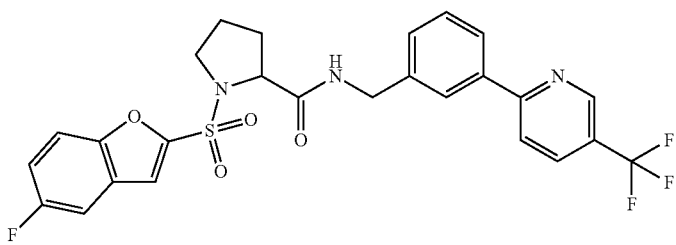 [SMILES: O=C(NCc1cccc(-c2ccc(C(F)(F)F)cn2)c1)C1CCCN1S(=O)(=O)c1cc2cc(F)ccc2o1] |
| 90 | 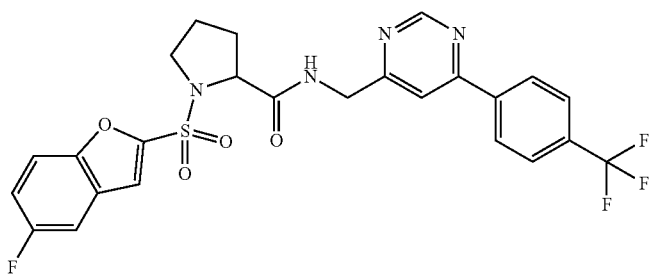 |
| 92 | 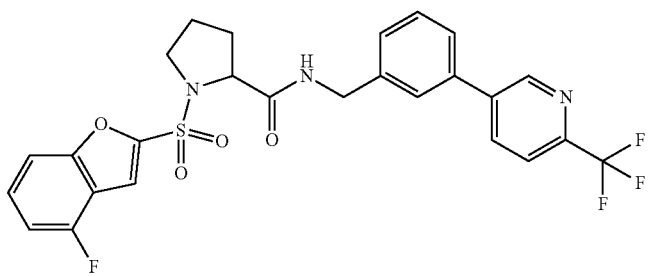 [SMILES: O=C(NCc1cccc(-c2ccc(C(F)(F)F)nc2)c1)C1CCCN1S(=O)(=O)c1cc2c(F)cccc2o1] |
| 93 | 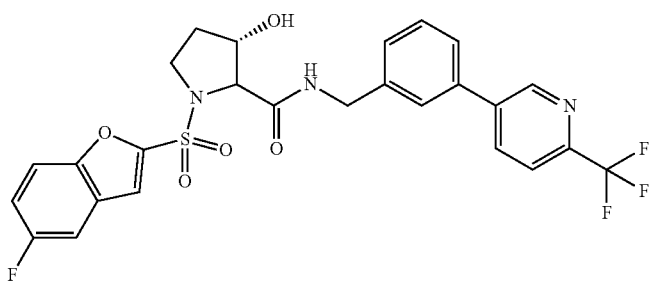 [SMILES: O=C(NCc1cccc(-c2ccc(C(F)(F)F)nc2)c1)C1[C@@H](O)CCN1S(=O)(=O)c1cc2cc(F)ccc2o1] |

TABLE 1-continued
| Example No. | Structural formula |
|---|---|
| 94 | 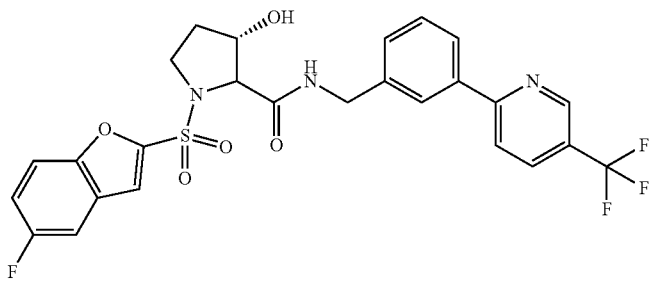 |
| 95 | 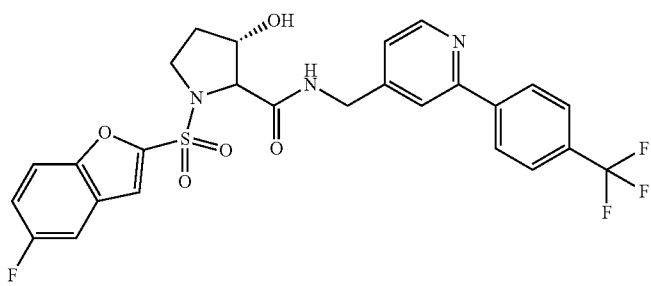 [SMILES: O=C(NCc1ccnc(-c2ccc(C(F)(F)F)cc2)c1)C1[C@@H](O)CCN1S(=O)(=O)c1cc2cc(F)ccc2o1] |
| 97 | 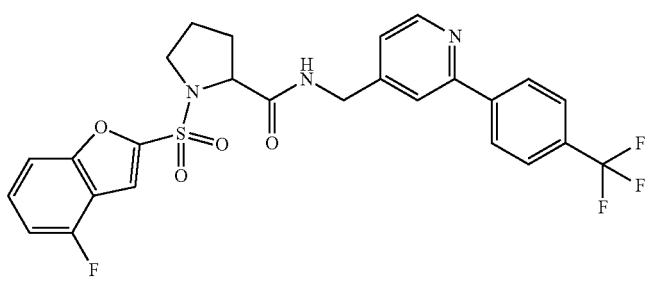 [SMILES: O=C(NCc1ccnc(-c2ccc(C(F)(F)F)cc2)c1)C1CCCN1S(=O)(=O)c1cc2c(F)cccc2o1] |
| 98 | 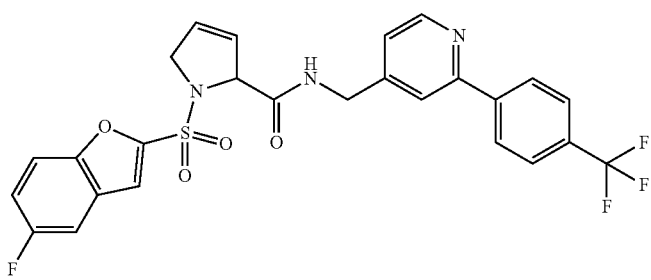 [SMILES: O=C(NCc1ccnc(-c2ccc(C(F)(F)F)cc2)c1)C1C=CCN1S(=O)(=O)c1cc2cc(F)ccc2o1] |
| 99 | 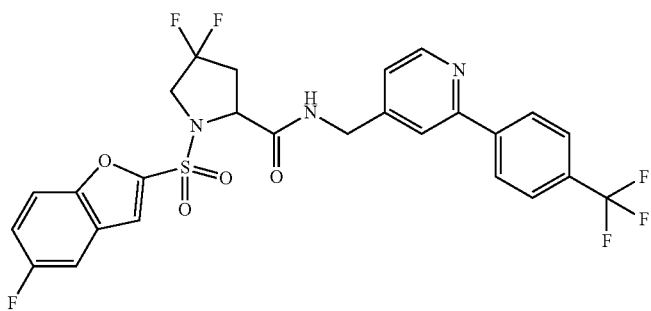 [SMILES: O=C(NCc1ccnc(-c2ccc(C(F)(F)F)cc2)c1)C1CC(F)(F)CN1S(=O)(=O)c1cc2cc(F)ccc2o1] |

TABLE 1-continued
| Example No. | Structural formula |
|---|---|
| 100 | 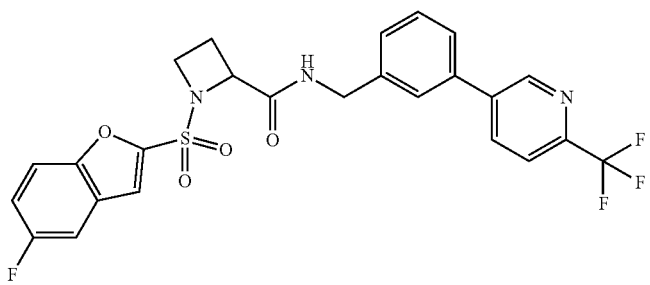 [SMILES: O=C(NCc1cccc(-c2ccc(C(F)(F)F)nc2)c1)C1CCN1S(=O)(=O)c1cc2cc(F)ccc2o1] |
| 101 | 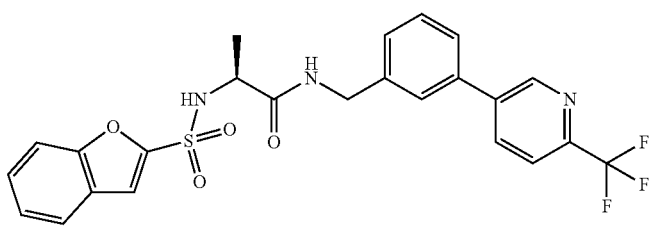 [SMILES: C[C@H](NS(=O)(=O)c1cc2ccccc2o1)C(=O)NCc1cccc(-c2ccc(C(F)(F)F)nc2)c1] |
| 102 | 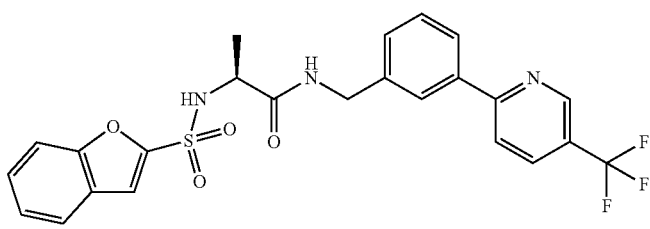 [SMILES: C[C@H](NS(=O)(=O)c1cc2ccccc2o1)C(=O)NCc1cccc(-c2ccc(C(F)(F)F)cn2)c1] |
| 104 | 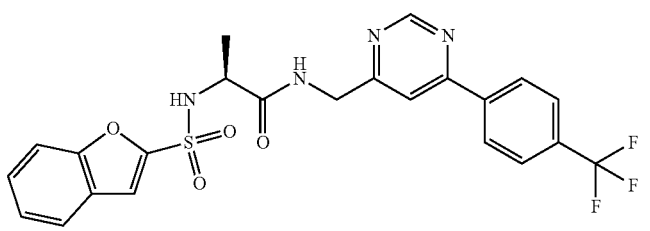 [SMILES: C[C@H](NS(=O)(=O)c1cc2ccccc2o1)C(=O)NCc1cc(-c2ccc(C(F)(F)F)cc2)ncn1] |
| 106 | 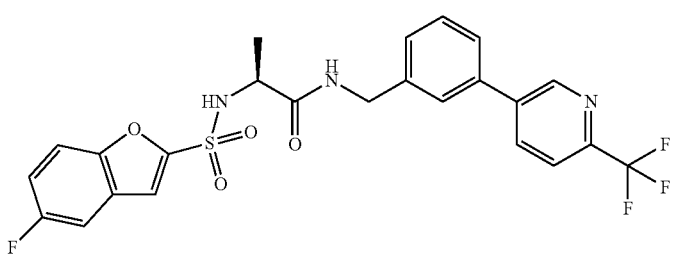 [SMILES: C[C@H](NS(=O)(=O)c1cc2cc(F)ccc2o1)C(=O)NCc1cccc(-c2ccc(C(F)(F)F)nc2)c1] |
| 107 | 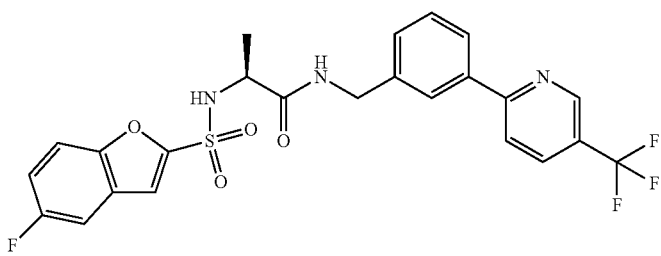 |

TABLE 1-continued
| Example No. | Structural formula |
|---|---|
| 108 | 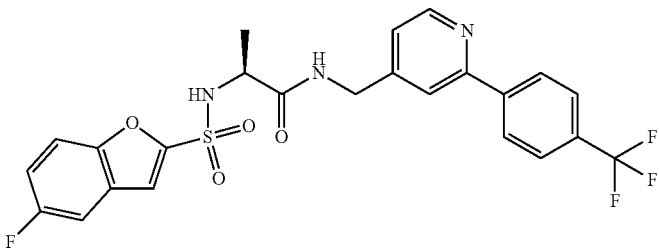 [SMILES: C[C@H](NS(=O)(=O)c1cc2cc(F)ccc2o1)C(=O)NCc1ccnc(-c2ccc(C(F)(F)F)cc2)c1] |
| 109 | 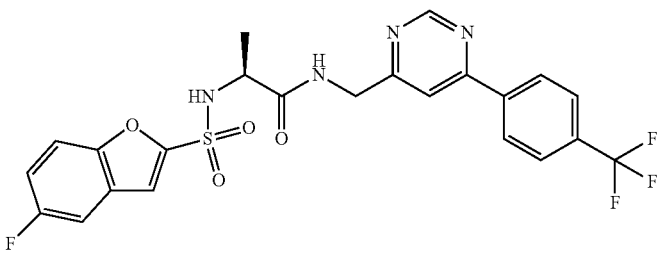 |
| 110 | 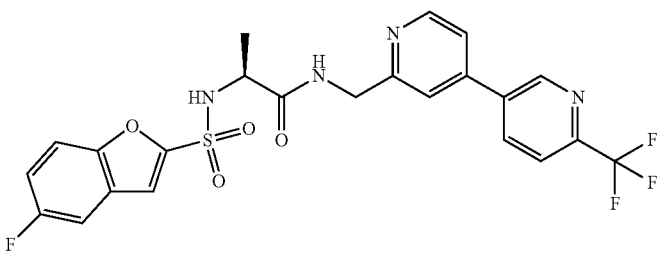 [SMILES: C[C@H](NS(=O)(=O)c1cc2cc(F)ccc2o1)C(=O)NCc1cc(-c2ccc(C(F)(F)F)nc2)ccn1] |
| 115 | 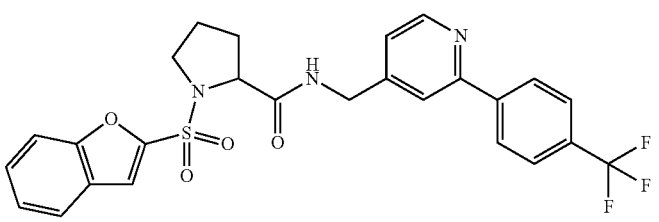 [SMILES: O=C(NCc1ccnc(-c2ccc(C(F)(F)F)cc2)c1)C1CCCN1S(=O)(=O)c1cc2ccccc2o1] |
| 116 | 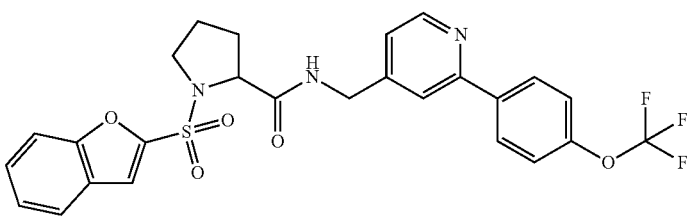 [SMILES: O=C(NCc1ccnc(-c2ccc(OC(F)(F)F)cc2)c1)C1CCCN1S(=O)(=O)c1cc2ccccc2o1] |
| 117 | 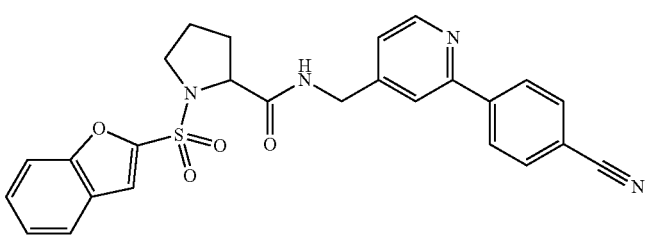 [SMILES: N#Cc1ccc(-c2cc(CNC(=O)C3CCCN3S(=O)(=O)c3cc4ccccc4o3)ccn2)cc1] |

TABLE 1-continued
| Example No. | Structural formula |
|---|---|
| 119 | 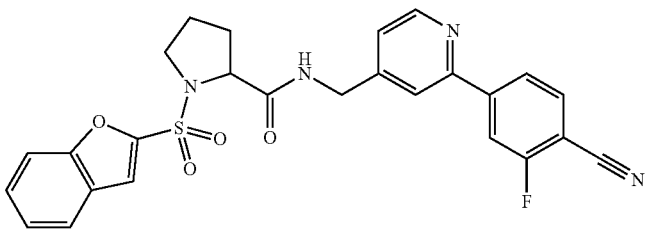 [SMILES: N#Cc1ccc(-c2cc(CNC(=O)C3CCCN3S(=O)(=O)c3cc4ccccc4o3)ccn2)cc1F] |
| 123 | 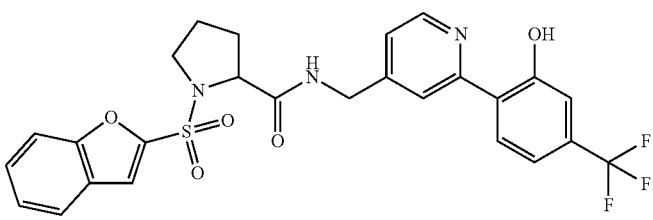 [SMILES: O=C(NCc1ccnc(-c2ccc(C(F)(F)F)cc2O)c1)C1CCCN1S(=O)(=O)c1cc2ccccc2o1] |
| 124 | 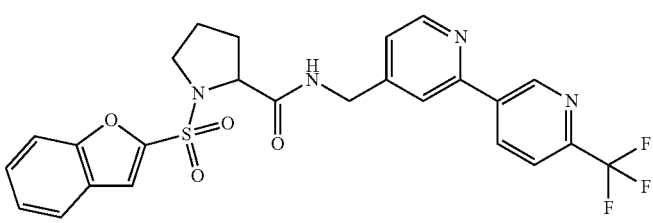 [SMILES: O=C(NCc1ccnc(-c2ccc(C(F)(F)F)nc2)c1)C1CCCN1S(=O)(=O)c1cc2ccccc2o1] |
| 127 | 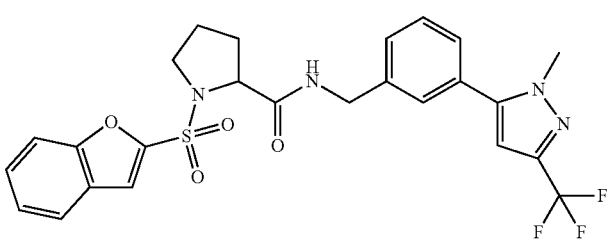 [SMILES: Cn1nc(C(F)(F)F)cc1-c1cccc(CNC(=O)C2CCCN2S(=O)(=O)c2cc3ccccc3o2)c1] |
| 128 | 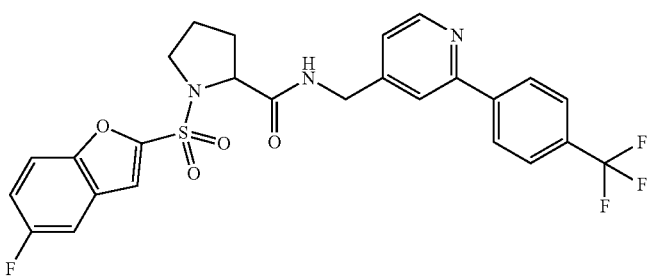 |
| 129 | 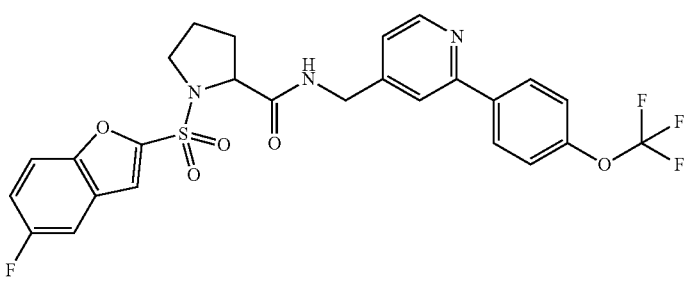 [SMILES: O=C(NCc1ccnc(-c2ccc(OC(F)(F)F)cc2)c1)C1CCCN1S(=O)(=O)c1cc2cc(F)ccc2o1] |

TABLE 1-continued
| Example No. | Structural formula |
|---|---|
| 130 | 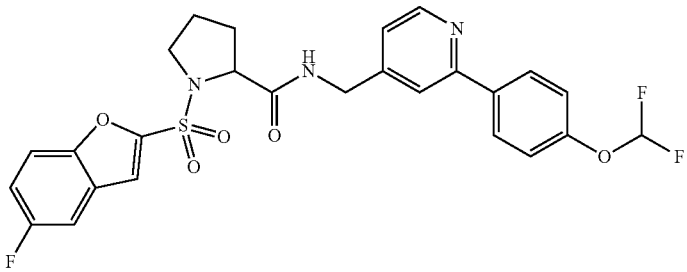 [SMILES: O=C(NCc1ccnc(-c2ccc(OC(F)F)cc2)c1)C1CCCN1S(=O)(=O)c1cc2cc(F)ccc2o1] |
| 132 | 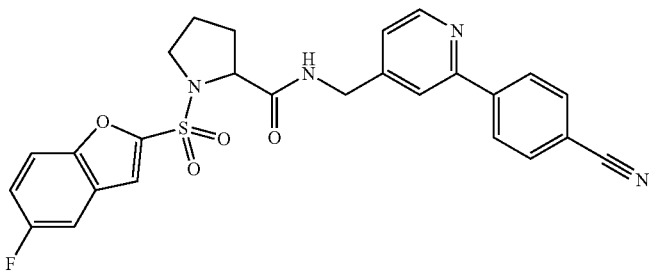 [SMILES: N#Cc1ccc(-c2cc(CNC(=O)C3CCCN3S(=O)(=O)c3cc4cc(F)ccc4o3)ccn2)cc1] |
| 133 | 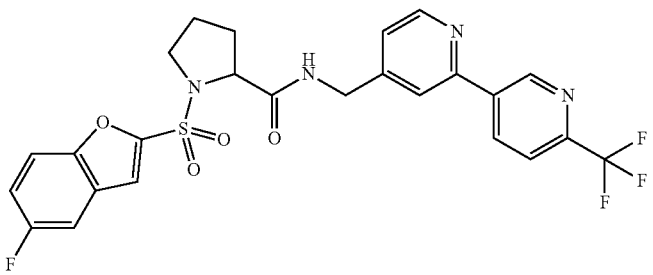 |
| 135 | 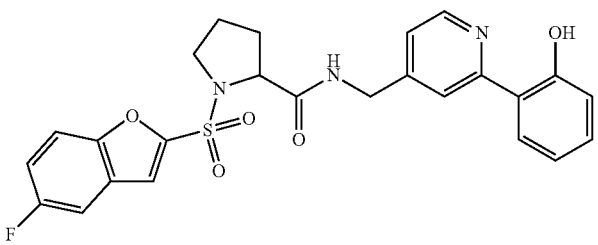 [SMILES: O=C(NCc1ccnc(-c2ccccc2O)c1)C1CCCN1S(=O)(=O)c1cc2cc(F)ccc2o1] |
| 136 | 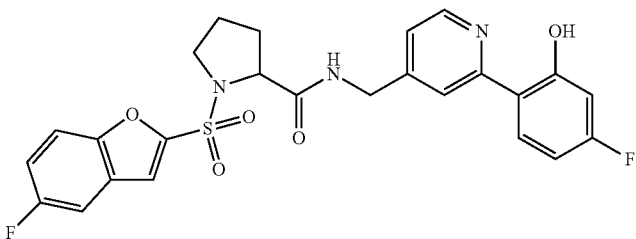 [SMILES: O=C(NCc1ccnc(-c2ccc(F)cc2O)c1)C1CCCN1S(=O)(=O)c1cc2cc(F)ccc2o1] |
| 137 | 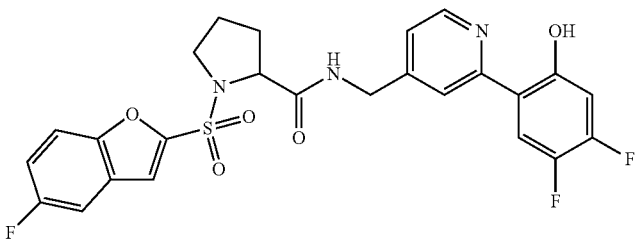 |

TABLE 1-continued
| Example No. | Structural formula |
|---|---|
| 138 | 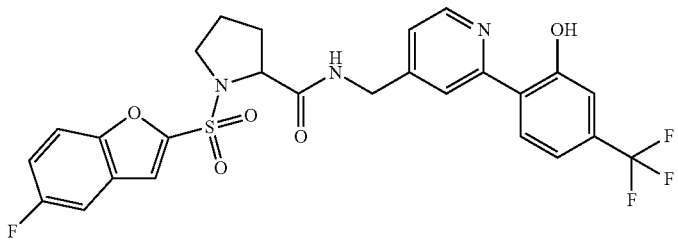 [SMILES: O=C(NCc1ccnc(-c2ccc(C(F)(F)F)cc2O)c1)C1CCCN1S(=O)(=O)c1cc2cc(F)ccc2o1] |
| 139 | 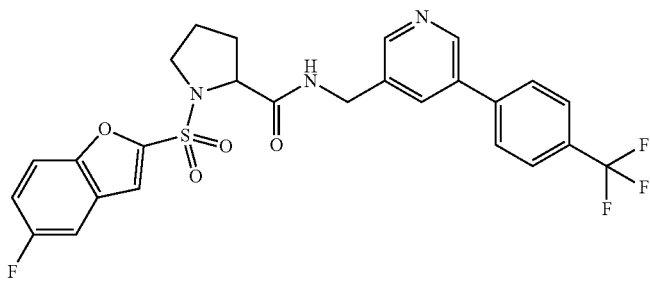 [SMILES: O=C(NCc1cncc(-c2ccc(C(F)(F)F)cc2)c1)C1CCCN1S(=O)(=O)c1cc2cc(F)ccc2o1] |
| 140 | 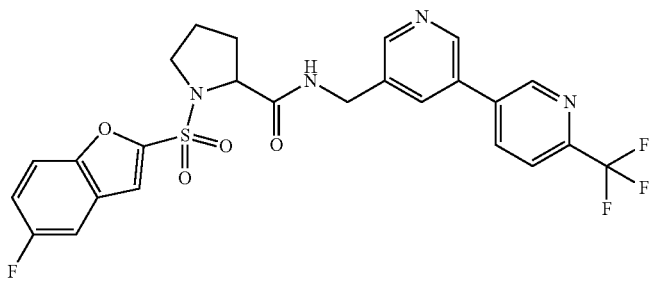 [SMILES: O=C(NCc1cncc(-c2ccc(C(F)(F)F)cn2)c1)C1CCCN1S(=O)(=O)c1cc2cc(F)ccc2o1] |
| 141 | 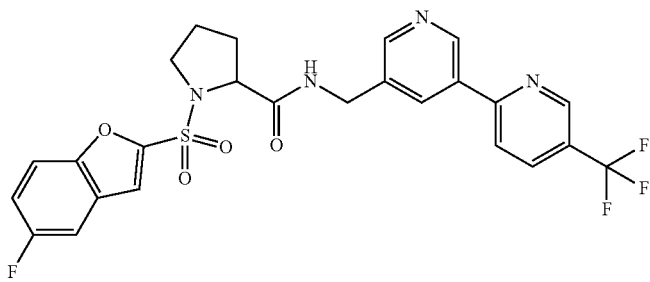 |
| 142 | 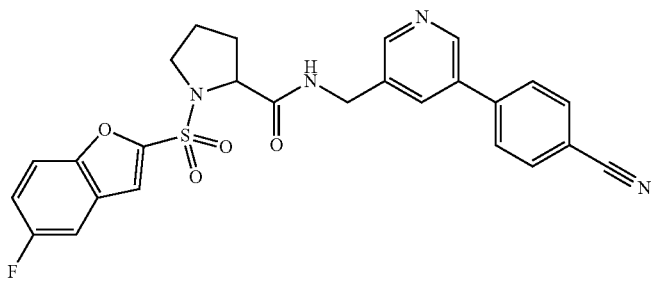 [SMILES: N#Cc1ccc(-c2cncc(CNC(=O)C3CCCN3S(=O)(=O)c3cc4cc(F)ccc4o3)c2)cc1] |

TABLE 1-continued
| Example No. | Structural formula |
|---|---|
| 145 | 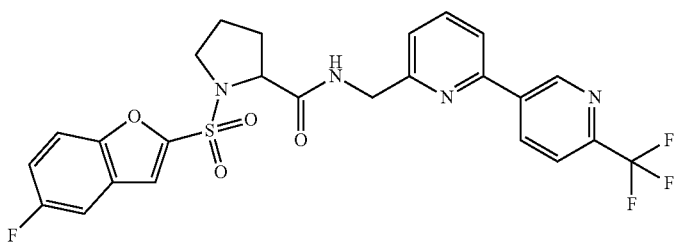 [SMILES: O=C(NCc1cccc(-c2ccc(C(F)(F)F)nc2)n1)C1CCCN1S(=O)(=O)c1cc2cc(F)ccc2o1] |
| 148 | 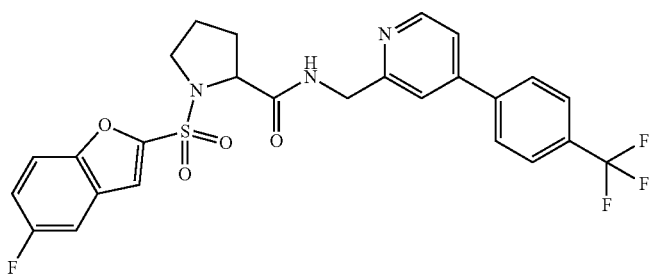 [SMILES: O=C(NCc1cc(-c2ccc(C(F)(F)F)cc2)ccn1)C1CCCN1S(=O)(=O)c1cc2cc(F)ccc2o1] |
| 149 | 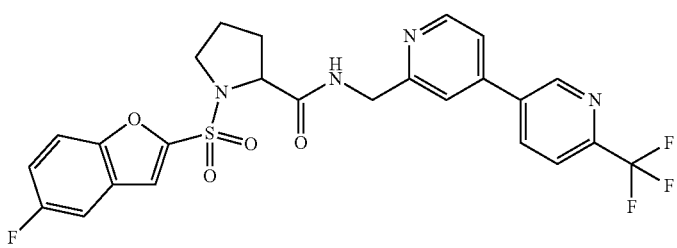 [SMILES: O=C(NCc1cc(-c2ccc(C(F)(F)F)nc2)ccn1)C1CCCN1S(=O)(=O)c1cc2cc(F)ccc2o1] |
| 150 | 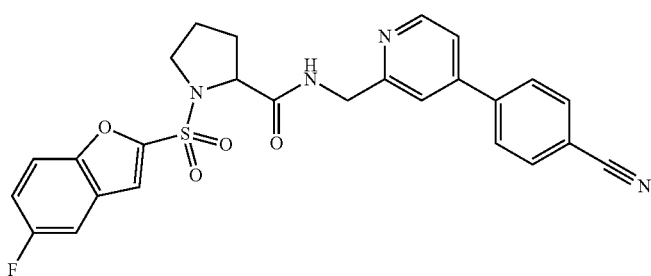 [SMILES: N#Cc1ccc(-c2ccnc(CNC(=O)C3CCCN3S(=O)(=O)c3cc4cc(F)ccc4o3)c2)cc1] |
| 151 | 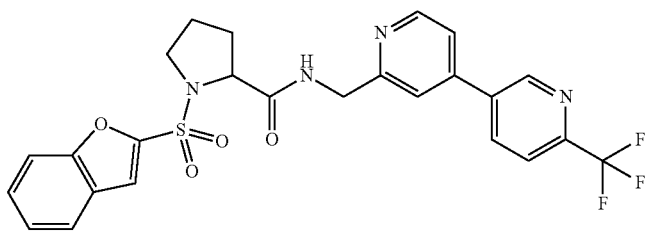 [SMILES: O=C(NCc1cc(-c2ccc(C(F)(F)F)nc2)ccn1)C1CCCN1S(=O)(=O)c1cc2ccccc2o1] |
| 153 | 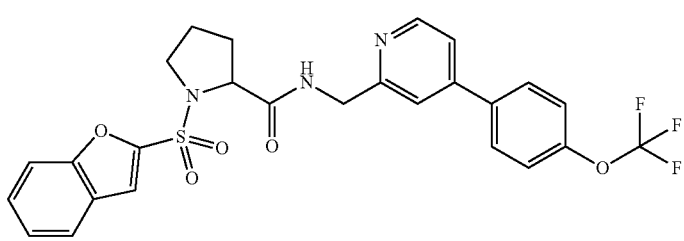 [SMILES: O=C(NCc1cc(-c2ccc(OC(F)(F)F)cc2)ccn1)C1CCCN1S(=O)(=O)c1cc2ccccc2o1] |

TABLE 1-continued
| Example No. | Structural formula |
|---|---|
| 155 | 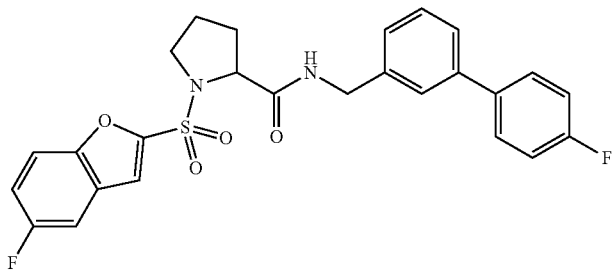 [SMILES: O=C(NCc1cccc(-c2ccc(F)cc2)c1)C1CCCN1S(=O)(=O)c1cc2cc(F)ccc2o1] |
| 156 | 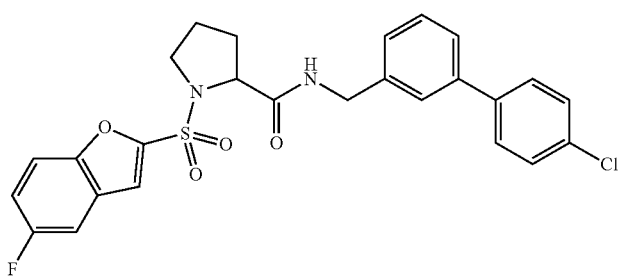 [SMILES: O=C(NCc1cccc(-c2ccc(Cl)cc2)c1)C1CCCN1S(=O)(=O)c1cc2cc(F)ccc2o1] |
| 157 | 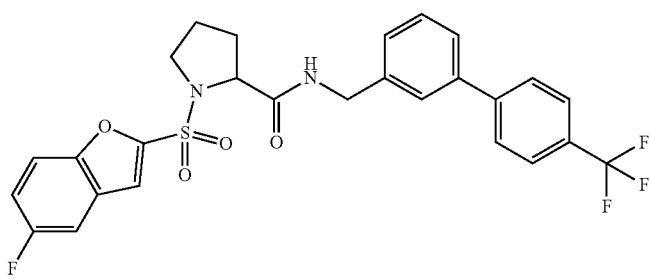 [SMILES: O=C(NCc1cccc(-c2ccc(C(F)(F)F)cc2)c1)C1CCCN1S(=O)(=O)c1cc2cc(F)ccc2o1] |
| 158 | 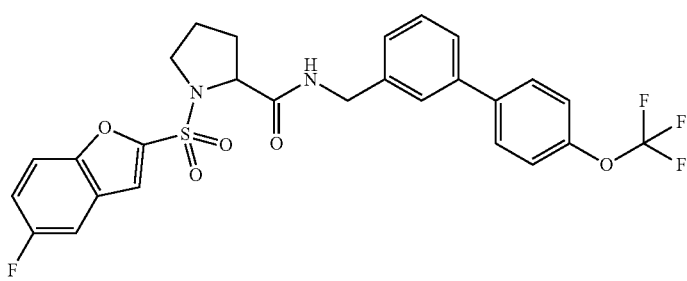 [SMILES: O=C(NCc1cccc(-c2ccc(OC(F)(F)F)cc2)c1)C1CCCN1S(=O)(=O)c1cc2cc(F)ccc2o1] |
| 159 | 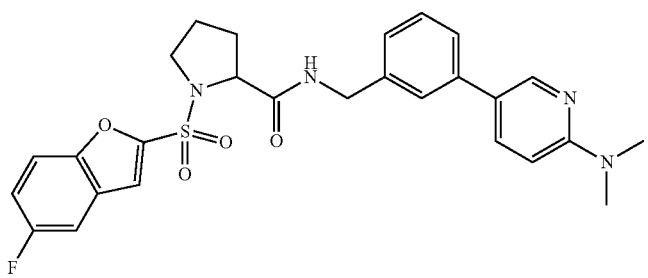 [SMILES: CN(C)c1ccc(-c2cccc(CNC(=O)C3CCCN3S(=O)(=O)c3cc4cc(F)ccc4o3)c2)cn1] |

TABLE 1-continued
| Example No. | Structural formula |
|---|---|
| 160 | 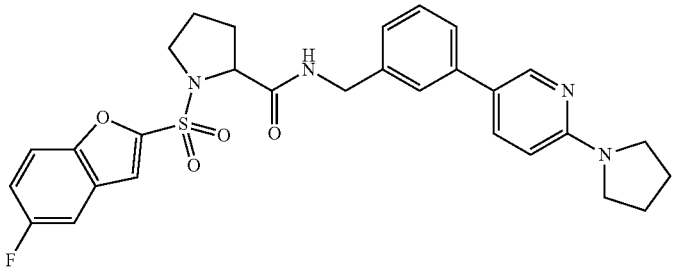 [SMILES: O=C(NCc1cccc(-c2ccc(N3CCCC3)nc2)c1)C1CCCN1S(=O)(=O)c1cc2cc(F)ccc2o1] |
| 161 | 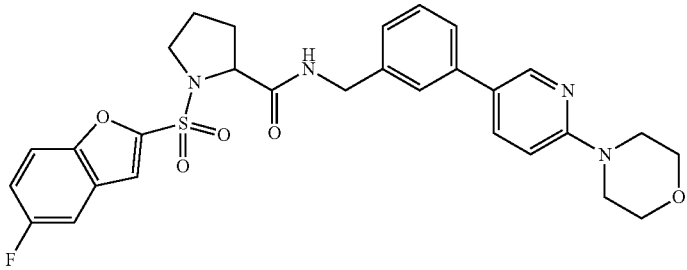 [SMILES: O=C(NCc1cccc(-c2ccc(N3CCOCC3)nc2)c1)C1CCCN1S(=O)(=O)c1cc2cc(F)ccc2o1] |
| 164 | 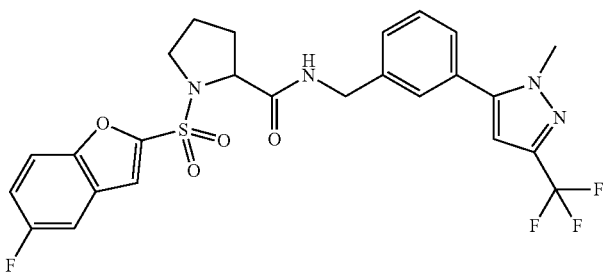 [SMILES: Cn1nc(C(F)(F)F)cc1-c1cccc(CNC(=O)C2CCCN2S(=O)(=O)c2cc3cc(F)ccc3o2)c1] |
| 172 | 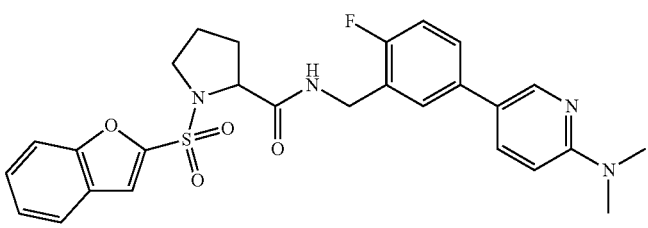 [SMILES: CN(C)c1ccc(-c2ccc(F)c(CNC(=O)C3CCCN3S(=O)(=O)c3cc4ccccc4o3)c2)cn1] |
| 173 | 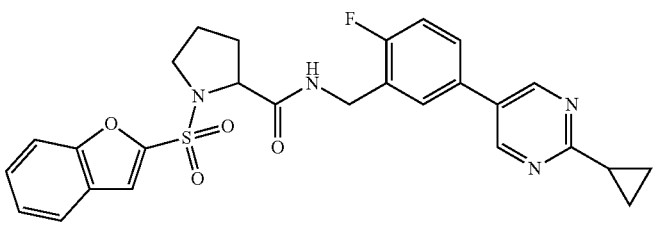 [SMILES: O=C(NCc1cc(-c2cnc(C3CC3)nc2)ccc1F)C1CCCN1S(=O)(=O)c1cc2ccccc2o1] |
| 174 | 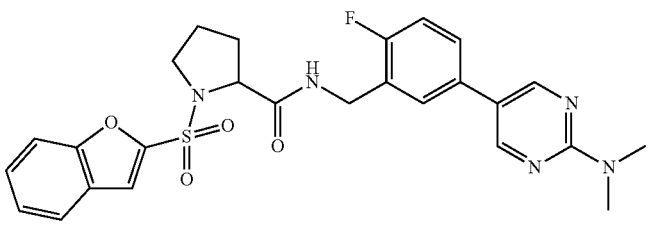 [SMILES: CN(C)c1ncc(-c2ccc(F)c(CNC(=O)C3CCCN3S(=O)(=O)c3cc4ccccc4o3)c2)cn1] |

TABLE 1-continued
| Example No. | Structural formula |
|---|---|
| 175 | 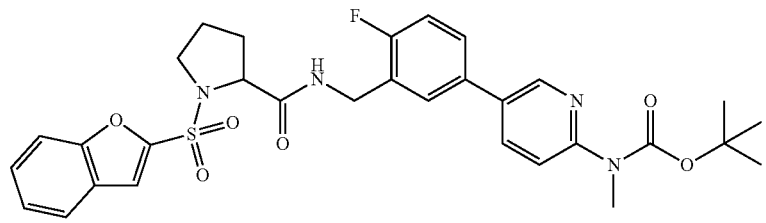 [SMILES: CN(C(=O)OC(C)(C)C)c1ccc(-c2ccc(F)c(CNC(=O)C3CCCN3S(=O)(=O)c3cc4ccccc4o3)c2)cn1] |
| 179 | 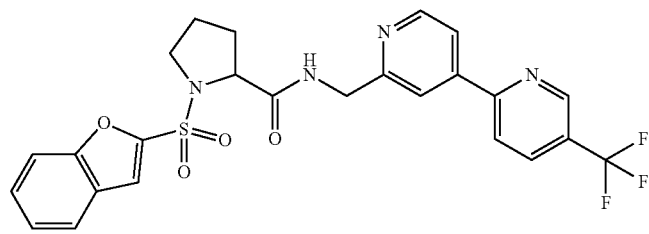 [SMILES: O=C(NCc1cc(-c2ccc(C(F)(F)F)cn2)ccn1)C1CCCN1S(=O)(=O)c1cc2ccccc2o1] |
| 181 | 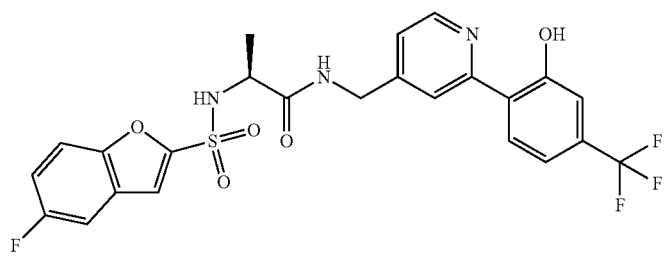 |
| 190 | 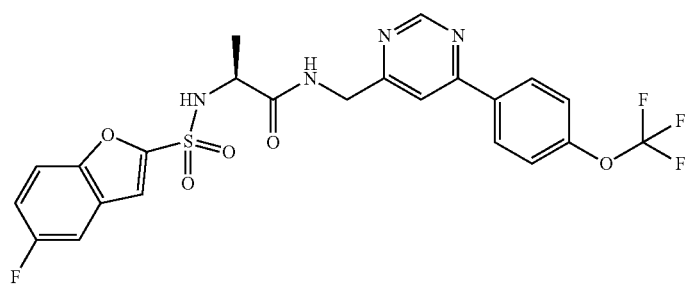 [SMILES: C[C@H](NS(=O)(=O)c1cc2cc(F)ccc2o1)C(=O)NCc1cc(-c2ccc(OC(F)(F)F)cc2)ncn1] |
| 191 | 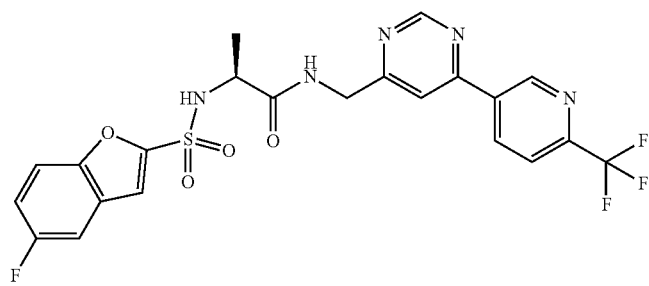 |
| 192 | 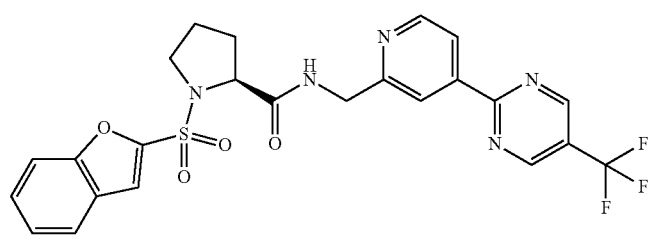 [SMILES: O=C(NCc1cc(-c2ncc(C(F)(F)F)cn2)ccn1)[C@@H]1CCCN1S(=O)(=O)c1cc2ccccc2o1] |

TABLE 1-continued
| Example No. | Structural formula |
|---|---|
| 193 | 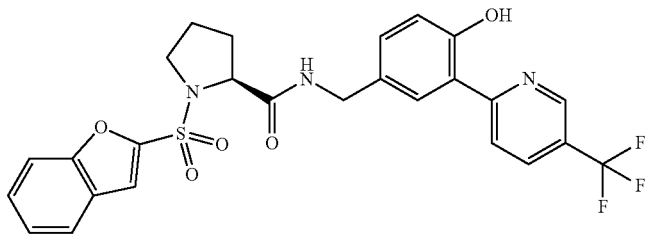 [SMILES: O=C(NCc1ccc(O)c(-c2ccc(C(F)(F)F)cn2)c1)[C@@H]1CCCN1S(=O)(=O)c1cc2ccccc2o1] |
| 194 | 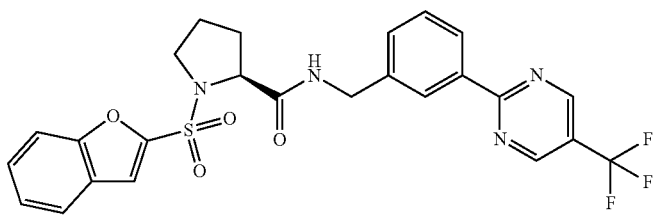 [SMILES: O=C(NCc1cccc(-c2ncc(C(F)(F)F)cn2)c1)[C@@H]1CCCN1S(=O)(=O)c1cc2ccccc2o1] |
| 195 | 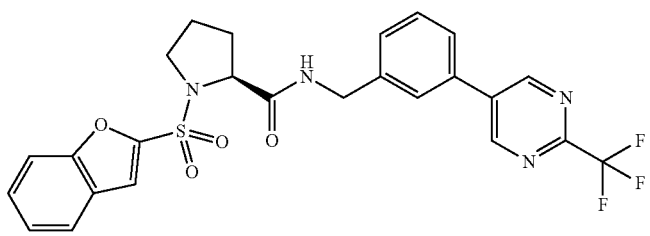 [SMILES: O=C(NCc1cccc(-c2cnc(C(F)(F)F)nc2)c1)[C@@H]1CCCN1S(=O)(=O)c1cc2ccccc2o1] |
| 196 | 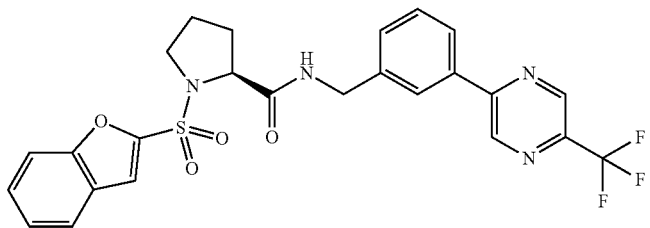 [SMILES: O=C(NCc1cccc(-c2cnc(C(F)(F)F)cn2)c1)[C@@H]1CCCN1S(=O)(=O)c1cc2ccccc2o1] |
| 197 | 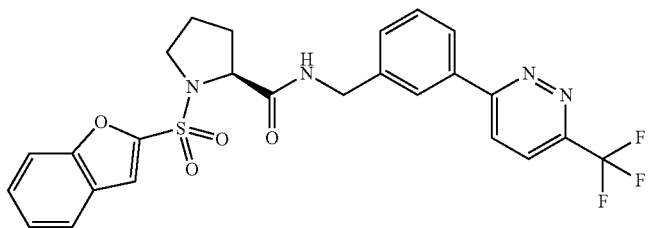 |
| 198 | 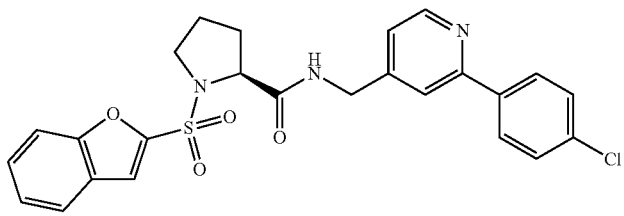 [SMILES: O=C(NCc1ccnc(-c2ccc(Cl)cc2)c1)[C@@H]1CCCN1S(=O)(=O)c1cc2ccccc2o1] |

TABLE 1-continued
| Example No. | Structural formula |
|---|---|
| 199 | 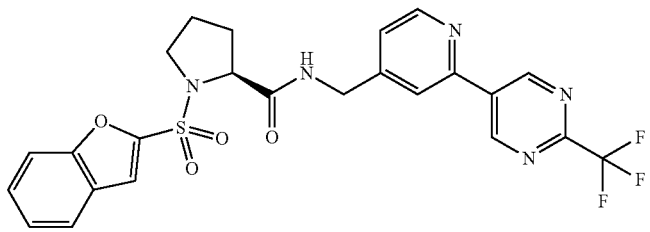 |
| 200 | 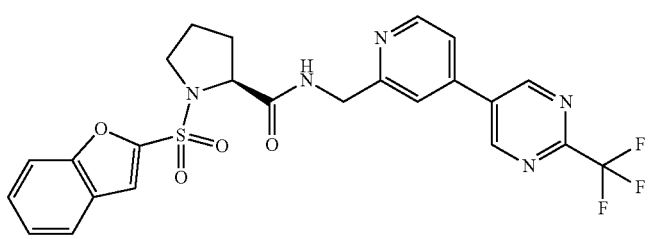 |
| 201 | 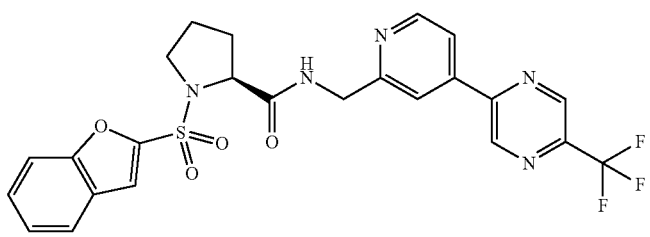 [SMILES: O=C(NCc1cc(-c2cnc(C(F)(F)F)cn2)ccn1)[C@@H]1CCCN1S(=O)(=O)c1cc2ccccc2o1] |
| 202 | 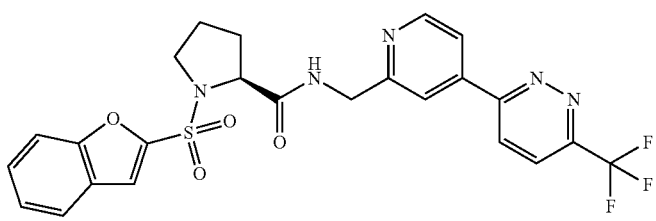 [SMILES: O=C(NCc1cc(-c2ccc(C(F)(F)F)nn2)ccn1)[C@@H]1CCCN1S(=O)(=O)c1cc2ccccc2o1] |
| 203 | 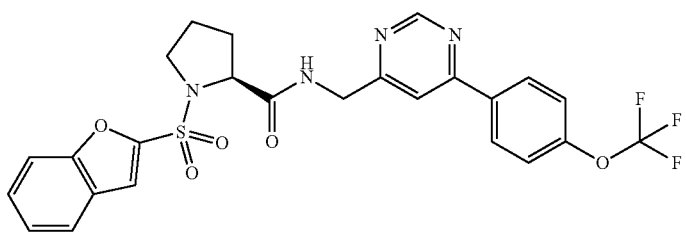 |
| 205 | 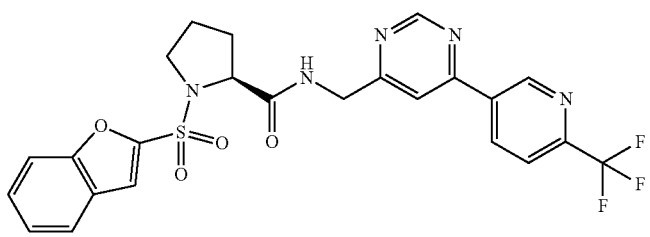 [SMILES: O=C(NCc1cc(-c2ccc(C(F)(F)F)nc2)ncn1)[C@@H]1CCCN1S(=O)(=O)c1cc2ccccc2o1] |

TABLE 1-continued
| Example No. | Structural formula |
| --- | --- |
| 206 | 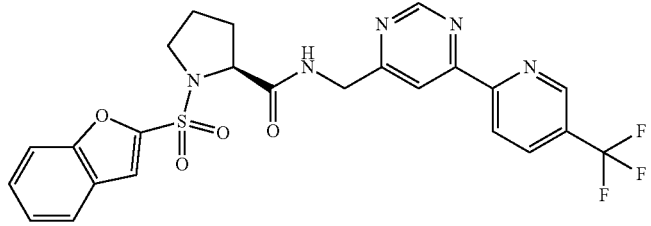 [SMILES: O=C(NCc1cc(-c2ccc(C(F)(F)F)cn2)ncn1)[C@@H]1CCCN1S(=O)(=O)c1cc2ccccc2o1] |
| 207 | 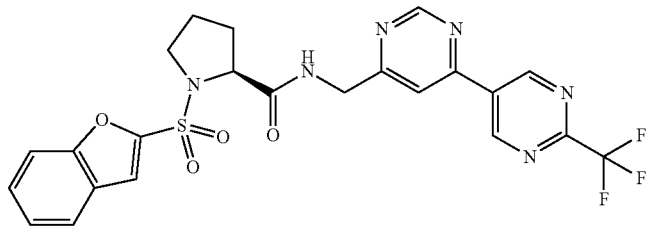 [SMILES: O=C(NCc1cc(-c2cnc(C(F)(F)F)nc2)ncn1)[C@@H]1CCCN1S(=O)(=O)c1cc2ccccc2o1] |
| 210 | 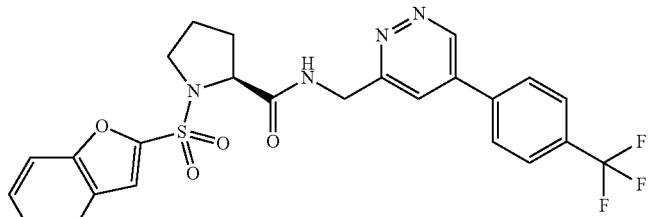 |
| 212 | 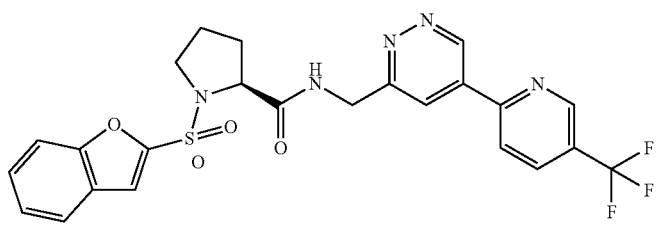 |
| 214 | 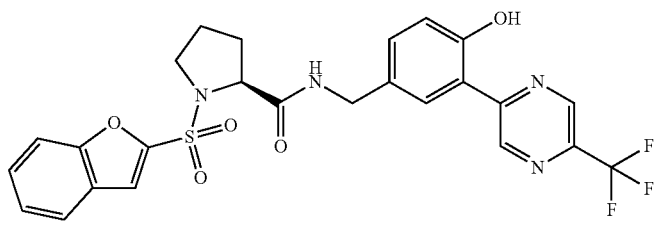 [SMILES: O=C(NCc1ccc(O)c(-c2cnc(C(F)(F)F)cn2)c1)[C@@H]1CCCN1S(=O)(=O)c1cc2ccccc2o1] |
| 215 | 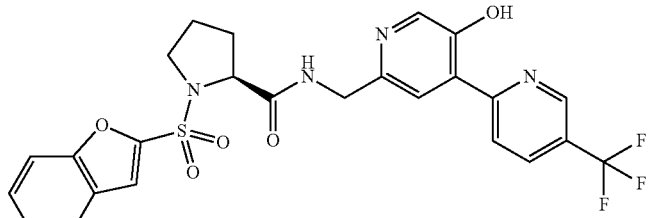 |

TABLE 1-continued
| Example No. | Structural formula |
|---|---|
| 216 | 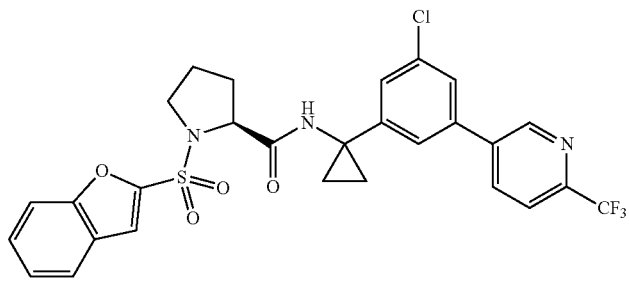 [SMILES: O=C(NC1(c2cc(Cl)cc(-c3ccc(C(F)(F)F)nc3)c2)CC1)[C@@H]1CCCN1S(=O)(=O)c1cc2ccccc2o1] |
| 221 | 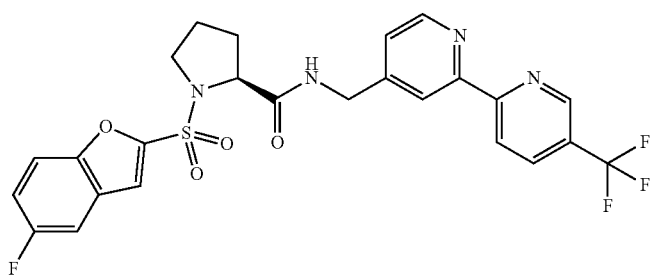 [SMILES: O=C(NCc1ccnc(-c2ccc(C(F)(F)F)cn2)c1)[C@@H]1CCCN1S(=O)(=O)c1cc2cc(F)ccc2o1] |
| 222 | 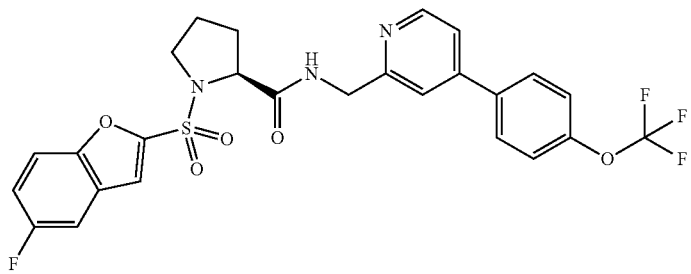 [SMILES: O=C(NCc1cc(-c2ccc(OC(F)(F)F)cc2)ccn1)[C@@H]1CCCN1S(=O)(=O)c1cc2cc(F)ccc2o1] |
| 223 | 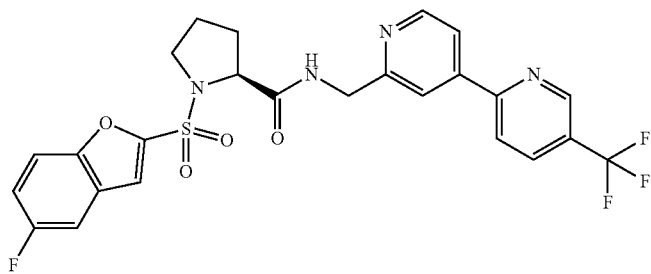 [SMILES: O=C(NCc1cc(-c2ccc(C(F)(F)F)cn2)ccn1)[C@@H]1CCCN1S(=O)(=O)c1cc2cc(F)ccc2o1] |
| 224 | 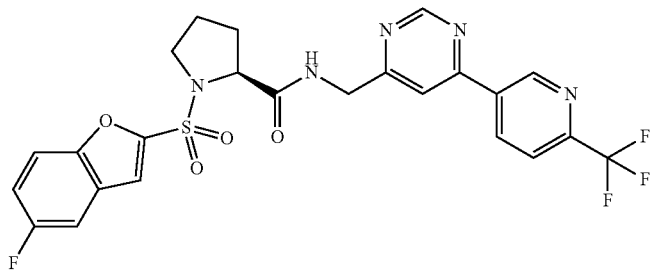 [SMILES: O=C(NCc1cc(-c2ccc(C(F)(F)F)nc2)ncn1)[C@@H]1CCCN1S(=O)(=O)c1cc2cc(F)ccc2o1] |

US 10,626,112 B2
TABLE 1-continued
| Example No. | Structural formula |
|---|---|
| 225 | 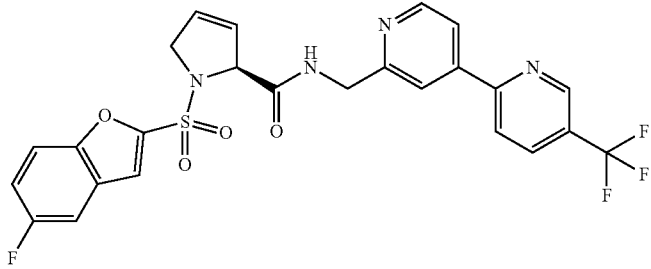 [SMILES: O=C(NCc1cc(-c2ccc(C(F)(F)F)cn2)ccn1)[C@@H]1C=CCN1S(=O)(=O)c1cc2cc(F)ccc2o1] |
| 226 | 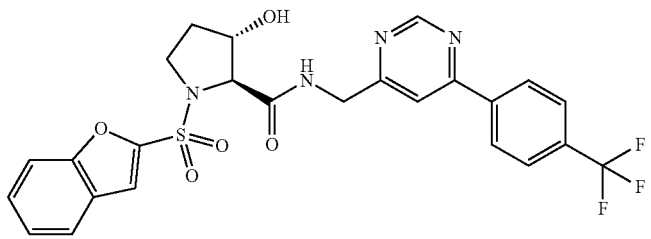 [SMILES: O=C(NCc1cc(-c2ccc(C(F)(F)F)cc2)ncn1)[C@@H]1[C@@H](O)CCN1S(=O)(=O)c1cc2ccccc2o1] |
| 229 | 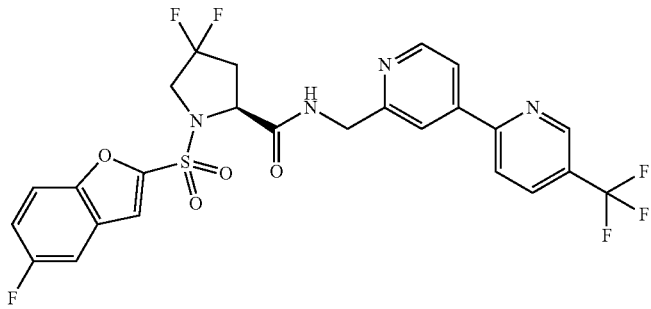 [SMILES: O=C(NCc1cc(-c2ccc(C(F)(F)F)cn2)ccn1)[C@@H]1CC(F)(F)CN1S(=O)(=O)c1cc2cc(F)ccc2o1] |
| 230 | 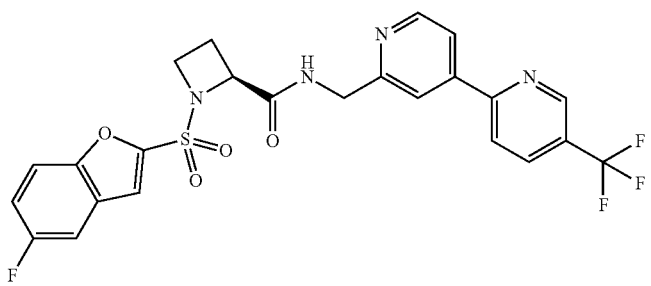 [SMILES: O=C(NCc1cc(-c2ccc(C(F)(F)F)cn2)ccn1)[C@@H]1CCN1S(=O)(=O)c1cc2cc(F)ccc2o1] |
| 231 | 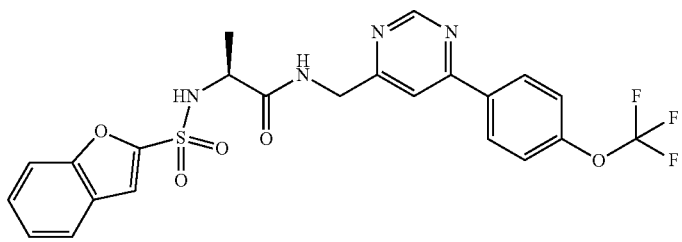 [SMILES: C[C@H](NS(=O)(=O)c1cc2ccccc2o1)C(=O)NCc1cc(-c2ccc(OC(F)(F)F)cc2)ncn1] |

US 10,626,112 B2
TABLE 1-continued
| Example No. | Structural formula |
|---|---|
| 233 | 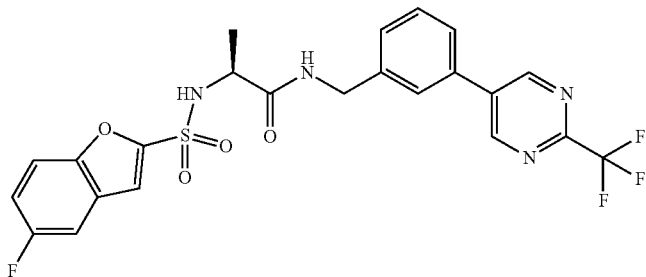 [SMILES: C[C@H](NS(=O)(=O)c1cc2cc(F)ccc2o1)C(=O)NCc1cccc(-c2cnc(C(F)(F)F)nc2)c1] |
| 235 | 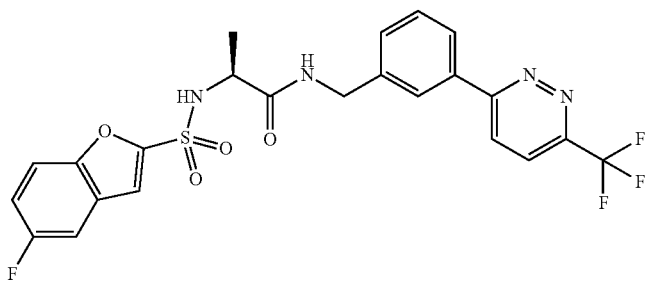 [SMILES: C[C@H](NS(=O)(=O)c1cc2cc(F)ccc2o1)C(=O)NCc1cccc(-c2ccc(C(F)(F)F)nn2)c1] |
| 239 | 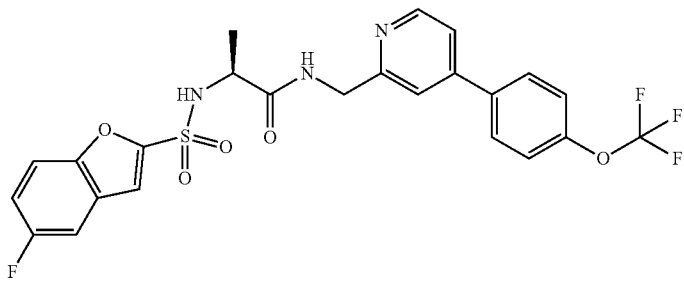 |
| 240 | 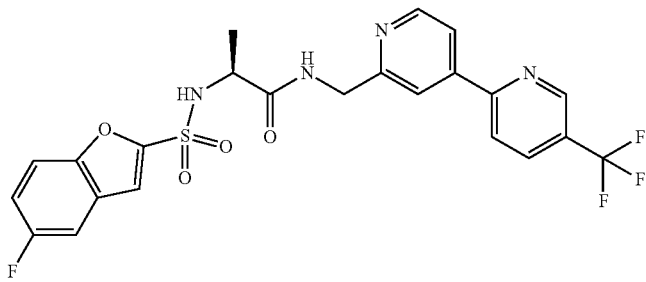 [SMILES: C[C@H](NS(=O)(=O)c1cc2cc(F)ccc2o1)C(=O)NCc1cc(-c2ccc(C(F)(F)F)cn2)ccn1] |
| 248 | 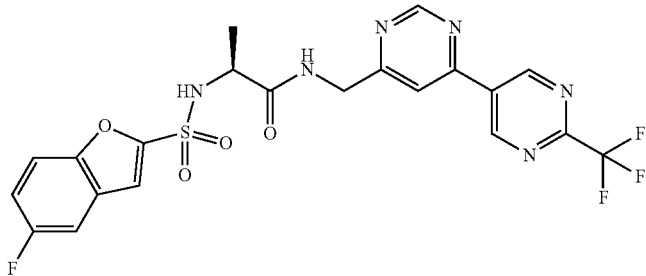 |

TABLE 1-continued
| Example No. | Structural formula |
|---|---|
| 252 | 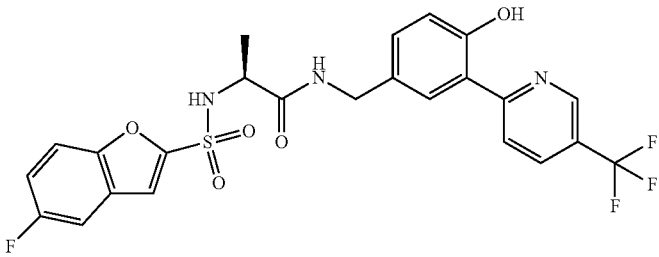 |
| 255 | 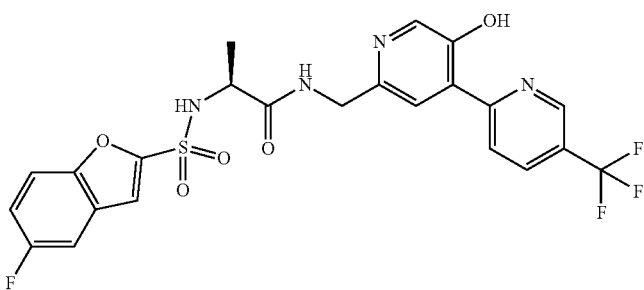 [SMILES: C[C@H](NS(=O)(=O)c1cc2cc(F)ccc2o1)C(=O)NCc1cc(-c2ccc(C(F)(F)F)cn2)c(O)cn1] |
| 258 | 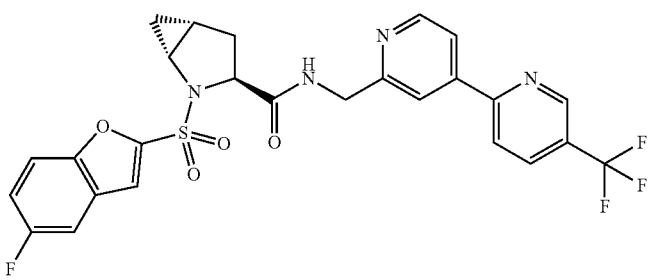 [SMILES: O=C(NCc1cc(-c2ccc(C(F)(F)F)cn2)ccn1)[C@@H]1C[C@H]2C[C@H]2N1S(=O)(=O)c1cc2cc(F)ccc2o1] |
| 259 | 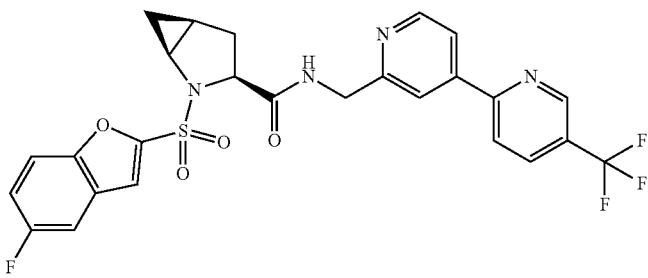 [SMILES: O=C(NCc1cc(-c2ccc(C(F)(F)F)cn2)ccn1)[C@@H]1C[C@@H]2C[C@@H]2N1S(=O)(=O)c1cc2cc(F)ccc2o1] |
| 262 | 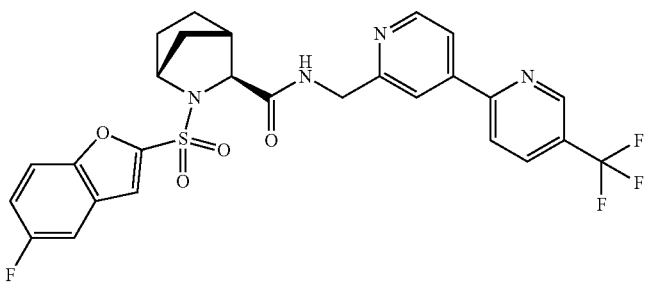 [SMILES: O=C(NCc1cc(-c2ccc(C(F)(F)F)cn2)ccn1)[C@@H]1[C@H]2CC[C@H](C2)N1S(=O)(=O)c1cc2cc(F)ccc2o1] |

TABLE 1-continued
| Example No. | Structural formula |
|---|---|
| 263 | 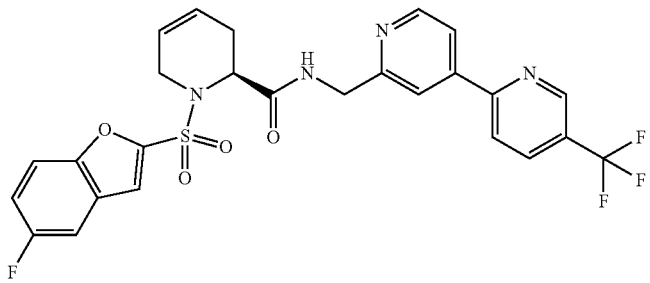 [SMILES: O=C(NCc1cc(-c2ccc(C(F)(F)F)cn2)ccn1)[C@@H]1CC=CCN1S(=O)(=O)c1cc2cc(F)ccc2o1] |
| 264 | 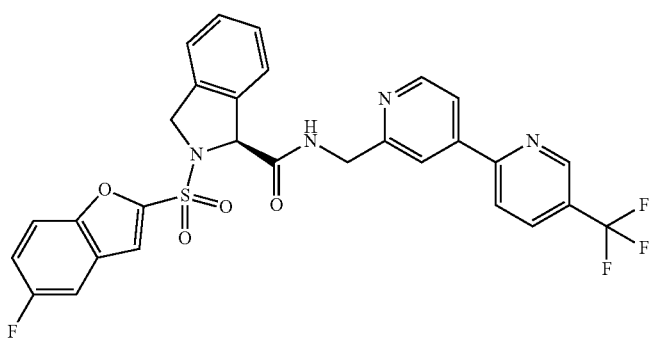 [SMILES: O=C(NCc1cc(-c2ccc(C(F)(F)F)cn2)ccn1)[C@@H]1c2ccccc2CN1S(=O)(=O)c1cc2cc(F)ccc2o1] |
| 265 | 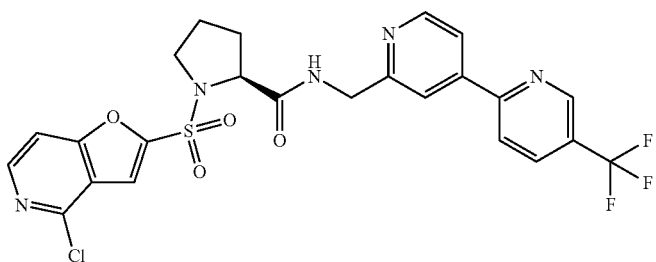 [SMILES: O=C(NCc1cc(-c2ccc(C(F)(F)F)cn2)ccn1)[C@@H]1CCCN1S(=O)(=O)c1cc2c(Cl)nccc2o1] |
| 267 | 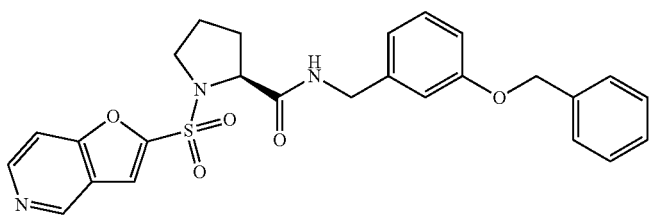 [SMILES: O=C(NCc1cccc(OCc2ccccc2)c1)[C@@H]1CCCN1S(=O)(=O)c1cc2cnccc2o1] |
| 268 | 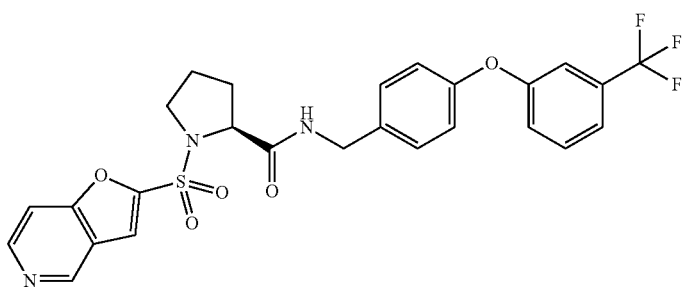 [SMILES: O=C(NCc1ccc(Oc2cccc(C(F)(F)F)c2)cc1)[C@@H]1CCCN1S(=O)(=O)c1cc2cnccc2o1] |

TABLE 1-continued
| Example No. | Structural formula |
|---|---|
| 269 | 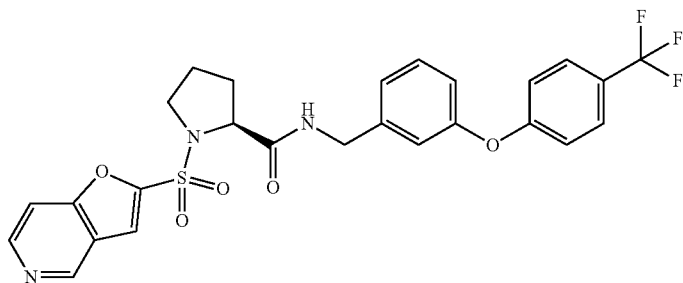 [SMILES: O=C(NCc1cccc(Oc2ccc(C(F)(F)F)cc2)c1)[C@@H]1CCCN1S(=O)(=O)c1cc2cnccc2o1] |
| 270 | 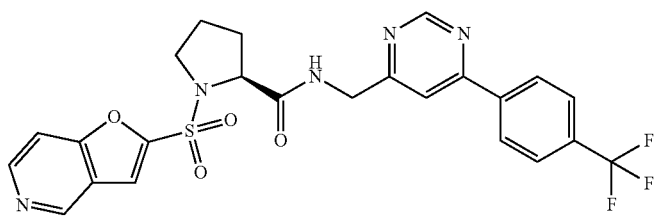 [SMILES: O=C(NCc1cc(-c2ccc(C(F)(F)F)cc2)ncn1)[C@@H]1CCCN1S(=O)(=O)c1cc2cnccc2o1] |
| 271 | 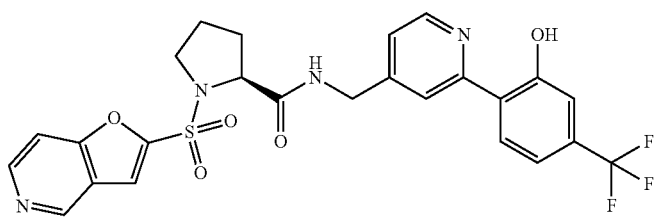 [SMILES: O=C(NCc1ccnc(-c2ccc(C(F)(F)F)cc2O)c1)[C@@H]1CCCN1S(=O)(=O)c1cc2cnccc2o1] |
| 272 | 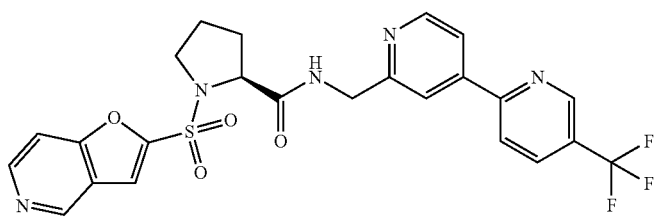 [SMILES: O=C(NCc1cc(-c2ccc(C(F)(F)F)cn2)ccn1)[C@@H]1CCCN1S(=O)(=O)c1cc2cnccc2o1] |
| 273 | 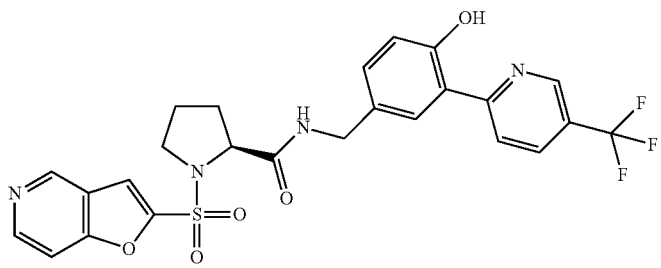 [SMILES: O=C(NCc1ccc(O)c(-c2ccc(C(F)(F)F)cn2)c1)[C@@H]1CCCN1S(=O)(=O)c1cc2cnccc2o1] |
| 274 | 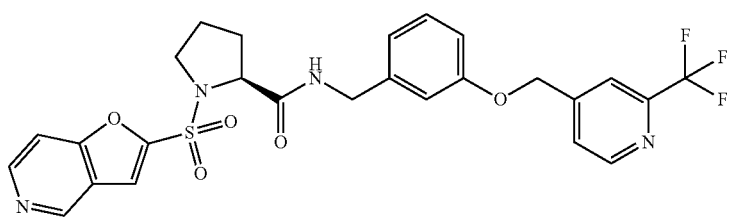 [SMILES: O=C(NCc1cccc(OCc2ccnc(C(F)(F)F)c2)c1)[C@@H]1CCCN1S(=O)(=O)c1cc2cnccc2o1] |

TABLE 1-continued
| Example No. | Structural formula |
|---|---|
| 275 | 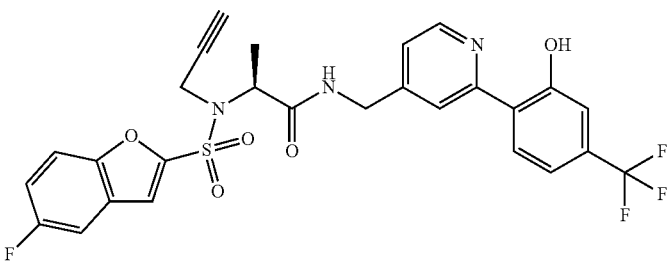 [SMILES: C#CCN([C@@H](C)C(=O)NCc1ccnc(-c2ccc(C(F)(F)F)cc2O)c1)S(=O)(=O)c1cc2cc(F)ccc2o1] |
| 278 | 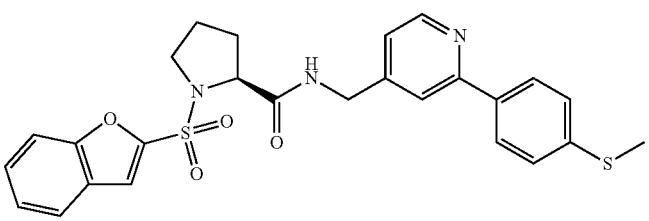 [SMILES: CSc1ccc(-c2cc(CNC(=O)[C@@H]3CCCN3S(=O)(=O)c3cc4ccccc4o3)ccn2)cc1] |
| 279 | 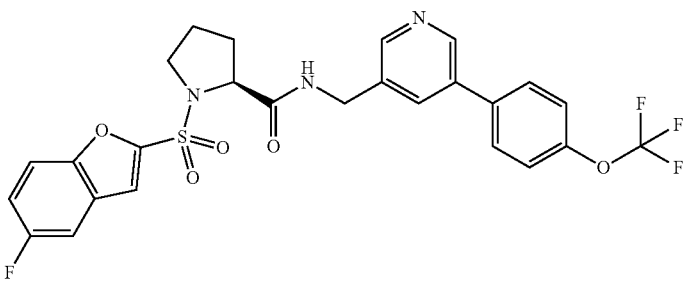 [SMILES: O=C(NCc1cncc(-c2ccc(OC(F)(F)F)cc2)c1)[C@@H]1CCCN1S(=O)(=O)c1cc2cc(F)ccc2o1] |
| 281 | 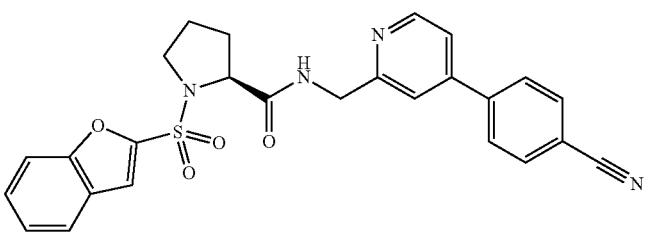 [SMILES: N#Cc1ccc(-c2ccnc(CNC(=O)[C@@H]3CCCN3S(=O)(=O)c3cc4ccccc4o3)c2)cc1] |
| 285 | 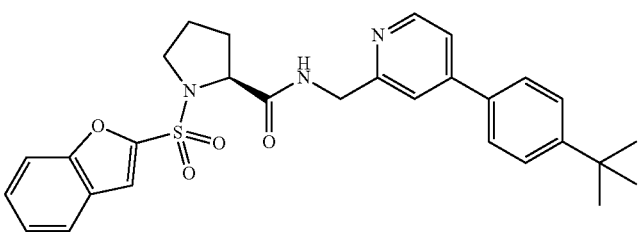 [SMILES: CC(C)(C)c1ccc(-c2ccnc(CNC(=O)[C@@H]3CCCN3S(=O)(=O)c3cc4ccccc4o3)c2)cc1] |
| 287 | 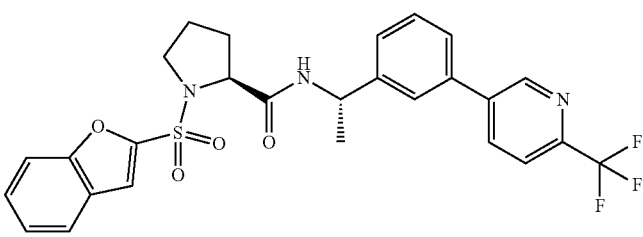 [SMILES: C[C@H](NC(=O)[C@@H]1CCCN1S(=O)(=O)c1cc2ccccc2o1)c1cccc(-c2ccc(C(F)(F)F)nc2)c1] |

US 10,626,112 B2
83	84
TABLE 1-continued
| Example No. | Structural formula |
|---|---|
| 288 | 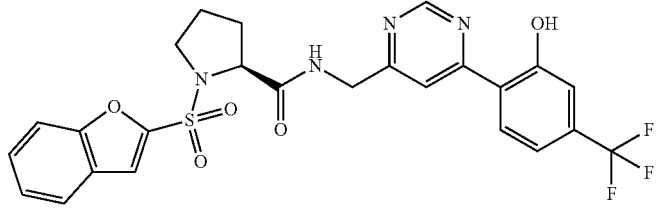 |
| 289 | 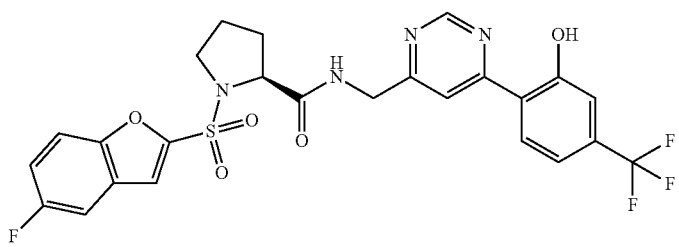 [SMILES: O=C(NCc1cc(-c2ccc(C(F)(F)F)cc2O)ncn1)[C@@H]1CCCN1S(=O)(=O)c1cc2cc(F)ccc2o1] |
| 290 | 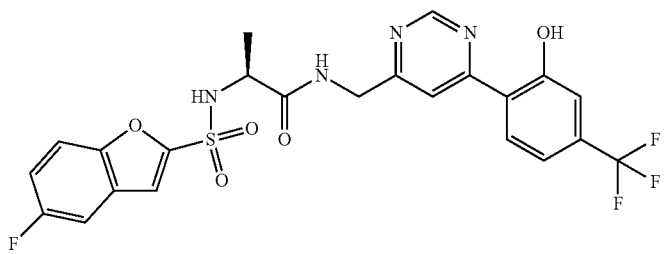 [SMILES: C[C@H](NS(=O)(=O)c1cc2cc(F)ccc2o1)C(=O)NCc1cc(-c2ccc(C(F)(F)F)cc2O)ncn1] |
| 291 | 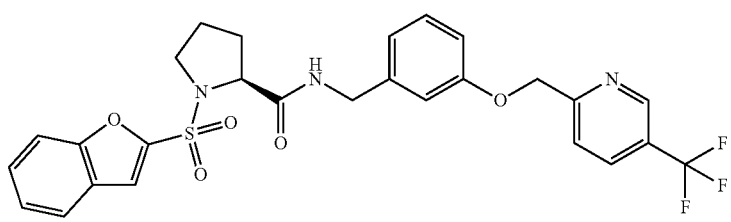 [SMILES: O=C(NCc1cccc(OCc2ccc(C(F)(F)F)cn2)c1)[C@@H]1CCCN1S(=O)(=O)c1cc2ccccc2o1] |
| 293 | 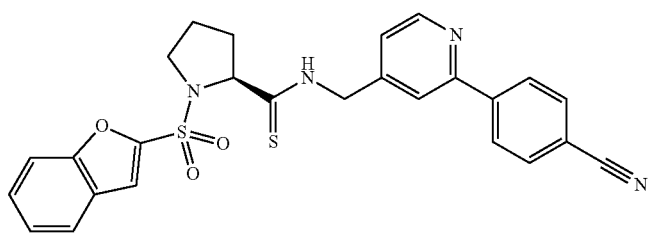 [SMILES: N#Cc1ccc(-c2cc(CNC(=S)[C@@H]3CCCN3S(=O)(=O)c3cc4ccccc4o3)ccn2)cc1] |
| 296 | 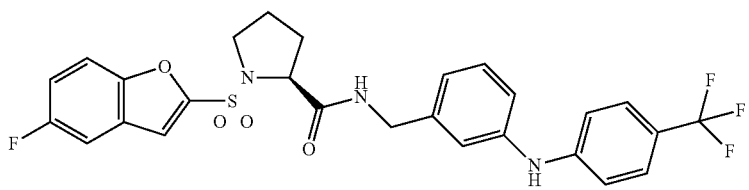 |

TABLE 1-continued
| Example No. | Structural formula |
|---|---|
| 297 | 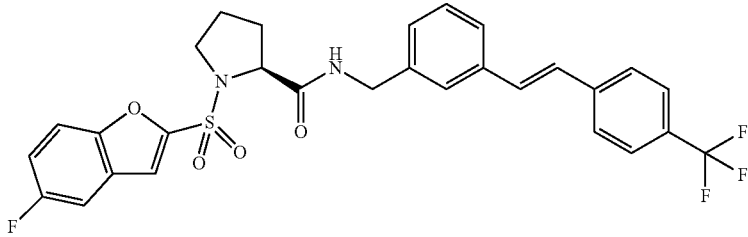 [SMILES: O=C(NCc1cccc(/C=C/c2ccc(C(F)(F)F)cc2)c1)[C@@H]1CCCN1S(=O)(=O)c1cc2cc(F)ccc2o1] |
| 298 | 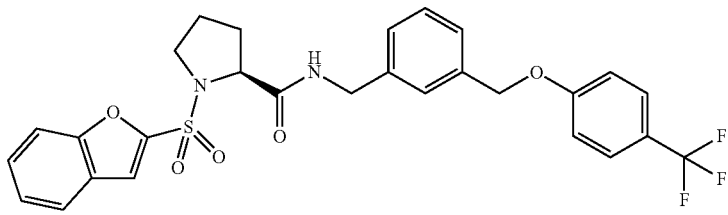 [SMILES: O=C(NCc1cccc(COc2ccc(C(F)(F)F)cc2)c1)[C@@H]1CCCN1S(=O)(=O)c1cc2ccccc2o1] |
| 299 | 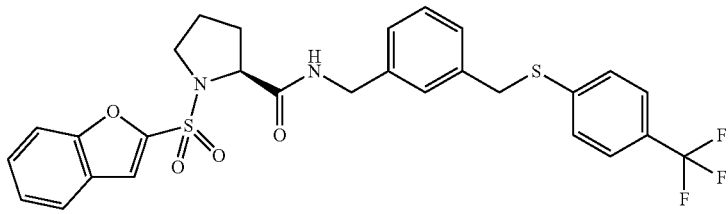 |
| 309 | 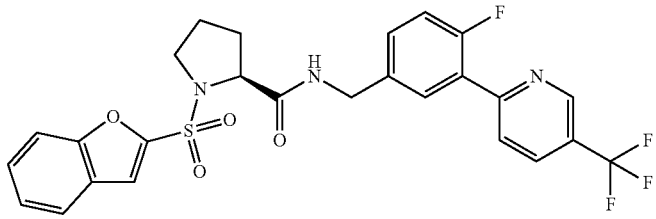 |
| 310 | 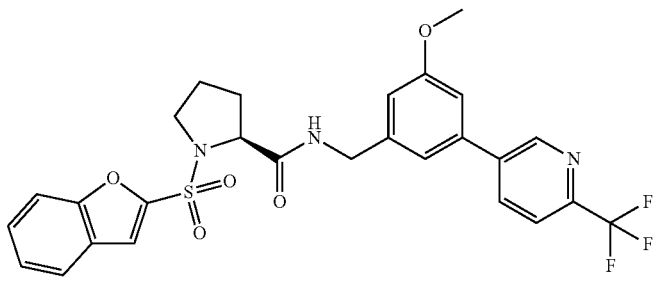 [SMILES: COc1cc(CNC(=O)[C@@H]2CCCN2S(=O)(=O)c2cc3ccccc3o2)cc(-c2ccc(C(F)(F)F)nc2)c1] |
| 311 | 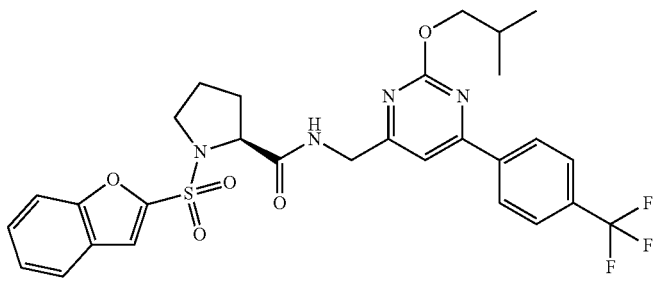 [SMILES: CC(C)COc1nc(CNC(=O)[C@@H]2CCCN2S(=O)(=O)c2cc3ccccc3o2)cc(-c2ccc(C(F)(F)F)cc2)n1] |

TABLE 1-continued
| Example No. | Structural formula |
|---|---|
| 312 | 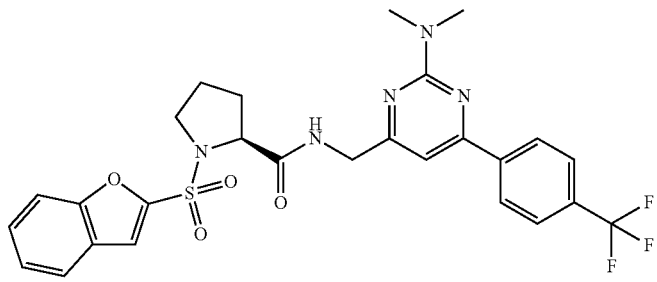 [SMILES: CN(C)c1nc(CNC(=O)[C@@H]2CCCN2S(=O)(=O)c2cc3ccccc3o2)cc(-c2ccc(C(F)(F)F)cc2)n1] |
| 315 | 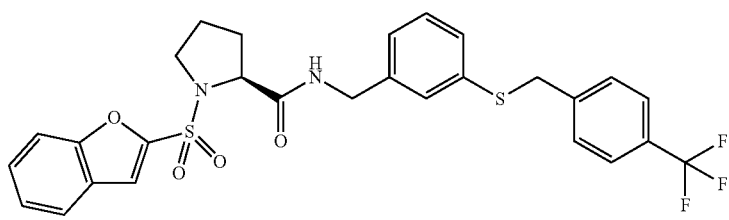 [SMILES: O=C(NCc1cccc(CCc2ccc(C(F)(F)F)cc2)c1)[C@@H]1CCCN1S(=O)(=O)c1cc2ccccc2o1] |
| 318 | 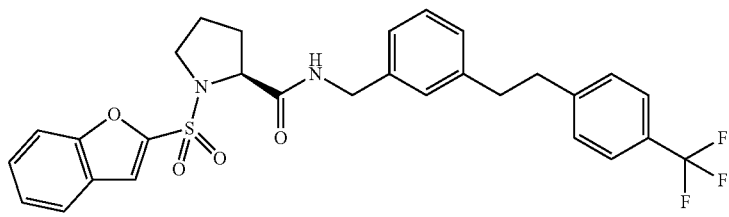 |
| 326 | 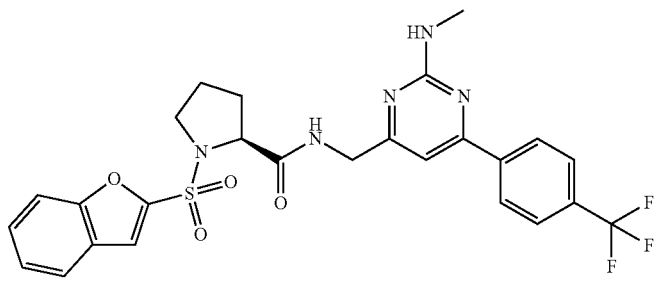 [SMILES: CNc1nc(CNC(=O)[C@@H]2CCCN2S(=O)(=O)c2cc3ccccc3o2)cc(-c2ccc(C(F)(F)F)cc2)n1] |
| 327 | 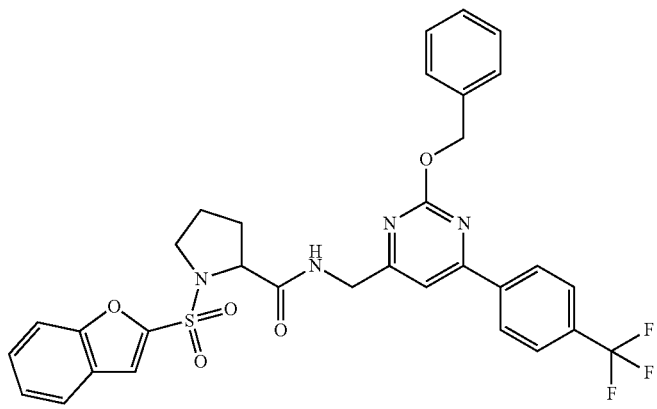 [SMILES: O=C(NCc1cc(-c2ccc(C(F)(F)F)cc2)nc(OCc2ccccc2)n1)C1CCCN1S(=O)(=O)c1cc2ccccc2o1] |

TABLE 1-continued
| Example No. | Structural formula |
| --- | --- |
| 328 | 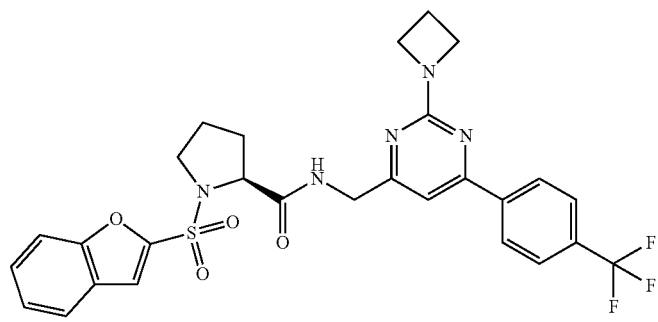 [SMILES: O=C(NCc1cc(-c2ccc(C(F)(F)F)cc2)nc(N2CCC2)n1)[C@@H]1CCCN1S(=O)(=O)c1cc2ccccc2o1] |
| 329 | 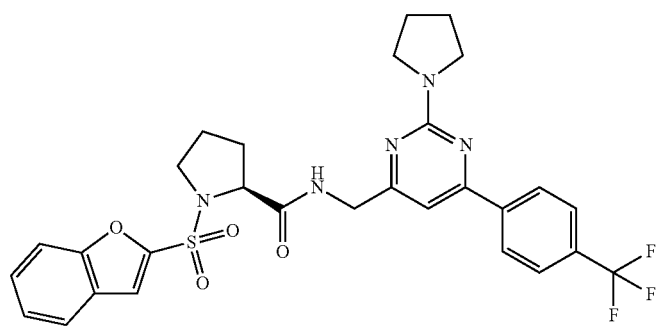 [SMILES: O=C(NCc1cc(-c2ccc(C(F)(F)F)cc2)nc(N2CCCC2)n1)[C@@H]1CCCN1S(=O)(=O)c1cc2ccccc2o1] |
| 330 | 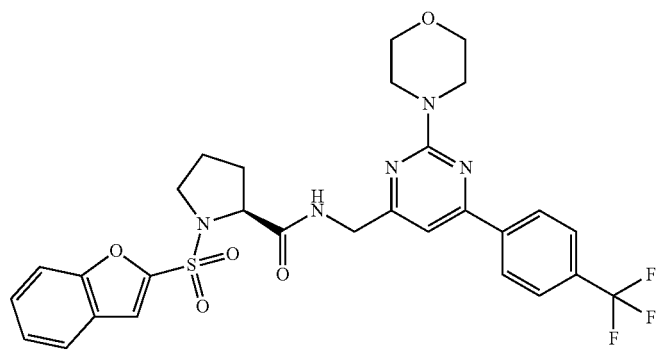 [SMILES: O=C(NCc1cc(-c2ccc(C(F)(F)F)cc2)nc(N2CCOCC2)n1)[C@@H]1CCCN1S(=O)(=O)c1cc2ccccc2o1] |
| 332 | 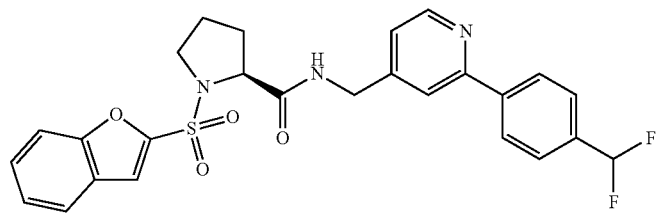 [SMILES: O=C(NCc1ccnc(-c2ccc(C(F)F)cc2)c1)[C@@H]1CCCN1S(=O)(=O)c1cc2ccccc2o1] |
| 333 | 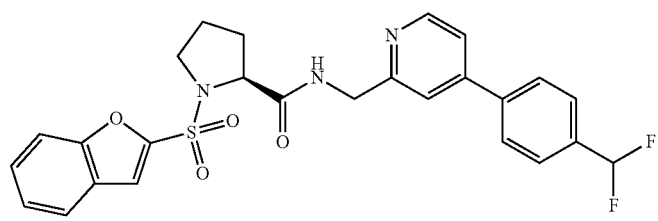 [SMILES: O=C(NCc1cc(-c2ccc(C(F)F)cc2)ccn1)[C@@H]1CCCN1S(=O)(=O)c1cc2ccccc2o1] |

TABLE 1-continued
| Example No. | Structural formula |
|---|---|
| 336 | 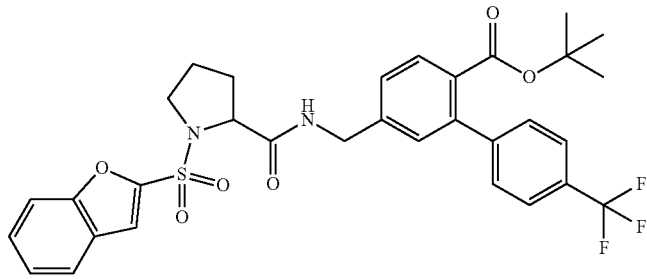 [SMILES: CC(C)(C)OC(=O)c1ccc(CNC(=O)C2CCCN2S(=O)(=O)c2cc3ccccc3o2)cc1-c1ccc(C(F)(F)F)cc1] |
| 337 | 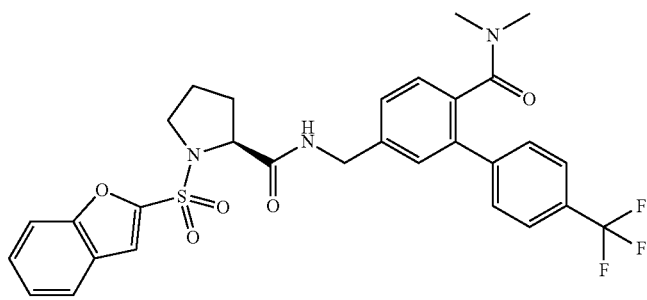 [SMILES: CN(C)C(=O)c1ccc(CNC(=O)[C@@H]2CCCN2S(=O)(=O)c2cc3ccccc3o2)cc1-c1ccc(C(F)(F)F)cc1] |
| 338 | 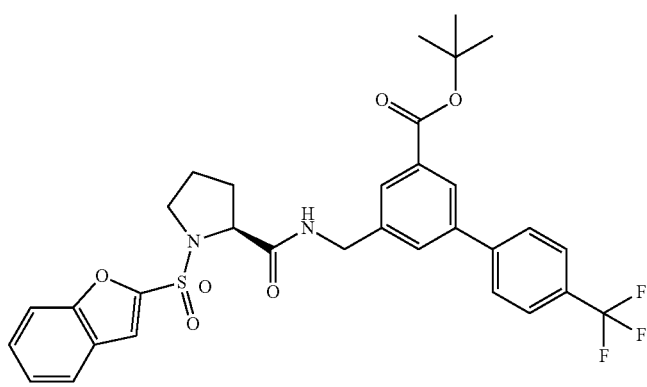 |
| 339 | 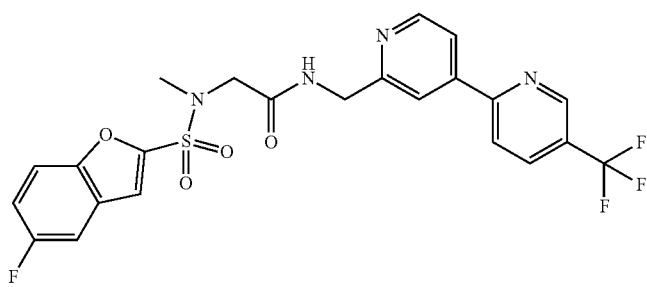 [SMILES: CN(CC(=O)NCc1cc(-c2ccc(C(F)(F)F)cn2)ccn1)S(=O)(=O)c1cc2cc(F)ccc2o1] |
| 341 | 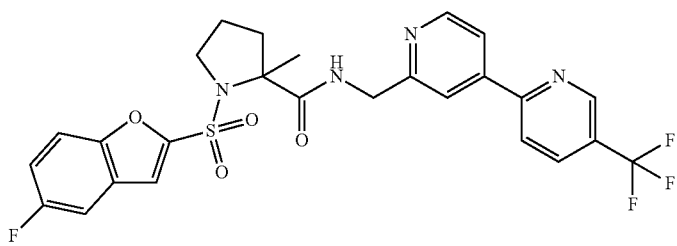 [SMILES: CC1(C(=O)NCc2cc(-c3ccc(C(F)(F)F)cn3)ccn2)CCCN1S(=O)(=O)c1cc2cc(F)ccc2o1] |

TABLE 1-continued
| Example No. | Structural formula |
|---|---|
| 344 | 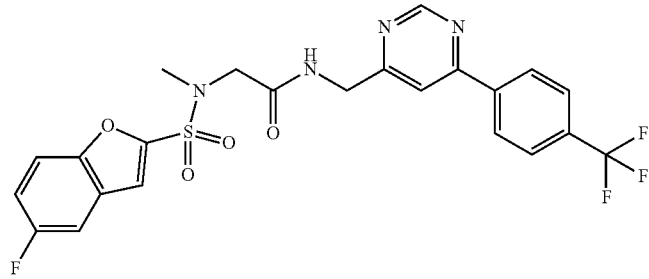 [SMILES: CN(CC(=O)NCc1cc(-c2ccc(C(F)(F)F)cc2)ncn1)S(=O)(=O)c1cc2cc(F)ccc2o1] |
| 348 | 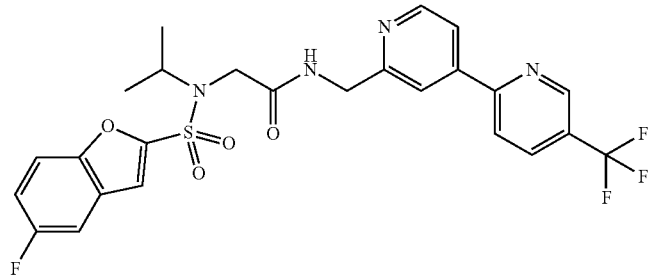 [SMILES: CC(C)N(CC(=O)NCc1cc(-c2ccc(C(F)(F)F)cn2)ccn1)S(=O)(=O)c1cc2cc(F)ccc2o1] |
| 349 | 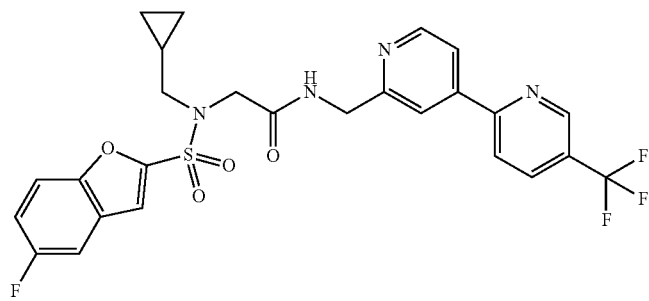 [SMILES: O=C(CN(CC1CC1)S(=O)(=O)c1cc2cc(F)ccc2o1)NCc1cc(-c2ccc(C(F)(F)F)cn2)ccn1] |
| 357 | 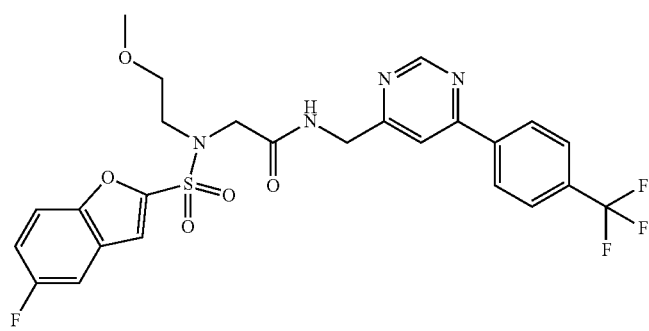 [SMILES: COCCN(CC(=O)NCc1cc(-c2ccc(C(F)(F)F)cc2)ncn1)S(=O)(=O)c1cc2cc(F)ccc2o1] |
| 359 | 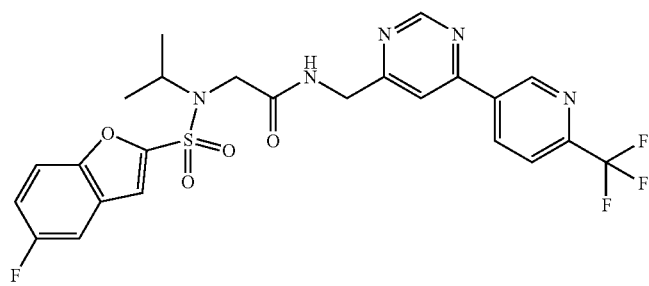 [SMILES: CC(C)N(CC(=O)NCc1cc(-c2ccc(C(F)(F)F)nc2)ncn1)S(=O)(=O)c1cc2cc(F)ccc2o1] |

TABLE 1-continued
| Example No. | Structural formula |
|---|---|
| 360 | 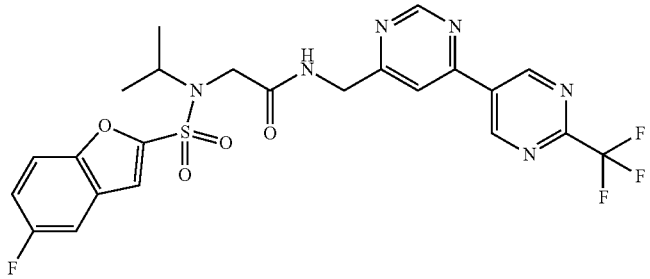 |
| 362 | 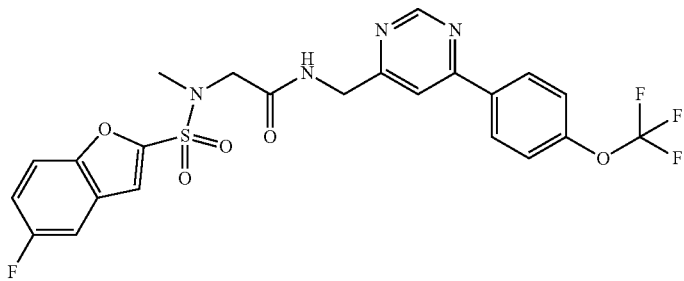 [SMILES: CN(CC(=O)NCc1cc(-c2ccc(OC(F)(F)F)cc2)ncn1)S(=O)(=O)c1cc2cc(F)ccc2o1] |
| 364 | 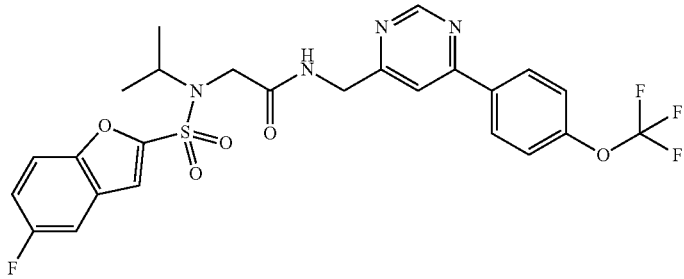 [SMILES: CC(C)N(CC(=O)NCc1cc(-c2ccc(OC(F)(F)F)cc2)ncn1)S(=O)(=O)c1cc2cc(F)ccc2o1] |
| 368 | 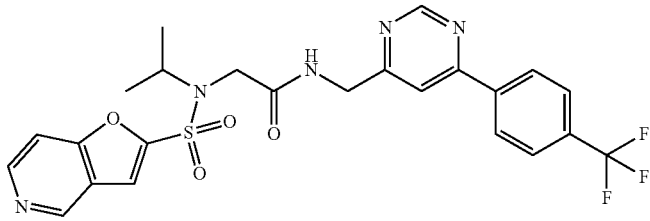 [SMILES: CC(C)N(CC(=O)NCc1cc(-c2ccc(C(F)(F)F)cc2)ncn1)S(=O)(=O)c1cc2cnccc2o1] |
| 369 | 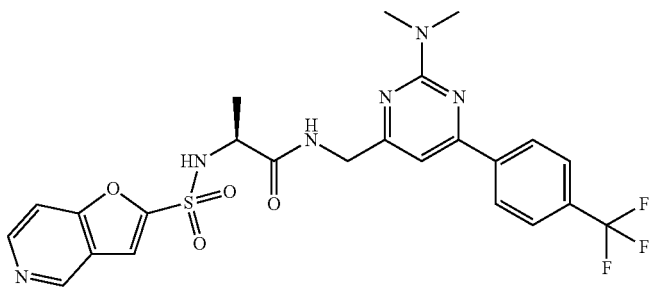 [SMILES: C[C@H](NS(=O)(=O)c1cc2cnccc2o1)C(=O)NCc1cc(-c2ccc(C(F)(F)F)cc2)nc(N(C)C)n1] |

TABLE 1-continued
| Example No. | Structural formula |
| --- | --- |
| 371 | 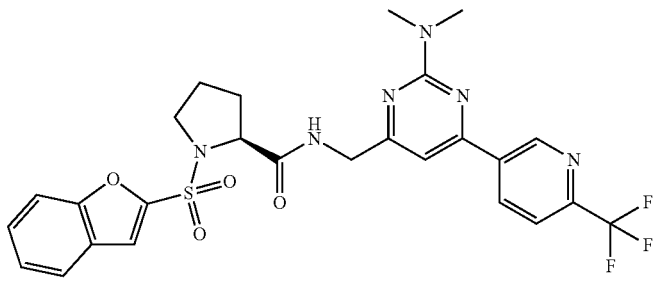 |
| 372 | 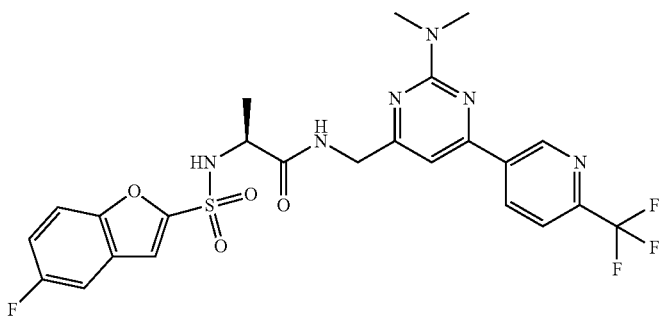 [SMILES: C[C@H](NS(=O)(=O)c1cc2cc(F)ccc2o1)C(=O)NCc1cc(-c2ccc(C(F)(F)F)nc2)nc(N(C)C)n1] |
| 374 | 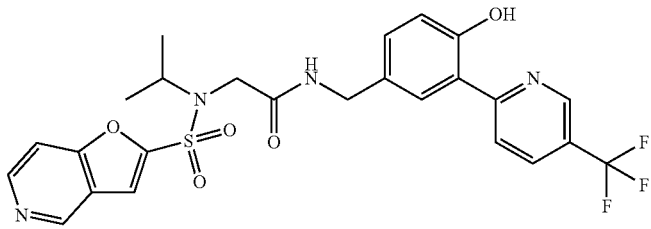 [SMILES: CC(C)N(CC(=O)NCc1ccc(O)c(-c2ccc(C(F)(F)F)cn2)c1)S(=O)(=O)c1cc2cnccc2o1] |
| 375 | 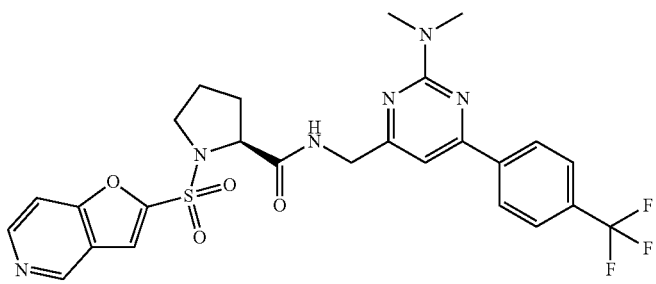 [SMILES: CN(C)c1nc(CNC(=O)[C@@H]2CCCN2S(=O)(=O)c2cc3cnccc3o2)cc(-c2ccc(C(F)(F)F)cc2)n1] |
| 376 | 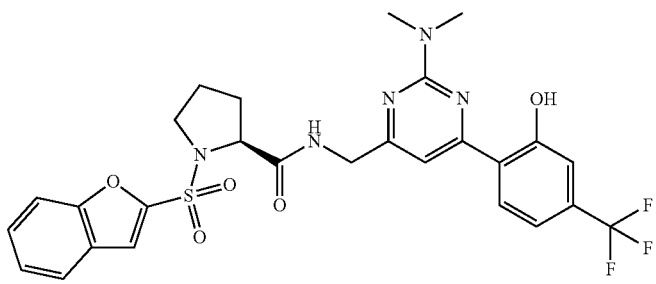 [SMILES: CN(C)c1nc(CNC(=O)[C@@H]2CCCN2S(=O)(=O)c2cc3ccccc3o2)cc(-c2ccc(C(F)(F)F)cc2O)n1] |

TABLE 1-continued
| Example No. | Structural formula |
|---|---|
| 378 | 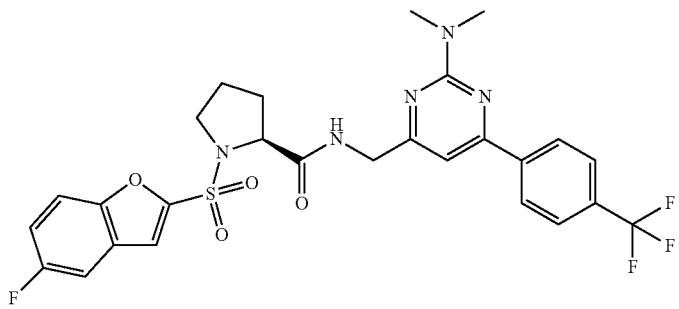 [SMILES: CN(C)c1nc(CNC(=O)[C@@H]2CCCN2S(=O)(=O)c2cc3cc(F)ccc3o2)cc(-c2ccc(C(F)(F)F)cc2)n1] |
| 379 | 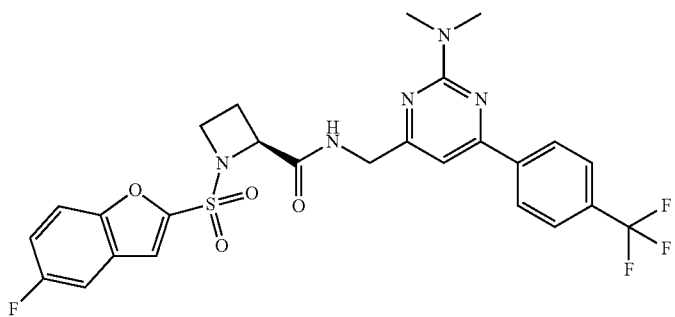 [SMILES: CN(C)c1nc(CNC(=O)[C@@H]2CCN2S(=O)(=O)c2cc3cc(F)ccc3o2)cc(-c2ccc(C(F)(F)F)cc2)n1] |
| 380 | 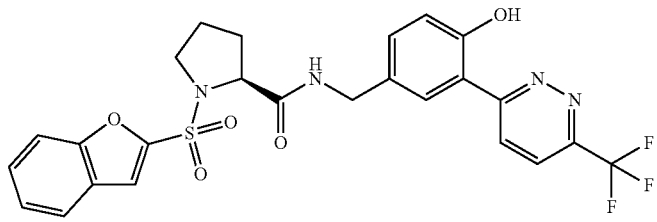 [SMILES: O=C(NCc1ccc(O)c(-c2ccc(C(F)(F)F)nn2)c1)[C@@H]1CCCN1S(=O)(=O)c1cc2ccccc2o1] |
| 381 | 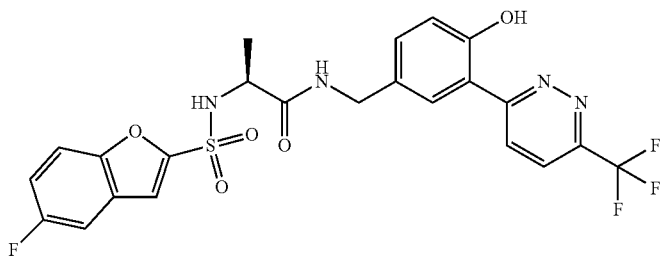 |
| 382 | 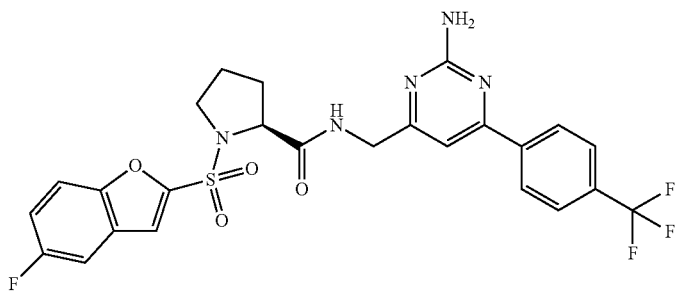 [SMILES: Nc1nc(CNC(=O)[C@@H]2CCCN2S(=O)(=O)c2cc3cc(F)ccc3o2)cc(-c2ccc(C(F)(F)F)cc2)n1] |

TABLE 1-continued
| Example No. | Structural formula |
|---|---|
| 383 | 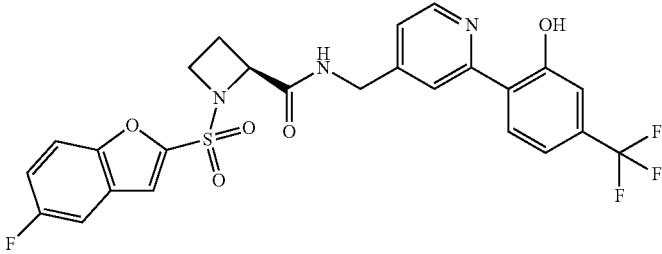 [SMILES: O=C(NCc1ccnc(-c2ccc(C(F)(F)F)cc2O)c1)[C@@H]1CCN1S(=O)(=O)c1cc2cc(F)ccc2o1] |
| 384 | 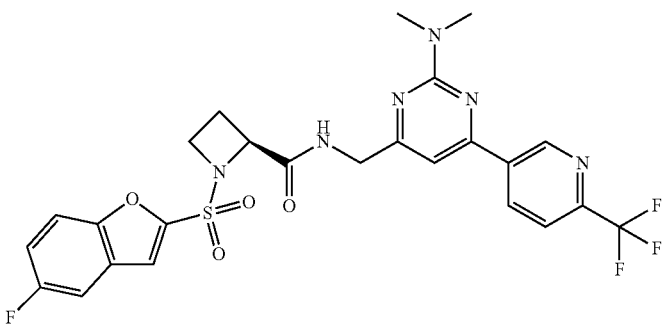 [SMILES: CN(C)c1nc(CNC(=O)[C@@H]2CCN2S(=O)(=O)c2cc3cc(F)ccc3o2)cc(-c2ccc(C(F)(F)F)nc2)n1] |
| 385 | 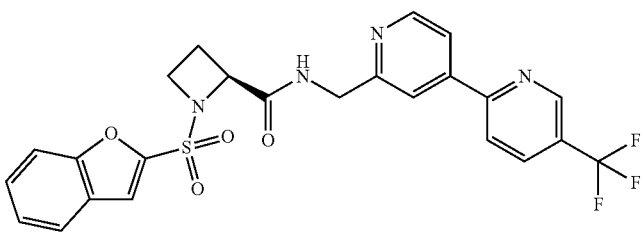 [SMILES: O=C(NCc1cc(-c2ccc(C(F)(F)F)cn2)ccn1)[C@@H]1CCN1S(=O)(=O)c1cc2ccccc2o1] |
| 386 | 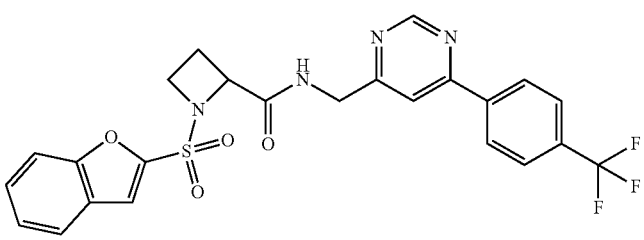 [SMILES: O=C(NCc1cc(-c2ccc(C(F)(F)F)cc2)ncn1)C1CCN1S(=O)(=O)c1cc2ccccc2o1] |
| 387 | 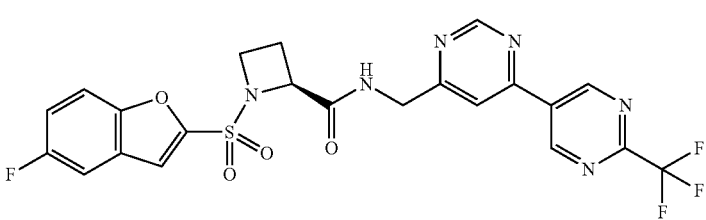 [SMILES: O=C(NCc1cc(-c2cnc(C(F)(F)F)nc2)ncn1)[C@@H]1CCN1S(=O)(=O)c1cc2cc(F)ccc2o1] |
| 388 | 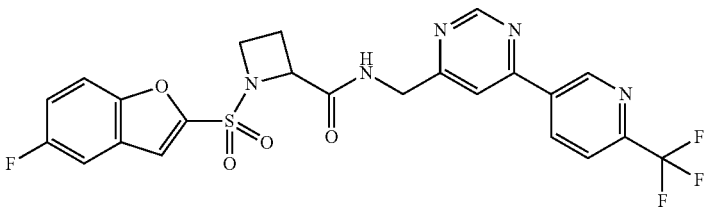 [SMILES: O=C(NCc1cc(-c2ccc(C(F)(F)F)nc2)ncn1)C1CCN1S(=O)(=O)c1cc2cc(F)ccc2o1] |

TABLE 1-continued
| Example No. | Structural formula |
|---|---|
| 389 | 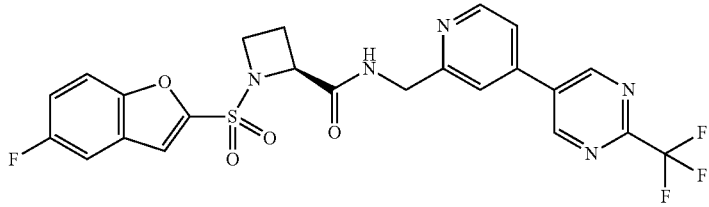 [SMILES: O=C(NCc1cc(-c2cnc(C(F)(F)F)nc2)ccn1)[C@@H]1CCN1S(=O)(=O)c1cc2cc(F)ccc2o1] |
| 390 | 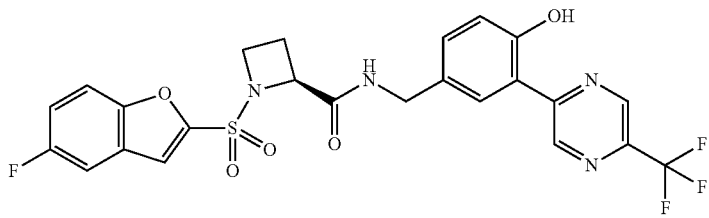 [SMILES: O=C(NCc1ccc(O)c(-c2cnc(C(F)(F)F)cn2)c1)[C@@H]1CCN1S(=O)(=O)c1cc2cc(F)ccc2o1] |
| 391 | 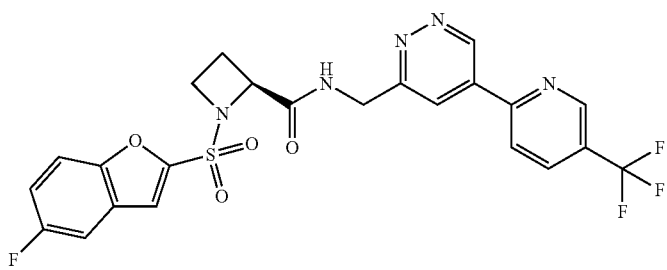 [SMILES: O=C(NCc1cc(-c2ccc(C(F)(F)F)cn2)cnn1)[C@@H]1CCN1S(=O)(=O)c1cc2cc(F)ccc2o1] |
| 392 | 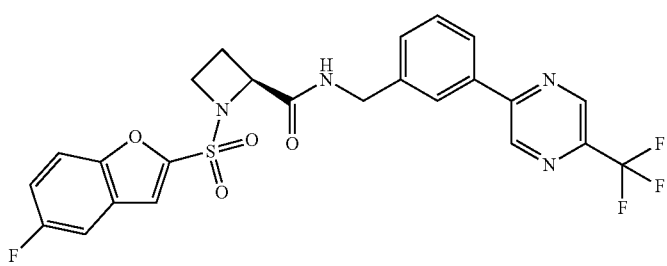 [SMILES: O=C(NCc1cccc(-c2cnc(C(F)(F)F)cn2)c1)[C@@H]1CCN1S(=O)(=O)c1cc2cc(F)ccc2o1] |
| 393 | 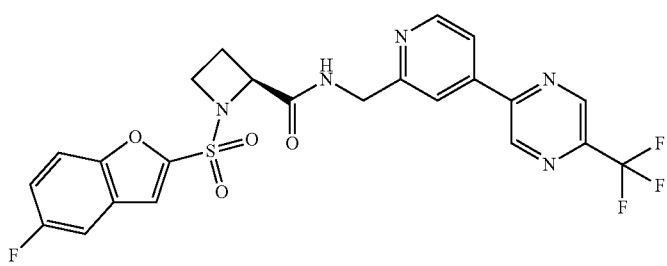 [SMILES: O=C(NCc1cc(-c2cnc(C(F)(F)F)cn2)ccn1)[C@@H]1CCN1S(=O)(=O)c1cc2cc(F)ccc2o1] |
| 394 | 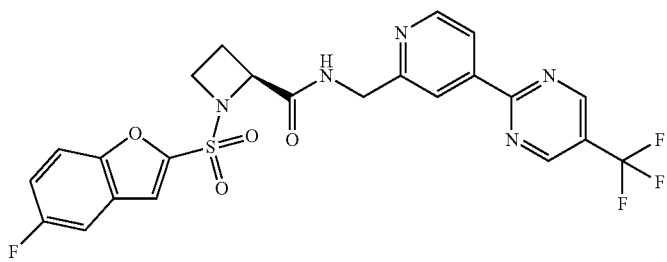 [SMILES: O=C(NCc1cc(-c2ncc(C(F)(F)F)cn2)ccn1)[C@@H]1CCN1S(=O)(=O)c1cc2cc(F)ccc2o1] |

TABLE 1-continued
| Example No. | Structural formula |
|---|---|
| 395 | 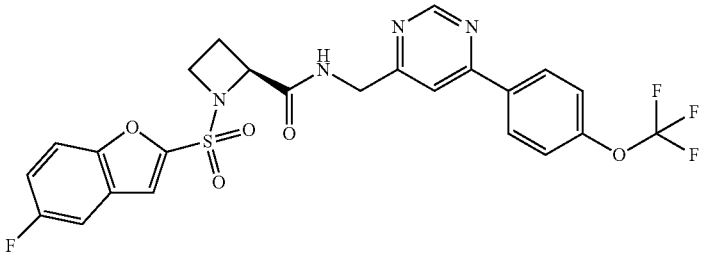 [SMILES: O=C(NCc1cc(-c2ccc(OC(F)(F)F)cc2)ncn1)[C@@H]1CCN1S(=O)(=O)c1cc2cc(F)ccc2o1] |
| 396 | 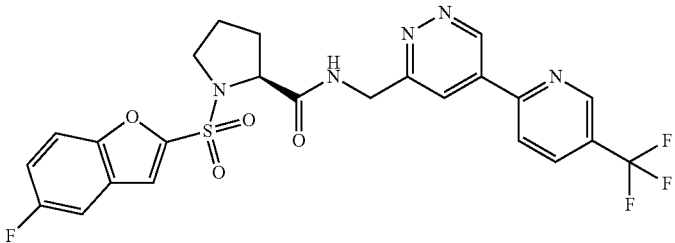 [SMILES: O=C(NCc1cc(-c2ccc(C(F)(F)F)cn2)cnn1)[C@@H]1CCCN1S(=O)(=O)c1cc2cc(F)ccc2o1] |
| 397 | 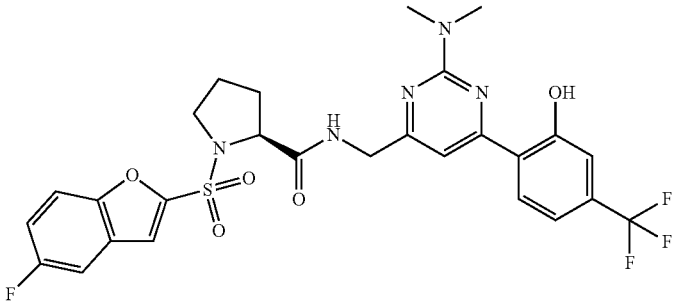 [SMILES: CN(C)c1nc(CNC(=O)[C@@H]2CCCN2S(=O)(=O)c2cc3cc(F)ccc3o2)cc(-c2ccc(C(F)(F)F)cc2O)n1] |
| 398 | 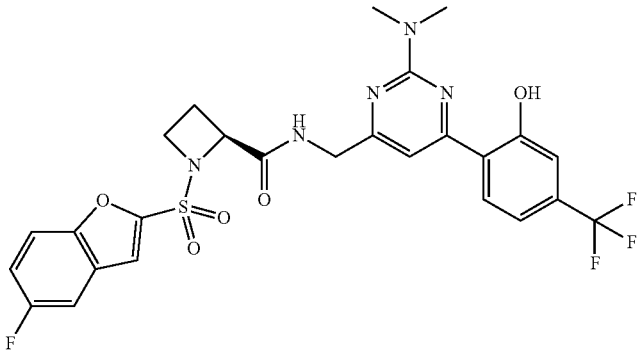 [SMILES: CN(C)c1nc(CNC(=O)[C@@H]2CCN2S(=O)(=O)c2cc3cc(F)ccc3o2)cc(-c2ccc(C(F)(F)F)cc2O)n1] |
| 399 | 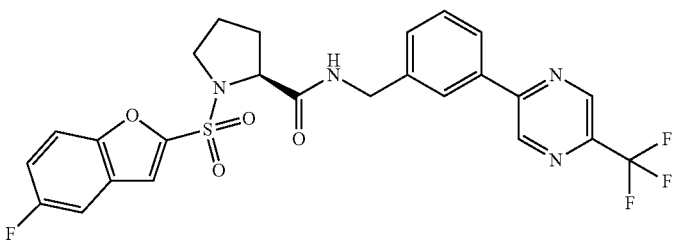 [SMILES: O=C(NCc1cccc(-c2cnc(C(F)(F)F)cn2)c1)[C@@H]1CCCN1S(=O)(=O)c1cc2cc(F)ccc2o1] |

US 10,626,112 B2
107                                                                                          108
TABLE 1-continued
| Example No. | Structural formula |
|---|---|
| 400 | 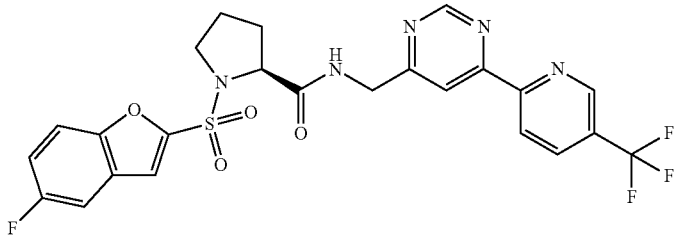 [SMILES: O=C(NCc1cc(-c2ccc(C(F)(F)F)cn2)ncn1)[C@@H]1CCCN1S(=O)(=O)c1cc2cc(F)ccc2o1] |
| 401 | 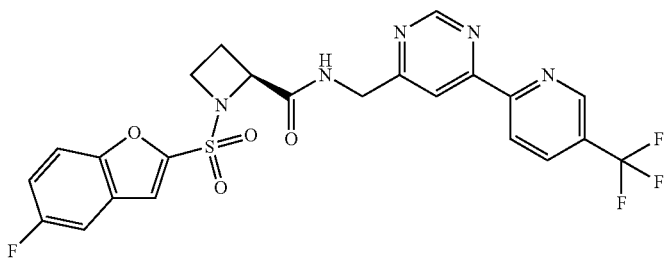 [SMILES: O=C(NCc1cc(-c2ccc(C(F)(F)F)cn2)ncn1)[C@@H]1CCN1S(=O)(=O)c1cc2cc(F)ccc2o1] |
| 402 | 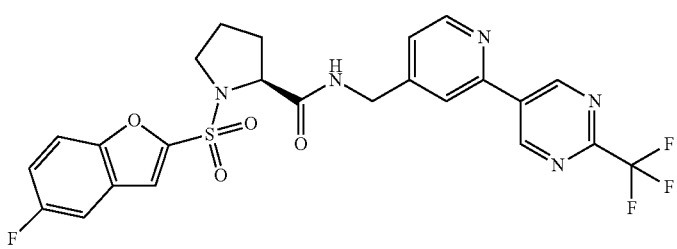 [SMILES: O=C(NCc1ccnc(-c2cnc(C(F)(F)F)nc2)c1)[C@@H]1CCCN1S(=O)(=O)c1cc2cc(F)ccc2o1] |
| 403 | 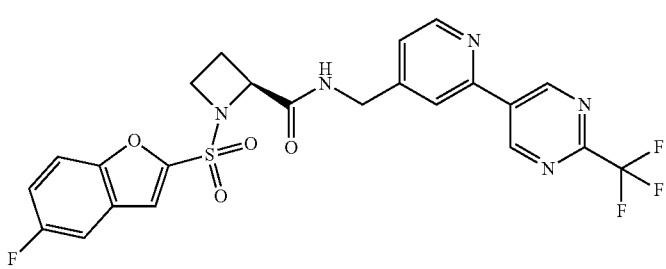 [SMILES: O=C(NCc1ccnc(-c2cnc(C(F)(F)F)nc2)c1)[C@@H]1CCN1S(=O)(=O)c1cc2cc(F)ccc2o1] |
| 404 | 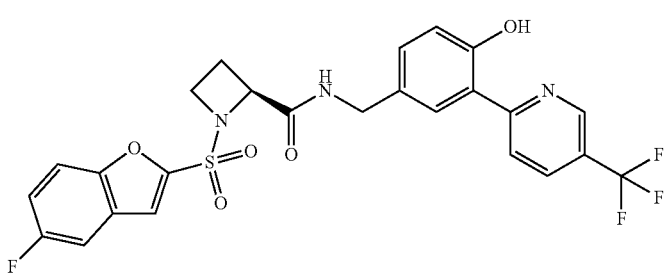 [SMILES: O=C(NCc1ccc(O)c(-c2ccc(C(F)(F)F)cn2)c1)[C@@H]1CCN1S(=O)(=O)c1cc2cc(F)ccc2o1] |
| 405 | 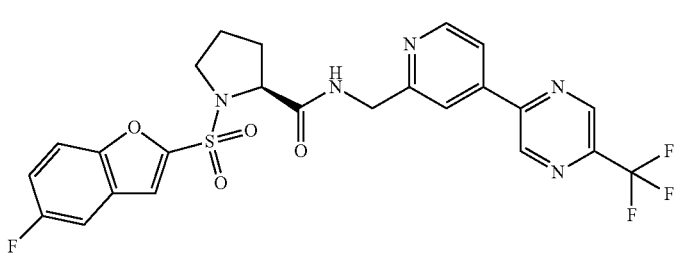 |

TABLE 1-continued
| Example No. | Structural formula |
|---|---|
| 406 | 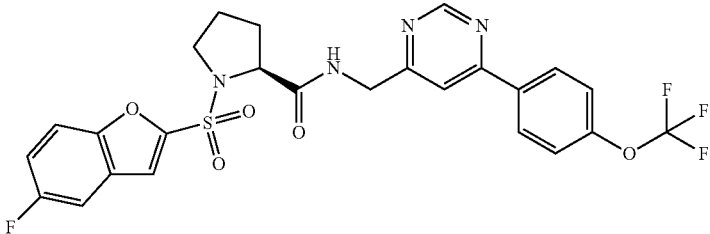 [SMILES: O=C(NCc1cc(-c2ccc(OC(F)(F)F)cc2)ncn1)[C@@H]1CCCN1S(=O)(=O)c1cc2cc(F)ccc2o1] |
| 407 | 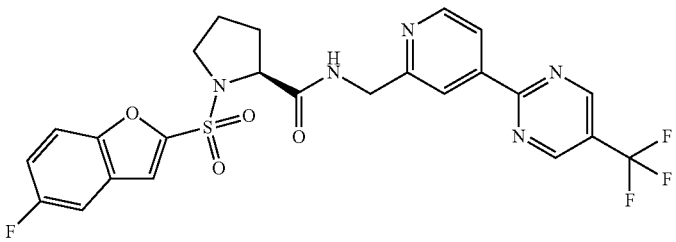 [SMILES: O=C(NCc1cc(-c2ncc(C(F)(F)F)cn2)ccn1)[C@@H]1CCCN1S(=O)(=O)c1cc2cc(F)ccc2o1] |
| 408 | 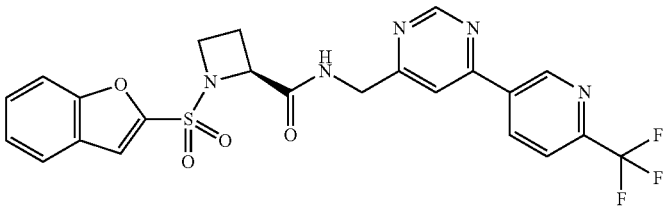 [SMILES: O=C(NCc1cc(-c2ccc(C(F)(F)F)nc2)ncn1)[C@@H]1CCN1S(=O)(=O)c1cc2ccccc2o1] |
| 409 | 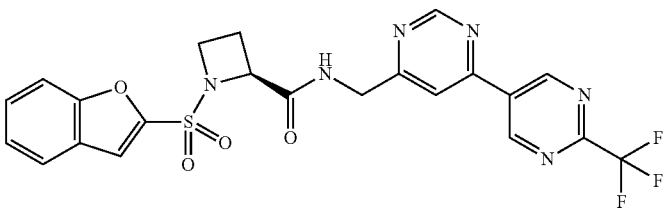 [SMILES: O=C(NCc1cc(-c2cnc(C(F)(F)F)nc2)ncn1)[C@@H]1CCN1S(=O)(=O)c1cc2ccccc2o1] |
| 410 | 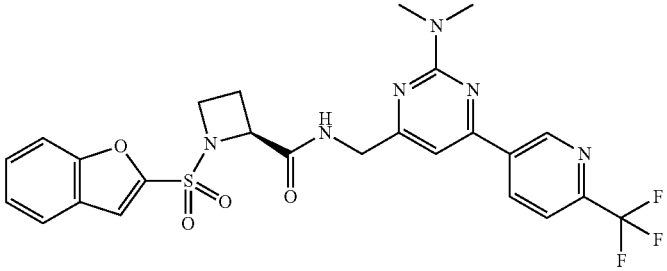 [SMILES: CN(C)c1nc(CNC(=O)[C@@H]2CCN2S(=O)(=O)c2cc3ccccc3o2)cc(-c2ccc(C(F)(F)F)nc2)n1] |
| 411 | 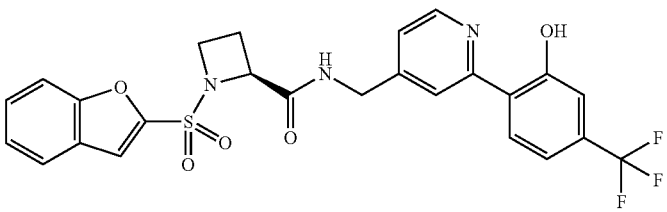 [SMILES: O=C(NCc1ccnc(-c2ccc(C(F)(F)F)cc2O)c1)[C@@H]1CCN1S(=O)(=O)c1cc2ccccc2o1] |

TABLE 1-continued
| Example No. | Structural formula |
|---|---|
| 412 | 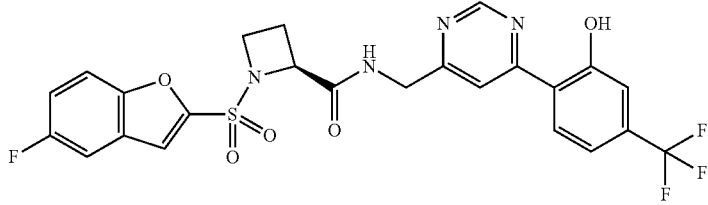 [SMILES: O=C(NCc1cc(-c2ccc(C(F)(F)F)cc2O)ncn1)[C@@H]1CCN1S(=O)(=O)c1cc2cc(F)ccc2o1] |
| 413 | 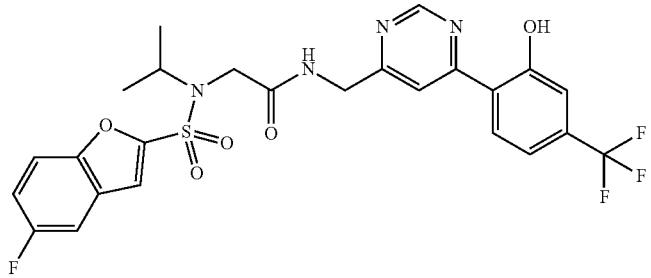 [SMILES: CC(C)N(CC(=O)NCc1cc(-c2ccc(C(F)(F)F)cc2O)ncn1)S(=O)(=O)c1cc2cc(F)ccc2o1] |
| 414 | 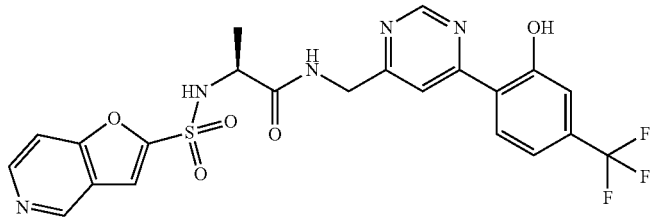 [SMILES: C[C@H](NS(=O)(=O)c1cc2cnccc2o1)C(=O)NCc1cc(-c2ccc(C(F)(F)F)cc2O)ncn1] |
| 416 | 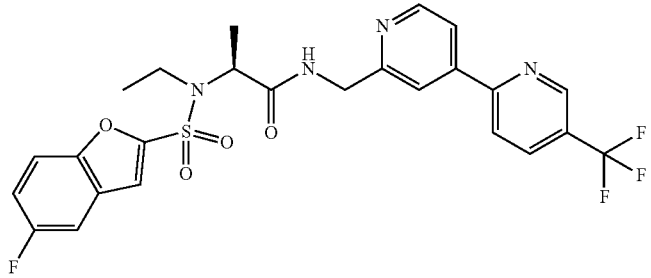 [SMILES: CCN([C@@H](C)C(=O)NCc1cc(-c2ccc(C(F)(F)F)cn2)ccn1)S(=O)(=O)c1cc2cc(F)ccc2o1] |
| 417 | 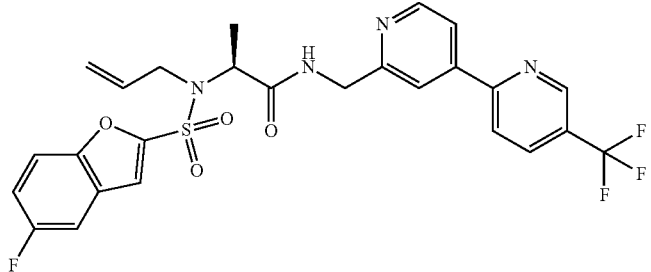 [SMILES: C=CCN([C@@H](C)C(=O)NCc1cc(-c2ccc(C(F)(F)F)cn2)ccn1)S(=O)(=O)c1cc2cc(F)ccc2o1] |
| 418 | 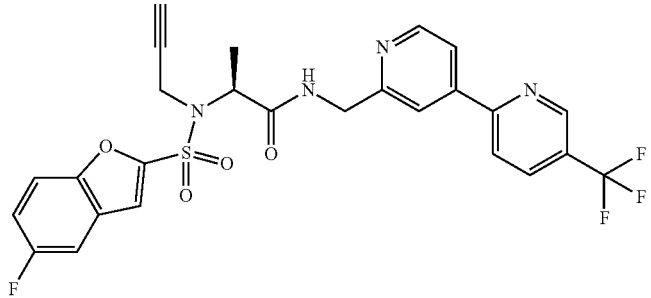 [SMILES: C#CCN([C@@H](C)C(=O)NCc1cc(-c2ccc(C(F)(F)F)cn2)ccn1)S(=O)(=O)c1cc2cc(F)ccc2o1] |

TABLE 1-continued
| Example No. | Structural formula |
|---|---|
| 419 | 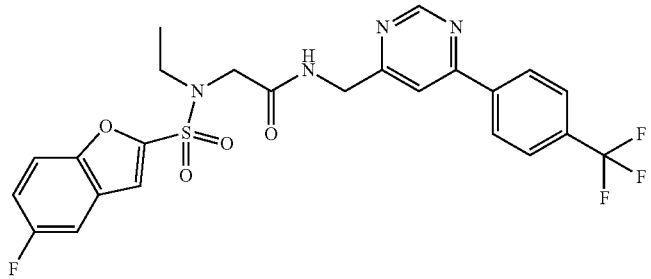 [SMILES: CCN(CC(=O)NCc1cc(-c2ccc(C(F)(F)F)cc2)ncn1)S(=O)(=O)c1cc2cc(F)ccc2o1] |
| 420 | 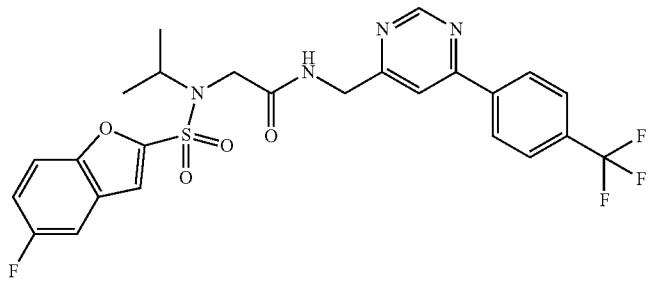 [SMILES: CC(C)N(CC(=O)NCc1cc(-c2ccc(C(F)(F)F)cc2)ncn1)S(=O)(=O)c1cc2cc(F)ccc2o1] |
| 421 | 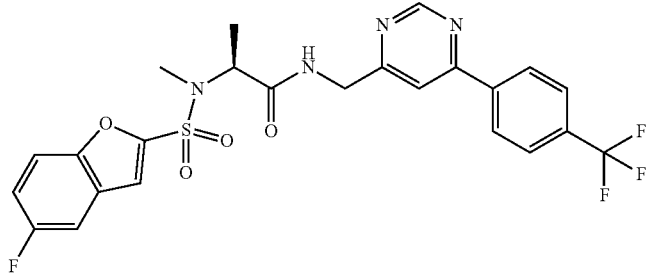 [SMILES: C[C@@H](C(=O)NCc1cc(-c2ccc(C(F)(F)F)cc2)ncn1)N(C)S(=O)(=O)c1cc2cc(F)ccc2o1] |
| 422 | 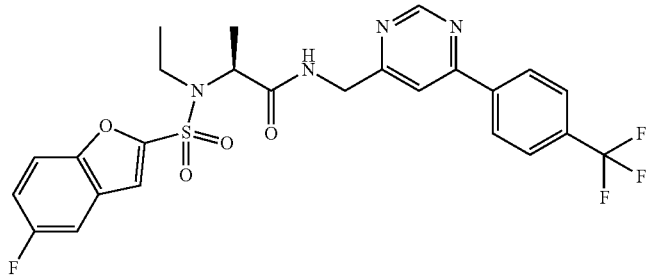 [SMILES: CCN([C@@H](C)C(=O)NCc1cc(-c2ccc(C(F)(F)F)cc2)ncn1)S(=O)(=O)c1cc2cc(F)ccc2o1] |
| 423 | 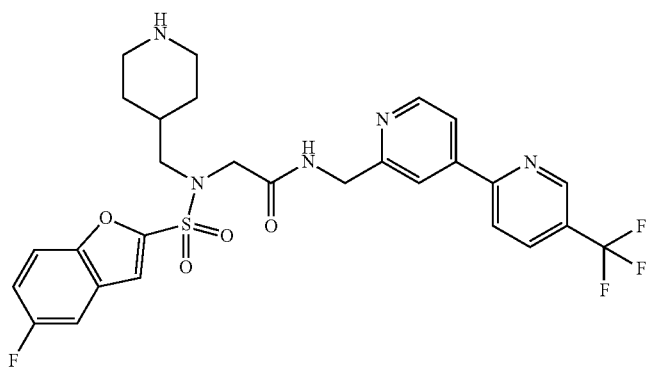 [SMILES: O=C(CN(CC1CCNCC1)S(=O)(=O)c1cc2cc(F)ccc2o1)NCc1cc(-c2ccc(C(F)(F)F)cn2)ccn1] |

TABLE 1-continued
| Example No. | Structural formula |
| --- | --- |
| 424 | 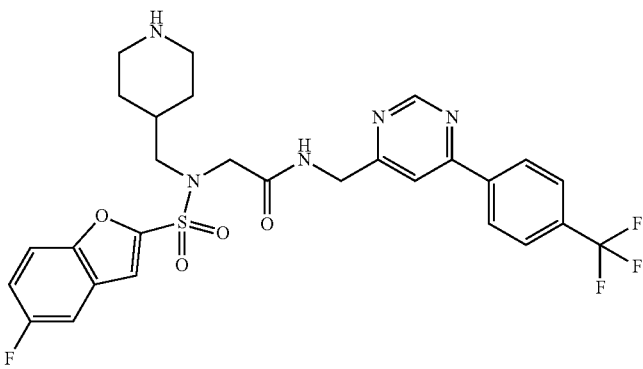 [SMILES: O=C(CN(CC1CCNCC1)S(=O)(=O)c1cc2cc(F)ccc2o1)NCc1cc(-c2ccc(C(F)(F)F)cc2)ncn1] |
| 426 | 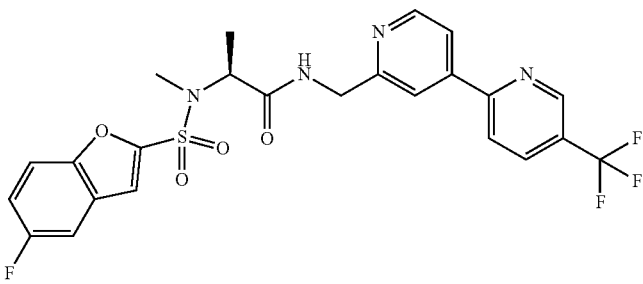 [SMILES: C[C@@H](C(=O)NCc1cc(-c2ccc(C(F)(F)F)cn2)ccn1)N(C)S(=O)(=O)c1cc2cc(F)ccc2o1] |
Further preferred are the compounds described in Examples 80, 84, 109, 116, 117, 123, 124, 138, 153, 179, 181, 190, 191, 192, 196, 199, 201, 203, 206, 224, 230, 248, 290, 312, 378, 379, 383, 384, 386, 387, 388, 389, 393, 395, 401, 405, 406, 411, 412 and in the following Tables (Table 1), and having the following structural formulas, and pharmaceutically acceptable salts thereof.
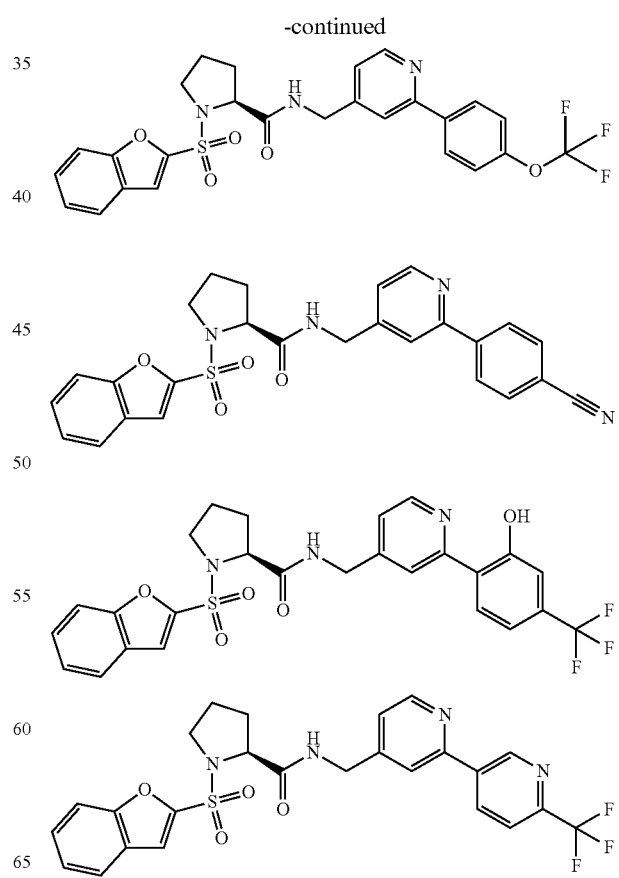

117
-continued
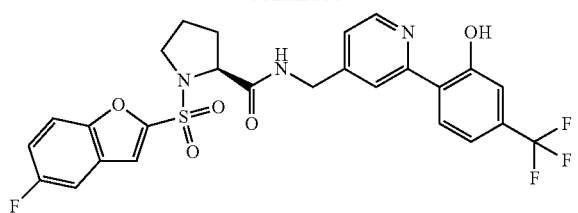
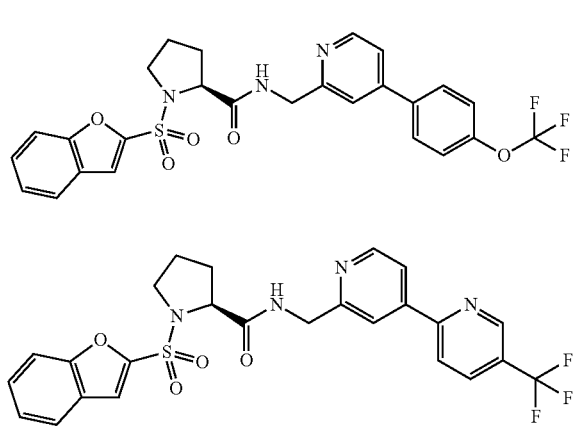
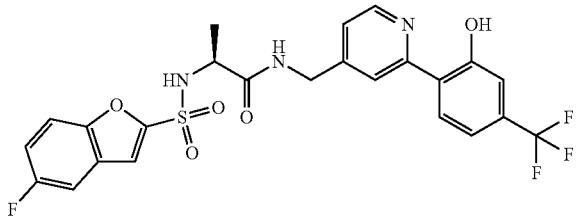
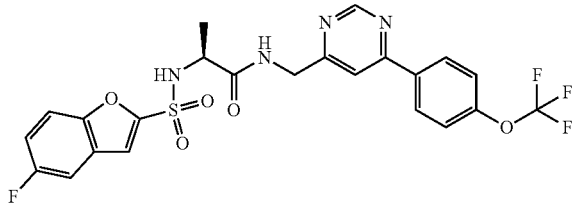
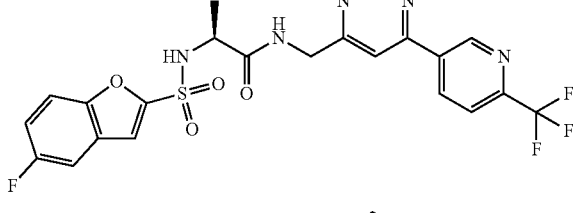
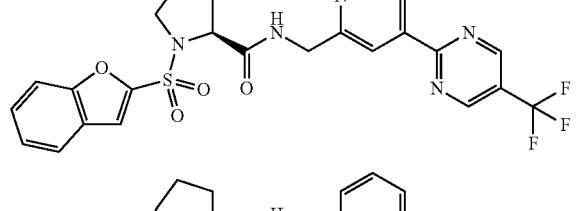
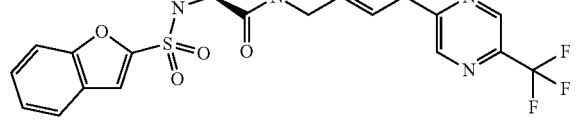
118
-continued
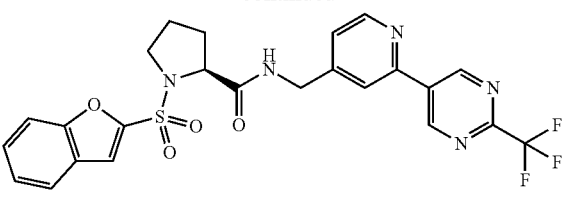
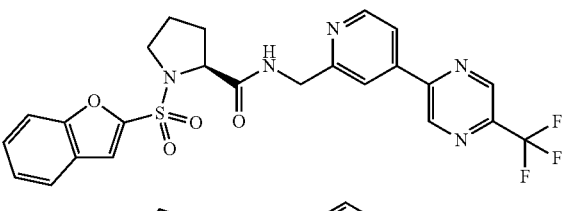
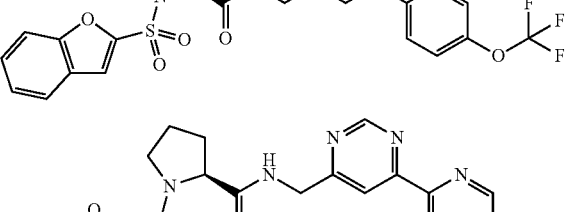
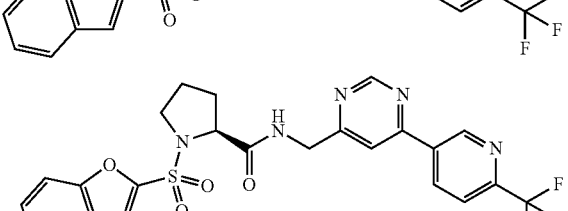
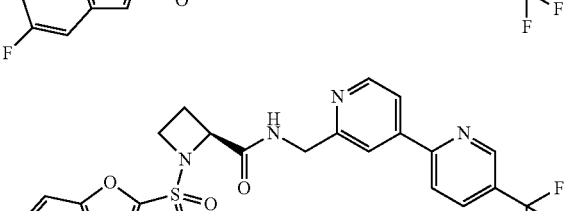
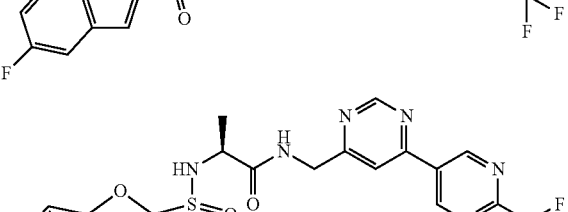
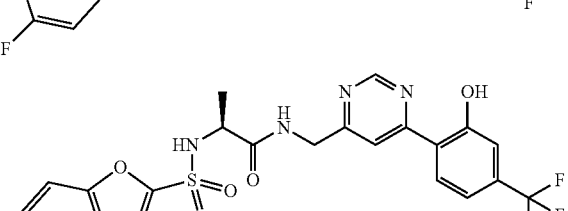
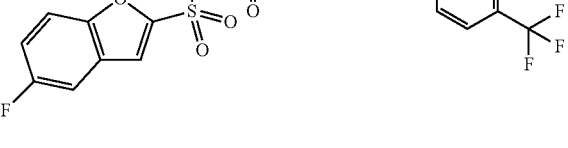

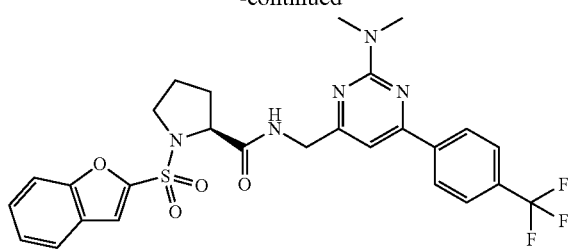
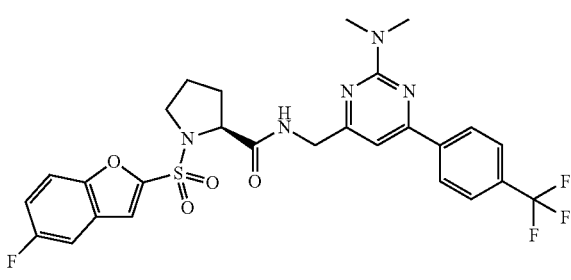
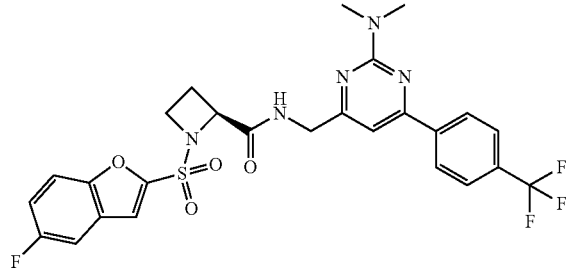
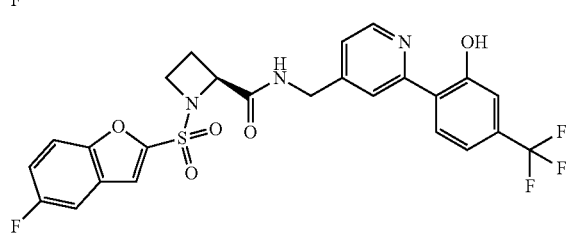
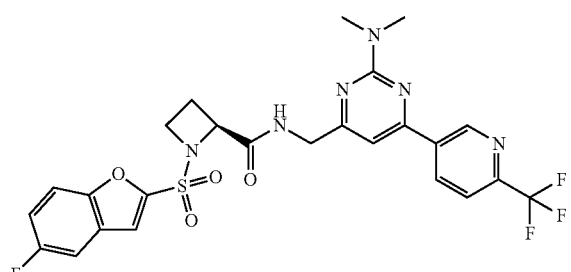
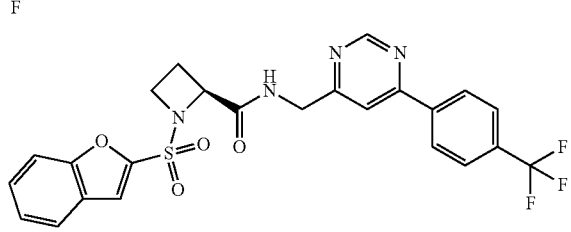
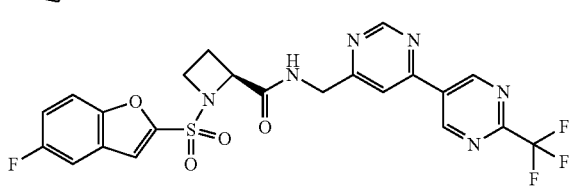
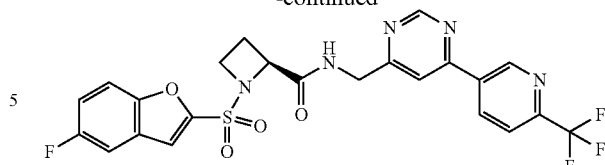
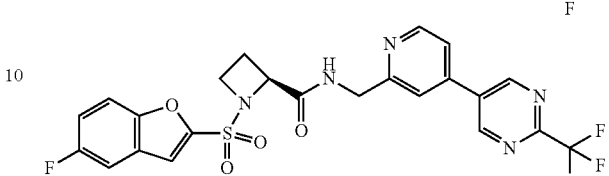
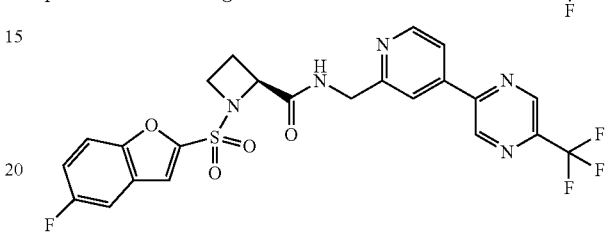
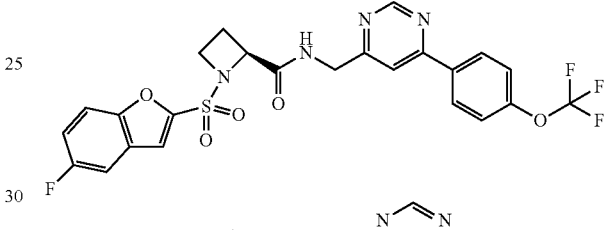
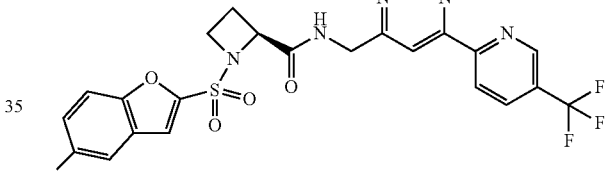
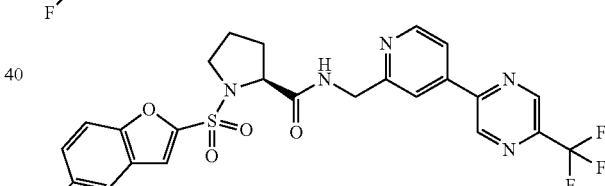
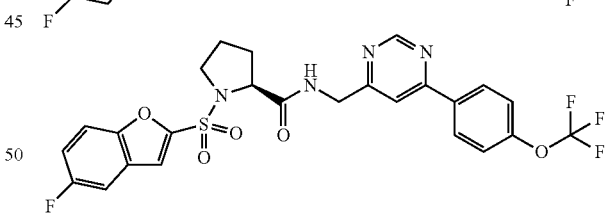
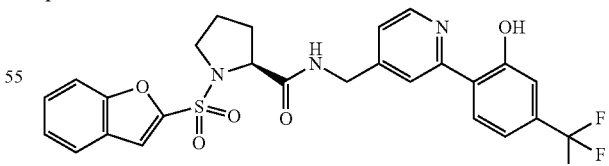
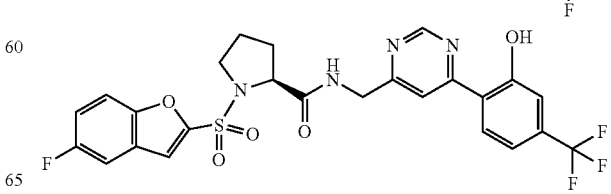

Effect of the Invention

The compound of the present invention has a superior TRPA1 antagonist activity, and useful for the prophylaxis and/or treatment of diseases involving TRPA1 (e.g., pain associated diseases, digestive tract diseases, lung diseases, bladder diseases, inflammatory diseases, dermatic diseases, and neurological diseases).

DETAILED DESCRIPTION OF THE PREFERRED EMBODIMENTS

The terms used in the present specification are defined below.

The "TRPA1 antagonist activity" refers to an activity capable of inhibiting activation of TRPA1, or down-regulating the biological activity of TRPA1 (e.g., intracellular inflow of ion). The TRPA1 antagonist activity can be evaluated by measuring the level of intracellular inflow of calcium ion into the cell expressing TRPA1.

The "halogen atom" is a fluorine atom, a chlorine atom, a bromine atom or an iodine atom.

The "halogeno group" is fluoro, chloro, bromo or iodo.

The "$C_{1-6}$ alkyl group" means a straight chain or branched alkyl group having 1-6 carbon atoms and, specifically, groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like can be mentioned.

The "$C_{2-6}$ alkenyl group" means a straight chain or branched alkenyl group having 2-6 carbon atoms and, specifically, groups such as vinyl, allyl, propenyl, butenyl, pentenyl, hexenyl, heptenyl, butadienyl, hexatrienyl, and each isomer thereof and the like can be mentioned.

The "cyclic $C_{3-6}$ alkyl group" means a cyclic alkyl group having 3-6 carbon atoms and, specifically, groups such as cyclopropyl, cyclobutyl, cyclopentyl, cyclohexyl and the like can be mentioned.

The "$C_{1-6}$ alkoxy group" means a straight chain or branched alkoxy group having 1-6 carbon atoms and, specifically, groups such as methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy and the like can be mentioned.

The $C_{6-10}$ aryl group means an aryl group having 6-10 carbon atoms and, specifically, groups such as phenyl, naphthyl group and the like can be mentioned.

The "$C_{1-6}$ alkyl group", "$C_{2-6}$ alkenyl group" and "$C_{1-6}$ alkoxy group" may have a substituent, and examples of such substituent include [substituent group A] below.

[Substituent Group A]
(1) halogeno group,
(2) hydroxy group,
(3) cyano group,
(4) nitro group,
(5) carboxyl group,
(6) alkenyl group ($C_{2-10}$ alkenyl group; e.g., vinyl, allyl, propenyl, butenyl, pentenyl, hexenyl, heptenyl, butadienyl, hexatrienyl, and each isomer thereof),
(7) alkynyl group ($C_{2-10}$ alkynyl group; e.g., ethynyl, propynyl, butynyl, pentynyl, hexynyl, and each isomer thereof),
(8) halogenoalkyl group (e.g., monofluoromethyl, difluoromethyl, trifluoromethyl, monofluoroethyl, difluoroethyl, trifluoroethyl, chloromethyl, chloroethyl, dichloroethyl, and each isomer thereof),
(9) cyclic alkyl group (optionally containing a hetero atom in the ring) (e.g., cyclopropyl, cyclobutyl, cyclopentyl, cyclohexyl, tetrahydrofuranyl, tetrahydropyranyl, aziridinyl, azetidinyl, pyrrolidinyl, piperidinyl, morpholinyl),
(10) an aryl group (e.g., phenyl, naphthyl),
(11) heteroaryl group (e.g., pyridyl, pyridazinyl, pyrimidinyl, pyrazinyl, furyl, thiophenyl, pyrrolyl, pyrazolyl, imidazolyl, triazolyl (e.g., 1,2,3-triazolyl, 1,2,4-triazolyl), tetrazolyl, oxazolyl, isoxazolyl, thiazolyl, isothiazolyl, oxadiazolyl (e.g., 1,2,3-oxadiazolyl, 1,2,4-oxadiazolyl, 1,3,4-oxadiazolyl), thiadiazolyl (e.g., 1,2,3-thiadiazolyl, 1,2,4-thiadiazolyl, 1,3,4-thiadiazolyl), benzofuryl, benzothiophenyl, indolyl, isoindolyl, benzoxazolyl, benzothiazolyl, benzimidazolyl, indazolyl, benzisoxazolyl, benzisothiazolyl, benzooxadiazolyl, benzothiadiazolyl, purinyl, quinolinyl, isoquinclinyl, cinnolinyl, phthalazinyl, quinazolinyl, quinoxalinyl, pteridinyl, imidazooxazolyl, imidazothiazolyl, imidazoimidazolyl),
(12) alkoxy group (e.g., methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy),
(13) alkylthio group (e.g., methylthio, ethylthio, n-propylthio, isopropylthio, n-butylthio, isobutylthio, sec-butylthio, tert-butylthio, n-pentylthio, isopentylthio, tert-pentylthio, neopentylthio, 2-pentylthio, 3-pentylthio, n-hexylthio, 2-hexylthio),
(14) alkoxy group (same as in the above-mentioned (12)) substituted by aryl group (same as in the above-mentioned (10)),
(15) alkylthio group (same as in the above-mentioned (13)) substituted by aryl group (same as in the above-mentioned (10)),
(16) alkoxy group (same as in the above-mentioned (12)) substituted by heteroaryl group (same as in the above-mentioned (11)),
(17) alkylthio group (same as in the above-mentioned (13)) substituted by heteroaryl group (same as in the above-mentioned (11)),
(18) cyclic alkyl (optionally containing a hetero atom in the ring)oxy group (e.g., cyclopropyloxy, cyclobutyloxy, cyclopentyloxy, cyclohexyloxy, tetrahydrofuranyloxy, tetrahydropyranyloxy, aziridinyloxy, azetidinyloxy, pyrrolidinyloxy, piperidinyloxy, morpholinyloxy),
(19) aryloxy group (e.g., group wherein aryl group (same as in the above-mentioned (10)) is bonded to oxygen atom),
(20) heteroaryloxy group (e.g., group wherein heteroaryl group (same as in the above-mentioned (11)) is bonded to oxygen atom),
(21) halogenoalkoxy group (e.g., group wherein halogenoalkyl group (same as in the above-mentioned (8)) is bonded to oxygen atom),
(22) halogenoalkylthio group (e.g., group wherein halogenoalkyl group (same as in the above-mentioned (8)) is bonded to sulfur atom),
(23) alkoxy group (same as in the above-mentioned (12)) substituted by hydroxy group,
(24) alkoxy group (same as in the above-mentioned (12)) substituted by alkoxy group (same as in the above-mentioned (12)),
(25) amino group,
(26) amino group mono- or di-substituted by alkyl group, Here, the "alkyl group" is a $C_{1-6}$ alkyl group, specifically, for example, methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like can be mentioned. As the amino group mono- or di-substituted by an alkyl group, specifically, an amino group monosubstituted by a $C_{1-6}$ alkyl such as methylamino, ethylamino, n-propylamino, isopropylamino, n-butylamino, isobutylamino, tert-butylamino, n-pentylamino, isopentylamino, hexylamino and the like; and an amino group di-substituted by a $C_{1-6}$ alkyl group such as dimethylamino, diethylamino, di-n-propylamino, methylethylamino, methylpropylamino, ethylpropylamino and the like can be mentioned.

(27) carbamoyl group,

(28) carbamoyl group mono- or di-substituted by alkyl group (same as the "alkyl group" in the above-mentioned (26)) (e.g., methylcarbamoyl, ethylcarbamoyl, dimethylcarbamoyl, diethylcarbamoyl, ethylmethylcarbamoyl)

(29) sulfamoyl group,

(30) sulfamoyl group mono- or di-substituted by alkyl group (same as the "alkyl group" in the above-mentioned (26)) (e.g., methylsulfamoyl, ethylsulfamoyl, dimethylsulfamoyl, diethylsulfamoyl, ethylmethylsulfamoyl),

(31) alkanoyl group (e.g., carbonyl group wherein hydrogen atom or alkyl group (same as the "alkyl group" in the above-mentioned (26)) is bonded to carbon atom),

(32) aroyl group (e.g., carbonyl group wherein aryl group (same as in the above-mentioned (10)) is bonded to carbon atom),

(33) alkylsulfonylamino group (e.g., sulfonylamino group substituted by alkyl group (same as the "alkyl group" in the above-mentioned (26)))

(34) arylsulfonylamino group (e.g., sulfonylamino group substituted by aryl group (same as in the above-mentioned (10))),

(35) heteroaryl sulfonylamino group (e.g., sulfonylamino group substituted by heteroaryl group (same as in the above-mentioned (11))),

(36) acylamino group (e.g., an amino group substituted by acyl group), wherein the "acyl group" is an acyl group having a $C_{1-6}$ alkyl group, a cyclic $C_{3-6}$ alkyl group, or $C_{6-10}$ aryl group; as the $C_{1-6}$ alkyl group, a cyclic $C_{3-6}$ alkyl group and $C_{6-10}$ aryl group, those recited above can be mentioned; as the acyl group, specifically, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group, naphthoyl group and the like can be mentioned,

(37) alkoxycarbonylamino group (e.g., carbonylamino group substituted by alkoxy group (same as in the above-mentioned (12))),

(38) alkylsulfonyl group (e.g., sulfonyl group substituted by alkyl group (same as the "alkyl group" in the above-mentioned (26))),

(39) alkylsulfinyl group (e.g., sulfinyl group substituted by alkyl group (same as the "alkyl group" in the above-mentioned (26))),

(40) alkoxycarbonyl group (e.g., methoxycarbonyl group, ethoxycarbonyl group), and the like can be mentioned.

When two or more substituents are present, they may be the same or different.

The "cyclic $C_{3-6}$ alkyl group (optionally containing a hetero atom in the ring)" means the above-mentioned cyclic $C_{3-6}$ alkyl group, or a cyclic alkyl group having 3-5 carbon atoms and containing at least one hetero atom and, specifically, those exemplified as the above-mentioned "cyclic $C_{3-6}$ alkyl group", as well as groups such as tetrahydrofuranyl, tetrahydropyranyl, aziridinyl, azetidinyl, pyrrolidinyl, piperidinyl, piperazinyl, morpholinyl and the like can be mentioned.

The "cycloalkane" means carbocycle having 3-10, preferably 3-8, more preferably 3-6 carbon atoms and, for example, cyclopropane, cyclobutane, cyclopentane, cyclohexane, cycloheptane, cyclooctane, cyclononane and cyclodecane and the like can be mentioned.

The "$C_{1-6}$ alkoxycarbonyl group" means a straight chain or branched alkoxycarbonyl group having 1-6 carbon atoms and, specifically, groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like can be mentioned. The "$C_{1-6}$ alkoxycarbonyl group" may have a substituent and, as such substituent, those exemplified as the above-mentioned [substituent group A] can be mentioned.

The "halogeno$C_{1-6}$ alkyl group" and "halogeno$C_{1-6}$ alkoxy group" mean $C_{1-6}$ alkyl group and $C_{1-6}$ alkoxy group, respectively, each substituted by one or more halogeno groups. As the halogeno$C_{1-6}$ alkyl group, specifically, groups such as monofluoromethyl, difluoromethyl, trifluoromethyl, monofluoroethyl, difluoroethyl, trifluoroethyl, chloromethyl, chloroethyl, dichloroethyl, and each isomer thereof and the like can be mentioned. The "halogeno$C_{1-6}$ alkoxy group" means, specifically, a $C_{1-6}$ alkoxy group substituted by one or more halogeno groups and, specifically, groups such as monofluoromethoxy, difluoromethoxy, trifluoromethoxy, monofluoroethoxy, difluoroethoxy, trifluoroethoxy, chloromethoxy, chloroethoxy, dichloroethoxy, and each isomer thereof and the like can be mentioned.

As the "$C_{1-6}$ alkylthio group", specifically, groups such as methylthio, ethylthio, n-propylthio, isopropylthio, n-butylthio, isobutylthio, sec-butylthio, tert-butylthio, n-pentylthio, isopentylthio, tert-pentylthio, neopentylthio, 2-pentylthio, 3-pentylthio, n-hexylthio, 2-hexylthio and the like can be mentioned.

As the "amino group mono- or di-substituted by $C_{1-6}$ alkyl group", specifically, an amino group monosubstituted by $C_{1-6}$ alkyl such as methylamino, ethylamino, n-propylamino, isopropylamino, n-butylamino, isobutylamino, tert-butylamino, n-pentylamino, isopentylamino, hexylamino and the like; and an amino group disubstituted by $C_{1-6}$ alkyl group such as dimethylamino, diethylamino, di-n-propylamino, methylethylamino, so methylpropylamino, ethylpropylamino and the like can be mentioned. The "amino group mono- or di-substituted by $C_{1-6}$ alkyl group" may have a substituent and, as such substituent, those exemplified as the above-mentioned [substituent group A] can be mentioned.

As the "carbamoyl group mono- or di-substituted by $C_{1-6}$alkyl group", specifically, groups such as methylcarbamoyl, ethylcarbamoyl, dimethylcarbamoyl, diethylcarbamoyl, ethylmethylcarbamoyl and the like can be mentioned. The "carbamoyl group mono- or di-substituted by $C_{1-6}$ alkyl group" may have a substituent and, as such substituent, those exemplified as the above-mentioned [substituent group A] can be mentioned.

As the "amino group substituted by acyl group", an amino group substituted by acyl group such as acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group, naphthoyl group and the like can be mentioned. The "amino group substituted by acyl group" may have a substituent and, as such substituent, those exemplified as the above-mentioned [substituent group A] can be mentioned.

The "saturated or unsaturated cyclic group (optionally containing a hetero atom)" means a group derived from saturated or unsaturated carbocycle (preferably having 5-15 carbon atoms) or heterocycle (preferably 5-membered to 15-membered).

As the saturated or unsaturated carbocycle, $C_{5-15}$ unsaturated monocyclic, bicyclic or tricyclic carbocycle, monocyclic, bicyclic or tricyclic carbocycle which is partly or entirely saturated, spiro-bonded bicyclic carbocycle and crosslinked bicyclic carbocycle can be mentioned. For example, cyclopentane, cyclohexane, cycloheptane, cyclopentene, cyclohexene, cycloheptene, cyclopentadiene, cyclohexadiene, cycloheptadiene, benzene, pentalene, perhydropentalene, azulene, perhydroazulene, inden, perhydroinden, indane, naphthalene, dihydronaphthalene, tetrahydronaphthalene, perhydronaphthalene, biphenylene, as-indacene, s-indacene, fluorene, phenanthrene, anthracene, spiro[4.4]nonane, spiro[4.5]decane, spiro[5.5]undecane, bicyclo[2.21]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane ring can be mentioned.

As the saturated or unsaturated heterocycle, 5-15-membered unsaturated monocyclic, bicyclic or tricyclic heterocycle containing, besides at least one carbon atom, 1-4 nitrogen atoms, 1-2 oxygen atoms and/or 1-2 sulfur atoms, or monocycle, bicyclic or tricyclic heterocycle which is partly or entirely saturated. For example, pyrrole, imidazole, triazole, tetrazole, pyrazole, pyridine, pyrazine, triazine, pyrimidine, pyridazine, azepine, diazepine, furan, pyran, oxepin, thiophene, thiopyran, thiepine, oxazole, isoxazole, thiazole, isothiazole, furazan, oxadiazole, oxazin, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridinee, naphthyridine, quinoxaline, quinazoline, cinnoline, benzooxazole, benzothiazole, benzoimidazole, chromene, benzooxepin, benzoxazepine, benzooxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxathiine, phenoxathiine, thianthrene, phenanthridine, phenanthrolin, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazin, tetrahydrooxazin, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzooxazole, perhydrobenzooxazole, dihydrobenzothiazole, perhydrobenzothiazole, dihydrobenzoimidazole, perhydrobenzoimidazole, dihydrobenzoazepine, tetrahydrobenzoazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithioran, dithiane, dioxaindane, benzodioxane, chromane, benzodithioran, benzodithiane and the like can be mentioned.

As the substituent that the "saturated or unsaturated cyclic group (optionally containing a hetero atom)" optionally has, the groups exemplified as the above-mentioned [substituent group A], as well as alkyl group (e.g., methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl) can be mentioned (hereinafter [substituent group B])

When two or more substituents are present, they may be the same or different.

The present invention provides a compound represented by the formula (I):

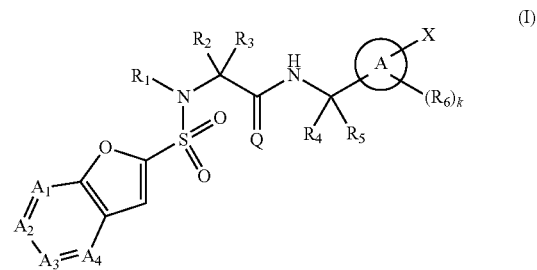

wherein each symbol is as defined above, (hereinafter to be also referred to as compound (I)), or a pharmaceutically acceptable salt thereof.

In the formula (I),
Q is =O or =S (preferably, Q is =O); $R_1$ is hydrogen or a $C_{1-6}$alkyl group optionally having substituent(s) (e.g., $C_{2-10}$ alkenyl group, $C_{2-10}$ alkynyl group, cyclic alkyl group (optionally containing a hetero atom in the ring), aryl group, heteroaryl group, alkoxy group) (preferably hydrogen or a C$_{1-6}$alkyl group); R$_2$ is hydrogen, a C$_{1-6}$ alkyl group (e.g., methyl, ethyl) optionally having substituent(s) (e.g., C$_{1-6}$ alkoxy group, halogen atom) or a C$_{2-6}$ alkenyl group optionally having substituent(s). R$_1$ and R$_2$ are optionally joined to form a nitrogen-containing ring optionally having substituent(s). Preferably, R$_1$ and R$_2$ are joined to form a nitrogen-containing ring optionally having substituent(s). As the nitrogen-containing ring optionally having substituent(s), which is jointly formed by R$_1$ and R$_2$, the following rings are recited as examples.

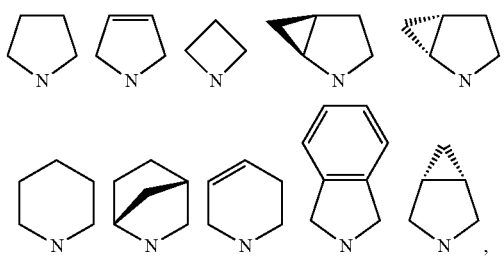

preferably

As the substituent that the nitrogen-containing ring jointly formed by R$_1$ and R$_2$ optionally has, those exemplified as the above-mentioned [substituent group A] can be mentioned. Preferably, a substituent is absent or an amino group mono- or di-substituted by an alkyl group (e.g., dimethylamino), a hydroxy group and a halogeno group (e.g., fluoro) are preferable. Further preferably, the nitrogen-containing ring does not have a substituent.

A derivative wherein R$_1$ is hydrogen and R$_2$ is a C$_{1-6}$ alkyl group is similarly preferable.

In the formula (I), partial structure (a):

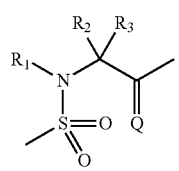

is preferably any of the following groups,

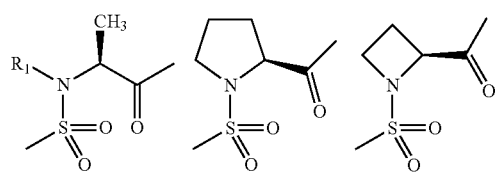

further preferably any of the following groups,

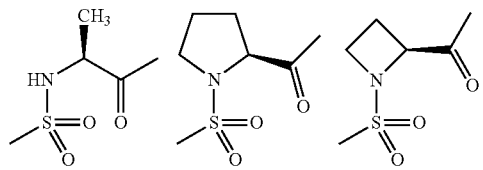

particularly preferably, any of the following groups.

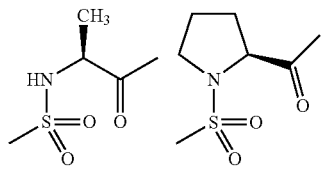

One embodiment of the compound of the present invention wherein, in the formula (I), R$_1$ and R$_2$ are joined to form a nitrogen-containing ring is represented by the following formula (II):

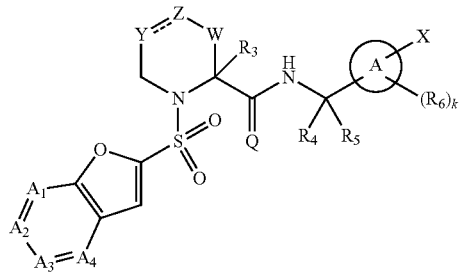

wherein
------
is a single bond or double bond;
Y is —CR$_{y1}$R$_{y2}$— or —CR$_{y3}$=;
Z is a bond, —O—, —CR$_{z1}$R$_{z2}$— or —CR$_{z3}$=;
W is a bond or —CR$_{w1}$R$_{w2}$—;
R$_{y1}$, R$_{y2}$, R$_{y3}$, R$_{z1}$, R$_{z2}$, R$_{z3}$, R$_{w1}$ and R$_{w2}$ are the same or different and each is hydrogen, a halogeno group, a hydroxy group or a C$_{1-6}$ alkyl group optionally having substituent(s); other symbols are each as defined in the formula (I).
Y is preferably —CR$_{y1}$R$_{y2}$—.
Z is preferably a bond, —CR$_{z1}$R$_{z2}$—, more preferably —CR$_{z1}$R$_{z2}$—.
W is preferably a bond.
R$_{y1}$ is preferably hydrogen, a hydroxy group, halogeno group (e.g., fluoro), more preferably hydrogen.
R$_{y2}$ is preferably hydrogen, a hydroxy group, halogeno group (e.g., fluoro), more preferably hydrogen.
R$_{y3}$ is preferably hydrogen.
R$_{z1}$ is preferably hydrogen, a hydroxy group, more preferably hydrogen.
R$_{z2}$ is preferably hydrogen, a hydroxy group, more preferably hydrogen.
R$_{z3}$ is preferably hydrogen.
R$_{w1}$ is preferably hydrogen.
R$_{w2}$ is preferably hydrogen.
In the formula (I) and the formula (II), ring A is a monocyclic aromatic ring or heteroaromatic ring, or a bicyclic aromatic ring or heteroaromatic ring.

As the monocyclic aromatic ring, an aromatic monocyclic carbocycle from the rings exemplified as the above-mentioned "saturated or unsaturated cyclic group (optionally containing a hetero atom)" can be mentioned, and specifically, benzene can be mentioned.

As the monocyclic heteroaromatic ring, an aromatic monocyclic heterocycle from the rings exemplified as the above-mentioned "saturated or unsaturated cyclic group (optionally containing a hetero atom)" can be mentioned, and a 6-membered one can be particularly mentioned. Specifically, pyridine, pyridazine, pyrimidine, pyrazine, triazine and the like can be mentioned.

As the bicyclic aromatic ring, an aromatic bicyclic carbocycle from the rings exemplified as the above-mentioned "saturated or unsaturated cyclic group (optionally containing a hetero atom)" can be mentioned and, specifically, naphthalene and the like can be mentioned.

As the bicyclicheteroaromatic ring, an aromatic bicyclic heterocycle from the rings exemplified as the "saturated or unsaturated cyclic group (optionally containing a hetero atom)" can be mentioned and, specifically, benzofuran, isobenzofuran, benzothiophene, indole, isoindole, indazoline, benzoimidazole, benzooxazole, benzoisoxazole, benzothiazole, benzoisothiazole, benzotriazole, quinoline, isoquinoline, cinnoline, quinazoline and the like can be mentioned.

Ring A is preferably a 6-membered monocyclic aromatic ring or heteroaromatic ring and a fused ring thereof, more preferably a 6-membered monocyclic aromatic ring or heteroaromatic ring. Specifically, benzene, pyridine, pyrimidine, pyridazine and benzofuran are preferable, and benzene, pyridine and pyrimidine are particularly preferable.

In the formula (I) and the formula (II),
$A_1$ is —C(Ra)═ or —N═, preferably —C(Ra)═;
$A_2$ is —C(Rb)═ or —N═, preferably —C(Rb)═;
$A_3$ is —C(Rc)═ or —N═, preferably —C(Rc)═;
$A_4$ is —C(Rd)═ or —N═, preferably —C(Rd)═.
At least two of $A_1$-$A_4$ are not —N═.

Ra, Rb, Rc and Rd are the same or different and each is hydrogen, a halogeno group (e.g., fluoro), a cyano group, a hydroxy group, a $C_{1-6}$ alkyl group, a $C_{1-6}$ alkoxy group, a halogeno$C_{1-6}$ alkyl group or a halogeno$C_{1-6}$ alkoxy group, preferably hydrogen or a halogeno group, more preferably, all are hydrogens, or any one of them is halogeno group.

In the formula (I) and the formula (II), partial structure (c):

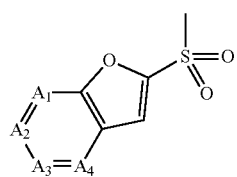

(c)

is preferably any of the groups of the following formulas:

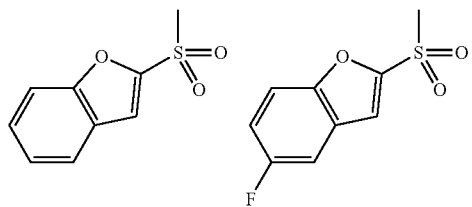

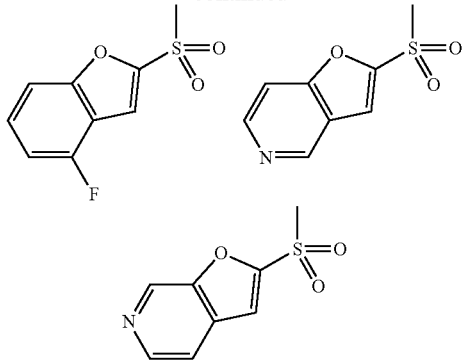

more preferably any of the groups of the following formulas:

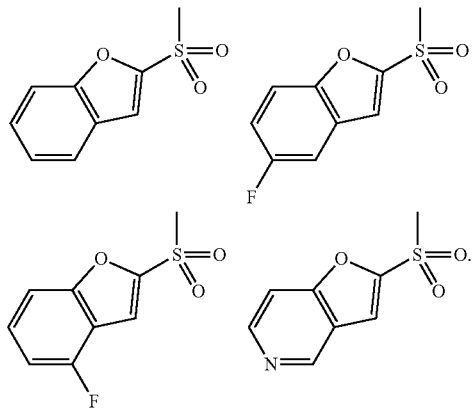

In the formula (I) and the formula (II), $R_3$ is hydrogen or a $C_{1-6}$ alkyl group, preferably hydrogen.

In the formula (I) and the formula (II), $R_4$ and $R_5$ are the same or different and each is hydrogen or a $C_{1-6}$ alkyl group, or $R_4$ and $R_5$ are optionally joined to form cycloalkane (e.g., cyclopropane). Preferably, $R_4$ and $R_5$ are the same or different and each is hydrogen or a $C_{1-6}$ alkyl group (wherein $R_4$ and $R_5$ are not joined to form cycloalkane), more preferably, $R_4$ and $R_5$ are both hydrogens.

In the formula (I) and the formula (II), X is
(a) hydrogen,
(b) -Cy,
(c) —C($R_{x1}R_{x2}$)-Cy,
(d) —C($R_{x1}R_{x2}$)—C($R_{x3}R_{x4}$)-Cy,
(e) —C($R_{x1}$)═C($R_{x2}$)-Cy,
(f) —O-Cy,
(g) —O—C($R_{x1}R_{x2}$)-Cy,
(h) —C($R_{x1}R_{x2}$)—O-Cy,
(i) —S(O)n-Cy,
(j) —S(O)n-C($R_{x1}R_{x2}$)-Cy,
(k) —C($R_{x1}R_{x2}$)—S(O)n-Cy,
(l) —N($R_{x5}$)-Cy,
(m) —N($R_{x5}$)—C($R_{x1}R_{x2}$)-Cy, —
(n) —C($R_{x1}R_{x2}$)—N($R_{x5}$)-Cy,
(o) —N($R_{x5}$)—N($R_{x6}$)-Cy,
(p) —O—N($R_{x5}$)-Cy,
(q) —N($R_{x5}$)—O-Cy,
(r) —C(O)—N($R_{x5}$)-Cy,
(s) —N($R_{x5}$)—C(O)-Cy,
(t) —S(O)m-N($R_{x5}$)-Cy,
(u) —N($R_{x5}$)—S(O)m-Cy, (v) —O—S(O)m-Cy, or
(w) —S(O)m-O-Cy,
preferably,
(a) hydrogen,
(b) -Cy,
(c) —C($R_{x1}R_{x2}$)-Cy,
(d) —C($R_{x1}R_{x2}$)—C($R_{x3}R_{x4}$)-Cy,
(e) —C($R_{x1}$)=C($R_{x2}$)-Cy,
(f) —O-Cy,
(g) —O—C($R_{x1}R_{x2}$)-Cy,
(h) —C($R_{x1}R_{x2}$)—O-Cy,
(i) —S(O)n-Cy,
(j) —S(O)n-C($R_{x1}R_{x2}$)-Cy,
(k) —C($R_{x1}R_{x2}$)—S(O)n-Cy,
(l) —N($R_{x5}$)-Cy,
(m) —N($R_{x5}$)—C($R_{x1}R_{x2}$)-Cy,
(n) —C($R_{x1}R_{x2}$)—N($R_{x5}$)-Cy,
(o) —N($R_{x5}$)—N($R_{x6}$)-Cy,
(p) —O—N($R_{x5}$)-Cy,
(q) —N($R_{x5}$)—O-Cy,
(r) —C(O)—N($R_{x5}$)-Cy,
(s) —N($R_{x5}$)—C(O)-Cy,
(t) —S(O)m-N($R_{x5}$)-Cy, or
(u) —N($R_{x5}$)—S(O)m-Cy,
more preferably,
(a) hydrogen,
(b) -Cy,
(f) —O-Cy,
(g) —O—C($R_{x1}R_{x2}$)-Cy,
(h) —C($R_{x1}R_{x2}$)—O-Cy,
(j) —S(O)n-C($R_{x1}R_{x2}$)-Cy, or
(m) —N($R_{x5}$)—C($R_{x1}R_{x2}$)-Cy
(each symbol is as defined in the formula (I)).

More preferably, X is hydrogen, -Cy, —O-Cy, or —O—$CH_2$—Cy, particularly preferably -Cy.

Cy is a saturated or unsaturated cyclic group optionally having substituent(s) (optionally containing a hetero atom), preferably a monocyclic or bicyclic, saturated or unsaturated cyclic group (optionally containing a hetero atom), more preferably a monocyclic saturated or unsaturated cyclic group (optionally containing a hetero atom). It is specifically cyclopentane, cyclohexane, cyclohexene, benzene, naphthalene, pyrrole, imidazole, triazole, tetrazole, pyrazole, pyridine, pyrazine, triazine, pyrimidine, pyridazine, furan, thiophene, oxazole, isoxazole, thiazole, isothiazole, oxadiazole, thiadiazole, indole, benzofuran, benzothiophene, quinoline, isoquinoline, quinazoline, benzooxazole, benzothiazole, benzoimidazole, tetrahydrofuran, dihydropyran, tetrahydropyran is preferable, further preferably, cyclopentane, cyclohexane, benzene, pyrazole, pyridine, pyrazine, pyrimidine, pyridazine, furan, thiophene, tetrahydrofuran, tetrahydropyran, particularly preferably benzene, pyridine, pyrazine, pyrimidine, pyridazine.

As for Cy, the substituent that the "saturated or unsaturated cyclic group (optionally containing a hetero atom)" optionally has is, for example, one exemplified as the above-mentioned [substituent group B]. Preferred are unsubstituted, alkyl group, alkenyl group, halogenoalkyl group, cyclic alkyl group (optionally containing a hetero atom in the ring), halogeno group, hydroxy group, alkoxy group, halogenoalkoxy group, alkyl group substituted by halogenoalkoxy group, amino group, amino group mono- or di-substituted by alkyl group, cyano group, alkylthio group, carboxyl group, alkoxycarbonyl group, carbamoyl group, carbamoyl group mono- or di-substituted by alkyl group, acylamino group and the like. Further preferred are unsubstituted, halogeno group, halogenoalkyl group, hydroxy group, halogenoalkoxy group, cyano group.

$R_{x1}$, $R_{x2}$, $R_{x3}$, $R_{x4}$, $R_{x5}$ and $R_{x6}$ are the same or different and each is hydrogen, a $C_{1-6}$ alkyl group optionally having substituent(s) or a $C_{1-6}$ alkoxycarbonyl group optionally having substituent(s). Preferred is hydrogen.

Cy is preferably any of the groups of the following formulas.

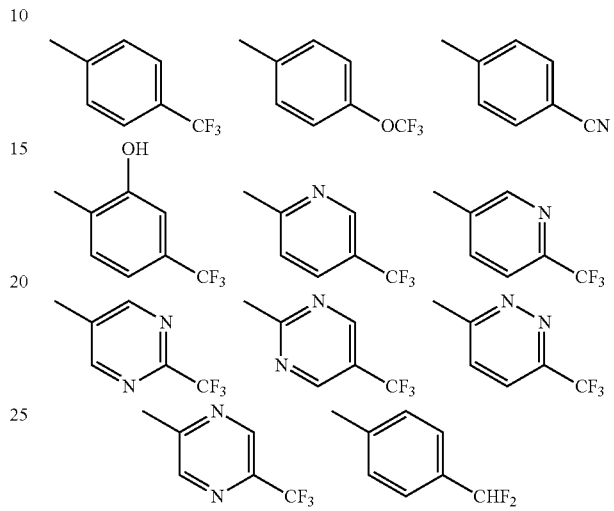

In the formula (I) and the formula (II), $R_6$ is a $C_{1-6}$ alkyl group optionally having substituent(s), a $C_{2-6}$ alkenyl group, a cyclic $C_{3-6}$ alkyl group (optionally containing a hetero atom), a halogeno group, a hydroxy group, a $C_{1-6}$ alkoxy group optionally having substituent(s), a halogeno$C_{1-6}$ alkyl group, a halogeno$C_{1-6}$ alkoxy group, an amino group, an amino group mono- or di-substituted by a $C_{1-6}$ alkyl group optionally having substituent(s), a cyano group, a $C_{1-6}$ alkylthio group, a carboxyl group, a $C_{1-6}$ alkoxycarbonyl group optionally having substituent(s), a carbamoyl group, a carbamoyl group mono- or di-substituted by a $C_{1-6}$ alkyl group optionally having substituent(s) or an amino group substituted by an acyl group optionally having substituent(s). When $R_6$ is present in plurality, they may be the same or different. As the substituent that the "$C_{1-6}$ alkyl group", "$C_{2-6}$ alkenyl group", "$C_{1-6}$ alkoxy group" optionally have, those exemplified as the above-mentioned [substituent group A] can be mentioned. Preferred are an alkyl group, an alkenyl group, an aryl group, a cyclic alkyl group (optionally containing a hetero atom in the ring), a halogeno group, a hydroxy group, alkoxy group, an amino group, an amino group mono- or di-substituted by alkyl group, a cyano group, an alkylthio group, a carboxyl group, an alkoxycarbonyl group, a carbamoyl group, a carbamoyl group mono- or di-substituted by alkyl group, an acylamino group and the like.

$R_6$ is preferably a $C_{1-6}$ alkyl group, a cyclic $C_{3-6}$ alkyl group (optionally containing a hetero atom), a halogeno group, a hydroxy group, a $C_{1-6}$ alkoxy group optionally having substituent(s), a halogeno$C_{1-6}$ alkoxy group, an amino group, a $C_{1-6}$ alkoxycarbonyl group or an amino group mono- or di-substituted by a $C_{1-6}$ alkyl group, more preferably a cyclic $C_{3-6}$ alkyl group (optionally containing a hetero atom), a halogeno group, a hydroxy group, a $C_{1-6}$ alkoxy group optionally having substituent(s), a halogeno$C_{1-6}$ alkoxy group, or an amino group mono- or di-substituted by a $C_{1-6}$ alkyl group.

k is an integer of 0-3, preferably an integer of 0-2, more preferably 0 or 1.

In the formula (I) and the formula (II), partial structure (b) containing ring A:

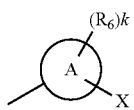

is preferably any of the groups of the following formulas:

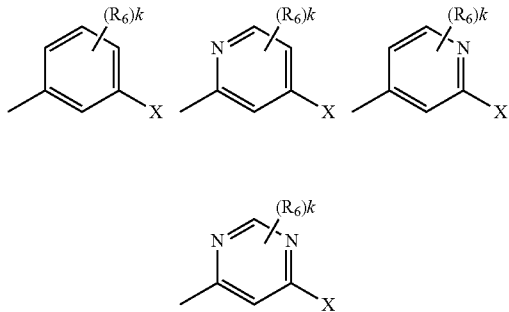

wherein each symbol is as defined in the formula (I).

A compound represented by the formula (I) and one embodiment thereof (a compound represented by the formula (II)) are also generically referred to as the compound of the present invention.

In the present invention, preferable compound of the present invention is, for example, the following compounds.

(I) A compound of the formula (I), wherein partial structure (b) containing ring A

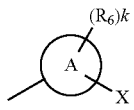

is any of the groups of the following formulas

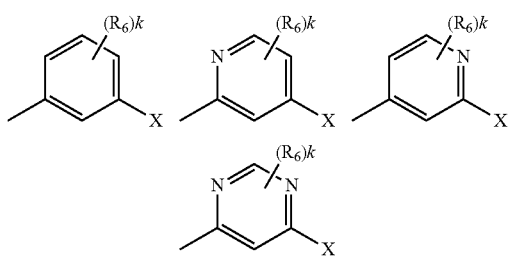

[compound I-1], a compound of the formula (I), wherein partial structure (c)

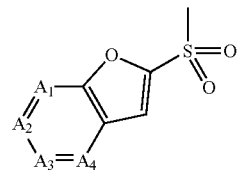

is any of the groups of the following formulas

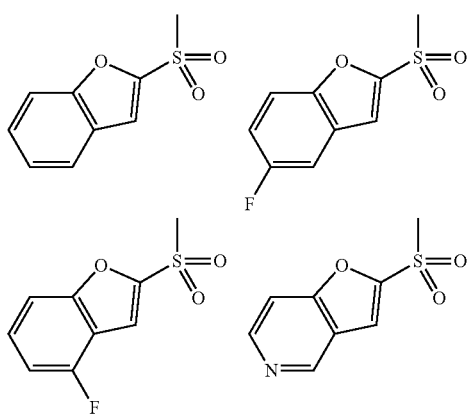

[compound I-2], a compound of the formula (I), wherein X is hydrogen, -Cy, —O-Cy or —O—CH$_2$—Cy [compound I-3], a compound of the formula (I), wherein X is -Cy; Cy is any of the groups of the following formulas

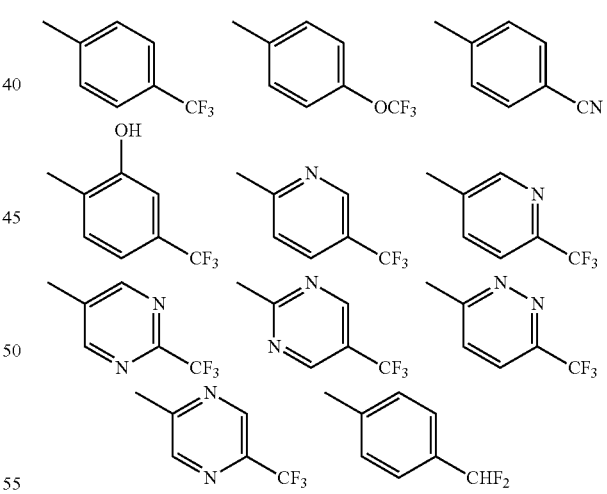

[compound I-4], a compound of the formula (I), wherein R$_4$ and R$_5$ are each hydrogen; partial structure (b) containing ring A

is any of the groups of the following formulas;

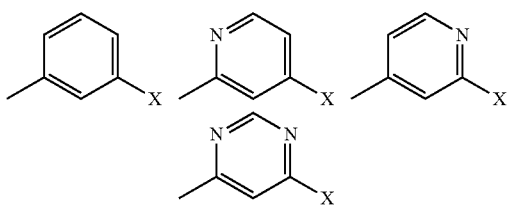

X is -Cy; Cy is any of the groups of the following formulas;

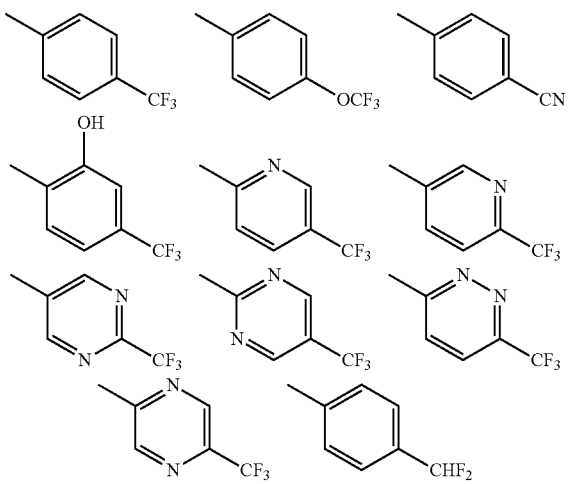

partial structure (c)

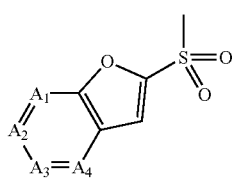

is any of the groups of the following formulas

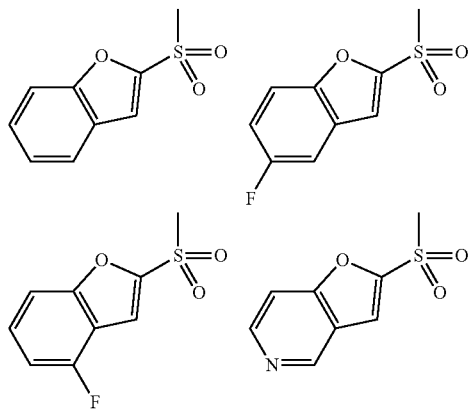

[compound 1-5].
(A) A compound of the formula (I), wherein
Q is =O;
$R_1$ is hydrogen or a $C_{1-6}$ alkyl group;
$R_4$ is hydrogen or a $C_{1-6}$ alkyl group;
$R_5$ is hydrogen or a $C_{1-6}$ alkyl group;
provided that $R_4$ and $R_5$ are not joined to form cycloalkane;
and
X is hydrogen,
—Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—N($R_{x5}$)—N($R_{x6}$)-Cy,
—O—N($R_{x5}$)-Cy,
—N($R_{x5}$)—O-Cy,
—C(O)—N($R_{x5}$)-Cy,
—N($R_{x5}$)—C(O)-Cy,
—S(O)m-N($R_{x5}$)-Cy, or
—N($R_{x5}$)—S(O)m-Cy
[compound A].

Preferable embodiments of compound A include
a compound, wherein $R_1$ is hydrogen, $R_2$ is a $C_{1-6}$ alkyl group, and $R_3$ is hydrogen [compound A-1],
a compound wherein partial structure (a)

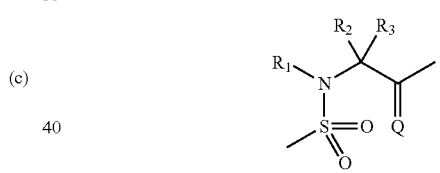

is any of the groups of the following formulas

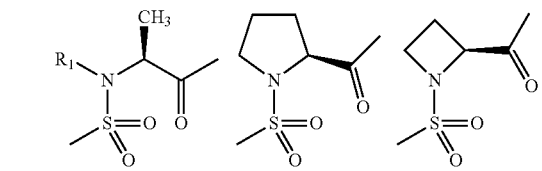

wherein $R_1$ is hydrogen or a $C_{1-6}$ alkyl group optionally having substituent (s) [compound A-2];
a compound wherein partial structure (a)

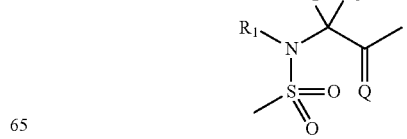

is any of the groups of the following formulas

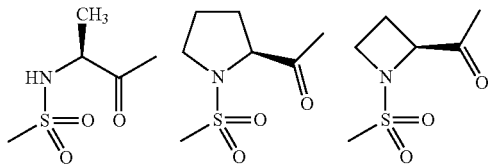

[compound A-2″];
a compound wherein partial structure (b) containing ring A

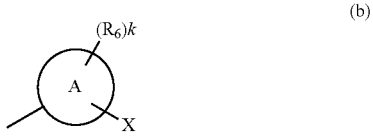
(b)

is any of the groups of the following formulas

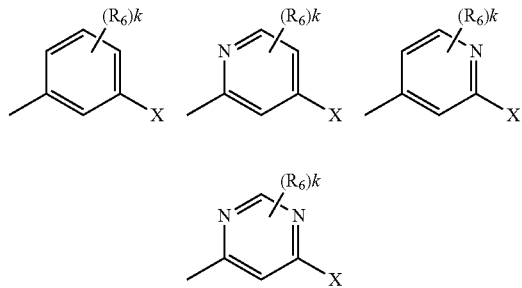

[compound A-3],
a compound wherein partial structure (c)

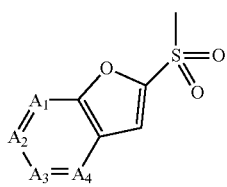
(c)

is any of the groups of the following formulas

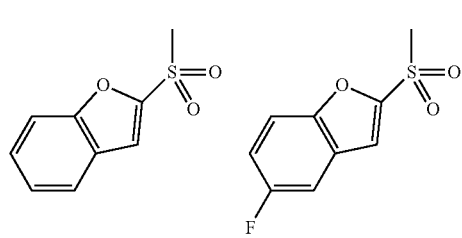

[compound A-4],
a compound wherein X is hydrogen, -Cy, —O-Cy or —O—CH₂—Cy [compound A-5],
a compound wherein X is -Cy; Cy is any of the groups of the following formulas

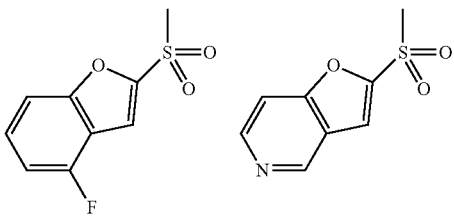

[compound A-6],
a compound wherein $R_4$ and $R_5$ are each hydrogen; partial structure (b) containing ring A

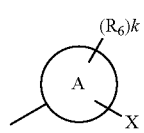
(b)

is any of the groups of the following formulas;

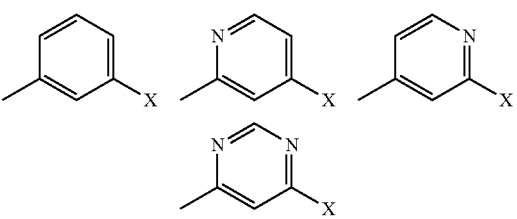

X is -Cy; Cy is any of the groups of the following formulas;

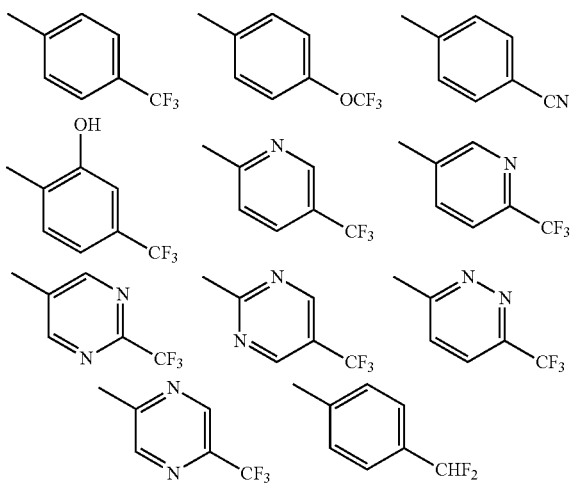

partial structure (c)

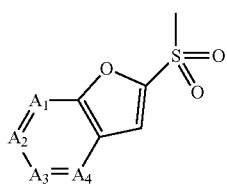

is any of the groups of the following formulas

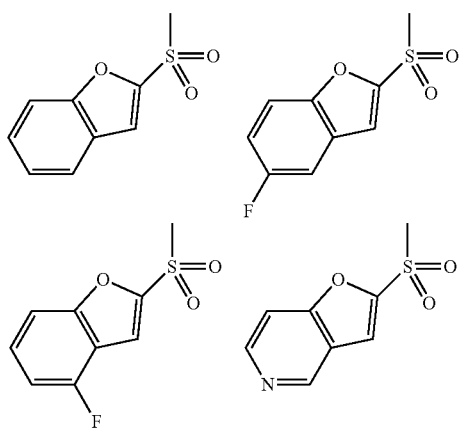

[compound A-7]

A preferable embodiment of compound A-2 is a compound wherein $R_1$ is hydrogen [compound A-2'].

A preferable embodiment of compound A-2 and compound A-2' is a compound wherein $R_4$ and $R_5$ are each hydrogen [compound A-2-1, compound A-2'-1, respectively], a compound wherein ring A is a 6-membered monocyclic aromatic ring or heteroaromatic ring [compound A-2-2, compound A-2'-2, respectively], and a compound wherein ring A is benzene, pyridine or pyrimidine [compound A-2-3, compound A-2'-3, respectively], a compound wherein partial structure (b) containing ring A

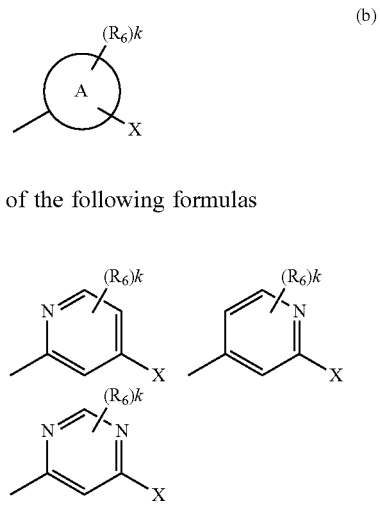

is any of the groups of the following formulas

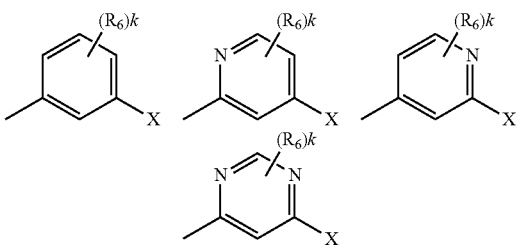

[compound A-2-4, compound A-2'-4, respectively], a compound wherein partial structure (b) containing ring A

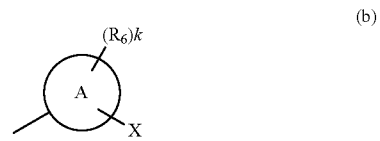

is a group of the following formula

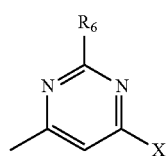

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$ alkyl group [compound A-2-4-1, compound A-2'-4-1, respectively], k is an integer of 0 to 2, RE is a $C_{1-6}$ alkyl group, a cyclic $C_{3-6}$ alkyl group (optionally containing a hetero atom), a halogeno group, a hydroxy group, a $C_{1-6}$ alkoxy group optionally having substituent (s), an amino group, a $C_{1-6}$ alkoxycarbonyl group or an amino group mono- or di-substituted by a $C_{1-6}$ alkyl group [compound A-2-5, compound A-2'-5, respectively], and k is 0 [compound A-2-6, compound A-2'-6, respectively], a compound wherein partial structure (b) containing ring A

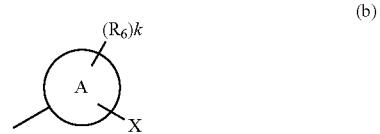

is any of the groups of the following formulas;

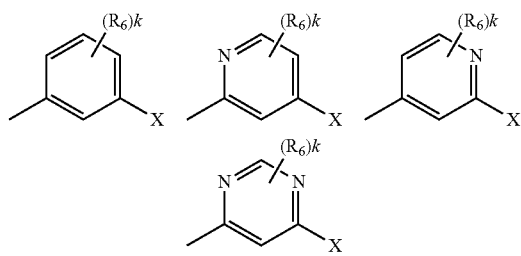

k is 0 or 1, RE is a halogeno group, a $C_{1-6}$ alkoxycarbonyl group, an amino group mono- or di-substituted by a $C_{1-6}$ alkyl group or a hydroxy group [compound A-2-7, compound A-2'-7, respectively], a compound wherein partial structure (b) containing ring A

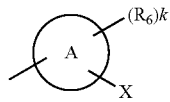 (b)

is any of the groups of the following formulas

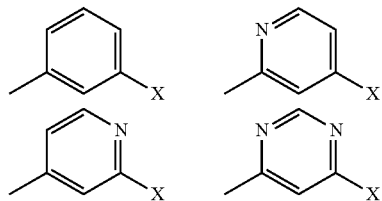

[compound A-2-8, compound A-2'-8, respectively], a compound wherein $A_1$ is —C(Ra)=, $A_2$ is —C(Rb)=, $A_3$ is —C(Rc)=, $A_4$ is —C(Rd)= [compound A-2-9, compound A-2'-9, respectively], a compound wherein $A_1$ is —C(Ra)=, $A_2$ is —C(Rb)=, $A_3$ is —C(Rc)=, $A_4$ is —C(Rd)=; Ra, Rb, Rc and Rd are all hydrogens, or any one of them is halogeno group [compound A-2-10, compound A-2'-10, respectively], a compound wherein partial structure (c)

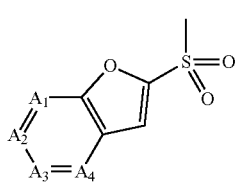 (c)

is any of the groups of the following formulas

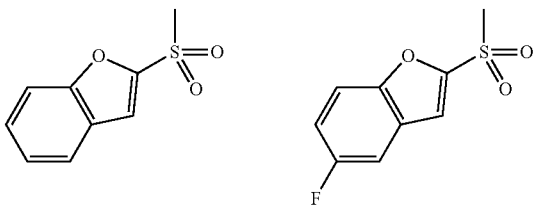

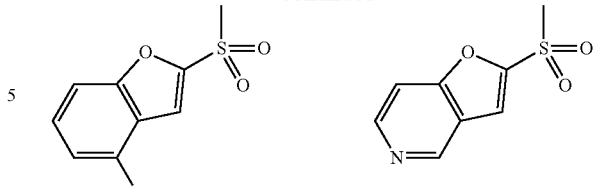

[compound A-2-11, compound A-2'-11, respectively], a compound wherein X is hydrogen, -Cy, —O-Cy or —O—CH$_2$—Cy

[compound A-2-12, compound A-2'-12, respectively], a compound wherein X is -Cy [compound A-2-13, compound A-2'-13, respectively], a compound wherein Cy is benzene optionally having substituent(s), pyridine optionally having substituent(s), pyrimidine optionally having substituent(s), pyridazine optionally having substituent(s) or pyrazine optionally having substituent(s) [compound A-2-14, compound A-2'-14, respectively], a compound wherein Cy is any of the groups of the following formulas

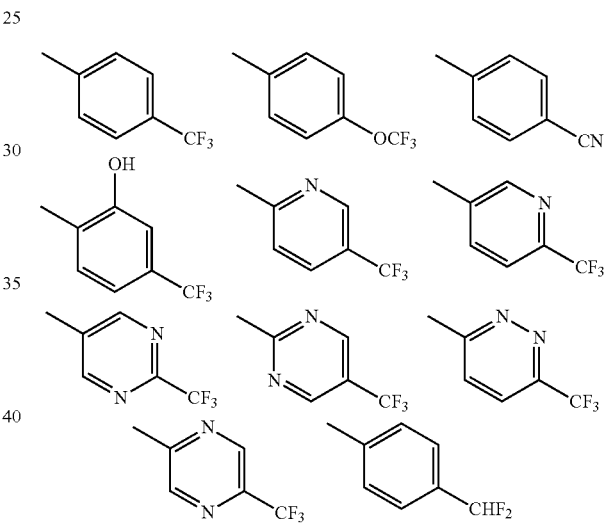

[compound A-2-15, compound A-2'-15, respectively], a compound wherein X is -Cy, Cy is benzene optionally having substituent(s), pyridine optionally having substituent(s), pyrimidine optionally having substituent(s), pyridazine optionally having substituent(s) or pyrazine optionally having substituent(s) [compound A-2-16, compound A-2'-16, respectively], a compound wherein X is -Cy, Cy is any of the groups of the following formulas

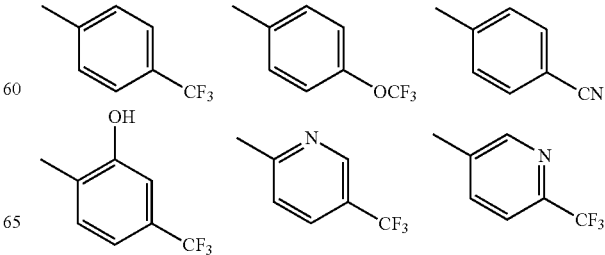

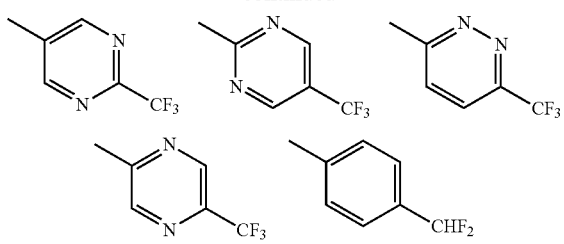

[compound A-2-17, compound A-2'-17, respectively],
a compound wherein $R_4$ and $R_5$ are each hydrogen, partial structure (b) containing ring A

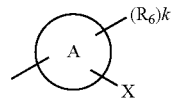

is any of the groups of the following formulas;

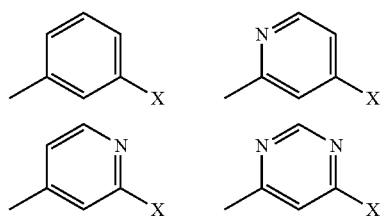

X is -Cy;
Cy is any of the groups of the following formulas

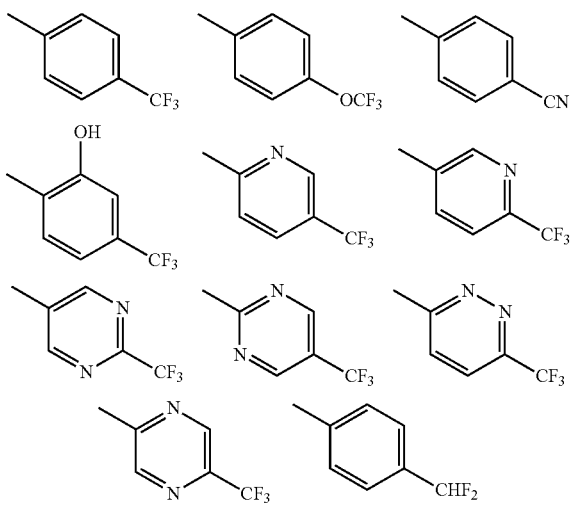

[compound A-2-18, compound A-2'-18, respectively],
a compound wherein $R_4$ and $R_5$ are each hydrogen, partial structure (b) containing ring A

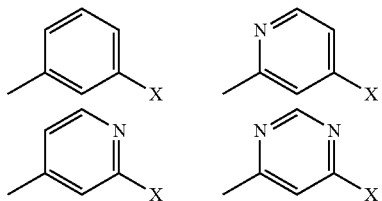

is any of the groups of the following formulas;

X is -Cy;
Cy is any of the groups of the following formulas;

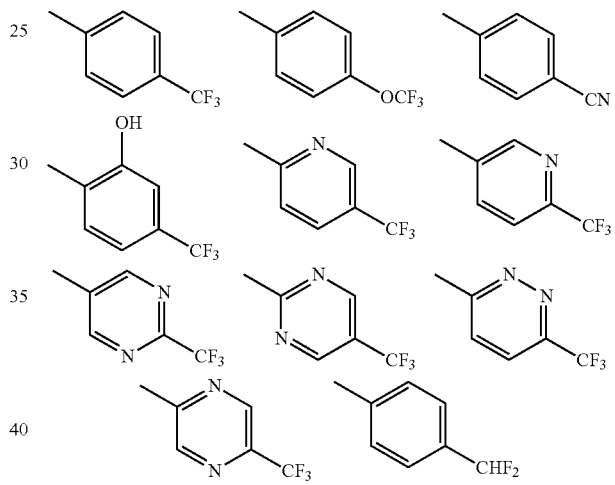

partial structure (c)

is any of the groups of the following formulas

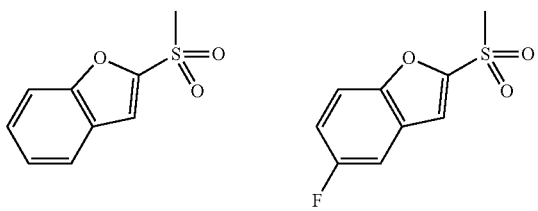

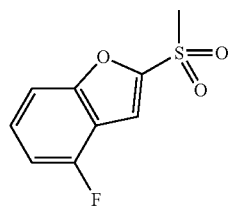 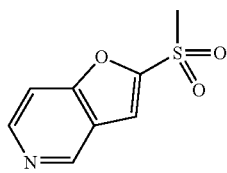

[compound A-2-19, compound A-2'-19, respectively],
a compound wherein $R_4$ and $R_5$ are each hydrogen, partial structure (b) containing ring A

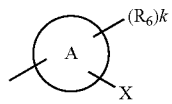

is a group of the following formula

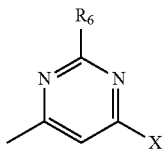

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$ alkyl group,
X is -Cy,
Cy is any of the groups of the following formulas;

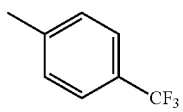 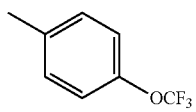 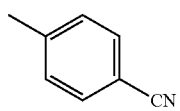
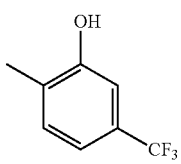 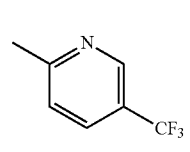 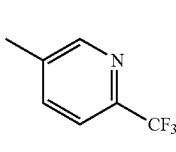
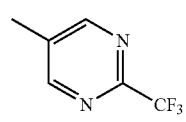 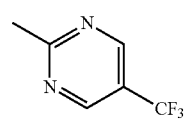 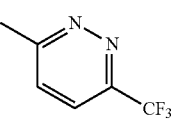
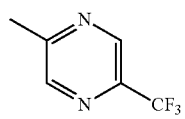 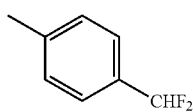

partial structure (c)

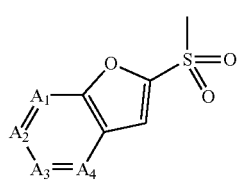

is any of the groups of the following formulas

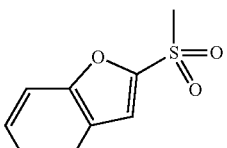 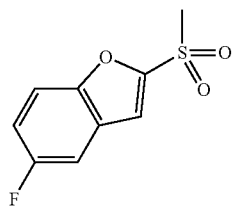
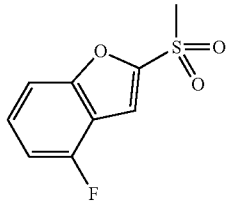 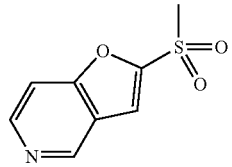

[compound A-2-19-1, compound A-2'-19-1, respectively] can be mentioned.
(B) A compound of the formula (II) wherein
Q is =O;
$R_4$ is hydrogen or a $C_{1-6}$ alkyl group;
$R_5$ is hydrogen or a $C_{1-6}$ alkyl group;
provided that $R_4$ and $R_5$ are not joined to form cycloalkane;
X is hydrogen,
-Cy,
—C($R_{x1}R_{x2}$)-Cy,
—C($R_{x1}R_{x2}$)—C($R_{x3}R_{x4}$)-Cy,
—C($R_{x1}$)=C($R_{x2}$)-Cy,
—O-Cy,
—O—C($R_{x1}R_{x2}$)-Cy,
—C($R_{x1}R_{x2}$)—O-Cy,
—S(O)n-Cy,
—S(O)n-C($R_{x1}R_{x2}$)-Cy,
—C($R_{x1}R_{x2}$)—S(O)n-Cy,
—N($R_{x5}$)-Cy,
—N($R_{x5}$)—C($R_{x1}R_{x2}$)-Cy,
—C($R_{x1}R_{x2}$)—N($R_{x5}$)-Cy,
—N($R_{x5}$)—N(Rx)-Cy,
—O—N($R_{x5}$)-Cy,
—N($R_{x5}$)—O-Cy,
—C(O)—N($R_{x5}$)-Cy,
—N($R_{x5}$)—C(O)-Cy,
—S(O)m-N($R_{x5}$)-Cy, or
—N($R_{x5}$)—S(O) m-Cy
[compound B]
As preferable embodiments of compound B,
a compound wherein Y is —$CH_2$—, Z is —$CH_2$—, W is a bond, $R_3$ is hydrogen [compound B-1], a compound wherein partial structure (b) containing ring A

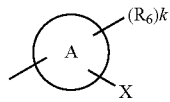
(b)

is any of the groups of the following formulas

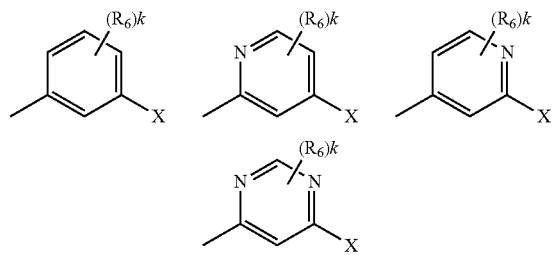

[compound B-2],
a compound wherein partial structure (b) containing ring A

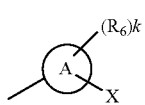
(b)

is a group of the following formula

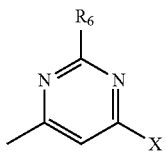

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$ alkyl group
[compound B-2-1],
a compound wherein partial structure (c)

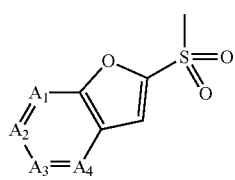
(c)

is any of the groups of the following formulas

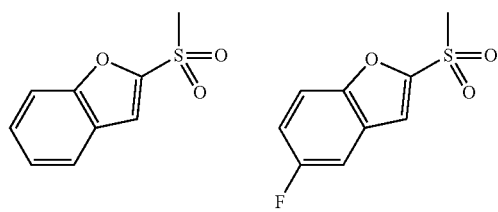

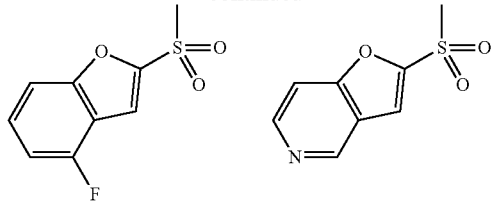

[compound B-3],
a compound wherein X is hydrogen, -Cy, —O-Cy or —O—CH$_2$—Cy [compound B-4],
a compound wherein X is -Cy, Cy is any of the groups of the following formulas

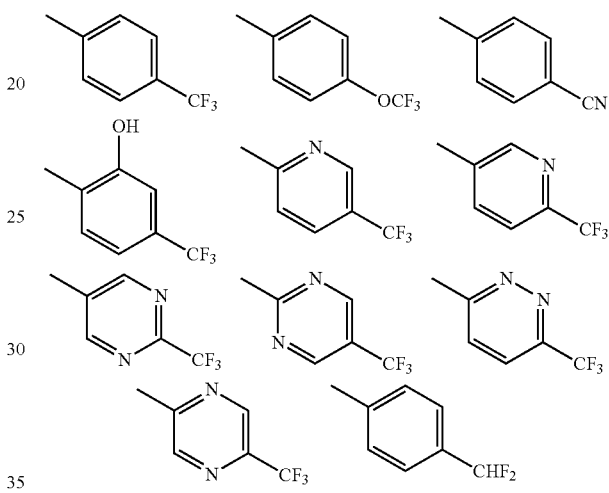

[compound B-5],
a compound wherein $R_4$ and $R_5$ is hydrogen, partial structure (b) containing ring A

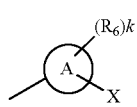
(b)

is any of the groups of the following formulas;

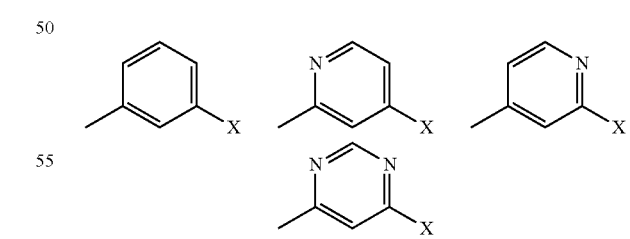

X is -Cy, Cy is any of the groups of the following formulas;

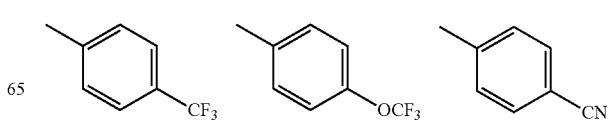

-continued

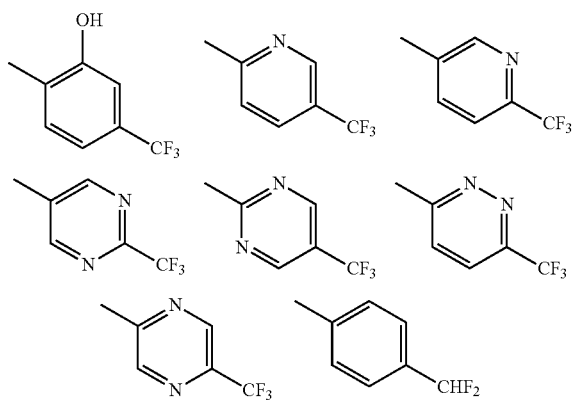

partial structure (c)

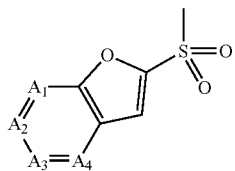

is any of the groups of the following formulas

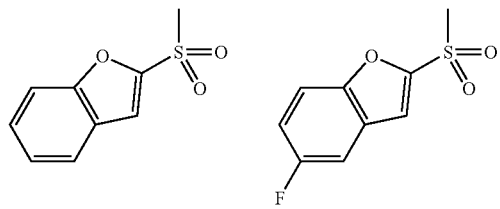

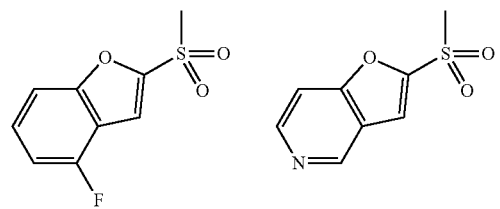

[compound B-6],
a compound wherein $R_4$ and $R_5$ is hydrogen, partial structure (b) containing ring A

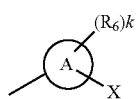

is a group of the following formula,

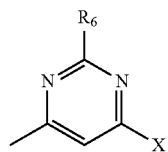

$R_6$ is a cyclic $C_{3-6}$ alkyl group (optionally containing a hetero atom), a $C_{1-6}$ alkoxy group optionally having substituent(s), an amino group or an amino group mono- or di-substituted by a $C_{1-6}$alkyl group, X is -Cy,
Cy is any of the groups of the following formulas;

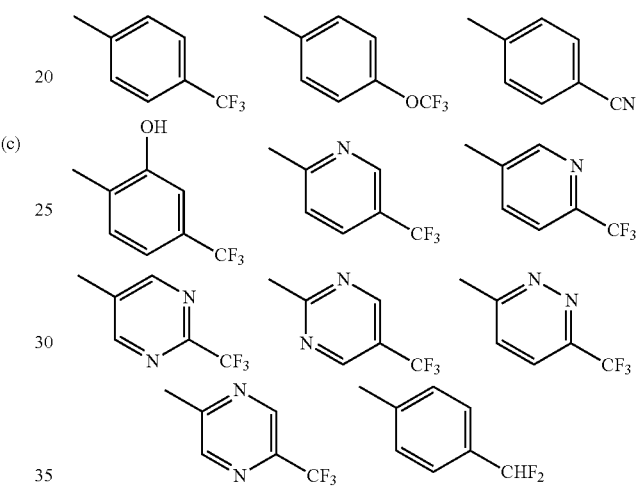

partial structure (c)

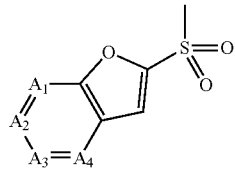

is any of the groups of the following formulas

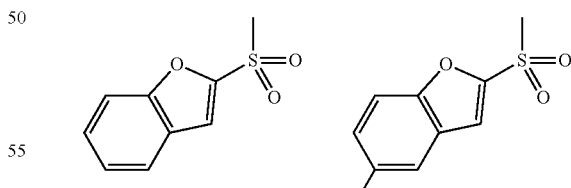

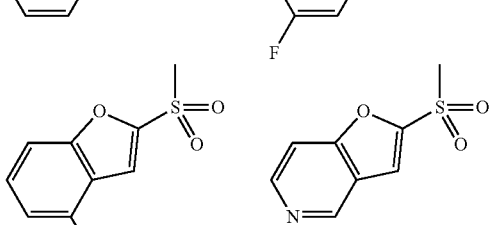

[compound B-6-1]
can be mentioned.
Preferable compounds of the present invention are the compounds described in the below-mentioned Examples, more preferably, the compounds of Examples 1, 2, 4, 5, 6, 7, 8, 9, 10, 11, 12, 13, 14, 16, 17, 18, 19, 20, 25, 26, 27, 30, 31, 34, 35, 36, 37, 38, 41, 42, 43, 44, 47, 48, 49, 51, 53, 54, 56, 57, 65, 66, 67, 69, 70, 71, 77, 79, 80, 84, 86, 87, 88, 89, 90, 92, 93, 94, 95, 97, 98, 99, 100, 101, 102, 104, 106, 107, 108, 109, 110, 115, 116, 117, 119, 123, 124, 127, 128, 129, 130, 132, 133, 135, 136, 137, 138, 139, 140, 141, 142, 145, 148, 149, 150, 151, 153, 155, 156, 157, 158, 159, 160, 161, 164, 172, 173, 174, 175, 179, 181, 190, 191, 192, 193, 194, 195, 196, 197, 198, 199, 200, 201, 202, 203, 205, 206, 207, 210, 212, 214, 215, 216, 221, 222, 223, 224, 225, 226, 229, 230, 231, 233, 235, 239, 240, 248, 252, 255, 258, 259, 262, 263, 264, 265, 267, 268, 269, 270, 271, 272, 273, 274, 275, 278, 279, 281, 285, 287, 288, 289, 290, 291, 293, 296, 297, 298, 299, 309, 310, 311, 312, 315, 318, 326, 327, 328, 329, 330, 332, 333, 336, 337, 338, 339, 341, 344, 348, 349, 357, 359, 360, 362, 364, 368, 369, 371, 372, 374, 375, 376, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 417, 418, 419, 420, 421, 422, 423, 424, 426.
Further preferred are the compounds described in Examples 80, 84, 109, 116, 117, 123, 124, 138, 153, 179, 181, 190, 191, 192, 196, 199, 203, 224, 230, 290, 312, 378, 379, 383, 384, 386, 387, 388, 389, 393, 395, 401, 405, 406, 411, 412 and having the following structural formulas, and pharmaceutically acceptable salts thereof.
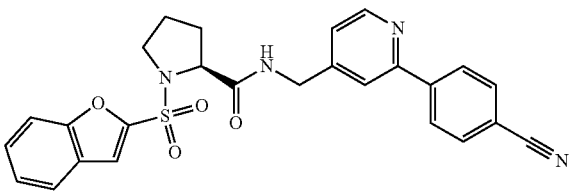
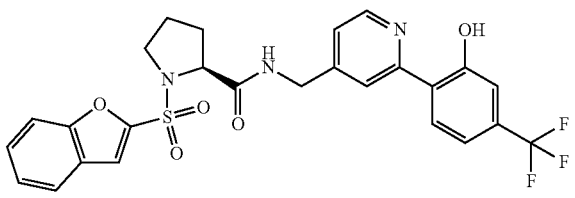
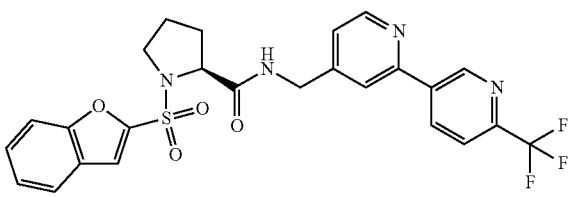
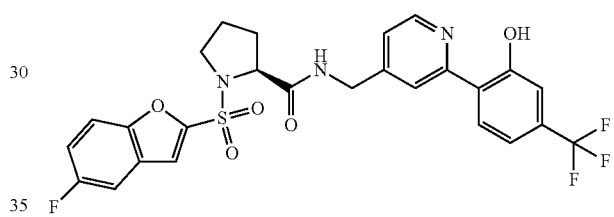
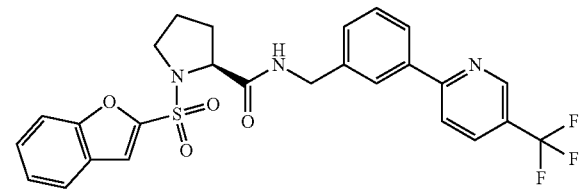
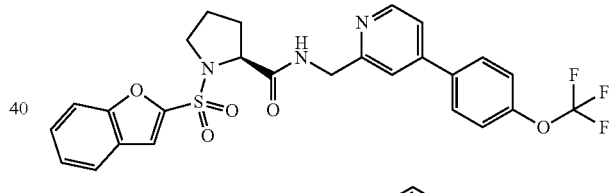
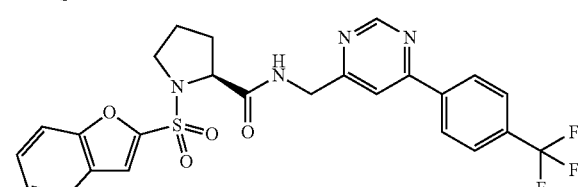
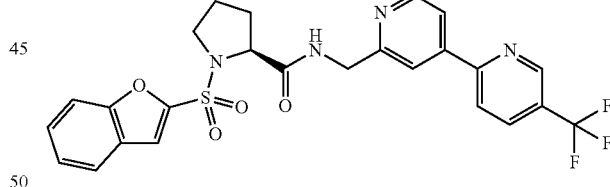
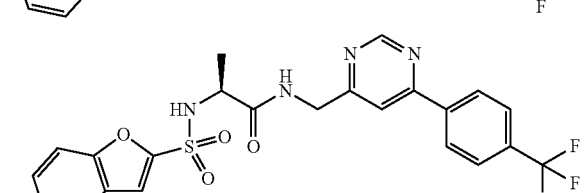
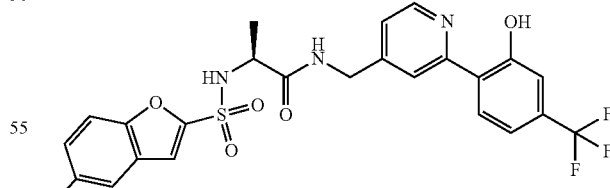
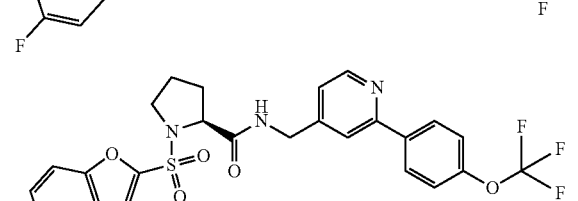
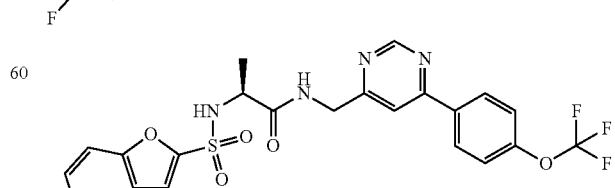

153
-continued
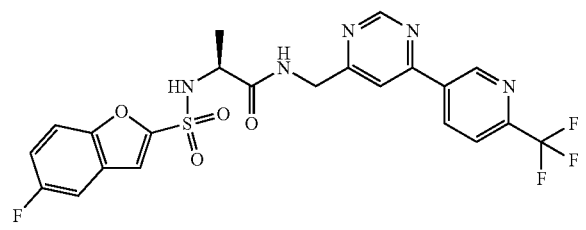
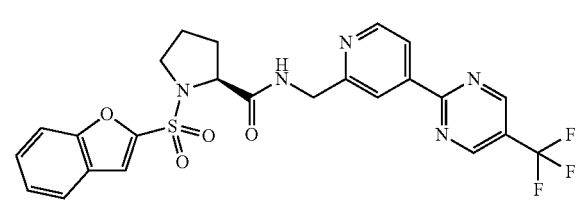
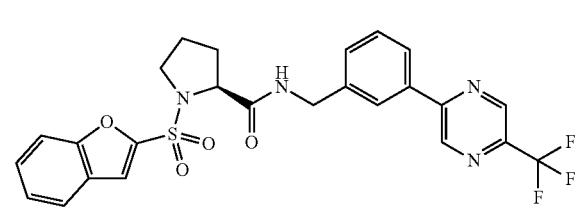

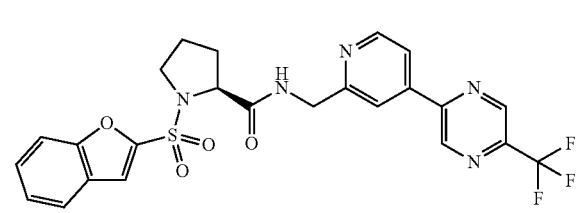
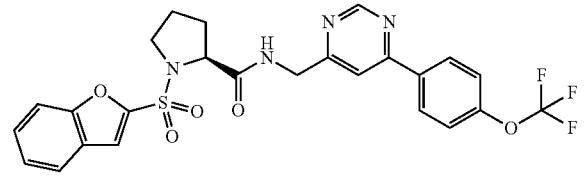
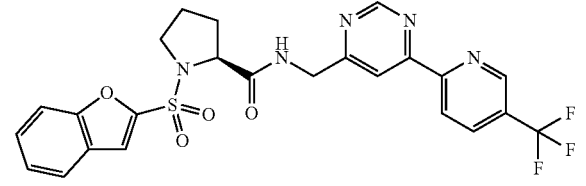
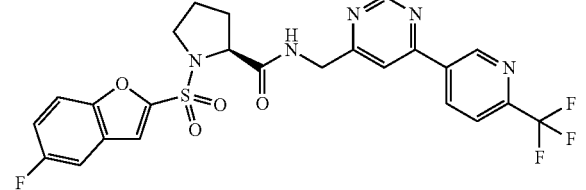
154
-continued
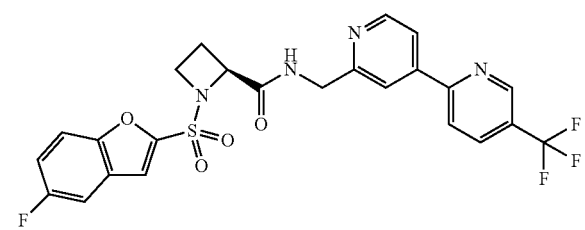
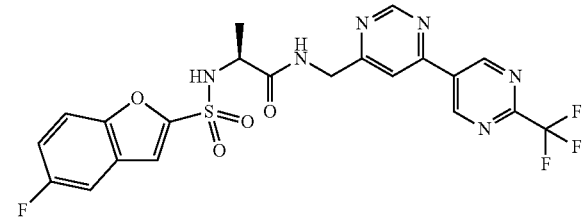
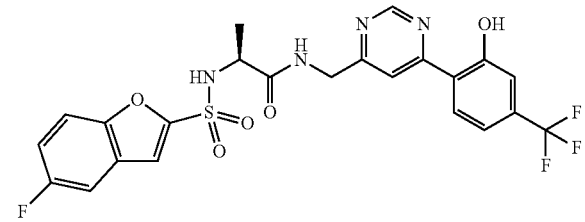
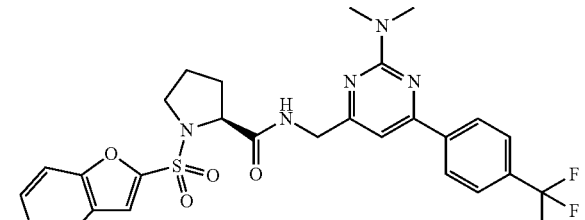
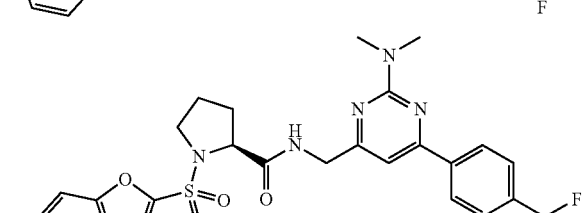
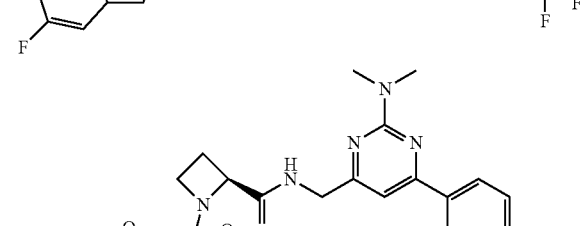
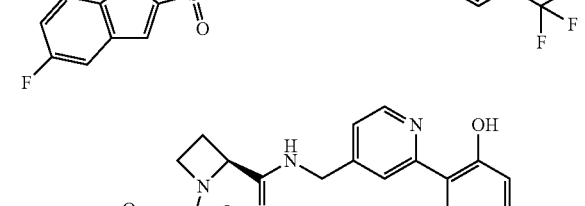

-continued

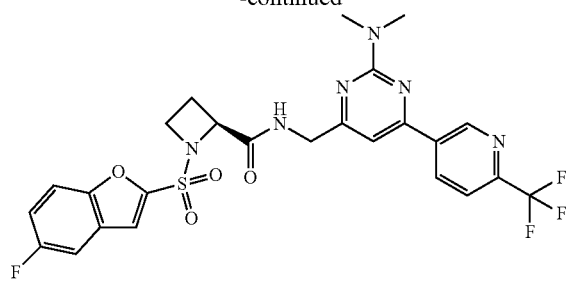
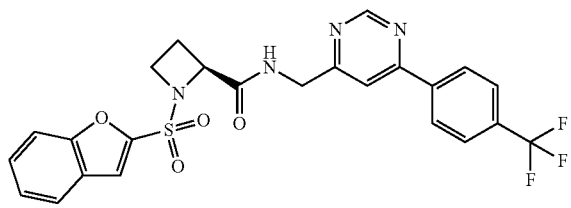
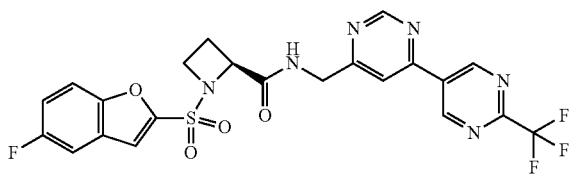
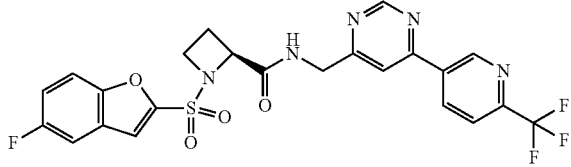
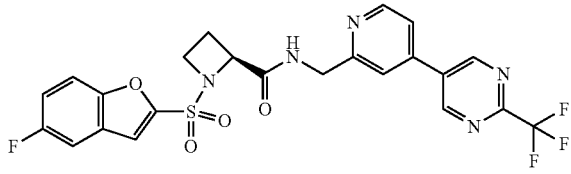
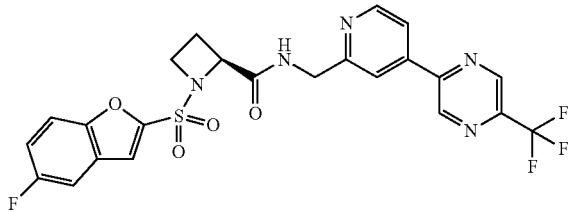

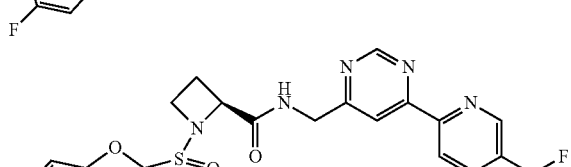

-continued

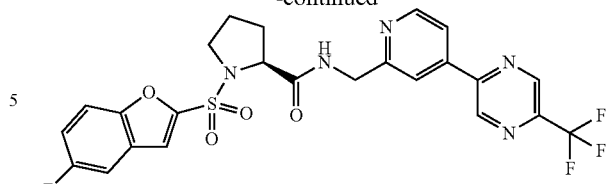
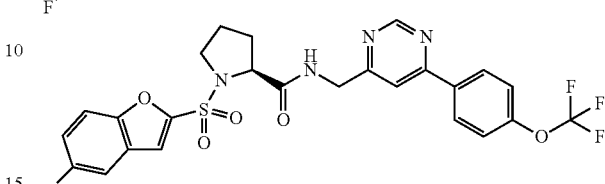
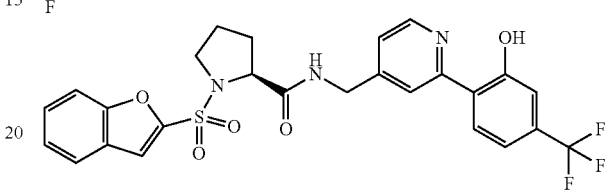
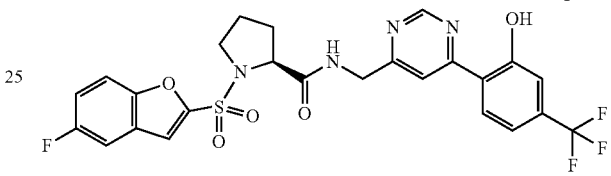

When the compound of the present invention can form a salt, the salt only needs to be pharmaceutically acceptable. For example, when an acidic group such as a carboxyl group and the like is present in the formula, ammonium salt, salts with alkali metal such as sodium, potassium and the like, salts with alkaline earth metal such as calcium, magnesium and the like, aluminum salt, zinc salt, salts with organic amine such as triethylamine, ethanolamine, morpholine, piperidine, dicyclohexylamine and the like, and salts with basic amino acid such as arginine, lysine and the like can be mentioned with regard to the acidic group. When a basic group is present in the formula, salts with inorganic acid such as hydrochloric acid, sulfuric acid, phosphoric acid, nitric acid, hydrobromic acid and the like, salts with organic carboxylic acid such as acetic acid, trifluoroacetic acid, citric acid, benzoic acid, maleic acid, fumaric acid, tartaric acid, succinic acid, tannic acid, butyric acid, hibenzoic acid, pamoic acid, enanthic acid, decanoic acid, teoclic acid, salicylic acid, lactic acid, oxalic acid, mandelic acid, malic acid and the like, and salts with organic sulfonic acid such as methanesulfonic acid, benzenesulfonic acid, p-toluenesulfonic acid and the like can be mentioned with regard to the basic group. As a method for forming a salt, the compound of the present invention and necessary acid or base are mixed at a suitable quantitative ratio in a solvent or a dispersing agent, or cation exchange or anion exchange of other salt form is employed.

The compound of the present invention also encompasses optical isomer, stereoisomer, tautomer, rotamer, and mixtures thereof at optional ratios. These can be obtained each as a single product according to a synthesis method and separation method known per se. For example, an optical isomer can be obtained by using an optically active synthetic intermediate or by optically resolving a racemate of a synthetic intermediate or final product by a conventional method.

Furthermore, it also encompasses a stable isotope and a radioactive isotope.

The compound of the present invention also includes solvates of the compound such as hydrate, alcohol adduct and the like.

The compound of the present invention can also be converted to a prodrug. The prodrug in the present invention is a compound that is converted in the body to produce the compound of the present invention. For example, when the active component contains a carboxyl group or a phosphate group, an ester, amide and the like thereof can be mentioned. When the active component contains an amino group, an amide, carbamate and the like thereof can be mentioned. When the active component contains a hydroxyl group, an ester, carbonate, carbamate and the like thereof can be mentioned. When the compound of the present invention is converted to a prodrug, it may be bonded to an amino acid or saccharides.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose or amino acid is bonded to the carboxylic acid moiety of the compound of the present invention or a hydroxyl group added by the metabolism, and the like can be mentioned.

The compound of the present invention has a superior TRPA1 antagonist activity for mammals such as human, bovine, horse, dog, mouse, rat and the like, and can be used as a medicament, which is administered as it is or as a pharmaceutical composition containing the same mixed with a pharmaceutically acceptable carrier according to a method known per se. While oral administration is generally preferable, parenteral administration (e.g., routes such as intravenous, subcutaneous, intramuscular, suppository, enema, ointment, patch, sublingual, eye drop, inhalation administrations and the like) can also be employed. While the dose used for the above-mentioned objects is determined according to the desired treatment effect, administration method, duration of treatment, age, body weight and the like, a daily dose of 1 μg-10 g for oral administration and 0.01 μg-1 g for parenteral administration is used, which is generally administered to an adult by an oral or parenteral route in one to several portions per day. In addition, the content of the compound of the present invention in the above-mentioned pharmaceutical composition is about 0.01 wt %-100 wt % of the whole composition.

Examples of the pharmaceutically acceptable carrier for the pharmaceutical composition of the present invention include various organic or inorganic carrier substances conventionally used as preparation materials. For example, excipient, lubricant, binder, disintegrant, water-soluble polymer and basic inorganic salt in solid preparation; solvent, solubilizing agents, suspending agent, isotonicity agent, buffering agent and soothing agent in liquid preparation, and the like can be mentioned. Where necessary, general additives such as preservative, antioxidant, colorant, sweetening agent, souring agent, foaming agent, flavor and the like can also be used.

The dosage form of such pharmaceutical composition may be tablet, powder, pill, granule, capsule, suppository, solution, so sugar-coated agent, depot, syrup, suspension, emulsion, troche, sublingual agent, adhesive preparation, oral disintegrant (tablet), inhalant, enema, ointment, patch, tape and eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, excipient and, where necessary, binder, disintegrant, lubricant, colorant, flavoring agent and the like are further added and the mixture is processed to give, for example, tablet, powder, pill, granule, capsule, solution, sugar-coated agent, depot, syrup and the like according to a conventional method. Examples of the excipient include lactose, cornstarch, sucrose, glucose, sorbitol, crystalline cellulose and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone and the like. Examples of the disintegrant include starch, agar, gelatin powder, crystalline cellulose, calcium carbonate, sodium hydrogen carbonate, calcium citrate, dextran, pectin and the like. Examples of the lubricant include magnesium stearate, talc, polyethylene glycol, silica, hydrogenated vegetable oil and the like. As the colorant, one allowed to add to a pharmaceutical product is used, and as the flavoring agent, cocoa powder, menthol, aromatic acid, peppermint oil, borneol, powdered cinnamon bark and the like are used. Where necessary, these tablets and granules are applied with a coating as appropriate such as sugar coating, gelatin coating, and the like.

When an injection is to be prepared, pH adjuster, buffering agent, stabilizer, preservative and the like are added where necessary and the mixture is processed to give subcutaneous, intramuscular or intravenous injection according to a conventional method.

As mentioned above, since the compound of the present invention shows a superior TRPA1 antagonist activity for mammals (e.g., mouse, rat, hamster, rabbit, cat, dog, swine, bovine, sheep, horse, monkey, human etc., preferably human), it is useful as a TRPA1 antagonist. Moreover, the compound of the present invention is useful for the prophylaxis and/or treatment of diseases involving TRPA1, and the compound of the present invention can be provided as a medicament for the prophylaxis and/or treatment of such diseases.

As the disease involving TRPA1, pain associated disease, digestive tract diseases, lung disease, bladder disease, inflammatory disease, dermatic diseases, and neurological disease and the like can be mentioned.

As the pain-associated disease, specifically, chronic pain, neuropathic pain, acute pain, inflammatory pain, postherpetic neuralgia, neuropathy, neuralgia, diabetic neuropathy, HIV related neuropathy, nerve damage, rheumatoid arthritis pain, osteoarthritis pain, back pain, low back pain, carcinomatous pain, toothache, headache, migraine, carpal-tunnel syndrome, fibromyalgia syndrome, neuritis, sciatic neuralgia, pelvic hypersensitivity, pelvic pain, menstrual pain, organ pain, pain after operation and the like can be mentioned.

As the digestive tract disease, functional gastrointestinal disorder {dysphagia, functional dyspepsia (FD), irritable bowel syndrome (IBS), functional abdominal pain syndrome}, reflux esophagitis (GERD), ulcer, inflammatory bowel disease (IBD), vomiting (cancer chemotherapy-induced vomiting), pancreatitis and the like can be mentioned.

As the lung disease, asthma, chronic coughing, chronic obstructive pulmonary diseases (COPD), bronchoconstriction and the like can be mentioned.

As the bladder disease, overactive bladder, abnormal urination, cystitis and the like can be mentioned.

As the inflammatory disease, burn, osteoarthritis and the like can be mentioned.

As the dermatic disease, allergic dermatitis including atopic dermatitis, pruritus and the like can be mentioned.

As the neurological disease, anticancer agent-induced neuropathy and the like can be mentioned.

As the disease involving TRPA1, preferably, chronic pain, neuropathic pain, acute pain, asthma, chronic obstructive pulmonary diseases, functional gastrointestinal disorder, reflux esophagitis, inflammatory bowel disease, pruritus, anticancer agent-induced neuropathy and the like can be mentioned.

The production methods of the representative compounds among the compounds of the present invention are shown below. The production methods of the compound of the present invention are not limited to these. Each symbol in the drawings is as defined above.

One embodiment of the synthesis method of compound (I) is shown below.

For example, compound (I-S) represented by

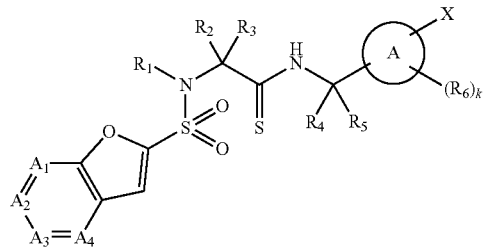

(I-S)

which is the formula (I)

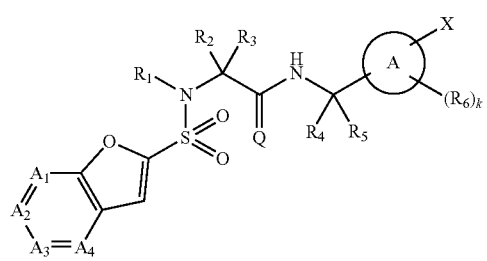

(I)

wherein Q is =S
can be synthesized from compound (I-O) represented by

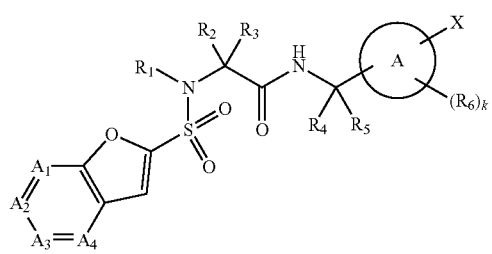

(I-O)

which is the formula (I)

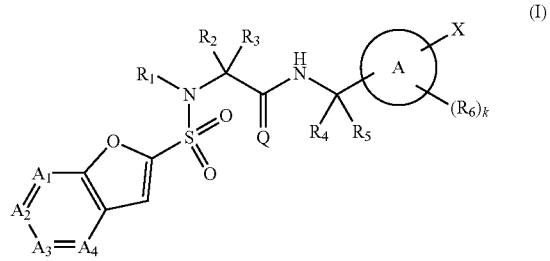

(I)

wherein Q is =O, and a representative synthesis method is shown below.

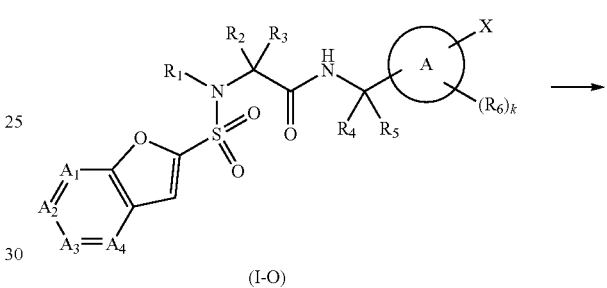

(I-O)

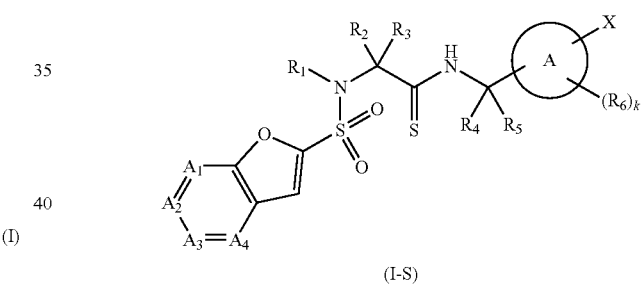

(I-S)

The object compound (I-S) can be synthesized by reaction of compound (I-O) with the Lawesson reagent and the like in a solvent that does not adversely influence the reaction such as tetrahydrofuran and the like.

A representative synthesis method is particularly shown below by taking the formula (I), wherein Q is =O, as an example. Compound (I-O) can be synthesized as follows.

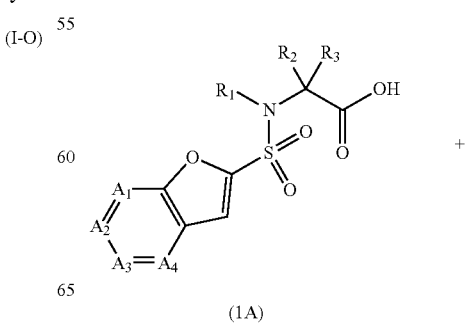

(1A)

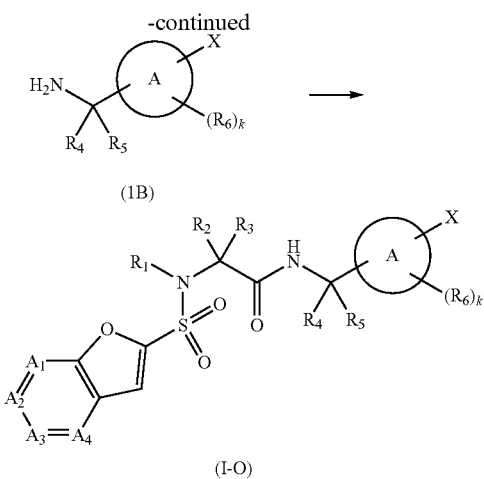

(1B)

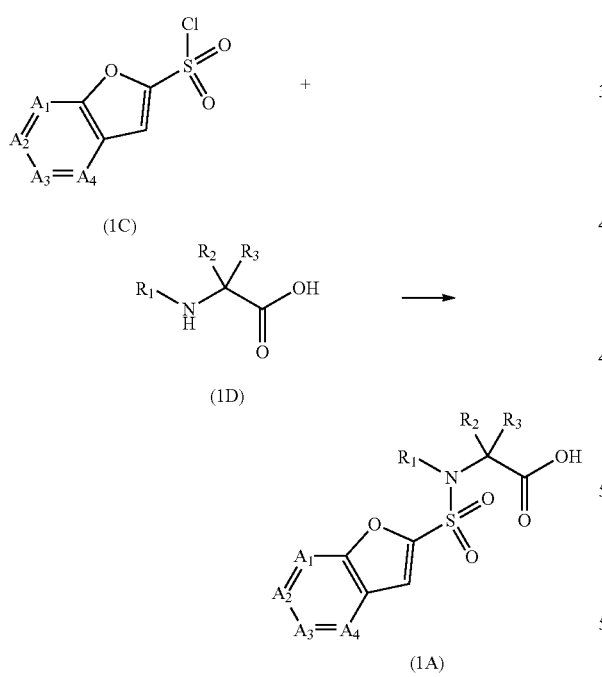

(I-O)

The object compound (I-O) can be produced by reaction of carboxylic acid derivative (1A) and amine derivative (1B) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like.

The above-mentioned carboxylic acid derivative (1A) can be synthesized as follows.

(1C)

(1D)

(1A)

Carboxylic acid derivative (1A) can be synthesized by reaction of sulfonylchloride derivative (1C) with amine derivative (1D) in a solvent that does not adversely influence the reaction such as a mixed solvent of tetrahydrofuran and water, and the like in the presence of a base such as sodium hydroxide and the like. Carboxylic acid derivative (1A) can also be synthesized by protected carboxylic acid of amine derivative (1D) with an appropriate protecting group such as methyl, ethyl, benzyl, tert-butyl and the like as necessary and removing the protecting group by an appropriate method such as an acid treatment and the like after the above-mentioned sulfonamidation.

Sulfonylchloride derivative (1C) can be synthesized as follows.

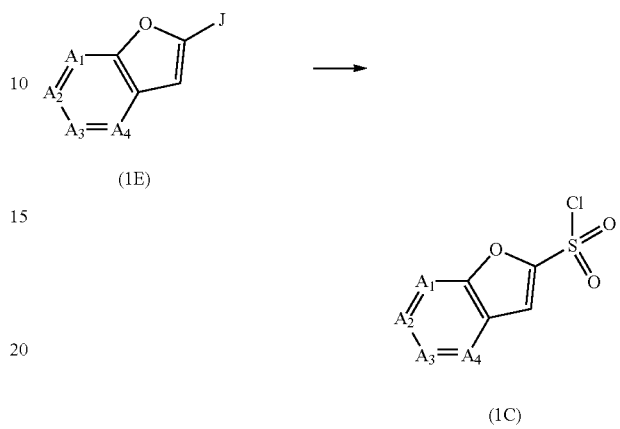

(1E)

(1C)

Sulfonylchloride derivative (1C) can be synthesized by reaction of furan derivative (1E) (wherein J is bromine atom, iodine atom, chlorine atom, hydrogen atom and the like) in a solvent that does not adversely influence the reaction such as diethyl ether, tetrahydrofuran and the like, for example, with n-butyllithium, sec-butyllithium, tert-butyllithium and the like, and then, for example, treatment with sulfur dioxide and N-chlorosuccinimide and the like.

A synthesis method of, for example, a compound represented by (1B-1)

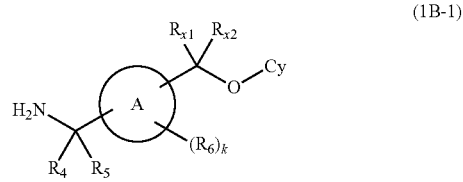

(1B-1)

which is the formula (1B)

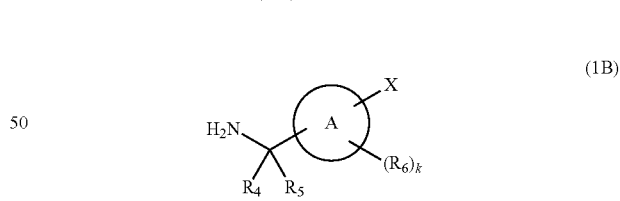

(1B)

wherein —X is a group represented by —C(R$_{x1}$R$_{x2}$)—O—Cy, is shown below.

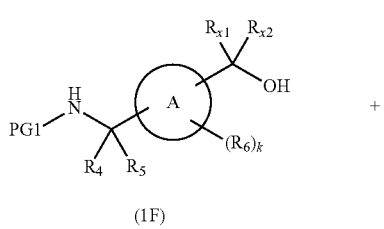

(1F)

-continued

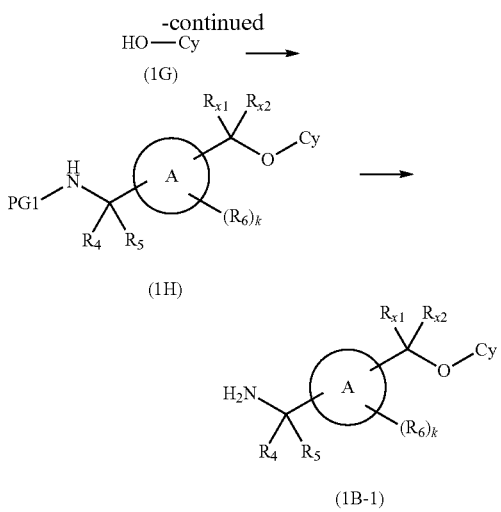

which is the formula (1B)

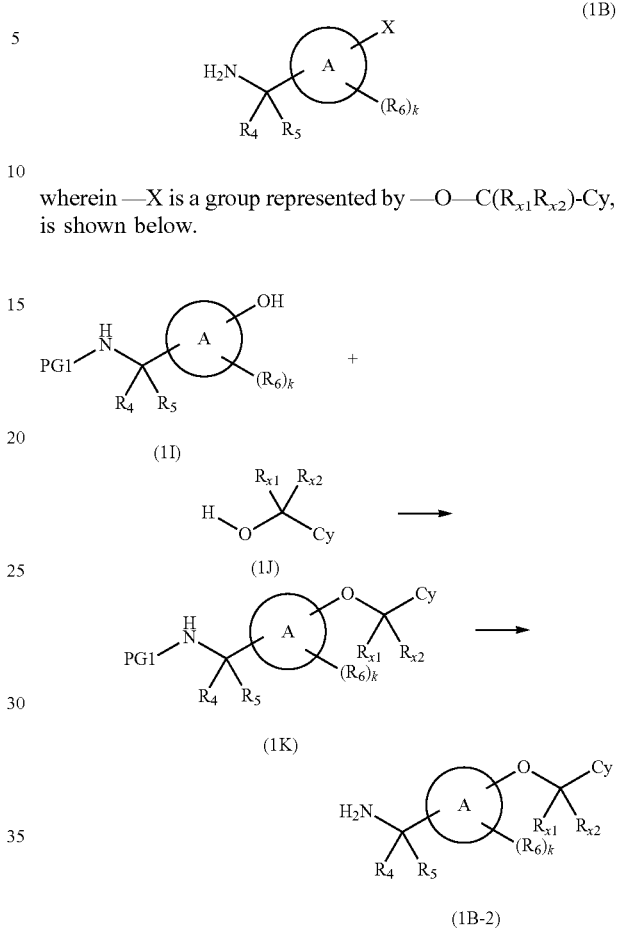

wherein —X is a group represented by —O—C($R_{x1}R_{x2}$)-Cy, is shown below.

Ether derivative (1H) can be synthesized by reaction of alcohol derivative (1F) (wherein PG1 is a suitable protecting group such as tert-butoxycarbonyl group (Boc group), benzyloxycarbonyl group (Cbz group) and the like. Where necessary, it is synthesized by reduction or alkylation and the like of the corresponding carboxylic acid derivative, ester derivative, aldehyde derivative, ketone derivative and the like) and alcohol derivative (1G) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like. The object compound (1B-1) can be produced by removing protecting group PG1 thereafter. The deprotection reaction is known and, for example, when PG1 is a tert-butoxycarbonyl group, a method using protic acid such as hydrochloric acid and trifluoroacetic acid, and a method using a Lewis acid such as boron trifluoride and tin tetrachloride can be mentioned. For example, when PG1 is a benzyloxycarbonyl group, a method using hydrogenation reaction under normal pressure or pressurization in a hydrogen atmosphere, a method using hydrobromic acid/acetic acid and the like, in the presence of a catalytic amount of palladium/carbon and the like can be mentioned. Ether derivative (1H) can also be produced by converting the hydroxyl group of alcohol derivative (1F) to a leaving group such as chlorine atom, bromine atom, iodine atom, methanesulfonyloxy group, p-toluenesulfonyloxy group and the like followed by reaction with alcohol derivative (1G) in a solvent that does not adversely influence the reaction such as tetrahydrofuran or N,N-dimethylformamide and the like in the presence of a base such as sodium hydride, potassium carbonate, cesium carbonate, triethylamine, N-ethyldiisopropylamine and the like in the presence or absence of, for example, potassium iodide, sodium iodide, tetra-n-butylammonium iodide and the like.

A synthesis method of, for example, a compound represented by (1B-2)

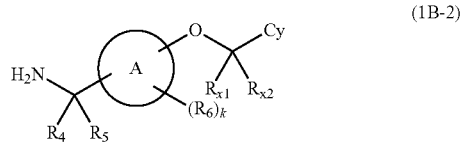

Ether derivative (1K) can be synthesized by reaction of alcohol derivative (1I) (wherein PG1 is a suitable protecting group such as tert-butoxycarbonyl group (Boc group), benzyloxycarbonyl group (Cbz group) and the like) and alcohol derivative (1J) (where necessary, it is synthesized by reduction or alkylation and the like of the corresponding carboxylic acid derivative, ester derivative, aldehyde derivative, ketone derivative and the like) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like. The object compound (1B-2) can be produced by removing protecting group PG1 by a suitable method such as an acid treatment, hydrogenolysis and the like. Ether derivative (1K) can also be produced by converting the hydroxyl group of alcohol derivative (1J) to a leaving group such as chlorine atom, bromine atom, iodine atom, methanesulfonyloxy group, p-toluenesulfonyloxy group and the like followed by reaction with alcohol derivative (1I) in a solvent that does not adversely influence the reaction such as tetrahydrofuran or N,N-dimethylformamide and the like in the presence of a base such as sodium hydride, potassium carbonate, cesium carbonate, triethylamine, N-ethyldiisopropylamine and the like in the presence or absence of, for example, potassium iodide, sodium iodide, tetra-n-butylammonium iodide and the like.

A synthesis method of, for example, a compound represented by (1B-3)

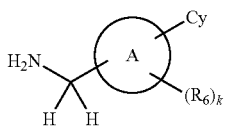
(1B-3)

which is the formula (1B)

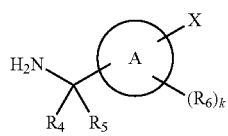
(1B)

wherein —X is a group represented by -Cy, and $R_4$ and $R_5$ are both hydrogen atoms,
is shown below.

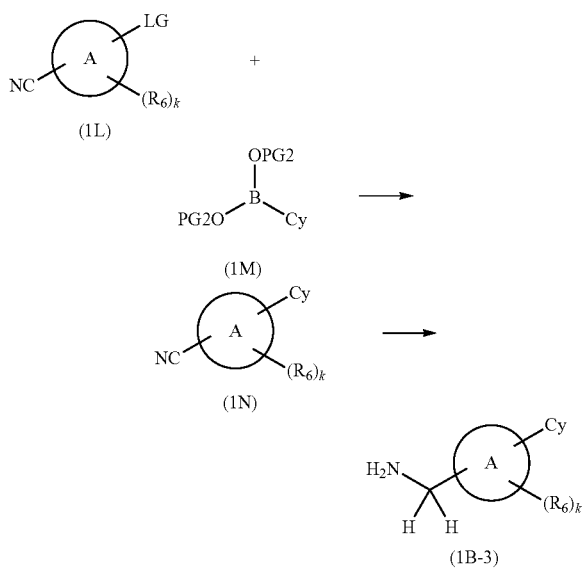

Nitrile derivative (1N) can be synthesized by reaction of nitrile derivative (1L) (wherein LG is a suitable leaving group such as chlorine atom, bromine atom, iodine atom, trifluoromethanesulfonyloxy group and the like) and boronic acid derivative (1M) (wherein —$B(OPG2)_2$ is —$B(OH)_2$ or a suitable boronic acid derivative such as catecholborane, pinacolborane, N-methyliminodiacetic acid boronate and the like) with a base such as sodium hydroxide, sodium carbonate, potassium carbonate, sodium hydrogen carbonate, potassium hydrogen carbonate, tripotassium phosphate and the like in a solvent that does not adversely influence the reaction such as 1,4-dioxane or toluene, butanol and the like, in the presence or absence of a co-solvent such as water and the like, in the presence or absence of copper acetate and the like, in the presence or absence of 2,4,6-triisopropyl-2'-(dicyclohexylphosphino)biphenyl and the like, in the presence of catalyst such as [1,1'-bis(diphenylphosphino)ferrocene]dichloropalladium, tris(dibenzylideneacetone) dipalladium, tetrakis(triphenylphosphine)palladium and the like. Amine derivative (1B-3) can be synthesized by reduction of the obtained nitrile derivative (1N) in a solvent that does not adversely influence the reaction such as water, methanol, ethanol, tetrahydrofuran and the like in the presence of a catalyst such as palladium/carbon, palladium hydroxide, platinum/carbon and the like in the presence or absence of an acid such as acetic acid, hydrochloric acid and the like under a hydrogen atmosphere at normal pressure or under pressurization. Also, amine derivative (1B-3) can be synthesized by reaction in a solvent that does not adversely influence the reaction such as tetrahydrofuran and the like with, for example, lithium aluminum hydride, borane•tetrahydrofuran complex and the like. Amine derivative (1B-3) can also be synthesized by reaction with sodium tetrahydroborate and the like in a solvent that does not adversely influence the reaction such as tetrahydrofuran and the like in the presence or absence of a co-solvent such as water and the like in the presence of a catalyst such as cobalt chloride and the like.

Amine derivative (1B-3) can also be synthesized as follows.

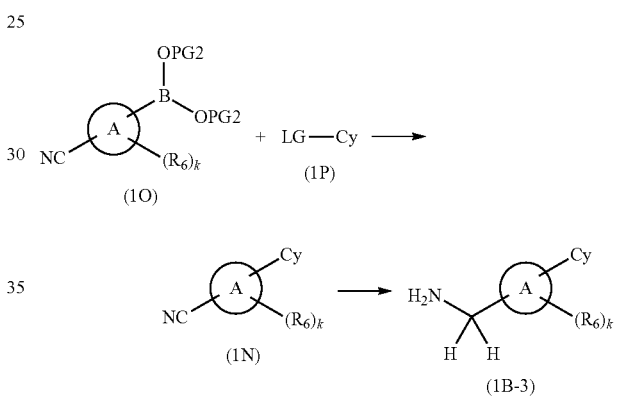

Nitrile derivative (1N) can be synthesized by reaction of nitrile derivative (1O) (wherein —$B(OPG2)_2$ is —$B(OH)_2$ or a suitable boronic acid derivative such as catecholborane, pinacolborane, N-methyliminodiacetic acid boronate and the like) and compound (1P) (wherein LG is a suitable leaving group such as chlorine atom, bromine atom, iodine atom, trifluoromethanesulfonyloxy group and the like) having an appropriate leaving group with a base such as sodium hydroxide, sodium carbonate, potassium carbonate, sodium hydrogen carbonate, potassium hydrogen carbonate, tripotassium phosphate and the like in a solvent that does not adversely influence the reaction such as 1,4-dioxane or toluene, butanol and the like, in the presence or absence of a co-solvent such as water and the like, in the presence or absence of copper acetate and the like, in the presence or absence of 2,4,6-triisopropyl-2'-(dicyclohexylphosphino)biphenyl and the like, in the presence of catalyst such as [1,1'-bis(diphenylphosphino)ferrocene]dichloropalladium, tris(dibenzylideneacetone)dipalladium, tetrakis(triphenylphosphine)palladium and the like, and amine derivative (1B-3) can be synthesized by reduction of nitrile group by the aforementioned method and the like.

A synthesis method of, for example, a compound represented by (1B-4)

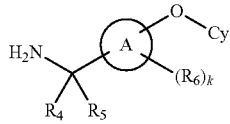

which is the formula (1B)

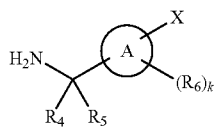

wherein —X is a group represented by —O-Cy, is shown below.

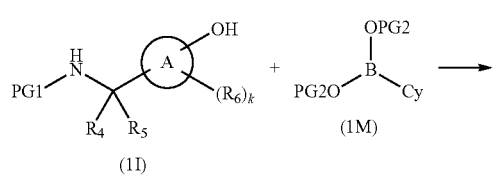

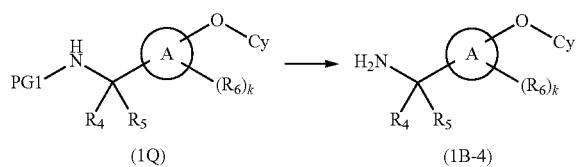

Ether derivative (1Q) is obtained by reaction of amine derivative (1I) (wherein PG1 is a suitable protecting group such as tert-butoxycarbonyl group (Boc group), benzyloxycarbonyl group (Cbz group) and the like) and boronic acid derivative (1M) (wherein —B(OPG2)$_2$ is —B(OH)$_2$ or a suitable boronic acid derivative such as catecholborane, pinacolborane, N-methyliminodiacetic acid boronate and the like) with copper acetate(I) and the like in a solvent that does not adversely influence the reaction such as dichloromethane, dichloroethane and the like in the presence or absence of a base such as triethylamine, N-ethyldiisopropylamine, pyridine and the like, in the presence or absence of molecular sieves 4 Å and the like. The object compound (1B-4) can be produced by removing protecting group PG1 by the aforementioned method and the like.

Amine derivative (1B-4) can also be synthesized as follows.

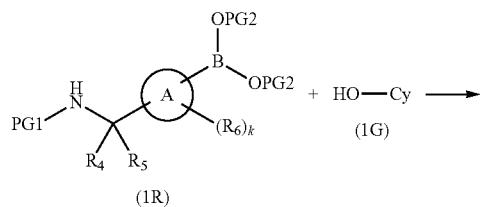

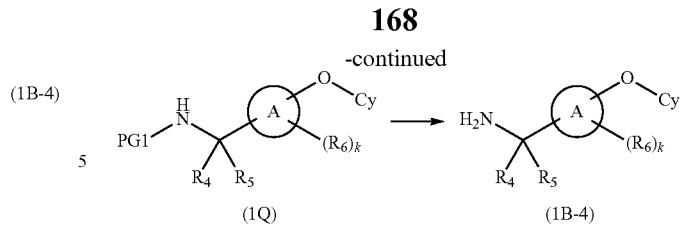

Ether derivative (1Q) can be synthesized by reaction of boronic acid derivative (1R) (wherein PG1 is a suitable protecting group such as tert-butoxycarbonyl group (Boc group), benzyloxycarbonyl group (Cbz group) and the like, wherein —B(OPG2)$_2$ is —B(OH)$_2$ or a suitable boronic acid derivative such as catecholborane, pinacolborane, N-methyliminodiacetic acid boronate and the like) and alcohol derivative (1G) with copper acetate(I) and the like in a solvent that does not adversely influence the reaction such as dichloromethane, dichloroethane and the like in the presence or absence of a base such as triethylamine, N-ethyldiisopropylamine or pyridine and the like, in the presence or absence of molecular sieves 4 Å and the like, and amine derivative (1B-4) can be synthesized by removing protecting group PG1 by the aforementioned method and the like.

A synthesis method of, for example, a compound represented by (1B-5)

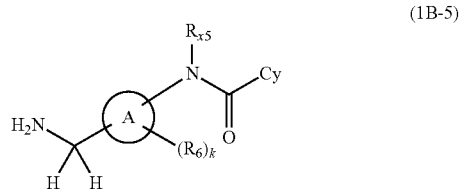

which is the formula (1B)

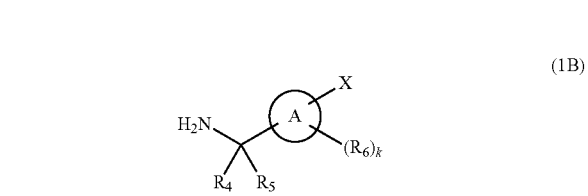

wherein —X is a group represented by —N(R$_{x5}$)—C(O)-Cy, and R$_4$ and R$_5$ are both hydrogen atoms, is shown below.

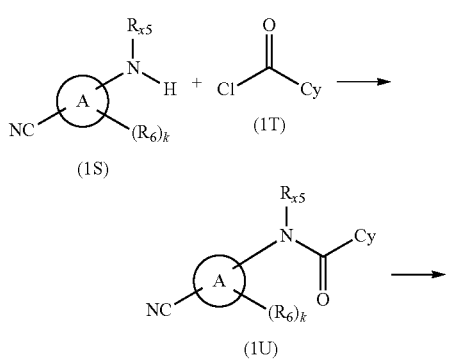

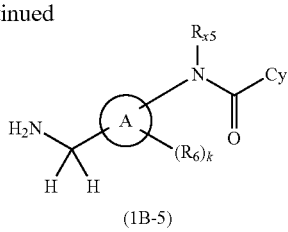

(1B-5)

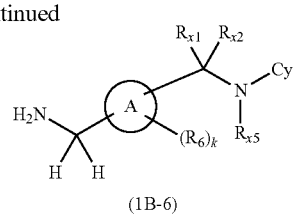

(1B-6)

Nitrile derivative (1U) can be synthesized by reaction of amine derivative (1S) and acid chloride derivative (1T) with a base such as triethylamine, pyridine, N,N-diisopropylethylamine and the like in a solvent that does not adversely influence the reaction such as dichloromethane and the like, in the presence or absence of an additive such as N,N-dimethyl-4-aminopyridine and the like. Amine derivative (1B-5) can be synthesized by reduction of the obtained nitrile derivative (1U) in a solvent that does not adversely influence the reaction such as water, methanol, ethanol, tetrahydrofuran and the like in the presence of a catalyst such as palladium/carbon, palladium hydroxide/carbon, platinum/carbon and the like in the presence or absence of an acid such as acetic acid, hydrochloric acid and the like, under a hydrogen atmosphere at normal pressure or under pressurization.

A synthesis method of, for example, a compound represented by (1B-6)

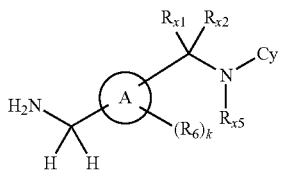

(1B-6)

which is the formula (1B)

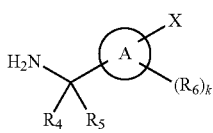

(1B)

wherein —X is a group represented by —C($R_{x1}R_{x2}$)—N($R_{x5}$)-Cy, and $R_4$ and $R_5$ are both hydrogen atoms, is shown below.

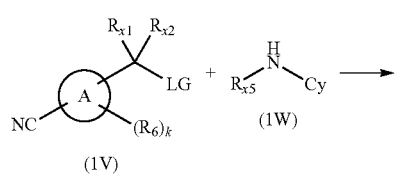

(1V)

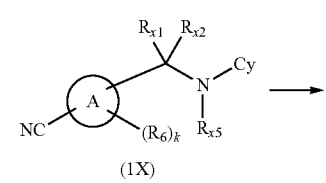

(1X)

nitrile derivative (1X) can be synthesized by reaction of nitrile derivative (1V) (wherein LG is a suitable leaving group such as chlorine atom, bromine atom, iodine atom, trifluoromethanesulfonyloxy group and the like) and amine derivative (1W) with a base such as triethylamine, N,N-diisopropylethylamine, sodium hydroxide, sodium carbonate and the like in a solvent that does not adversely influence the reaction such as acetonitrile, N,N-dimethylformamide, acetone and the like in the presence or absence of additive such as tetra-n-butylammonium iodide, lithium chloride and the like. Amine derivative (1B-6) can be synthesized by reaction of the obtained nitrile derivative (1X) in a solvent that does not adversely influence the reaction such as tetrahydrofuran and the like with, for example, lithium aluminum hydride, borane-tetrahydrofuran complex and the like.

Amine derivative (1B-6) can also be synthesized as follows.

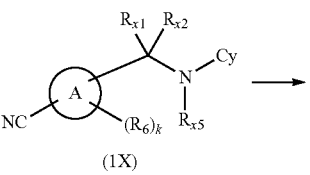

(1Y)    (1W)

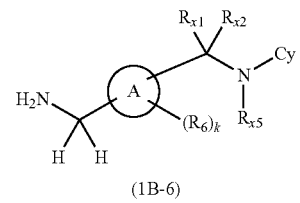

(1X)

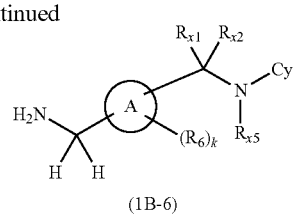

(1B-6)

Nitrile derivative (1X) can be synthesized by reaction of alcohol derivative (1Y) and amine derivative (1W) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like. Amine derivative (1B-6) can also be synthesized by reaction of the obtained nitrile derivative (1X) in a solvent that does not adversely influence the reaction such as tetrahydrofuran and the like with, for example, lithium aluminum hydride, borane-tetrahydrofuran complex and the like.

A synthesis method of, for example, a compound represented by (1B-7)

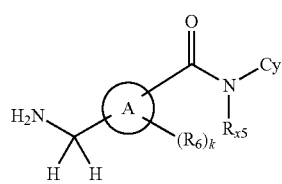
(1B-7)

which is the formula (1B)

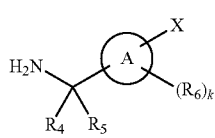
(1B)

wherein —X is a group represented by —C(O)—N(R$_{x5}$)-Cy, and R$_4$ and R$_5$ are both hydrogen atoms, is shown below.

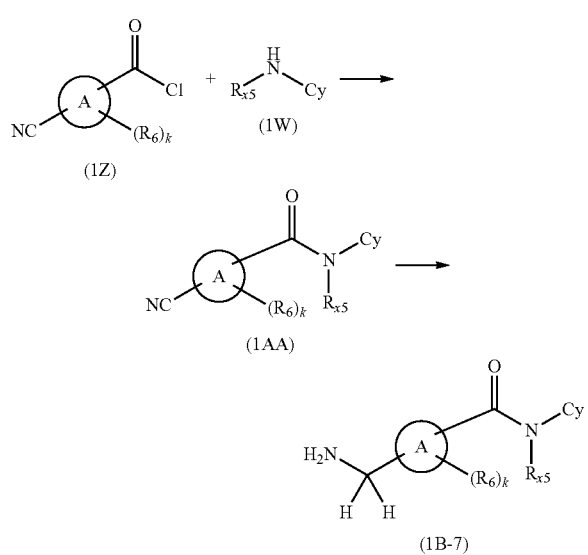
(1B-7)

Amide derivative (1AA) can be synthesized by reaction of acid chloride derivative (1Z) and amine derivative (1W) within a base such as triethylamine, N,N-diisopropylethylamine, pyridine and the like in a solvent that does no adversely influence the reaction such as dichloromethane and the like, in the presence or absence of an additive such as N,N-dimethyl-4-aminopyridine and the like. Amine derivative (1B-7) can be synthesized by reduction of the obtained amide derivative (1AA) in a solvent that does not adversely influence the reaction such as water, methanol, ethanol, tetrahydrofuran and the like in the presence of a catalyst such as palladium/carbon, palladium hydroxide/carbon, platinum/carbon and the like in the presence or absence of an acid such as acetic acid, hydrochloric acid and the like, under a hydrogen atmosphere at normal pressure or under pressurization.

A synthesis method of, for example, a compound represented by (1B-8)

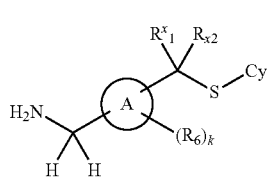
(1B-8)

which is the formula (1B)

(1B)

wherein —X is a group represented by —C(R$_{x1}$R$_{x2}$)—S(O)n-Cy, n=0, and R$_4$ and R$_5$ are both hydrogen atoms, is shown below.

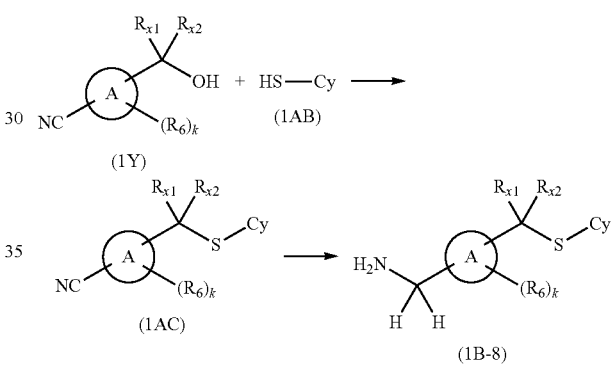

Nitrile derivative (1AC) can be synthesized by reaction of alcohol derivative (1Y) and thiol derivative (1AB) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like. Amine derivative (1B-8) can be synthesized by reaction of the obtained nitrile derivative (1AC) in a solvent that does not adversely influence the reaction such as tetrahydrofuran and the like with, for example, lithium aluminum hydride, borane-tetrahydrofuran complex and the like.

A synthesis method of, for example, a compound represented by (1B-9)

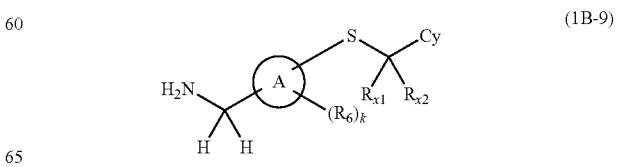
(1B-9)

which is the formula (1B)

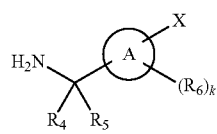

wherein —X is a group represented by —S(O)n-C(R$_{x1}$R$_{x2}$)-Cy, n=0, and R$_4$ and R$_5$ are both hydrogen atoms, is shown below.

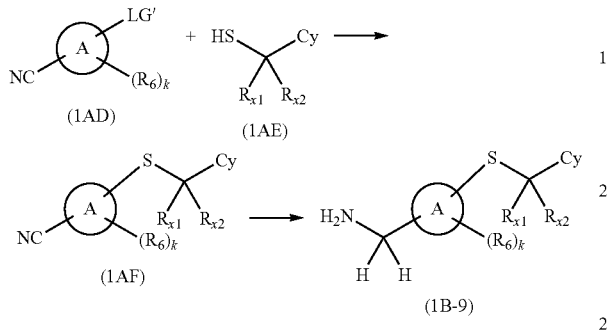

Sulfide derivative (1AF) can be synthesized by reaction of nitrile derivative (1AD) (wherein LG' is a chlorine atom, a bromine atom or an iodine atom) and thiol derivative (1AE) in a solvent that does not adversely influence the reaction such as N,N-dimethylformamide, dimethyl sulfoxide and the like with, for example, sodium hydride, potassium hydroxide and potassium tert-butoxide and the like. Amine derivative (1B-9) can be synthesized by reaction of the obtained sulfide derivative (1AF) in a solvent that does not adversely influence the reaction such as tetrahydrofuran and the like with, for example, lithium aluminum hydride, borane-tetrahydrofuran complex and the like.

A synthesis method of, for example, a compound represented by (2E)

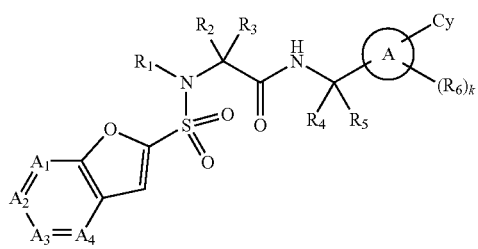

which is the formula (I)

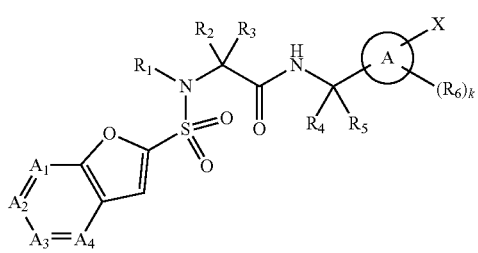

wherein Q is =O and —X is a group represented by -Cy, is shown below.

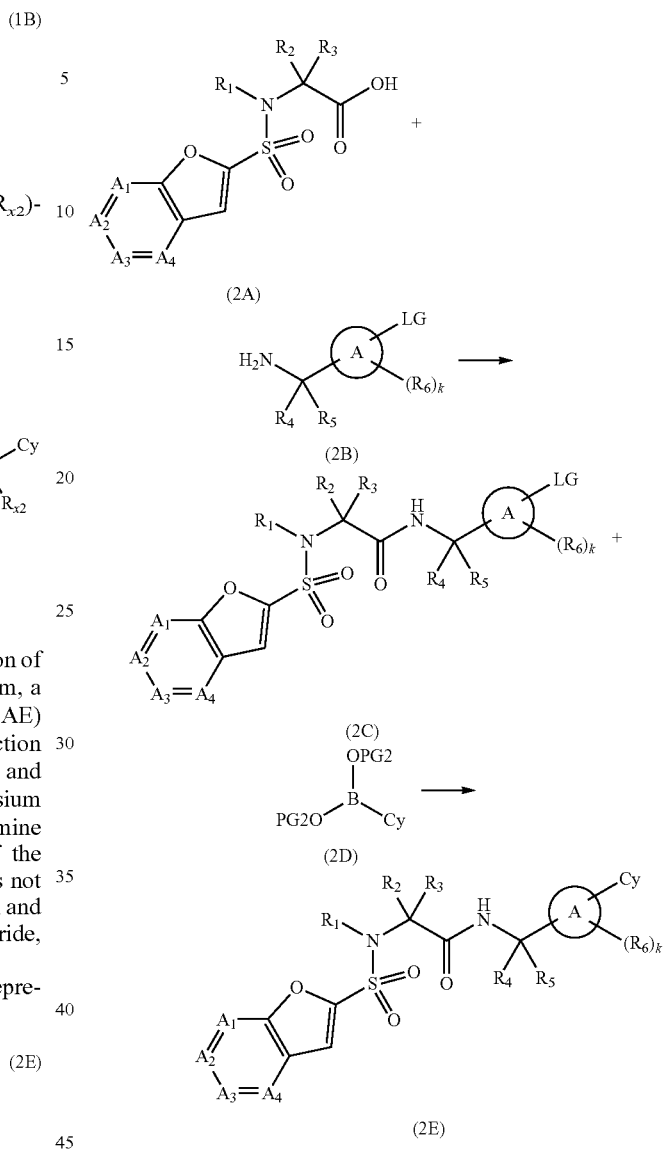

The object amide derivative (2C) can be produced by reaction of carboxylic acid derivative (2A) that can be synthesized in the same manner as carboxylic acid derivative (1A) obtained by the aforementioned method, and amine derivative (2B) (wherein LG is a suitable leaving group such as chlorine atom, bromine atom, iodine atom, trifluoromethanesulfonyloxy group and the like) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. The object compound (2E) can be synthesized by reaction of the obtained amide derivative (2C) and boronic acid derivative (2D) (wherein —B(OPG2)$_2$ is —B(OH)$_2$ or a suitable boronic acid derivative such as catecholborane, pinacolborane, N-methyliminodiacetic acid boronate and the like) with a base such as sodium hydroxide, sodium carbonate, potassium carbonate, sodium hydrogen carbonate, potassium hydrogen carbonate, tripotassium phosphate and the like in a solvent that does not adversely influence the reaction such as 1,4-dioxane or toluene, butanol and the like, in the presence or absence of a co-solvent such as water and the like, in the presence or absence of copper acetate and the like in the presence or absence of 2,4,6-triisopropyl-2'-(dicyclohexylphosphino)biphenyl and the like, in the presence of a catalyst such as [1,1'-bis(diphenylphosphino)ferrocene]dichloropalladium, tris(dibenzylideneacetone)dipalladium, tetrakis(triphenylphosphine)palladium and the like.

Compound (2E) can also be synthesized as follows.

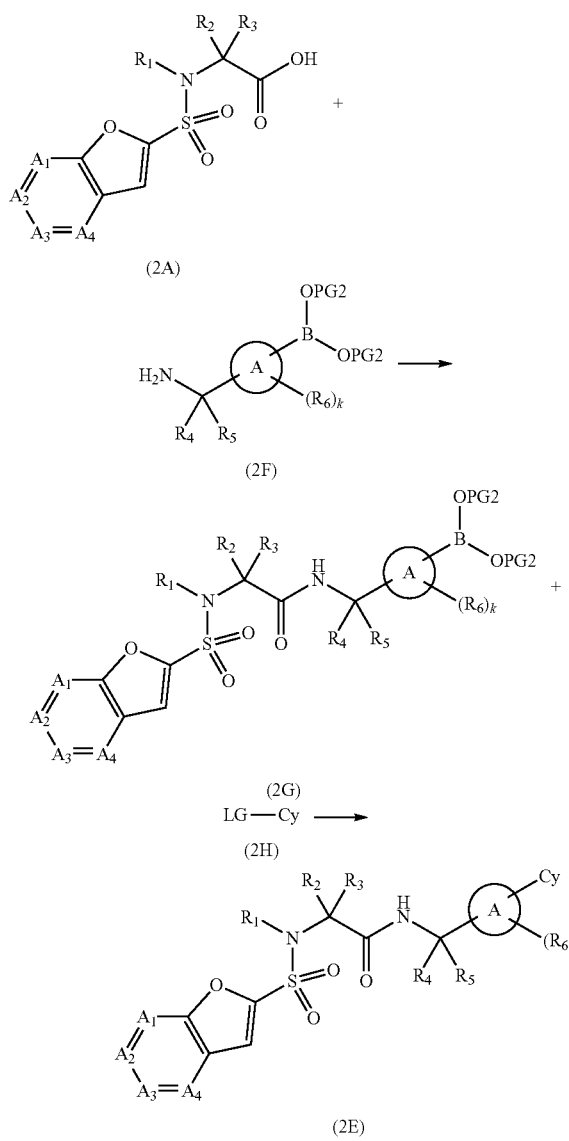

The object amide derivative (2G) can be produced by reaction of carboxylic acid derivative (2A) and amine derivative (2F) (wherein —B(OPG2)$_2$ is —B(OH)$_2$ or a suitable boronic acid derivative such as catecholborane, pinacolborane, N-methyliminodiacetic acid boronate and the like) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. The object compound (2E) can be synthesized by reaction of the obtained amide derivative (2G) and compound (2H) (wherein LG is a suitable leaving group such as chlorine atom, bromine atom, iodine atom, trifluoromethanesulfonyloxy group and the like) having an appropriate leaving group with a base such as sodium hydroxide, sodium carbonate, potassium carbonate, sodium hydrogen carbonate, potassium hydrogen carbonate, tripotassium phosphate and the like in a solvent that does not adversely influence the reaction such as 1,4-dioxane or toluene, butanol and the like, in the presence or absence of a co-solvent such as water and the like, in the presence or absence of copper acetate and the like in the presence or absence of 2,4,6-triisopropyl-2'-(dicyclohexylphosphino)biphenyl and the like, in the presence of a catalyst such as [1,1'-bis(diphenylphosphino)ferrocene]dichloropalladium, tris(dibenzylideneacetone)dipalladium, tetrakis(triphenylphosphine)palladium and the like.

A synthesis method of, for example, a compound represented by (2J)

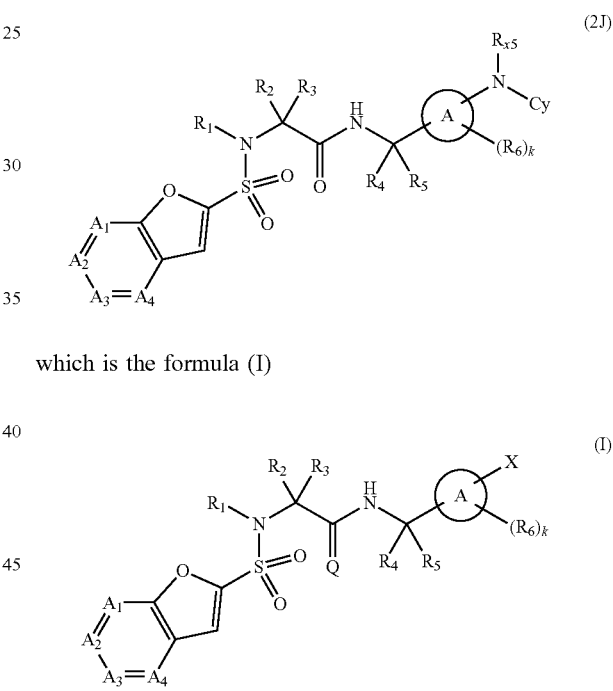

which is the formula (I)

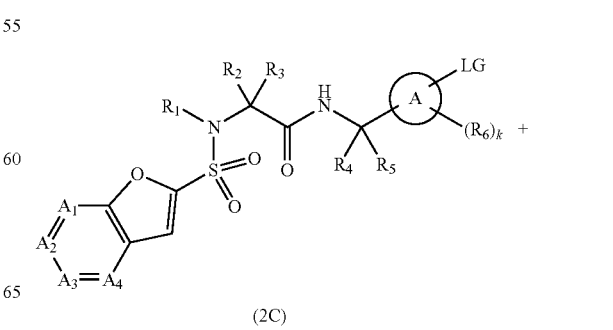

wherein Q is =O and —X is a group represented by —N(R$_{x5}$)-Cy,
is shown below.

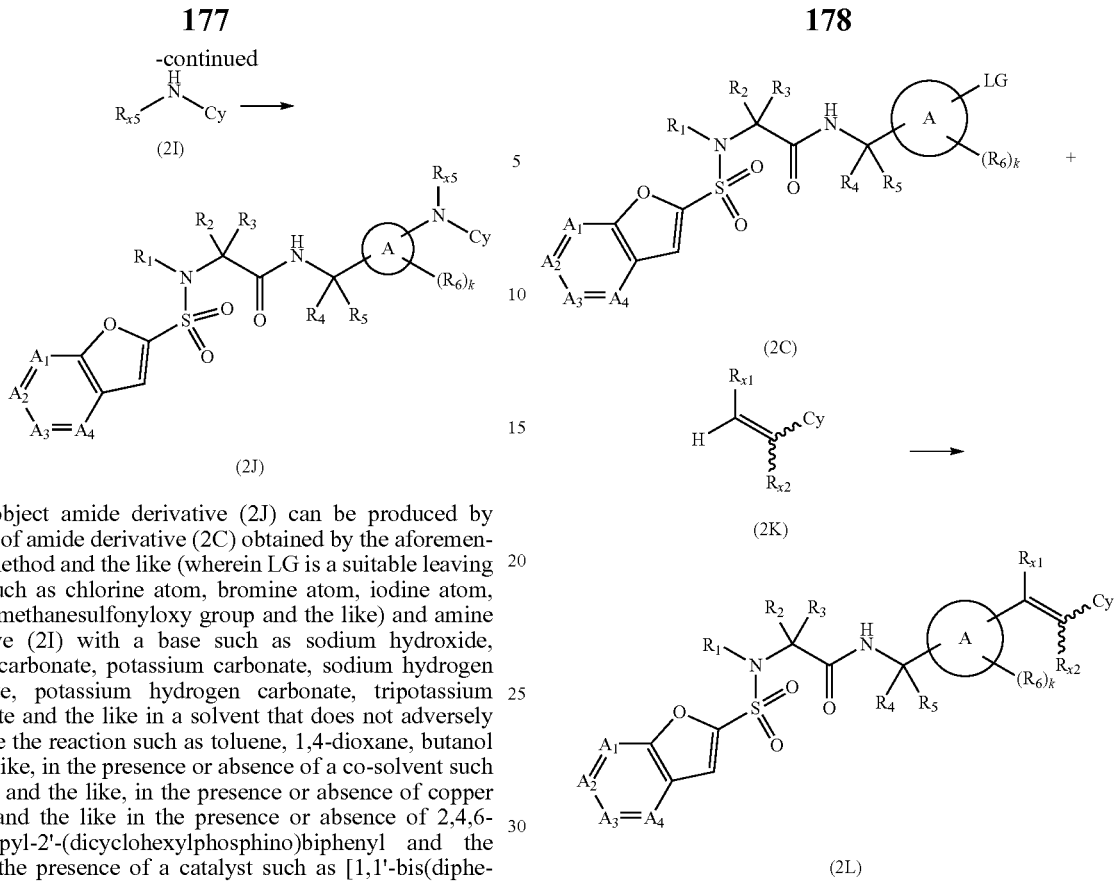

The object amide derivative (2J) can be produced by reaction of amide derivative (2C) obtained by the aforementioned method and the like (wherein LG is a suitable leaving group such as chlorine atom, bromine atom, iodine atom, trifluoromethanesulfonyloxy group and the like) and amine derivative (2I) with a base such as sodium hydroxide, sodium carbonate, potassium carbonate, sodium hydrogen carbonate, potassium hydrogen carbonate, tripotassium phosphate and the like in a solvent that does not adversely influence the reaction such as toluene, 1,4-dioxane, butanol and the like, in the presence or absence of a co-solvent such as water and the like, in the presence or absence of copper acetate and the like in the presence or absence of 2,4,6-triisopropyl-2'-(dicyclohexylphosphino)biphenyl and the like, in the presence of a catalyst such as [1,1'-bis(diphenylphosphino)ferrocene]dichloropalladium, tris(dibenzylideneacetone)dipalladium, tetrakis(triphenylphosphine)palladium and the like.

A synthesis method of, for example, a compound represented by (2L)

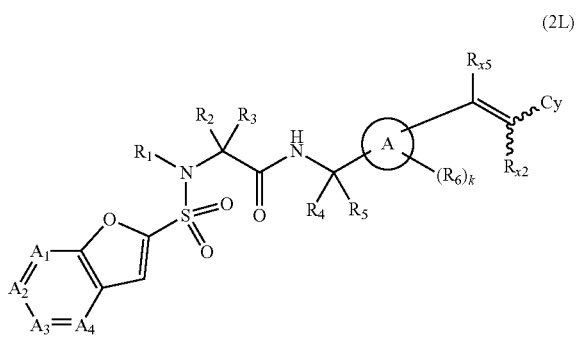

which is the formula (I)

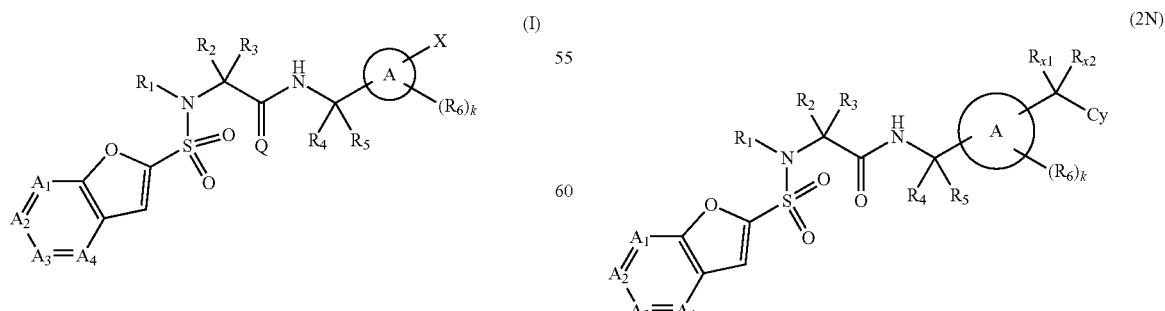

wherein Q is =O and —X is a group represented by —C($R_{x1}$)=C($R_{x2}$)-Cy, is shown below.

The object compound (2L) can be synthesized by reaction of amide derivative (2C) obtained by the aforementioned method and the like (wherein LG is a suitable leaving group such as chlorine atom, bromine atom, iodine atom, trifluoromethanesulfonyloxy group and the like) and alkene derivative (2K) in a solvent that does not adversely influence the reaction such as N,N-dimethylformamide, tetrahydrofuran and the like, in the presence or absence of a base such as triethylamine, potassium carbonate, silver carbonate(I), sodium acetate and the like in the presence or absence of for example, triphenylphosphine and the like, in the presence of a catalyst such as palladium(II) acetate, tris(dibenzylideneacetone)dipalladium, tetrakis(triphenylphosphine)palladium and the like.

A synthesis method of, for example, a compound represented by (2N)

which is the formula (I)

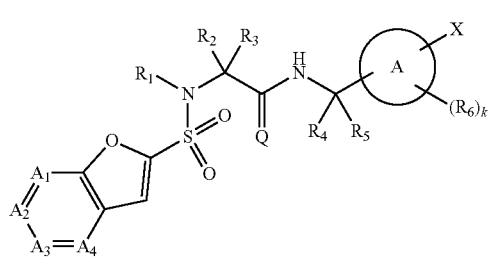

wherein Q is =O and —X is a group represented by —C(R$_{x1}$R$_{x2}$)-Cy, is shown below.

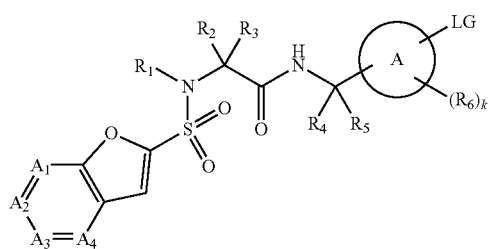

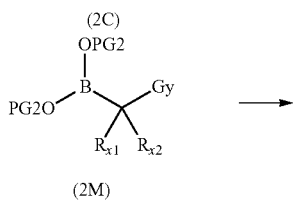

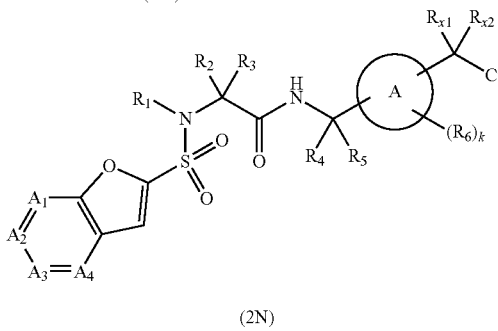

The object compound (2N) can be synthesized by reaction of amide derivative (2C) (wherein LG is a suitable leaving group such as chlorine atom, bromine atom, iodine atom, trifluoromethanesulfonyloxy group and the like) obtained by the aforementioned method and the like and boronic acid derivative (2M) (wherein —B(OPG2)$_2$ is —B(OH)$_2$ or a suitable boronic acid derivative such as catecholborane, pinacolborane, N-methyliminodiacetic acid boronate and the like) with a base such as sodium hydroxide, sodium carbonate, potassium carbonate, sodium hydrogen carbonate, potassium hydrogen carbonate, tripotassium phosphate and the like in a solvent that does not adversely influence the reaction such as 1,4-dioxane or toluene, butanol and the like, in the presence or absence of a co-solvent such as water and the like, in the presence or absence of copper acetate and the like, in the presence or absence of 2,4,6-triisopropyl-2'-(dicyclohexylphosphino)biphenyl and the like, in the presence of catalyst such as [1,1'-bis(diphenylphosphino)ferrocene]dichloropalladium, tris(dibenzylideneacetone)dipalladium, tetrakis(triphenylphosphine)palladium and the like.

A synthesis method of, for example, a compound represented by (3E)

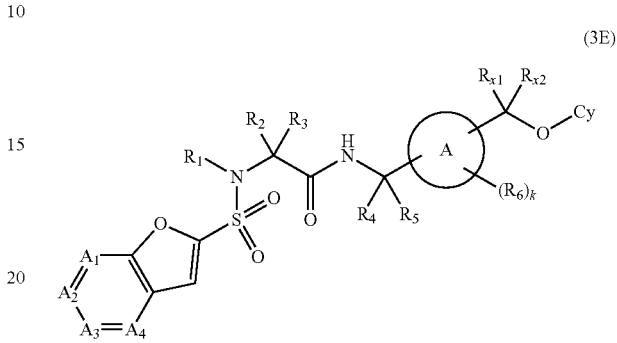

which is the formula (I)

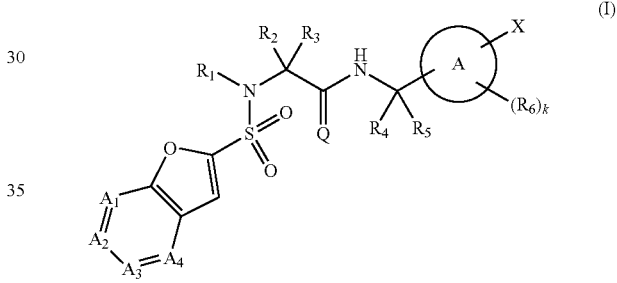

wherein Q is =O and —X is a group represented by —C(R$_{x1}$R$_{x2}$)—O-Cy, is shown below.

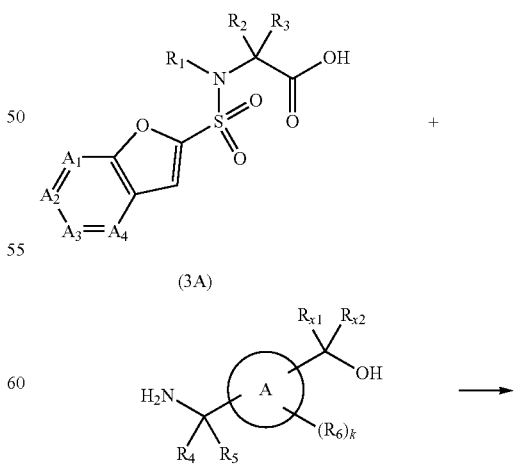

-continued

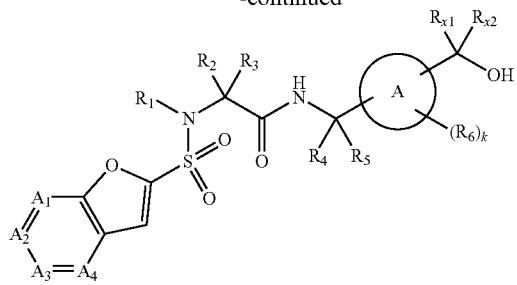

(3C)

HO—Cy (3D)

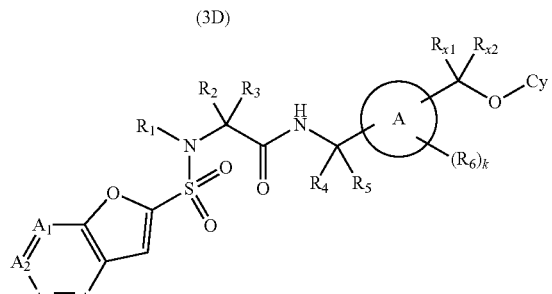

(3E)

The object amide derivative (3C) can be produced by reaction of carboxylic acid derivative (3A) that can be synthesized in the same manner as carboxylic acid derivative (1A) obtained by the aforementioned method, and amine derivative (3B) (where necessary, it is synthesized by reduction or alkylation and the like of the corresponding carboxylic acid derivative, ester derivative, aldehyde derivative, ketone derivative and the like) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. The object compound (3E) can be produced by reaction of the obtained amide derivative (3C) and alcohol derivative (3D) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like.

A synthesis method of, for example, a compound represented by (4E)

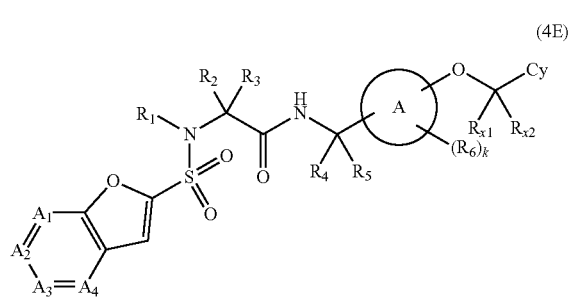

(4E)

which is the formula (I)

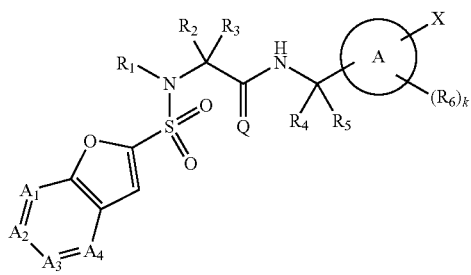

(I)

wherein Q is =O and —X is a group represented by —O—C($R_{x1}R_{x2}$)-Cy, is shown below.

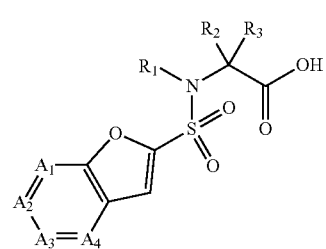

(4A)

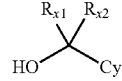

(4B)

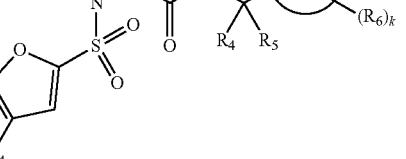

(4C)

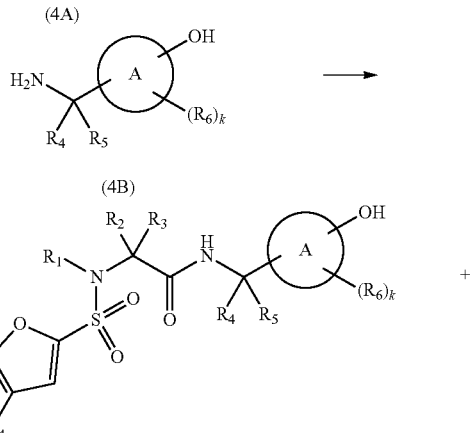

(4D)

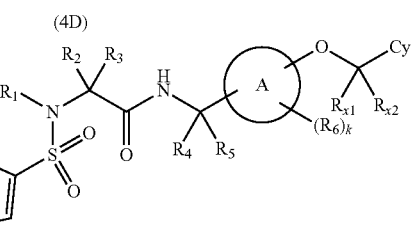

(4E)

The object amide derivative (4C) can be produced by reaction of carboxylic acid derivative (4A) that can be synthesized in the same manner as carboxylic acid derivative (1A) obtained by the aforementioned method, and amine derivative (4B) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. The object compound (4E) can be produced by reaction of the obtained amide derivative (4C) and alcohol derivative (4D) (where necessary, it is synthesized by reduction or alkylation and the like of the corresponding carboxylic acid derivative, ester derivative, aldehyde derivative, ketone derivative and the like) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like.

A synthesis method of, for example, a compound represented by (5F)

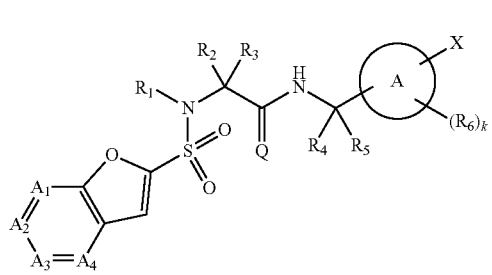

(5F)

which is the formula (I)

(I)

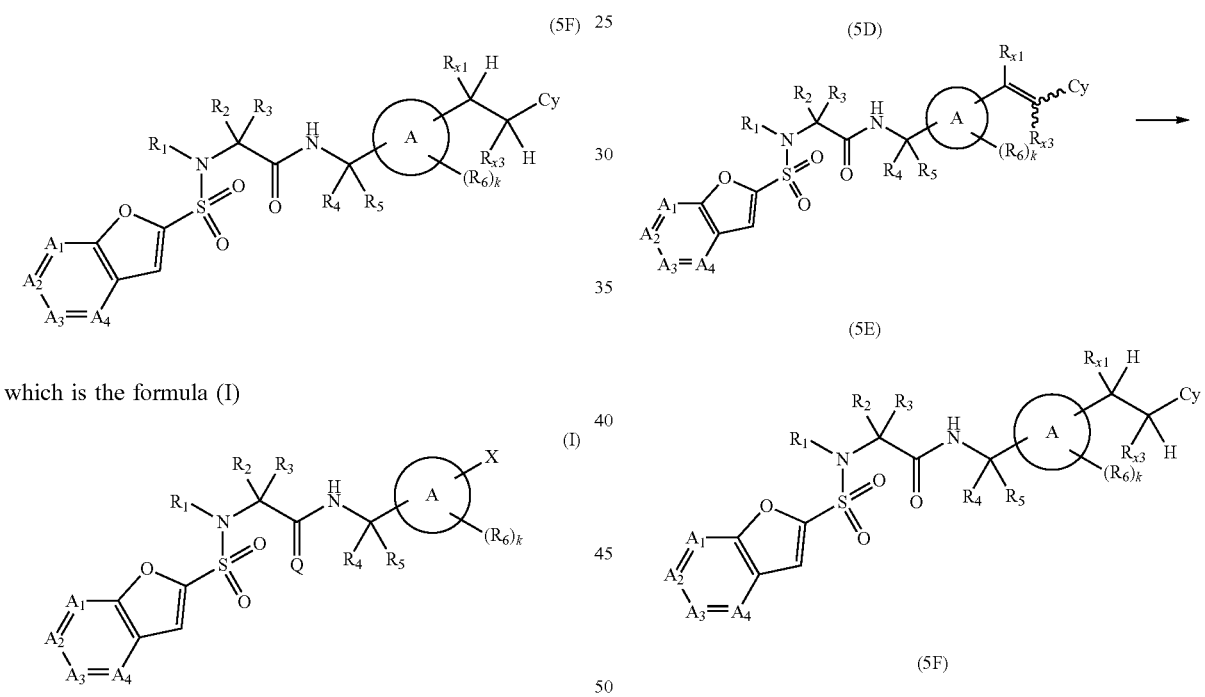

wherein Q is =O and —X is a group represented by —C($R_{x1}R_{x2}$)—C($R_{x3}R_{x4}$)-Cy, and both $R_{x2}$ and $R_{x4}$ are hydrogens, is shown below.

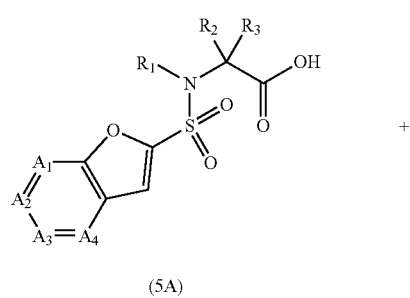

(5A)

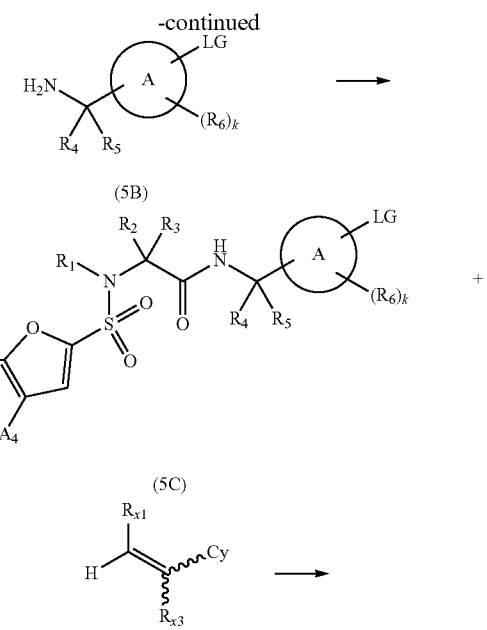

The object amide derivative (5C) can be produced by reaction of carboxylic acid derivative (5A) that can be synthesized in the same manner as carboxylic acid derivative (1A) obtained by the aforementioned method, and amine derivative (5B) (wherein LG is a suitable leaving group such as chlorine atom, bromine atom, iodine atom, trifluoromethanesulfonyloxy group and the like) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. Alkene derivative (5E) can be synthesized by reaction of the obtained amide derivative (5C) and alkene derivative (5D) in a solvent that does not adversely influence the reaction such as N,N-dimethylformamide, tetrahydrofuran and the like, in the presence or absence of a base such as triethylamine, potassium carbonate, silver carbonate(I), sodium acetate and the like, in the presence or absence of triphenylphosphine and the like, in the presence of a catalyst such as palladium(II) acetate, tris(dibenzylideneacetone)dipalladium, tetrakis(triphenylphosphine)palladium and the like. Amide derivative (5F) can be synthesized by reduction of the obtained alkene derivative (5E) in a solvent that does not adversely influence the reaction such as water, methanol, ethanol, tetrahydrofuran and the like, in the presence of a catalyst such as palladium/carbon, palladium hydroxide/carbon, platinum/carbon and the like in the presence or absence of an acid such as acetic acid, hydrochloric acid and the like, under a hydrogen atmosphere at normal pressure or under pressurization.

A synthesis method of, for example, compounds represented by (6E), (6F), (6G)

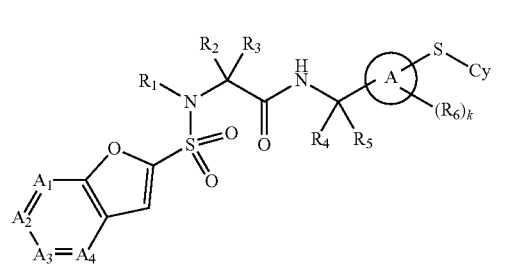
(6E)

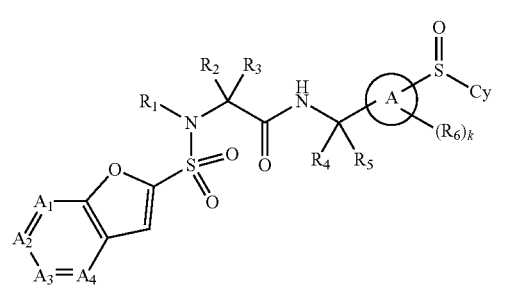
(6F)

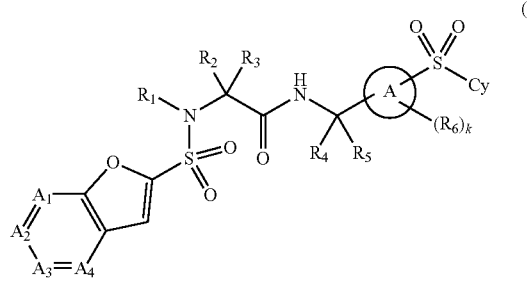
(6G)

which are represented by the formula (I)

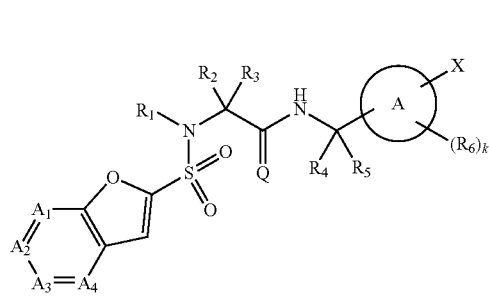
(I)

wherein Q is =O and —X is a group represented by —S(O)n-Cy, n=0, 1, 2, is shown below.

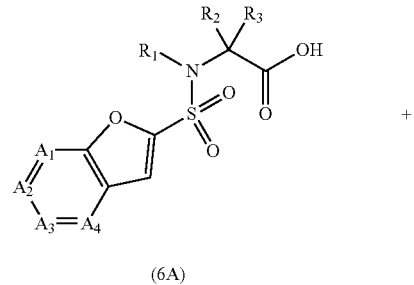
(6A)

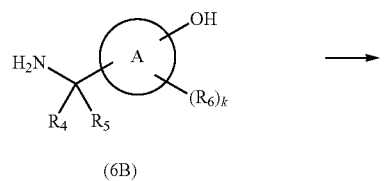
(6B)

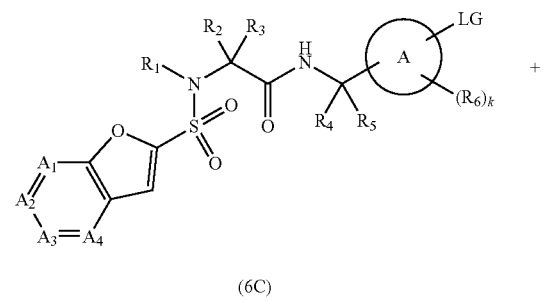
(6C)

HS—Cy
(6D)

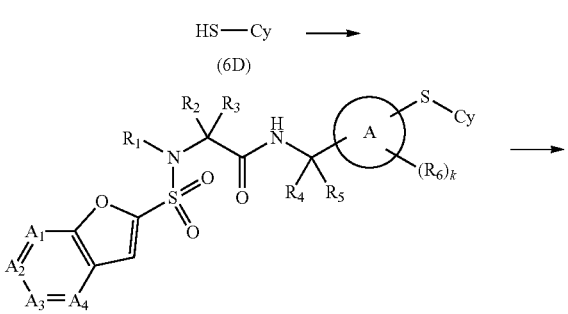
(6E)

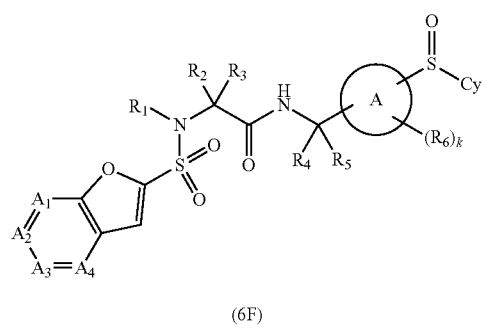
(6F)

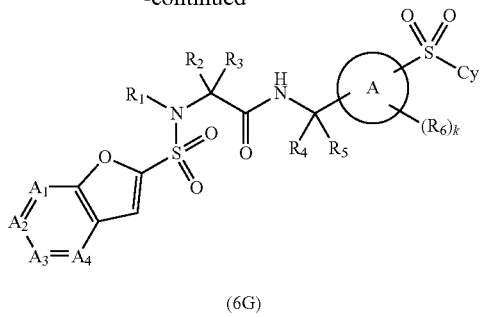

(6G)

Amide derivative ((6E) can be produced by reaction of carboxylic acid derivative (6A) that can be synthesized in the same manner as carboxylic acid derivative (1A) obtained by the aforementioned method, and amine derivative (6B) (wherein LG is a suitable leaving group such as chlorine atom, bromine atom, iodine atom, otrifluoromethanesulfonyloxy group and the like) with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazoie and the like in the presence or absence of a base such as triethylamine and the like. The object compound (6E) can be synthesized by reaction of the obtained amide derivative (6C) and thiol derivative (6D) with a base such as N,N-diisopropylethylamine, sodium tert-butoxide, potassium carbonate and the like in a solvent that does not adversely influence the reaction such as toluene or 1,4-dioxane, butanol and the like, in the presence or absence of a co-solvent such as water and the like, in the presence or absence of, for example, 4,5-bis(diphenylphosphino)-9,9-dimethylxanthene, 2,4,6-triisopropyl-2'-(dicyclohexylphosphino)biphenyl and the like, in the presence of a catalyst such as tris(dibenzylideneacetone)dipalladium, [1,1'-bis(diphenylphosphino)ferrocene]dichloropalladium, tetrakis(triphenylphosphine)palladium and the like. Sulfoxide derivative (6F) and sulfone derivative (6G) can be synthesized by reaction of sulfide derivative (6E) obtained by the aforementioned method and the like with, for example, 3-chloroperbenzoic acid, aqueous hydrogen peroxide and the like in a solvent that does not adversely influence the reaction such as dichloromethane and the like.

A synthesis method of, for example, compounds represented by (6L), (6M)

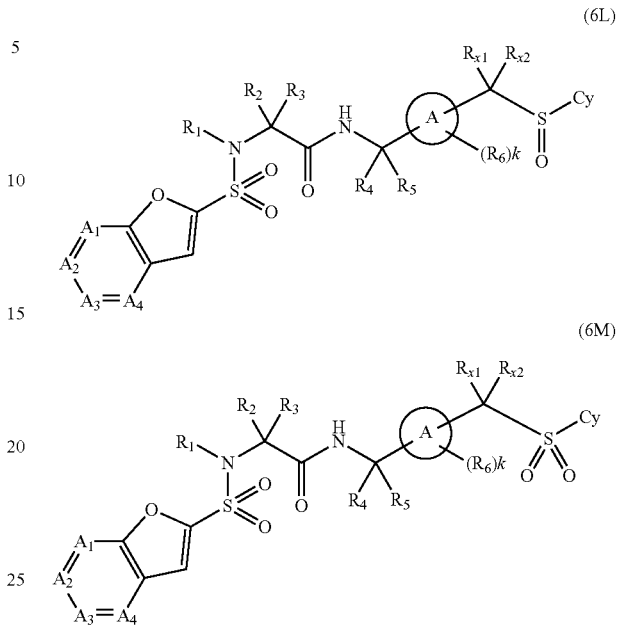

which are represented by the formula (I)

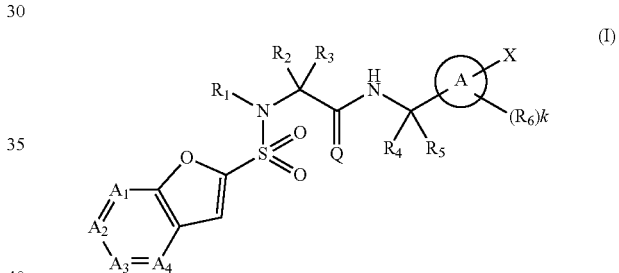

wherein Q is =O and —X is a group represented by —C($R_{x1}R_{x2}$)—S(O)n-Cy, n=1, 2,
is shown below.

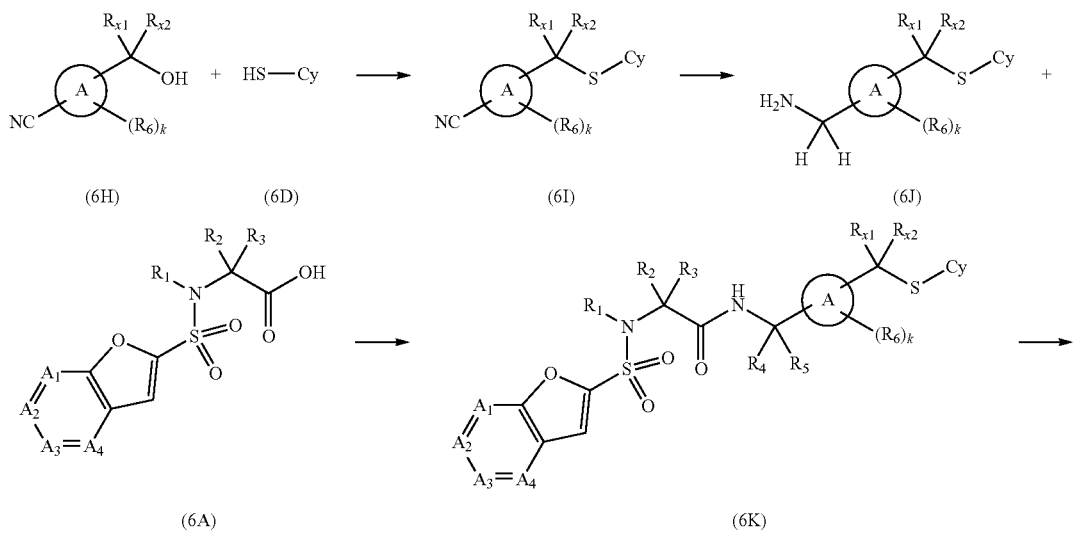

-continued

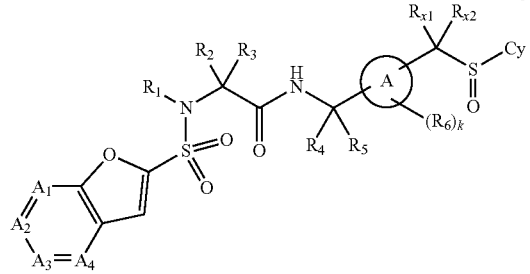

(6L)

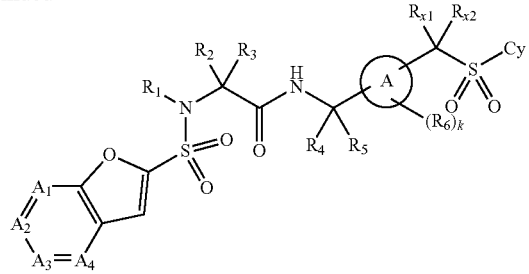

(6M)

Nitrile derivative (6I) can be synthesized by reaction of alcohol derivative (6H) and thiol derivative (6D) with diisopropyl azodicarboxylate (DIAD), diethyl azodicarboxylate (DEAD) and the like in a solvent that does not adversely influence the reaction such as dichloromethane, tetrahydrofuran and the like in the presence of, for example, triphenylphosphine and the like. Amine derivative (6J) can be synthesized by reaction of the obtained nitrile derivative (6I) with, for example, lithium aluminum hydride, borane-tetrahydrofuran complex and the like in a solvent that does not adversely influence the reaction such as tetrahydrofuran and the like. Amide derivative (6K) can be produced by reaction of the obtained amine derivative (6J) and carboxylic acid derivative (6A) that can be synthesized in the same manner as carboxylic acid derivative (1A) obtained by the aforementioned method with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. Sulfoxide derivative (6L) and sulfone derivative (6M) can be synthesized by reaction of the obtained amide derivative (6K) with, for example, 3-chloroperbenzoic acid, aqueous hydrogen peroxide and the like in a solvent that does not adversely influence the reaction such as dichloromethane and the like.

A synthesis method of, for example, compounds represented by (6S), (6T)

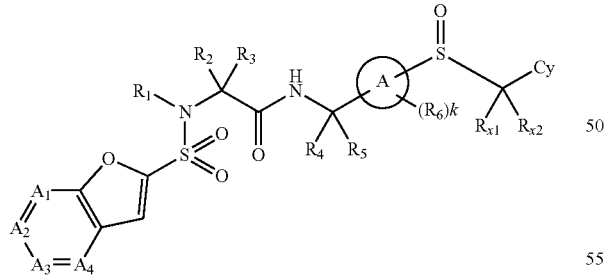

(6S)

-continued

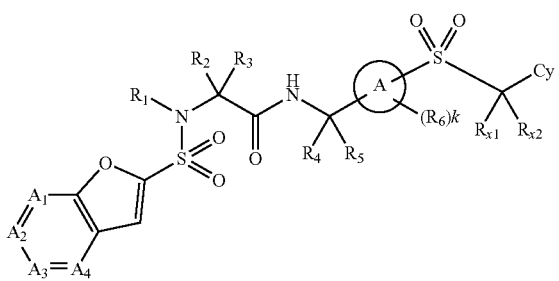

(6T)

which are represented by the formula (I)

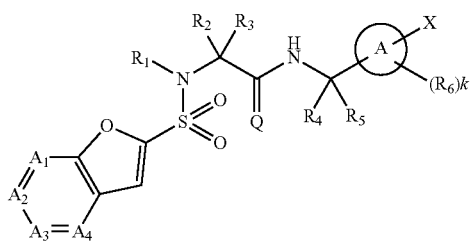

(I)

wherein Q is =O and —X is a group represented by —S(O)n-C($R_{x1}R_{x2}$)-Cy, n=1, 2,
is shown below.

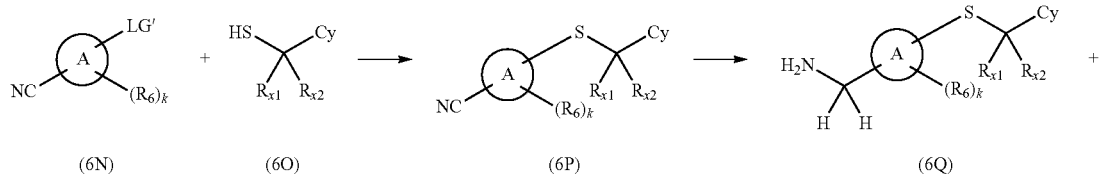

(6N)        (6O)        (6P)        (6Q)

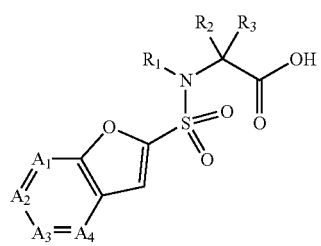

(6A)

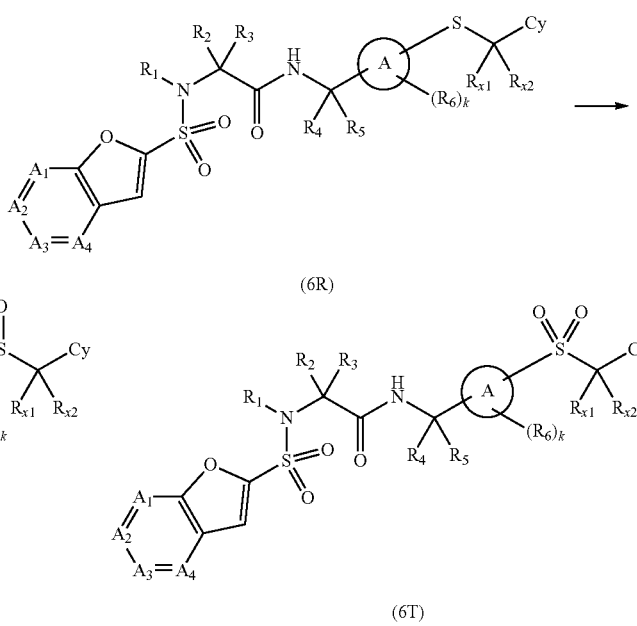

(6R)

(6S)

(6T)

Sulfide derivative (6P) can be synthesized by reaction of nitrile derivative (6N) (wherein LG' is a chlorine atom, a bromine atom or an iodine atom) and thiol derivative (6O) with, for example, sodium hydride, potassium hydroxide and potassium tert-butoxide and the like in a solvent that does not adversely influence the reaction such as N,N-dimethylformamide, dimethyl sulfoxide and the like. Amine derivative (6Q) can be synthesized by reaction of the obtained sulfide derivative (6P) with, for example, lithium aluminum hydride, borane-tetrahydrofuran complex and the like in a solvent that does not adversely influence the reaction such as tetrahydrofuran and the like. Amide derivative (6R) can be produced by reaction of the obtained amine derivative (6Q) and carboxylic acid derivative (6A) that can be synthesized in the same manner as carboxylic acid derivative (1A) obtained by the aforementioned method with a condensation reagent represented by 1-ethyl-3-(3'-dimethylaminopropyl)carbodiimide (WSC) in a solvent that does not adversely influence the reaction such as dichloromethane and the like in the presence or absence of, for example, 1-hydroxybenzotriazole and the like in the presence or absence of a base such as triethylamine and the like. The object sulfoxide derivative (6S) and sulfone derivative (6T) can be synthesized by reaction of the obtained amide derivative (6R) with, for example, 3-chloroperbenzoic acid, aqueous hydrogen peroxide and the like in a solvent that does not adversely influence the reaction such as dichloromethane and the like.

EXAMPLES

The present invention is explained in detail in the following by referring to Reference Examples, Examples and Experimental Examples, which are not to be construed as limitative. Unless particularly indicated, the apparatuses, reagents and the like to be used in the Examples can be easily prepared according to a method generally practiced in the pertinent field or are commercially available. In addition, % in the title compound means the yield.

Reference Example A-1

Synthesis of 7-fluorobenzofuran-2-ylsulfonylchloride (A-1)

A solution of 7-fluorobenzofuran (0.90 g, 6.6 mmol) in diethyl ether (10 mL) was cooled to 0° C., 1.3 mol/L tert-butyllithium (n-pentane solution, 6.1 mL, 7.9 mmol) was added dropwise over 20 min. Sulfur dioxide was blown into the reaction mixture for 20 min, N-chlorosuccinimide (1.1 g, 9.7 mmol) was added and the mixture was stirred for 1 hr. The reaction mixture was poured into ice water, extracted with ethyl acetate, and the organic layer was washed with saturated brine, and dried over sodium sulfate. The desiccant was filtered off, the solvent was evaporated and the obtained residue was purified by silica gel column chromatography (petroleum ether) to give the title compound (0.40 g, 1.7 mmol, 26%).

MS (ESI) m/z 235 (M+H)$^+$

Reference Example A-2

Synthesis of 6-fluorobenzofuran-2-ylsulfonylchloride (A-2)

(step 1) Synthesis of 2-(2,2-dibromovinyl)-5-fluorophenol

A solution of carbon tetrabromide (22.4 g, 68.4 mmol) in dichloromethane (80 mL) was cooled to 0° C., triphenylphosphine (27.7 g, 106 mmol) was added and the mixture was stirred for 30 min. To the reaction mixture was added triethylamine (23.8 mL, 171 mmol) and 4-fluoro-2-hydroxybenzaldehyde (4.00 g, 28.6 mmol) was slowly added while maintaining the reaction temperature at 5° C. or below. The reaction mixture was stirred at 30° C. for 2 hr, concentrated under reduced pressure and the obtained residue was purified by silica gel column chromatography (hexane/ethyl acetate) to give the title compound (2.66 g, 8.99 mmol, 31%).

$^1$H NMR (400 MHz, CDCl$_3$) δ 7.51-7.44 (m, 2H), 6.69-6.64 (m, 1H), 6.58-6.55 (m, 1H), 5.56 (s, 1H).

(step 2) Synthesis of 2-bromo-6-fluorobenzofuran

To the compound (2.40 g, 8.14 mmol) obtained in step 1, copper(I) iodide (123 mg, 0.648 mmol) and potassium phosphate (3.26 g, 15.4 mmol) was added tetrahydrofuran (80 mL) and the mixture was stirred at 80° C. for 2 hr. The insoluble material was filtered off, concentrated under reduced pressure and the obtained residue was purified by silica gel column chromatography (hexane) to give the title compound (1.15 g, 5.34 mmol, 66%).

$^1$H NMR (400 MHz, CDCl$_3$) δ7.42-7.38 (m, 1H), 7.18-7.15 (m, 1H), 7.02-6.96 (m, 1H), 6.68 (s, 1H).

(step 3) Synthesis of 6-fluorobenzofuran-2-ylsulfonylchloride (A-2)

An operation similar to that in Reference Example A-1 was performed using the compound (1.0 g, 4.7 mmol) obtained in step 2 instead of 7-fluorobenzofuran to give the title compound (0.10 g, 0.43 mmol, 9%).

MS (ESI) m/z 235 (M+H)$^+$

A-3 to A-4 described in Table 2 were synthesized by using corresponding commercially available reagents and by an operation similar to that in Reference Example A-2.

A solution of 5-methylbenzofuran (5.2 g, 39 mmol) in tetrahydrofuran (75 mL) was cooled to −40° C., 2.5 mol/L n-butyllithium (hexane solution, 19 mL, 48 mmol) was added and the mixture was stirred for 40 min. Sulfur dioxide was blown into the reaction mixture for 20 min while maintaining the temperature at −40° C.--30° C., and the mixture was stirred at room temperature for 90 min. To the reaction mixture was added hexane, and the insoluble material was collected by filtration, and dried. To the obtained solid were added dichloromethane (300 mL) and N-chlorosuccinimide (31 g, 0.23 mol), and the mixture was stirred at room temperature overnight, and the insoluble material was filtered off. The filtrate was concentrated under reduced pressure to give the title compound (3.0 g, 13 mmol, 33%).

MS (ESI) m/z 231 (M+H)$^+$

Reference Example A-6

Synthesis of 4-chlorofuro[3,2-c]pyridine-2-sulfonylchloride (A-6)

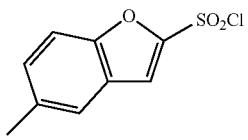

A solution of 4-chlorofuro[3,2-c]pyridine (3.0 g, 20 mmol) in tetrahydrofuran (80 mL) was cooled to −40° C.,

TABLE 2

| Ref. Example No. | Structural formula | MS(ESI) m/z (M + H)$^+$ | NMR |
|---|---|---|---|
| A-2 | ![structure] | 235 | |
| A-3 | ![structure] | 235 | $^1$H NMR (400 MHz, CD$_3$OD) δ 7.67-7.63 (m, 2H), 7.47-7.34 (m, 2H). |
| A-4 | ![structure] | 235 | $^1$H NMR (400 MHz, CDCl$_3$) δ 7.72 (s, 1H), 7.60-7.55 (m, 1H), 7.47 (d, J = 8.8 Hz, 1H), 7.12 (t, J = 8.8 Hz, 1H). |

Reference Example A-5

Synthesis of 5-methylbenzofuran-2-ylsulfonylchloride (A-2)

2.5 mol/L n-butyllithium (hexane solution, 9.4 mL, 24 mmol) was added and the mixture was stirred for 1 hr. Sulfur dioxide was blown into the reaction mixture for 30 min while maintaining the temperature at −40° C.--30° C., and the mixture was stirred at room temperature for 1.5 hr. To the reaction mixture was added hexane (100 mL), and the insoluble material was collected by filtration, and dried. To the obtained solid was added dichloromethane (75 mL) and N-chlorosuccinimide (3.1 g, 23 mmol) was added at 0° C., and the mixture was stirred at room temperature for 1 hr. The reaction mixture was washed 5 times with water. The organic layer was dried over sodium sulfate, the desiccant was filtered off, and the solvent was evaporated to give the title compound (3.5 g, 14 mmol, 71%).

MS (ESI) m/z 252 (M+H)$^+$ $^1$H NMR (400 MHz, CDCl$_3$) δ 8.55 (d, J=6.0 Hz, 1H), 7.74 (d, J=1.0 Hz, 1H), 7.59 (dd, J=6.0, 1.0 Hz, 1H).

Reference Example B-1

Synthesis of (2S)-1-(benzofuran-2-ylsulfonyl)pyrrolidine-2-carboxylic acid (B-1)

L-proline (53 mg, 0.46 mmol) was dissolved in 2 mol/L aqueous sodium hydroxide solution (2 mL) and tetrahydrofuran (2 mL), benzofuran-2-sulfonylchloride (120 mg, 0.56 mmol) was added and the mixture was stirred at room temperature for a few hours. The reaction mixture was extracted with dichloromethane, and the aqueous layer was neutralized with 2 mol/L hydrochloric acid, and extracted with dichloromethane. The obtained organic layer was dried over sodium sulfate. The desiccant was filtered off, and the solvent was evaporated to give the title compound as pale yellow white crystals (110 mg, 0.37 mmol, 81%)

MS (ESI) m/z 296 (M+H)$^+$ $^1$H NMR (400 MHz, DMSO-d) δ 12.91 (s, 1H), 7.82 (d, J=8.0 Hz, 1H), 7.75 (d, J=8.0 Hz, 1H), 7.67 (s, 1H), 7.56-7.52 (m, 1H), 7.42-7.37 (m, 1H), 4.29-4.26 (m, 1H), 3.54-3.47 (m, 1H), 3.41-3.35 (m, 1H), 2.10-1.82 (m, 3H), 1.73-1.64 (m, 1H).

B-2 to B-6, B-8, B-10 to B-11, B-13 and B-32 to B-37 described in Table 3 were synthesized by using A-1, A-2, A-3 and corresponding commercially available reagents and by an operation similar to that in Reference Example B-1.

TABLE 3

| Ref. Example No. | Structural formula | MS(ESI) m/z (M + H)$^+$ | NMR |
| --- | --- | --- | --- |
| B-1 | | 296 | $^1$H NMR (400 MHz, DMSO-d$_6$) δ 12.91 (s, 1H), 7.82 (d, J = 8.0 Hz, 1H), 7.75 (d, J = 8.0 Hz, 1H), 7.67 (s, 1H), 7.56-7.62 (m, 1H), 7.42-7.37 (m, 1H), 4.29-4.26 (m, 1H), 3.64-3.47 (m, 1H), 3.41-3.35 (m, 1H), 2.10-1.82 (m, 3H), 1.73-1.64 (m, 1H). |
| B-2 | | 314 | $^1$H NMR (400 MHz, CD$_3$OD): δ 7.62-7.60 (m, 2H), 7.40-7.33 (m, 2H), 4.44 (dd, J = 8.8, 4.0 Hz, 1H), 3.68-3.67 (m, 1H), 3.58-3.53 (m, 1H), 2.19-2.17 (m, 1H), 2.09-2.00 (m, 2H), 1.86-1.83 (m, 1H). |
| B-3 | | 314 | $^1$H NMR (400 MHz, CD$_3$OD) δ 7.61 (dd, J = 8.8, 5.6 Hz, 1H), 7.32 (s, 1H), 7.28 (dd, J = 8.8, 2.0 Hz, 1H), 7.02 (dt, J = 8.8, 2.0 Hz, 1H), 4.06 (t, J = 6.0 Hz, 1H), 3.53-3.49 (m, 1H), 3.38-3.34 (m, 1H), 1.85-1.78 (m, 3H), 1.51-1.45 (m, 1H). |
| B-4 | | 314 | $^1$H NMR (300 MHz, CD$_3$OD) δ 7.68-7.66 (m, 1H), 7.52-7.50 (m, 2H), 7.33-7.28 (m, 1H), 4.45-4.42 (m, 1H), 3.67-3.64 (m, 1H), 3.55-3.51 (m, 1H), 2.18-2.05 (m, 3H), 1.84-1.81 (m, 1H). |

TABLE 3-continued

| Ref. Example No. | Structural formula | MS(ESI) m/z (M + H)+ | NMR |
|---|---|---|---|
| B-5 | | 314 | ¹H NMR (400 MHz, CD₃OD) δ 7.59-7.60 (m, 3H), 7.16-7.12 (m, 1H), 4.47-4.44 (m, 1H), 3.69-3.64 (m, 1H), 3.56-3.52 (m, 1H), 2.20-2.00 (m, 3H), 1.85-1.81 (m, 1H). |
| B-6 | | 294 | ¹H NMR (400 MHz, DMSO-d₆) δ 13.16 (s, 1H), 7.82 (ddd, J = 7.8, 1.3, 0.9 Hz, 1H), 7.75 (dd, J = 8.4, 0.9 Hz, 1H), 7.73 (d, J = 1.0 Hz, 1H), 7.55 (ddd, J = 8.4, 7.2, 1.3 Hz, 1H), 7.41 (ddd, J = 7.8, 7.2, 0.9 Hz, 1H), 6.01-5.97 (m, 1H), 5.85-5.81 (m, 1H), 5.10-5.03 (m, 1H), 4.33-4.19 (m, 2H). |
| B-7 | | 312 | ¹H NMR (300 MHz, CD₃OD) δ 7.63 (dd, J = 9.3, 3.9 Hz, 1H), 7.64 (s, 1H), 7.49 (dd, J = 8.1, 2.7 Hz, 1H), 7.29 (ddd, J = 9.3, 9.0, 2.7 Hz, 1H), 5.98-5.96 (m, 1H), 5.82-5.78 (m, 1H), 5.20-5.18 (m, 1H), 4.37-4.35 (m, 2H). |
| B-8 | | 312 | ¹H NMR (400 MHz, DMSO-d₆) δ 13.03 (brs, 1H), 7.81 (ddd, J = 7.8, 1.3, 0.9 Hz, 1H), 7.72 (dd, J = 8.5, 0.8 Hz, 1H), 7.65 (d, J = 0.9 Hz, 1H), 7.53 (ddd, J = 8.5, 7.2, 1.3 Hz, 1H), 7.39 (ddd, J = 7.8, 7.2, 0.8 Hz, 1H), 5.35 (s, 1H), 4.25 (d, J = 4.0 Hz, 1H), 4.08 (brs, 1H), 3.58 (ddd, J = 8.9, 8.6, 1.8 Hz, 1H), 3.47 (ddd, J = 10.7, 8.9, 6.7 Hz, 1H), 2.02-1.89 (m, 1H), 1.81-1.73 (m, 1H). |
| B-10 | | 312 | ¹H NMR (400 MHz, DMSO-d₆) δ 12.84 (brs, 1H), 7.82-7.79 (m, 1H), 7.73 (dd, J = 8.4, 1.0 Hz, 1H), 7.63 (d, J = 1.0 Hz, 1H), 7.52 (ddd, J = 8.4, 7.2, 1.4 Hz, 1H), 7.38 (ddd, J = 8.0, 7.2, 1.0 Hz, 1H), 4.78 (d, J = 2.9 Hz, 1H), 4.31 (dd, J = 9.0, 7.5 Hz, 1H), 4.23-4.18 (m, 1H), 3.56 (dd, J = 11.2, 3.7 Hz, 1H), 3.32-3.24 (m, 1H), 2.14-2.06 (m, 1H), 2.00-1.91 (m, 1H). |
| B-11 | | 332 | ¹H NMR (400 MHz, DMSO-d₆) δ 13.33 (brs, 1H), 7.84 (dd, J = 7.8, 1.3 Hz, 1H), 7.78-7.75 (m, 2H), 7.57 (ddd, J = 8.5, 7.2, 1.3 Hz, 1H), 7.47-7.38 (m, 1H), 4.55 (dd, J = 9.4, 5.6 Hz, 1H), 3.97-3.88 (m, 2H), 2.94-2.79 (m, 1H), 2.61-2.52 (m, 1H). |

TABLE 3-continued

| Ref. Example No. | Structural formula | MS(ESI) m/z (M + H)+ | NMR |
|---|---|---|---|
| B-13 | | 282 | — |
| B-32 | | 302 | $^1$H NMR (400 MHz, DMSO-d$_6$) δ 12.93 (brs, 1H), 7.80 (dd, J = 9.1, 4.1 Hz, 1H), 7.64-7.59 (m, 2H), 7.40 (td, J = 9.3, 2.8 Hz, 1H), 4.07 (s, 2H), 2.98 (s, 3H). |
| B-33 | | 238 | $^1$H NMR (400 MHz, DMSO-d$_6$) δ 12.73 (brs, 1H), 8.86 (d, J = 8.9 Hz, 1H), 7.75 (dd, J = 9.1, 4.1 Hz, 1H), 7.60 (dd, J = 8.5, 2.7 Hz, 1H), 7.48 (d, J = 0.9 Hz, 1H), 7.37 (td, J = 9.2, 2.8 Hz, 1H), 3.83-3.71 (m, 1H), 1.78-1.65 (m, 1H), 1.63-1.60 (m, 1H), 0.81 (dd, J = 7.3 Hz, 3H). |
| B-34 | | 316 | $^1$H NMR (400 MHz, DMSO-d$_6$) δ 12.73 (brs, 1H), 7.79 (dd, J = 9.1, 4.1 Hz, 1H), 7.64-7.59 (m, 2H), 7.40 (td, J = 9.3, 2.7 Hz, 1H), 2.93 (s, 3H), 1.48 (s, 6H). |
| B-35 | | 328 | $^1$H NMR (400 MHz, DMSO-d$_6$) δ 12.84 (brs, 1H), 7.78 (dd, J = 9.1, 4.1 Hz, 1H), 7.60 (dd, J = 8.5, 2.7 Hz, 1H), 7.54 (d, J = 0.9 Hz, 1H), 7.39 (td, J = 9.3, 2.8 Hz, 1H), 3.69-3.60 (m, 1H), 3.55-3.48 (m, 1H), 2.24-2.15 (m, 1H), 2.02-1.82 (m, 3H), 1.54 (s, 3H). |
| B-36 | | 302 | — |

TABLE 3-continued

| Ref. Example No. | Structural formula | MS(ESI) m/z (M + H)+ | NMR |
|---|---|---|---|
| B-37 | ![structure] | 274 | $^1$H NMR (400 MHz, DMSO-d$_6$) δ 12.75 (brs, 1H), 8.82 (s, 1H), 7.76 (dd, J = 9.1, 4.1 Hz, 1H), 7.60 (dd, J = 8.5, 2.7 Hz, 1H), 7.51 (d, J = 0.9 Hz, 1H), 7.38 (td, J = 9.2, 2.7 Hz, 1H), 3.79 (s, 2H). |

Reference Example B-7

Synthesis of (2S)-1-(5-fluorobenzofuran-2-ylsulfonyl)-2,5-dihydropyrrole-2-carboxylic acid (B-7)

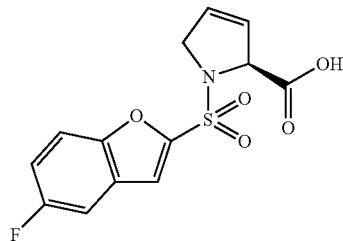 [SMILES: O=C(O)[C@@H]1C=CCN1S(=O)(=O)c1cc2cc(F)ccc2o1]

(step 1) Synthesis of (4R)—N-(5-fluorobenzofuran-2-yl)sulfonyl-4-hydroxy-L-proline methyl ester To (4R)-4-hydroxy-L-proline methyl ester hydrochloride (2.3 g, 13 mmol) were added dichloromethane (35 mL), triethylamine (5.4 mL, 39 mmol) and 4-dimethylaminopyridine (0.16 g, 1.3 mmol). The reaction mixture was cooled to 0° C., A-3 (3.0 g, 13 mmol) was added and the mixture was stirred at room temperature overnight. The reaction mixture was washed successively with water and saturated brine, and the organic layer was dried over sodium sulfate. The desiccant was filtered off, and the solvent was evaporated to give the title compound (3.5 g, 10 mmol, 80%).

MS (ESI) m/z 344 (M+H)+

$^1$H NMR (300 MHz, CDCl$_3$): δ 7.50-7.43 (m, 1H), 7.37 (s, 1H), 7.33-7.30 (m, 1H), 7.18-7.10 (m, 1H), 4.59 (t, J=9.0 Hz, 1H), 4.48-4.41 (m, 1H), 3.80-3.75 (m, 1H), 3.77 (s, 3H), 3.62-3.58 (m, 1H), 2.28-2.16 (m, 2H).

(step 2) Synthesis of (4R)—N-(5-fluorobenzofuran-2-yl)sulfonyl-4-methylsulfonyloxy-L-proline methyl ester To the compound (7.0 g, 20 mmol) obtained in step 1, triethylamine (4.3 mL, 31 mmol) and 4-dimethylaminopyridine (0.50 g, 4.1 mmol) was added dichloromethane (100 mL). The reaction mixture was cooled to 0° C., methanesulfonylchloride (3.5 g, 31 mmol) was added dropwise, and the mixture was stirred at 0° C. for 1 hr. The reaction mixture was washed successively with water and saturated brine, and the organic layer was dried over sodium sulfate. The desiccant was filtered off, and the solvent was evaporated to give the title compound (8.5 g, 20 mmol, 99%).

MS (ESI) m/z 421 (M+H)+

(step 3) Synthesis of (2S)-1-(5-fluorobenzofuran-2-ylsulfonyl)-2,5-dihydropyrrole-2-carboxylic acid methyl ester To the compound (8.5 g, 20 mmol) obtained in step 2 and diphenyl diselenide (3.8 g, 12 mmol) was added methanol (100 mL). To the reaction mixture was added sodium tetrahydroborate (1.0 g, 26 mmol) and the mixture was heated under reflux overnight. The reaction mixture was concentrated under reduced pressure and the obtained residue was purified by silica gel column chromatography (petroleum ether/ethyl acetate). The obtained oil was dissolved in dichloromethane (50 mL), pyridine (6 mL)/hydrogen peroxide water (12 mL) was added and the mixture was stirred at room temperature for 2 hr. The reaction mixture was washed successively with water, 1 mol/L aqueous citric acid solution and saturated aqueous sodium sulfite solution, and the organic layer was dried over sodium sulfate. The desiccant was filtered off, the solvent was evaporated and the residue was purified by silica gel column chromatography (dichloromethane/methanol) to give the title compound (1.8 g, 5.5 mmol, 27%).

MS (ESI) m/z 326 (M+H)+

(step 4) Synthesis of (2S)-1-(5-fluorobenzofuran-2-ylsulfonyl)-2,5-dihydropyrrole-2-carboxylic acid (B-7)

To the compound (1.8 g, 5.5 mmol) obtained in step 3 and trimethyltin hydroxide (5.0 g, 28 mmol) was added 1,2-dichloroethane (35 mL), and the mixture was stirred with heating in a sealed tube at 80° C. for 5 hr. The reaction mixture was concentrated under reduced pressure and the obtained residue was dissolved in ethyl acetate and washed successively with 1 mol/L aqueous hydrochloric acid solution and saturated brine. The organic layer was dried over sodium sulfate, the desiccant was filtered off, and the solvent was evaporated to give the title compound (1.4 g, 4.5 mmol, 81%).

MS (ESI) m/z 312 (M+H)+

$^1$H NMR (300 MHz, CD$_3$OD): δ 7.63 (dd, J=9.3, 3.9 Hz, 1H), 7.54 (s, 1H), 7.49 (dd, J=8.1, 2.7 Hz, 1H), 7.29 (ddd, J=9.3, 9.0, 2.7 Hz, 1H), 5.98-5.96 (m, 1H), 5.82-5.78 (m, 1H), 5.20-5.18 (m, 1H), 4.37-4.35 (m, 2H).

Reference Example B-9

Synthesis of (2S,3S)-1-(5-fluorobenzofuran-2-ylsulfonyl)-3-hydroxypyrrolidine-2-carboxylic acid (B-9)

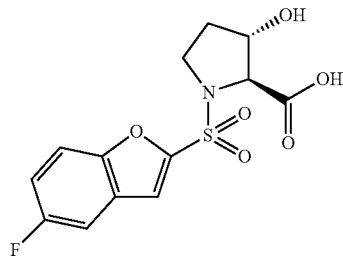 [SMILES: O=C(O)[C@@H]1[C@@H](O)CCN1S(=O)(=O)c1cc2cc(F)ccc2o1]

(step 1) Synthesis of (3S)-3-hydroxy-L-proline methyl ester hydrochloride

To a solution of (3S)-3-hydroxy-L-proline (1.5 g, 12 mmol) in methanol (20 mL) was added thionyl chloride (1.4 g, 0.12 mol) at 000, and the mixture was stirred at room temperature overnight. The resulting insoluble material was collected by filtration, and washed with diethyl ether to give the title compound (1.9 g, 10 mmol, 91%).
MS (ESI) m/z 146 (M+H)$^+$
$^1$H NMR (CDCl$_3$, 300 MHz): δ6.01-5.99 (m, 1H), 4.49-4.46 (m, 1H), 4.13 (d, J=2.7 Hz, 1H), 3.76 (s, 3H), 3.38-3.28 (m, 2H), 2.01-1.84 (m, 2H).

(step 2) Synthesis of (2S,3S)-1-(5-fluorobenzofuran-2-ylsulfonyl)-3-hydroxypyrrolidine-2-carboxylic acid methyl ester To the compound (1.2 g, 6.7 mmol) obtained in step 1 were added dichloromethane (20 mL), triethylamine (2.8 mL, 20 mmol) and 4-dimethylaminopyridine (82 mg, 0.67 mmol). The reaction mixture was cooled to 0° C., A-3 (1.6 g, 6.7 mmol) was added, and the mixture was stirred for 1 hr and concentrated under reduced pressure. The obtained residue was purified by silica gel column chromatography (petroleum ether/ethyl acetate) to give the title compound (1.4 g, 4.1 mmol, 61%).
MS (ESI) m/z 344 (M+H)$^+$
$^1$H NMR (300 MHz, DMSO-d$_6$): δ7.81-7.67 (m, 1H), 7.65-7.61 (m, 2H), 7.44-7.37 (m, 1H), 5.43 (s, 1H), 4.27-4.25 (m, 1H), 4.16 (s, $^1$H), 3.67 (s, 3H), 3.63-3.44 (m, 2H), 1.97-1.94 (m, 1H), 1.80-1.74 (m, 1H).

(step 3) Synthesis of (2S,3S)-1-(5-fluorobenzofuran-2-ylsulfonyl)-3-hydroxypyrrolidine-2-carboxylic acid (B-9)

To a solution of the compound (1.2 g, 3.5 mmol) obtained in step 2 in methanol (20 mL) was added 2 mol/L aqueous lithium hydroxide solution (10 mL), and the mixture was stirred at room temperature for 1 hr. Methanol was evaporated from the reaction mixture, concentrated hydrochloric acid was added and the resulting precipitate was collected by filtration, and dried to give the title compound (0.78 g, 2.4 mmol, 68%).
MS (ESI) m/z 330 (M+H)$^+$
$^1$H NMR (300 MHz, CD$_3$OD): δ 7.63 (dd, J=9.0, 3.9 Hz, 1H), 7.50-7.45 (m, 2H), 7.28 (ddd, J=9.3, 9.0, 2.7 Hz, 1H), 4.38 (s, 1H), 4.28 (s, 1H), 3.75-3.58 (m, 2H), 2.15-2.05 (m, 1H), 1.90-1.84 (m, 1H).

Reference Example B-12

Synthesis of (2S)-1-(5-fluorobenzofuran-2-ylsulfonyl)-4,4-difluoropyrrolidine-2-carboxylic acid (B-12)

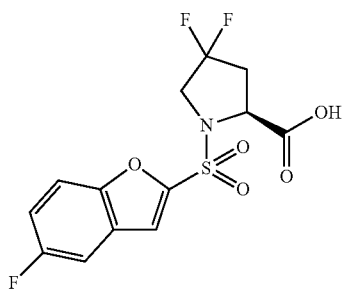 [SMILES: O=C(O)[C@@H]1CC(F)(F)CN1S(=O)(=O)c1cc2cc(F)ccc2o1]

To a solution of 4,4-difluoro-L-proline methyl ester (0.81 g, 4.9 mmol) in pyridine (20 mL) was added A-3 (1.2 g, 4.9 mmol), and the mixture was stirred at room temperature for 2 hr. To the reaction mixture was added 6 mol/L aqueous hydrochloric acid solution to adjust to pH4, and the mixture was extracted with dichloromethane. The organic layer was dried over sodium sulfate, and the desiccant was filtered off. The solvent was evaporated and the obtained residue was purified by silica gel column chromatography (hexane/ethyl acetate) to give methyl ester of the title compound. To the obtained methyl ester were added methanol (20 mL) and 2 mol/L aqueous lithium hydroxide solution (20 mL), and the mixture was stirred at room temperature for 30 min. Methanol was evaporated from the reaction mixture, concentrated hydrochloric acid was added and the resulting precipitate was collected by filtration, and dried to give the title compound (0.72 g, 2.1 mmol, 42%).
MS (ESI) m/z 350 (M+H)$^+$
$^1$H NMR (300 MHz, CD$_3$OD) δ 7.64 (dd, J=9.0, 4.2 Hz, 1H), 7.55 (d, J=1.2 Hz, 1H), 7.49 (dd, J=8.4, 2.7 Hz, 1H), 7.30 (ddd, J=9.3, 9.0, 2.7 Hz, 1H), 4.70-4.64 (m, 1H), 3.98-3.90 (m, 2H), 2.83-2.71 (m, 1H), 2.59-2.49 (m, 1H).

Reference Example B-14

Synthesis of (2S)-1-(5-fluorobenzofuran-2-ylsulfonyl)azetidine-2-carboxylic acid (B-14)

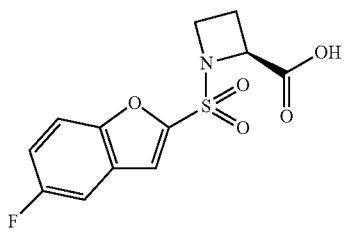 [SMILES: O=C(O)[C@@H]1CCN1S(=O)(=O)c1cc2cc(F)ccc2o1]

To (S)-azetidine-2-carboxylic acid (1.9 g, 19 mmol) were added saturated aqueous sodium hydroxide solution (15 mL)

and a solution of A-3 (4.5 g, 19 mmol) in tetrahydrofuran (15 mL) and the mixture was stirred at room temperature for 30 min. Tetrahydrofuran was evaporated, adjusted to pH3-4 with 1 mol/L aqueous hydrochloric acid solution, and the precipitate was collected by filtration, and dried to give the title compound (4.0 g, 13 mmol, 71%).

MS (ESI) m/z 300 (M+H)$^+$ $^1$H NMR (300 MHz, CD$_3$OD) δ 7.71 (dd, J=9.2, 4.1 Hz, 1H), 7.61 (s, 1H), 7.54 (dd, J=8.4, 2.7 Hz, 1H), 7.34 (ddd, J=9.3, 9.0, 2.7 Hz, 1H), 4.76 (t, J=8.4 Hz, 1H), 4.03-3.96 (m, 2H), 2.45-2.36 (m, 2H)

Reference Example B-15

Synthesis of (2S)-2-{(benzofuran-2-ylsulfonyl)amino}propionic acid (B-15)

To alanine tert-butyl ester hydrochloride (0.36 g, 2.0 mmol) were added acetonitrile (10 mL), benzofuran-2-sulfonylchloride (0.52 g, 2.4 mmol) and triethylamine (0.60 mL, 4.4 mmol) and the mixture was stirred at room temperature overnight. The reaction mixture was concentrated under reduced pressure, trifluoroacetic acid (3 mL) was added to the obtained residue and the mixture was stirred at room temperature for 2 hr, concentrated under reduced pressure and the obtained residue was purified by high performance liquid chromatography (water-acetonitrile, each containing 0.1% trifluoroacetic acid) to give the title compound (0.45 g, 1.7 mmol, 84%).

MS (ESI) m/z 270 (M+H)$^+$ $^1$H NMR (400 MHz, DMSO-d$_6$) δ 12.76 (br-s, 1H), 8.84 (d, J=8.7 Hz, 1H), 7.79 (d, J=7.8 Hz, 1H), 7.70 (d, J=8.4 Hz, 1H), 7.57-7.48 (m, 2H), 7.38 (dd, J=7.8, 7.5 Hz, 1H), 4.02-3.90 (m, 1H), 1.26 (d, J=7.2 Hz, 3H).

B-16 described in Table 4 was synthesized by using A-3 and by an operation similar to that in Reference Example B-15.

Reference Example B-17

Synthesis of (2S)-1-(5-methylbenzofuran-2-ylsulfonyl)pyrrolidine-2-carboxylic acid (B-17)

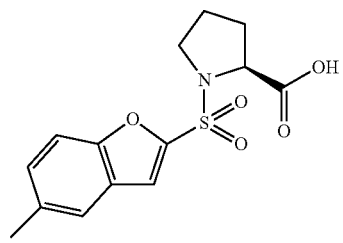 [SMILES: Cc1ccc2oc(S(=O)(=O)N3CCC[C@H]3C(=O)O)cc2c1]

L-proline (0.42 g, 3.6 mmol) was dissolved by adding saturated aqueous sodium hydroxide solution (10 mL), and a solution of A-5 (0.91 g, 4.0 mmol) in tetrahydrofuran (5 mL) was added dropwise at 0° C. After stirring for 30 min, the reaction mixture was partitioned by adding dichloromethane. The organic layer was discarded, and the aqueous layer was concentrated under reduced pressure and the remaining dichloromethane was removed, and the residue was acidified by slowly adding 10 mol/L aqueous hydrochloric acid solution. The precipitate was collected by filtration, and dried to give the title compound (0.78 g, 2.5 mmol, 70%).

MS (ESI) m/z 310 (M+H)$^+$ $^1$H NMR (400 MHz, CD$_3$OD): δ 7.56 (s, 1H), 7.52-7.49 (m, 1H), 7.44 (d, J=0.8 Hz, 1H), 7.35 (dd, J=11.2, 1.6 Hz, 1H), 4.43-4.39 (m, 1H), 3.64-3.60 (m, 1H), 3.58-3.31 (m, 1H), 2.46 (s, 3H), 2.18-1.82 (m, 3H), 1.72-1.71 (m, 1H).

B-18 to B-23 described in Table 5 were synthesized by using A-3 and corresponding commercially available reagents and by an operation similar to that in Reference Example B-1.

TABLE 4

| Ref Example No. | Structural formula | MS(ESI) m/z (M + H)$^+$ | NMR |
|---|---|---|---|
| B-15 | | 270 | $^1$H NMR (400 MHz, DMSO-d$_6$) δ 12.76 (br-s, 1H), 8.84 (d, J = 8.7 Hz, 1H), 7.79 (d, J = 7.8 Hz, 1H), 7.70 (d, J = 8.4 Hz, 1H), 7.57-7.48 (m, 2H), 7.38 (dd, J = 7.8, 7.5 Hz, 1H), 4.02-3.90 (m, 1H), 1.26 (d, J = 7.2 Hz, 3H). |
| B-16 | | 288 | $^1$H NMR (400 MHz, DMSO-d$_6$) δ 12.75 (br-s, 1H), 8.91 (d, J = 8.7 Hz, 1H), 7.75 (dd, J = 9.1, 4.1 Hz, 1H), 7.60 (dd, J = 8.5, 2.8 Hz, 1H), 7.49 (s, 1H), 7.38 (ddd, J = 9.3, 9.3, 2.8 Hz, 1H), 3.96 (dq, J = 8.9, 7.2 Hz, 1H), 1.26 (d, J = 7.2 Hz, 3H). |

TABLE 5

| Ref. Example No. | Structural formula | MS(ESI) m/z (M + H)+ | NMR |
|---|---|---|---|
| B-18 | | 330 | ¹H NMR (400 MHz, DMSO-d₆) δ 12.89 (s, 1H), 7.78 (dd, J = 8.9, 3.9 Hz, 1H), 7.63-7.59 (m, 2H), 7.39 (ddd, J = 9.3, 8.9, 2.7 Hz, 1H), 4.78 (d, J = 2.9 Hz, 1H), 4.30 (dd, J = 9.1, 7.5 Hz, 1H), 4.23-4.16 (m, 1H), 3.56 (dd, J = 11.3, 3.5 Hz, 1H), 3.36-3.35 (m, 1H), 2.16-2.07 (m, 1H), 2.00-1.91 (m, 1H). |
| B-19 | | 326 | ¹H NMR (400 MHz, DMSO-d₆) δ 12.84 (s, 1H), 7.85 (dd, J = 9.2, 4.4 Hz, 1H), 7.67 (d, J = 0.9 Hz, 1H), 7.65 (dd, J = 8.5, 2.8 Hz, 1H), 7.44 (ddd, J = 9.3, 9.2, 2.8 Hz, 1H), 4.32 (d, J = 5.1 Hz, 1H), 3.53 (d, J = 9.4 Hz, 1H), 3.42 (dd, J = 9.4, 4.9 Hz, 1H), 2.02-1.93 (m, 1H), 1.74-1.65 (m, 1H), 0.79-0.73 (m, 1H), 0.70-0.63 (m, 1H). |
| B-20 | | 326 | ¹H NMR (400 MHz, DMSO-d₆) δ 12.90 (s, 1H), 7.85 (ddd, J = 9.2, 4.0, 0.9 Hz, 1H), 7.69 (d, J = 0.9 Hz, 1H), 7.66 (dd, J = 8.5, 2.7 Hz, 1H), 7.45 (ddd, J = 9.3, 9.2, 2.7 Hz, 1H), 3.88 (dd, J = 8.3, 8.3 Hz, 1H), 3.39 (ddd, J = 6.5, 5.5, 2.6 Hz, 1H), 2.38 (dd, J = 12.8, 8.6 Hz, 1H), 2.21-2.10 (m, 1H), 1.76-1.65 (m, 1H), 0.50-0.40 (m, 1H), −0.11 (ddd, J = 6.1, 5.0, 2.6 Hz, 1H). |
| B-21 | | 326 | ¹H NMR (400 MHz, DMSO-d₆) δ 13.04 (s, 1H), 7.82 (ddd, J = 9.1, 4.0, 0.9 Hz, 1H), 7.66 (d, J = 0.9 Hz, 1H), 7.64 (dd, J = 8.5, 2.8 Hz, 1H), 7.42 (ddd, J = 9.3, 9.1, 2.8 Hz, 1H), 4.62 (dd, J = 11.3, 2.6 Hz, 1H), 3.61 (ddd, J = 6.4, 6.4, 2.5 Hz, 1H), 2.36-2.21 (m, 1H), 2.01 (dd, J = 13.5, 2.6 Hz, 1H), 1.58-1.46 (m, 1H), 0.83-0.72 (m, 1H), 0.73-0.64 (m, 1H). |
| B-22 | | 390 | ¹H NMR (400 MHz, DMSO-d₆) δ 13.04 (s, 1H), 7.81 (dd, J = 9.1, 4.1 Hz, 1H), 7.66 (d, J = 0.9 Hz, 1H), 7.61 (dd, J = 8.5, 2.8 Hz, 1H), 7.42 (ddd, J = 9.3, 9.1, 2.8 Hz, 1H), 7.24-7.14 (m, 5H), 4.48 (dd, J = 8.7, 2.7 Hz, 1H), 4.01 (dd, J = 9.2, 7.6 Hz, 1H), 3.63-3.55 (m, 1H), 3.31-3.25 (m, 1H), 2.38-2.24 (m, 2H). |

TABLE 5-continued

| Ref. Example No. | Structural formula | MS(ESI) m/z (M + H)⁺ | NMR |
|---|---|---|---|
| B-23 | | 328 | ¹H NMR (400 MHz, DMSO-d₆) δ 13.01 (s, 1H), 7.79 (ddd, J = 9.1, 4.1, 0.9 Hz, 1H), 7.60 (dd, J = 8.5, 2.7 Hz, 1H), 7.56 (d, J = 0.9 Hz, 1H), 7.38 (ddd, J = 9.2, 9.1, 2.7 Hz, 1H), 4.58 (d, J = 3.9 Hz, 1H), 3.84-3.75 (m, 1H), 3.31-3.25 (m, 1H), 2.13-2.01 (m, 1H), 1.71-1.55 (m, 3H), 1.40-1.09 (m, 2H). |

Reference Example B-24

Synthesis of (1S,2S,4R)-3-(5-fluorobenzofuran-2-ylsulfonyl)-3-azabicyclo[2.2.1]heptane-2-carboxylic acid (B-24)

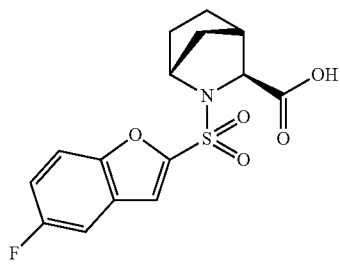

To (1S,2S,4R)-3-tert-butoxycarbonyl-3-azabicyclo[2.2.1]heptane-2-carboxylic acid (100 mg, 0.41 mmol) were added trifluoroacetic acid (0.50 mL), dichloromethane (1 mL) and the mixture was stirred at room temperature for a few hours. The reaction mixture was concentrated under reduced pressure and the obtained residue was dissolved in 2 mol/L aqueous sodium hydroxide solution (2 mL) and tetrahydrofuran (2 mL), A-3 (96 mg, 0.41 mmol) was added, and the mixture was stirred at room temperature for a few hours. The reaction mixture was extracted with dichloromethane, and the aqueous layer was neutralized with 1 mol/L hydrochloric acid, and extracted with dichloromethane. The obtained organic layer was dried over sodium sulfate. The desiccant was filtered off, and the solvent was evaporated to give the title compound (139 mg, 0.41 mmol, 99%).

MS (ESI) m/z 340 (M+H)±

¹H NMR (400 MHz, DMSO-d₆) δ 12.85 (s, 1H), 7.84 (dd, J=8.9, 3.8 Hz, 1H), 7.64-7.60 (m, 2H), 7.42 (ddd, J=9.3, 8.9, 2.8 Hz, 1H), 4.26 (s, 1H), 3.95 (s, 1H), 2.72 (d, J=4.4 Hz, 1H), 1.98-1.89 (m, 1H), 1.73-1.59 (m, 1H), 1.50-1.37 (m, 2H), 1.30-1.20 (m, 2H).

B-25 and B-26 described in Table 6 were synthesized by using corresponding commercially available reagents and by an operation similar to that in Reference Example B-24.

TABLE 6

| Ref. Example No. | Structural formula | MS(ESI) m/z (M + H)⁺ | NMR |
|---|---|---|---|
| B-25 | | 326 | ¹H NMR, (400 MHz, DMSO-d₆) δ 12.95 (s, 1H), 7.78 (dd, J = 9.2, 4.0 Hz, 1H), 7.65-7.57 (m, 2H), 7.39 (td, J = 9.3, 9.2, 2.8 Hz, 1H), 5.79-5.67 (m, 2H), 4.73 (dd, J = 4,9, 3.5 Hz, 1H), 4.11-3.92 (m, 2H), 2.58-2.44 (m, 2H). |
| B-26 | | 362 | ¹H NMR (400 MHz, DMSO-d₆) δ 13.33 (s, 1H), 7.75 (dd, J = 9.1, 4.2 Hz, 1H), 7.71 (d, J = 0.9 Hz, 1H), 7.60 (dd, J = 8.5, 2.7 Hz, 1H), 7.4.1-7.31 (m, 5H), 5.57 (d, J = 2.7 Hz, 1H), 4.89 (dd, J = 13.9, 2,7 Hz, 1H), 4.80 (d, J = 13.9 Hz, 1H). |

Reference Example B-27

Synthesis of (2S)-1-(4-chlorofuro[3,2-c]pyridin-2-yl)sulfonylpyrrolidine-2-carboxylic acid (B-27)

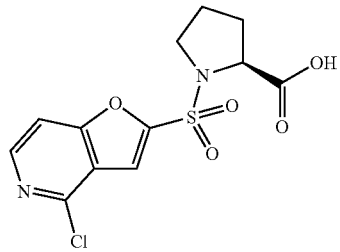 [SMILES: O=C(O)[C@@H]1CCCN1S(=O)(=O)c1cc2c(Cl)nccc2o1]

Water (12 mL) was added to L-proline (1.0 g, 8.8 mmol) and sodium hydroxide (0.64 g, 16 mmol) to dissolve them, and the mixture was stirred at 0° C. for 25 min. A solution of A-6 (2.0 g, 8.0 mmol) in tetrahydrofuran (18 mL) was slowly added, and the mixture was stirred for 40 min. To the reaction mixture was added 6 mol/L aqueous hydrochloric acid solution to adjust to pH4, and the insoluble material was collected by filtration, and dried to give the title compound (1.1 g, 3.3 mmol, 42%) as a white solid.

MS (ESI) m/z 331 (M+H)$^+$ $^1$H NMR (400 MHz, DMSO-d$_6$) δ 8.49 (d, J=6.0 Hz, 1H), 7.93 (dd, J=6.0, 0.8 Hz, 1H), 7.80 (d, J=0.8 Hz, 1H), 4.34-4.31 (m, 1H), 3.60-3.53 (m, 1H), 3.48-3.43 (m, 1H), 2.17-2.12 (m, 1H), 1.96-1.75 (m, 3H).

Reference Example B-28

Synthesis of (2S)-1-furo[3,2-c]pyridin-2-ylsulfonylpyrrolidine-2-carboxylic acid (B-28)

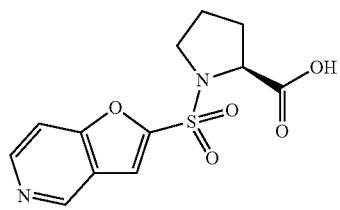 [SMILES: O=C(O)[C@@H]1CCCN1S(=O)(=O)c1cc2cnccc2o1]

B-27 (0.80 g, 2.4 mmol) was dissolved by adding acetic acid (25 mL) and tetrahydrofuran (25 mL), and 10% palladium/carbon (150 mg) was added. The reaction mixture was stirred under a hydrogen atmosphere at 70° C. for 4 hr, the catalyst was filtered off, ethyl acetate was added to the filtrate and the mixture was washed with water. The organic layer was dried over sodium sulfate, the desiccant was filtered off, and the solvent was evaporated and methanol (8 mL) was added to the obtained residue. The insoluble material was collected by filtration, and dried to give the title compound (0.30 g, 1.0 mmol, 42%) as a white solid.

MS (ESI) m/z 297 (M+H)$^+$ $^1$H NMR (400 MHz, DMSO-d$_6$) δ 12.92 (s, 1H), 9.12 (s, 1H), 8.66 (d, J=7.4 Hz, 1H), 7.87 (d, J=7.4 Hz, 1H), 7.82 (s, 1H), 4.31-4.28 (m, 1H), 3.57-3.52 (m, 1H), 3.44-3.38 (m, 1H), 2.14-2.09 (m, 1H), 1.96-1.84 (m, 2H), 1.76-1.72 (m, 1H).

Reference Example B-29

Synthesis of (2S)-2-(furo[3,2-c]pyridin-2-ylsulfonylamino)propanoic acid hydrochloride (B-29)

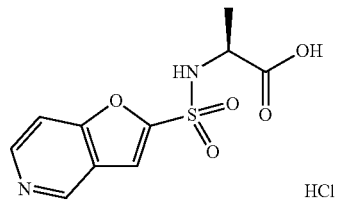 [SMILES: C[C@H](NS(=O)(=O)c1cc2cnccc2o1)C(=O)O ; Cl]

(step 1) Synthesis of (2S)-2-[(4-chlorofuro[3,2-c]pyridin-2-yl)sulfonylamino]propanoic acid To L-alanine tert-butyl hydrochloride (0.12 g, 0.67 mmol) and A-6 (0.20 g, 0.80 mmol) were added acetonitrile (10 mL) and triethylamine (0.21 mL, 1.5 mmol), and the mixture was stirred at room temperature for 2 hr. The reaction mixture was concentrated under reduced pressure and ethyl acetate (50 mL) was added to the obtained residue. The mixture was washed successively with saturated aqueous sodium hydrogen carbonate and saturated brine. The organic layer was dried over sodium sulfate, the desiccant was filtered off, and the solvent was evaporated. To the obtained residue was added trifluoroacetic acid (20 mL), and the mixture was stirred at room temperature for 1 hr. The reaction mixture was concentrated under reduced pressure and water was added to the obtained residue. The mixture was adjusted to pH10 with 2 mol/L aqueous sodium hydroxide solution and washed with dichloromethane. The aqueous layer was acidified with 6 mol/L hydrochloric acid, and the mixture was extracted with dichloromethane. The organic layer was dried over sodium sulfate, the desiccant was filtered off, and the solvent was evaporated to give the title compound (0.11 g, 0.36 mmol, 54%)

MS (ESI) m/z 305 (M+H)$^+$ $^1$H NMR (400 MHz, DMSO-d$_6$) δ 12.82-12.79 (m, 1H), 9.15 (d, J=11.6 Hz, 1H), 8.47 (d, J=7.6 Hz, 1H), 7.91-7.89 (m, 1H), 7.61 (d, J=0.8 Hz, 1H), 3.99-4.04 (m, 1H), 1.32-1.21 (m, 3H).

(step 2) Synthesis of (2S)-2-(furo[3,2-c]pyridin-2-ylsulfonylamino)propanoic acid hydrochloride (B-29)

To a solution of the compound (1.0 g, 3.3 mmol) obtained in step 1 in acetic acid (80 mL) was added zinc (0.67 g, 10 mmol) and the mixture was heated under reflux for 2 hr. The insoluble material was filtered off, the filtrate was concentrated under reduced pressure and the obtained residue was purified by high performance liquid chromatography (water-acetonitrile-hydrochloric acid) to give the title compound (0.14 g, 0.46 mmol, 14%).

MS (ESI) m/z 271 (M+H)$^+$ $^1$H NMR (400 MHz, DMSO-d$_6$) δ9.46 (s, 1H), 9.31 (d, J=8.4 Hz, 1H), 8.92 (d, J=6.4 Hz, 1H), 8.37 (d, J=6.4 Hz, 1H), 7.86 (s, 1H), 4.03 (dq, J=8.4, 7.2 Hz, 1H), 1.30 (d, J=7.2 Hz, 3H).

Reference Example B-30

Synthesis of (2S)-2-[(5-fluorobenzofuran-2-yl)sulfonyl-prop-2-ynl-amino]propanoic acid (B-30)

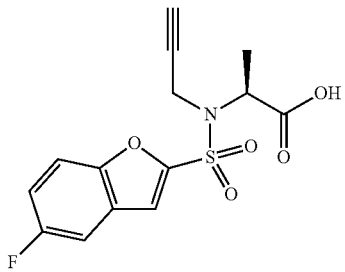 [SMILES: C#CCN([C@@H](C)C(=O)O)S(=O)(=O)c1cc2cc(F)ccc2o1]

To B-16 (0.10 g, 0.35 mmol) and potassium carbonate (0.14 g, 1.0 mmol) were added N,N-dimethylformamide (3 mL) and propargylbromide (28 L, 0.37 mmol) and the mixture was stirred at room temperature overnight. Using dichloromethane, the mixture was filtered through celite, and the solvent was evaporated. To the residue containing N,N-dimethylformamide was added 1 mol/L aqueous lithium hydroxide solution and the mixture was stirred at room temperature for 1 hr. The reaction mixture was neutralized with 1 mol/L aqueous trifluoroacetic acid solution, and purified by high performance liquid chromatography (water-acetonitrile, each containing 0.1% trifluoroacetic acid) to give the title compound (22 mg, 0.068 mmol, 20%)
MS (ESI) m/z 326 (M+H)$^+$

Reference Example B-31

Synthesis of (2S,4R)-1-(benzofuran-2-ylsulfonyl)-4-(dimethylamino)pyrrolidine-2-carboxylic acid (B-31)

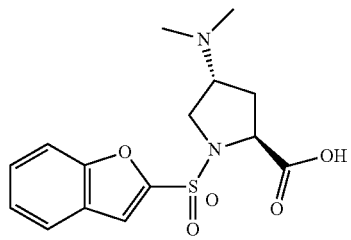

(step 1) Synthesis of (2S,4S)-4-(p-tolylsulfonyloxy)pyrrolidine-1,2-dicarboxylic acid O2-methyl O1-tert-butyl To a solution of N-Boc-cis-4-hydroxy-L-proline methyl ester (0.50 g, 2.0 mmol) in dichloromethane (10 mL) were added triethylamine (0.85 mL, 6.1 mmol), 4-dimethylaminopyridine (25 mg, 0.20 mmol) and p-toluenesulfonyl chloride (0.58 g, 3.1 mmol), and the mixture was stirred at room temperature overnight. 4-Dimethylaminopyridine (25 mg, 0.20 mmol) was added and the mixture was stirred for one more night, extracted with dichloromethane and 0.1 mol/L hydrochloric acid, washed with saturated sodium bicarbonate water, and saturated brine, and dried over anhydrous magnesium sulfate. The mixture was concentration under reduced pressure, and the obtained residue was purified by silica gel chromatography (hexane/ethyl acetate) to give the title compound (800 mg, 2.0 mmol, 98%).

(step 2) Synthesis of methyl (2S,4R)-4-(dimethylamino)pyrrolidine-2-carboxylate hydrochloride To the compound (110 mg, 0.28 mmol) obtained in step 1 were added acetonitrile (1 mL), 2 mol/L dimethylamine (tetrahydrofuran solution, 1.5 mL) and the mixture was stirred using a microwave reactor at 160° C. for 1 hr. A similar operation was performed 3 times in total, and 3 batches of the reaction mixture were combined and the solvent was evaporated under reduced pressure. The obtained residue was purified by high performance liquid chromatography (water-acetonitrile-hydrochloric acid), and dissolved in dichloromethane (1.3 mL). 4 mol/L Hydrochloric acid/1,4-dioxane (2.3 mL) was added and the mixture was stirred at room temperature for 6 hr. The mixture was concentration under reduced pressure, acetonitrile and water were added, and the mixture was freeze-dried to give the title compound.
MS (ESI) m/z 273 [M+H]$^+$ (step 3) Synthesis of (2S,4R)-1-(benzofuran-2-ylsulfonyl)-4-(dimethylamino)pyrrolidine-2-carboxylic acid (B-31)

The compound obtained in step 2 was diluted with dichloromethane (7 mL), N,N-diisopropylethylamine (0.54 mL, 3.1 mmol) and benzofuran-2-sulfonylchloride (0.13 g, 0.62 mmol) were added and the mixture was stirred at room temperature for 1 hr 45 min The reaction mixture was extracted with saturated sodium bicarbonate water and dichloromethane, washed with saturated brine, and dried over anhydrous magnesium sulfate. The mixture was concentrated under reduced pressure and the obtained compound was dissolved in 1,4-dioxane (6 mL), 1 mol/L aqueous lithium hydroxide solution (0.62 mL) was added and the mixture was stirred at room temperature for 1 hr. Furthermore, 1 mol/L aqueous lithium hydroxide solution (0.62 mL) was added and the mixture was stirred for 1 hr, and neutralized with 1 mol/L aqueous trifluoroacetic acid solution. The solvent was evaporated under reduced pressure. The obtained residue was purified by high performance liquid chromatography (water-acetonitrile, each containing 0.1% trifluoroacetic acid) to give trifluoroacetate of the title compound (164 mg, 0.36 mmol, 42%).
MS (ESI) m/z 339 [M+H]$^+$

Reference Example B-38

Synthesis of (2S)-1-furo[2,3-c]pyridin-2-ylsulfonylpyrrolidine-2-carboxylic acid (B-38)

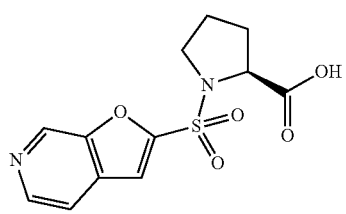 [SMILES: O=C(O)[C@@H]1CCCN1S(=O)(=O)c1cc2ccncc2o1]

(step 1) Synthesis of (E)-3-(3-furyl)prop-2-enoic acid

3-Furaldehyde (10.0 g, 104 mmol) and malonic acid (15.0 g, 144 mmol) were dissolved in pyridine (12 mL) and the mixture was stirred at 85° C. for 2 hr, poured into ice water, and weakly acidified with 1 mol/L hydrochloric acid. The precipitated crystals were collected by filtration, dissolved in ethyl acetate, washed with 1 mol/L hydrochloric acid, and the organic layer was dried over magnesium sulfate. The desiccant was filtered off, and the solvent was evaporated to give the title compound (10.0 g, 72.4 mmol, 70%) as a white solid.

$^1$H NMR (400 MHz, DMSO-$d_6$) δ 12.26 (s, 1H), 8.08 (s, 1H), 7.73 (s, 1H), 7.49 (d, J=15.6 Hz, 1H), 6.94-6.93 (m, 1H), 6.25 (d, J=15.6 Hz, 1H).

(step 2) Synthesis of 6H-furo[2,3-c]pyridin-7-one

The compound (5.00 g, 36.2 mmol) obtained in step 1 and triethylamine (4.30 g, 42.5 mmol) were dissolved in acetone (50 mL). Ethyl chloroformate (5.20 g, 47.9 mmol) was added and the mixture was stirred at 0° C. for 1 hr, an aqueous solution (15 mL) of sodium azide (3.50 g, 53.8 mmol) was added dropwise and the mixture was stirred at 0° C. for 1 hr. 150 mL of ice water was added and the mixture was extracted with toluene. The organic layer was dried over magnesium sulfate, the desiccant was filtered off. The solvent was evaporated to about 20 mL while maintaining the liquid temperature at less than 30° C. The obtained solution was added dropwise to a mixed solution of diphenylmethane (40 mL) and tributylamine (7 mL), and the mixture was heated at 220° C. for 1.5 hr. To maintain 220° C. during heating, heating was performed while removing toluene. The mixture was cooled, hexane was added and the precipitated crystals were collected by filtration, washed with ethyl acetate, and dried to give the title compound (750 mg, 5.55 mmol, 15%) as a white solid.

(step 3) Synthesis of 7-chlorofuro[2,3-c]pyridine

The compound (750 mg, 5.55 mmol) obtained in step 2 and phosphorus oxychloride (1.30 g, 8.48 mmol) were placed in a two necked pear-shaped flask after drying by heating, and the mixture was heated under reflux under a nitrogen atmosphere for about 3-4 hr. The reaction mixture was cooled to room temperature, poured into 100 mL of ice water, basified with 10% aqueous sodium hydroxide solution and extracted 3 times with diethyl ether (100 mL). The organic layer was dried over sodium sulfate, the desiccant was filtered off, and the solvent was evaporated and the obtained residue was purified by silica gel chromatography (pentane/ethyl acetate) to give the title compound (700 mg, 4.56 mmol, 82%).

$^1$H NMR (300 MHz, CDCl$_3$) δ 8.22 (d, J=5.1 Hz, 1H), 7.83 (d, J=2.4 Hz, 1H), 7.52 (d, J=5.1 Hz, 1H), 6.89 (d, J=2.1 Hz, 1H).

(step 4) Synthesis of 7-chlorofuro[2,3-c]pyridine-2-sulfonyl chloride

A solution of the compound (760 mg, 4.95 mmol) obtained in step 3 in tetrahydrofuran (40 mL) was cooled to −40° C. under a nitrogen atmosphere, 2.5 mol/L n-butyllithium (hexane solution, 2.2 mL, 5.5 mmol) was added and the mixture was stirred for 1 hr. While maintaining the temperature at −40° C.--70° C., sulfur dioxide was blown into the reaction mixture for 30 min, and the mixture was stirred at room temperature for 90 min. Hexane was added to the reaction mixture, and the insoluble material was collected by filtration and dried. To the obtained solid were added dichloromethane (50 mL) and N-chlorosuccinimide (748 mg, 5.4 mmol) at 0° C. and the mixture was stirred at room temperature for 1 hr, and the insoluble material was filtered off. The filtrate was concentrated under reduced pressure to give the title compound (600 mg, 2.38 mmol, 48%).

(step 5) Synthesis of (2S)-1-(7-chlorofuro[2,3-c]pyridin-2-yl)sulfonylpyrrolidine-2-carboxylic acid Water (3 mL) was added to L-proline (275 mg, 2.39 mmol) and sodium hydroxide (240 mg, 6.00 mmol) to dissolve them, and the mixture was stirred at 0° C. for 25 min. A solution of the compound (600 mg, 2.38 mmol) obtained in step 4 in tetrahydrofuran (10 mL) was slowly added, and the mixture was stirred for 40 min. The reaction mixture was concentrated, and extracted with dichloromethane. To the organic layer was adjusted to pH3-4 by slowly adding 1 mol/L aqueous hydrochloric acid solution, and the insoluble material was collected by filtration, and the filtrate was concentrated under reduced pressure to give the title compound (196 mg, 0.593 mmol, 25%) as a white solid.

$^1$H NMR (300 MHz, DMSO-$d_6$) δ 12.9 (s, 1H), 8.36 (d, J=5.2 Hz, 1H), 7.88 (d, J=5.2 Hz, 1H), 7.84 (s, 1H), 4.32-4.29 (m, 1H), 3.59-3.56 (m, 1H), 3.48-3.32 (m, 1H), 2.17-2.16 (m, 1H), 1.99-1.81 (m, 3H).

(step 6) Synthesis of (2S)-1-furo[2,3-c]pyridin-2-ylsulfonylpyrrolidine-2-carboxylic acid (B-38)

To the compound (196 mg, 0.593 mmol) obtained in step 5 was dissolved in acetic acid (10 mL) and tetrahydrofuran (10 mL), and 10% palladium/carbon (196 mg) was added. The reaction mixture was stirred under a hydrogen atmosphere at 70° C. for 10 hr, and the catalyst was filtered off. The filtrate was concentrated under reduced pressure, and the residue was purified by high performance liquid chromatography (water-acetonitrile) to give the title compound (0.30 g, 1.0 mmol, 42%) as a white solid.

MS (ESI) m/z 297 (M+H)$^+$ $^1$H NMR (400 MHz, DMSO-$d_6$) δ 12.92-12.91 (m, 1H), 9.15 (s, 1H), 8.54 (d, J=5.2 Hz, 1H), 7.89-7.86 (m, 1H), 7.75 (s, 1H), 4.32-4.30 (m, 1H), 3.59-3.54 (m, 1H), 3.52-3.41 (m, 1H), 2.18-2.09 (m, 1H), 1.98-1.78 (m, 2H), 1.77-1.71 (m, 1H)

Reference Example B-39

Synthesis of 2-[(5-fluorobenzofuran-2-yl)sulfonylisopropylamino]acetic acid (B-39)

(step 1) Synthesis of 5-fluoro-N-isopropyl-benzofuran-2-sulfonamide

To isopropylamine (85.9 mg, 1.0 mmol) and A-3 (234 mg, 1.0 mmol) were added acetonitrile (10 mL), triethylamine (0.21 mL, 1.5 mmol) and the mixture was stirred at room temperature for 30 min. Water was added to the reaction mixture, and the mixture was extracted with dichloromethane. The organic layer was dried over sodium sulfate. The desiccant was filtered off, and the solvent was evaporated to give the title compound (122 mg, 0.475 mmol, 48%).

MS (ESI) m/z 258 (M+H)$^+$ (step 2) 2-[(5-fluorobenzofuran-2-yl)sulfonylisopropylamino]acetic acid (B-39)

The compound (122 mg, 0.475 mmol) obtained in step 1, methyl bromoacetate (43.8 μL, 0.475 mmol) and potassium carbonate (65.6 mg, 0.475 mmol) were dissolved in acetonitrile (5 mL) and the mixture was stirred at 40° C. overnight. 2 mol/L Aqueous sodium hydroxide solution (500 μL) was added at room temperature and the mixture was stirred for 3 hr. The mixture was washed with dichloromethane, and the aqueous layer was acidified with 1 mol/L hydrochloric acid to about pH3, and extracted with dichloromethane. The organic layer was dried over sodium sulfate. The desiccant was filtered off, and the solvent was evaporated to give the title compound (117 mg, 0.372 mmol, 78%).

MS (ESI) m/z 316 (M+H)$^+$ $^1$H NMR (400 MHz, DMSO-d$_6$) δ 12.76 (s, 1H), 7.80 (dd, J=9.1, 4.1 Hz, 1H), 7.65-7.57 (m, 2H), 7.40 (td, J=9.2, 2.8 Hz, 1H), 4.13 (h, J=6.7 Hz, 1H), 3.99 (s, 2H), 1.03 (d, J=6.7 Hz, 6H).

B-40 described in Table 7 was synthesized by using corresponding commercially available reagents and A-3 and by an operation similar to that in Reference Example B-39.

(step 1) Synthesis of benzyl 2-(benzylamino)acetate

To a solution of benzylamine (54 mg, 0.50 mmol) in acetonitrile (4 mL) was added potassium carbonate (69 mg, 0.50 mmol) and the mixture was cooled to −10° C. to −15° C. Benzyl bromoacetate (0.078 mL, 0.50 mmol) diluted with acetonitrile (1 mL) was added dropwise, and the mixture was warmed to room temperature and stirred overnight. The insoluble material was filtered off, and the solvent was evaporated under reduced pressure to give the title compound.

(step 2) Synthesis of 2-[benzyl-(5-fluorobenzofuran-2-yl)sulfonyl-amino]acetic acid (B-41)

To the compound (0.13 g, 0.50 mmol) obtained in step 1 and A-3 (0.14 g, 0.60 mmol), triethylamine (0.10 mL, 0.75

TABLE 7

| Ref. Example No. | Structural formula | MS(ESI) m/z (M + H)$^+$ | NMR |
|---|---|---|---|
| B-39 | | 316 | $^1$H NMR (400 MHz, DMSO-d$_5$) δ 12.76 (s, 1H), 7.80 (dd, J = 9.1, 4.1 Hz, 1H), 7.65-7.57 (m, 2H), 7.40 (td, J = 9.2, 2.8 Hz, 1H), 4.13 (h, J = 6.7 Hz. 1H), 3.99 (s, 2H), 1.03 (d, J = 6.7 Hz, 6H). |
| B-40 | | 328 | — |

Reference Example B-41

Synthesis of 2-[benzyl-(5-fluorobenzofuran-2-yl)sulfonyl-amino]acetic acid (B-41)

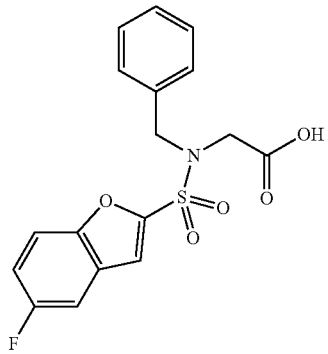 [SMILES: O=C(O)CN(Cc1ccccc1)S(=O)(=O)c1cc2cc(F)ccc2o1]

mmol) was added acetonitrile (3 mL) and the mixture was stirred at room temperature for 3 hr. Thereafter, saturated aqueous sodium hydrogen carbonate solution was added, and the mixture was extracted with dichloromethane. The organic layer was dried over sodium sulfate. The desiccant was filtered off, and the solvent was evaporated. To the obtained residue were added tetrahydrofuran (1 mL) and 2 mol/L aqueous sodium hydroxide solution (1 mL), several drops of methanol were added and the mixture was stirred for 30 min. The mixture was acidified with 1 mol/L hydrochloric acid, water was added and the mixture was extracted with dichloromethane. The organic layer was dried over sodium sulfate, and the desiccant was filtered off, and the solvent was evaporated to give the title compound (0.14 g, 0.38 mmol, 76%).

MS (ESI) m/z 364 (M+H)$^+$

B-42 to B-48 described in Table 8 were synthesized by using corresponding commercially available reagents and by an operation similar to that in Reference Example B-41,

TABLE 8

| Ref. Example No. | Structural formula | MS(ESI) m/z (M + H)+ | NMR |
|---|---|---|---|
| B-42 | | 355 | — |
| B-43 | | 365 | — |
| B-44 | | 332 | — |
| B-45 | | 360 | — |
| B-46 | | 366 | — |
| B-47 | | 471 | — |
| B-48 | | 457 | — |

Reference Example B-49

Synthesis of 2-[furo[3,2-c]pyridin-2-ylsulfonyl(isopropyl)amino]acetic acid hydrochloride (B-49)

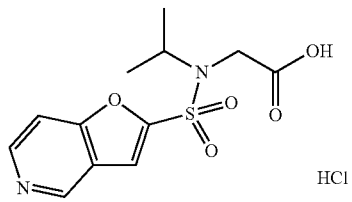 [SMILES: CC(C)N(CC(=O)O)S(=O)(=O)c1cc2cnccc2o1 ; Cl]

(step 1) Synthesis of ethyl 2-(isopropylamino)acetate

To a solution of isopropylamine (4.4 g, 75 mmol) in ether (100 mL) was added ethyl bromoacetate (6.26 g, 37.5 mmol) and the mixture was stirred at room temperature for 12 hr. The insoluble material was filtered off, and the filtrate was concentrated under reduced pressure to give the title compound (4.89 g, 33.7 mmol, 90%).

$^1$H NMR (300 MHz, CDCl$_3$) δ 4.16-4.11 (m, 2H), 3.47 (s, 2H), 2.79-2.71 (m, 1H), 1.25-1.19 (m, 3H), 1.03 (d, J=3.9 Hz, 6H).

(step 2) Synthesis of ethyl 2-[(4-chlorofuro[3,2-c]pyridin-2-yl)sulfonyl-isopropyl-amino]acetate A solution of the compound (1.74 g, 12.0 mmol) obtained in step 1, A-6 (3.02 g, 24.0 mmol) and pyridine (9 mL) in dichloromethane (25 mL) was stirred at room temperature overnight, and the solvent was evaporated. The residue was purified by silica gel chromatography (pentane/ethyl acetate) to give the title compound (800 mg, 2.21, 18%).

MS (ESI) m/z 361 (M+H)$^+$ (step 3) Synthesis of ethyl 2-[furo[3,2-c]pyridin-2-ylsulfonyl(isopropyl)amino]acetate The compound (600 mg, 1.67 mmol) obtained in step 2 was dissolved in acetic acid (25 mL) and tetrahydrofuran (25 mL), and 10% palladium/carbon (120 mg) was added. The reaction mixture was stirred under a hydrogen atmosphere at 70° C. for 1 hr, and the catalyst was filtered off. Ethyl acetate was added and the mixture was washed with water. The organic layer was dried over sodium sulfate, the desiccant was filtered off, and the solvent was evaporated. To the obtained residue was added methanol (8 mL), and the insoluble material was collected by filtration. The filtrate was dried to give the title compound (210 mg, 0.643 mmol, 38%) as a white solid.

MS (ESI) m/z 327 (M+H)$^+$ (step 4) Synthesis of 2-[furo[3,2-c]pyridin-2-ylsulfonyl(isopropyl)amino]acetic acid hydrochloride (B-49)

To the compound (210 mg, 0.643 mmol) obtained in step 3 was added methanol (5 mL) and 2 mol/L aqueous lithium hydroxide solution (3 mL), and the mixture was stirred at room temperature for 2 hr. The mixture was acidified to pH4-5 with 4 mol/L hydrochloric acid and the resulting precipitate was collected by filtration. The filtrate was dried to give the title compound (120 mg, 0.402 mmol, 63%) as a white solid.

MS (ESI) m/z 299 (M+H)$^+$ $^1$H NMR (300 MHz, DMSO-d$_6$) δ 9.36 (s, 1H), 8.84 (d, J=6.3 Hz, 1H), 8.23 (d, J=4.5 Hz, 1H), 7.79 (s, 1H), 4.19-4.15 (m, 1H), 4.03 (s, 2H), 1.06 (d, J=6.9 Hz, 6H).

Reference Example C-1

Synthesis of (2S)-1-(benzofuran-2-ylsulfonyl)-N-[(3-hydroxyphenyl)methyl]pyrrolidine-2-carboxyamide (C-1)

To B-1 (15 g, 51 mmol), 3-(aminomethyl)phenol (9.7 g, 61 mmol), WSC hydrochloride (8.7 g, 56 mmol) and 1-hydroxybenzotriazole (7.6 g, 56 mmol) were added dichloromethane (300 mL) and N-ethyldiisopropylamine (14.4 g, 172 mmol) and the mixture was stirred at room temperature overnight. Water was added to the reaction mixture, and the mixture was extracted with dichloromethane. The organic layer was dried over sodium sulfate, the desiccant was filtered off, and the solvent was evaporated. The obtained residue was purified by silica gel column chromatography (hexane/ethyl acetate) to give the title compound (4.63 g, 11.6 mmol, 23%).

MS (ESI) m/z 401 (M+H)$^+$ $^1$H NMR (400 MHz, CD$_3$OD) δ 7.81 (d, J=8.0 Hz, 1H), 7.64 (dd, J=8.4, 0.8 Hz, 1H), 7.59 (d, J=0.8 Hz, 1H), 7.55 (td, J=8.4, 1.2 Hz, 1H), 7.44-7.40 (m, 1H), 7.15 (t, J=8.0 Hz, 1H), 6.82 (d, J=7.6 Hz, 1H), 6.78 (d, J=2.0 Hz, 1H), 6.70 (dd, J=8.0, 1.6 Hz, 1H), 4.43-4.39 (m, 3H), 3.71-3.68 (m, 1H), 3.57-3.52 (m, 1H), 2.07-1.94 (m, 3H), 1.76-1.72 (m, 1H)

C-2 described in Table 9 was synthesized by using B-4 and corresponding commercially available reagents and by an operation similar to that in Reference Example C-1.

TABLE 9

| Ref. Example No. | Structural formula | MS(ESI) m/z (M + H)$^+$ | NMR |
|---|---|---|---|
| C-1 | | 401 | $^1$H NMR (400 MHz, CD$_3$OD) δ 7.81 (d, J = 8.0 Hz, 1H), 7.64 (dd, J = 8.4, 0.8 Hz, 1H), 7.59 (d, J = 0.8 Hz, 1H), 7.55 (td, J = 8.4, 1.2 Hz, 1H), 7.44-7.40 (m, 1H), 7.15 (t, J = 8.0 Hz, 1H), 6.82 (d, J = 7.6 Hz, 1H), 6.78 (d, J = 2.0 Hz, 1H), 6.70 (dd, J = 8.0, 1.6 Hz, 1H), 4.43-4.39 (m, 3H), 3.71-3.68 (m, 1H), 3.57-3.52 (m, 1H), 2.07-1.94 (m, 3H), 1.76-1.72 (m, 1H). |

| Ref. Example No. | Structural formula | MS(ESI) m/z (M + H)+ | NMR |
|---|---|---|---|
| C-2 | | 419 | ¹H NMR (400 MHz, CD₃OD) δ 7.65 (dd, J = 8.8, 4.0 Hz, 1H), 7.57 (d, J = 0.8 Hz, 1H), 7.52 (dd, J = 8.0, 2.8 Hz, 1H), 7.32 (dt, J = 9.2, 2.8 Hz, 1H), 7.15 (t, J = 8.0 Hz, 1H), 6.81 (d, J = 7.6 Hz, 1H), 6.77 (d, J = 2.0 Hz, 1H), 6.70 (dd, J = 8.0, 2.0 Hz, 1H), 4.42-4.38 (m, 3H), 3.73-3.68 (m, 1H), 3.57-3.52 (m, 1H), 2.08-1.94 (m, 3H), 1.78-1.74 (m, 1H). |

Reference Example C-3

Synthesis of (2S)-1-(5-fluorobenzofuran-2-ylsulfonyl)-N-[(3-fluoro-5-hydroxyphenyl)methyl]pyrrolidine-2-carboxyamide (C-3)

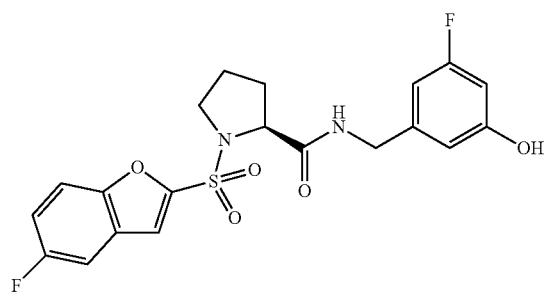 [SMILES: O=C(NCc1cc(O)cc(F)c1)[C@@H]1CCCN1S(=O)(=O)c1cc2cc(F)ccc2o1]

(step 1) Synthesis of 3-(aminomethyl)-5-fluorophenol

To a solution of 3-fluoro-5-hydroxybenzonitrile (4.5 g, 33 mmol) in ethanol (50 mL) were added 10%-palladium/carbon (0.45 g) and concentrated hydrochloric acid (12 mL), and the mixture was stirred under a hydrogen atmosphere at room temperature overnight. The catalyst was filtered off and the mixture was concentrated under reduced pressure to give the title compound (4.52 g, 25 mmol, 77%).

MS (ESI) m/z 143 (M+H)+

(step 2) Synthesis of (2S)-1-(5-fluorobenzofuran-2-ylsulfonyl)-N-[(3-fluoro-5-hydroxyphenyl)methyl]pyrrolidine-2-carboxyamide (C-3)

To the compound (1.7 g, 9.6 mmol) obtained in step 1, B-4 (1.5 g, 4.8 mmol), WSC hydrochloride (0.97 g, 6.2 mmol) and 1-hydroxybenzotriazole (0.84 g, 6.2 mmol) were added dichloromethane (50 mL) and triethylamine (1.5 g, 14 mmol) and the mixture was stirred at room temperature overnight. Water was added to the reaction mixture, and the mixture was extracted with dichloromethane. The organic layer was dried over sodium sulfate, the desiccant was filtered off, and the solvent was evaporated. The obtained residue was purified by silica gel column chromatography (hexane/ethyl acetate) to give the title compound (0.39 g, 0.89 mmol, 18%).

MS (ESI) m/z 437 (M+H)+

¹H NMR (400 MHz, DMSO-d₆) δ 9.93 (s, 1H), 8.67 (t, J=6.1 Hz, 1H), 7.80 (dd, J=9.2, 4.2 Hz, 1H), 7.69 (d, J=0.9 Hz, 1H), 7.65 (dd, J=8.5, 2.7 Hz, 1H), 7.43 (td, J=9.2, 2.7 Hz, 1H), 6.56-6.48 (m, 2H), 6.43 (dt, J=10.8, 2.3 Hz, 1H), 4.34-4.12 (m, 3H), 3.66-3.55 (m, 1H), 3.43-3.34 (m, 1H), 2.01-1.81 (m, 3H), 1.72-1.60 (m, 1H).

Reference Example C-4

Synthesis of (2S)-1-(benzofuran-2-ylsulfonyl)-N-[(2-chloro-4-pyridyl)methyl]pyrrolidine-2-carboxyamide (C-4)

To B-1 (4.11 g, 13.9 mmol), 4-aminomethyl-2-chloropyridine hydrochloride (3.00 g, 16.8 mmol), WSC hydrochloride (2.38 g, 15.3 mmol) and 1-hydroxybenzotriazole (2.07 g, 15.3 mmol) were added dichloromethane (100 mL) and N-ethyldiisopropylamine (7.19 g, 55.7 mmol) and the mixture was stirred at room temperature overnight. Water was added to the reaction mixture, and the mixture was extracted with dichloromethane. The organic layer was dried over sodium sulfate, the desiccant was filtered off, and the solvent was evaporated. The obtained residue was purified by silica gel column chromatography (hexane/ethyl acetate) to give the title compound (3.50 g, 8.35 mmol, 60%).

MS (ESI) m/z 420 (M+H)+

¹H NMR (400 MHz, CD₃OD): δ 8.30 (d, J=5.2 Hz, 1H), 7.81 (d, J=7.6 Hz, 1H), 7.66-7.62 (m, 2H), 7.58-7.53 (m, 1H), 7.48 (s, 1H), 7.43-7.36 (m, 2H), 4.59-4.43 (m, 2H), 4.42-4.40 (m, 1H), 3.75-3.69 (m, 1H), 3.58-3.52 (m, 1H), 2.10-1.93 (m, 3H), 1.77-1.71 (m, 1H).

C-5 and C-10 to C-12 described in Table 10 were synthesized by using B-1, B-4, and corresponding commercially available reagents and by an operation similar to that in Reference Example C-4.

TABLE 10

| Ref. Example No | Structural formula | MS(ESI) m/z (M + H)+ | NMR |
|---|---|---|---|
| C-4 | | 420 | ¹H NMR (400 MHz, CD₃OD): δ 8.30 (d, J = 5.2 Hz, 1H), 7.81 (d, J = 7.6 Hz, 1H), 7.66-7.62 (m, 2H), 7.56-7.53 (m, 1H), 7.48 (s, 1H), 7.43-7.36 (m, 2H), 4.59-4.43 (m, 2H), 4.42-4.40 (m, 1H), 3.75-3.69 (m, 1H), 3.58-3.52 (m, 1H), 2.10-1.93 (m, 3H), 1.77-1.71 (m, 1H). |
| C-5 | | 438 | ¹H NMR (300 MHz, CD₃OD): δ 8.30 (d, J = 5.4 Hz, 1H), 7.66 (dd, J = 9.0, 4.2 Hz, 1H). 7.61 (s, 1H), 7.52 (dd, J = 8.7, 2.7 Hz, 1H), 7.48 (s, 1H), 7.37-7.29 (m, 2H), 4.59-4.37 (m, 3H), 3.74-3.70 (m, 1H), 3.58-3.52 (m, 1H), 2.09-1.94 (m, 3H), 1.77-1.73 (m, 1H). |
| C-10 | | 523 | — |
| C-11 | | 463 | ¹H NMR (400 MHz, DMSO-d₆) δ 8.70 (t, J = 6.1, 6.1 Hz, 1H), 7.83 (d, J = 7.8 Hz, 1H), 7.78-7.69 (m, 2H), 7.60-7.48 (m, 3H), 7,46-7.38 (m, 1H), 7.24 (d, J = 8.4 Hz, 2H), 4.35-4.20 (m, 3H), 3.59 (q, J = 7.1, 5.5, 5.4 Hz, 1H), 3.44-3.38 (m, 1H), 1.98-1.78 (m. 3H), 1.70-1.57 (m, 1H). |
| C-12 | | 481 | ¹H NMR (400 MHz, DMSO-d₆) δ 8.73 (t, J = 6.0, 6.0 Hz, 1H), 7.99-7.88 (m, 1H), 7.84 (d, J = 7.6 Hz, 1H), 7.80-7.69 (m, 2H), 7.60-7.37 (m, 2H), 7.19 (dd, J = 9.9, 8.6 Hz, 1H), 6.98-6.79 (m, 1H), 4.45-4.23 (m, 3H), 3.65-3.57 (m, 1H), 3.45-3.37 (m, 1H), 2.02-1.79 (m, 3H), 1.74-1.57 (m, 1H). |

Reference Example C-6

Synthesis of (2S)—N-[(5-bromo-3-pyridyl)methyl]-1-(5-fluorobenzofuran-2-ylsulfonyl)-pyrrolidine-2-carboxyamide (C-6)

(step 1) Synthesis of 3-aminomethyl-5-bromopyridine

To 5-bromo-3-cyanopyridine (15 g, 82 mmol) and cobalt (II) chloride 6 hydrate (2.0 g, 8.2 mmol) were added tetrahydrofuran (100 mL) and water (50 mL), and the mixture was cooled to 0° C. and sodium tetrahydroborate (6.3 g, 0.17 mol) was added. The mixture was stirred at room temperature for 1.5 hr, the reaction mixture was acidified with 3 mol/L aqueous hydrochloric acid solution and stirred for 1 hr. Tetrahydrofuran was evaporated from the reaction mixture under reduced pressure, and washed with diethyl ether. The aqueous layer was alkalified with aqueous ammonia, and extracted with dichloromethane. The organic layer was washed with saturated brine, dried over sodium sulfate, the desiccant was filtered off and the solvent was evaporated to give the title compound (5.0 g, 27 mmol, 33%).

MS (ESI) m/z 187 (M+H)$^+$ (step 2) Synthesis of (2S)—N-[(5-bromo-3-pyridyl)methyl]-1-(5-fluorobenzofuran-2-ylsulfonyl)-pyrrolidine-2-carboxyamide (C-6)

To a solution of B-4 (4.0 g, 13 mmol) in dichloromethane (20 mL) was added thionyl chloride (5 mL), and the mixture was stirred at 50° C. for 2 hr. The reaction mixture was concentrated under reduced pressure and, to the obtained residue were added dichloromethane (40 mL), the compound (4.7 g, 26 mmol) obtained in step 1 and pyridine (5 mL)/dichloromethane (20 mL). After stirring at room temperature for 30 min, the mixture was concentrated under reduced pressure and the obtained residue was purified by high performance liquid chromatography (water-acetonitrile, each containing 0.1% trifluoroacetic acid) to give the title compound (1.4 g, 2.9 mmol, 23%).

MS (ESI) m/z 482 (M+H)$^+$ $^1$H NMR (300 MHz, CD$_3$OD): δ 8.53 (dd, J=10.8, 1.8 Hz, 2H), 8.03 (d, J=1.8 Hz, 1H), 7.65 (dd, J=9.3, 0.9 Hz, 1H), 7.58 (s, 1H), 7.52 (dd, J=8.4, 2.7 Hz, 1H), 7.32 (td, J=9.0, 2.7 Hz, 1H), 4.57-4.34 (m, 3H), 3.74-3.67 (m, 1H), 3.57-3.49 (m, 1H), 2.10-1.90 (m, 3H), 1.78-1.70 (m, 1H).

C-7 described in Table 11 was synthesized by using B-4 and corresponding commercially available reagents and by an operation similar to that in Reference Example C-6.

TABLE 11

| Ref. Example No. | Structural formula | MS(ESI) m/z (M + H)$^+$ | NMR |
|---|---|---|---|
| C-6 | | 482 | $^1$H NMR (300 MHz, CD$_3$OD): δ 8.53 (dd, J = 10.8, 1.8 Hz, 2H), 8.03 (d, J = 1.8 Hz, 1H), 7.65 (dd, J = 9.3, 0.9 Hz, 1H), 7.58 (s, 1H), 7.52 (dd, J = 8.4, 2.7 Hz, 1H), 7.32 (td, J = 9.0, 2.7 Hz, 1H), 4.57-4.34 (m, 3H), 3.74-3.67 (m, 1H), 3.57-3.49 (m, 1H), 2.10-1.90 (m, 3H), 1.78-1.70 (m, 1H). |
| C-7 | | 438 | $^1$H NMR (300 MHz, CD$_3$OD): δ 7.79 (t, J = 7.8 Hz, 1H), 7.66 (dd, J = 9.0, 3.3 Hz, 1H), 7.60 (d, J = 0.6 Hz, 1H), 7.52 (dd, J = 8.1, 2.4 Hz, 1H), 7.43-7.40 (m, 1H), 7.36-7.23 (m, 2H), 4.59-4.40 (m, 3H), 3.77-3.70 (m, 1H), 3.57-3.51 (m, 1H), 2.11-1.97 (m, 3H), 1.80-1.72 (m, 1H). |

Reference Example C-8

Synthesis of (2S)—N-[(4-chloro-2-pyridyl)methyl]-1-(5-fluorobenzofuran-2-ylsulfonyl)-pyrrolidine-2-carboxyamide (C-8)

Using 3-aminomethyl-5-bromopyridine instead of 2-aminomethyl-4-chloropyridine, and by an operation similar to that in Reference Example C-6, step 2, the title compound (yield 19%) was obtained. MS (ESI) m/z 438 (M+H)$^+$ $^1$H NMR (300 MHz, CD$_3$OD): δ 8.31 (d, J=5.4 Hz, 1H), 7.65 (dd, J=9.0, 3.9 Hz, 1H), 7.60 (s, 1H), 7.56 (s, 1H), 7.51 (dd, J=7.8, 2.4 Hz, 1H), 7.37-7.30 (m, 2H), 4.63-4.38 (m, 3H), 3.75-3.68 (m, 1H), 3.58-3.52 (m, 1H), 2.07-1.94 (m, 3H), 1.77-1.73 (m, 1H).

C-9 described in Table 12 was synthesized by using B-1 and corresponding commercially available reagents and by an operation similar to that in Reference Example C-8.

TABLE 12

| Ref. Example No. | Structural formula | MS(ESI) m/z (M + H)+ | NMR |
|---|---|---|---|
| C-8 | | 438 | ¹H NMR (300 MHz, CD₃OD): δ 8.31 (d, J = 5.4 Hz, 1H), 7.65 (dd, J = 9.0, 3.9 Hz, 1H), 7.60 (s, 1H), 7.56 (s, 1H), 7.51 (dd, J = 7.8, 2,4 Hz, 1H), 7.37-7.30 (m, 2H), 4.63-4.38 (m, 3H), 3.75-3.68 (m, 1H), 3.58-3.52 (m, 1H), 2.07-1.94, (m, 3H), 1.77-1.73 (m, 1H). |
| C-9 | | 420 | ¹H NMR (300 MHz, CD₃OD): δ 8.44 (d, J = 5.1 Hz, 1H), 7.81 (d, J = 7.5 Hz, 1H), 7.67-7.52 (m, 4H), 744-7.36 (m, 2H), 4.66- 452 (m, 2H), 446-4.40 (m, 1H), 3.75-3.72 (rn, 1H), 3.56-3.53 (m, 1H), 2.09-1.96 (m, 3H), 1.75-1.72 (m, 1H). |

Reference Example D-1

Synthesis of 3-(benzyloxy)benzylamine hydrochloride (D-1)

(step 1) Synthesis of 3-benzyloxybenzonitrile

To 3-hydroxybenzonitrile (10.0 g, 84.0 mmol), benzyl bromide (15.8 g, 92.8 mmol) and potassium carbonate (40.6 g, 294 mmol) was added N,N-dimethylformamide (200 mL), and the mixture was stirred at 80° C. overnight. To the reaction mixture was added water, and the mixture was extracted with ethyl acetate. The organic layer was washed with saturated brine, and dried over sodium sulfate. The desiccant was filtered off, and the solvent was evaporated. The obtained residue was purified by silica gel column chromatography (petroleum ether/ethyl acetate) to give the title compound (16.0 g, 76.6 mmol, 91%).
MS(ESI) m/z 210 (M+H)⁺
¹H NMR (400 MHz, CDCl₃): δ7.41-7.35 (m, 6H), 7.26-7.19 (m, 3H), 5.08 (s, 2H).

(step 2) Synthesis of 3-(benzyloxy)benzylamine

To a solution of the compound (5.0 g, 24 mmol) obtained in step 1 in tetrahydrofuran (50 mL) was added 1 mol/L lithium aluminum hydride (tetrahydrofuran solution, 36 mL, 36 mmol) at 0° C., and the mixture was stirred for 3 hr. The reaction mixture was poured into ice water, and the mixture was extracted with ethyl acetate. The organic layer was washed with saturated brine, and dried over sodium sulfate. The desiccant was filtered off, and the solvent was evaporated. The obtained residue was purified by silica gel column chromatography (petroleum ether/ethyl acetate) to give the title compound (4.5 g, 21 mmol, 88%).
MS(ESI) m/z 214 (M+H)⁺

(step 3) Synthesis of 3-(benzyloxy)benzylamine hydrochloride (D-1)

To the compound (1.6 g, 7.6 mmol) obtained in step 2 was added 3 mol/L hydrogen chloride (dichloromethane solution, 5 mL), and the mixture was stirred at room temperature for 1 hr, and concentrated under reduced pressure to give the title compound (1.5 g, 6.0 mmol, 79%).
MS(ESI) m/z 214 (M+H)⁺
¹H NMR (400 MHz, CD₃OD): δ7.47-7.30 (m, 6H), 7.09 (s, 1H), 7.01-6.99 (m, 2H), 5.12 (s, 2H), 3.95 (s, 2H).

D-2 described in Table 13 was synthesized by using corresponding commercially available reagents and by an operation similar to that in Reference Example D-1.

TABLE 13

| Ref. Example No. | Structural formula | MS(ESI) m/z (M + H)+ | NMR |
|---|---|---|---|
| D-1 | | 214 | ¹H MMR (400 MHz, CD₃OD): δ 7.47-7.30 (m, 6H), 7.09 (s, 1H), 7.01-6.99 (m, 2H), 5.12 (s, 2H), 3.95 (s, 2H). |

TABLE 13-continued

| Ref. Example No. | Structural formula | MS(ESI) m/z (M + H)+ | NMR |
|---|---|---|---|
| D-2 | H₂N–⟨benzyl⟩–O–CH₂–⟨phenyl⟩–CF₃ · HCl | 282 | ¹H NMR (400 MHz, CD₃OD): δ 7.67~7.51 (m, 4H), 7.36 (t, J = 8.0 Hz, 1H), 7.11~7.02 (m, 3H), 5.20 (s, 2H), 4.07 (s, 2H). |

Reference Example D-3

Synthesis of {4-[3-(trifluoromethyl)phenoxy]phenyl}methanamine hydrochloride (D-3)

(step 1) Synthesis of tert-butyl N-[(4-hydroxyphenyl)methyl]carbamate

To 4-hydroxybenzylamine (500 mg, 4.1 mmol) were added di-tert-butyl dicarbonate (1.1 g, 4.9 mmol), triethylamine (840 µL), water (2 mL) and THF (10 mL), and the mixture was stirred at room temperature for 4 hr was stirred. The reaction mixture was diluted with ethyl acetate and washed with 0.1 mol/L aqueous hydrochloric acid solution. The organic layer was dried over sodium sulfate, and then the desiccant was filtered off, and the solvent was evaporated. The obtained residue was purified by silica gel column chromatography (hexane/ethyl acetate) to give the title compound (980 mg).
MS(ESI) m/z 224 (M+H)+

(step 2) Synthesis of tert-butyl N-({4-[3-(trifluoromethyl)phenoxy]phenyl}methyl) carbamate To the compound (500 mg, 2.2 mmol) obtained in step 1 were added 3-trifluoromethylphenylboronic acid (420 mg, 2.2 mmol), copper acetate (410 mg, 2.2 mmol), triethylamine (1.5 mL, 11 mmol), molecular sieves 4 Å (1.5 g), dichloromethane (15 mL), and the mixture was stirred at room temperature overnight. The reaction mixture was filtered, the insoluble material was removed, and the solvent was evaporated. To the residue was added ethyl acetate, and the mixture was washed with 0.1 mol/L aqueous hydrochloric acid solution. The organic layer was dried over sodium sulfate, the desiccant was filtered off, and the solvent was evaporated. The obtained residue was purified by silica gel column chromatography (hexane/ethyl acetate) to give the title compound (380 mg).
MS(ESI) m/z 368 (M+H)+

(step 3) Synthesis of {4-[3-(trifluoromethyl)phenoxy]phenyl}methanamine hydrochloride (D-3)

To the compound (380 mg) obtained in step was added 4 mol/L hydrochloric acid/1,4-dioxane solution (5 mL), and the mixture was stirred at room temperature for 3 hr was stirred. The solvent was evaporated to give the title compound was obtained.
MS(ESI) m/z 268 (M+H)+
¹H NMR (400 MHz, DMSO-d₆) δ 8.40 (brs, 3H), 7.65 (t, J=8.0 Hz, 1H), 7.56 (d, J=6.8 Hz, 2H), 7.52 (d, J=7.6 Hz, 1H), 7.30 (dd, J=8.0, 2.0 Hz, 1H), 7.27 (s, 1H), 7.15 (d, J=9.6 Hz, 2H), 4.03 (s, 2H).

D-4 to D-6 described in Table 14 were synthesized by using corresponding commercially available reagents and by an operation similar to that in Reference Example D-3.

TABLE 14

| Ref. Example No. | Structural formula | MS(ESI) m/z (M + H)+ | NMR |
|---|---|---|---|
| D-3 | H₂N–CH₂–⟨phenyl⟩–O–⟨phenyl⟩–CF₃ · HCl | 268 | ¹H MHR (400 MHz, DMSO-d₆) δ 8.40 (brs, 3H), 7.65 (t, J = 8.0 Hz, 1H), 7.56 (d, J = 6.8 Hz., 2H), 7.52 (d, J = 7.6 Hz, 1H), 7.30 (dd, J = 8.0, 2.0 Hz, 1H), 7.27 (s, 1H), 7.15 (d, J = 9.6 Hz, 2H), 4.03 (s, 2H). |
| D-4 | H₂N–CH₂–⟨phenyl⟩–O–⟨phenyl⟩–CF₃ · HCl | 268 | ¹H NMR (400 MHz. DMSO-d₆) δ 8.45 (brs, 3H), 7.76 (d, J = 8.4 Hz, 2H), 7.50 (t, J = 7.8 Hz, 1H), 7.37 (brd, J = 8.0 Hz, 1H), 7.31 (brs, 1H), 7.17 (d, J = 8.4 Hz, 2H), 7.16-7.14 (m, 1H), 4.04 (s, 2H). |
| D-5 | H₂N–CH₂–⟨phenyl⟩–O–⟨pyridyl⟩–CF₃ · HCl | 269 | — |

TABLE 14-continued

| Ref. Example No. | Structural formula | MS(ESI) m/z (M + H)+ | NMR |
|---|---|---|---|
| D-6 | H₂N—⟨phenyl⟩—O—⟨pyridine⟩—CF₃ · HCl | 269 | 1H NMR (400 MHz, DMSO-d₆) δ 8.67 (d, J = 5.7 Hz, 1H), 8.25 (br-s, 3H), 7.66-7.58 (m, 2H), 7.40-7.31 (m, 3H), 7.17 (dd, J = 5.7, 2.4 Hz, 1H), 4.09 (s, 2H). |

Reference Example D-7

Synthesis of 3-(benzylthio)benzylamine hydrochloride (D-7)

H₂N—⟨phenyl⟩—S—⟨phenyl⟩ · HCl (step 1) Synthesis of tert-butyl N-[(3-bromophenyl)methyl]carbamate To 3-bromobenzylamine hydrochloride (1.0 g, 4.5 mmol) and di-tert-butyl dicarbonate (0.98 g, 4.5 mmol) were added dichloromethane (10 mL) and triethylamine (0.63 mL, 4.5 mmol), and the mixture was stirred at room temperature overnight. To the reaction mixture was added water and the mixture was extracted with dichloromethane. The organic layer was dried over sodium sulfate, the desiccant was filtered off, and the solvent was evaporated to give the title compound (1.3 g, 4.5 mmol, 100%).
MS(ESI) m/z 286 (M+H)⁺

(step 2) Synthesis of 3-(benzylthio)benzylamine hydrochloride (D-7)

To the compound (0.20 g, 0.70 mmol) obtained in step 1, tris(dibenzylideneacetone)dipalladium(0) (16 mg, 0.017 mmol) and Xantphos (20 mg, 0.035 mmol) were added 1,4-dioxane (2 mL), benzylmercaptan (0.090 mL, 0.77 mmol) and N-ethyldiisopropylamine (0.24 mL, 1.4 mmol), and the mixture was stirred at 90° C. overnight. To the reaction mixture was added ethyl acetate, and the mixture was washed successively with 0.5 mol/L aqueous hydrochloric acid solution, saturated aqueous sodium hydrogen carbonate and saturated brine. The organic layer was dried over sodium sulfate, the desiccant was filtered off, and the solvent was evaporated. To the obtained residue was added trifluoroacetic acid (5 mL), and the mixture was stirred at room temperature for 5 min. To the reaction mixture was added dichloromethane, and the mixture was washed successively with 2 mol/L aqueous sodium hydroxide solution, saturated aqueous sodium hydrogen carbonate. The organic layer was dried over sodium sulfate, the desiccant was filtered off, and the solvent was evaporated. To the obtained residue was added 4 mol/L hydrochloric acid (1,4-dioxane solution, 0.25 mL, 1.0 mmol). The solvent was evaporated and the obtained residue was suspended in ethyl acetate, a small amount of dichloromethane and methanol, and the mixture was stirred at room temperature for 10 min. The precipitate was collected by filtration to give the title compound (0.14 g, 0.50 mmol, 73%).
MS(ESI) m/z 230 (M+H)⁺
¹H NMR (400 MHz, DMSO-d₆) δ 8.32 (br-s, 3H), 7.58-7.47 (m, 1H), 7.43-7.19 (m, 8H), 4.28 (s, 2H), 3.99 (s, 2H).

Reference Example D-8

Synthesis of [4-(phenoxymethyl)phenyl]methanamine trifluoroacetate (D-8)

H₂N—⟨phenyl⟩—CH₂—O—⟨phenyl⟩ · TFA (step 1) Synthesis of tert-butyl N-{[4-(hydroxymethyl)phenyl]methyl}carbamate An operation similar to that in Reference Example D-3, step 1 was performed using [4-(aminomethyl)phenyl]methanol (1.2 g, 9.7 mmol) instead of 4-hydroxybenzylamine to give the title compound (2.0 g, 8.4 mmol, 87%).
MS(ESI) m/z 238 (M+H)⁺

(step 2) Synthesis of tert-butyl N-{[4-(phenoxymethyl)phenyl]methyl}carbamate

The compound (2.0 g, 8.4 mmol) obtained in step 1, phenol (900 μL, 10 mmol) and triphenylphosphine (2.2 g, 13 mmol) were dissolved in dichloromethane (84 mL), diisopropyl azodicarboxylate (2.7 mL, 13 mmol) was added dropwise, and the mixture was stirred for a few hours. The solvent was evaporated and the obtained residue was purified by silica gel column chromatography (hexane/ethyl acetate) to give the title compound (1.8 g, 5.9 mmol, 70%).
MS (ESI) m/z 314 (M+H)⁺

(step 3) Synthesis of [4-(phenoxymethyl)phenyl]methanamine trifluoroacetate (D-8)

To the compound (1.8 g, 5.9 mmol) obtained in step 2 was added 4 mol/L hydrochloric acid/1,4-dioxane solution (20 mL) and the mixture was stirred for a few hours. The solvent was evaporated and the obtained residue was purified by high performance liquid chromatography (water-acetonitrile, each containing 0.1% trifluoroacetic acid) to give the title compound (1.7 g, 5.1 mmol, 86%).
MS(ESI) m/z 214 (M+H)⁺
¹H NMR (400 MHz, DMSO-d₆) δ 7.97 (br-s, 3H), 7.53-7.42 (m, 4H), 7.35-7.25 (m, 2H), 7.02-6.97 (m, 2H), 6.95 (tt, J=7.3, 1.0 Hz, 1H), 5.13 (s, 2H), 4.03 (s, 2H)

Reference Example D-9

Synthesis of 3-[6-(trifluoromethyl)-3-pyridyl]benzylamine trifluoroacetate (D-9)

(step 1) Synthesis of 3-[6-(trifluoromethyl)-3-pyridyl]benzonitrile

To 3-cyanophenylboronic acid (500 mg, 3.4 mmol), 5-bromo-2-(trifluoromethyl)pyridine (850 mg, 3.7 mmol) and 1,1'-bis(diphenylphosphino)ferrocenedichloropalladium(II) (250 mg, 0.34 mmol) were added 1,4-dioxane (5 mL) and 1 mol/L aqueous sodium carbonate solution (5 mL), and the mixture was stirred with heating using a microwave reactor at 100° C. for 30 min. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (643 mg, 2.6 mmol, 76%).

MS (ESI) m/z 249 (M+H)+

(step 2) Synthesis of 3-[6-(trifluoromethyl)-3-pyridyl]benzylamine trifluoroacetate (D-9)

The compound (446 mg, 1.8 mmol) obtained in step 1 was dissolved in ethanol (10 mL), and the mixture was reduced by using a Flow Hydrogenation apparatus (H-cube, manufactured by ThalesNano Nanotechnology) under the conditions of 10% Pd/C (30 mm), 70° C., 50 bar, flow rate 1 mL/min. The reaction mixture was concentrated under reduced pressure, and the obtained residue was purified by high performance liquid chromatography (water-acetonitrile, each containing 0.1% trifluoroacetic acid) to give the title compound (307 g, 1.2 mmol, 67%).

MS (ESI) m/z 253 (M+H)+

1H NMR (400 MHz, DMSO-de) δ 9.12 (d, J=2.2 Hz, 1H), 8.40-8.36 (m, 1H), 8.20 (br-s, 3H), 8.07 (dd, J=8.3, 1.0 Hz, 1H), 7.94 (s, 1H), 7.90-7.84 (m, 1H), 7.67-7.55 (m, 2H), 4.15 (s, 2H).

D-10 to D-11 described in Table 15 were synthesized by using corresponding commercially available reagents and by an operation similar to that in Reference Example D-9.

TABLE 15

| Ref. Example No. | Structural formula | MS(ESI) m/z (M + H)+ | NMR |
|---|---|---|---|
| D-9 | | 253 | 1H NMR (400 MHz, DMSO-d6) δ 9.12 (d, J = 2.2 Hz, 1H), 8.40-8.36 (m, 1H), 8.20 (br-s, 3H), 8.07 (dd, J = 8.3, 1.0 Hz, 1H), 7.94 (s, 1H), 7.90-7.84 (m, 1H), 7.67-7.55 (m, 2H), 4.15 (s, 2H). |
| D-10 | | 253 | 1H NMR (400 MHz, DMSO-d6) δ 9.07 (s, 1H), 8.36 (d, J = 8.6 Hz, 1H), 8.40-8.25 (m, 3H), 8.31 (s, 1H), 8.22 (d, J = 8.5 Hz, 1H), 8.18 (td, J = 4.4, 1.8 Hz, 1H), 7.65-7.58 (m, 2H), 4.22-4.12 (m, 2H). |
| D-11 | | 253 | — |

Reference Example D-12

Synthesis of 3-[2-(dimethylamino)-4-pyridyl]benzylamine hydrochloride (D-12)

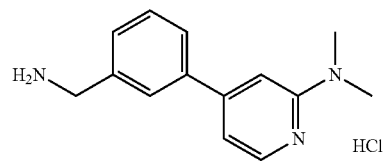 [SMILES: CN(C)c1cc(-c2cccc(CN)c2)ccn1 ; Cl]

(step 1) Synthesis of 4-chloro-2-dimethylaminopyridine

To 2-amino-4-chloropyridine (5.0 g, 39 mmol) and sodium cyanoborohydride (7.6 g, 0.12 mol) were dissolved in acetonitrile (100 mL) and water (20 mL), and formalin and acetic acid (32 mL) were added at 0° C. The mixture was warmed to room temperature and stirred overnight. The reaction mixture was adjusted to pH>4 with sodium hydroxide. The mixture was extracted with dichloromethane, and the organic layer was washed with saturated brine, and dried over sodium sulfate. The desiccant was filtered off, and the solvent was evaporated to give the title compound (3.9 g, 25 mmol, 64%).

MS (ESI) m/z 157 (M+H)+

1H NMR (300 MHz, CDCl3): δ 8.03 (d, J=5.4 Hz, 1H), 6.54 (d, J=5.4 Hz, 1H), 6.47 (s, 1H), 3.07 (s, 6H).

(step 2) Synthesis of 3-(2-dimethylamino-4-pyridyl)benzonitrile

To the compound (2.7 g, 17 mmol) obtained in step 1, 3-cyanophenylboronic acid (2.3 g, 16 mmol), potassium carbonate (4.3 g, 35 mmol) and 1,1'-bis(di-tert-butylphosphino)ferrocenedichloropalladium (Pd-118, 1.1 g, 1.7 mmol) were added N,N-dimethylformamide (50 mL) and water (1 mL) and the mixture was stirred at 90° C. overnight. The reaction mixture was concentrated under reduced pressure and the obtained residue was purified by silica gel column chromatography (petroleum ether/ethyl acetate) to give the title compound (1.7 g, 7.6 mmol, 48%).

MS (ESI) m/z 224 (M+H)+

(step 3) Synthesis of 3-[2-(dimethylamino)-4-pyridyl]benzylamine (D-12)

To the compound (1.0 g, 4.5 mmol) obtained in step 2 and palladium/carbon (0.2 g) were added ethanol (50 mL) and concentrated hydrochloric acid (5 mL), and the mixture was stirred at normal pressure under a hydrogen atmosphere at room temperature overnight. The catalyst was filtered off and the mixture was concentrated under reduced pressure to give the title compound (0.50 g, 2.2 mmol, 49%).

MS (ESI) m/z 228 (M+H)+

1H NMR (300 MHz, CD3OD): δ 8.06 (s, 1H), 7.98 (d, J=6.9 Hz, 1H), 7.93-7.90 (m, 1H), 7.67-7.65 (m, 2H), 7.43 (d, J=1.2 Hz, 1H), 7.30 (dd, J=6.9, 1.2 Hz, 1H), 4.26 (s, 2H), 3.38 (s, 6H).

Reference Example D-16

Synthesis of [6-[4-(trifluoromethyl)phenyl]pyrimidin-4-yl]methylamine (D-16)

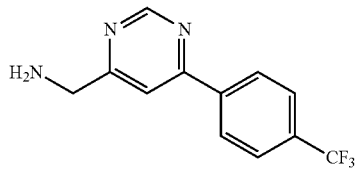 [SMILES: NCc1cc(-c2ccc(C(F)(F)F)cc2)ncn1]

(step 1) Synthesis of 4-methyl-6-[4-(trifluoromethyl)phenyl]pyrimidine

To 4-chloro-6-methylpyrimidine (4.78 g, 37.4 mmol), 4-trifluoromethylphenylboronic acid (8.47 g, 44.6 mmol) and tetrakis(triphenylphosphine)palladium(0) (1.40 g, 1.21 mmol) was added acetonitrile (50 mL). To the reaction mixture was added a solution of sodium carbonate (12.9 g, 121 mmol) in water (9 mL), and the mixture was heated under reflux under an argon atmosphere for 3 hr, and poured into water. The mixture was extracted with ethyl acetate, and the organic layer was washed with saturated brine, and dried over sodium sulfate. The desiccant was filtered off, and the solvent was evaporated. The obtained residue was purified by silica gel column chromatography (petroleum ether/ethyl acetate) to give the title compound (6.13 g, 25.8 mmol, 69%).

MS (ESI) m/z 239 (M+H)+

1H NMR (300 MHz, CDCl3): δ 9.17 (s, 1H), 8.17 (d, J=8.1 Hz, 2H), 7.74 (d, J=8.1 Hz, 2H), 7.60 (s, 1H), 2.61 (s, 3H).

(step 2) Synthesis of 4-bromomethyl-6-[4-(trifluoromethyl)phenyl]pyrimidine

To the compound (5.92 g, 24.7 mmol) obtained in step 1, N-bromosuccinimide (39.2 g, 223 mmol) and benzoyl peroxide (4.86 g, 20.1 mmol) was added carbon tetrachloride (100 mL), and the mixture was stirred at 100° C. overnight. To the reaction mixture was added saturated aqueous sodium hydrogen carbonate, and the mixture was extracted with ethyl acetate, and the organic layer was washed with saturated brine, and dried over sodium sulfate. The desiccant was filtered off, and the solvent was evaporated. The obtained residue was purified by silica gel column chromatography (petroleum ether/ethyl acetate) to give the title compound (0.73 g, 2.3 mmol, 9%).

MS (ESI) m/z 317 (M+H)+

1H NMR (300 MHz, CDCl3): δ 9.23 (s, 1H), 8.22 (d, J=8.1 Hz, 2H), 7.91 (s, 1H), 7.80 (d, J=8.1 Hz, 2H), 4.47 (s, 2H).

(step 3) Synthesis of [6-[4-(trifluoromethyl)phenyl]pyrimidin-4-yl]methylamine (D-16)

To a solution of the compound (0.73 g, 2.3 mmol) obtained in step 2 in ethanol (10 mL) was added dropwise concentrated aqueous ammonia (15 mL) over 10 min, and the mixture was stirred at room temperature for 1 hr. The reaction mixture was concentrated under reduced pressure and the obtained residue was purified by silica gel column chromatography (petroleum ether/ethyl acetate) to give the title compound (0.17 g, 0.69 mmol, 30%).

MS (ESI) m/z 254 (M+H)+

1H NMR (300 MHz, CD3OD): δ 9.26 (s, 1H), 8.40 (d, J=8.1 Hz, 2H), 8.13 (s, 1H), 7.88 (d, J=8.1 Hz, 2H), 4.26 (s, 2H).

Reference Example D-18

Synthesis of [4-[6-(trifluoromethyl)-3-pyridyl]-2-pyridyl]methylamine (D-18)

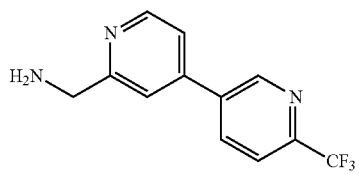

(step 1) Synthesis of [4-[6-(trifluoromethyl)-3-pyridyl]-2-pyridyl]methanol

To (4-chloro-2-pyridyl)methanol (1.51 g, 10.5 mmol), [6-(trifluoromethyl)-3-pyridyl]boronic acid (1.99 g, 10.5 mmol), sodium carbonate (3.40 g, 32.1 mmol) and 1,1'-bis(di-tert-butylphosphino)ferrocenedichloropalladium (Pd- 118, 0.70 g, 1.07 mmol) were added 1,4-dioxane (50 mL) and water (5 mL) and the mixture was stirred at 100° C. for 3 hr. The reaction mixture was concentrated under reduced pressure and the obtained residue was purified by silica gel column chromatography (petroleum ether/ethyl acetate) to give the title compound (1.36 g, 5.35 mmol, 51%).

MS (ESI) m/z 255 (M+H)$_+$ (step 2) Synthesis of [4-[6-(trifluoromethyl)-3-pyridyl]-2-pyridyl]methylamine (D-18)

To the compound (1.36 g, 5.38 mmol) obtained in step 1 was added thionyl chloride (25 mL) and the mixture was heated under reflux for 2 hr, concentrated under reduced pressure and the obtained residue was added to aqueous ammonia (25 mL), and the mixture was stirred at 70° C. for 2 hr. The reaction mixture was concentrated under reduced pressure and the obtained residue was purified by silica gel column chromatography (petroleum ether/ethyl acetate) to give the title compound (286 mg, 1.13 mmol, 21%).

MS (ESI) m/z 254 (M+H)$^+$ with ethyl acetate. The organic layer was dried over sodium sulfate. The desiccant was filtered off, and the solvent was evaporated. The obtained residue was purified by silica gel column chromatography (hexane/ethyl acetate) to give the title compound (235 mg, 0.94 mmol, 67%).

MS (ESI) m/z 249 (M+H)$^+$ (step 2) Synthesis of [5-[6-(trifluoromethyl)-3-pyridyl]-3-pyridyl]methylamine ditrifluoroacetate (D-19)

the compound (235 mg, 0.94 mmol) obtained in step 1 was dissolved in ethanol (5 mL), and the mixture was reduced by using a Flow Hydrogenation apparatus (H-cube, manufactured by ThalesNano Nanotechnology) under the conditions of 10% Pd/C (30 mm), 65° C., 50 bar, flow rate 1 mL/min. The reaction mixture was concentrated under reduced pressure, and the obtained residue was purified by high performance liquid chromatography (water-acetonitrile, each containing 0.1% trifluoroacetic acid) to give the title compound (37 g, 0.11 mmol, 12%). MS (ESI) m/z 253 (M+H)$^+$ D-20 described in Table 16 was synthesized by using corresponding commercially available reagents and by an operation similar to that in Reference Example D-19.

TABLE 16

| Ref. Example No. | Structural formula | MS(ESI) m/z (M + H)$^+$ | NMR |
|---|---|---|---|
| D-19 | H$_2$N─⟨pyridyl⟩─⟨pyridyl-CF$_3$⟩ · 2TFA | 254 | — |
| D-20 | H$_2$N─⟨pyridyl⟩─⟨pyridyl-CF$_3$⟩ · 2TFA | 254 | — |

$^1$H NMR (300 MHz, CD$_3$OD): δ 9.12 (d, J=1.5 Hz, 1H), 8.66 (d, J=5.1 Hz, 1H), 8.43 (dd, J=8.1, 1.5 Hz, 1H), 7.98 (d, J=8.1 Hz, 1H), 7.87 (s, 1H), 7.70 (dd, J=5.1, 1.5 Hz, 1H), 4.03 (s, 2H).

Reference Example D-19

Synthesis of [5-[6-(trifluoromethyl)-3-pyridyl]-3-pyridyl]methylamine ditrifluoroacetate (D-19)

(step 1) Synthesis of [5-[6-(trifluoromethyl)-3-pyridyl]-pyridine-3-carbonitrile To 5-bromopyridine-3-carbonitrile (250 mg, 1.4 mmol), [6-(trifluoromethyl)-3-pyridyl]boronic acid (290 mg, 1.5 mmol) and 1,1-bis(diphenylphosphino)ferrocenedichloropalladium(II) (50 mg, 0.068 mmol) were added 1,4-dioxane (2.5 mL) and 1 mol/L aqueous sodium carbonate solution (2.5 mL) and the mixture was stirred with heating using a microwave reactor at 110° C. for 15 min. To the reaction mixture was added water, and the mixture was extracted Reference Example D-21

Synthesis of [3-[5-(trifluoromethyl)pyrimidin-2-yl]phenyl]methylamine hydrochloride (D-21)

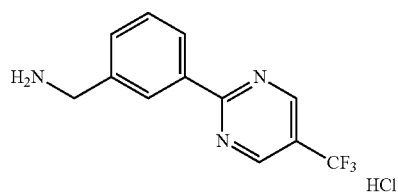 [SMILES: NCc1cccc(-c2ncc(C(F)(F)F)cn2)c1 ; Cl]

(step 1) Synthesis of 3-[5-(trifluoromethyl)pyrimidin-2-yl]benzonitrile

To 2-bromo-5-trifluoromethylpyrimidine (1.3 g, 5.5 mmol), 3-cyanophenylboronic acid (0.97 g, 6.6 mmol), and 1,1'-bis(diphenylphosphino)ferrocenedichloropalladium(II) (0.20 g, 0.27 mmol) were added 1,4-dioxane (50 mL) and saturated aqueous sodium hydrogen carbonate solution (30 mL) and the mixture was stirred at 105° C. for 1.5 hr. The insoluble material was filtered off, ethyl acetate was added to the filtrate, washed successively with water and saturated brine, and dried over sodium sulfate. The desiccant was filtered off and the solvent was evaporated and the obtained residue was purified by silica gel column chromatography (petroleum ether/ethyl acetate) to give the title compound (1.0 g, 4.0 mmol, 73%).
MS (ESI) m/z 250 (M+H)$^+$
$^1$H NMR (400 MHz, CDCl$_3$) δ 9.08 (s, 2H), 8.85 (s, 1H), 8.76 (d, J=8.0 Hz, 1H), 7.83 (d, J=7.6 Hz, 1H), 7.65 (dd, J=8.0, 7.6 Hz, 1H).

(step 2) Synthesis of [3-[5-(trifluoromethyl)pyrimidin-2-yl]phenyl]methylamine hydrochloride (D-21)

To a solution of the compound (1.0 g, 4.0 mmol) obtained in step 1 in acetic acid (30 mL) was added 10% palladium/carbon (0.30 g), and the mixture was stirred under a hydrogen atmosphere at 25° C. for 3 hr. The catalyst was filtered off, and the filtrate was dissolved by adding dichloromethane (15 mL). Triethylamine (0.50 mL, 3.6 mmol) and di-tert-butyl dicarbonate (1.0 g, 4.6 mmol) were added, and the mixture was stirred at room temperature for 40 min. The reaction mixture was washed with water, dried over sodium sulfate, and the desiccant was filtered off. The solvent was evaporated and the obtained residue was purified by silica gel column chromatography (petroleum ether/ethyl acetate). To the obtained compound was added 4 mol/L hydrogen chloride (dichloromethane solution, 10 mL, 40 mmol), and the mixture was stirred at room temperature for 30 min, and concentrated under reduced pressure to give the title compound (0.13 g, 0.45 mmol, 11%).
MS (ESI) m/z 254 (M+H)$^+$
$^1$H NMR (300 MHz, DMSO-ds) δ 9.39 (s, 2H), 8.59 (s, 1H), 8.48-8.38 (m, 4H), 7.76-7.73 (m, 1H), 7.65 (dd, J=7.8, 7.8 Hz, 1H), 4.18-4.17 (m, 2H)°

Reference Example D-22

Synthesis of [3-[2-(trifluoromethyl)pyrimidin-5-yl]phenyl]methylamine (D-22)

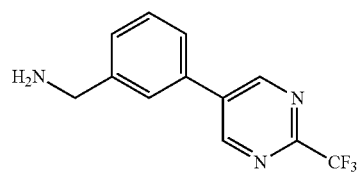 [SMILES: NCc1cccc(-c2cnc(C(F)(F)F)nc2)c1]

(step 1) Synthesis of 3-[2-(trifluoromethyl)pyrimidin-5-yl]benzonitrile

To 5-bromo-2-trifluoromethylpyrimidine (3.0 g, 13 mmol), 3-cyanophenylboronic acid (2.3 g, 16 mmol), sodium carbonate (2.8 g, 26 mmol) and 1,1'-bis(diphenylphosphino) ferrocenedichloropalladium(II) (0.47 g, 0.65 mmol) were added N,N-dimethylformamide (80 mL) and water (20 mL) and the mixture was stirred at 110° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (2.4 g, 9.6 mmol, 73%).
MS (ESI) m/z 250 (M+H)$^+$
$^1$H NMR (300 MHz, CDCl$_3$) δ 9.12 (s, 2H), 7.93-7.85 (m, 3H), 7.74 (dd, J=7.8, 7.8 Hz, 1H).

(step 2) Synthesis of [3-[2-(trifluoromethyl)pyrimidin-5-yl]phenyl]methylamine (D-22)

To the compound (2.0 g, 8.0 mmol) obtained in step 1 and cobalt(II) chloride 6 hydrate (0.10 g, 0.80 mmol) were added tetrahydrofuran (28 mL) and water (4 mL). Sodium tetrahydroborate (0.61 g, 16 mmol) was added to the reaction mixture at 0° C., and the mixture was stirred at room temperature for 2 hr and adjusted to pH1 with 3 mol/L hydrochloric acid. The mixture was stirred at room temperature for 1 hr, tetrahydrofuran was evaporated under reduced pressure from the reaction mixture, and adjusted to pH8-9 with aqueous ammonia. The reaction mixture was extracted with ethyl acetate, and the organic layer was washed with saturated brine, and dried over sodium sulfate. The desiccant was filtered off. The solvent was evaporated and the obtained residue was purified by high performance liquid chromatography (water-acetonitrile) to give the title compound (0.11 g, 0.41 mmol, 5%).
MS (ESI) m/z 254 (M+H)$^+$
$^1$H NMR (300 MHz, CD$_3$OD) δ 9.28 (s, 2H), 7.83 (s, 1H), 7.76-7.32 (m, 1H), 7.59-7.56 (m, 2H), 3.99 (s, 2H).

Reference Example D-23

Synthesis of [3-[5-(trifluoromethyl)pyrazin-2-yl]phenyl]methylamine (D-23)

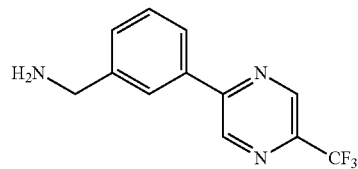 [SMILES: NCc1cccc(-c2cnc(C(F)(F)F)cn2)c1]

(step 1) Synthesis of 3-[5-(trifluoromethyl)pyrazin-2-yl]benzonitrile

To 2-chloro-5-trifluoromethylpyrazine (1.0 g, 5.5 mmol), 3-cyanophenylboronic acid (0.81 g, 5.47 mmol), potassium carbonate (2.3 g, 16 mmol) and so tetrakis(triphenylphosphine)palladium(0) (0.36 g, 0.31 mmol) were added 1,4-dioxane (40 mL) and water (10 mL) and the mixture was stirred at 85° C. for 5 hr. The reaction mixture was added to aqueous ammonium chloride solution, and the mixture was extracted with ethyl acetate. The organic layer was washed with saturated brine, dried over sodium sulfate, and the desiccant was filtered off. The solvent was evaporated and the obtained residue was purified by silica gel column chromatography (petroleum ether/ethyl acetate) to give the title compound (0.92 g, 3.7 mmol, 67%). MS (ESI) m/z 250 (M+H)$^+$ $^1$H NMR (400 MHz, CDCl$_3$) δ 9.15 (s, 1H), 9.04 (s, 1H), 8.43 (s, 1H), 8.32 (d, J=8.0 Hz, 1H), 7.84 (d, J=8.0 Hz, 1H), 7.70 (dd, J=8.0, 8.0 Hz, 1H)

(step 2) Synthesis of [3-[5-(trifluoromethyl)pyrazin-2-yl]phenyl]methylamine (D-23)

To a solution of the compound (0.72 g, 2.9 mmol) obtained in step 1 in acetic acid (22 mL) was added 10% palladium/carbon (0.22 g), and the mixture was stirred under a hydrogen atmosphere at room temperature for 3 hr. The catalyst was filtered off, ethyl acetate was added to the filtrate and the mixture was washed successively with water and saturated brine. The organic layer was dried over sodium sulfate, and the desiccant was filtered off, and the solvent was evaporated and the obtained residue was purified by high performance liquid chromatography (water-acetonitrile) to give the title compound (0.12 g, 0.47 mmol, 16%).

MS (ESI) m/z 254 (M+H)$^+$ $^1$H NMR (400 MHz, CD$_3$OD) δ 9.37 (s, 1H), 9.13 (s, 1H), 8.36 (s, 1H), 8.32-8.30 (m, 1H), 7.73-7.69 (m, 2H), 4.28 (s, 2H).

Reference Example D-24

Synthesis of [3-[6-(trifluoromethyl)pyridazin-3-yl]phenyl]methylamine (D-24)

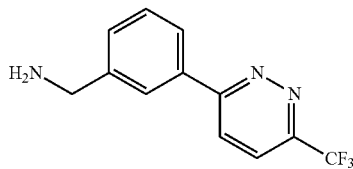 [SMILES: NCc1cccc(-c2ccc(C(F)(F)F)nn2)c1]

Using the compound obtained in Reference Example D-35, step 1 instead of 5-bromo-2-trifluoromethylpyrimidine, and by an operation similar to that in Reference Example, D-22, the title compound (yield 19%) was obtained.

MS (ESI) m/z 254 (M+H)$^+$ $^1$H NMR (400 MHz, CD$_3$OD) δ 8.43 (d, J=8.8 Hz, 1H), 8.20-8.18 (m, 2H), 8.10 (d, J=6.4 Hz, 1H), 7.60-7.57 (m, 2H), 3.98 (s, 2H).

Reference Example D-25

Synthesis of [2-(4-chlorophenyl)-4-pyridyl]methylamine hydrochloride (D-25)

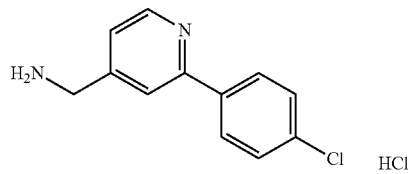 [SMILES: NCc1ccnc(-c2ccc(Cl)cc2)c1 ; Cl]

(step 1) Synthesis of tert-butyl N-[(2-chloro-4-pyridyl)methyl]carbamate (2-Chloro-4-pyridyl)methylamine (14 g, 0.10 mol) was dissolved by adding dichloromethane (120 mL), triethylamine (28 mL, 0.20 mol) and di-tert-butyl dicarbonate (26 g, 0.12 mol) were added, and the mixture was stirred at room temperature for 2 hr. The solvent was evaporated from the reaction mixture and the obtained residue was purified by silica gel column chromatography (petroleum ether/ethyl acetate) to give the title compound (22 g, 0.091 mmol, 91%).

MS (ESI) m/z 243 (M+H)$^+$ (step 2) Synthesis of tert-butyl N-[[2-(4-chlorophenyl)-4-pyridyl]methyl]carbamate To the compound (1.4 g, 5.9 mmol) obtained in step 1, 4-chlorophenylboronic acid (1.0 g, 6.4 mmol), sodium carbonate (1.6 g, 15 mmol) and tetrakis(triphenylphosphine)palladium(0) (0.21 g, 0.18 mmol) were added N,N-dimethylformamide (20 mL) and water (5 mL) and the mixture was stirred at 100° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (1.0 g, 3.1 mmol, 54%).

MS (ESI) m/z 319 (M+H)$^+$ $^1$H NMR (400 MHz, CDCl$_3$) δ 8.62 (d, J=4.8 Hz, 1H), 7.92 (d, J=8.4 Hz, 2H), 7.60 (s, 1H), 7.43 (d, J=8.4 Hz, 2H), 7.15 (d, J=4.8 Hz, 1H), 5.01 (s, 1H), 4.37-4.39 (m, 2H), 1.48 (s, 9H).

(step 3) Synthesis of [2-(4-chlorophenyl)-4-pyridyl]methylamine hydrochloride (D-25)

To the compound (1.0 g, 3.1 mmol) obtained in step 2 was added 4 mol/L hydrogen chloride (dichloromethane solution, 80 mL, 0.32 mol), and the mixture was stirred at room temperature for 1 hr, and concentrated under reduced pressure. To the obtained residue was added dichloromethane, and the insoluble material was collected by filtration, and dried to give the title compound (0.49 g, 1.9 mmol, 61%).

MS (ESI) m/z 219 (M+H)$^+$ $^1$H NMR (400 MHz, DMSO-d$_6$) δ 8.79 (brs, 3H), 8.74 (d, J=4.8 Hz, 1H), 8.31 (s, 1H), 8.15 (d, J=8.8 Hz, 2H), 7.63 (d, J=8.8 Hz, 2H), 7.58 (d, J=4.8 Hz, 1H), 4.17-4.22 (m, 2H).

Reference Example D-26

Synthesis of [2-[6-(trifluoromethyl)-3-pyridyl]-4-pyridyl]methylamine hydrochloride (D-26)

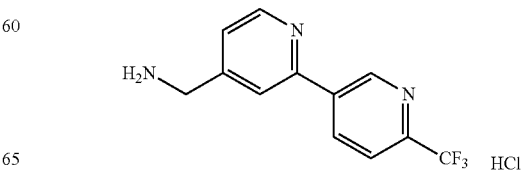

(step 1) Synthesis of tert-butyl [[2-[6-(trifluoromethyl)-3-pyridyl]-4-pyridyl]methyl]carbamate To the compound (12 g, 50 mmol) obtained in Reference Example D-25, step 1 and [6-(trifluoromethyl)-3-pyridyl] boronic acid (11 g, 60 mmol), sodium carbonate (21 g, 0.10 mol) and 1,1'-bis(diphenylphosphino) ferrocenedichloropalladium(II) (1.8 g, 2.5 mmol) were added 1,4-dioxane (100 mL) and water (20 mL) and the mixture was stirred at 110° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (11 g, 31 mmol, 62%).

MS (ESI) m/z 354 (M+H)$^+$ (step 2) Synthesis of [2-[6-(trifluoromethyl)-3-pyridyl]-4-pyridyl]methylamine hydrochloride (D-26)

To the compound (11 g, 31 mmol) obtained in step 1 was added 4 mol/L hydrogen chloride (dichloromethane solution, 120 mL, 0.48 mol), and the mixture was stirred at room temperature for 1 hr, and concentrated under reduced pressure to give the title compound (8.0 g, 28 mmol, 90%).

MS (ESI) m/z 254 (M+H)$^+$ $^1$H NMR (400 MHz, DMSO-$d_6$) δ 10.91 (s, 1H), 9.48 (s, 1H), 8.90 (s, 2H), 8.84-8.80 (m, 1H), 8.76-8.74 (m, 1H), 8.52 (s, 1H), 8.11 (d, J=8.4 Hz, 1H), 7.66 (d, J=4.8 Hz, 1H), 4.23-4.19 (m, 2H).

Reference Example D-27

Synthesis of [2-[5-(trifluoromethyl)-2-pyridyl]-4-pyridyl]methylamine (D-27)

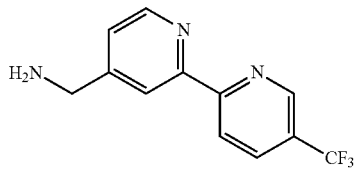

(step 1) Synthesis of [2-[5-(trifluoromethyl)-2-pyridyl]-4-pyridyl]methanol

To (2-chloro-4-pyridyl)methanol (3.00 g, 20.9 mmol), E-4 (7.57 g, 25.1 mmol), 1,1'-bis(diphenylphosphino)ferrocene (1.15 g, 2.09 mmol), palladium acetate (0.23 g, 1.05 mmol), cesium carbonate (13.6 g, 41.8 mmol) and copper(I) chloride (2.06 g, 20.9 mmol) was added N,N-dimethylformamide (300 mL) and the mixture was stirred at 100° C. overnight. The insoluble material was filtered off, ethyl acetate was added to the filtrate and the mixture was washed successively with water and saturated brine. The organic layer was dried over sodium sulfate, and the desiccant was filtered off, and the solvent was evaporated and the obtained residue was purified by silica gel column chromatography (petroleum ether/ethyl acetate) to give the title compound (4.12 g, 16.2 mmol, 77%).

$^1$H NMR (400 MHz, CDCl$_3$) δ 8.91 (s, 1H), 8.65 (d, J=5.0 Hz, 1H), 8.53 (d, J=8.2 Hz, 1H), 8.42 (s, 1H), 8.04 (d, J=8.2 Hz, 1H), 7.41 (d, J=5.0 Hz, 1H), 4.83 (s, 2H).

(step 2) Synthesis of [2-[5-(trifluoromethyl)-2-pyridyl]-4-pyridyl]methylamine (D-27)

To a solution of the compound (2.2 g, 8.5 mmol) obtained in step 1 in toluene (20 mL) was added thionyl chloride (5 mL) at 0° C., and the mixture was stirred at room temperature for 2 hr. The insoluble material was collected by filtration, washed with petroleum ether and post-dried. To the obtained solid was added aqueous ammonia (50 mL). The reaction mixture was stirred with heating at 70° C. for 5 hr, concentrated under reduced pressure and the obtained residue was purified by high performance liquid chromatography (water-acetonitrile) to give the title compound (0.30 g, 1.2 mmol, 14%).

MS (ESI) m/z 254 (M+H)$^+$ $^1$H NMR (400 MHz, CD$_3$OD) δ 9.22 (s, 1H), 9.02 (m, 2H), 8.70 (d, J=8.6 Hz, 1H), 8.52 (d, J=8.6 Hz, 1H), 8.13 (d, J=5.6 Hz, 1H), 4.60 (s, 2H).

Reference Example D-28

Synthesis of [2-[2-(trifluoromethyl)pyrimidin-5-yl]-4-pyridyl]methylamine hydrochloride (D-28)

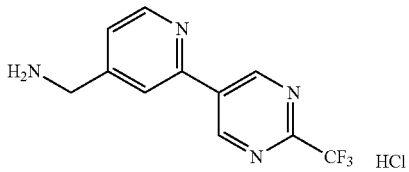 [SMILES: NCc1ccnc(-c2cnc(C(F)(F)F)nc2)c1 ; Cl]

(step 1) Synthesis of 5-(4,4,5,5-tetramethyl-1,3,2-dioxaborolan-2-yl)-2-(trifluoromethyl)pyrimidine To 5-bromo-2-trifluoromethylpyrimidine (6.8 g, 30 mmol), bis(pinacolato)diboron (11 g, 40 mmol), potassium acetate (8.8 g, 90 mmol) and 1,1'-bis(diphenylphosphino) ferrocenedichloropalladium(II) (0.10 g, 0.14 mmol) was added 1,4-dioxane (100 mL) and the mixture was stirred at 110° C. for 4 hr. The insoluble material was filtered off, and the solvent was evaporated. The obtained residue was purified by silica gel column chromatography (petroleum ether/ethyl acetate) to give the title compound (5.0 g, 18 mmol, 61%).

MS (ESI) m/z 275 (M+H)$^+$ (step 2) Synthesis of tert-butyl N-[[2-[2-(trifluoromethyl)pyrimidin-5-yl]-4-pyridyl]methyl]carbamate To the compound (1.7 g, 6.0 mmol) obtained in step 1 and the compound (2.5 g, 10 mmol) obtained in Reference Example D-25, step 1, sodium carbonate (2.4 g, 17 mmol) and 1,1'-bis(diphenylphosphino) ferrocenedichloropalladium(II) (30 mg, 0.041 mmol) were added 1,4-dioxane (25 mL) and water (5 mL) and the mixture was stirred at 110° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (1.1 g, 3.0 mmol, 50%).

MS (ESI) m/z 355 (M+H)+

(step 3) Synthesis of [2-[2-(trifluoromethyl)pyrimidin-5-yl]-4-pyridyl]methylamine hydrochloride (D-28)

To the compound (1.1 g, 3.0 mmol) obtained in step 2 was added 4 mol/L hydrogen chloride (dichloromethane solution, 25 mL, 0.10 mol), and the mixture was stirred at room temperature for 1 hr, and concentrated under reduced pressure to give the title compound (0.68 g, 2.3 mmol, 79%).

MS (ESI) m/z 255 (M+H)+
$^1$H NMR (400 MHz, CD$_3$OD) δ 9.51 (s, 2H), 8.83 (d, J=5.0 Hz, 1H), 8.24 (s, 1H), 7.68 (d, J=5.0 Hz, 1H), 4.31 (s, 2H).

Reference Example D-29

Synthesis of 2-[4-(aminomethyl)-2-pyridyl]-5-(trifluoromethyl)phenol (D-29)

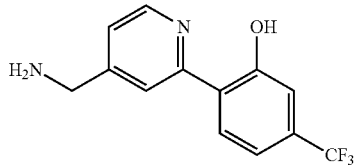 [SMILES: NCc1ccnc(-c2ccc(C(F)(F)F)cc2O)c1]

(step 1) Synthesis of 2-[2-methoxy-4-(trifluoromethyl)phenyl]pyridine-4-carbonitrile To 2-chloropyridine-4-carbonitrile (26 g, 0.19 mol) and [2-methoxy-4-(trifluoromethyl)phenyl]boronic acid (44 g, 0.23 mol) were added sodium carbonate (40 g, 0.38 mol) and 1,1'-bis(diphenylphosphino) ferrocenedichloropalladium(II) (7.0 g, 9.5 mmol) were added N,N-dimethylformamide (400 mL) and water (100 mL) and the mixture was stirred at 100° C. for 4 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (40 g, 0.14 mol, 76%).

MS (ESI) m/z 279 (M+H)+
$^1$H NMR (400 MHz, DMSO-d$_6$) δ 8.96 (d, J=5.0 Hz, 1H), 8.30 (d, J=1.2 Hz, 1H), 7.95 (d, J=8.2 Hz, 1H), 7.86 (dd, J=5.0, 1.2 Hz, 1H), 7.48 (s, 1H), 7.45 (d, J=8.2 Hz, 1H), 3.97 (s, 3H).

(step 2) Synthesis of 2-[2-hydroxy-4-(trifluoromethyl)phenyl]pyridine-4-carbonitrile To a solution of the compound (40 g, 0.14 mol) obtained in step 1 in dichloromethane (4 L) was added 1 mol/L boron tribromide (dichloromethane solution, 0.25 L, 0.25 mol) at −70° C. and the mixture was stirred at −20° C. for 3 hr. The reaction mixture was poured into ice water, and extracted with dichloromethane. The organic layer was washed successively with saturated aqueous sodium hydrogen carbonate and saturated brine, dried over sodium sulfate, and the desiccant was filtered off. The solvent was evaporated and the obtained residue was purified by silica gel column chromatography (petroleum ether/ethyl acetate) to give the title compound (24 g, 0.091 mol, 63%).

MS (ESI) m/z 265 (M+H)+

(step 3) Synthesis of 2-[4-(aminomethyl)-2-pyridyl]-5-(trifluoromethyl)phenol (D-29)

To a solution of the compound (24 g, 91 mmol) obtained in step 2 in ethanol (1.0 L) was added 10% palladium/carbon (3.0 g), and the mixture was stirred at 50 psi pressurization under a hydrogen atmosphere, at 70° C. for 3 hr. The catalyst was filtered off, the filtrate was concentrated under reduced pressure and the obtained residue was purified by silica gel column chromatography (petroleum ether/ethyl acetate/dichloromethane) to give the title compound (15 g, 56 so mmol, 62%)

MS (ESI) m/z 269 (M+H)+
$^1$H NMR (400 MHz, DMSO-d$_6$) δ 8.59 (d, J=5.0 Hz, 1H), 8.30 (s, 1H), 8.27 (d, J=8.2 Hz, 1H), 7.51 (d, J=5.0 Hz, 1H), 7.25 (d, J=8.2 Hz, 1H), 7.23 (s, 1H), 3.88 (s, 2H).

Reference Example D-30

Synthesis of [4-[4-(trifluoromethoxy)phenyl]-2-pyridyl]methylamine (D-30)

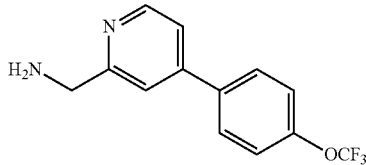 [SMILES: NCc1cc(-c2ccc(OC(F)(F)F)cc2)ccn1]

(step 1) Synthesis of 4-[4-(trifluoromethoxy)phenyl]pyridine-2-carbonitrile

To 4-chloro-2-cyanopyridine (0.50 g, 3.6 mmol), 4-trifluoromethoxyphenylboronic acid (0.74 g, 3.6 mmol) and 1,1'-bis(diphenylphosphino)ferrocenedichloropalladium(II) (0.13 g, 0.18 mmol) were added 1,4-dioxane (20 mL) and 1 mol/L aqueous sodium carbonate solution (20 mL) and the mixture was stirred with heating using a microwave reactor at 100° C. for 20 min. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (0.71 g, 2.7 mmol, 74%).

MS (ESI) m/z 265 (M+H)+

(step 2) Synthesis of [4-[4-(trifluoromethoxy)phenyl]-2-pyridyl]methylamine (D-30)

To a solution of the compound (0.67 g, 2.5 mmol) obtained in step 1 in acetic acid (28 mL) was added 10% palladium/carbon (0.19 g) and the mixture was stirred under a hydrogen atmosphere at room temperature for 30 min. The catalyst was filtered off, ethyl acetate was added to the filtrate and the mixture was washed with saturated aqueous sodium hydrogen carbonate. The organic layer was dried over sodium sulfate, and the desiccant was filtered off, and the solvent was evaporated to give the title compound (0.51 g, 1.9 mmol, 75%).

MS (ESI) m/z 269 (M+H)+

Reference Example D-31

Synthesis of [4-[5-(trifluoromethyl)-2-pyridyl]-2-pyridyl]methylamine hydrochloride (D-31)

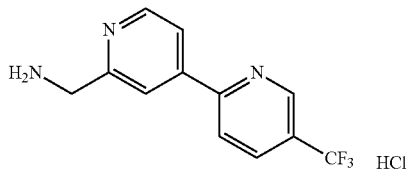 [SMILES: NCc1cc(-c2ccc(C(F)(F)F)cn2)ccn1 ; Cl]

(step 1) Synthesis of tert-butyl N-[(4-chloro-2-pyridyl)methyl]carbamate

To a solution of (4-chloro-2-pyridyl)methylamine (28 g, 0.20 mol) in dichloromethane (250 mL) were added triethylamine (56 mL, 0.40 mol) and di-tert-butyl dicarbonate (52 g, 0.24 mol), and the mixture was stirred at room temperature for 2 hr. The solvent was evaporated and the obtained residue was purified by silica gel column chromatography (petroleum ether/ethyl acetate) to give the title compound (45 g, 0.18 mol, 92%).

MS (ESI) m/z 243 (M+H)+

(step 2) Synthesis of [4-[5-(trifluoromethyl)-2-pyridyl]-2-pyridyl]methylamine hydrochloride (D-31)

To the compound (21 g, 88 mmol) obtained in step 1, E-4 (36 g, 0.12 mol), 1,1'-bis(diphenylphosphino)ferrocene (5.6 g, 10 mmol), palladium acetate (1.1 g, 4.9 mmol), cesium carbonate (66 g, 0.20 mol) and copper(I) chloride (10 g, 0.10 mol) was added N,N-dimethylformamide (450 mL) and the mixture was stirred at 100° C. for 4 hr. The insoluble material was filtered off, ethyl acetate was added to the filtrate and the mixture was washed successively with water and saturated brine. The organic layer was dried over sodium sulfate, and the desiccant was filtered off, and the solvent was evaporated. To the obtained residue was added 4 mol/L hydrogen chloride (dichloromethane solution, 10 mL, 40 mmol), and the mixture was concentrated under reduced pressure. To the obtained residue was added dichloromethane, and the insoluble material was collected by filtration, and dried to give the title compound (22 g, 74 mmol, 84%).

MS (ESI) m/z 254 (M+H)+

$^1$H NMR (400 MHz, CD$_3$OD) δ 9.14 (s, 1H), 8.95 (d, J=5.4 Hz, 1H), 8.61 (s, 1H), 8.45 (d, J=5.4 Hz, 1H), 8.44-8.40 (m, 2H), 4.56 (s, 2H).

Reference Example D-32

Synthesis of [4-[2-(trifluoromethyl)pyrimidin-5-yl]-2-pyridyl]methylamine 2 hydrochloride (D-32)

(step 1) Synthesis of tert-butyl N-[[4-(4,4,5,5-tetramethyl-1,3,2-dioxaborolan-2-yl)-2-pyridyl]methyl]carbamate To the compound (11 g, 47 mmol) obtained in Reference Example D-31, step 1, bis(pinacolato)diboron (14 g, 56 mmol), potassium acetate (3.8 g, 14 mmol) and 1,1'-bis(diphenylphosphino)ferrocenedichloropalladium(II) (3.4 g, 4.2 mmol) was added N,N-dimethylformamide (200 mL) and the mixture was stirred at 100° C. for 2 hr. The insoluble material was filtered off, ethyl acetate was added to the filtrate and the mixture was washed successively with water and saturated brine. The organic layer was dried over sodium sulfate, and the desiccant was filtered off, and the solvent was evaporated to give the title compound as a crudely purified product (13 g)

(step 2) Synthesis of [4-[2-(trifluoromethyl)pyrimidin-5-yl]-2-pyridyl]methylamine 2 hydrochloride (D-32)

To the crudely purified product (0.60 g) obtained in step 1, 5-bromo-2-(trifluoromethyl)pyrimidine (0.50 g, 2.2 mmol), sodium carbonate (0.47 g, 4.4 mmol) and 1,1'-bis(diphenylphosphino) ferrocenedichloropalladium(II) (90 mg, 0.11 mmol) were added N,N-dimethylformamide (16 mL) and water (4 mL) and the mixture was stirred at 100° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate). To the obtained compound were added dichloromethane (20 mL) and 6 mol/L hydrogen chloride (dichloromethane solution, 10 mL, 60 mmol), and the mixture was stirred at room temperature for 1 hr, and concentrated under reduced pressure to give the title compound (0.36 g, 1.2 mmol, 57%).

MS (ESI) m/z 255 (M+H)+

$^1$H NMR (400 MHz, DMSO-d$_6$) δ 12.84 (br s, 1H), 9.61 (s, 2H), 8.93-8.78 (m, 4H), 8.36 (s, 1H), 8.06 (d, J=5.2 Hz, 1H), 4.40-4.28 (m, 2H).

D-33 to D-34 described in Table 17 were synthesized by using corresponding commercially available reagents and by an operation similar to that in Reference Example D-32.

TABLE 17

| Ref. Example No. | Structural formula | MS(ESI) m/z (M + H)+ | NMR |
|---|---|---|---|
| D-32 | H₂N pyridyl-pyrimidine-CF₃ · 2HCl | 255 | ¹H NMR (400 MHz, DMSO-d₆) δ 12.84 (br s, 1H), 9.61 (s, 2H), 8.93-8.78 (m, 4H), 8.36 (s, 1H), 8.06 (d, J = 5.2 Hz, 1H), 4.40-4.28 (m, 2H). |
| D-33 | H₂N pyridyl-pyrimidine-CF₃ · 2HCl | 255 | ¹H NMR (400 MHz, DMSO-d₆) δ 11.15 (br s, 1H), 9.51 (s, 2H), 8.89 (d, J = 5.0 Hz, 1H), 8.69 (s, 3H), 8.48 (br s, 1H): 8.34 (dd, J = 5.0, 1.6 Hz, 1H), 4.38-4.28 (m, 2H). |
| D-34 | H₂N pyridyl-pyrazine-CF₃ · 2HCl | 255 | ¹H NMR (400 MHz, CD₃OD) δ 9.49 (s, 1H), 9.23 (s, 1H), 8.90 (d, J = 5.4 Hz, 1H), 8.36 (br s, 1H), 8.27 (dd, J = 5.4, 1.6 Hz, 1H), 4.47 (s, 2H). |

Reference Example D-35

Synthesis of [4-[6-(trifluoromethyl)pyridazin-3-yl]-2-pyridyl]methylamine hydrochloride (D-35)

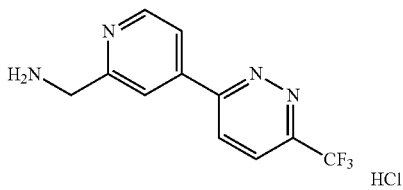 [SMILES: NCc1cc(-c2ccc(C(F)(F)F)nn2)ccn1 ; Cl]

(step 1) Synthesis of 3-chloro-6-(trifluoromethyl)pyridazine

To 3-(trifluoromethyl)-1H-pyridazin-6-one (1.1 g, 6.7 mmol) was added phosphorus oxychloride (10 mL) and the mixture was stirred at 100° C. for 2.5 hr, and concentrated under reduced pressure. To the obtained residue were added dichloromethane and water, and the mixture was stirred at room temperature for 5 min. The mixture was alkalified by adding potassium carbonate to partition the mixture. The organic layer was washed with saturated brine, dried over sodium sulfate, and the desiccant was filtered off, and the solvent was evaporated and the obtained residue was purified by silica gel column chromatography (petroleum ether/ethyl acetate) to give the title compound (0.77 g, 4.2 mmol, 63%).

MS (ESI) m/z 182 (M+H)⁺

¹H NMR (400 MHz, CDCl₃) δ 7.82 (d, J=8.8 Hz, 1H), 7.74 (d, J=8.8 Hz, 1H).

(step 2) Synthesis of [4-[6-(trifluoromethyl)pyridazin-3-yl]-2-pyridyl]methylamine hydrochloride (D-35)

Using the compound obtained in step 1 instead of 5-bromo-2-(trifluoromethyl)pyrimidine, and by an operation similar to that in Reference Example D-32, step 2, the title compound was obtained (yield 54%).

MS (ESI) m/z 255 (M+H)⁺

¹H NMR (400 MHz, CD₃OD) δ 8.92 (d, J=5.3 Hz, 1H), 8.59 (d, J=9.0 Hz, 1H), 8.37 (br s, 1H), 8.33 (d, J=9.0 Hz, 1H), 8.24 (dd, J=5.3, 1.4 Hz, 1H), 4.49 (s, 2H).

Reference Example D-36

Synthesis of [5-[6-(trifluoromethyl)-3-pyridyl]-3-pyridyl]methylamine (D-36)

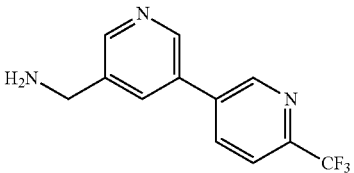 [SMILES: NCc1cncc(-c2ccc(C(F)(F)F)nc2)c1]

Using 5-bromo-2-trifluoromethylpyridine and (5-cyano-3-pyridyl)boronic acid instead of 5-bromo-2-trifluoromethylpyrimidine and 3-cyanophenylboronic acid, and by an operation similar to that in Reference Example D-22, the title compound (yield 9%) was obtained.

MS (ESI) m/z 254 (M+H)⁺

¹H NMR (400 MHz, CD₃OD) δ 9.10 (s, 1H), 8.87 (d, J=1.6 Hz, 1H), 8.68 (s, 1H), 8.41 (dd, J=8.0, 1.6 Hz, 1H), 8.27 (s, 1H), 7.99 (d, J=8.0 Hz, 1H), 4.02 (s, 2H).

Reference Example D-37

Synthesis of [5-[5-(trifluoromethyl)-2-pyridyl]-3-pyridyl]methylamine (D-37)

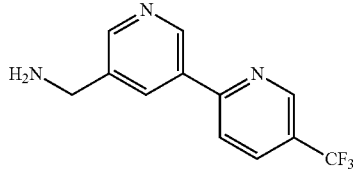 [SMILES: NCc1cncc(-c2ccc(C(F)(F)F)cn2)c1]

(step 1) Synthesis of 5-[5-(trifluoromethyl)-2-pyridyl]pyridine-3-carbonitrile

To 2-bromo-5-(trifluoromethyl)pyridine (4.0 g, 18 mmol) and 5-cyano-3-pyridylboronic acid (3.1 g, 21 mmol) were added sodium carbonate (3.8 g, 35 mmol) and 1,1'-bis(diphenylphosphino)ferrocenedichloropalladium(II) (0.66 g, 0.90 mmol), N,N-dimethylformamide (160 mL) and water (40 mL) and the mixture was stirred at 110° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (3.3 g, 13 mmol, 73%).

MS (ESI) m/z 250 (M+H)⁺

¹H NMR (400 MHz, CDCl₃) δ 9.44 (s, 1H), 9.03 (s, 1H), 8.98 (s, 1H), 8.71 (s, 1H), 8.12 (d, J=8.4 Hz, 1H). 7.94 (d, J=8.4 Hz, 1H).

(step 2) Synthesis of [5-[5-(trifluoromethyl)-2-pyridyl]-3-pyridyl]methylamine (D-37)

To a solution of the compound (3.0 g, 12 mmol) obtained in step 1 in methanol (30 mL) was added nickel (50 mg) and the mixture was stirred under a hydrogen atmosphere at room temperature for 2 hr. The catalyst was filtered off, and the solvent was evaporated. The obtained residue was purified by high performance liquid chromatography (water-acetonitrile) to give the title compound (0.42 g, 1.7 mmol, 14%).

MS (ESI) m/z 254 (M+H)⁺

¹H NMR (400 MHz, CD₃OD) δ 9.74 (s, 1H), 9.60 (s, 1H), 9.18 (s, 1H), 9.16 (s, 1H) 8.48-8.42 (m, 2H), 4.58 (s, 2H).

Reference Example D-38

Synthesis of [6-[4-(trifluoromethoxy)phenyl]pyrimidin-4-yl]methylamine hydrochloride (D-38)

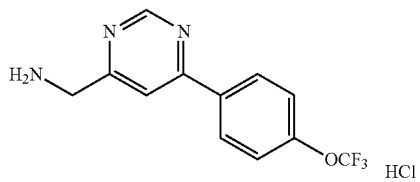 [SMILES: NCc1cc(-c2ccc(OC(F)(F)F)cc2)ncn1 ; Cl]

(step 1) Synthesis of 4-chloro-6-[4-(trifluoromethoxy)phenyl]pyrimidine

To 4,6-dichloropyrimidine (131 g, 879 mmol), 4-(trifluoromethoxy)phenylboronic acid (200 g, 970 mol), potassium carbonate (244 g, 1.77 mol) and tetrakis(triphenylphosphine)palladium(0) (21.5 g, 18.6 mmol) were added 1,4-dioxane (3.0 L) and water (200 mL) and the mixture was stirred at 105° C. for 6 hr. The insoluble material was filtered off, the filtrate was concentrated under reduced pressure and the obtained residue was purified by silica gel column chromatography (petroleum ether/ethyl acetate) to give the title compound (78.0 g, 284 mmol, 32%).

MS (ESI) m/z 275 (M+H)⁺

¹H NMR (400 MHz, CDCl₃) δ 9.04 (s, 1H), 8.13 (d, J=8.6 Hz, 2H), 7.73 (s, 1H), 7.36 (d, J=8.6 Hz, 2H).

(step 2) Synthesis of 6-[4-(trifluoromethoxy)phenyl]pyrimidine-4-carbonitrile

To the compound (1.0 g, 3.6 mmol) obtained in step 1, sodium cyanide (0.22 g, 4.4 mmol) and 1,4-diazabicyclo[2.2.2]octane (41 mg, 0.37 mmol) were added water (2 mL) and dimethyl sulfoxide (6 mL) and the mixture was stirred at 38° C. for 7 hr. The reaction mixture was poured into water, and extracted with ethyl acetate. The organic layer was washed with saturated brine, and dried over sodium sulfate. The desiccant was filtered off, and the solvent was evaporated. To the obtained residue was added petroleum ether, the insoluble material was collected by filtration, and dried to give the title compound (0.80 g, 3.0 mmol, 83%).

MS (ESI) m/z 266 (M+H)⁺

¹H NMR (300 MHz, CDCl₃) δ 9.38 (s, 1H), 8.20 (d, J=8.5 Hz, 2H), 8.04 (s, 1H), 7.42 (d, J=8.5 Hz, 2H).

(step 3) Synthesis of [6-[4-(trifluoromethoxy)phenyl]pyrimidin-4-yl]methylamine hydrochloride (D-38)

To a solution of the compound (10 g, 38 mmol) obtained in step 2 in acetic acid (150 mL) was added 10% palladium/carbon (0.15 g), and the mixture was stirred under a hydrogen atmosphere at room temperature for 1.5 hr. The catalyst was filtered off, to the filtrate was added dichloromethane and the mixture was washed with aqueous sodium hydrogen carbonate solution. The organic layer was dried over sodium sulfate, and the desiccant was filtered off. The solvent was evaporated and the obtained residue was dissolved by adding dichloromethane (120 mL), di-tert-butyl dicarbonate (11 g, 49 mmol) and triethylamine (10 mL, 72 mmol) were added, and the mixture was stirred at room temperature for 30 min. The solvent was evaporated from the reaction mixture and the obtained residue was purified by silica gel column chromatography (petroleum ether/ethyl acetate). To the obtained compound was added 4 mol/L hydrogen chloride (dichloromethane solution, 10 mL, 40 mmol), and the mixture was stirred at room temperature for 20 min, and concentrated under reduced pressure to give the title compound (4.1 g, 13 mmol, 35%).

MS (ESI) m/z 270 (M+H)⁺

¹H NMR (400 MHz, DMSO-d₆) δ 9.31 (s, 1H), 8.73 (s, 3H), 8.37-8.34 (m, 3H), 7.61 (d, J=8.4 Hz, 2H), 4.32-4.28 (m, 2H).

Reference Example D-39

Synthesis of [2-[4-(2,2,2-trifluoroethoxy)phenyl]-4-pyridyl]methylamine hydrochloride (D-39)

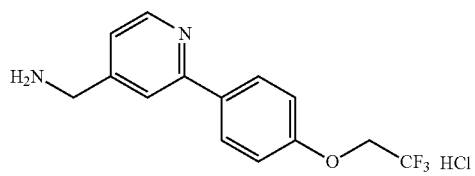 [SMILES: NCc1ccnc(-c2ccc(OCC(F)(F)F)cc2)c1 ; Cl]

(step 1) Synthesis of 1-bromo-4-(2,2,2-trifluoroethoxy)benzene

To a solution of 4-bromophenol (10 g, 58 mmol) in acetone (230 mL) were added potassium carbonate (24 g, 0.17 mol) and 2,2,2-trifluoroethyl trifluoromethanesulfonate (17 g, 72 mmol), and the mixture was stirred at room temperature overnight. The insoluble material was filtered off, acetone was evaporated from the filtrate under reduced pressure (300 mbar, 30° C.). To the obtained residue was added dichloromethane (200 mL) and the mixture was filtered. The filtrate was concentrated under reduced pressure to give the title compound (13 g, 51 mmol, 88%).

$^1$H NMR (400 MHz, CDCl$_3$) δ 7.44-7.40 (m, 2H), 6.85-6.81 (m, 2H), 4.35-4.29 (m, 2H).

(step 2) Synthesis of 4,4,5,5-tetramethyl-2-[4-(2,2,2-trifluoroethoxy)phenyl]-1,3,2-dioxaborolane To the compound (5.0 g, 20 mmol) obtained in step 1, bis(pinacolato)diboron (7.4 g, 29 mmol), potassium acetate (5.7 g, 58 mmol) and 1,1'-bis(diphenylphosphino)ferrocenedichloropalladium(II) (1.4 g, 1.9 mmol) was added N,N-dimethylformamide (100 mL) and the mixture was stirred at 100° C. for 2 hr. The insoluble material was filtered off, diethyl ether was added to the filtrate and the mixture was washed with water, dried over sodium sulfate, and the desiccant was filtered off. The solvent was evaporated and the obtained residue was purified by silica gel column chromatography (petroleum ether) to give the title compound (5.0 g, 17 mmol, 85%).

MS (ESI) m/z 303 (M+H)$^+$ $^1$H NMR (400 MHz, CDCl$_3$) δ 7.82-7.79 (m, 2H), 6.97-6.93 (m, 2H), 4.43-4.35 (m, 2H), 1.36 (s, 12H).

(step 3) Synthesis of tert-butyl N-[[2-[4-(2,2,2-trifluoroethoxy)phenyl]-4-pyridyl]methyl]carbamate To the compound (2.0 g, 6.6 mmol) obtained in step 1, the compound (1.5 g, 6.2 mmol) obtained in Reference Example D-25, step 1, sodium carbonate (1.7 g, 16 mmol) and 1,1'-bis(diphenylphosphino) ferrocenedichloropalladium(II) (0.22 g, 0.30 mmol) were added N,N-dimethylformamide (20 mL) and water (5 mL) and the mixture was stirred at 100° C. for 2 hr. The insoluble material was filtered off, diethyl ether was added to the filtrate and the mixture was washed with water, dried over sodium sulfate, and the desiccant was filtered off. The solvent was evaporated and the obtained residue was purified by silica gel column chromatography (petroleum ether/ethyl acetate) to give the title compound (1.1 g, 2.9 mmol, 47%).

MS (ESI) m/z 383 (M+H)$^+$ $^1$H NMR (400 MHz, DMSO-d$_6$) δ 8.55 (d, J=4.8 Hz, 1H), 8.03 (d, J=8.8 Hz, 2H), 7.77 (s, 1H), 7.55-7.52 (m, 1H), 7.18 (d, J=8.8 Hz, 2H), 7.15 (d, J=5.8 Hz, 1H), 4.88-4.81 (m, 2H), 4.21 (d, J=5.8 Hz, 2H), 1.41 (s, 9H).

(step 4) Synthesis of [2-[4-(2,2,2-trifluoroethoxy)phenyl]-4-pyridyl]methylamine hydrochloride (D-39)

To the compound (1.1 g, 2.9 mmol) obtained in step 3 was added 4 mol/L hydrogen chloride (dichloromethane solution, 100 mL, 0.40 mol), and the mixture was stirred at room temperature for 1 hr, and concentrated under reduced pressure. To the obtained residue was added dichloromethane, and the insoluble material was collected by filtration, and dried to give the title compound (0.74 g, 2.3 mmol, 80%).

MS (ESI) m/z 283 (M+H)$^+$ $^1$H NMR (400 MHz, DMSO-d$_6$) δ 8.90 (br s, 3H), 8.75 (d, J=5.4 Hz, 1H), 8.40 (s, 1H), 8.17 (d, J=8.8 Hz, 2H), 7.67 (d, J=5.4 Hz, 1H), 7.29 (d, J=8.8 Hz, 2H), 4.90 (q, J=8.8 Hz, 2H), 4.25 (q, J=5.6 Hz, 2H).

Reference Example D-40

Synthesis of [6-[6-(trifluoromethyl)-3-pyridyl]pyrimidin-4-yl]methylamine hydrochloride (D-40)

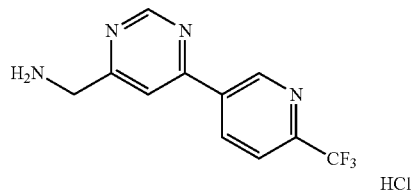 [SMILES: NCc1cc(-c2ccc(C(F)(F)F)nc2)ncn1 ; Cl]

(step 1) Synthesis of 4-chloro-6-[6-(trifluoromethyl)-3-pyridyl]pyrimidine

To 2,4-dichloropyrimidine (6.0 g, 40 mmol), [(6-trifluoromethyl)-3-pyridyl]boronic acid (8.5 g, 44 mmol), potassium carbonate (11 g, 81 mmol) and tetrakis(triphenylphosphine)palladium(0) (1.2 g, 1.0 mmol) were added 1,4-dioxane (150 mL) and water (15 mL) and the mixture was stirred with heating at 110° C. for 4 hr. The reaction mixture was filtered, and the filtrate was diluted with ethyl acetate and washed successively with water and saturated brine. The organic layer was dried over sodium sulfate, and the desiccant was filtered off, and the solvent was evaporated and the obtained residue was purified by silica gel column chromatography (petroleum ether/ethyl acetate) to give the title compound (3.5 g, 14 mmol, 34%).

$^1$H NMR (400 MHz, DMSO-d$_6$) δ 9.37 (s, 1H), 9.14 (s, 1H), 8.61 (dd, J=8.4, 1.6 Hz, 1H), 7.87 (d, J=8.4 Hz, 1H), 7.85 (s, 1H).

(step 2) Synthesis of 6-[6-(trifluoromethyl)-3-pyridyl]pyrimidine-4-carbonitrile To the compound (3.5 g, 14 mmol) obtained in step 1, sodium cyanide (0.79 g, 16 mmol) and 1,4-diazabicyclo[2.2.2]octane (0.15 g, 1.2 mmol) were added water (9 mL) and dimethyl sulfoxide (25 mL), and the mixture was stirred at room temperature for 4 hr. The reaction mixture was added to water, and the mixture was extracted with diethyl ether. The organic layer was washed with saturated brine, and dried over sodium sulfate. The desiccant was filtered off, and the solvent was evaporated and the obtained residue was purified by silica gel column chromatography (petroleum ether/ethyl acetate) to give the title compound (2.2 g, 8.8 mmol, 65%).

$^1$H NMR (400 MHz, CDCl$_3$) δ 9.49 (s, 1H), 9.44 (s, 1H), 8.67 (d, J=8.4 Hz, 1H), 8.15 (s, 1H), 7.92 (d, J=8.4 Hz, 1H).

(step 3) Synthesis of [6-[6-(trifluoromethyl)-3-pyridyl]pyrimidin-4-yl]methylamine hydrochloride (D-40)

To a solution of the compound (2.2 g, 8.8 mmol) obtained in step 2 in acetic acid (120 mL) was added 10% palladium/carbon (660 mg), and the mixture was stirred under a hydrogen atmosphere at room temperature for 1.5 hr. The catalyst was filtered off, dichloromethane was added to the filtrate and washed with aqueous sodium carbonate solution. The organic layer was dried over sodium sulfate, and the desiccant was filtered off, and the solvent was evaporated. To the obtained residue was added 4 mol/L hydrogen chloride (dichloromethane solution, 10 mL, 40 mmol), and the mixture was concentrated under reduced pressure. To the obtained residue was added dichloromethane, and the insoluble material was collected by filtration, and dried to give the title compound (1.0 g, 3.4 mmol, 40%).

MS (ESI) m/z 255 (M+H)$^+$ $^1$H NMR (400 MHz, CD$_3$OD) δ 9.53 (s, 1H), 9.37 (s, 1H), 8.67 (d, J=8.0 Hz, 1H), 8.30 (s, 1H), 8.04 (d, J=8.0 Hz, 1H), 4.51 (s, 2H)

Reference Example D-41

Synthesis of [6-[5-(trifluoromethyl)-2-pyridyl]pyrimidin-4-yl]methylamine hydrochloride (D-41)

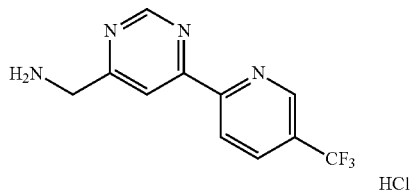 [SMILES: NCc1cc(-c2ccc(C(F)(F)F)cn2)ncn1 ; Cl]

(step 1) Synthesis of 4-chloro-6-[5-(trifluoromethyl)-2-pyridyl]pyrimidine

To 4-chloro-1H-pyrimidin-6-one (3.0 g, 23 mmol), E-4 (9.0 g, 30 mmol), 1,1'-bis(diphenylphosphino)ferrocene (1.3 g, 2.3 mmol), palladium acetate (0.26 g, 1.2 mmol), cesium carbonate (15 g, 46 mmol) and copper(I) chloride (2.3 g, 23 mmol) was added N,N-dimethylformamide (100 mL) and the mixture was stirred at 100° C. overnight. The insoluble material was filtered off, the filtrate was concentrated under reduced pressure. To the obtained residue was added phosphorus oxychloride (40 mL), and the mixture was stirred at 105° C. for 3 hr. The reaction mixture was concentrated under reduced pressure. To the obtained residue was added dichloromethane and the mixture was washed successively with water and saturated brine. The organic layer was dried over sodium sulfate, and the desiccant was filtered off, and the solvent was evaporated and the obtained residue was purified by silica gel column chromatography (petroleum ether/ethyl acetate) to give the title compound (0.55 g, 2.1 mmol, 9%).

MS (ESI) m/z 260 (M+H)$^+$ $^1$H NMR (400 MHz, CDCl$_3$) δ 9.09 (s, 1H), 8.98 (s, 1H), 8.63 (d, J=8.0 Hz, 1H), 8.49 (s, 1H), 8.13 (dd, J=8.0, 1.6 Hz, 1H).

(step 2) Synthesis of 6-[5-(trifluoromethyl)-2-pyridyl]pyrimidine-4-carbonitrile Sodium cyanide (0.17 g, 3.4 mmol) and 1,4-diazabicyclo[2.2.2]octane (24 mg, 0.21 mmol) were dissolved in water (15 mL), a solution of the compound (0.55 g, 2.1 mmol) obtained in step 1 in dimethyl sulfoxide (50 mL) was added and the mixture was stirred at room temperature for 7 hr. The reaction mixture was added to water, and the mixture was extracted with dichloromethane. The organic layer was dried over sodium sulfate, and the desiccant was filtered off, and the solvent was evaporated and the obtained residue was purified by silica gel column chromatography (petroleum ether/ethyl acetate) to give the title compound (0.35 g, 1.4 mmol, 66%)

MS (ESI) m/z 251 (M+H)$^+$ $^1$H NMR (400 MHz, CDCl$_3$) δ 9.44 (s, 1H), 9.02 (s, 1H), 8.80 (s, 1H), 8.68 (d, J=8.8 Hz, 1H), 8.17 (dd, J=8.0, 2.0 Hz, 1H).

(step 3) Synthesis of [6-[5-(trifluoromethyl)-2-pyridyl]pyrimidin-4-yl]methylamine hydrochloride (D-41)

To a solution of the compound (0.32 g, 1.3 mmol) obtained in step 2 in acetic acid (15 mL) was added 10% palladium/carbon (90 mg), and the mixture was stirred under a hydrogen atmosphere at room temperature for 30 min. The catalyst was filtered off, and the filtrate was adjusted to pH8 with aqueous sodium carbonate solution, and extracted with dichloromethane. The organic layer was dried over sodium sulfate, and the desiccant was filtered off, and the solvent was evaporated. To the obtained residue was dissolved in dichloromethane (15 mL), triethylamine (0.60 mL, 4.3 mmol) and di-tert-butyl dicarbonate (0.34 g, 1.5 mmol) were added, and the mixture was stirred at room temperature for 1 hr. The reaction mixture was washed with water, dried over sodium sulfate, and the desiccant was filtered off. The solvent was evaporated and the obtained residue was purified by silica gel column chromatography (petroleum ether/ethyl acetate). To the obtained compound were added dichloromethane (2 mL) and 4 mol/L hydrogen chloride (dichloromethane solution, 10 mL, 40 mmol), and the mixture was stirred at room temperature for 30 min, and concentrated under reduced pressure to give the title compound (0.10 g, 0.34 mmol, 27%).

MS (ESI) m/z 255 (M+H)$^+$ $^1$H NMR (400 MHz, CD$_3$OD) δ 9.37 (s, 1H), 9.08 (s, 1H), 8.76 (d, J=8.2 Hz, 1H), 8.59 (s, 1H), 8.36 (dd, J=8.2, 1.5 Hz, 1H), 4.49 (s, 2H).

Reference Example D-42

Synthesis of [6-[2-(trifluoromethyl)pyrimidin-5-yl]pyrimidin-4-yl]methylamine hydrochloride (D-42)

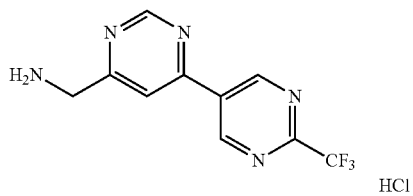 [SMILES: NCc1cc(-c2cnc(C(F)(F)F)nc2)ncn1 ; Cl]

(step 1) Synthesis of 4-chloro-6-[2-(trifluoromethyl)pyrimidin-5-yl]pyrimidine

To the compound (2.5 g, 9.1 mmol) obtained in Reference Example D-28, step 1, 4,6-dichloropyrimidine (2.4 g, 16 mmol), potassium carbonate (3.3 g, 24 mmol) and tetrakis(triphenylphosphine)palladium(0) (0.68 g, 0.60 mmol) were added 1,4-dioxane (150 mL) and water (15 mL) and the mixture was stirred at 110° C. for 2 hr. The insoluble material was filtered off, ethyl acetate was added to the filtrate and the mixture was washed with saturated brine, dried over sodium sulfate, and the desiccant was filtered off. The solvent was evaporated and the obtained residue was purified by silica gel column chromatography (petroleum ether/ethyl acetate) to give the title compound (0.87 g, 3.3 mmol, 37%).

MS (ESI) m/z 261 (M+H)$^+$ $^1$H NMR (400 MHz, CDCl$_3$) δ 9.55 (s, 2H), 9.18 (s, 1H), 7.87 (s, 1H).

(step 2) Synthesis of 6-[2-(trifluoromethyl)pyrimidin-5-yl]pyrimidine-4-carbonitrile To a solution of sodium cyanide (0.19 g, 4.0 mmol) and 1,4-diazabicyclo[2.2.2]octane (41 mg, 0.37 mmol) in water (2 mL) was added a solution of the compound (0.85 g, 3.3 mmol) obtained in step 1 in dimethyl sulfoxide (6 mL) and the mixture was stirred at 38° C. for 7 hr. The reaction mixture was added to water (30 mL) and the mixture was extracted with ethyl acetate. The organic layer was washed with saturated brine, dried over sodium sulfate, and the desiccant was filtered off. The solvent was evaporated. To the obtained residue was added petroleum ether, and the insoluble material was collected by filtration, and dried to give the title compound (0.55 g, 2.2 mmol, 67%)

MS (ESI) m/z 252 (M+H)$^+$ (step 3) Synthesis of [6-[2-(trifluoromethyl)pyrimidin-5-yl]pyrimidin-4-yl]methylamine hydrochloride (D-42)

To a solution of the compound (0.55 g, 2.2 mmol) obtained in step 2 in acetic acid (20 mL) was added 10% palladium/carbon (20 mg), and the mixture was stirred under a hydrogen atmosphere at room temperature for 1.5 hr. The catalyst was filtered off, dichloromethane was added to the filtrate and the mixture was washed with saturated aqueous sodium hydrogen carbonate. The organic layer was dried over sodium sulfate, and the desiccant was filtered off. The solvent was evaporated. To the obtained residue was added 4 mol/L hydrogen chloride (dichloromethane solution, 20 mL, 80 mmol), and the mixture was stirred at room temperature for 30 min, and concentrated under reduced pressure. To the obtained residue was added dichloromethane, and the insoluble material was collected by filtration, and dried to give the title compound (0.18 g, 0.62 mmol, 28%).

MS (ESI) m/z 256 (M+H)$^+$ $^1$H NMR (400 MHz, DMSO-d) δ 9.78 (s, 2H), 9.46 (d, J=0.8 Hz, 1H), 8.73 (brs, 3H), 8.60 (d, J=0.8 Hz, 1H), 4.37 (q, J=5.6 Hz, 2H)

Reference Example D-43

Synthesis of [6-[4-(trifluoromethyl)phenyl]pyridazin-4-yl]methylamine hydrochloride (D-43)

(step 1) Synthesis of tert-butyl N-[(3,6-dichloropyridazin-4-yl)methyl]carbamate To N-Boc-glycine (10 g, 57 mmol), 3,6-dichloropyridazine (5.0 g, 34 mmol) and silver nitrate (I) (0.57 g, 3.4 mmol) were added water (60 mL) and trifluoroacetic acid (0.50 mL, 6.7 mmol). The reaction mixture was heated to 70° C., and a solution of ammonium persulfate (14 g, 61 mmol) in water (20 mL) was slowly added over 20 min. After stirring for 30 min, isopropyl acetate (200 mL) was added to the reaction mixture. The mixture was cooled to 20° C., adjusted to pH9 with aqueous ammonia and the mixture was partitioned. The aqueous layer was extracted with isopropyl acetate (50 mL), and the combined organic layer was washed with 1 mol/L aqueous sodium hydrogen carbonate solution. The organic layer was dried over magnesium sulfate, and the desiccant was filtered off. Hexane was added and the resulting insoluble material was collected by filtration, and dried to give the title compound (2.0 g, 7.2 mmol, 21%).

MS (ESI) m/z 278 (M+H)$^+$ (step 2) Synthesis of tert-butyl N-[[3-chloro-6-[6-(trifluoromethyl)phenyl]pyridazin-4-yl]methyl]carbamate To the compound (0.90 g, 3.2 mmol) obtained in step 1, 4-(trifluoromethyl)phenylboronic acid (0.58 g, 3.0 mmol), sodium carbonate (2.1 g, 20 mmol) and 1,1'-bis(diphenylphosphino)ferrocenedichloropalladium(II) (0.20 g, 0.28 mmol) were added 1,4-dioxane (20 mL) and water (5 mL) and the mixture was stirred with heating at 110° C. for 2 hr. To the reaction mixture was added ethyl acetate, and the mixture was washed successively with water and saturated brine. The organic layer was dried over sodium sulfate, the desiccant was filtered off, and the solvent was evaporated. The obtained residue was purified by silica gel column chromatography (petroleum ether/ethyl acetate) to give the title compound (0.60 g, 1.5 mmol, 51%).

MS (ESI) m/z 388 (M+H)$^+$ (step 3) Synthesis of [6-[4-(trifluoromethyl)phenyl]pyridazin-4-yl]methylamine hydrochloride (D-43)

To a solution of the compound (0.60 g, 1.5 mmol) obtained in step 2 in acetic acid (20 mL) was added 10% palladium/carbon (22 mg), and the mixture was stirred under a hydrogen atmosphere at room temperature for 3 hr. The catalyst was filtered off, ethyl acetate was added to the filtrate and the mixture was washed with saturated brine. The organic layer was dried over sodium sulfate, and the desiccant was filtered off. The solvent was evaporated. To the obtained residue was added 4 mol/L hydrogen chloride (dichloromethane solution, 5 mL, 20 mmol), and the mixture was concentrated under reduced pressure. The obtained residue was purified by high performance liquid chromatography (water-acetonitrile) to give the title compound (0.16 g, 0.49 mmol, 32%).

MS (ESI) m/z 254 (M+H)$^+$ $^1$H NMR (400 MHz, DMSO-ds) δ 9.44 (d, J=1.8 Hz, 1H), 8.95 (s, 3H), 8.68 (d, J=1.8 Hz, 1H), 8.40 (d, J=8.4 Hz, 2H), 8.24-8.19 (m, 1H), 8.00 (d, J=8.4 Hz, 2H), 4.27-4.23 (m, 2H).

D-44 described in Table 18 was synthesized by using corresponding commercially available reagents and by an operation similar to that in Reference Example D-43.

insoluble material was collected by filtration, and dried to give the title compound (1.2 g, 5.0 mmol, 33%).

MS (ESI) m/z 241 (M+H)$^+$ $^1$H NMR (400 MHz, DMSO-d$_6$) δ 13.24 (s, 1H), 8.34 (s, 1H), 8.04 (d, J=8.2 Hz, 2H), 7.88 (d, J=8.2 Hz, 2H), 7.26 (s, 1H).

(step 2) Synthesis of 3-chloro-5-[4-(trifluoromethyl)phenyl]pyridazine

To the compound (1.2 g, 5.0 mmol) obtained in step 1 was added phosphorus oxychloride (15 mL) and the mixture was stirred with heating at 105° C. for 3 hr. The reaction mixture was concentrated under reduced pressure. To the obtained residue was added dichloromethane, and the mixture was

TABLE 18

| Ref. Example No. | Structural formula | MS(ESI) m/z (M + H)$^+$ | NMR |
|---|---|---|---|
| D-43 | | 254 | $^1$H NMR (400 MHz, DMSO-d$_6$) δ 9.44 (d, J = 1.8 Hz, 1H), 8.95 (s, 3H), 8.68 (d, J = 1.8 Hz, 1H), 8.40 (d, J = 8.4 Hz, 2H), 8.24-8.19 (m, 1H), 8.00 (d, J = 8.4 Hz, 2H), 4.27-4.23 (m, 2H). |
| D-44 | | 255 | $^1$H NMR (400 MHz, CD$_3$OD) δ 9.56 (d, J = 2.0 Hz, 1H), 9.50 (d, J = 2.0 Hz, 1H), 8.84 (dd, J = 8.2, 2.0 Hz, 1H), 8.76 (d, J = 2.0 Hz, 1H), 8.10 (d, J = 8.2 Hz, 1H), 4.50 (s, 2H). |

Reference Example D-45

Synthesis of [5-[4-(trifluoromethyl)phenyl]pyridazin-3-yl]methylamine (D-45)

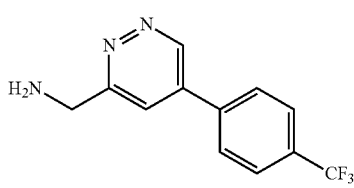

(step 1) Synthesis of 4-[4-(trifluoromethyl)phenyl]-1H-pyridazin-6-one

To 4-chloro-1H-pyridazin-6-one (2.0 g, 15 mmol), 4-(trifluoromethyl)phenylboronic acid (3.5 g, 18 mmol) and 1,1'-bis(diphenylphosphino)ferrocenedichloropalladium(II) (0.58 g, 0.79 mmol) were added 1,4-dioxane (20 mL) and saturated aqueous sodium hydrogen carbonate (16 mL) and the mixture was stirred with heating at 105° C. for 3 hr. To the reaction mixture was added ethyl acetate, and the mixture was washed successively with water and saturated brine. The organic layer was dried over sodium sulfate, the desiccant was filtered off, and the solvent was evaporated. To the obtained residue was added diethyl ether, and the washed successively with water and saturated brine. The organic layer was dried over sodium sulfate, and the desiccant was filtered off. The solvent was evaporated and the obtained residue was purified by silica gel column chromatography (petroleum ether/ethyl acetate) to give the title compound (0.50 g, 1.5 mmol, 51%)

MS (ESI) m/z 259 (M+H)$^+$ $^1$H NMR (400 MHz, CDCl$_3$) δ 9.39 (s, 1H), 7.84 (d, J=8.6 Hz, 2H), 7.79 (d, J=8.6 Hz, 2H), 7.72 (s, 1H).

(step 3) Synthesis of 5-[4-(trifluoromethyl)phenyl]pyridazine-3-carbonitrile

The compound (0.42 g, 1.6 mmol) obtained in step 2 was dissolved by adding N,N-Dimethylformamide (25 mL). Zinc cyanide (0.37 g, 3.2 mmol), tris(dibenzylideneacetone)dipalladium(0) (75 mg, 0.080 mmol) and 1,1'-bis(diphenylphosphino)ferrocene (45 mg, 0.080 mmol) were added under a nitrogen atmosphere and the mixture was stirred heating at 110° C. for 3 hr. To the reaction mixture was added dichloromethane and the mixture was washed successively with water and saturated brine. The organic layer was dried over sodium sulfate, and the desiccant was filtered off. The solvent was evaporated and the obtained residue was purified by silica gel column chromatography (petroleum ether/ethyl acetate) to give the title compound (0.32 g, 1.3 mmol, 80%).

MS (ESI) m/z 250 (M+H)$^+$ $^1$H NMR (400 MHz, CDCl$_3$) δ 9.64 (s, 1H), 8.04 (s, 1H), 7.88 (d, J=8.2 Hz, 2H), 7.82 (d, J=8.2 Hz, 2H).

(step 4) Synthesis of [5-[4-(trifluoromethyl)phenyl]pyridazin-3-yl]methylamine (D-45)

To a solution of the compound (0.36 g, 1.5 mmol) obtained in step 3 in methanol (15 mL) was added 10% palladium/carbon (0.30 g), and the mixture was stirred under a hydrogen atmosphere at 25° C. for 30 min. The catalyst was filtered off, and the filtrate was concentrated under reduced pressure. To a the obtained residue was added dichloromethane, and the insoluble material was collected by filtration, and dried to give the title compound (0.23 g, 0.91 mmol, 63%).

MS (ESI) m/z 254 (M+H)$^+$ $^1$H NMR (400 MHz, CD$_3$OD) δ 9.72 (s, 1H), 8.26 (s, 1H), 8.13 (d, J=8.2 Hz, 2H), 7.94 (d, J=8.2 Hz, 2H), 4.64 (s, 2H).

Reference Example D-46

Synthesis of [5-[6-(trifluoromethyl)-3-pyridyl]pyridazin-3-yl]methylamine hydrochloride (D-46)

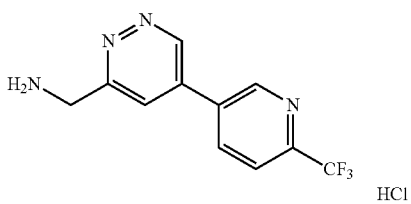 [SMILES: NCc1cc(-c2ccc(C(F)(F)F)nc2)cnn1 ; Cl]

To a solution of a compound (1.0 g, 4.0 mmol) obtained using [6-(trifluoromethyl)-3-pyridyl]boronic acid instead of 4-(trifluoromethyl)phenylboronic acid, and by an operation similar to that in Reference Example D-45, steps 1-3, in methanol (40 mL) were added concentrated hydrochloric acid (1 mL) and 10% palladium/carbon (0.30 g), and the mixture was stirred under a hydrogen atmosphere at 25° C. for 1 hr. The catalyst was filtered off, and the filtrate was concentrated under reduced pressure. To the obtained residue were added dichloromethane (30 mL), triethylamine (1.5 mL, 11 mmol) and di-tert-butyl dicarbonate (1.1 g, 5.2 mmol), and the mixture was stirred at room temperature for 1 hr. The reaction mixture was washed successively with water and saturated brine, the organic layer was dried over sodium sulfate, and the desiccant was filtered off. The solvent was evaporated and the obtained residue was purified by silica gel column chromatography (petroleum ether/ethyl acetate). To the obtained compound was added 4 mol/L hydrogen chloride (dichloromethane solution, 10 mL, 40 mmol), and the mixture was stirred at room temperature for 30 min, concentrated under reduced pressure to give the title compound (0.65 g, 2.2 mmol, 56%).

MS (ESI) m/z 255 (M+H)$^+$ $^1$H NMR (400 MHz, CD$_3$OD) δ 9.96-9.95 (m, 1H), 9.30 (s, 1H), 8.66-8.58 (m, 2H), 8.10 (d, J=8.4 Hz, 2H), 4.73 (s, 2H).

Reference Example D-47

Synthesis of [5-[5-(trifluoromethyl)-2-pyridyl]pyridazin-3-yl]methylamine hydrochloride (D-47)

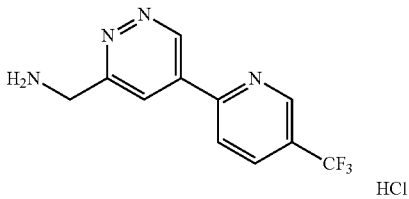 [SMILES: NCc1cc(-c2ccc(C(F)(F)F)cn2)cnn1 ; Cl]

(step 1) Synthesis of 3-chloro-5-[5-(trifluoromethyl)-2-pyridyl]pyridazine

To 4-chloro-1H-pyridazin-6-one (4.5 g, 35 mmol), E-4 (13 g, 41 mmol), 1,1'-bis(diphenylphosphino)ferrocene (1.9 g, 3.5 mmol), palladium acetate (0.39 g, 1.7 mmol), cesium carbonate (23 g, 69 mmol) and copper(I) chloride (3.4 g, 35 mmol) was added N,N-dimethylformamide (100 mL) and the mixture was stirred at 105° C. for 6 hr. The insoluble material was filtered off, and the filtrate was concentrated under reduced pressure. To the obtained residue was added phosphorus oxychloride (30 mL), and the mixture was stirred at 105° C. for 2 hr. The reaction mixture was concentrated under reduced pressure. To the obtained residue was added dichloromethane and the mixture was washed successively with water and saturated brine. The organic layer was dried over sodium sulfate, and the desiccant was filtered off. The solvent was evaporated and the obtained residue was purified by silica gel column chromatography (petroleum ether/ethyl acetate) to give the title compound (2.1 g, 8.1 mmol, 23%).

MS (ESI) m/z 260 (M+H)$^+$ $^1$H NMR (400 MHz, DMSO-d$_6$) δ 9.96 (d, J=1.6 Hz, 1H), 9.20 (s, 1H), 8.62-8.51 (m, 3H).

(step 2) Synthesis of 5-[5-(trifluoromethyl)-2-pyridyl]pyridazine-3-carbonitrile The compound (1.0 g, 3.9 mmol) obtained in step 1 was dissolved by adding N,N-Dimethylformamide (20 mL). Zinc cyanide (0.27 g, 2.3 mmol), tris(dibenzylideneacetone)dipalladium(0) (0.14 g, 0.15 mmol) and 1,1'-bis(diphenylphosphino)ferrocene (0.16 g, 0.29 mmol) were added under a nitrogen atmosphere and the mixture was stirred with heating at 110° C. for 4.5 hr. To the reaction mixture was added dichloromethane and the mixture was washed successively with water and saturated brine. The organic layer was dried over sodium sulfate, and the desiccant was filtered off. The solvent was evaporated and the obtained residue was purified by silica gel column chromatography (petroleum ether/ethyl acetate) to give the title compound (0.30 g, 1.2 mmol, 31%).

MS (ESI) m/z 251 (M+H)$^+$ (step 3) Synthesis of [5-[5-(trifluoromethyl)-2-pyridyl]pyridazin-3-yl]methylamine hydrochloride (D-47)

To a solution of the compound (0.60 g, 2.4 mmol) obtained in step 2 in acetic acid (15 mL) was added 10% palladium/carbon (0.18 g), and the mixture was stirred under a hydrogen atmosphere at 25° C. for 1.5 hr. The catalyst was filtered off, and the filtrate was concentrated under reduced pressure. To the obtained residue were added dichloromethane (30 mL), triethylamine (3.5 mL, 25 mmol) and di-tert-butyl dicarbonate (2.0 g, 9.2 mmol), and the mixture was stirred at room temperature for 1 hr. To the reaction mixture was added dichloromethane and the mixture was washed with water. The organic layer was dried over sodium sulfate, and the desiccant was filtered off. The solvent was evaporated and the obtained residue was purified by silica gel column chromatography (petroleum ether/ethyl acetate). To the obtained compound was added 4 mol/L hydrogen chloride (dichloromethane solution, 25 mL, 0.10 mol), and the mixture was stirred at room temperature for 1 hr, and concentrated under reduced pressure to give the title compound (0.50 g, 1.7 mmol, 71%).

MS (ESI) m/z 255 (M+H)$^+$ $^1$H NMR (400 MHz, DMSO-d$_6$) δ 9.98 (d, J=2.1 Hz, 1H), 9.22 (s, 1H), 8.75 (s, 3H), 8.59-8.52 (m, 3H), 4.54-4.50 (m, 2H).

Reference Example D-48

Synthesis of 4-(aminomethyl)-2-[5-(trifluoromethyl)-2-pyridyl]phenol hydrochloride (D-48)

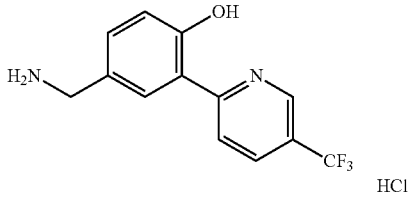 [SMILES: NCc1ccc(O)c(-c2ccc(C(F)(F)F)cn2)c1 ; Cl]

(step 1) Synthesis of (5-cyano-2-methoxy-phenyl)boronic acid

3-Bromo-4-methoxybenzonitrile (7.7 g, 36 mmol) and triisopropyl borate (14 g, 73 mmol) were dissolved by adding tetrahydrofuran (150 mL), and 2.5 mol/L n-butyllithium (hexane solution, 22 mL, 55 mmol) was slowly added over 20 min at −78° C. After stirring at −78° C. for 2 hr, to the reaction mixture was added 7% phosphoric acid (100 mL), and the mixture was heated to room temperature. The reaction mixture was partitioned, to the organic layer was added dichloromethane, and the mixture was extracted with 5% aqueous sodium hydroxide solution (200 mL). The aqueous layer was washed with diethyl ether, adjusted to pH2.5 with 85% phosphoric acid and the insoluble material was collected by filtration. The obtained solid was washed with water, and dried to give the title compound (5.1 g, 29 mmol, 79%)

MS (ESI) m/z 178 (M+H)$^+$ $^1$H NMR (300 MHz, DMSO-d$_6$) δ 8.03 (s, 2H), 7.86-7.78 (m, 2H), 7.13 (d, J=11.6 Hz, 1H), 3.85 (s, 3H).

(step 2) Synthesis of 4-methoxy-3-[5-(trifluoromethyl)-2-pyridyl]benzonitrile

To the compound (1.1 g, 6.0 mmol) obtained in step 1, 2-bromo-5-(trifluoromethyl)pyridine (1.2 g, 5.5 mmol), sodium carbonate (1.2 g, 11 mmol) and 1,1′-bis(diphenylphosphino)ferrocenedichloropalladium(II) (0.20 g, 0.27 mmol) were added N,N-dimethylformamide (16 mL) and water (4 mL) and the mixture was stirred at 100° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (1.4 g, 5.1 mmol, 92%).

MS (ESI) m/z 279 (M+H)$^+$ (step 3) Synthesis of tert-butyl N-[[4-hydroxy-3-[5-(trifluoromethyl)-2-pyridyl]phenyl]methyl]carbamate To the compound (1.5 g, 5.4 mmol) obtained in step 2 and cobalt(II) chloride 6 hydrate (0.70 g, 5.4 mmol) were added tetrahydrofuran (60 mL) and water (40 mL). To the reaction mixture was added sodium tetrahydroborate (0.51 g, 14 mmol) at 0° C., and the mixture was stirred at room temperature for 3 hr, and 3 mol/L hydrochloric acid (150 mL) was added. Tetrahydrofuran was evaporated from the reaction mixture under reduced pressure, and the mixture was adjusted to pH8-9 with aqueous ammonia. To the reaction mixture was added and extracted with ethyl acetate, and the organic layer was washed with saturated brine, dried over sodium sulfate, and the desiccant was filtered off. The solvent was evaporated. The obtained residue was dissolved in dichloromethane (5 mL), and 1 mol/L boron tribromide (dichloromethane solution, 10 mL, 10 mmol) was added. After stirring at room temperature for 7 hr, the reaction mixture was adjusted to pH8 with saturated aqueous sodium carbonate solution, and the mixture was extracted with ethyl acetate. The organic layer was washed with saturated brine, dried over sodium sulfate, and the desiccant was filtered off. The solvent was evaporated. The obtained residue was dissolved by adding dichloromethane (5 mL), di-tert-butyl dicarbonate (−70° C., 0.46 g, 2.1 mmol) was added, and the mixture was stirred at room temperature for 30 min. The solvent was evaporated from the reaction mixture and the obtained residue was purified by silica gel column chromatography (dichloromethane) to give the title compound (0.28 g, 0.76 mmol, 14%).

MS (ESI) m/z 369 (M+H)$^+$ $^1$H NMR (400 MHz, CDCl$_3$) δ 13.59 (s, 1H), 8.80 (s, 1H), 8.08-8.02 (m, 2H), 7.75 (s, 1H), 7.29 (dd, J=8.8, 0.8 Hz, 1H), 7.02 (d, J=8.8 Hz, 1H), 4.86 (s, 1H), 4.45-4.15 (m, 2H), 1.47 (s, 9H).

(step 4) Synthesis of 4-(aminomethyl)-2-[5-(trifluoromethyl)-2-pyridyl]phenol hydrochloride (D-48)

To the compound (0.28 g, 0.76 mmol) obtained in step 3 were added dichloromethane (3 mL) and 4 mol/L hydrogen chloride (dichloromethane solution, 10 mL, 40 mmol), and the mixture was stirred at room temperature for 30 min, and concentrated under reduced pressure to give the title compound (0.21 g, 0.67 mmol, 88%).

MS (ESI) m/z 269 (M+H)$^+$ $^1$H NMR (400 MHz, DMSO-d$_6$) δ 9.08 (s, 1H), 8.46-8.41 (m, 5H), 8.30 (d, J=2.0 Hz, 1H), 7.50 (dd, J=8.4, 2.0 Hz, 1H), 7.05 (d, J=8.4 Hz, 1H), 4.03-3.99 (m, 2H).

Reference Example D-49

Synthesis of 4-(aminomethyl)-2-[5-(trifluoromethyl)pyrimidin-2-yl]phenol hydrochloride (D-49)

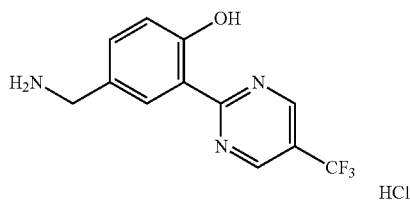 [SMILES: NCc1ccc(O)c(-c2ncc(C(F)(F)F)cn2)c1 ; Cl]

Using 2-chloro-5-(trifluoromethyl)pyrimidine instead of 2-bromo-5-(trifluoromethyl)pyridine, and by an operation similar to that in Reference Example D-48, the title compound (yield 6%) was obtained.

MS (ESI) m/z 270 (M+H)$^+$ $^1$H NMR (400 MHz, CD$_3$OD) δ 9.29 (s, 2H), 8.72 (d, J=2.4 Hz, 1H), 7.58 (dd, J=8.4, 2.4 Hz, 1H), 7.12 (d, J=8.0 Hz, 1H), 4.16 (s, 2H).

Reference Example D-50

Synthesis of 4-(aminomethyl)-2-[5-(trifluoromethyl)pyrazin-2-yl]phenol hydrochloride (D-50)

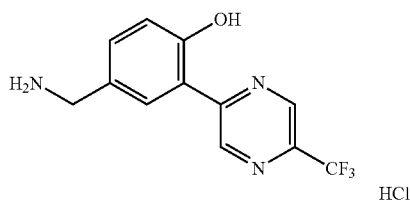 [SMILES: NCc1ccc(O)c(-c2cnc(C(F)(F)F)cn2)c1 ; Cl]

(step 1) Synthesis of 4-methoxy-3-[5-(trifluoromethyl)pyrazin-2-yl]benzonitrile

Using 2-chloro-5-(trifluoromethyl)pyrazine instead of 2-bromo-5-(trifluoromethyl)pyridine, and by an operation similar to that in Reference Example D-48, step 2, the title compound was obtained (yield 92%).

MS (ESI) m/z 280 (M+H)$^+$ $^1$H NMR (400 MHz, CDCl$_3$) δ 9.31 (d, J=0.8 Hz, 1H), 9.03 (d, J=0.8 Hz, 1H), 8.28 (d, J=0.8 Hz, 1H), 7.78 (dd, J=8.8, 0.8 Hz, 1H), 7.15 (d, J=8.8 Hz, 1H), 4.02 (s, 3H).

(step 2) Synthesis of [4-methoxy-3-[5-(trifluoromethyl)pyrazin-2-yl]phenyl]methylamine To a solution of the compound (1.2 g, 4.3 mmol) obtained in step 1 in acetic acid (120 mL) was added 10% palladium/carbon (0.50 g), and the mixture was stirred under a hydrogen atmosphere at room temperature for 3 hr. The catalyst was filtered off, to the filtrate was added dichloromethane (100 mL) and the mixture was washed with aqueous sodium carbonate solution. The organic layer was dried over sodium sulfate, and the desiccant was filtered off. The solvent was evaporated and the obtained residue was purified by high performance liquid chromatography (water-acetonitrile) to give the title compound (0.20 g, 0.71 mmol, 16%).

MS (ESI) m/z 284 (M+H)$^+$ (step 3) Synthesis of 4-(aminomethyl)-2-[5-(trifluoromethyl)pyrazin-2-yl]phenol hydrochloride (D-50)

The compound (0.20 g, 0.71 mmol) obtained in step 2 was dissolved by adding dichloromethane (25 mL) and 1 mol/L boron tribromide (dichloromethane solution, 3 mL, 3 mmol) was added at −78° C. After stirring at room temperature for 4 hr, the reaction mixture was adjusted to pH8 with saturated aqueous sodium carbonate solution, extracted with dichloromethane. The organic layer was dried over sodium sulfate, and the desiccant was filtered off. The solvent was evaporated. To the obtained residue was added 4 mol/L hydrogen chloride (dichloromethane solution, 10 mL, 40 mmol), and the mixture was stirred at room temperature for 30 min, and concentrated under reduced pressure. To the obtained residue was added dichloromethane, and the insoluble material was collected by filtration, and dried to give the title compound (0.19 g, 0.61 mmol, 87%).

MS (ESI) m/z 270 (M+H)$^+$ $^1$H NMR (300 MHz, DMSO-d$_6$) δ 11.30 (br s, 1H), 9.52 (s, 1H), 9.25 (s, 1H), 8.30 (br s, 3H), 8.13 (d, J=2.1 Hz, 1H), 7.52 (dd, J=8.4, 2.1 Hz, 1H), 7.13 (d, J=8.4 Hz, 1H), 4.03-3.97 (m, 2H).

Reference Example D-51

Synthesis of 6-(aminomethyl)-4-[5-(trifluoromethyl)-2-pyridyl]pyridin-3-ol hydrochloride (D-51)

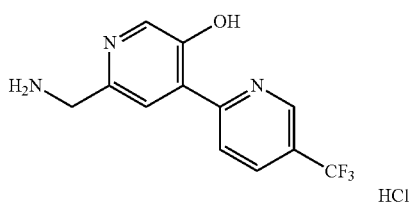 [SMILES: NCc1cc(-c2ccc(C(F)(F)F)cn2)c(O)cn1 ; Cl]

(step 1) Synthesis of 2-chloro-5-(methoxymethoxy)pyridine

N,N-Dimethylformamide (25 mL) was added to suspend sodium hydride (60% in oil, 1.8 g, 45 mmol), and a solution of 2-chloro-5-hydroxypyridine (5.0 g, 39 mmol) in N,N-dimethylformamide (10 mL) was slowly added dropwise over 45 min. The reaction mixture was stirred at room temperature for 1.5 hr, chloromethylmethylether (3.3 mL, 43 mmol) was added dropwise over 10 min, and the mixture was stirred at room temperature for 12 hr. To the reaction mixture was added ethyl acetate and the mixture was washed successively with water and saturated brine. The organic layer was dried over sodium sulfate, and the desiccant was filtered off. The solvent was evaporated and the obtained residue was purified by silica gel column chromatography (petroleum ether/ethyl acetate) to give the title compound (5.4 g, 31 mmol, 80%).

MS (ESI) m/z 174 (M+H)$^+$ $^1$H NMR (400 MHz, CDCl$_3$) δ 8.17 (d, J=2.8 Hz, 1H), 7.36 (dd, J=2.8, 9.2 Hz, 1H), 7.24 (d, J=9.2 Hz, 1H), 5.18 (s, 2H), 3.46 (s, 3H).

(step 2) Synthesis of [2-chloro-5-(methoxymethoxy)-4-pyridyl]boronic acid

To a solution of the compound (4.5 g, 26 mmol) obtained in step 1 in tetrahydrofuran (500 mL) was added 1.3 mol/L tert-butyllithium (40 mL, 52 mmol) at −78° C. and the mixture was stirred for 30 min. A solution of triisopropyl borate (9.7 g, 52 mmol) in tetrahydrofuran (20 mL) was added dropwise at −78° C. over 1 hr. To the reaction mixture were added ethyl acetate (100 mL) and water (60 mL) to partition the mixture, and the aqueous layer was washed with diethyl ether. The aqueous layer was adjusted to pH1 with 1 mol/L hydrochloric acid, and the insoluble material was collected by filtration, and dried to give the title compound (3.0 g, 14 mmol, 54%).

MS (ESI) m/z 218 (M+H)$^1$ $^1$H NMR (300 MHz, CDCl$_3$) δ 8.45 (s, 2H), 8.13 (s, 1H), 7.37 (s, 1H), 5.24 (s, 2H), 3.40 (s, 3H).

(step 3) Synthesis of 2-chloro-5-(methoxymethoxy)-4-[5-(trifluoromethyl)-2-pyridyl]pyridine To the compound (5.0 g, 22 mmol) obtained in step 2, 2-bromo-5-(trifluoromethyl)pyridine (6.2 g, 29 mmol), sodium carbonate (4.7 g, 44 mmol) and 1,1'-bis(diphenylphosphino)ferrocenedichloropalladium(II) (0.80 g, 1.1 mmol) were added N,N-dimethylformamide (80 mL) and water (20 mL) and the mixture was stirred at 110° C. for 2 hr. The insoluble material was filtered off, ethyl acetate was added to the filtrate and the mixture was washed successively with water and saturated brine, dried over sodium sulfate, and the desiccant was filtered off. The solvent was evaporated and the obtained residue was purified by silica gel column chromatography (petroleum ether/ethyl acetate) to give the title compound (2.0 g, 6.3 mmol, 28%).

MS (ESI) m/z 319 (M+H)$^+$ $^1$H NMR (400 MHz, DMSO-d$_6$) δ 9.14 (s, 1H), 8.44 (s, 1H), 8.41 (dd, J=2.0, 8.4 Hz, 1H), 8.22 (d, J=8.4 Hz, 1H), 7.84 (s, 1H), 5.39 (s, 2H), 3.36 (s, 3H).

(step 4) Synthesis of 5-hydroxy-4-[5-(trifluoromethyl)-2-pyridyl]pyridine-2-carbonitrile The compound (4.8 g, 15 mmol) obtained in step 3 was dissolved by adding N,N-dimethylformamide (300 mL). Zinc cyanide (1.1 g, 9.1 mmol), tris(dibenzylideneacetone)dipalladium(0) (0.30 g, 0.32 mmol) and 1,1'-bis(diphenylphosphino)ferrocene (0.60 g, 1.1 mmol) were added under a nitrogen atmosphere and the mixture was stirred with heating at 110° C. for 12 hr. To the reaction mixture was added dichloromethane and the mixture was washed successively with water and saturated brine. The organic layer was dried over sodium sulfate, and the desiccant was filtered off. The solvent was evaporated and the obtained residue was so purified by silica gel column chromatography (petroleum ether/ethyl acetate) to give the title compound (1.3 g, 4.9 mmol, 33%).

MS (ESI) m/z 266 (M+H)$^+$ $^1$H NMR (400 MHz, CDCl$_3$) δ 14.10 (s, 1H), 8.94 (s, 1H), 8.60 (s, 1H), 8.26 (d, J=8.0 Hz, 1H), 8.16 (d, J=8.0 Hz, 1H), 8.09 (s, 1H).

(step 5) Synthesis of 6-(aminomethyl)-4-[5-(trifluoromethyl)-2-pyridyl]pyridin-3-ol hydrochloride (D-51)

To a solution of the compound (0.90 g, 3.4 mmol) obtained in step 4 in methanol (150 mL) were added 10% palladium/carbon (270 mg) and concentrated hydrochloric acid (2 mL), and the mixture was stirred under a hydrogen atmosphere at room temperature for 1.5 hr. The catalyst was filtered off, the filtrate was concentrated under reduced pressure and the obtained residue was purified by high performance liquid chromatography (water-acetonitrile) to give the title compound (0.36 g, 1.2 mmol, 35%).

MS (ESI) m/z 270 (M+H)$^+$ $^1$H NMR (400 MHz, DMSO-d$_6$) δ 9.16 (s, 1H), 8.49-8.38 (m, 6H), 8.19 (s, 1H), 4.18-4.14 (m, 2H).

Reference Example D-52

Synthesis of 1-[3-chloro-5-[6-(trifluoromethyl)-3-pyridyl]phenyl]cyclopropanamine hydrochloride (D-52)

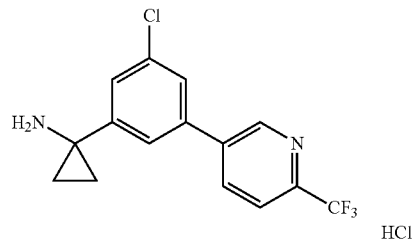 [SMILES: NC1(c2cc(Cl)cc(-c3ccc(C(F)(F)F)nc3)c2)CC1 ; Cl]

(step 1) Synthesis of tert-butyl N-[1-(3-bromo-5-chlorophenyl)cyclopropyl]carbamate To a solution of 3-bromo-5-chlorobenzonitrile (0.22 g, 1.0 mmol) in diethyl ether (3 mL) was added titanium tetraisopropoxide (0.21 mL, 1.1 mmol). 3 mol/L Ethylmagnesium bromide (diethylether solution, 0.73 mL, 2.2 mmol) was added dropwise at −70° C. and the mixture was stirred for 10 min, heated to room temperature and stirred for 1 hr. To the reaction mixture was added dropwise boron trifluoride diethylether complex (0.25 mL, 2.0 mmol), and the mixture was stirred for 30 min. 1 mol/L Hydrochloric acid (3 mL) was added, and the mixture was stirred at room temperature overnight. The reaction mixture was concentrated under reduced pressure and the obtained residue was purified by high performance liquid chromatography (water-acetonitrile, each containing 0.1% trifluoroacetic acid) to give an intermediate (60 mg, 0.17 mmol). To the obtained intermediate (60 mg) were added dichloromethane (2 mL), triethylamine (0.070 mL, 0.50 mmol) and di-tert-butyl dicarbonate (40 mg, 0.18 mmol), and the mixture was stirred at room temperature overnight. The solvent was evaporated from the reaction mixture, and the mixture was purified by silica gel column chromatography to give the title compound (30 mg, 0.095 mmol, 10%).

$^1$H NMR (400 MHz, CDCl$_3$) δ 7.33 (s, 1H), 7.21 (s, 1H), 7.11 (s, 1H), 5.14 (m, 1H), 1.45 (s, 9H), 1.36-1.12 (m, 4H)

(step 2) Synthesis of tert-butyl N-[1-[3-chloro-5-[6-(trifluoromethyl)-3-pyridyl]phenyl]cyclopropyl]carbamate To the compound (30 mg, 0.095 mmol) obtained in step 1, [6-(trifluoromethyl)-3-pyridyl]boronic acid (23 mg, 0.11 mmol) and 1,1'-bis(diphenylphosphino)ferrocenedichloropalladium(II) (7.0 mg, 0.0096 mmol) were added 1,4-dioxane (1 mL) and 1 mol/L aqueous sodium carbonate solution (0.3 mL) and the mixture was stirred with heating using a microwave reactor at 115° C. for 20 min. The reaction mixture was purified by high performance liquid chromatography (water-acetonitrile, each containing 0.1% trifluoroacetic acid) to give the title compound (22 mg, 0.053 mmol, 56%).

$^1$H NMR (400 MHz, CDCl$_3$) δ 8.88 (d, J=2.2 Hz, 1H), 8.04-7.93 (m, 1H), 7.76 (d, J=8.2 Hz, 1H), 7.39 (s, 1H), 7.36-7.30 (m, 1H), 7.25 (s, 1H), 5.30 (s, 1H), 1.53-1.21 (m, 13H).

(step 3) Synthesis of 1-[3-chloro-5-[6-(trifluoromethyl)-3-pyridyl]phenyl]cyclopropanamine hydrochloride (D-52)

To the compound (22 mg, 0.053 mmol) obtained in step 2 were added dichloromethane (2 mL), 4 mol/L hydrochloric acid (1,4-dioxane solution, 2 mL), and the mixture was stirred at room temperature for 8 hr. The solvent was evaporated from the reaction mixture, and the residue was dissolved in water-acetonitrile and lyophilized to give the title compound (16 mg, 0.045 mmol, 85%).

MS (ESI) m/z 313 (M+H)$^+$ $^1$H NMR (400 MHz, DMSO-d$_6$) δ 9.19 (s, 1H), 9.02 (s, 3H), 8.49 (d, J=8.2 Hz, 1H), 8.05 (d, J=8.2 Hz, 1H), 7.94 (s, 1H), 7.84 (s, 1H), 7.62 (s, 1H), 1.49-1.36 (m, 4H).

Reference Example D-53

Synthesis of 1-[2-[4-(trifluoromethyl)phenyl]-4-pyridyl]cyclopropanamine (D-53)

(step 1) Synthesis of 2-[4-(trifluoromethyl)phenyl]pyridine 4-carbonitrile

To 2-chloropyridine-4-carbonitrile (0.15 g, 1.1 mmol), [4-(trifluoromethyl)phenyl]boronic acid (0.27 g, 1.4 mmol), 1,1'-bis(diphenylphosphino)ferrocenedichloropalladium(II) (40 mg, 0.054 mmol) were added 1,4-dioxane (7.5 mL) and 1 mol/L aqueous sodium carbonate solution (2.5 mL) and the mixture was stirred with heating using a microwave reactor at 120° C. for 20 min. The solvent was evaporated and the obtained residue was purified by silica gel column chromatography (hexane/ethyl acetate) to give the title compound (0.27 g, 1.1 mmol, 99%).

MS (ESI) m/z 249 (M+H)$^+$ (step 2) Synthesis of 1-[2-[4-(trifluoromethyl)phenyl]-4-pyridyl]cyclopropanamine (D-53)

To a solution of the compound (0.27 mg, 1.1 mmol) obtained in step 1 in tetrahydrofuran (6.5 mL) was added titanium tetraisopropoxide (0.48 mL, 1.61 mmol), and the mixture was cooled to −78° C. under an argon atmosphere. To the so reaction mixture was added dropwise 0.95 mol/L ethylmagnesium bromide (tetrahydrofuran solution, 3.3 mL, 3.2 mmol) and the mixture was stirred for 10 min, and at room temperature for 1 hr. To the reaction mixture was added boron trifluoride•diethylether complex (0.33 mL, 2.7 mmol) and the mixture was stirred at room temperature for 2 hr. 1 mol/L Hydrochloric acid (3.3 mL) was added and the mixture was stirred for 5 min. 2 mol/L Aqueous sodium hydroxide solution (21 mL) was added. Using dichloromethane, the insoluble material was filtered off through celite, and the obtained filtrate was extracted with dichloromethane, washed with saturated brine, and the organic layer was dried over anhydrous magnesium sulfate. The desiccant was filtered off, and the solvent was evaporated. The obtained residue was purified by silica gel column chromatography (hexane/ethyl acetate) to give the title compound (19 mg, 0.067 mmol, 6%).

MS (ESI) m/z 279 (M+H)$^+$

D-54 described in Table 19 was synthesized by using corresponding commercially available reagents and by an operation similar to that in Reference Example D-53.

TABLE 19

| Ref. Example No. | Structural formula | MS(ESI) m/z (M + H)$^+$ | NMR |
|---|---|---|---|
| D-53 | | 279 | — |
| D-54 | | 280 | — |

Reference Example D-55

Synthesis of [3-[[2-(trifluoromethyl)-4-pyridyl]methoxy]phenyl]methylamine hydrochloride (D-55)

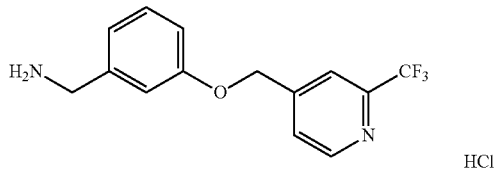 [SMILES: NCc1cccc(OCc2ccnc(C(F)(F)F)c2)c1 ; Cl]

tert-Butyl N-[(3-hydroxyphenyl)methyl]carbamate (0.18 g, 1.0 mmol), E-1 (0.22 g, 1.0 mmol) and triphenylphosphine (0.39 g, 1.5 mmol) were dissolved in dichloromethane (3 mL), diisopropyl azodicarboxylate (0.32 mL, 1.5 mmol) was added, and the mixture was stirred at room temperature for 1 hr. The reaction mixture was concentrated under reduced pressure and the obtained residue was purified by silica gel column chromatography (hexane/ethyl acetate). To the obtained compound was added 4 mol/L hydrochloric acid (1,4-dioxane solution, 3 mL), and the mixture was stirred at room temperature for 1 hr, and concentrated under reduced pressure to give the title compound (0.13 g, 0.40 mmol, 40%)

MS (ESI) m/z 283 (M+H)+

Reference Example D-56

Synthesis of tert-butyl 4-(aminomethyl)-2-[4-(trifluoromethyl)phenyl]benzoate (D-56)

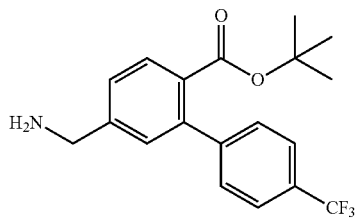

(step 1) Synthesis of 4-bromo-2-[4-(trifluoromethyl)phenyl]benzoic acid 2,4-Dibromobenzoic acid (10.0 g, 36.0 mmol), 4-trifluoromethylphenylboronic acid (7.50 g, 39.6 mmol), lithium hydroxide (3.30 g, 79.2 mmol) and tris(dibenzylideneacetone)dipalladium(0) (1.0 g, 1.09 mmol) were dissolved in water (108 mL) and N-methyl-2-pyrrolidone (108 mL), and the mixture was stirred with heating at 65° C. for 24 hr. After filtration, water (200 mL) was added, to the filtrate was added 4 mol/L aqueous potassium hydroxide solution to pH11, and the mixture was washed with dichloromethane. To the aqueous layer was added 1 mol/L hydrochloric acid at 0° C. to pH4-5, and the precipitated solid was washed with water and dried to give the title compound (6.2 g, 18.0 mmol, 50%).

$^1$H NMR (300 MHz, CDCl$_3$) δ 7.90 (d, J=8.8 Hz, 1H), 7.64 (d, J=8.4 Hz, 2H), 7.63-7.61 (m, 1H), 7.50 (d, J=2.0 Hz, 1H), 7.40 (d, J=8.4 Hz, 2H).

(step 2) Synthesis of tert-butyl 4-bromo-2-[4-(trifluoromethyl)phenyl]benzoate

To the compound (3.00 g, 8.69 mmol) obtained in step 1 were added tert-butyl alcohol (42 mL) and dichloromethane (30 mL), 4-dimethylaminopyridine (0.54 g, 4.3 mmol) and pyridine (9 mL) and di-tert-butyl dicarbonate (2.2 g, 4.7 mmol) were added at room temperature and the mixture was stirred at overnight. The solvent was evaporated from the reaction mixture, and the residue was adjusted to pH5 with 0.5 mol/L hydrochloric acid and the mixture was extracted with ethyl acetate. The organic layer was washed successively with saturated aqueous sodium hydrogen carbonate solution and saturated brine. The organic layer was dried over sodium sulfate, and the desiccant was filtered off. The solvent was evaporated and the obtained residue was purified by silica gel column chromatography (pentane) to give the title compound (1.55 g, 3.86 mmol, 44%).

$^1$H NMR (300 MHz, CDCl$_3$) δ 7.73 (d, J=8.0 Hz, 1H), 7.66 (d, J=8.0 Hz, 2H), 7.58 (dd, J=8.4, 2.0 Hz, 1H), 7.45 (d, J=2.0 Hz, 1H), 7.40 (d, J=8.4 Hz, 2H), 1.23 (s, 9H).

(step 3) Synthesis of tert-butyl 4-cyano-2-[4-(trifluoromethyl)phenyl]benzoate

The compound (1.40 g, 3.5 mmol) obtained in step 2, zinc cyanide (410 mg, 3.5 mmol) and tetrakis(triphenylphosphine)palladium(0) (438 mg, 0.379 mmol) were added and the mixture was stirred with heating at 100° C. for 2 hr. The solvent was evaporated and the obtained residue was purified by silica gel column chromatography (pentane) to give the title compound (1.0 g, 2.88 mmol, 83%).

$^1$H NMR (300 MHz, CDCl$_3$) δ 7.92 (d, J=8.0 Hz, 1H), 7.74 (dd, J=8.0, 1.6 Hz, 1H), 7.70 (d, J=8.0 Hz, 2H), 7.61 (d, J=1.6 Hz, 1H), 7.42 (d, J=8.0 Hz, 2H), 1.26 (s, 9H).

(step 4) Synthesis of tert-butyl 4-(aminomethyl)-2-[4-(trifluoromethyl)phenyl]benzoate (D-56)

To a solution of the compound (1.0 g, 2.88 mmol) obtained in step 3 in methanol (200 mL) was added 10% palladium/carbon (1.0 g), and the mixture was stirred under a hydrogen atmosphere at room temperature for 2 hr. The solvent was evaporated. To the obtained residue was added methanol (8 mL), and the insoluble material was collected by filtration, and the filtrate was concentrated under reduced pressure and the obtained residue was purified by silica gel column chromatography (dichloromethane/methanol) to give the title compound (307 mg, 0.874 mmol, 30%) as a brown solid.

MS (ESI) m/z 352 (M+H)+

$^1$H NMR (400 MHz, DMSO-d$_6$) δ 7.80 (d, J=8.0 Hz, 2H), 7.74 (d, J=8.0 Hz, 1H), 7.51-7.49 (m, 3H), 7.42 (s, 1H), 3.87 (s, 2H), 1.19 (s, 9H).

Reference Example D-57

Synthesis of 4-(aminomethyl)-N,N-dimethyl-2-[4-(trifluoromethyl)phenyl]benzamide (D-57)

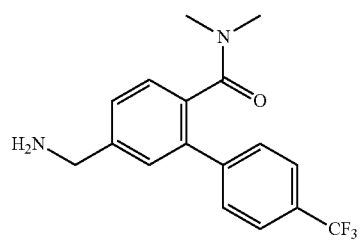 [SMILES: CN(C)C(=O)c1ccc(CN)cc1-c1ccc(C(F)(F)F)cc1]

(step 1) Synthesis of 4-bromo-N,N-dimethyl-2-[4-(trifluoromethyl)phenyl]benzamide To a solution of the compound (3.30 g, 9.56 mmol) obtained in Reference Example D-56, step 1 in dichloromethane (60 mL) was added oxalyl chloride (2.5 g, 19.2 mmol), and the mixture was stirred at room temperature for 4 hr. The solvent was evaporated and dissolved in THF (50 mL). 2 mol/L Dimethylamine (tetrahydrofuran solution, 1.45 mL, 2.90 mmol) was added at 00° C., and the mixture was stirred at room temperature for 3 hr. The mixture was concentrated under reduced pressure and the obtained residue was purified by silica gel column chromatography (pentane/ethyl acetate) to give the title compound (2.20 g, 0.591 mmol, 62%).

$^1$H NMR (400 MHz, CDCl$_3$) δ 7.67 (d, J=8.0 Hz, 2H), 7.60-7.56 (m, 4H), 7.30 (d, J=8.0 Hz, 1H), 2.86 (s, 3H), 2.46 (s, 3H).

(step 2) Synthesis of 4-cyano-N,N-dimethyl-2-[4-(trifluoromethyl)phenyl]benzamide Using 4-bromo-N,N-dimethyl-2-[4-(trifluoromethyl)phenyl]benzamide instead of tert-butyl 4-bromo-2-[4-(trifluoromethyl)phenyl]benzoate, and by an operation similar to that in Reference Example D-56, step 3, the title compound (yield 90%) was obtained.

$^1$H NMR (300 MHz, CDCl$_3$) δ 7.78-7.71 (m, 4H), 7.60-7.54 (m, 3H), 2.89 (s, 3H), 2.47 (s, 3H).

(step 3) Synthesis of 4-(aminomethyl)-N,N-dimethyl-2-[4-(trifluoromethyl)phenyl]benzamide (D-57)

Using 4-cyano-N,N-dimethyl-2-[4-(trifluoromethyl)phenyl]benzamide instead of tert-butyl 4-cyano-2-[4-(trifluoromethyl)phenyl]benzoate, and by an operation similar to that in Reference Example D-56, step 4, the title compound (yield 44%) was obtained.

MS (ESI) m/z 323 (M+H)$^+$ $^1$H NMR (400 MHz, DMSO-d$_6$) δ 7.80 (d, J=8.4 Hz, 2H), 7.59 (d, J=8.4 Hz, 2H), 7.48 (s, 1H), 7.45 (d, J=8.0 Hz, 1H), 7.30 (d, J=8.0 Hz, 1H), 3.82 (s, 2H), 2.78 (s, 3H), 2.50 (s, 3H).

Reference Example D-58

Synthesis of tert-butyl 3-(aminomethyl)-5-[4-(trifluoromethyl)phenyl]benzoate (D-58)

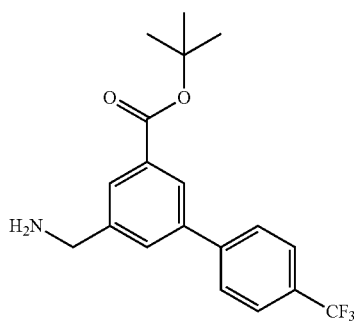 [SMILES: CC(C)(C)OC(=O)c1cc(CN)cc(-c2ccc(C(F)(F)F)cc2)c1]

(step 1) Synthesis of tert-butyl 3-bromo-5-iodobenzoate

3-Bromo-5-iodobenzoic acid (1.0 g, 3.1 mmol) was dissolved in tert-butyl alcohol (14 mL) and dichloromethane (10 mL), di-tert-butyl dicarbonate (0.80 g, 5.2 mmol), 4-dimethylaminopyridine (0.19 g, 2.3 mmol) and pyridine (3 mL) were added and the mixture was stirred at room temperature overnight. The reaction mixture was concentrated under reduced pressure. To the obtained residue was added ethyl acetate and 0.5 mol/L aqueous hydrochloric acid solution to partition the mixture, and the organic layer was washed successively with saturated aqueous sodium hydrogen carbonate solution and saturated brine. The organic layer was dried, concentrated under reduced pressure and the obtained residue was purified by silica gel column chromatography (petroleum ether) to give the title compound (0.50 g, 1.3 mmol, 43%).

$^1$H NMR (400 MHz, CDCl$_3$) δ 8.22 (s, 1H), 8.06 (s, 1H), 7.99 (s, 1H), 1.59 (s, 9H).

(step 2) Synthesis of tert-butyl 3-bromo-5-cyanobenzoate

To the compound (0.98 g, 2.6 mmol) obtained in step 1, zinc cyanide (0.15 g, 1.3 mmol), tetrakistriphenylphosphinepalladium(0) (0.18 g, 0.16 mmol) was added N,N-dimethylformamide (75 mL) and the mixture was stirred at 80° C. for 2 hr. The reaction mixture was concentrated under reduced pressure and the obtained residue was purified by silica gel column chromatography (petroleum ether) to give the title compound (0.58 g, 2.1 mmol, 81%).

$^1$H NMR (400 MHz, CDCl$_3$) δ 8.32 (s, 1H), 8.17 (s, 1H), 7.92 (s, 1H), 1.60 (s, 9H).

(step 3) Synthesis of tert-butyl 3-cyano-5-[4-(trifluoromethyl)phenyl]benzoate

To the compound (0.58 g, 2.1 mmol) obtained in step 2, 4-trifluoromethylphenylboronic acid (0.47 g, 2.5 mmol), potassium carbonate (0.71 g, 5.2 mmol) and tetrakistriphenylphosphinepalladium(0) (0.15 g, 0.13 mmol) were added 1,4-dioxane (20 mL) and water (2 mL) and the mixture was stirred at under a nitrogen atmosphere at 85° C. for 2 hr. The reaction mixture was filtered, water was added to the filtrate and the mixture was extracted with diethyl ether. The organic layer was washed with water, and dried over sodium sulfate. The desiccant was filtered off, concentrated under reduced pressure and the obtained residue was purified by silica gel column chromatography (petroleum ether/ethyl acetate) to give the title compound (0.62 g, 1.8 mmol, 86%).

$^1$H NMR (400 MHz, CDCl$_3$) δ 8.42 (dd, J=2.8, 2.8 Hz, 1H), 8.28 (dd, J=2.8, 2.8 Hz, 1H), 8.00 (dd, J=2.8, 2.8 Hz, 1H), 7.76 (d, J=8.2 Hz, 2H), 7.71 (d, J=8.2 Hz, 2H), 1.63 (s, 9H).

(step 4) Synthesis of tert-butyl 3-(aminomethyl)-5-[4-(trifluoromethyl)phenyl]benzoate (D-58)

To a solution of the compound (0.45 g, 1.3 mmol) obtained in step 3 in methanol (200 mL) was added 10% palladium/carbon (0.50 g), and the mixture was stirred under a hydrogen atmosphere at room temperature for 2 hr. The reaction mixture was filtered, and the filtrate was concentrated under reduced pressure and the obtained residue was purified by silica gel column chromatography (dichloromethane/methanol) to give the title compound (0.24 g, 0.69 mmol, 53%).

MS (ESI) m/z 352 (M+H)$^+$ $^1$H NMR (400 MHz, DMSO-d$_6$) δ 8.03 (s, 1H), 7.96-7.92 (m, 4H), 7.86-7.84 (m, 2H), 3.86 (s, 2H), 1.58 (s, 9H).

Reference Example D-59

Synthesis of 4-(aminomethyl)-N,N-dimethyl-6-[4-(trifluoromethyl)phenyl]pyrimidin-2-amine hydrochloride (D-59)

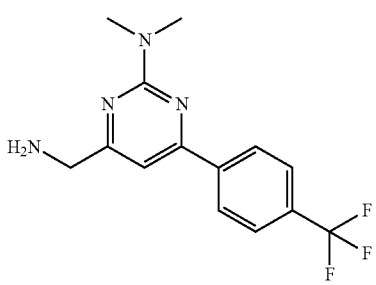 [SMILES: CN(C)c1nc(CN)cc(-c2ccc(C(F)(F)F)cc2)n1]

(step 1) Synthesis of tert-butyl N-[[2-benzylsulfonyl-6-[4-(trifluoromethyl)phenyl]pyrimidin-4-yl]methyl]carbamate To a solution of the compound (1.08 g, 2.27 mmol) obtained in Example 311, step 1 in dichloromethane (20 mL) was added 3-chloroperbenzoic acid (1.56 g, 9.08 mmol) at 0° C., and the mixture was stirred at room temperature for 6 hr. To the reaction mixture was added saturated aqueous sodium hydrogen carbonate, and the mixture was extracted with dichloromethane. The organic layer was dried over sodium sulfate. The desiccant was filtered off, and the solvent was evaporated to give the title compound (1.01 g, 1.99 mmol, 88%).

MS (ESI) m/z 508 (M+H)$^+$ (step 2) Synthesis of 4-(aminomethyl)-N,N-dimethyl-6-[4-(trifluoromethyl)phenyl]pyrimidin-2-amine hydrochloride (D-59)

To a solution of the compound (152 mg, 0.30 mmol) obtained in step 1 in N,N-dimethylformamide (2 mL) was added 2 mol/L dimethylamine (tetrahydrofuran solution, 0.30 mL, 0.60 mmol) and the mixture was stirred with heating by using a microwave reactor at 100° C. for 10 min. The reaction mixture was concentrated under reduced pressure, water was added and the mixture was extracted with dichloromethane. The organic layer was dried over sodium sulfate, and the desiccant was filtered off. The solvent was evaporated. To the obtained residue was added 4 mol/L hydrochloric acid (1,4-dioxane solution, 2 mL), and the mixture was stirred at room temperature for 1.5 hr. The reaction mixture was concentrated under reduced pressure to give the title compound (96 mg, 0.29 mmol, 96%).

MS (ESI) m/z 297 (M+H)$^+$

Reference Example D-60

Synthesis of 4-(aminomethyl)-N,N-dimethyl-6-[6-(trifluoromethyl)-3-pyridyl]pyrimidin-2-amine (D-60)

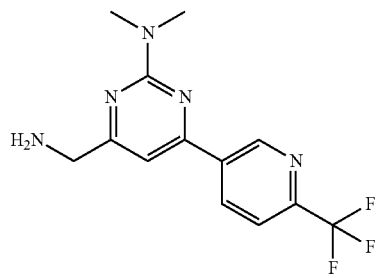 [SMILES: CN(C)c1nc(CN)cc(-c2ccc(C(F)(F)F)nc2)n1]

(step 1) Synthesis of 4,6-dichloro-N,N-dimethyl-pyrimidin-2-amine

A solution of 2,4,6-trichloropyrimidine (16 g, 87 mmol) in acetonitrile (280 mL) was cooled to −15° C., 2 mol/L dimethylamine (tetrahydrofuran solution, 92 mL, 0.18 mol) was slowly added, and the mixture was stirred for 2 hr. The reaction mixture was concentrated under reduced pressure and the obtained residue was purified by silica gel column chromatography (petroleum ether) to give the title compound (4.2 g, 22 mmol, 25%).

$^1$H NMR (300 MHz, CDCl$_3$) δ 6.50 (s, 1H), 3.18 (s, 6H)

(step 2) Synthesis of 4-chloro-N,N-dimethyl-6-[6-(trifluoromethyl)-3-pyridyl]pyrimidin-2-amine To the compound (2.0 g, 10 mmol) obtained in step 1 and 6-trifluoromethyl-3-pyridineboronic acid (2.0 g, 10 mmol) were added saturated aqueous sodium hydrogen carbonate solution (20 mL) and tetrahydrofuran (20 mL), and the mixture was stirred. To the reaction mixture was added tetrakistriphenylphosphinepalladium(0) (0.60 g, 0.52 mmol), and the mixture was stirred under a nitrogen atmosphere at 100° C. for 6 hr. The reaction mixture was filtered, and the filtrate was extracted with ethyl acetate. The organic layer was washed with saturated brine, and dried over sodium sulfate. The desiccant was filtered off, concentrated under reduced pressure and the obtained residue was purified by silica gel column chromatography (petroleum ether) to give the title compound (1.2 g, 4.0 mmol, 38%).

$^1$H NMR (300 MHz, CDCl$_3$) δ 9.31 (d, J=1.2 Hz, 1H), 8.44-8.48 (m, 1H), 7.78 (d, J=8.1 Hz, 1H), 6.93 (s, 1H), 3.27 (s, 6H)

(step 3) Synthesis of 2-(dimethylamino)-6-[6-(trifluoromethyl)-3-pyridyl]pyrimidine-4-carbonitrile To a solution of the compound (1.2 g, 4.0 mmol) obtained in step 2 in dimethyl sulfoxide (26 mL) was added a solution of sodium cyanide (0.24 g, 4.8 mmol) and 1,4-diazabicyclo[2.2.2]octane (44 mg, 0.40 mmol) in water (8 mL). After stirring at 60° C. for 9 hr, the reaction mixture was added to water, and the mixture was extracted with diethyl ether. The organic layer was washed with saturated brine, and dried over sodium sulfate. The desiccant was filtered off, concentrated under reduced pressure and the obtained residue was purified by silica gel column chromatography (petroleum ether/ethyl acetate) to give the title compound (1.0 g, 3.4 mmol, 86%).

$^1$H NMR (300 MHz, CDCl$_3$) δ 9.34 (br s, 1H), 8.46-8.49 (m, 1H), 7.81 (d, J=8.4 Hz, 1H), 7.19 (s, 1H), 3.21 (s, 6H).

(step 4) Synthesis of 4-(aminomethyl)-N,N-dimethyl-6-[6-(trifluoromethyl)-3-pyridyl]pyrimidin-2-amine (D-60)

To a solution of the compound (0.64 g, 2.2 mmol) obtained in step 3 in acetic acid (100 mL) was added 10% palladium/carbon (0.30 g), and the mixture was stirred under a hydrogen atmosphere at room temperature for 30 min. The reaction mixture was filtered, dichloromethane was added to the filtrate and the mixture was washed with aqueous sodium carbonate solution. The organic layer was dried over sodium sulfate, the desiccant was filtered off, concentrated under reduced pressure and the obtained residue was dissolved in dichloromethane (30 mL). di-tert-Butyl dicarbonate (0.65 g, 3.0 mmol) and triethylamine (1.0 mL, 7.2 mmol) were added and the mixture was stirred for 30 min. The reaction mixture was concentrated under reduced pressure and the obtained residue was purified by silica gel column chromatography (petroleum ether/ethyl acetate) to give the title compound as a protected form. To the obtained protected form was added 4 mol/L hydrochloric acid (dichloromethane solution, 150 mL) and the mixture was stirred for 20 min, and concentrated under reduced pressure to give 2 hydrochloride of the title compound (0.42 g, 1.1 mmol, 53%).

MS (ESI) m/z 298 (M+H)$^+$ $^1$H NMR (400 MHz, DMSO-d$_6$) δ 9.46 (s, 1H), 8.75 (d, J=7.6 Hz, 1H), 8.63 (br, 2H), 8.10 (d, J=8.4 Hz, 1H), 7.52 (s, 1H), 5.79 (br s, 2H), 4.11-4.15 (m, 2H), 3.26 (s, 6H).

Reference Example D-61

Synthesis of 2-[6-(aminomethyl)-2-(dimethylamino)pyrimidin-4-yl]-5-(trifluoromethyl)phenol (D-61)

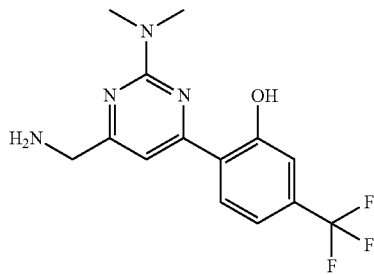 [SMILES: CN(C)c1nc(CN)cc(-c2ccc(C(F)(F)F)cc2O)n1]

(step 1) Synthesis of 4-chloro-6-[2-methoxy-4-(trifluoromethyl)phenyl]-N,N-dimethyl-pyrimidin-2-amine To 4,6-dichloro-N,N-dimethyl-pyrimidin-2-amine (2.0 g, 10 mmol) obtained in Reference Example D-60, step 1, [2-methoxy-4-(trifluoromethyl)phenyl]boronic acid (2.3 g, 10 mmol) were added saturated aqueous sodium hydrogen carbonate solution (20 mL) and tetrahydrofuran (20 mL). To the reaction mixture was added tetrakistriphenylphosphinepalladium(0) (0.60 g, 0.52 mmol), and the mixture was stirred under a nitrogen atmosphere at 100° C. for 6 hr. The reaction mixture was filtered, and the filtrate was extracted with ethyl acetate. The organic layer was washed with saturated brine, and dried over sodium sulfate. The desiccant was filtered off, concentrated under reduced pressure and the obtained residue was purified by silica gel column chromatography (petroleum ether) to give the title compound (2.6 g, 7.8 mmol, 76%).

$^1$H NMR (300 MHz, CDCl$_3$) δ 8.08 (d, J=8.3 Hz, 1H), 7.30 (dd, J=8.3, 1.2 Hz, 1H), 7.19 (br s, 1H), 7.14 (s, 1H), 3.95 (s, 3H), 3.23 (s, 6H).

(step 2) Synthesis of 4-chloro-6-[2-hydroxy-4-(trifluoromethyl)phenyl]-N,N-dimethyl-pyrimidin-2-amine A solution of the compound (0.30 g, 0.91 mmol) obtained in step 1 in dichloromethane (20 mL) was cooled to −78° C., and 1 mol/L boron tribromide (dichloromethane solution, 9.1 mL, 9.1 mmol) was added. The mixture was heated to room temperature and stirred for 16 hr. The reaction mixture was adjusted to pH8 with a saturated aqueous sodium carbonate solution. The mixture was extracted with dichloromethane, and the organic layer was dried over sodium sulfate. The desiccant was filtered off, concentrated under reduced pressure and the obtained residue was purified by silica gel column chromatography (petroleum ether/ethyl acetate) to give the title compound (0.25 g, 0.78 mmol, 86%).

$^1$H NMR (300 MHz, CDCl$_3$) δ 7.78 (d, J=8.7 Hz, 1H), 7.24 (br s, 1H), 7.12-7.15 (m, 1H), 7.01 (s, 1H), 3.26 (br s, 6H).

(step 3) Synthesis of 2-(dimethylamino)-6-[2-hydroxy-4-(trifluoromethyl)phenyl]pyrimidine-4-carbonitrile To a solution of the compound (0.80 g, 2.5 mmol) obtained in step 2 in dimethyl sulfoxide (40 mL) was added a solution of sodium cyanide (0.74 g, 15 mmol) and 1,4-diazabicyclo[2.2.2]octane (0.28 g, 2.5 mmol) in water (8 mL). After stirring at 27° C. for 16 hr, the reaction mixture was added to water, and the mixture was extracted with diethyl ether. The organic layer was washed with saturated brine, and dried over sodium sulfate. The desiccant was filtered off, concentrated under reduced pressure and the obtained residue was purified by silica gel column chromatography (petroleum ether/ethyl acetate) to give the title compound (0.35 g, 1.1 mmol, 45%).

$^1$H NMR (300 MHz, CDCl$_3$) δ 13.72 (s, 1H), 7.82-7.85 (m, 1H), 7.29 (br s, 1H), 7.27 (s, 1H), 7.18-7.21 (m, 1H), 3.27-3.31 (m, 6H)

(step 4) Synthesis of 2-[6-(aminomethyl)-2-(dimethylamino)pyrimidin-4-yl]-5-(trifluoromethyl)phenol (D-61)

To a solution of the compound (0.47 g, 1.5 mmol) obtained in step 3 in acetic acid (100 mL) was added 10% palladium/carbon (0.25 g), and the mixture was stirred under a hydrogen atmosphere at room temperature for 30 min. The reaction mixture was filtered, dichloromethane was added to the filtrate and the mixture was washed with aqueous sodium carbonate solution. The organic layer was dried over sodium sulfate, the desiccant was filtered off, concentrated under reduced pressure and the obtained residue was dissolved in dichloromethane (30 mL). di-tert-Butyl dicarbonate (0.52 g, 2.4 mmol) and triethylamine (0.70 mL, 5.0 mmol) were added and the mixture was stirred for 30 min. The reaction mixture was concentrated under reduced pressure and the obtained residue was purified by silica gel column chromatography (petroleum ether/ethyl acetate) to give the title compound as a protected form. To the obtained protected form was added 4 mol/L hydrochloric acid (dichloromethane solution, 150 mL) and the mixture was stirred for 2.5 hr, and concentrated under reduced pressure to give 2 hydrochloride of the title compound (0.32 g, 0.84 mmol, 55%).

MS (ESI) m/z 313 (M+H)$^+$ $^1$H NMR (300 MHz, CDCl$_3$) δ 8.48 (br s, 3H), 8.14-8.17 (m, 1H), 7.50 (s, 1H), 7.27-7.29 (m, 1H), 4.10-4.16 (m, 2H), 3.21 (s, 6H).

Reference Example D-62

Synthesis of 4-(aminomethyl)-2-[6-(trifluoromethyl)pyridazin-3-yl]phenol (D-62)

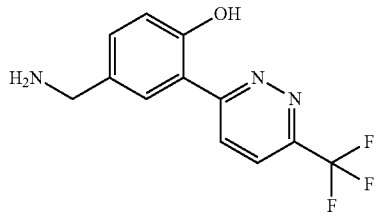 [SMILES: NCc1ccc(O)c(-c2ccc(C(F)(F)F)nn2)c1]

(step 1) Synthesis of 5-cyano-2-methoxyphenylboronic acid

To a solution of 3-bromo-4-methoxybenzonitrile (15 g, 71 mmol) and triisopropyl borate (27 g, 0.14 mol) in tetrahydrofuran (250 mL) was added 2.5 mol/L n-butyllithium solution (43 mL, 0.11 mol) at −78° C. and the mixture was stirred for 2 hr. To the reaction mixture was added 7% aqueous phosphoric acid solution (150 mL), and the mixture was heated to room temperature. After partition, the organic layer was diluted with dichloromethane and extracted with 5% aqueous sodium hydroxide solution (300 mL). The aqueous layer was washed with diethyl ether, and adjusted to pH2.5 with 85% aqueous phosphoric acid solution. The insoluble material was collected by filtration, washed with water and post-dried to give the title compound (9.5 g, 54 mmol, 76%).

$^1$H NMR (300 MHz, CDCl$_3$) δ 8.15 (d, J=2.1 Hz, 1H), 7.73 (dd, J=8.9, 2.1 Hz, 1H), 6.98 (d, J=8.9 Hz, 1H), 5.70 (s, 2H), 3.99 (s, 3H).

(step 2) Synthesis of 3-chloro-6-(trifluoromethyl)pyridazine

To 6-(trifluoromethyl)pyridazin-3-ol (3.0 g, 18 mmol) was added phosphorus oxychloride (18 mL) and the mixture was stirred at 90° C. overnight, and concentrated under reduced pressure. To the obtained residue were added dichloromethane and ice, and the mixture was stirred for 30 min, and saturated aqueous potassium carbonate solution was added. The reaction mixture was extracted with dichloromethane. The organic layer was dried over sodium sulfate, and the desiccant was filtered off. The filtrate was concentrated under reduced pressure to give the title compound (2.8 g, 15 mmol, 85%).

$^1$H NMR (300 MHz, CDCl$_3$) δ 7.82 (d, J=9.0 Hz, 1H), 7.74 (d, J=9.0 Hz, 1H).

(step 3) Synthesis of 4-methoxy-3-[6-(trifluoromethyl)pyridazin-3-yl]benzonitrile To the compound (2.0 g, 11 mmol) obtained in step 1, the compound (1.9 g, 10 mmol) obtained in step 2 and sodium carbonate (2.2 g, 20 mmol) were added N,N-dimethylformamide (40 mL) and water (10 mL). To the reaction mixture was added 1,1'-bis(diphenylphosphino)ferrocenedichloropalladium(II) (0.37 g, 0.50 mmol), and the mixture was stirred under a nitrogen atmosphere at 100° C. for 2.5 hr. The insoluble material was filtered off, and the filtrate was extracted with ethyl acetate. The organic layer was washed with saturated brine, and dried over sodium sulfate. The desiccant was filtered off, and the filtrate was concentrated under reduced pressure and the obtained residue was purified by silica gel column chromatography (petroleum ether/ethyl acetate) to give the title compound (1.4 g, 5.0 mmol, 50%).

$^1$H NMR (300 MHz, CDCl$_3$) δ 8.39 (d, J=2.1 Hz, 1H), 8.23 (d, J=8.7 Hz, 1H), 7.84 (d, J=9.0 Hz, 1H), 7.80 (dd, J=8.7, 2.1 Hz, 1H), 7.14 (d, J=8.7 Hz, 1H), 3.98 (s, 3H).

(step 3) Synthesis of tert-butyl N-[[4-methoxy-3-[6-(trifluoromethyl)pyridazin-3-yl]phenyl]methyl]carbamate The compound (1.6 g, 5.7 mmol) obtained in step 2 was dissolved by adding 2 mol/L ammonia (methanol solution, 100 mL), Raney-nickel (0.80 g) was added and the mixture was stirred under a hydrogen atmosphere at room temperature for 1.5 hr. The reaction mixture was filtered, and the filtrate was concentrated under reduced pressure. The obtained residue was dissolved by adding dichloromethane (20 mL). To the reaction solution were added di-tert-butyl dicarbonate (1.9 g, 8.7 mmol) and triethylamine (2.4 mL, 17 mmol), and the mixture was stirred for 30 min. The reaction mixture was concentrated under reduced pressure and the obtained residue was purified by silica gel column chromatography (petroleum ether/ethyl acetate) to give the title compound (1.3 g, 3.3 mmol, 58%).

$^1$H NMR (300 MHz, CDCl$_3$) δ 8.25 (d, J=8.7 Hz, 1H), 7.98-7.97 (m, 1H), 7.79 (d, J=9.3 Hz, 1H), 7.47-7.44 (m, 1H), 7.02 (d, J=8.4 Hz, 1H), 4.89 (br s, 1H), 4.36-4.34 (m, 2H), 3.89 (s, 3H), 1.46 (s, 9H).

(step 4) Synthesis of 4-(aminomethyl)-2-[6-(trifluoromethyl)pyridazin-3-yl]phenol (D-62)

To a solution of the compound (1.1 g, 2.9 mmol) obtained in step 3 in dichloromethane (15 mL) was added 1 mol/L boron tribromide (dichloromethane solution, 57 mL, 57 mmol) at −78° C. The mixture was heated to room temperature and stirred for 2 days. To the reaction mixture was added methanol (30 mL), and the mixture was adjusted to pH7-8 with saturated aqueous sodium carbonate solution, and extracted with dichloromethane. The organic layer was dried over sodium sulfate, and the desiccant was filtered off. The filtrate was concentrated under reduced pressure. The obtained residue was dissolved by adding dichloromethane (20 mL). di-tert-Butyl dicarbonate (0.68 g, 3.1 mmol) and triethylamine (1.1 mL, 8.1 mmol) were added and the mixture was stirred for 30 min. The reaction mixture was concentrated under reduced pressure and the obtained residue was purified by silica gel column chromatography (petroleum ether/ethyl acetate) to give the title compound as a protected form (0.60 g). To a solution of the obtained protected form (0.60 g) in dichloromethane (50 mL) was added 2 mol/L hydrochloric acid (dichloromethane solution, 200 mL) and the mixture was stirred for 2 hr, and concentrated under reduced pressure to give hydrochloride of the title compound (0.50 g, 1.6 mmol, 57%).

MS (ESI) m/z 270 (M+H)$^+$ $^1$H NMR (400 MHz, DMSO-d$_6$) δ 8.58 (d, J=9.0 Hz, 1H), 8.36-8.28 (m, 4H), 8.16 (d, J=1.8 Hz, 1H), 7.51 (dd, J=8.1, 1.8 Hz, 1H), 7.12 (d, J=8.4 Hz, 1H), 4.03-3.99 (m, 2H).

Reference Example D-63

Synthesis of 4-(aminomethyl)-6-[4-(trifluoromethyl)phenyl]pyrimidin-2-amine ditrifluoroacetate (D-63)

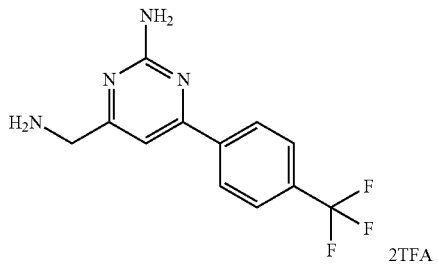 [SMILES: NCc1cc(-c2ccc(C(F)(F)F)cc2)nc(N)n1]

To a solution of the compound (253 mg, 0.50 mmol) obtained in Reference Example D-59, step 1 in N,N-dimethylformamide (4 mL) was added 4-methoxybenzylamine (0.50 mL, 3.6 mmol) and the mixture was stirred with heating at 100° C. for 10 min by using a microwave reactor. The reaction mixture was concentrated under reduced pressure, water was added and the mixture was extracted with dichloromethane. The organic layer was dried over sodium sulfate. The desiccant was filtered off, and the solvent was evaporated. To the obtained residue was added trifluoroacetic acid (7 mL) and the mixture was stirred at 80° C. for 3 hr. The reaction mixture was concentrated under reduced pressure and the obtained residue was purified by high performance liquid chromatography (water-acetonitrile, each containing 0.1% trifluoroacetic acid) to give the title compound (54 mg, 0.11 mmol, 22%).

MS (ESI) m/z 269 (M+H)$^+$

Reference Example E-1

Synthesis of [2-(trifluoromethyl)-4-pyridyl]methanol (E-1)

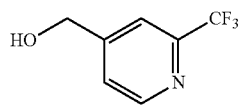 [SMILES: OCc1ccnc(C(F)(F)F)c1]

A solution of 2-(trifluoromethyl)isonicotinic acid (10.0 g, 52.4 mmol) in tetrahydrofuran (150 mL) was cooled to 0° C., 1 mol/L borane-tetrahydrofuran solution (105 mL, 105 mmol) was added under a nitrogen atmosphere and the mixture was stirred at 75° C. for 2 hr. The reaction mixture was poured into ice water, and extracted with ethyl acetate. The organic layer was washed with saturated brine, and dried over sodium sulfate. The desiccant was filtered off, and the filtrate was concentrated under reduced pressure and the obtained residue was purified by silica gel column chromatography (hexane/ethyl acetate) to give the title compound (5.60 g, 31.6 mmol, 60%).

MS (ESI) m/z 178 (M+H)$^+$ $^1$H NMR (300 MHz, CDCl$_3$): δ 8.68 (d, J=4.8 Hz, 1H), 7.79 (s, 1H), 7.64 (d, J=4.8 Hz, 1H). 5.62 (br-s, 1H), 4.66 (s, 2H),

Reference Example E-2

Synthesis of [2-(dimethylamino)-4-pyridyl]methanol (E-2)

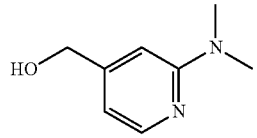

To a solution of (2-chloro-4-pyridyl)methanol (1.0 g, 7.0 mmol) in tetrahydrofuran (5 mL) was added 2 mol/L dimethylamine-tetrahydrofuran solution (20 mL, 40 mmol), and the mixture was stirred with heating in an autoclave under a nitrogen atmosphere at 200° C. for 2 days. The reaction mixture was concentrated under reduced pressure and the obtained residue was purified by high performance liquid chromatography (water-acetonitrile) to give the title compound (0.27 g, 1.7 mmol, 25%).

MS (ESI) m/z 153 (M+H)$^+$ $^1$H NMR (400 MHz, CD$_3$OD): δ 7.98 (d, J=5.2 Hz, 1H), 6.69 (s, 1H), 6.59 (d, J=5.2 Hz, 1H), 4.58 (s, 2H), 3.09 (s, 6H).

Reference Example E-3

Synthesis of [5-(dimethylamino)-3-pyridyl]methanol (E-3)

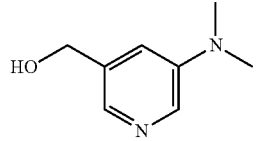

5-(Dimethylamino)pyridine-3-carboxylic acid methyl ester (0.10 g, 0.56 mmol) was dissolved by adding tetrahydrofuran (5.6 mL), and 2 mol/L lithium borohydride (tetrahydrofuran solution, 2 mL, 4 mmol) was added at 0° C. After stirring for 2 hr, the mixture was heated to 23° C. and further stirred overnight. 1 mol/L Hydrochloric acid was slowly added, and the mixture was dried over sodium sulfate, the desiccant was filtered off, and concentrated under reduced pressure to give the title compound as a crude product.

MS (ESI) m/z 153 (M+H)$^+$

Reference Example E-4

Synthesis of 6-methyl-2-[5-trifluoromethyl]-2-pyridyl-1,3,6,2-dioxazaborocane-4,8-dione (E-4)

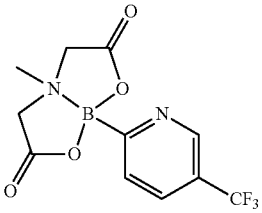

To 2-bromo-5-trifluoromethylpyridine (7.79 g, 34.4 mmol) and triisopropyl boronate (9.6 mL, 40 mmol) was added tetrahydrofuran (100 mL), and the mixture was cooled to −78° C., and 2.5 mol/L n-butyllithium (hexane solution, 13.8 mL, 34.4 mmol) was added dropwise. After stirring at −78° C. for 1 hr, the mixture was warmed to 23° C. and further stirred for 3 hr. A solution of N-methyliminodiacetic acid (8.61 g, 58.5 mmol) in dimethyl sulfoxide (68 mL) was separately prepared and placed in a three-necked flask equipped with a dropping funnel and a distillation apparatus, and the flask was heated until the inside temperature reached 115°. The earlier reaction mixture was placed in a dropping funnel, and added dropwise over about 1 hr while controlling the addition rate such that the inside temperature would be 110-120° C. In this case, tetrahydrofuran was rapidly evaporated. After completion of the dropwise addition, the temperature was lowered to 50° C., and dimethyl sulfoxide was evaporated under reduced pressure (250 mTorr). The residue was washed with diethyl ether and the obtained solid was dried under reduced pressure to give the title compound (3.43 g, 11.4 mmol, 33%).

MS (ESI) m/z 303 (M+H)$^+$ $^1$H NMR (400 MHz, CD$_3$OD): δ 8.92 (s, 1H), 8.17 (dd, J=8.0, 1.6 Hz, 1H), 7.65 (d, J=8.0 Hz, 1H), 4.13 (s, 2H), 4.12 (s, 2H), 3.00 (s, 3H).

Example 1

Synthesis of (2S)-1-(benzofuran-2-ylsulfonyl)-N-[[3-[(4-cyanophenyl)methoxy]phenyl]methyl]pyrrolidine-2-carboxamide (1)

To a solution of C-1 (40 mg, 0.10 mmol), 4-hydroxybenzonitrile (20 mg, 0.15 mmol) in dichloromethane (1.5 mL) were added triphenylphosphine (52 mg, 0.20 mmol) and diisopropyl azodicarboxylate (0.039 mL, 0.20 mmol), and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (40 mg, 0.077 mmol, 77%).

MS (ESI) m/z 516 (M+H)$^+$ $^1$H NMR (400 MHz, DMSO-d$_6$) δ 8.65 (t, J=6.0 Hz, 1H), 7.89-7.80 (m, 3H), 7.75 (dt, J=8.5, 0.8, 0.8 Hz, 1H), 7.72 (d, J=0.9 Hz, 1H), 7.62 (dt, J=8.2, 1.4, 1.3 Hz, 2H), 7.56 (ddd, J=8.5, 7.3, 1.3 Hz, 1H), 7.42 (ddd, J=8.0, 7.2, 0.9 Hz, 1H), 7.24 (dd, J=7.9, 7.9 Hz, 1H), 6.96 (dd, J=2.0, 2.0 Hz, 1H), 6.91-6.85 (m, 2H), 5.21 (s, 2H), 4.37-4.20 (m, 3H), 3.64-3.55 (m, 2H), 1.96-1.79 (m, 3H), 1.68-1.58 (m, 1H).

Example 2 to Example 36 described in Table 20 were synthesized by using the compounds described in Reference Examples and corresponding commercially available reagents and by an operation similar to that in Example 1.

TABLE 20

| Ex. No. | structure | compound name |
|---|---|---|
| 1 | 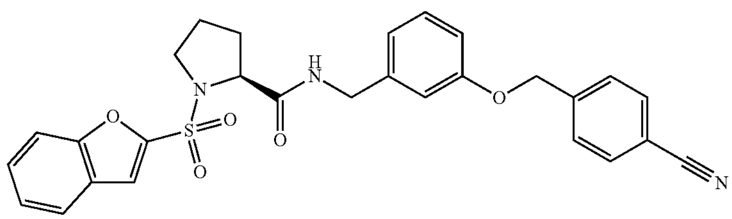 [SMILES: N#Cc1ccc(COc2cccc(CNC(=O)[C@@H]3CCCN3S(=O)(=O)c3cc4ccccc4o3)c2)cc1] | (2S)-1-(benzofuran-2-ylsulfonyl)-N-[[3-[(4-cyanophenyl)methoxy]-phenyl]methyl]-pyrrolidine-2-carboxamide |
| 2 | 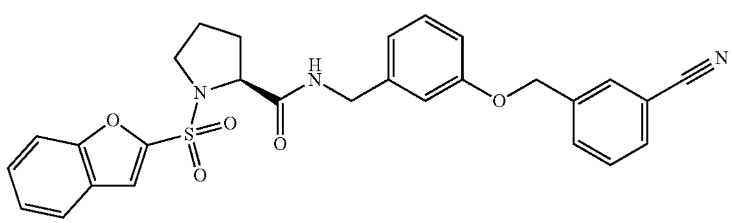 [SMILES: N#Cc1cccc(COc2cccc(CNC(=O)[C@@H]3CCCN3S(=O)(=O)c3cc4ccccc4o3)c2)c1] | (2S)-1-(benzofuran-2-ylsulfonyl)-N-[[3-[(3-cyanophenyl)methoxy]phenyl]methyl]pyrrolidine-2-carboxamide |
| 3 | 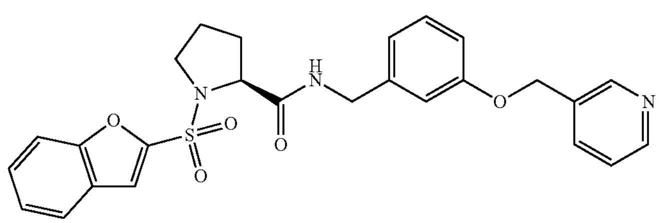 [SMILES: O=C(NCc1cccc(OCc2cccnc2)c1)[C@@H]1CCCN1S(=O)(=O)c1cc2ccccc2o1] | (2S)-1-(benzofuran-2-ylsulfonyl)-N-[[3-(3-pyridylmethoxy)phenyl]methyl]pyrrolidine-2-carboxamide |
| 4 | 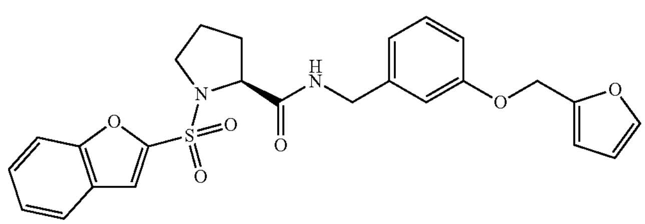 [SMILES: O=C(NCc1cccc(OCc2ccco2)c1)[C@@H]1CCCN1S(=O)(=O)c1cc2ccccc2o1] | (2S)-1-(benzofuran-2-ylsulfonyl)-N-[[3-(2-furylmethoxy)phenyl]methyl]pyrrolidine-2-carboxamide |

TABLE 20-continued

| Ex. No. | structure | compound name |
|---|---|---|
| 5 | 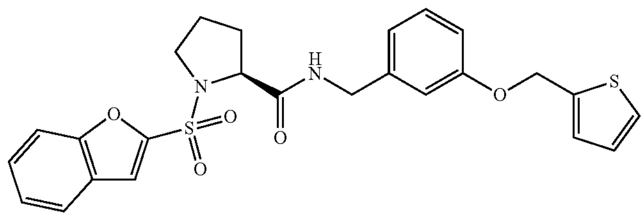 [SMILES: O=C(NCc1cccc(OCc2cccs2)c1)[C@@H]1CCCN1S(=O)(=O)c1cc2ccccc2o1] | (2S)-1-(benzofuran-2-ylsulfonyl)-N-[[3-(2-thienylmethoxy)phenyl]methyl]pyrrolidine-2-carboxamide |
| 6 | 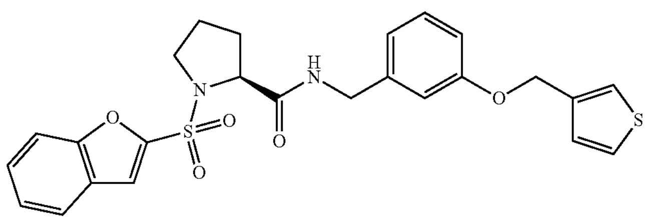 [SMILES: O=C(NCc1cccc(OCc2ccsc2)c1)[C@@H]1CCCN1S(=O)(=O)c1cc2ccccc2o1] | (2S)-1-(benzofuran-2-ylsulfonyl)-N-[[3-(3-thienylmethoxy)phenyl]methyl]pyrrolidine-2-carboxamide |
| 7 | 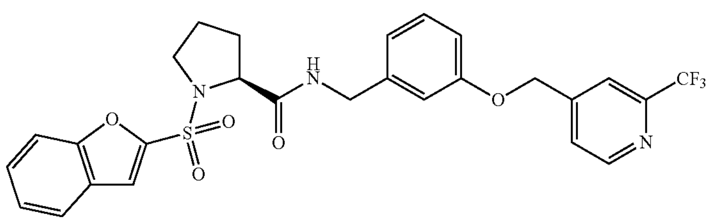 [SMILES: O=C(NCc1cccc(OCc2ccnc(C(F)(F)F)c2)c1)[C@@H]1CCCN1S(=O)(=O)c1cc2ccccc2o1] | (2S)-1-(benzofuran-2-ylsulfonyl)-N-[[3-[[2-(trifluoromethyl)-4-phenyl]methoxy]phenyl]methyl]pyrrolidine-2-carboxamide |
| 8 | 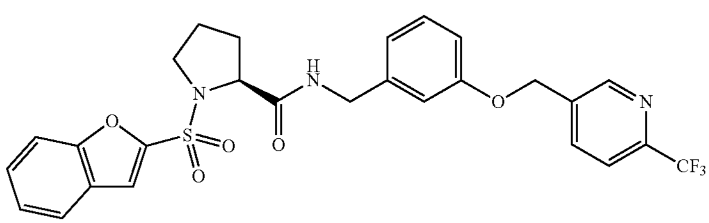 [SMILES: O=C(NCc1cccc(OCc2ccc(C(F)(F)F)nc2)c1)[C@@H]1CCCN1S(=O)(=O)c1cc2ccccc2o1] | (2S)-1-(benzofuran-2-ylsulfonyl)-N-[[3-[[6-(trifluoromethyl)-3-pyridyl]methoxy]phenyl]methyl]pyrrolidine-2-carboxamide |
| 9 | 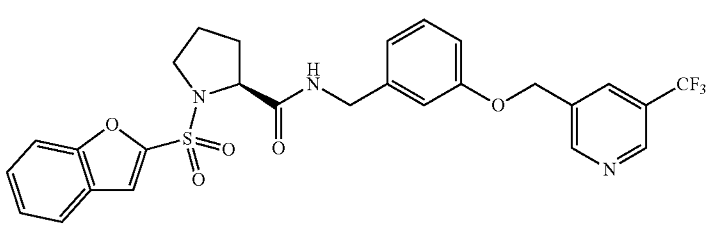 | (2S)-1-(benzofuran-2-ylsulfonyl)-N-[[3-[[5-(trifluoromethyl)-3-pyridyl]methoxy]phenyl]methyl]pyrrolidine-2-carboxamide |
| 10 | 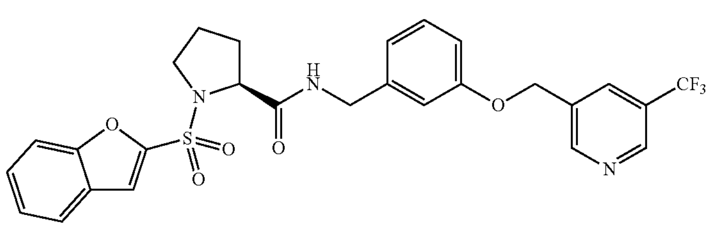 | (2S)-1-(benzofuran-2-ylsulfonyl)-N-[[3-[(5-chloro-3-pyridyl)methoxy]phenyl]methyl]pyrrolidine-2-carboxamide |

TABLE 20-continued

| Ex. No. | structure | compound name |
|---|---|---|
| 11 | 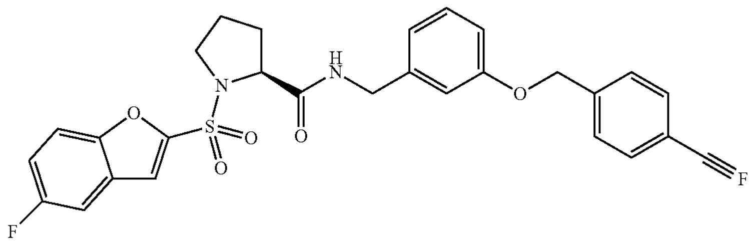 | (2S)-N-[[3-[(4-cyanophenyl)methoxy]phenyl]methyl]-1-(5-fluorobenzofuran-2-yl)sulfonyl-pyrrolidine-2-carboxamide |
| 12 | 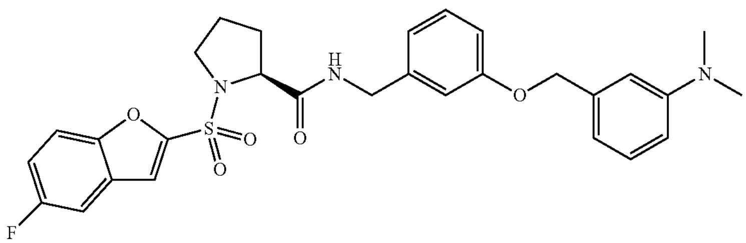 [SMILES: CN(C)c1cccc(COc2cccc(CNC(=O)[C@@H]3CCCN3S(=O)(=O)c3cc4cc(F)ccc4o3)c2)c1] | (2S)-N-[[3-[[3-(dimethylamino)phenyl]methoxy]phenyl]-methyl]-1-(5-fluorobenzofuran-2-yl)sulfonyl-pyrrolidine-2-carboxamide |
| 13 | 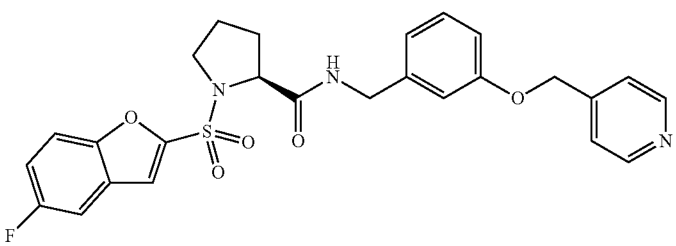 [SMILES: O=C(NCc1cccc(OCc2ccncc2)c1)[C@@H]1CCCN1S(=O)(=O)c1cc2cc(F)ccc2o1] | (2S)-1-(5-fluorobenzofuran-2-yl)sulfonyl-N-[[3-(4-pyridylmethoxy)phenyl]methyl]pyrrolidine-2-carboxamide |
| 14 | 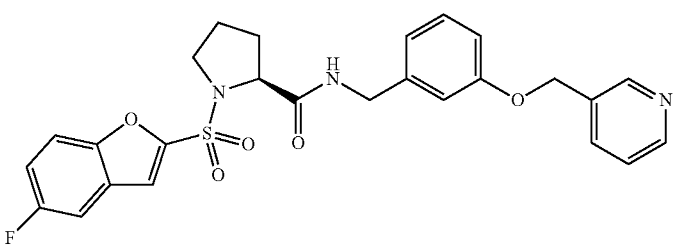 | (2S)-1-(5-fluorobenzofuran-2-yl)sulfonyl-N-[[3-(3-pyridylmethoxy)phenyl]-methyl]pyrrolidine-2-carboxamide |
| 15 | 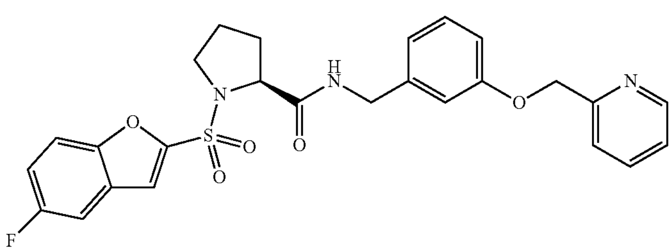 [SMILES: O=C(NCc1cccc(OCc2ccccn2)c1)[C@@H]1CCCN1S(=O)(=O)c1cc2cc(F)ccc2o1] | (2S)-1-(5-fluorobenzofuran-2-yl)sulfonyl-N-[[3-(2-pyridylmethoxy)phenyl]-methyl]pyrrolidine-2-carboxamide |
| 16 | 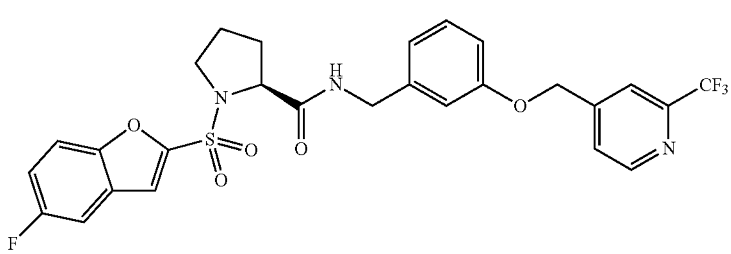 [SMILES: O=C(NCc1cccc(OCc2ccnc(C(F)(F)F)c2)c1)[C@@H]1CCCN1S(=O)(=O)c1cc2cc(F)ccc2o1] | (2S)-1-(5-fluorobenzofuran-2-yl)sulfonyl-N-[[3-[[2-(trifluoromethyl)-4-pyridyl]methoxy]phenyl]-methyl]pyrrolidine-2-carboxamide |

TABLE 20-continued

| Ex. No. | structure | compound name |
|---|---|---|
| 17 | 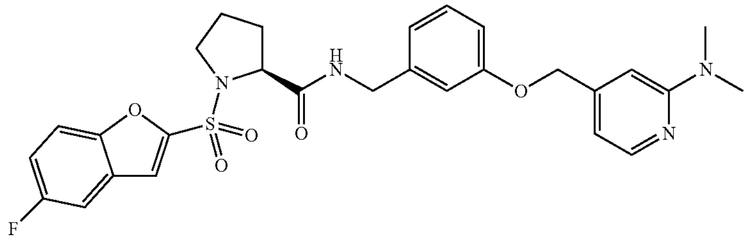 | (2S)-N-[[3-[[2-(dimethylamino)-4-pyridyl]methoxy]phenyl]-methyl]-1-(5-fluorobenzofuran-2-yl)sulfonyl-pyrrolidine-2-carboxamide |
| 18 | 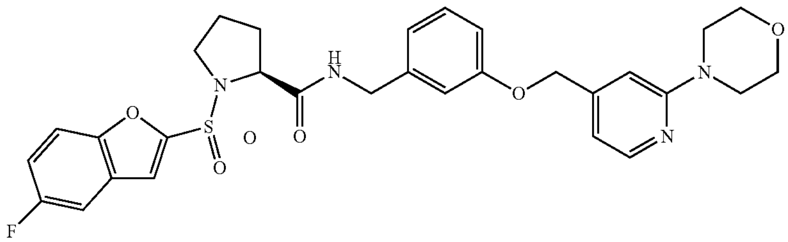 | (2S)-1-(5-fluorobenzofuran-2-yl)sulfonyl-N-[[3-[[2-morpholino-4-pyridyl)-methoxy]phenyl]-methyl]pyrrolidine-2-carboxamide |
| 19 | 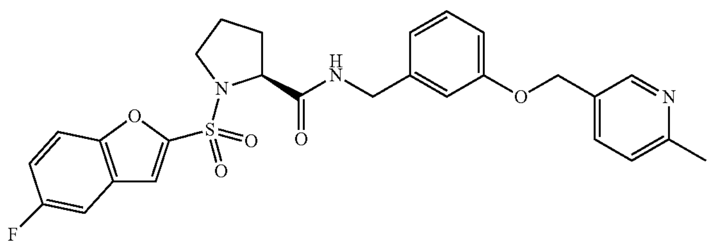 [SMILES: Cc1ccc(COc2cccc(CNC(=O)[C@@H]3CCCN3S(=O)(=O)c3cc4cc(F)ccc4o3)c2)cn1] | (2S)-1-(5-fluorobenzofuran-2-yl)sulfonyl-N-[[3-[(6-methyl-3-pyridyl)methoxy]phenyl]-methyl]pyrrolidine-2-carboxamide |
| 20 | 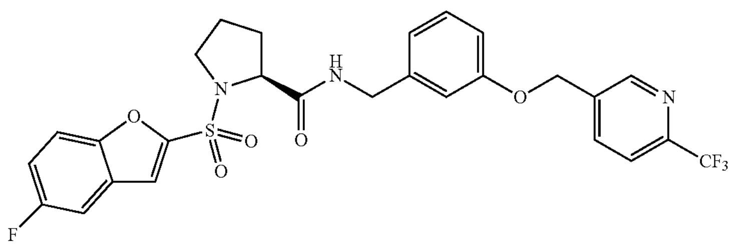 [SMILES: O=C(NCc1cccc(OCc2ccc(C(F)(F)F)nc2)c1)[C@@H]1CCCN1S(=O)(=O)c1cc2cc(F)ccc2o1] | (2S)-1-(5-fluorobenzofuran-2-yl)sulfonyl-N-[[3-[[6-(trifluoromethyl)-3-pyridyl]methoxy]phenyl]-methyl]pyrrolidine-2-carboxamide |
| 21 | 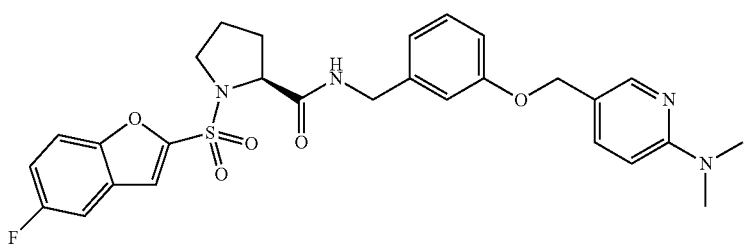 [SMILES: CN(C)c1ccc(COc2cccc(CNC(=O)[C@@H]3CCCN3S(=O)(=O)c3cc4cc(F)ccc4o3)c2)cn1] | (2S)-N-[[3-[[6-(dimethylamino)-3-pyridyl]methoxy]phenyl]-methyl]-1-(5-fluorobenzofuran-2-yl)sulfonyl-pyrrolidine-2-carboxamide |
| 22 | 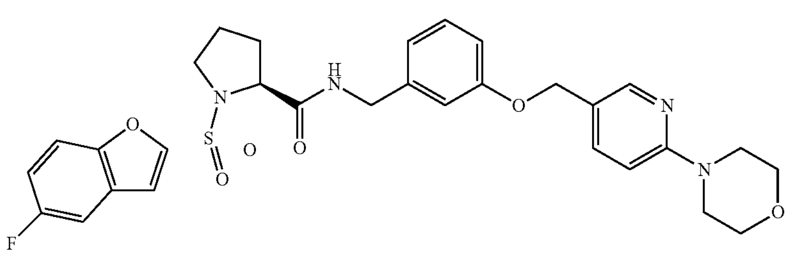 | (2S)-1-(5-fluorobenzofuran-2-yl)sulfonyl-N-[[3-[(6-morpholino-3-pyridyl)methoxy]phenyl]-methyl]pyrrolidine-2-carboxamide |

TABLE 20-continued

| Ex. No. | structure | compound name |
|---|---|---|
| 23 | 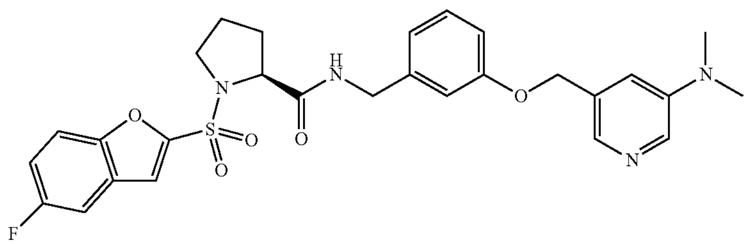 | (2S)-N-[[3-[[5-(dimethylamino)-3-pyridyl]methoxy]phenyl]-methyl]-1-(5-fluorobenzofuran-2-yl)sulfonyl-pyrrolidine-2-carboxamide |
| 24 | 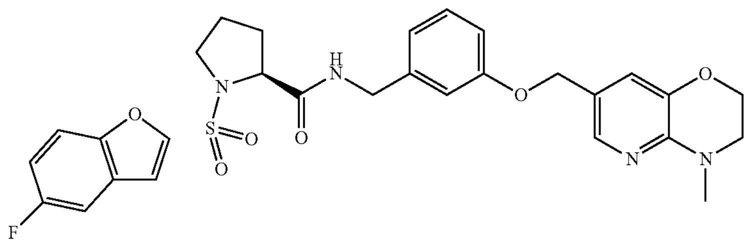 | (2S)-1-(5-fluorobenzofuran-2-yl)sulfonyl-N-[[3-[(4-methyl-2,3-dihydropyrido[3,2-b][1,4]oxazin-7-yl)methoxy]-phenyl]methyl]pyrrolidine-2-carboxamide |
| 25 | 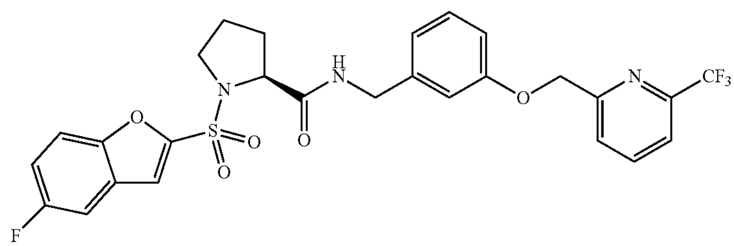 [SMILES: O=C(NCc1cccc(OCc2cccc(C(F)(F)F)n2)c1)[C@@H]1CCCN1S(=O)(=O)c1cc2cc(F)ccc2o1] | (2S)-1-(5-fluorobenzofuran-2-yl)sulfonyl-N-[[3-[[6-(trifluoromethyl)-2-pyridyl]methoxy]phenyl]-methyl]pyrrolidine-2-carboxamide |
| 26 | 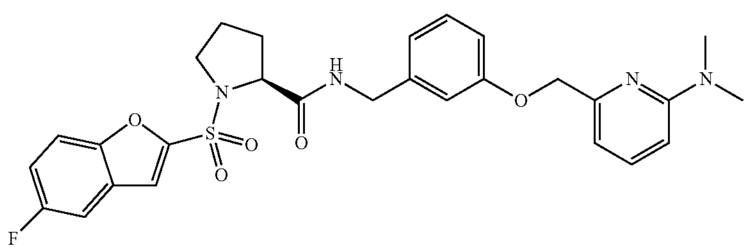 [SMILES: CN(C)c1cccc(COc2cccc(CNC(=O)[C@@H]3CCCN3S(=O)(=O)c3cc4cc(F)ccc4o3)c2)n1] | (2S)-N-[[3-[[6-(dimethylamino)-2-pyridyl]methoxy]phenyl]-methyl]-1-(5-fluorobenzofuran-2-yl)sulfonyl-pyrrolidine-2-carboxamide |
| 27 | 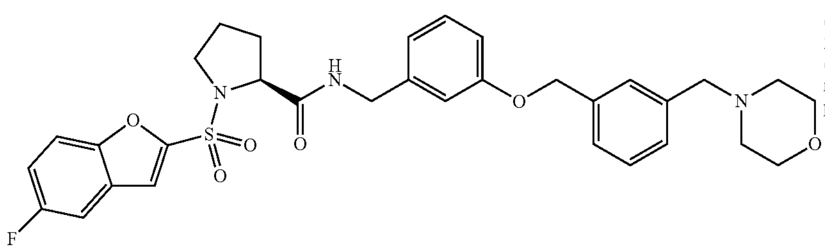 [SMILES: O=C(NCc1cccc(OCc2cccc(CN3CCOCC3)c2)c1)[C@@H]1CCCN1S(=O)(=O)c1cc2cc(F)ccc2o1] | (2S)-1-(5-fluorobenzofuran-2-yl)sulfonyl-N-[[3-[[3-(morpholinomethyl)phenyl]-methoxy]phenyl]methyl]-pyrrolidine-2-carboxamide |
| 28 | 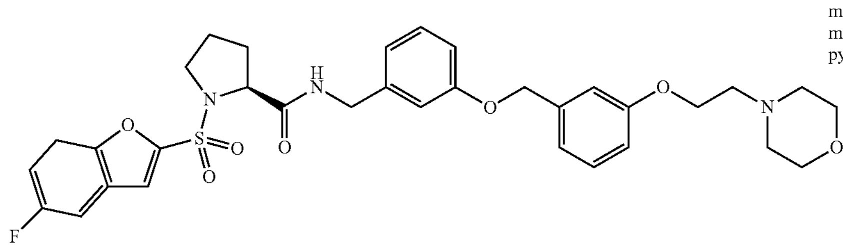 | (2S)-1-(5-fluorobenzofuran-2-yl)sulfonyl-N-[[3-[[3-(2-morpholinoethoxy)phenyl]-methoxy]phenyl]methyl]-pyrrolidine-2-carboxamide |

TABLE 20-continued

| Ex. No. | structure | compound name |
| --- | --- | --- |
| 29 | 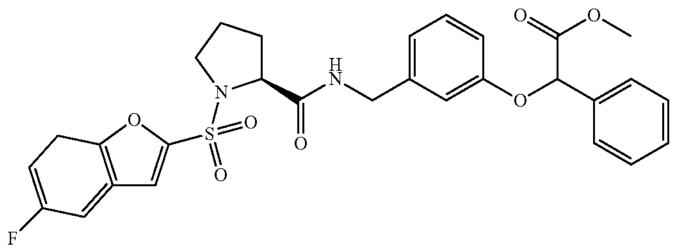 | methyl 2-[3-[[[(2S)-1-(5-fluorobenzofuran-2-yl)sulfonylpyrrolinidine-2-carbonyl]amino]methyl]-phenoxy]-2-phenylacetate |
| 30 | 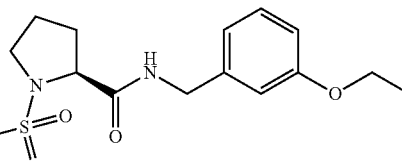 | (2S)-1-(5-fluorobenzofuran-2-yl)sulfonyl-N-[[3-(tetrahydropyran-4-ylmethoxy)phenyl]-methyl]pyrrolidine-2-carboxamide |
| 31 | 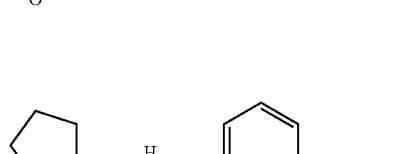 | (2S)-1-(5-fluorobenzofuran-2-yl)sulfonyl-N-[[3-(tetrahydropyran-3-ylmethoxy)phenyl]-methyl]pyrrolidine-2-carboxamide |
| 32 | 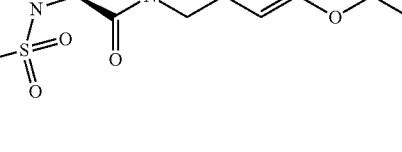 | (2S)-1-(5-fluorobenzofuran-2-yl)sulfonyl-N-[[3-(tetrahydrofuran-3-ylmethoxy)phenyl]-methyl]pyrrolidine-2-carboxamide |
| 33 | 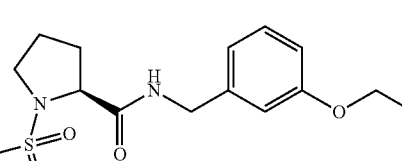 | (2S)-1-(5-fluorobenzofuran-2-yl)sulfonyl-N-[(3-tetrahydropyran-4-yloxyphenyl)methyl]-pyrrolidine-2-carboxamide |
| 34 | 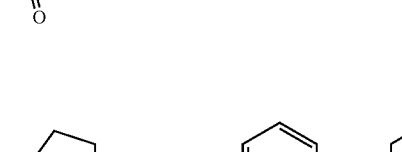 | (2S)-N-[(3-benzyloxy-5-fluoro-phenyl)methyl]-1-(5-fluorobenzofuran-2-yl)sulfonyl-pyrrolidine-2-carboxamide |

TABLE 20-continued

| Ex. No. | structure | compound name |
|---|---|---|
| 35 | 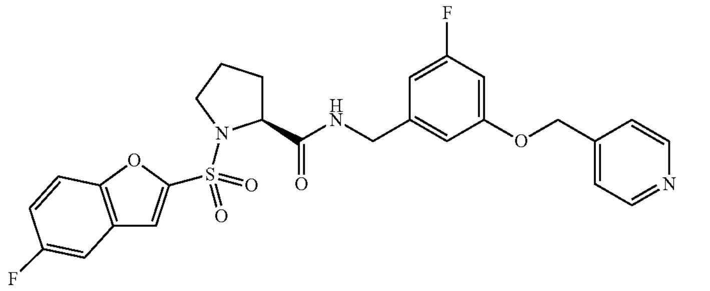 [SMILES: O=C(NCc1cc(F)cc(OCc2ccncc2)c1)[C@@H]1CCCN1S(=O)(=O)c1cc2cc(F)ccc2o1] | (2S)-1-(5-fluorobenzofuran-2-yl)sulfonyl-N-[[3-fluoro-5-(4-pyridylmethoxy)-phenyl]methyl]-pyrrolidine-2-carboxamide |
| 36 | 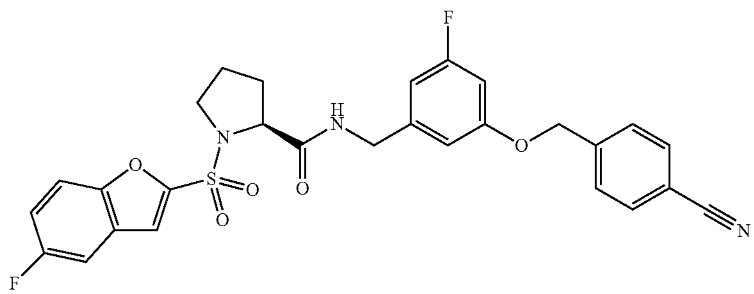 [SMILES: N#Cc1ccc(COc2cc(F)cc(CNC(=O)[C@@H]3CCCN3S(=O)(=O)c3cc4cc(F)ccc4o3)c2)cc1] | (2S)-N-[[3-[(4-cyanophenyl)methoxy]-5-fluoro-phenyl]methyl]-1-(5-fluorobenzofuran-2-yl)sulfonyl-pyrrolidine-2-carboxamide |

Example 37

Synthesis of (2S)-1-(benzofuran-2-ylsulfonyl)-N-[(3-benzyloxyphenyl)methyl]pyrrolidine-2-carboxamide (37)

To B-1 (2.00 g, 6.76 mmol), D-1 (1.69 g, 6.76 mmol), WSC hydrochloride (1.43 g, 7.44 mmol) and 1-hydroxy-7-azabenzotriazole (0.92 g, 6.76 mmol) were added dichloromethane (35 mL) and triethylamine (1.23 mL, 9.80 mmol) and the mixture was stirred at room temperature overnight. Water was added to the reaction mixture, and the mixture was extracted with dichloromethane. The organic layer was dried over sodium sulfate, the desiccant was filtered off, and the solvent was evaporated. The obtained residue was purified by high performance liquid chromatography (water-acetonitrile, each containing 0.1% trifluoroacetic acid) to give the title compound (2.25 g, 4.597 mmol, 69%).

MS (ESI) m/z 491 (M+H)$^+$ $^1$H NMR (400 MHz, DMSO-d$_6$) δ 8.65 (t, J=6.1 Hz, 1H), 7.83 (ddd, J=7.9, 1.4, 0.8 Hz, 1H), 7.75 (dd, J=8.4, 0.9 Hz, 1H), 7.71 (d, J=0.9 Hz, 1H), 7.55 (ddd, J=8.5, 7.2, 1.3 Hz, 1H), 7.47-7.28 (m, 6H), 7.23 (dd, J=8.2, 7.5 Hz, 1H), 6.99-6.94 (m, 1H), 6.91-6.83 (m, 2H), 5.09 (s, 2H), 4.38-4.20 (m, 3H), 3.64-3.55 (m, 1H), 3.44-3.35 (m, 1H), 1.97-1.80 (m, 3H), 1.70-1.57 (m, 1H).

Example 84

Synthesis of (2S)-1-(benzofuran-2-ylsulfonyl)-N-[[6-[4-(trifluoromethyl)phenyl]pyrimidin-4-yl]methyl]pyrrolidine-2-carboxamide (84)

To B-1 (30 mg, 0.10 mmol), D-16 (25 mg, 0.10 mmol), WSC hydrochloride (38 mg, 0.20 mmol) and 1-hydroxy-7-azabenzotriazole (27 mg, 0.20 mmol) were added dichloromethane (1 mL) and triethylamine (42 L, 0.30 mmol) and the mixture was stirred at room temperature overnight. The solvent was evaporated and the obtained residue was purified by high performance liquid chromatography (water-acetonitrile, each containing 0.1% trifluoroacetic acid) to give trifluoroacetate of the title compound (34 mg, 0.064 mmol, 64%).

MS (ESI) m/z 531 (M+H)$^+$ $^1$H NMR (400 MHz, DMSO-d$_6$) δ 9.25 (d, J=1.3 Hz, 1H), 8.99 (dd, J=6.2, 5.7 Hz, 1H), 8.40 (d, J=8.2 Hz, 2H), 8.06 (d, J=1.3 Hz, 1H), 7.92 (d, J=8.2 Hz, 2H), 7.85 (ddd, J=7.8, 1.3, 1.0 Hz, 1H), 7.80 (d, J=1.0 Hz, 1H), 7.76 (dd, J=8.4, 1.0 Hz, 1H), 7.57 (ddd, J=8.4, 7.4, 1.3 Hz, 1H), 7.43 (ddd, J=7.8, 7.4, 1.0 Hz, 1H), 4.56 (dd, J=17.3, 6.2 Hz, 1H), 4.45 (dd, J=17.3, 5.7 Hz, 1H), 4.38 (dd, J=8.2, 3.8 Hz, 1H), 3.69-3.60 (m, 1H), 3.49-3.39 (m, 1H), 2.10-1.87 (m, 3H), 1.74-1.62 (m, 1H).

Example 104

Synthesis of (2S)-2-(benzofuran-2-ylsulfonylamino)-N-[[6-[4-(trifluoromethyl)phenyl]pyrimidin-4-yl]methyl]propanamide (104)

To B-15 (16 mg, 0.059 mmol), D-16 (15 mg, 0.059 mmol), WSC hydrochloride (14 mg, 0.071 mmol) and 1-hydroxy-7-azabenzotriazole (8 mg, 0.06 mmol) were added dichloromethane (2 mL) and triethylamine (0.012 mL, 0.089 mmol) and the mixture was stirred at room temperature overnight. The reaction mixture was concentrated under reduced pressure and the obtained residue was purified by high performance liquid chromatography (water-acetonitrile, each containing 0.1% trifluoroacetic acid) to give trifluoroacetate of the title compound (19 mg, 0.030 mmol, 51%).

MS (ESI) m/z 505 (M+H)$^+$ $^1$H NMR (400 MHz, DMSO-ds) δ 9.21 (d, J=1.3 Hz, 1H), 8.89 (d, J=7.8 Hz, 1H), 8.75 (dd, J=6.0, 5.9 Hz, 1H), 8.36 (d, J=8.1 Hz, 2H), 7.95 (d, J=1.3 Hz, 1H), 7.93 (d, J=8.1 Hz, 2H), 7.73 (ddd, J=7.9, 1.3, 1.0 Hz, 1H), 7.65 (dd, J=8.5, 0.9

Hz, 1H), 7.55 (d, J=1.0 Hz, 1H), 7.49 (ddd, J=8.5, 7.2, 1.3 Hz, 1H), 7.35 (ddd, J=7.9, 7.2, 0.9 Hz, 1H), 4.39 (dd, J=17.2, 5.9 Hz, 1H), 4.33 (dd, J=17.2, 6.0 Hz, 1H), 4.10 (dq, J=7.8, 7.1 Hz, 1H), 1.25 (d, J=7.1 Hz, 3H).

Example 109

Synthesis of (2S)-2-[(5-fluorobenzofuran-2-yl)sulfonylamino]-N-[[6-[4-(trifluoromethyl)phenyl]pyrimidin-4-yl]methyl]propanamide (109)

To B-16 (20 mg, 0.070 mmol), D-16 (18 mg, 0.070 mmol), WSC hydrochloride (16 mg, 0.084 mmol) and 1-hydroxy-7-azabenzotriazole (9 mg, 0.07 mmol) were added dichloromethane (2 mL) and triethylamine (0.015 mL, 0.11 mmol) and the mixture was stirred at room temperature overnight. The reaction mixture was concentrated under reduced pressure and the obtained residue was purified by high performance liquid chromatography (water-acetonitrile, each containing 0.1% trifluoroacetic acid) to give trifluoroacetate of the title compound (28 mg, 0.043 mmol, 62%).

MS (ESI) m/z 523 (M+H)$^+$ $^1$H NMR (400 MHz, DMSO-d$_6$) δ 9.21 (d, J=1.3 Hz, 1H), 8.95 (d, J=7.8 Hz, 1H), 8.76 (t, J=5.9 Hz, 1H), 8.35 (d, J=8.2 Hz, 2H), 7.99-7.89 (m, 3H), 7.70 (dd, J=9.1, 4.0 Hz, 1H), 7.57-7.48 (m, 2H), 7.34 (ddd, J=9.3, 9.1, 2.8 Hz, 1H), 4.44-4.28 (m, 2H), 4.11 (dq, J=7.8, 7.1 Hz, 1H), 1.26 (d, J=7.1 Hz, 3H).

Example 38 to Example 74, Example 76 to Example 80, Example 84, Example 86 to Example 103, Example 105 to Example 108 and Example 110 to Example 111 described in Table 21 were synthesized by using the compounds described in Reference Examples and corresponding commercially available reagents and by an operation similar to that in Example 37.

TABLE 21

| Ex. No. | structure | compound name |
|---|---|---|
| 37 | 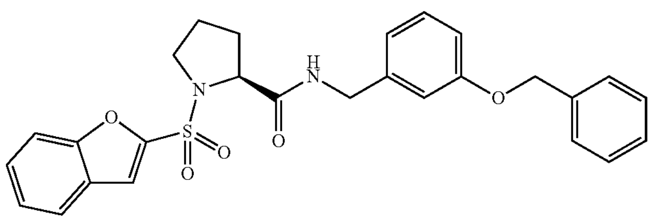 [SMILES: O=C(NCc1cccc(OCc2ccccc2)c1)[C@@H]1CCCN1S(=O)(=O)c1cc2ccccc2o1] | (2S)-1-(benzofuran-2-ylsulfonyl)-N-[(3-benzyloxyphenyl)methyl]-pyrrolidine-2-carboxamide |
| 38 | 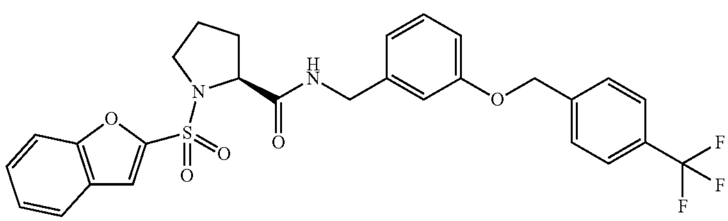 [SMILES: O=C(NCc1cccc(OCc2ccc(C(F)(F)F)cc2)c1)[C@@H]1CCCN1S(=O)(=O)c1cc2ccccc2o1] | (2S)-1-(benzofuran-2-ylsulfonyl)-N-[[3-[[4-(trifluoromethyl)phenyl]methoxy]-phenyl]methyl]pyrrolidine-2-carboxamide |
| 39 | 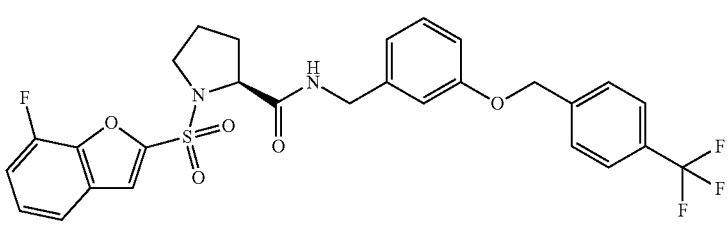 [SMILES: O=C(NCc1cccc(OCc2ccc(C(F)(F)F)cc2)c1)[C@@H]1CCCN1S(=O)(=O)c1cc2cccc(F)c2o1] | (2S)-1-(7-fluorobenzofuran-2-yl)sulfonyl-N-[[3-[[4-(trifluoromethyl)phenyl]methoxy]-phenyl]methyl]pyrrolidine-2-carboxamide |
| 40 | 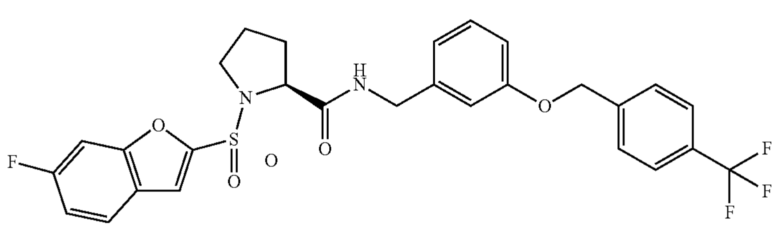 | (2S)-1-(6-fluorobenzofuran-2-yl)sulfonyl-N-[[3-[[4-(trifluoromethyl)phenyl]methoxy]-phenyl]methyl]pyrrolidine-2-carboxamide |

TABLE 21-continued

| Ex. No. | structure | compound name |
|---|---|---|
| 41 | 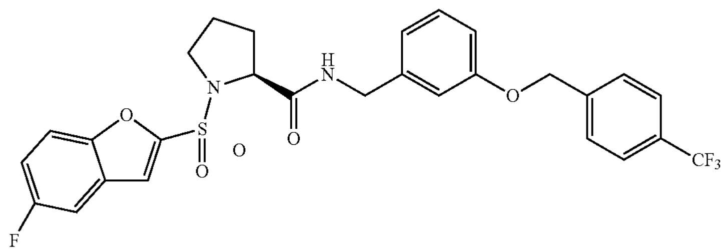 | (2S)-1-(5-fluorobenzofuran-2-yl)sulfonyl-N-[[3-[[4-(trifluoromethyl)phenyl]methoxy]-phenyl]methyl]pyrrolidine-2-carboxamide |
| 42 | 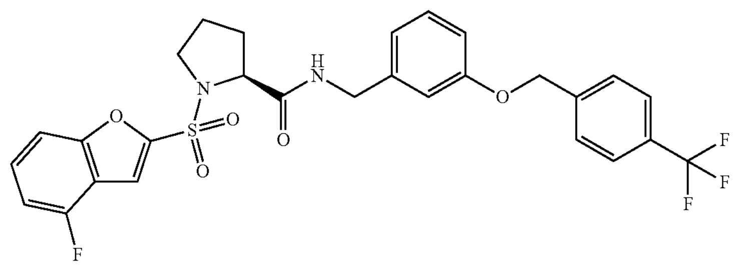 [SMILES: O=C(NCc1cccc(OCc2ccc(C(F)(F)F)cc2)c1)[C@@H]1CCCN1S(=O)(=O)c1cc2c(F)cccc2o1] | (2S)-1-(4-fluorobenzofuran-2-yl)sulfonyl-N-[[3-[[4-(trifluoromethyl)phenyl]methoxy]-phenyl]methyl]pyrrolidine-2-carboxamide |
| 43 | 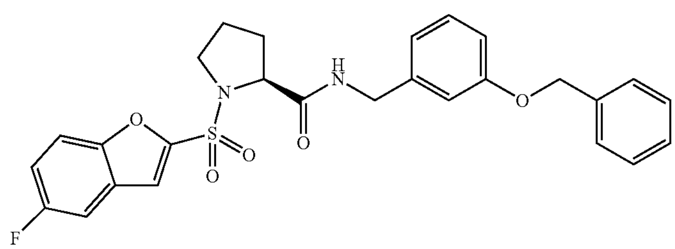 [SMILES: O=C(NCc1cccc(OCc2ccccc2)c1)[C@@H]1CCCN1S(=O)(=O)c1cc2cc(F)ccc2o1] | (2S)-N-[(3-benzyloxyphenyl)methyl]-1-(5-fluorobenzofuran-2-yl)sulfonyl-pyrrolidine-2-carboxamide |
| 44 | 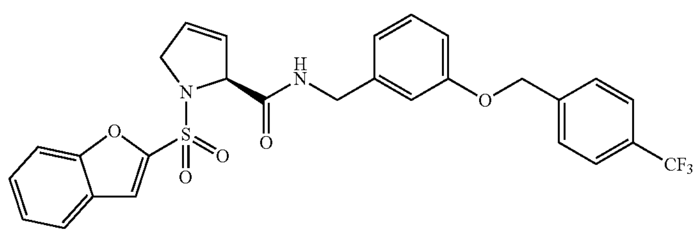 [SMILES: O=C(NCc1cccc(OCc2ccc(C(F)(F)F)cc2)c1)[C@@H]1C=CCN1S(=O)(=O)c1cc2ccccc2o1] | (2S)-1-(benzofuran-2-ylsulfonyl)-N-[[3-[[4-(trifluoromethyl)phenyl]methoxy]-phenyl]methyl]-2,5-dihydropyrrole-2-carboxamide |
| 45 | 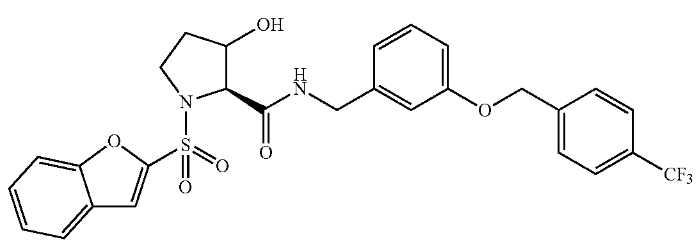 [SMILES: O=C(NCc1cccc(OCc2ccc(C(F)(F)F)cc2)c1)[C@@H]1C(O)CCN1S(=O)(=O)c1cc2ccccc2o1] | (2S,3S)-1-(benzofuran-2-ylsulfonyl)-3-hydroxy-N-[[3-[[4-(trifluoromethyl)phenyl]methoxy]-phenyl]methyl]pyrrolidine-2-carboxamide |
| 46 | 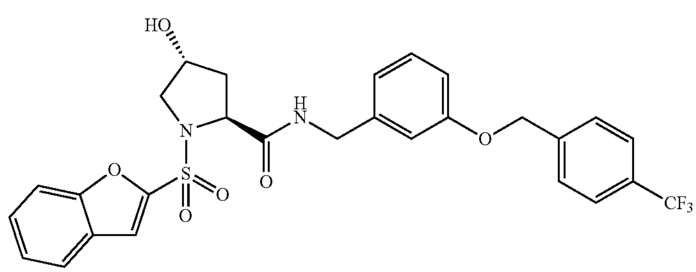 [SMILES: O=C(NCc1cccc(OCc2ccc(C(F)(F)F)cc2)c1)[C@@H]1C[C@@H](O)CN1S(=O)(=O)c1cc2ccccc2o1] | (2S,4R)-1-(benzofuran-2-ylsulfonyl)-4-hydroxy-N-[[3-[[4-(trifluoromethyl)phenyl]methoxy]-phenyl]methyl]pyrrolidine-2-carboxamide |

TABLE 21-continued

| Ex. No. | structure | compound name |
|---|---|---|
| 47 | 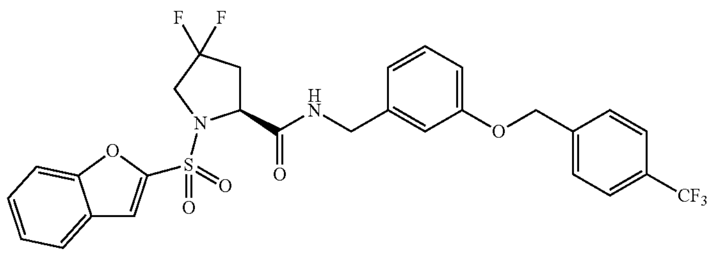 [SMILES: O=C(NCc1cccc(OCc2ccc(C(F)(F)F)cc2)c1)[C@@H]1CC(F)(F)CN1S(=O)(=O)c1cc2ccccc2o1] | (2S)-1-(benzofuran-2-ylsulfonyl)-4,4-difluoro-N-[[3-[[4-(trifluoromethyl)phenyl]methoxy]-phenyl]methyl]pyrrolidine-2-carboxamide |
| 48 | 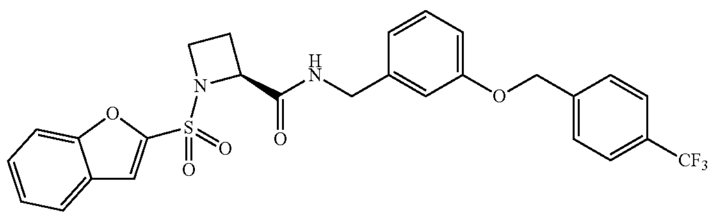 [SMILES: O=C(NCc1cccc(OCc2ccc(C(F)(F)F)cc2)c1)[C@@H]1CCN1S(=O)(=O)c1cc2ccccc2o1] | (2S)-1-(benzofuran-2-ylsulfonyl)-N-[[3-[[4-(trifluoromethyl)phenyl]methoxy]-phenyl]methyl]azetidine-2-carboxamide |
| 49 | 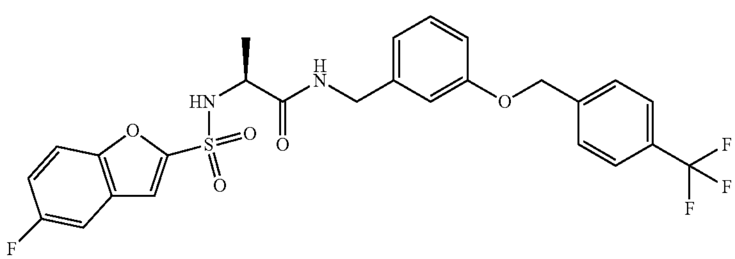 [SMILES: C[C@H](NS(=O)(=O)c1cc2cc(F)ccc2o1)C(=O)NCc1cccc(OCc2ccc(C(F)(F)F)cc2)c1] | (2S)-2-[(5-fluorobenzofuran-2-yl)sulfonylamino]-N-[[3-[[4-(trifluoromethyl)phenyl]methoxy]-phenyl]methyl]propanamide |
| 50 | 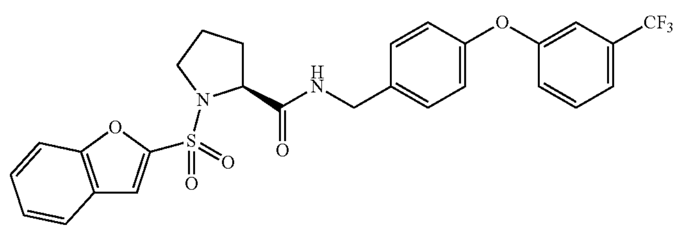 [SMILES: O=C(NCc1ccc(Oc2cccc(C(F)(F)F)c2)cc1)[C@@H]1CCCN1S(=O)(=O)c1cc2ccccc2o1] | (2S)-1-(benzofuran-2-ylsulfonyl)-N-[[4-[3-(trifluoromethyl)phenoxy]phenyl]-methyl]pyrrolidine-2-carboxamide |
| 51 | 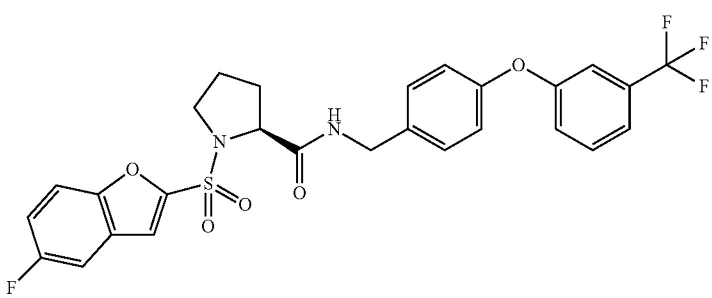 [SMILES: O=C(NCc1ccc(Oc2cccc(C(F)(F)F)c2)cc1)[C@@H]1CCCN1S(=O)(=O)c1cc2cc(F)ccc2o1] | (2S)-1-(5-fluorobenzofuran-2-yl)sulfonyl-N-[[4-[3-(trifluoromethyl)phenoxy]phenyl]-methyl]pyrrolidine-2-carboxamide |
| 52 | 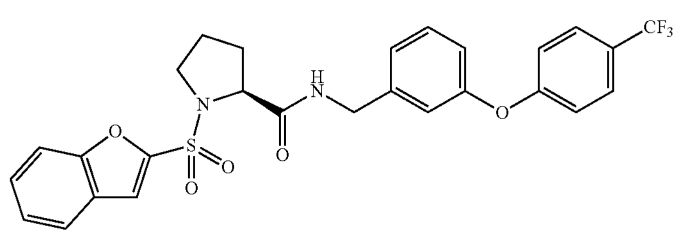 [SMILES: O=C(NCc1cccc(Oc2ccc(C(F)(F)F)cc2)c1)[C@@H]1CCCN1S(=O)(=O)c1cc2ccccc2o1] | (2S)-1-(benzofuran-2-ylsulfonyl)-N-[[3-[4-(trifluoromethyl)phenoxy]phenyl]-methyl]pyrrolidine-2-carboxamide |

TABLE 21-continued

| Ex. No. | structure | compound name |
| --- | --- | --- |
| 53 | 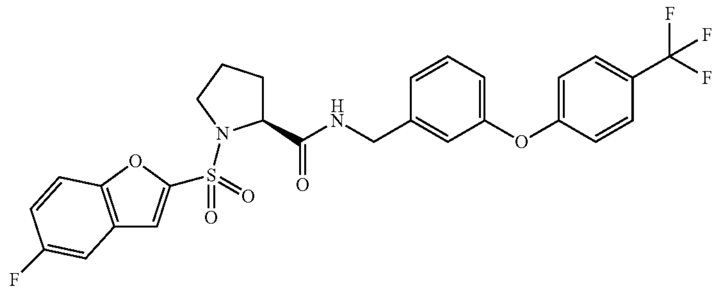 [SMILES: O=C(NCc1cccc(Oc2ccc(C(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[3-[4-(trifluoromethyl)phenoxy]phenyl]-methyl]pyrrolidine-2-carboxamide |
| 54 | 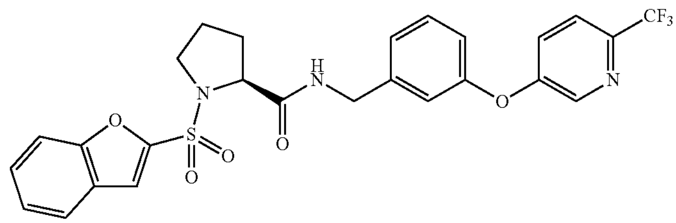 [SMILES: O=C(NCc1cccc(Oc2ccc(C(F)(F)F)nc2)c1)[C@@H]1CCCN1S(=O)(=O)c1cc2ccccc2o1] | (2S)-1-(benzofuran-2-ylsulfonyl)-N-[[3-[[6-(trifluoromethyl)-3-pyridyl]oxy]phenyl]methyl]-pyrrolidine-2-carboxamide |
| 55 | 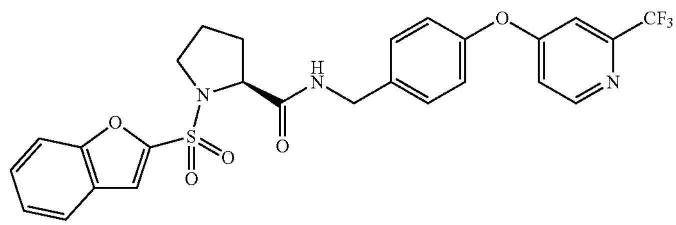 [SMILES: O=C(NCc1ccc(Oc2ccnc(C(F)(F)F)c2)cc1)[C@@H]1CCCN1S(=O)(=O)c1cc2ccccc2o1] | (2S)-1-(benzofuran-2-ylsulfonyl)-N-[[4-[[2-(trifluoromethyl)-4-pyridyl]oxy]phenyl]methyl]-pyrrolidine-2-carboxamide |
| 56 | 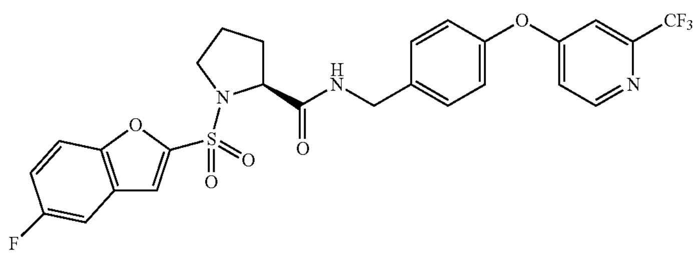 [SMILES: O=C(NCc1ccc(Oc2ccnc(C(F)(F)F)c2)cc1)[C@@H]1CCCN1S(=O)(=O)c1cc2cc(F)ccc2o1] | (2S)-1-(5-fluorobenzofuran-2-yl)sulfonyl-N-[[4-[[2-(trifluoromethyl)-4-pyridyl]oxy]phenyl]methyl]-pyrrolidine-2-carboxamide |
| 57 | 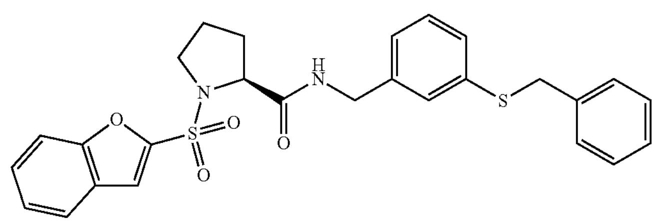 [SMILES: O=C(NCc1cccc(SCc2ccccc2)c1)[C@@H]1CCCN1S(=O)(=O)c1cc2ccccc2o1] | (2S)-1-(benzofuran-2-ylsulfonyl)-N-[(3-benzylsulfanylphenyl)methyl]-pyrrolidine-2-carboxamide |
| 58 | 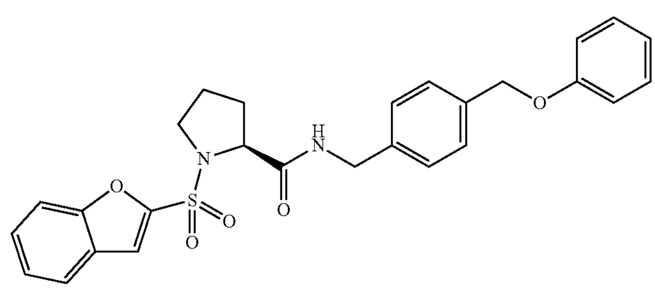 [SMILES: O=C(NCc1ccc(COc2ccccc2)cc1)[C@@H]1CCCN1S(=O)(=O)c1cc2ccccc2o1] | (2S)-1-(benzofuran-2-ylsulfonyl)-N-[[4-(phenoxymethyl)phenyl]methyl]-pyrrolidine-2-carboxamide |

TABLE 21-continued

| Ex. No. | structure | compound name |
|---|---|---|
| 59 | 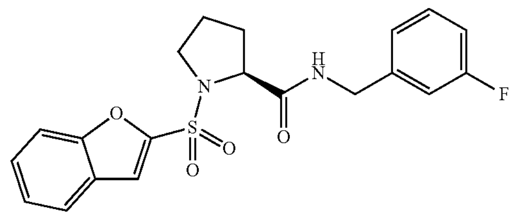 [SMILES: O=C(NCc1cccc(F)c1)[C@@H]1CCCN1S(=O)(=O)c1cc2ccccc2o1] | (2S)-1-(benzofuran-2-ylsulfonyl)-N-[(3-fluorophenyl)methyl]pyrrolidine-2-carboxamide |
| 60 | 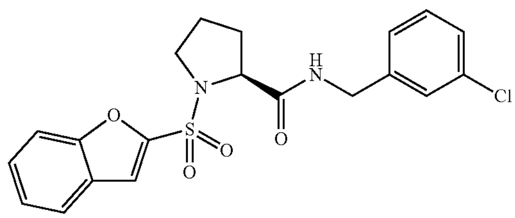 [SMILES: O=C(NCc1cccc(Cl)c1)[C@@H]1CCCN1S(=O)(=O)c1cc2ccccc2o1] | (2S)-1-(benzofuran-2-ylsulfonyl)-N-[(3-chlorophenyl)methyl]pyrrolidine-2-carboxamide |
| 61 | 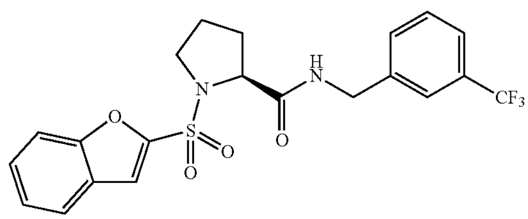 [SMILES: O=C(NCc1cccc(C(F)(F)F)c1)[C@@H]1CCCN1S(=O)(=O)c1cc2ccccc2o1] | (2S)-1-(benzofuran-2-ylsulfonyl)-N-[[3-(trifluoromethyl)phenyl]methyl]-pyrrolidine-2-carboxamide |
| 62 | 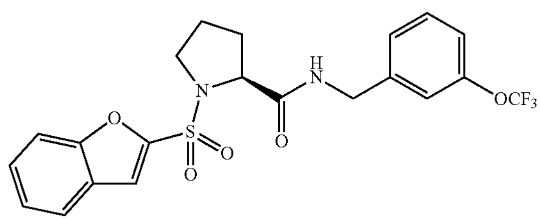 [SMILES: O=C(NCc1cccc(OC(F)(F)F)c1)[C@@H]1CCCN1S(=O)(=O)c1cc2ccccc2o1] | (2S)-1-(benzofuran-2-ylsulfonyl)-N-[[3-(trifluoromethoxy)phenyl]methyl]-pyrrolidine-2-carboxamide |
| 63 | 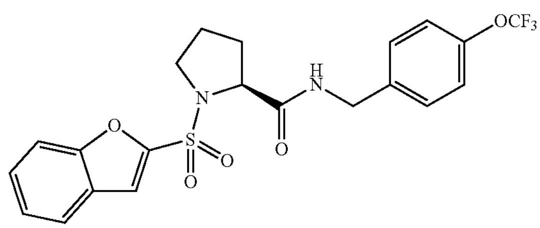 [SMILES: O=C(NCc1ccc(OC(F)(F)F)cc1)[C@@H]1CCCN1S(=O)(=O)c1cc2ccccc2o1] | (2S)-1-(benzofuran-2-ylsulfonyl)-N-[[4-(trifluoromethoxy)phenyl]methyl]-pyrrolidine-2-carboxamide |
| 64 | 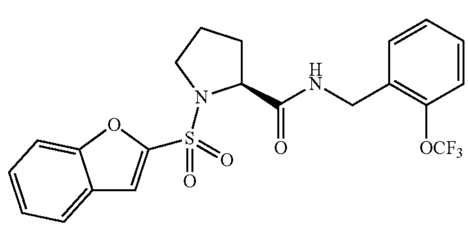 [SMILES: O=C(NCc1ccccc1OC(F)(F)F)[C@@H]1CCCN1S(=O)(=O)c1cc2ccccc2o1] | (2S)-1-(benzofuran-2-ylsulfonyl)-N-[[2-(trifluoromethoxy)phenyl]methyl]-pyrrolidine-2-carboxamide |
| 65 | 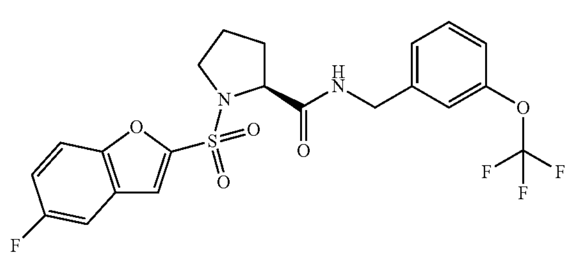 [SMILES: O=C(NCc1cccc(OC(F)(F)F)c1)[C@@H]1CCCN1S(=O)(=O)c1cc2cc(F)ccc2o1] | (2S)-1-(5-fluorobenzofuran-2-yl)sulfonyl-N-[[3-(trifluoromethoxy)phenyl]methyl]-pyrrolidine-2-carboxamide |

TABLE 21-continued

| Ex. No. | structure | compound name |
|---|---|---|
| 66 | 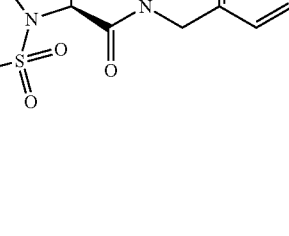 | (2S)-1-(5-fluorobenzofuran-2-yl)sulfonyl-N-[[4-(trifluoromethoxy)phenyl]methyl]-pyrrolidine-2-carboxamide |
| 67 | 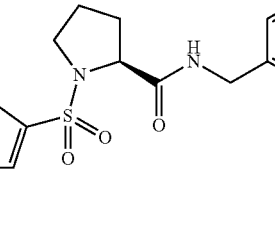 | (2S)-1-(benzofuran-2-ylsulfonyl)-N-[[2-chloro-5-(trifluoromethyl)phenyl]methyl]-pyrrolidine-2-carboxamide |
| 68 | 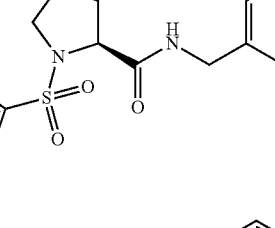 | (2S)-1-(benzofuran-2-ylsulfonyl)-N-[(2,4-difluoro-3-methoxy-phenyl)methyl]pyrrolidine-2-carboxamide |
| 69 | 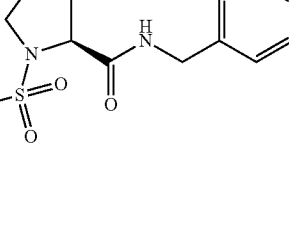 | (2S)-1-(5-fluorobenzofuran-2-yl)sulfonyl-N-[[3-fluoro-4-(trifluoromethoxy)phenyl]methyl]-pyrrolidine-2-carboxamide |
| 70 | 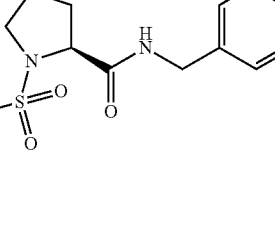 | (2S)-1-(5-fluorobenzofuran-2-yl)sulfonyl-N-[[4-fluoro-3-(trifluoromethoxy)phenyl]methyl]-pyrrolidine-2-carboxamide |
| 71 | 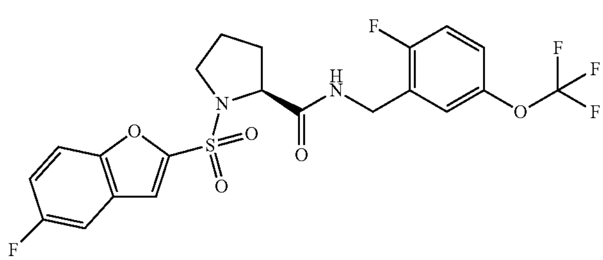 [SMILES: O=C(NCc1cc(OC(F)(F)F)ccc1F)[C@@H]1CCCN1S(=O)(=O)c1cc2cc(F)ccc2o1] | (2S)-1-(5-fluorobenzofuran-2-yl)sulfonyl-N-[[2-fluoro-5-(trifluoromethoxy)phenyl]methyl]-pyrrolidine-2-carboxamide |

TABLE 21-continued

| Ex. No. | structure | compound name |
|---|---|---|
| 72 | 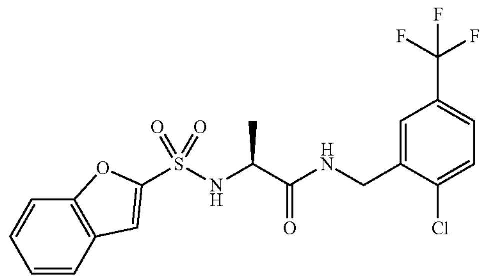 [SMILES: C[C@H](NS(=O)(=O)c1cc2ccccc2o1)C(=O)NCc1cc(C(F)(F)F)ccc1Cl] | (2S)-2-(benzofuran-2-ylsulfonylamino)-N-[[2-chloro-5-(trifluoromethyl)phenyl]methyl]-propanamide |
| 73 | 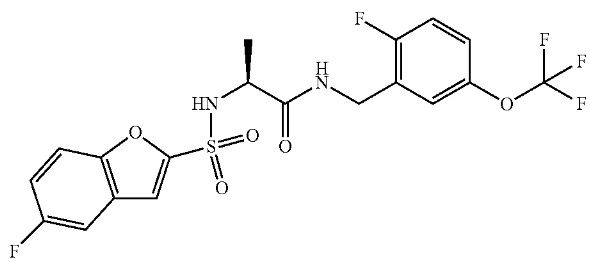 [SMILES: C[C@H](NS(=O)(=O)c1cc2cc(F)ccc2o1)C(=O)NCc1cc(OC(F)(F)F)ccc1F] | (2S)-2-[(5-fluorobenzofuran-2-yl)sulfonylamino]-N-[[2-fluoro-5-(trifluoromethoxy)phenyl]methyl]-propanamide |
| 74 | 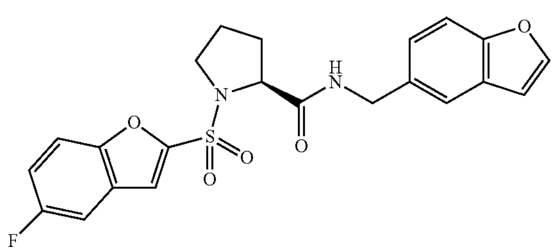 [SMILES: O=C(NCc1ccc2occc2c1)[C@@H]1CCCN1S(=O)(=O)c1cc2cc(F)ccc2o1] | (2S)-N-(benzofuran-5-ylmethyl)-1-(5-fluorobenzofuran-2-yl)sulfonyl-pyrrolidine-2-carboxamide |
| 76 | 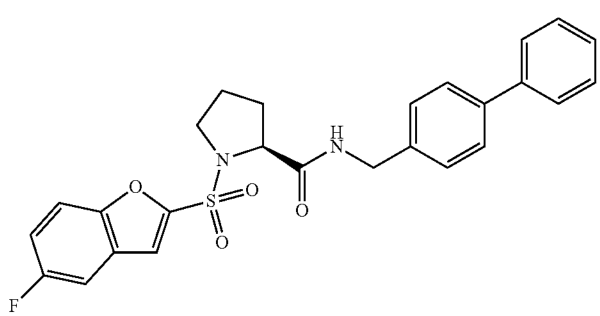 [SMILES: O=C(NCc1ccc(-c2ccccc2)cc1)[C@@H]1CCCN1S(=O)(=O)c1cc2cc(F)ccc2o1] | (2S)-1-(5-fluorobenzofuran-2-yl)sulfonyl-N-[(4-phenylphenyl)methyl]pyrrolidine-2-carboxamide |
| 77 | 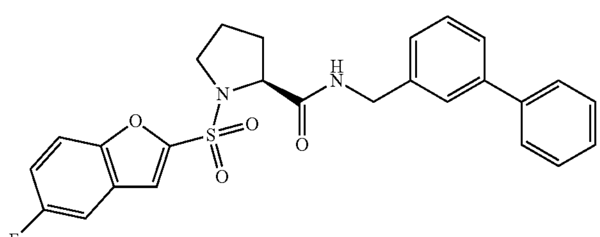 | (2S)-1-(5-fluorobenzofuran-2-yl)sulfonyl-N-[(3-phenylphenyl)methyl]pyrrolidine-2-carboxamide |

TABLE 21-continued

| Ex. No. | structure | compound name |
|---|---|---|
| 78 | 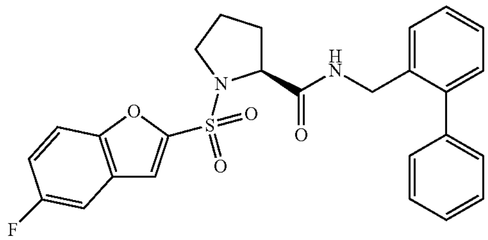 [SMILES: O=C(NCc1ccccc1-c1ccccc1)[C@@H]1CCCN1S(=O)(=O)c1cc2cc(F)ccc2o1] | (2S)-1-(5-fluorobenzofuran-2-yl)sulfonyl-N-[(2-phenylphenyl)methyl]pyrrolidine-2-carboxamide |
| 79 | 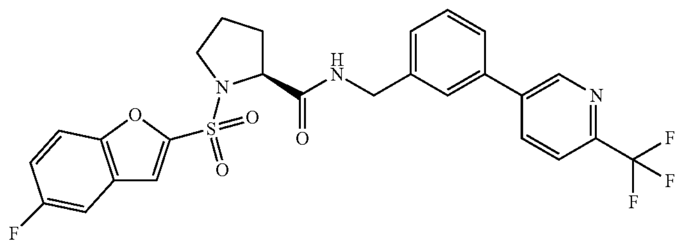 [SMILES: O=C(NCc1cccc(-c2ccc(C(F)(F)F)nc2)c1)[C@@H]1CCCN1S(=O)(=O)c1cc2cc(F)ccc2o1] | (2S)-1-(benzofuran-2-ylsulfonyl)-N-[[3-[6-(trifluoromethyl)-3-pyridyl]phenyl]methyl]pyrrolidine-2-carboxamide |
| 80 | 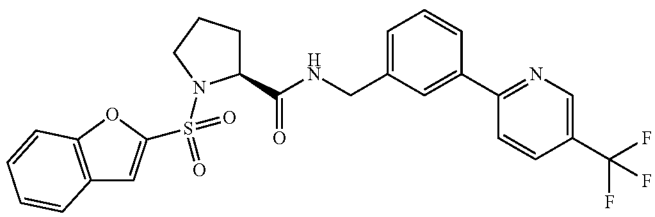 [SMILES: O=C(NCc1cccc(-c2ccc(C(F)(F)F)cn2)c1)[C@@H]1CCCN1S(=O)(=O)c1cc2ccccc2o1] | (2S)-1-(benzofuran-2-ylsulfonyl)-N-[[3-[5-(trifluoromethyl)-2-pyridyl]phenyl]methyl]pyrrolidine-2-carboxamide |
| 84 | 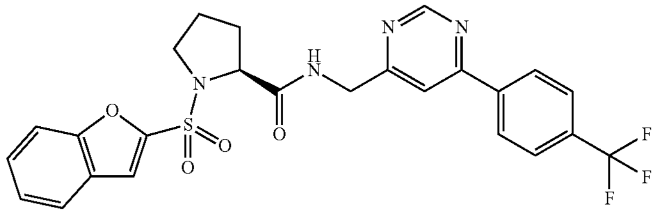 [SMILES: O=C(NCc1cc(-c2ccc(C(F)(F)F)cc2)ncn1)[C@@H]1CCCN1S(=O)(=O)c1cc2ccccc2o1] | (2S)-1-(benzofuran-2-ylsulfonyl)-N-[[6-[4-(trifluoromethyl)phenyl]pyrimidin-4-yl]methyl]pyrrolidine-2-carboxamide |
| 86 | 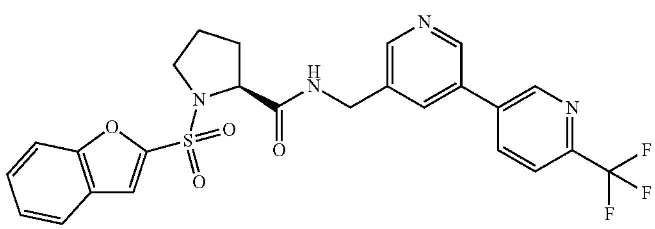 [SMILES: O=C(NCc1cncc(-c2ccc(C(F)(F)F)nc2)c1)[C@@H]1CCCN1S(=O)(=O)c1cc2ccccc2o1] | (2S)-1-(benzofuran-2-ylsulfonyl)-N-[[5-[6-(trifluoromethyl)-3-pyridyl]-3-pyridyl]methyl]pyrrolidine-2-carboxamide |
| 87 | 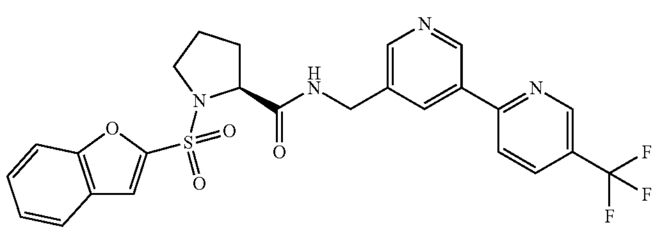 [SMILES: O=C(NCc1cncc(-c2ccc(C(F)(F)F)cn2)c1)[C@@H]1CCCN1S(=O)(=O)c1cc2ccccc2o1] | (2S)-1-(benzofuran-2-ylsulfonyl)-N-[[5-[5-(trifluoromethyl)-2-pyridyl]-3-pyridyl]methyl]pyrrolidine-2-carboxamide |

TABLE 21-continued

| Ex. No. | structure | compound name |
|---|---|---|
| 88 | 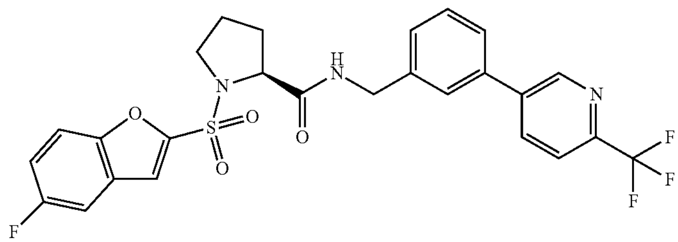 [SMILES: O=C(NCc1cccc(-c2ccc(C(F)(F)F)nc2)c1)[C@@H]1CCCN1S(=O)(=O)c1cc2cc(F)ccc2o1] | (2S)-1-(5-fluorobenzofuran-2-yl)sulfonyl-N-[[3-[6-(trifluoromethyl)-3-pyridyl]phenyl]methyl]pyrrolidine-2-carboxamide |
| 89 | 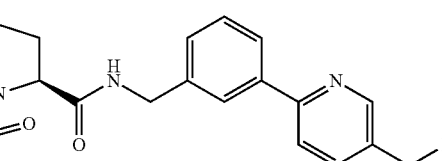 | (2S)-1-(5-fluorobenzofuran-2-yl)sulfonyl-N-[[3-[5-(trifluoromethyl)-2-pyridyl]phenyl]methyl]pyrrolidine-2-carboxamide |
| 90 | 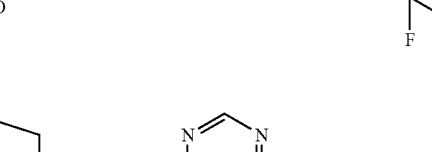 | (2S)-1-(5-fluorobenzofuran-2-yl)sulfonyl-N-[[6-[4-(trifluoromethyl)phenyl]pyrimidin-4-yl]methyl]pyrrolidine-2-carboxamide |
| 92 | 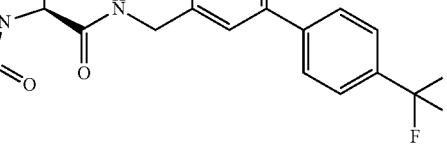 | (2S)-1-(4-fluorobenzofuran-2-yl)sulfonyl-N-[[3-[6-(trifluoromethyl)-3-pyridyl]phenyl]methyl]pyrrolidine-2-carboxamide |
| 93 | 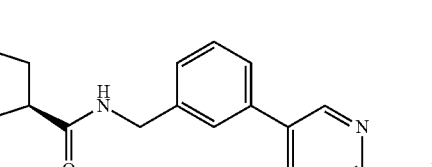 | (2S,3S)-1-(5-fluorobenzofuran-2-yl)sulfonyl-3-hydroxy-N-[[3-[6-(trifluoromethyl)-3-pyridyl]phenyl]methyl]pyrrolidine-2-carboxamide |
| 94 | 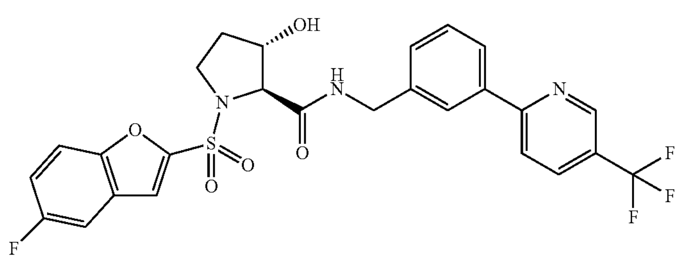 [SMILES: O=C(NCc1cccc(-c2ccc(C(F)(F)F)cn2)c1)[C@@H]1[C@@H](O)CCN1S(=O)(=O)c1cc2cc(F)ccc2o1] | (2S,3S)-1-(5-fluorobenzofuran-2-yl)sulfonyl-3-hydroxy-N-[[3-[5-(trifluoromethyl)-2-pyridyl]phenyl]methyl]pyrrolidine-2-carboxamide |

TABLE 21-continued

| Ex. No. | structure | compound name |
|---|---|---|
| 95 | 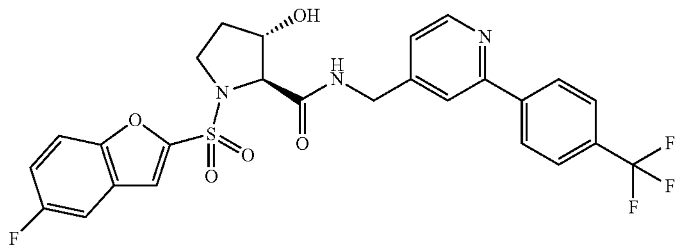 [SMILES: O=C(NCc1ccnc(-c2ccc(C(F)(F)F)cc2)c1)[C@@H]1[C@@H](O)CCN1S(=O)(=O)c1cc2cc(F)ccc2o1] | (2S,3S)-1-(5-fluorobenzofuran-2-yl)sulfonyl-3-hydroxy-N-[[2-[4-(trifluoromethyl)phenyl]-4-pyridyl]methyl]pyrrolidine-2-carboxamide |
| 96 | 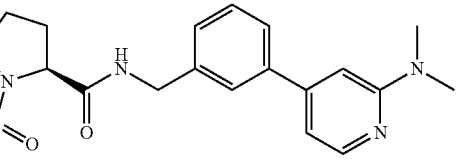 | (2S)-N-[[3-[2-(dimethylamino)-4-pyridyl]phenyl]methyl]-1-(5-fluorobenzofuran-2-yl)sulfonyl-pyrrolidine-2-carboxamide |
| 97 | 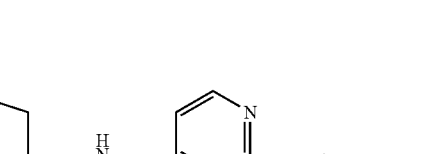 | (2S)-1-(4-fluorobenzofuran-2-yl)sulfonyl-N-[[2-[4-(trifluoromethyl)phenyl]-4-pyridyl]methyl]pyrrolidine-2-carboxamide |
| 98 | 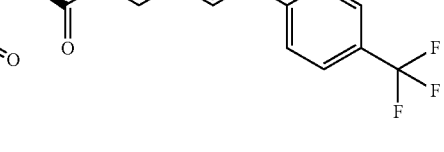 | (2S)-1-(5-fluorobenzofuran-2-yl)sulfonyl-N-[[2-[4-(trifluoromethyl)phenyl]-4-pyridyl]methyl]-2,5-dihydropyrrole-2-carboxamide |
| 99 | 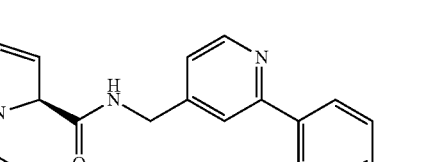 | (2S)-4,4-difluoro-1-(5-fluorobenzofuran-2-yl)sulfonyl-N-[[2-[4-(trifluoromethyl)phenyl]-4-pyridyl]methyl]pyrrolidine-2-carboxamide |
| 100 | 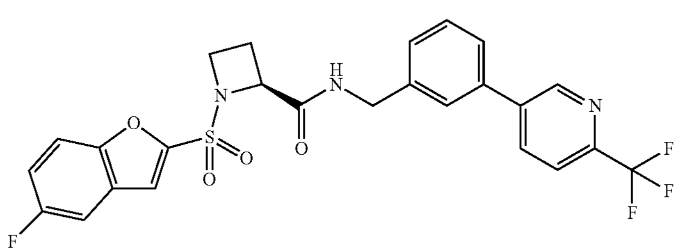 [SMILES: O=C(NCc1cccc(-c2ccc(C(F)(F)F)nc2)c1)[C@@H]1CCN1S(=O)(=O)c1cc2cc(F)ccc2o1] | (2S)-1-(5-fluorobenzofuran-2-yl)sulfonyl-N-[[3-[6-(trifluoromethyl)-3-pyridyl]phenyl]methyl]azetidine-2-carboxamide |

TABLE 21-continued

| Ex. No. | structure | compound name |
| --- | --- | --- |
| 101 | 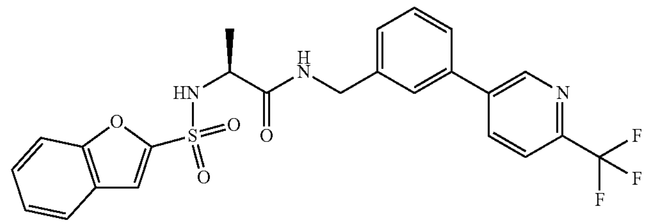 [SMILES: C[C@H](NS(=O)(=O)c1cc2ccccc2o1)C(=O)NCc1cccc(-c2ccc(C(F)(F)F)nc2)c1] | (2S)-2-(benzofuran-2-ylsulfonylamino)-N-[[3-[6-(trifluoromethyl)-3-pyridyl]phenyl]methyl]propanamide |
| 102 | 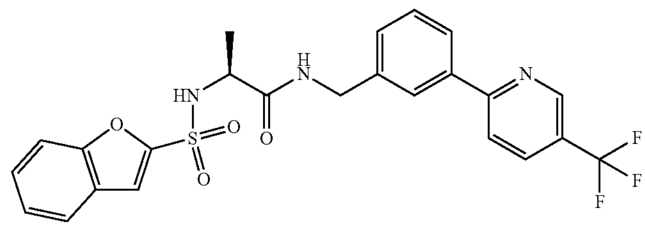 [SMILES: C[C@H](NS(=O)(=O)c1cc2ccccc2o1)C(=O)NCc1cccc(-c2ccc(C(F)(F)F)cn2)c1] | (2S)-2-(benzofuran-2-ylsulfonylamino)-N-[[3-[5-(trifluoromethyl)-2-pyridyl]phenyl]methyl]propanamide |
| 103 | 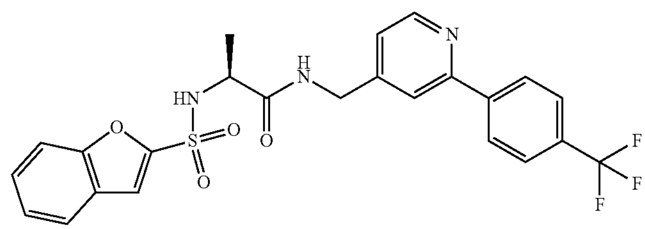 | (2S)-2-(benzofuran-2-ylsulfonylamino)-N-[[2-[4-(trifluoromethyl)phenyl]-4-pyridyl]methyl]propanamide |
| 104 | 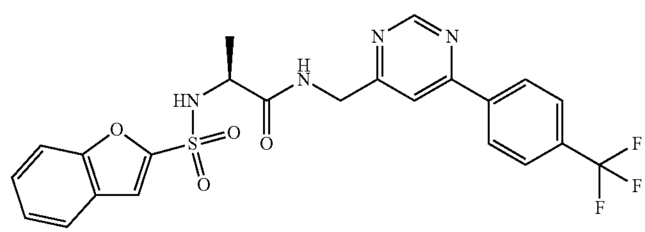 [SMILES: C[C@H](NS(=O)(=O)c1cc2ccccc2o1)C(=O)NCc1cc(-c2ccc(C(F)(F)F)cc2)ncn1] | (2S)-2-(benzofuran-2-ylsulfonylamino)-N-[[6-[4-(trifluoromethyl)phenyl]pyrimidin-4-yl]methyl]propanamide |
| 105 | 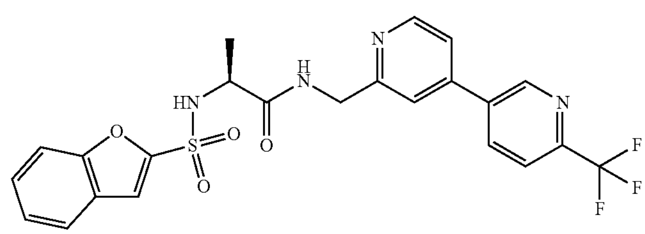 [SMILES: C[C@H](NS(=O)(=O)c1cc2ccccc2o1)C(=O)NCc1cc(-c2ccc(C(F)(F)F)nc2)ccn1] | (2S)-2-(benzofuran-2-ylsulfonylamino)-N-[[4-[6-(trifluoromethyl)-3-pyridyl]-2-pyridyl]methyl]propanamide |
| 106 | 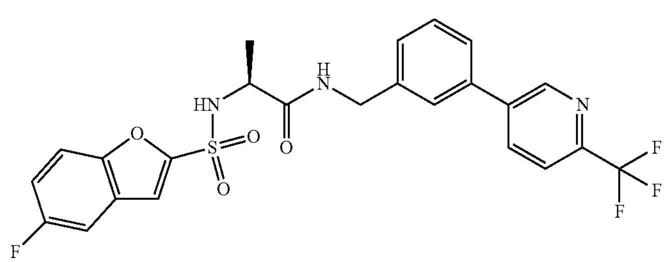 [SMILES: C[C@H](NS(=O)(=O)c1cc2cc(F)ccc2o1)C(=O)NCc1cccc(-c2ccc(C(F)(F)F)nc2)c1] | (2S)-2-[(5-fluorobenzofuran-2-yl)sulfonylamino]-N-[[3-[6-(trifluoromethyl)-3-pyridyl]phenyl]methyl]propanamide |

TABLE 21-continued

| Ex. No. | structure | compound name |
|---|---|---|
| 107 | 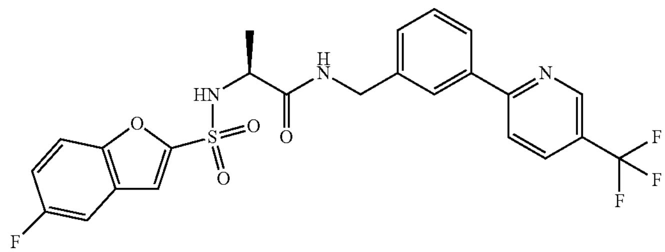 [SMILES: C[C@H](NS(=O)(=O)c1cc2cc(F)ccc2o1)C(=O)NCc1cccc(-c2ccc(C(F)(F)F)cn2)c1] | (2S)-2-[(5-fluorobenzofuran-2-yl)sulfonylamino]-N-[[3-[5-(trifluoromethyl)-2-pyridyl]phenyl]methyl]propanamide |
| 108 | 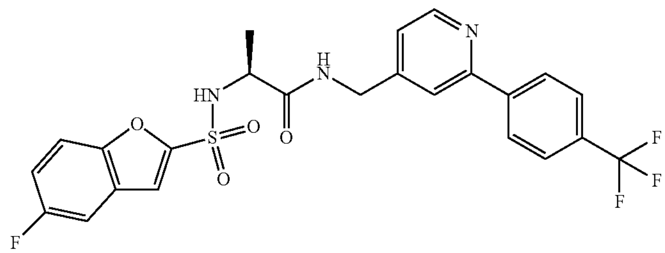 [SMILES: C[C@H](NS(=O)(=O)c1cc2cc(F)ccc2o1)C(=O)NCc1ccnc(-c2ccc(C(F)(F)F)cc2)c1] | (2S)-2-[(5-fluorobenzofuran-2-yl)sulfonylamino]-N-[[2-[4-(trifluoromethyl)phenyl]-4-pyridyl]methyl]propanamide |
| 109 | 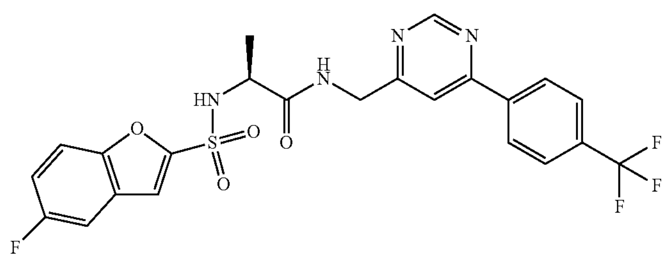 [SMILES: C[C@H](NS(=O)(=O)c1cc2cc(F)ccc2o1)C(=O)NCc1cc(-c2ccc(C(F)(F)F)cc2)ncn1] | (2S)-2-[(5-fluorobenzofuran-2-yl)sulfonylamino]-N-[[6-[4-(trifluoromethyl)phenyl]pyrimidin-4-yl]methyl]propanamide |
| 110 | 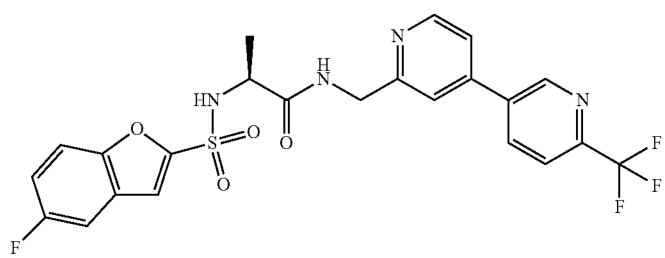 [SMILES: C[C@H](NS(=O)(=O)c1cc2cc(F)ccc2o1)C(=O)NCc1cc(-c2ccc(C(F)(F)F)nc2)ccn1] | (2S)-2-[(5-fluorobenzofuran-2-yl)sulfonylamino]-N-[[4-[6-(trifluoromethyl)-3-pyridyl]-2-pyridyl]methyl]propanamide |
| 111 | 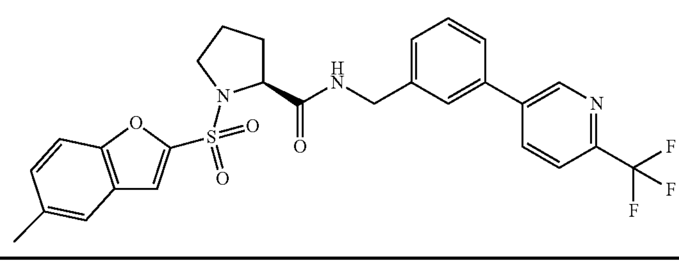 | (2S)-1-(5-methylbenzofuran-2-yl)sulfonyl-N-[[3-[6-(trifluoromethyl)-3-pyridyl]phenyl]methyl]pyrrolidine-2-carboxamide |

Example 112

Synthesis of (2S)-1-(benzofuran-2-ylsulfonyl)-N-[(2-phenyl-4-pyridyl)methyl]pyrrolidine-2-carboxamide (112)

To C-4 (30 mg, 0.072 mmol), phenylboronic acid (17 mg, 0.14 mmol) and 1,1'-bis(diphenylphosphino)ferrocenedichloropalladium(II) (5 mg, 0.007 mmol) were added 1,4-dioxane (1 mL) and 1 mol/L aqueous sodium carbonate solution (1 mL) and the mixture was stirred with heating by using a microwave reactor at 100° C. for 10 min. To the reaction mixture was added acetonitrile (2 mL), the organic layer was taken out, concentrated under reduced pressure and the obtained residue was purified by high performance liquid chromatography (water-acetonitrile, each containing 0.1% trifluoroacetic acid) to give trifluoroacetate of the title compound (40 mg, 0.069 mmol, 96%).

MS (ESI) m/z 462 (M+H)$^+$ $^1$H NMR (400 MHz, DMSO-d$_6$) δ 8.90 (dd, J=5.9, 5.8 Hz, 1H), 8.66 (d, J=5.2 Hz, 1H), 8.07 (ddd, J=8.0, 1.4, 1.4 Hz, 2H), 7.98-7.91 (m, 1H), 7.88-7.81 (m, 1H), 7.79-7.73 (m, 2H), 7.60-7.33 (m, 6H), 4.52 (dd, J=16.7, 5.9 Hz, 1H), 4.43 (dd, J=16.7, 5.8 Hz, 1H), 4.34 (dd, J=8.3, 3.7 Hz, 1H), 3.67-3.59 (m, 1H), 3.47-3.37 (m, 1H), 2.06-1.83 (m, 3H), 1.71-1.60 (m, 1H).

Example 117

Synthesis of (2S)-1-(benzofuran-2-ylsulfonyl)-N-[[2-(4-cyanophenyl)-4-pyridyl]methyl]pyrrolidine-2-carboxamide (117)

To C-4 (42 mg, 0.10 mmol), 4-cyanophenylboronic acid (29 mg, 0.20 mmol) and 1,1'-bis(diphenylphosphino)ferrocenedichloropalladium(II) (7.3 mg, 0.010 mmol) were added 1,4-dioxane (1 mL) and 1 mol/L aqueous sodium carbonate solution (1 mL) and the mixture was stirred with heating by using a microwave reactor at 100° C. for 10 min. The reaction mixture was concentrated under reduced pressure and the obtained residue was purified by high performance liquid chromatography (water-acetonitrile, each containing 0.1% trifluoroacetic acid) to give trifluoroacetate of the title compound (38 mg, 0.069 mmol, 96%).

MS (ESI) m/z 487 (M+H)$^+$ $^1$H NMR (400 MHz, DMSO-d$_6$) δ 8.89 (dd, J=6.2, 5.8 Hz, 1H), 8.67 (d, J=5.2 Hz, 1H), 8.31-8.24 (m, 2H), 8.03-7.93 (m, 3H), 7.88-7.82 (m, 1H), 7.79-7.72 (m, 2H), 7.57 (ddd, J=8.3, 7.4, 1.4 Hz, 1H), 7.47-7.40 (m, 1H), 7.39-7.33 (m, 1H), 4.50 (dd, J=16.5, 6.2 Hz, 1H), 4.41 (dd, J=16.5, 5.8 Hz, 1H), 4.33 (dd, J=8.3, 3.7 Hz, 1H), 3.67-3.58 (m, 1H), 3.51-3.45 (m, 1H), 2.05-1.84 (m, 3H), 1.73-1.61 (m, 1H).

Example 123

Synthesis of (2S)-1-(benzofuran-2-ylsulfonyl)-N-[[2-[2-hydroxy-4-(trifluoromethyl)phenyl]-4-pyridyl]methyl]pyrrolidine-2-carboxamide (123)

To C-4 (21 mg, 0.050 mmol), 2-hydroxy-4-trifluoromethylphenylboronic acid (21 mg, 0.10 mmol) and 1,1'-bis(diphenylphosphino)ferrocenedichloropalladium(II) (4 mg, 0.005 mmol) were added 1,4-dioxane (0.7 mL) and 1 mol/L aqueous sodium carbonate solution (0.7 mL) and the mixture was stirred with heating by using a microwave reactor at 120° C. for 20 min. The reaction mixture was neutralized with trifluoroacetic acid, and purified by high performance liquid chromatography (water-acetonitrile, each containing 0.1% trifluoroacetic acid) to give trifluoroacetate of the title compound (24 mg, 0.036 mmol, 72%).

MS (ESI) m/z 546 (M+H)$^+$ $^1$H NMR (400 MHz, DMSO-d$_6$) δ 14.67 (brs, 1H), 8.93 (dd, J=6.3, 5.9 Hz, 1H), 8.64 (d, J=5.3 Hz, 1H), 8.24 (d, J=8.2 Hz, 1H), 8.20 (s, 1H), 7.84 (d, J=7.9 Hz, 1H), 7.78 (d, J=0.9 Hz, 1H), 7.76 (dd, J=8.5, 0.9 Hz, 1H), 7.57 (ddd, J=8.5, 7.2, 1.3 Hz, 1H), 7.46-7.40 (m, 2H), 7.26-7.21 (m, 2H), 4.54 (dd, J=16.7, 6.3 Hz, 1H), 4.45 (dd, J=16.7, 5.9 Hz, 1H), 4.34 (dd, J=8.3, 3.8 Hz, 1H), 3.67-3.59 (m, 1H), 3.45-3.41 (m, 1H), 2.07-1.85 (m, 3H), 1.72-1.61 (m, 1H).

Example 124

Synthesis of (2S)-1-(benzofuran-2-ylsulfonyl)-N-[[2-[6-(trifluoromethyl)-3-pyridyl]-4-pyridyl]methyl]pyrrolidine-2-carboxamide (124)

To C-4 (42 mg, 0.10 mmol), [6-(trifluoromethyl)-3-pyridyl]boronic acid (38 mg, 0.20 mmol) and 1,1'-bis(diphenylphosphino)ferrocenedichloropalladium(II) (7 mg, 0.01 mmol) were added 1,4-dioxane (1 mL) and 1 mol/L aqueous sodium carbonate solution (1 mL) and the mixture was stirred with heating by using a microwave reactor at 100° C. for 10 min. To the reaction mixture was added ethyl acetate, and the mixture was washed with saturated brine. The organic layer was dried over sodium sulfate, the desiccant was filtered off, and the solvent was evaporated. The obtained residue was purified by high performance liquid chromatography (water-acetonitrile, each containing 0.1% trifluoroacetic acid) to give trifluoroacetate of the title compound (44 mg, 0.068 mmol, 68%).

MS (ESI) m/z 531 (M+H)$^+$ $^1$H NMR (400 MHz, DMSO-d$_6$) δ 9.42 (d, J=2.1 Hz, 1H), 8.90 (dd, J=6.2, 5.9 Hz, 1H), 8.74-8.66 (m, 2H), 8.07 (s, 1H), 8.05 (dd, J=8.4, 0.8 Hz, 1H), 7.84 (ddd, J=7.9, 1.3, 0.9 Hz, 1H), 7.77 (d, J=0.9 Hz, 1H), 7.75 (dd, J=8.5, 1.0 Hz, 1H), 7.56 (ddd, J=8.5, 7.3, 1.3 Hz, 1H), 7.45-7.39 (m, 2H), 4.52 (dd, J=16.6, 6.2 Hz, 1H), 4.42 (dd, J=16.6, 5.9 Hz, 1H), 4.34 (dd, J=8.3, 3.8 Hz, 1H), 3.66-3.59 (m, 1H), 3.47-3.40 (m, 1H), 2.04-1.85 (m, 3H), 1.71-1.61 (m, 1H).

Example 113 to Example 116, Example 118 to Example 122 and Example 125 to Example 175 described in Table 22 were synthesized by using the compounds described in Reference Examples and corresponding commercially available reagents and by an operation similar to that in Example 112.

TABLE 22

| Ex. No. | structure | compound name |
|---|---|---|
| 112 | 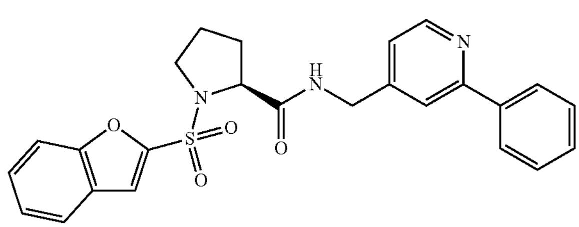 [SMILES: O=C(NCc1ccnc(-c2ccccc2)c1)[C@@H]1CCCN1S(=O)(=O)c1cc2ccccc2o1] | (2S)-1-(benzofuran-2-ylsulfonyl)-N-[(2-phenyl-4-pyridyl)methyl]pyrrolidine-2-carboxamide |

TABLE 22-continued

| Ex. No. | structure | compound name |
|---|---|---|
| 113 | 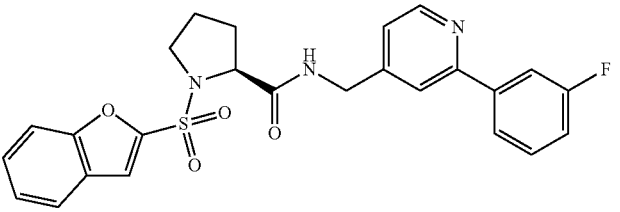 [SMILES: O=C(NCc1ccnc(-c2cccc(F)c2)c1)[C@@H]1CCCN1S(=O)(=O)c1cc2ccccc2o1] | (2S)-1-(benzofuran-2-ylsulfonyl)-N-[[2-(3-fluorophenyl)-4-pyridyl]methyl]pyrrolidine-2-carboxamide |
| 114 | 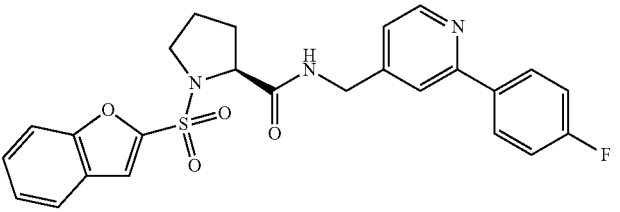 [SMILES: O=C(NCc1ccnc(-c2ccc(F)cc2)c1)[C@@H]1CCCN1S(=O)(=O)c1cc2ccccc2o1] | (2S)-1-(benzofuran-2-ylsulfonyl)-N-[[2-(4-fluorophenyl)-4-pyridyl]methyl]pyrrolidine-2-carboxamide |
| 115 | 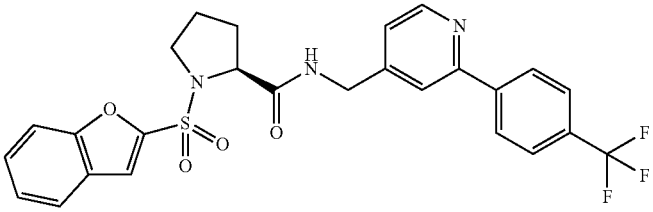 | (2S)-1-(benzofuran-2-ylsulfonyl)-N-[[2-[4-(trifluoromethyl)phenyl]-4-pyridyl]methyl]pyrrolidine-2-carboxamide |
| 116 | 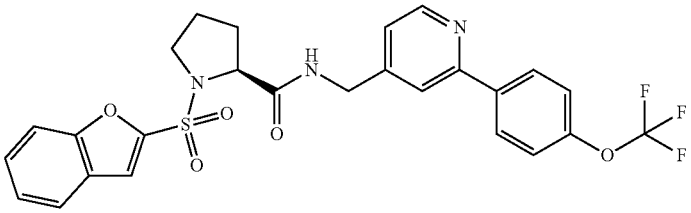 [SMILES: O=C(NCc1ccnc(-c2ccc(OC(F)(F)F)cc2)c1)[C@@H]1CCCN1S(=O)(=O)c1cc2ccccc2o1] | (2S)-1-(benzofuran-2-ylsulfonyl)-N-[[2-[4-(trifluoromethoxy)phenyl]-4-pyridyl]methyl]pyrrolidine-2-carboxamide |
| 117 | 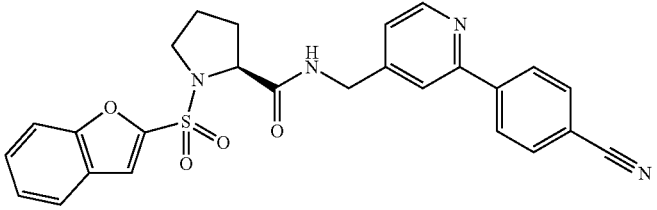 [SMILES: N#Cc1ccc(-c2cc(CNC(=O)[C@@H]3CCCN3S(=O)(=O)c3cc4ccccc4o3)ccn2)cc1] | (2S)-1-(benzofuran-2-ylsulfonyl)-N-[[2-(4-cyanophenyl)-4-pyridyl]methyl]pyrrolidine-2-carboxamide |
| 118 | 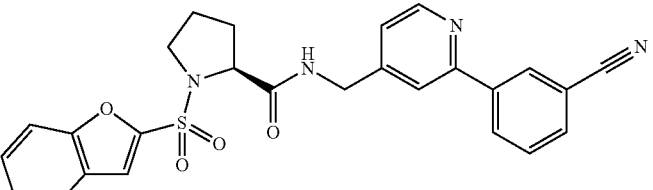 | (2S)-1-(benzofuran-2-ylsulfonyl)-N-[[2-(3-cyanophenyl)-4-pyridyl]methyl]pyrrolidine-2-carboxamide |
| 119 | 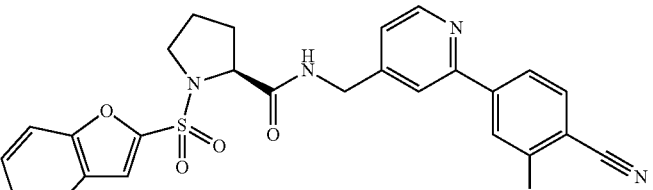 | (2S)-1-(benzofuran-2-ylsulfonyl)-N-[[2-(4-cyano-3-fluoro-phenyl)-4-pyridyl]methyl]pyrrolidine-2-carboxamide |

TABLE 22-continued

| Ex. No. | structure | compound name |
|---|---|---|
| 120 | 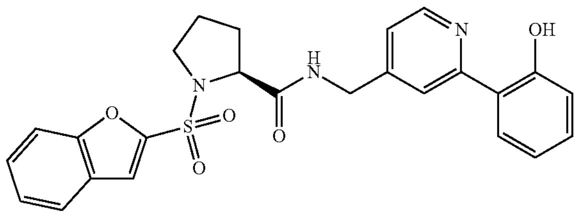 [SMILES: O=C(NCc1ccnc(-c2ccccc2O)c1)[C@@H]1CCCN1S(=O)(=O)c1cc2ccccc2o1] | (2S)-1-(benzofuran-2-ylsulfonyl)-N-[[2-(2-hydroxyphenyl)-4-pyridyl]methyl]pyrrolidine-2-carboxamide |
| 121 | 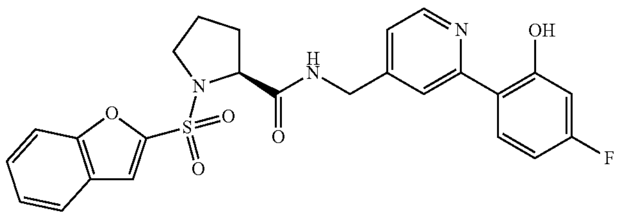 [SMILES: O=C(NCc1ccnc(-c2ccc(F)cc2O)c1)[C@@H]1CCCN1S(=O)(=O)c1cc2ccccc2o1] | (2S)-1-(benzofuran-2-ylsulfonyl)-N-[[2-(4-fluoro-2-hydroxy-phenyl)-4-pyridyl]methyl]pyrrolidine-2-carboxamide |
| 122 | 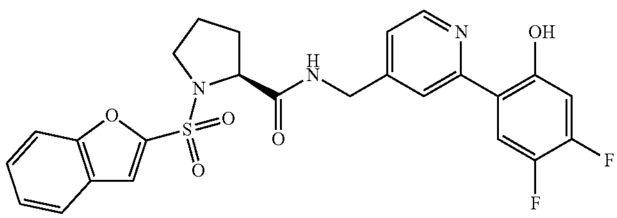 [SMILES: O=C(NCc1ccnc(-c2cc(F)c(F)cc2O)c1)[C@@H]1CCCN1S(=O)(=O)c1cc2ccccc2o1] | (2S)-1-(benzofuran-2-ylsulfonyl)-N-[[2-(4,5-difluoro-2-hydroxy-phenyl)-4-pyridyl]methyl]pyrrolidine-2-carboxamide |
| 123 | 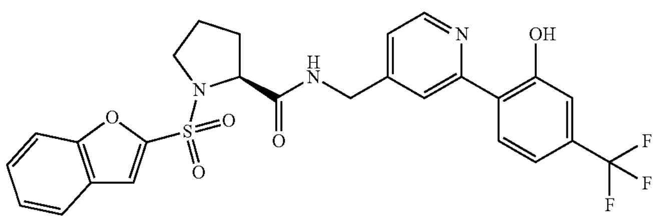 | (2S)-1-(benzofuran-2-ylsulfonyl)-N-[[2-[2-hydroxy-4-(trifluoromethyl)phenyl]-4-pyridyl]methyl]pyrrolidine-2-carboxamide |
| 124 | 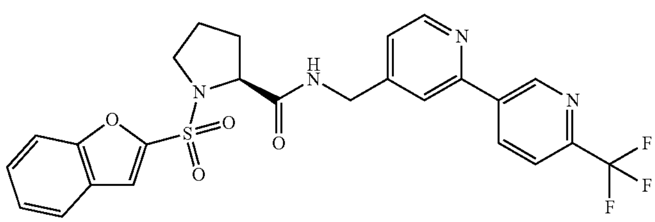 | (2S)-1-(benzofuran-2-ylsulfonyl)-N-[[2-[6-(trifluoromethyl)-3-pyridyl]-4-pyridyl]methyl]pyrrolidine-2-carboxamide |
| 125 | 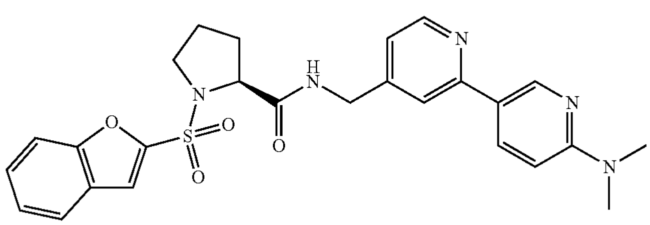 [SMILES: CN(C)c1ccc(-c2cc(CNC(=O)[C@@H]3CCCN3S(=O)(=O)c3cc4ccccc4o3)ccn2)cn1] | (2S)-1-(benzofuran-2-ylsulfonyl)-N-[[2-[6-(dimethylamino)-3-pyridyl]-4-pyridyl]methyl]pyrrolidine-2-carboxamide |
| 126 | 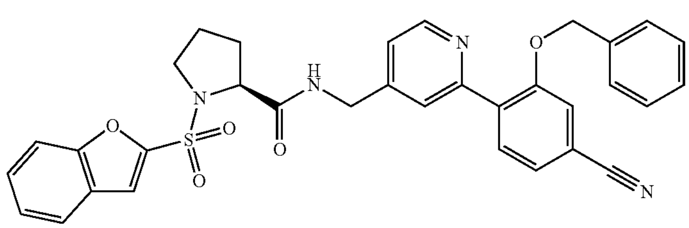 [SMILES: N#Cc1ccc(-c2cc(CNC(=O)[C@@H]3CCCN3S(=O)(=O)c3cc4ccccc4o3)ccn2)c(OCc2ccccc2)c1] | (2S)-1-(benzofuran-2-ylsulfonyl)-N-[[2-(2-benzyloxy-4-cyano-phenyl)-4-pyridyl]methyl]pyrrolidine-2-carboxamide |

TABLE 22-continued

| Ex. No. | structure | compound name |
| --- | --- | --- |
| 127 | 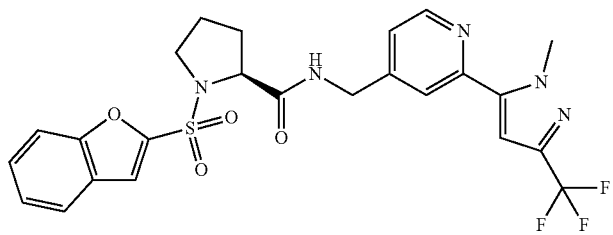 [SMILES: CN/C(=C\C(=N)C(F)(F)F)c1cc(CNC(=O)[C@@H]2CCCN2S(=O)(=O)c2cc3ccccc3o2)ccn1] | (2S)-1-(benzofuran-2-yl)sulfonyl)-N-[[2-[2-methyl-5-(trifluoromethyl)pyrazol-3-yl]-4-pyridyl]methyl]pyrrolidine-2-carboxamide |
| 128 | 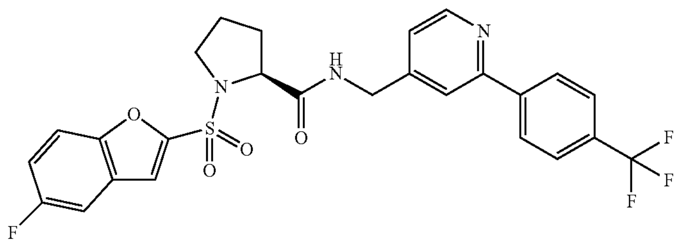 [SMILES: O=C(NCc1ccnc(-c2ccc(C(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[2-[4-(trifluoromethyl)phenyl]-4-pyridyl]methyl]pyrrolidine-2-carboxamide |
| 129 | 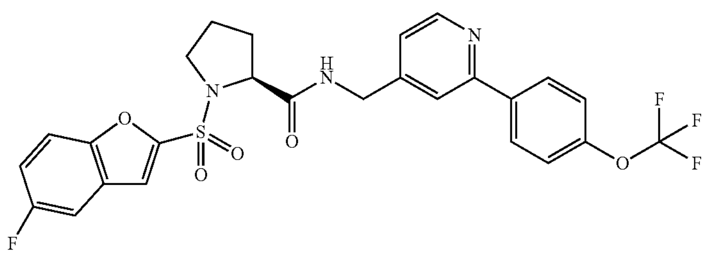 [SMILES: O=C(NCc1ccnc(-c2ccc(OC(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[2-[4-(trifluoromethoxy)phenyl]-4-pyridyl]methyl]pyrrolidine-2-carboxamide |
| 130 | 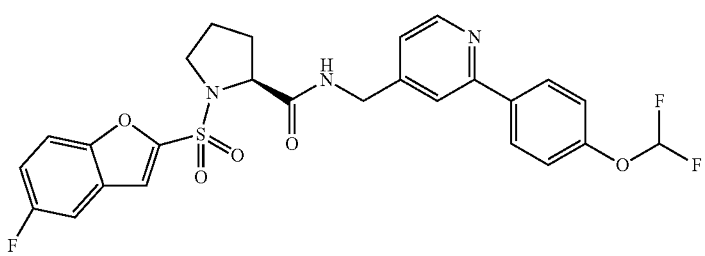 [SMILES: O=C(NCc1ccnc(-c2ccc(OC(F)F)cc2)c1)[C@@H]1CCCN1S(=O)(=O)c1cc2cc(F)ccc2o1] | (2S)-N-[[2-[4-(difluoromethoxy)phenyl]-4-pyridyl]methyl]-1-(5-fluorobenzofuran-2-yl)sulfonyl-pyrrolidine-2-carboxamide |
| 131 | 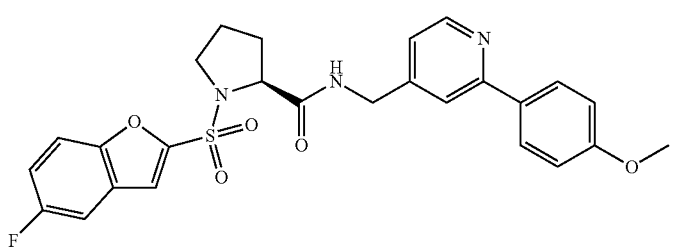 [SMILES: COc1ccc(-c2cc(CNC(=O)[C@@H]3CCCN3S(=O)(=O)c3cc4cc(F)ccc4o3)ccn2)cc1] | (2S)-1-(5-fluorobenzofuran-2-yl)sulfonyl-N-[[2-(4-methoxyphenyl)-4-pyridyl]methyl]pyrrolidine-2-carboxamide |
| 132 | 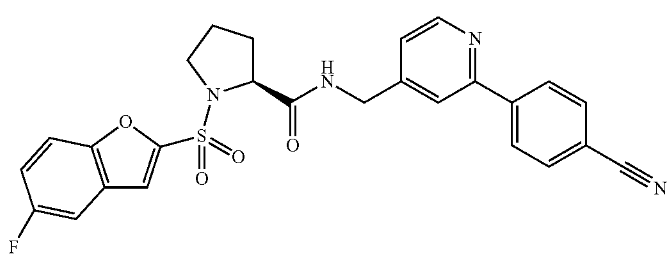 [SMILES: N#Cc1ccc(-c2cc(CNC(=O)[C@@H]3CCCN3S(=O)(=O)c3cc4cc(F)ccc4o3)ccn2)cc1] | (2S)-N-[[2-(4-cyanophenyl)-4-pyridyl]methyl]-1-(5-fluorobenzofuran-2-yl)sulfonyl-pyrrolidine-2-carboxamide |

TABLE 22-continued

| Ex. No. | structure | compound name |
|---|---|---|
| 133 | 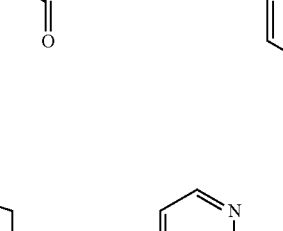 | (2S)-1-(5-fluorobenzofuran-2-yl)sulfonyl-N-[[2-[6-(trifluoromethyl)-3-pyridyl]-4-pyridyl]methyl]pyrrolidine-2-carboxamide |
| 134 | 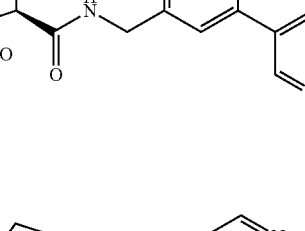 | (2S)-N-[[2-(2-cyclopropylpyrimidin-5-yl)-4-pyridyl]methyl]-1-(5-fluorobenzofuran-2-yl)sulfonyl-pyrrolidine-2-carboxamide |
| 135 | 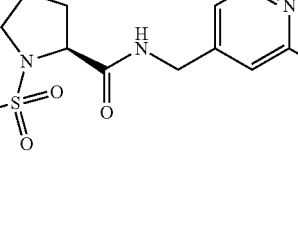 | (2S)-1-(5-fluorobenzofuran-2-yl)sulfonyl-N-[[2-(2-hydroxyphenyl)-4-pyridyl]methyl]pyrrolidine-2-carboxamide |
| 136 | 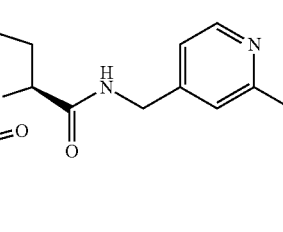 | (2S)-1-(5-fluorobenzofuran-2-yl)sulfonyl-N-[[2-(4-fluoro-2-hydroxy-phenyl)-4-pyridyl]methyl]pyrrolidine-2-carboxamide |
| 137 | 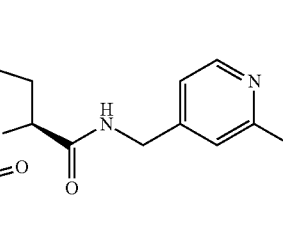 | (2S)-N-[[2-(4,5-difluoro-2-hydroxy-phenyl)-4-pyridyl]methyl]-1-(5-fluorobenzofuran-2-yl)sulfonyl-pyrrolidine-2-carboxamide |
| 138 | 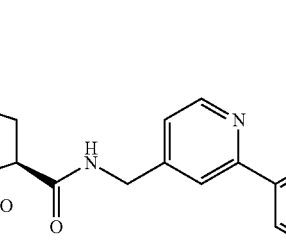 | (2S)-1-(5-fluorobenzofuran-2-yl)sulfonyl-N-[[2-[2-hydroxy-4-(trifluoromethyl)phenyl]-4-pyridyl]methyl]pyrrolidine-2-carboxamide |

TABLE 22-continued

| Ex. No. | structure | compound name |
|---|---|---|
| 139 | 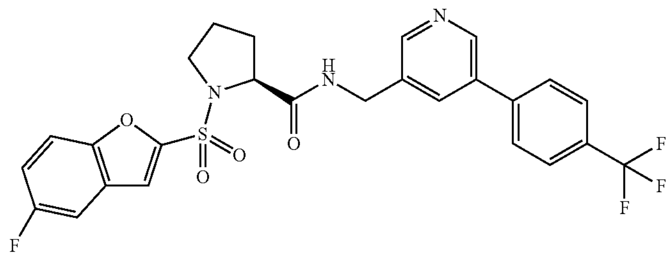 [SMILES: O=C(NCc1cncc(-c2ccc(C(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[5-[4-(trifluoromethyl)phenyl]-3-pyridyl]methyl]pyrrolidine-2-carboxamide |
| 140 | 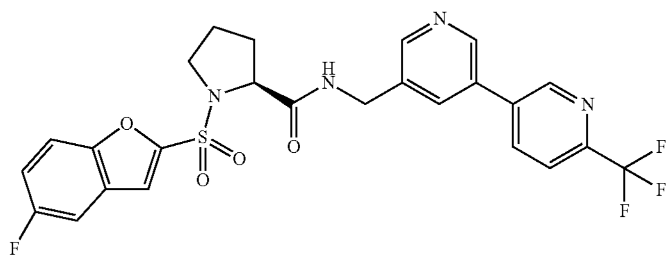 [SMILES: O=C(NCc1cncc(-c2ccc(C(F)(F)F)nc2)c1)[C@@H]1CCCN1S(=O)(=O)c1cc2cc(F)ccc2o1] | (2S)-1-(5-fluorobenzofuran-2-yl)sulfonyl-N-[[5-[6-(trifluoromethyl)-3-pyridyl]-3-pyridyl]methyl]pyrrolidine-2-carboxamide |
| 141 | 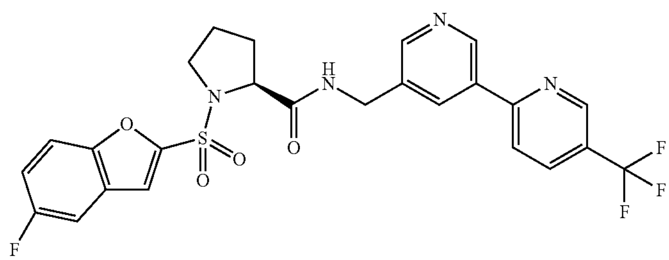 [SMILES: O=C(NCc1cncc(-c2ccc(C(F)(F)F)cn2)c1)[C@@H]1CCCN1S(=O)(=O)c1cc2cc(F)ccc2o1] | (2S)-1-(5-fluorobenzofuran-2-yl)sulfonyl-N-[[5-[5-(trifluoromethyl)-2-pyridyl]-3-pyridyl]methyl]pyrrolidine-2-carboxamide |
| 142 | 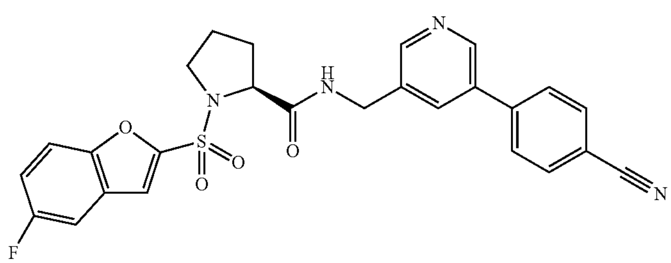 [SMILES: N#Cc1ccc(-c2cncc(CNC(=O)[C@@H]3CCCN3S(=O)(=O)c3cc4cc(F)ccc4o3)c2)cc1] | (2S)-N-[[5-(4-cyanophenyl)-3-pyridyl]methyl]-1-(5-fluorobenzofuran-2-yl)sulfonyl-pyrrolidine-2-carboxamide |
| 143 | 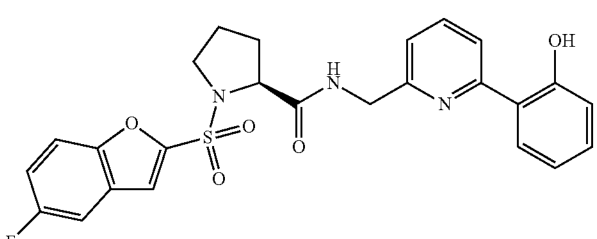 | (2S)-1-(5-fluorobenzofuran-2-yl)sulfonyl-N-[[6-(2-hydroxyphenyl)-2-pyridyl]methyl]pyrrolidine-2-carboxamide |
| 144 | 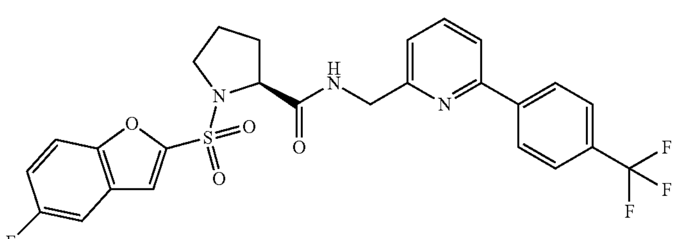 | (2S)-1-(5-fluorobenzofuran-2-yl)sulfonyl-N-[[6-[4-(trifluoromethyl)phenyl]-2-pyridyl]methyl]pyrrolidine-2-carboxamide |

TABLE 22-continued

| Ex. No. | structure | compound name |
|---|---|---|
| 145 | 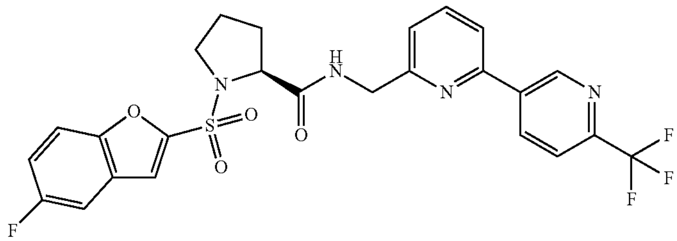 [SMILES: O=C(NCc1cccc(-c2ccc(C(F)(F)F)nc2)n1)[C@@H]1CCCN1S(=O)(=O)c1cc2cc(F)ccc2o1] | (2S)-1-(5-fluorobenzofuran-2-yl)sulfonyl-N-[[6-[6-(trifluoromethyl)-3-pyridyl]-2-pyridyl]methyl]pyrrolidine-2-carboxamide |
| 146 | 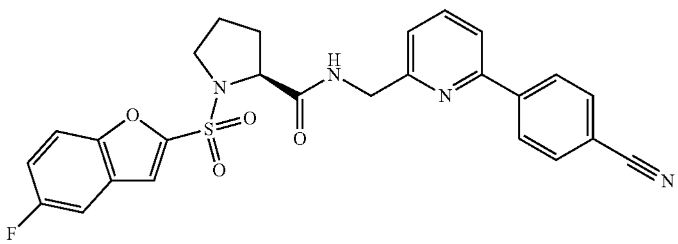 [SMILES: N#Cc1ccc(-c2cccc(CNC(=O)[C@@H]3CCCN3S(=O)(=O)c3cc4cc(F)ccc4o3)n2)cc1] | (2S)-N-[[6-(4-cyanophenyl)-2-pyridyl]methyl]-1-(5-fluorobenzofuran-2-yl)sulfonyl-pyrrolidine-2-carboxamide |
| 147 | 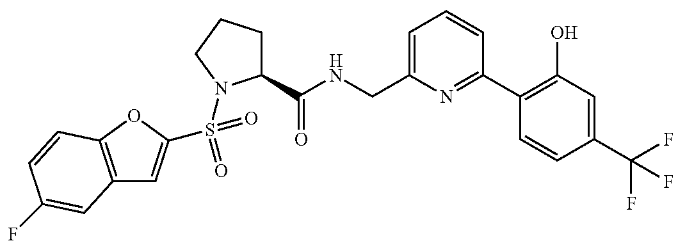 [SMILES: O=C(NCc1cccc(-c2ccc(C(F)(F)F)cc2O)n1)[C@@H]1CCCN1S(=O)(=O)c1cc2cc(F)ccc2o1] | (2S)-1-(5-fluorobenzofuran-2-yl)sulfonyl-N-[[6-[2-hydroxy-4-(trifluoromethyl)phenyl]-2-pyridyl]methyl]pyrrolidine-2-carboxamide |
| 148 | 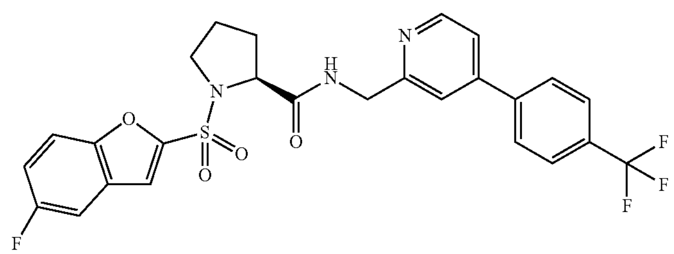 [SMILES: O=C(NCc1cc(-c2ccc(C(F)(F)F)cc2)ccn1)[C@@H]1CCCN1S(=O)(=O)c1cc2cc(F)ccc2o1] | (2S)-1-(5-fluorobenzofuran-2-yl)sulfonyl-N-[[4-[4-(trifluoromethyl)phenyl]-2-pyridyl]methyl]pyrrolidine-2-carboxamide |
| 149 | 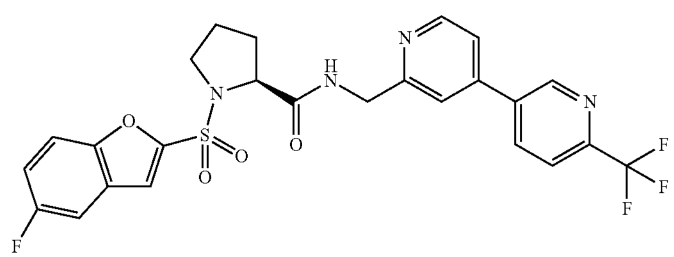 [SMILES: O=C(NCc1cc(-c2ccc(C(F)(F)F)nc2)ccn1)[C@@H]1CCCN1S(=O)(=O)c1cc2cc(F)ccc2o1] | (2S)-1-(5-fluorobenzofuran-2-yl)sulfonyl-N-[[4-[6-(trifluoromethyl)-3-pyridyl]-2-pyridyl]methyl]pyrrolidine-2-carboxamide |
| 150 | 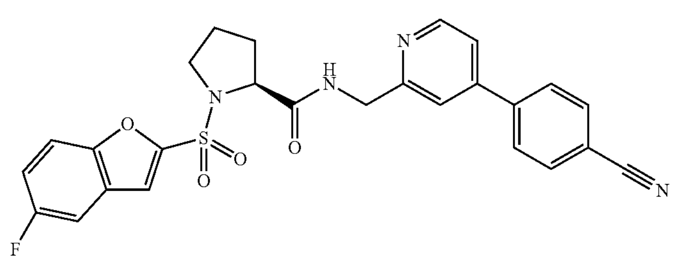 [SMILES: N#Cc1ccc(-c2ccnc(CNC(=O)[C@@H]3CCCN3S(=O)(=O)c3cc4cc(F)ccc4o3)c2)cc1] | (2S)-N-[[4-(4-cyanophenyl)-2-pyridyl]methyl]-1-(5-fluorobenzofuran-2-yl)sulfonyl-pyrrolidine-2-carboxamide |

TABLE 22-continued

| Ex. No. | structure | compound name |
|---|---|---|
| 151 | 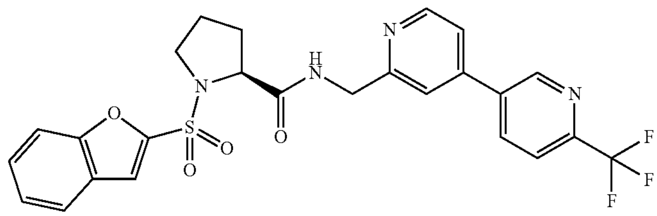 [SMILES: O=C(NCc1cc(-c2ccc(C(F)(F)F)nc2)ccn1)[C@@H]1CCCN1S(=O)(=O)c1cc2ccccc2o1] | (2S)-1-(benzofuran-2-ylsulfonyl)-N-[[4-[6-(trifluoromethyl)-3-pyridyl]-2-pyridyl]methyl]pyrrolidine-2-carboxamide |
| 152 | 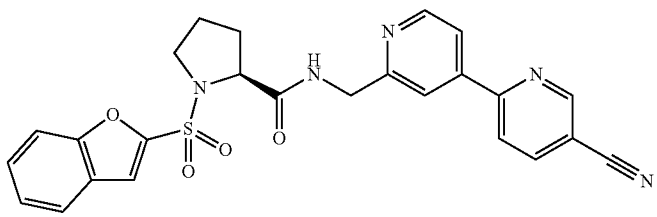 [SMILES: N#Cc1ccc(-c2ccnc(CNC(=O)[C@@H]3CCCN3S(=O)(=O)c3cc4ccccc4o3)c2)nc1] | (2S)-1-(benzofuran-2-ylsulfonyl)-N-[[4-(5-cyano-2-pyridyl)-2-pyridyl]methyl]pyrrolidine-2-carboxamide |
| 153 | 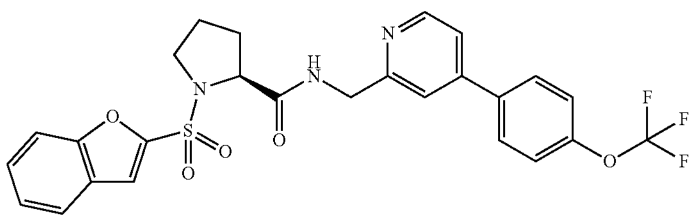 | (2S)-1-(benzofuran-2-ylsulfonyl)-N-[[4-[4-(trifluoromethoxy)phenyl]-2-pyridyl]methyl]pyrrolidine-2-carboxamide |
| 154 | 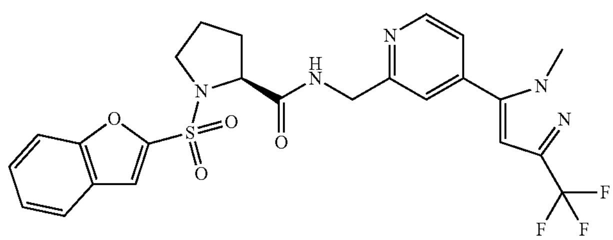 [SMILES: CN/C(=C\C(=N)C(F)(F)F)c1ccnc(CNC(=O)[C@@H]2CCCN2S(=O)(=O)c2cc3ccccc3o2)c1] | (2S)-1-(benzofuran-2-ylsulfonyl)-N-[[4-[2-methyl-5-(trifluoromethyl)pyrazol-3-yl]-2-pyridyl]methyl]pyrrolidine-2-carboxamide |
| 155 | 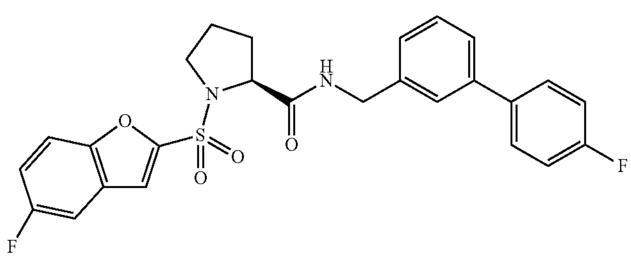 [SMILES: O=C(NCc1cccc(-c2ccc(F)cc2)c1)[C@@H]1CCCN1S(=O)(=O)c1cc2cc(F)ccc2o1] | (2S)-1-(5-fluorobenzofuran-2-yl)sulfonyl-N-[[3-(4-fluorophenyl)phenyl]methyl]-pyrrolidine-2-carboxamide |
| 156 | 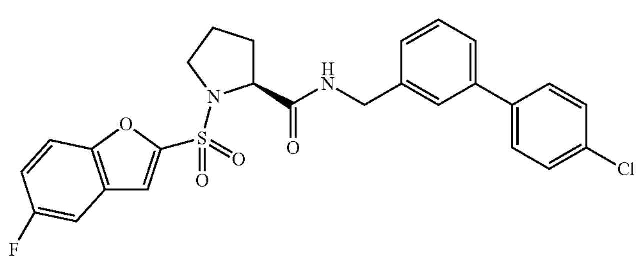 [SMILES: O=C(NCc1cccc(-c2ccc(Cl)cc2)c1)[C@@H]1CCCN1S(=O)(=O)c1cc2cc(F)ccc2o1] | (2S)-N-[[3-(4-chlorophenyl)phenyl]methyl]-1-(5-fluorobenzofuran-2-yl)sulfonyl-pyrrolidine-2-carboxamide |

TABLE 22-continued

| Ex. No. | structure | compound name |
|---|---|---|
| 157 | 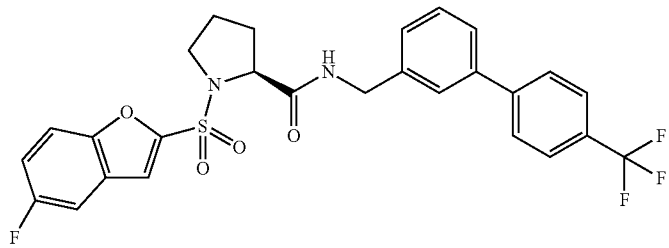 [SMILES: O=C(NCc1cccc(-c2ccc(C(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[3-[4-(trifluoromethyl)phenyl]-phenyl]methyl]pyrrolidine-2-carboxamide |
| 158 | 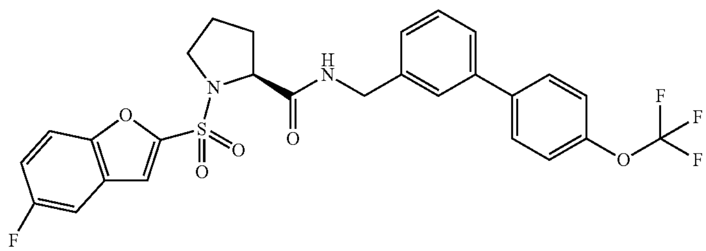 [SMILES: O=C(NCc1cccc(-c2ccc(OC(F)(F)F)cc2)c1)[C@@H]1CCCN1S(=O)(=O)c1cc2cc(F)ccc2o1] | (2S)-1-(5-fluorobenzofuran-2-yl)sulfonyl-N-[[3-[4-(trifluoromethoxy)phenyl]-phenyl]methyl]pyrrolidine-2-carboxamide |
| 159 | 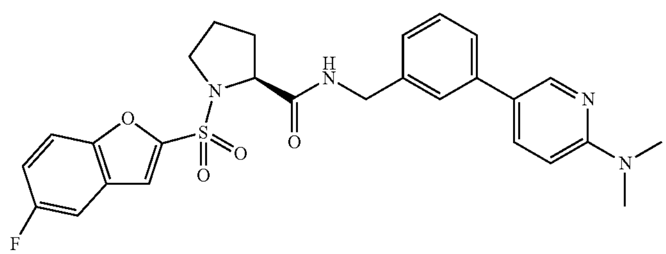 [SMILES: CN(C)c1ccc(-c2cccc(CNC(=O)[C@@H]3CCCN3S(=O)(=O)c3cc4cc(F)ccc4o3)c2)cn1] | (2S)-N-[[3-[6-(dimethylamino)-3-pyridyl]phenyl]methyl]-1-(5-fluorobenzofuran-2-yl)sulfonyl-pyrrolidine-2-carboxamide |
| 160 | 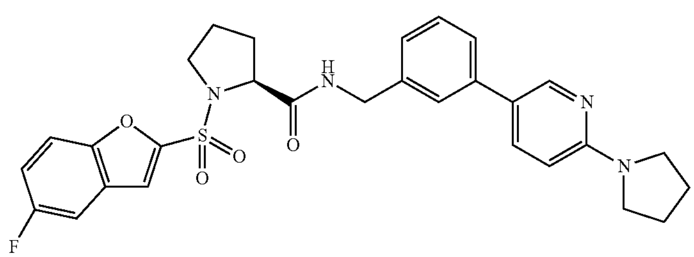 [SMILES: O=C(NCc1cccc(-c2ccc(N3CCCC3)nc2)c1)[C@@H]1CCCN1S(=O)(=O)c1cc2cc(F)ccc2o1] | (2S)-1-(5-fluorobenzofuran-2-yl)sulfonyl-N-[[3-(6-pyrrolidin-1-yl-3-pyridyl)phenyl]methyl]-pyrrolidine-2-carboxamide |
| 161 | 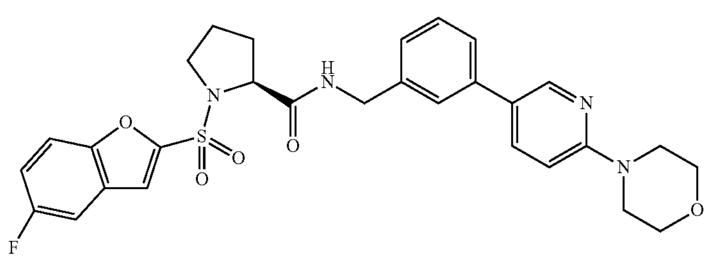 [SMILES: O=C(NCc1cccc(-c2ccc(N3CCOCC3)nc2)c1)[C@@H]1CCCN1S(=O)(=O)c1cc2cc(F)ccc2o1] | (2S)-1-(5-fluorobenzofuran-2-yl)sulfonyl-N-[[3-(6-morpholino-3-pyridyl)phenyl]methyl]-pyrrolidine-2-carboxamide |
| 162 | 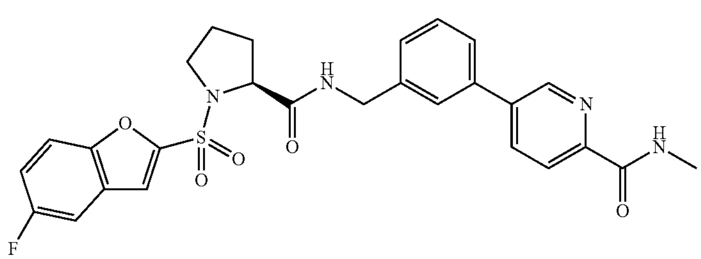 [SMILES: CNC(=O)c1ccc(-c2cccc(CNC(=O)[C@@H]3CCCN3S(=O)(=O)c3cc4cc(F)ccc4o3)c2)cn1] | 5-[3-[[[(2S)-1-(5-fluorobenzofuran-2-yl)sulfonylpyrrolidine-2-carbonyl]amino]methyl]phenyl]-N-methyl-pyridine-2-carboxamide |

TABLE 22-continued

| Ex. No. | structure | compound name |
|---|---|---|
| 163 | 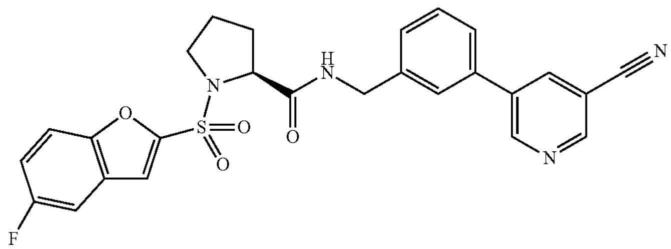 [SMILES: N#Cc1cncc(-c2cccc(CNC(=O)[C@@H]3CCCN3S(=O)(=O)c3cc4cc(F)ccc4o3)c2)c1] | (2S)-N-[[3-(5-cyano-3-pyridyl)phenyl]methyl]-1-(5-fluorobenzofuran-2-yl)sulfonyl-pyrrolidine-2-carboxamide |
| 164 | 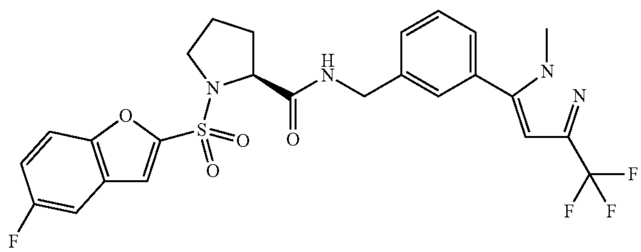 [SMILES: CN/C(=C\C(=N)C(F)(F)F)c1cccc(CNC(=O)[C@@H]2CCCN2S(=O)(=O)c2cc3cc(F)ccc3o2)c1] | (2S)-1-(5-fluorobenzofuran-2-yl)sulfonyl-N-[[3-[2-methyl-5-(trifluoromethyl)pyrazol-3-yl]phenyl]methyl]pyrrolidine-2-carboxamide |
| 165 | 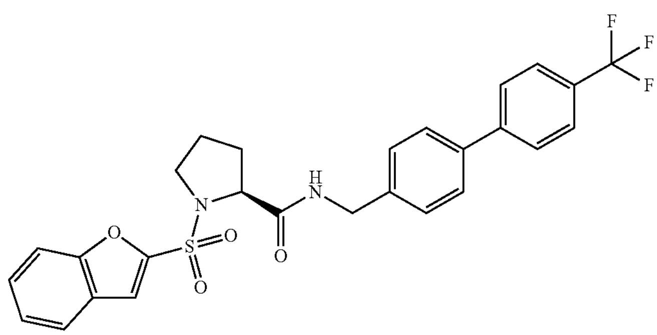 [SMILES: O=C(NCc1ccc(-c2ccc(C(F)(F)F)cc2)cc1)[C@@H]1CCCN1S(=O)(=O)c1cc2ccccc2o1] | (2S)-1-(benzofuran-2-ylsulfonyl)-N-[[4-[4-(trifluoromethyl)phenyl]-phenyl]methyl]pyrrolidine-2-carboxamide |
| 166 | 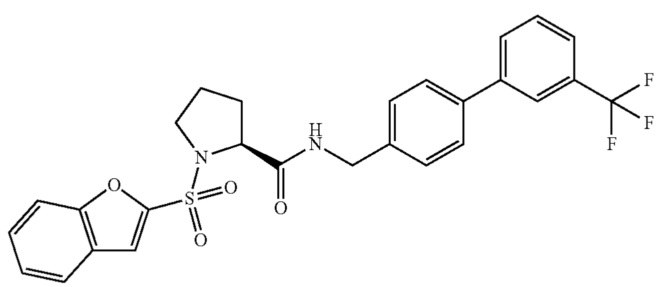 [SMILES: O=C(NCc1ccc(-c2cccc(C(F)(F)F)c2)cc1)[C@@H]1CCCN1S(=O)(=O)c1cc2ccccc2o1] | (2S)-1-(benzofuran-2-ylsulfonyl)-N-[[4-[3-(trifluoromethyl)phenyl]-phenyl]methyl]pyrrolidine-2-carboxamide |
| 167 | 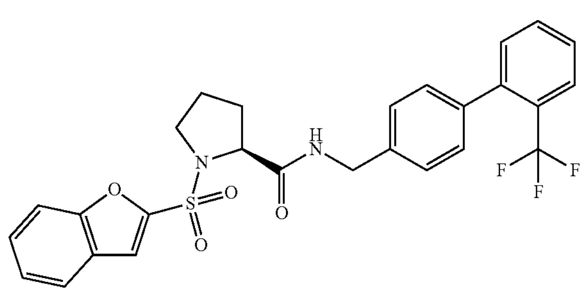 [SMILES: O=C(NCc1ccc(-c2ccccc2C(F)(F)F)cc1)[C@@H]1CCCN1S(=O)(=O)c1cc2ccccc2o1] | (2S)-1-(benzofuran-2-ylsulfonyl)-N-[[4-[2-(trifluoromethyl)phenyl]-phenyl]methyl]pyrrolidine-2-carboxamide |

TABLE 22-continued

| Ex. No. | structure | compound name |
|---|---|---|
| 168 | 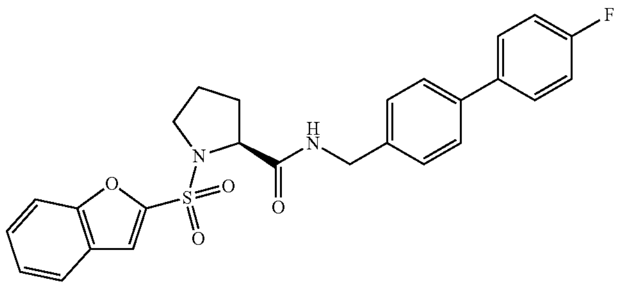 [SMILES: O=C(NCc1ccc(-c2ccc(F)cc2)cc1)[C@@H]1CCCN1S(=O)(=O)c1cc2ccccc2o1] | (2S)-1-(benzofuran-2-ylsulfonyl)-N-[[4-(4-fluorophenyl)phenyl]methyl]-pyrrolidine-2-carboxamide |
| 169 | 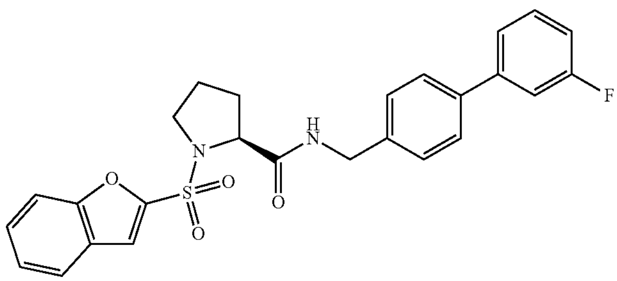 [SMILES: O=C(NCc1ccc(-c2cccc(F)c2)cc1)[C@@H]1CCCN1S(=O)(=O)c1cc2ccccc2o1] | (2S)-1-(benzofuran-2-ylsulfonyl)-N-[[4-(3-fluorophenyl)phenyl]methyl]-pyrrolidine-2-carboxamide |
| 170 | 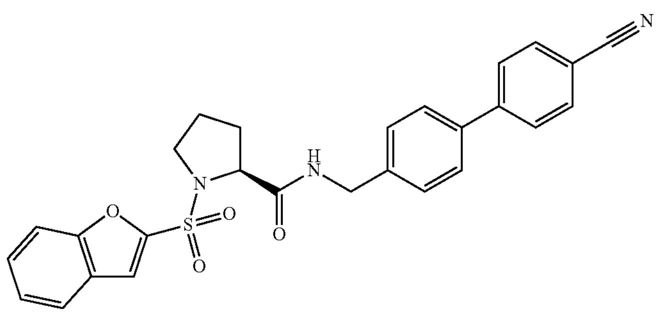 [SMILES: N#Cc1ccc(-c2ccc(CNC(=O)[C@@H]3CCCN3S(=O)(=O)c3cc4ccccc4o3)cc2)cc1] | (2S)-1-(benzofuran-2-ylsulfonyl)-N-[[4-(4-cyanophenyl)phenyl]methyl]-pyrrolidine-2-carboxamide |
| 171 | 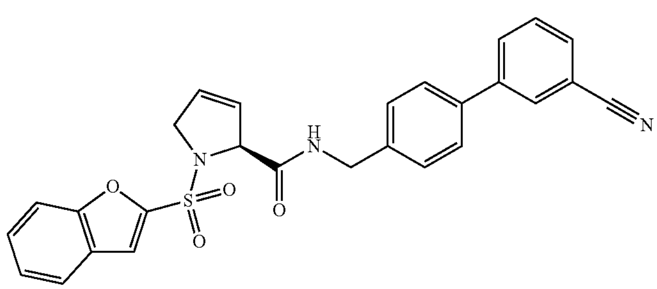 [SMILES: N#Cc1cccc(-c2ccc(CNC(=O)[C@@H]3C=CCN3S(=O)(=O)c3cc4ccccc4o3)cc2)c1] | (2S)-1-(benzofuran-2-ylsulfonyl)-N-[[4-(3-cyanophenyl)phenyl]methyl]-pyrrolidine-2-carboxamide |
| 172 | 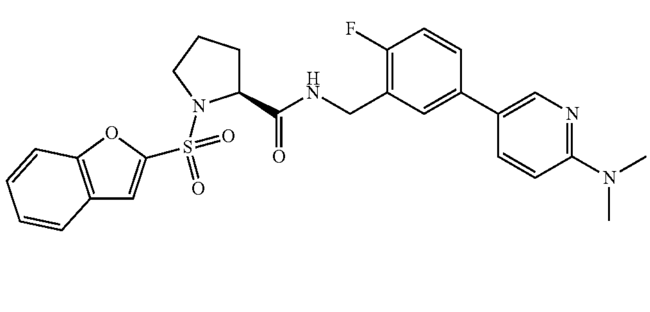 [SMILES: CN(C)c1ccc(-c2ccc(F)c(CNC(=O)[C@@H]3CCCN3S(=O)(=O)c3cc4ccccc4o3)c2)cn1] | (2S)-1-(benzofuran-2-ylsulfonyl)-N-[[5-[6-(dimethylamino)-3-pyridyl]-2-fluoro-phenyl]methyl]pyrrolidine-2-carboxamide |

TABLE 22-continued

| Ex. No. | structure | compound name |
|---|---|---|
| 173 | 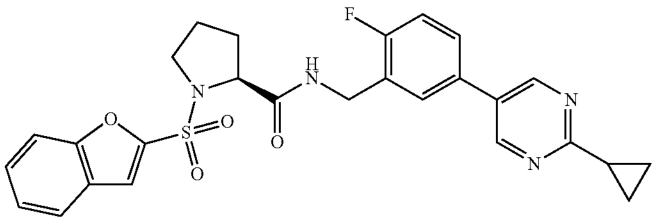 [SMILES: O=C(NCc1cc(-c2cnc(C3CC3)nc2)ccc1F)[C@@H]1CCCN1S(=O)(=O)c1cc2ccccc2o1] | (2S)-1-(benzofuran-2-ylsulfonyl)-N-[[5-(2-cyclopropylpyrimidin-5-yl)-2-fluoro-phenyl]methyl]pyrrolidine-2-carboxamide |
| 174 | 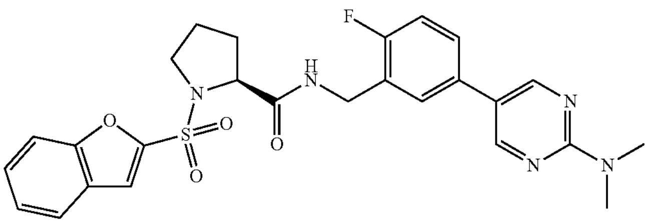 [SMILES: CN(C)c1ncc(-c2ccc(F)c(CNC(=O)[C@@H]3CCCN3S(=O)(=O)c3cc4ccccc4o3)c2)cn1] | (2S)-1-(benzofuran-2-ylsulfonyl)-N-[[5-[2-(dimethylamino)pyrimidin-5-yl]-2-fluoro-phenyl]methyl]pyrrolidine-2-carboxamide |
| 175 | 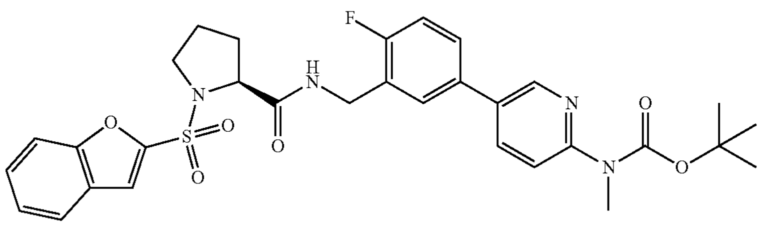 [SMILES: CN(C(=O)OC(C)(C)C)c1ccc(-c2ccc(F)c(CNC(=O)[C@@H]3CCCN3S(=O)(=O)c3cc4ccccc4o3)c2)cn1] | tert-butyl N-[5-[3-[[[(2S)-1-benzofuran-2-ylsulfonyl)pyrrolidine-2-carbonyl]amino]methyl]-4-fluoro-phenyl]-2-pyridyl]-N-methylcarbamate |

Example 176

Synthesis of (2S)-1-(benzofuran-2-ylsulfonyl)-N-[[2-(1H-indol-2-yl)-4-pyridyl]methyl]pyrrolidine-2-carboxamide (176)

To C-4 (21 mg, 0.050 mmol), N-Boc-indole-2-boronic acid (26 mg, 0.10 mmol) and 1,1'-bis(diphenylphosphino)ferrocenedichloropalladium(II) (4 mg, 0.005 mmol) were added 1,4-dioxane (0.8 mL) and 1 mol/L aqueous sodium carbonate solution (0.8 mL) and the mixture was stirred with heating by using a microwave reactor at 100° C. for 10 min. To the reaction mixture was added trifluoroacetic acid (3 mL), and the mixture was stirred at room temperature overnight, concentrated under reduced pressure and the obtained residue was purified by high performance liquid chromatography (water-acetonitrile, each containing 0.1% trifluoroacetic acid) to give trifluoroacetate of the title compound (19 mg, 0.031 mmol, 61%).

MS (ESI) m/z 501 (M+H)$^+$ $^1$H NMR (400 MHz, DMSO-d$_6$) δ 11.67 (s, 1H), 8.87 (t, J=6.0 Hz, 1H), 8.57 (dd, J=5.1, 0.8 Hz, 1H), 7.91 (s, 1H), 7.87-7.82 (m, 1H), 7.80-7.74 (m, 2H), 7.60-7.53 (m, 2H), 7.48-7.40 (m, 2H), 7.26-7.20 (m, 1H), 7.16-7.08 (m, 2H), 6.99 (ddd, J=8.0, 7.0, 1.0 Hz, 1H), 4.52-4.33 (m, 3H), 3.68-3.60 (m, 1H), 3.47-3.38 (m, 1H), 2.04-1.86 (m, 3H), 1.73-1.62 (m, 1H).

Example 177 described in Table 23 was synthesized by using the compounds described in Reference Examples and corresponding commercially available reagents and by an operation similar to that in Example 176.

TABLE 23

| Example No. | structure | compound name |
|---|---|---|
| 176 | 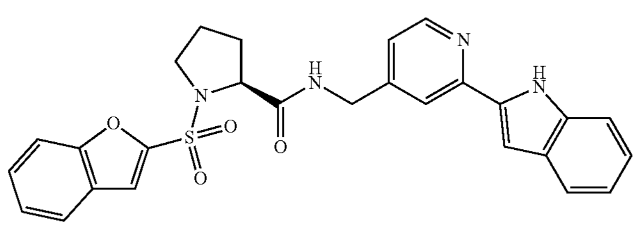 [SMILES: O=C(NCc1ccnc(-c2cc3ccccc3[nH]2)c1)[C@@H]1CCCN1S(=O)(=O)c1cc2ccccc2o1] | (2S)-1-(benzofuran-2-ylsulfonyl)-N-[[2-(1H-indol-2-yl)-4-pyridyl]methyl]pyrrolidine-2-carboxamide |

TABLE 23-continued

| Example No. | structure | compound name |
|---|---|---|
| 177 | 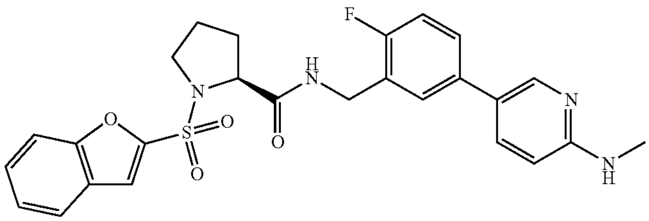 [SMILES: CNc1ccc(-c2ccc(F)c(CNC(=O)[C@@H]3CCCN3S(=O)(=O)c3cc4ccccc4o3)c2)cn1] | (2S)-1-(benzofuran-2-ylsulfonyl)-N-[[2-fluoro-5-[6-(methylamino)-3-pyridyl]phenyl]methyl]pyrrolidine-2-carboxamide |

Example 178

Synthesis of (2S)-1-(benzofuran-2-ylsulfonyl)-N-[[2-[5-(trifluoromethyl)-2-pyridyl]-4-pyridyl]methyl]pyrrolidine-2-carboxamide (178)

To C-5 (42 mg, 0.10 mmol), E-4 (30 mg, 0.10 mmol) and tris(dibenzylideneacetone)dipalladium(0) (1.4 mg, 0.0015 mol) and 2-dicyclohexylphosphino-2',4',6'-triisopropylbiphenyl (2.9 mg, 0.006 mmol), copper acetate (9.1 mg, 0.05 mmol), potassium carbonate (69 mg, 0.5 mmol) were added N,N-dimethylformamide (0.8 mL) and 2-propanol (0.2 mL) and the mixture was stirred with heating by using a microwave reactor at 130° C. for 20 min. The reaction mixture was concentrated under reduced pressure and the obtained residue was purified by high performance liquid chromatography (water-acetonitrile, each containing 0.1% trifluoroacetic acid) to give trifluoroacetate of the title compound (15 mg, 0.028 mmol, 28%). MS (ESI) m/z 531 (M+H)$^+$ Example 179

Synthesis of (2S)-1-(benzofuran-2-ylsulfonyl)-N-[[4-[5-(trifluoromethyl)-2-pyridyl]-2-pyridyl]methyl]pyrrolidine-2-carboxamide (179)

To C-9 (42 mg, 0.10 mmol), E-4 (30 mg, 0.10 mmol) and tris(dibenzylideneacetone)dipalladium(0) (1.4 mg, 0.0015 mmol) and 2-dicyclohexylphosphino-2',4',6'-triisopropylbiphenyl (2.9 mg, 0.006 mmol), copper acetate (9.1 mg, 0.05 mmol), potassium carbonate (69 mg, 0.5 mmol) were added N,N-dimethylformamide (0.8 mL) and 2-propanol (0.2 mL) and the mixture was stirred with heating by using a microwave reactor at 130° C. for 20 min. The reaction mixture was concentrated under reduced pressure and the obtained residue was purified by high performance liquid chromatography (water-acetonitrile, each containing 0.1% trifluoroacetic acid) to give trifluoroacetate of the title compound (10 mg, 0.019 mmol, 19%).

MS (ESI) m/z 531 (M+H)$^+$ $^1$H NMR (400 MHz, DMSO-ds) δ 9.12 (d, J=2.4 Hz, 1H), 8.89 (dd, J=6.1, 5.9 Hz, 1H), 8.73 (d, J=5.1 Hz, 1H), 8.41 (dd, J=8.5, 2.4 Hz, 1H), 8.32 (d, J=8.5 Hz, 1H), 8.11-8.02 (m, 2H), 7.83 (dd, J=7.7, 1.1 Hz, 1H), 7.79-7.71 (m, 2H), 7.56 (ddd, J=8.6, 7.4, 1.4 Hz, 1H), 7.42 (ddd, J=7.7, 7.4, 0.8 Hz, 1H), 4.57 (dd, J=16.3, 6.1 Hz, 1H), 4.50 (dd, J=16.3, 5.9 Hz, 1H), 4.38 (dd, J=7.4, 4.1 Hz, 1H), 3.68-3.58 (m, 1H), 3.43-3.38 (m, 1H), 2.03-1.88 (m, 3H), 1.75-1.62 (m, 1H).

TABLE 24

| Example No. | structure | compound name |
|---|---|---|
| 178 | 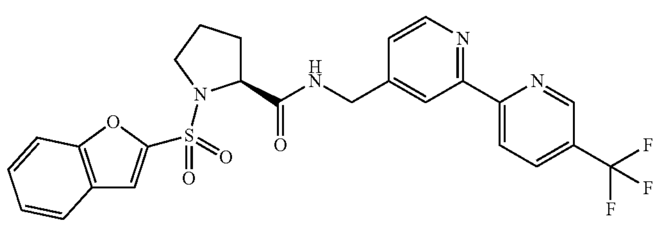 | (2S)-1-(benzofuran-2-ylsulfonyl)-N-[[2-[5-(trifluoromethyl)-2-pyridyl]-4-pyridyl]methyl]pyrrolidine-2-carboxamide |
| 179 | 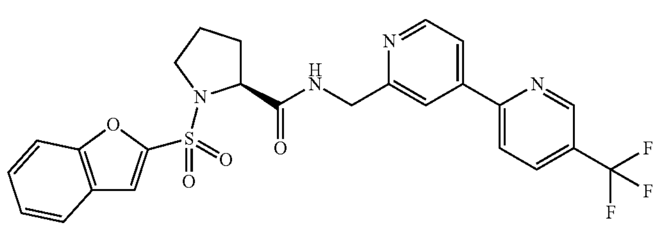 | (2S)-1-(benzofuran-2-ylsulfonyl)-N-[[4-[5-(trifluoromethyl)-2-pyridyl]-2-pyridyl]methyl]pyrrolidine-2-carboxamide |

Example 180

Synthesis of (2S)-2-(benzofuran-2-ylsulfonylamino)-N-[[2-[2-hydroxy-4-(trifluoromethyl)phenyl]-4-pyridyl]methyl]propanamide (180)

(step 1) Synthesis of 2-[2-hydroxy-4-(trifluoromethyl)phenyl]pyridine-4-carbonitrile To 2-chloro-4-cyanopyridine (69 mg, 0.50 mmol), 2-hydroxy-4-trifluoromethylphenylboronic acid (0.10 g, 0.50 mmol) and 1,1'-bis(diphenylphosphino)ferrocenedichloropalladium(II) (37 mg, 0.050 mmol) were added 1,4-dioxane (1 mL) and 1 mol/L aqueous sodium carbonate solution (1 mL) and the mixture was stirred with heating by using a microwave reactor at 120° C. for 20 min. The reaction mixture was neutralized with trifluoroacetic acid (0.2 mL), and purified by high performance liquid chromatography (water-acetonitrile, each containing 0.1% trifluoroacetic acid) to give the title compound (66 mg, 0.25 mmol, 50%)

MS (ESI) m/z 265 (M+H)$^+$ (step 2) Synthesis of 2-[4-(aminomethyl)-2-pyridyl]-5-(trifluoromethyl)phenol The compound (66 mg, 0.25 mmol) obtained in step 1 was dissolved in ethanol (10 mL), and the mixture was reduced by using a Flow Hydrogenation apparatus (H-cube, manufactured by ThalesNano Nanotechnology) under the conditions of 10% Pd/C (30 mm), 65° C., 50 bar, flow rate 1 mL/min. The reaction mixture was concentrated under reduced pressure to give the title compound (45 mg, 0.17 mmol, 67%).

MS (ESI) m/z 269 (M+H)$^+$ (step 3) Synthesis of (2S)-2-(benzofuran-2-ylsulfonylamino)-N-[[2-[2-hydroxy-4-(trifluoromethyl)phenyl]-4-pyridyl]methyl]propanamide(180)

Using the compound obtained in step 2 instead of D-1, and by an operation similar to that in Example 37, trifluoroacetate of the title compound (yield 60%) was obtained.

MS (ESI) m/z 520 (M+H)$^+$ $^1$H NMR (400 MHz, DMSO-d$_6$) δ 14.47 (s, 1H), 8.87 (d, J=7.9 Hz, 1H), 8.73 (dd, J=6.0, 5.9 Hz, 1H), 8.57 (dd, J=5.3, 0.7 Hz, 1H), 8.21-8.15 (m, 1H) 8.11 (s, 1H), 7.76 (ddd, J=7.9, 1.3, 0.9 Hz, 1H), 7.66 (dd, J=8.5, 0.9 Hz, 1H), 7.54 (d, J=0.9 Hz, 1H), 7.50 (ddd, J=8.5, 7.3, 1.3 Hz, 1H), 7.37 (ddd, J=7.9, 7.3, 0.9 Hz, 1H), 7.30 (dd, J=5.3, 1.4 Hz, 1H), 7.27-7.21 (m, 2H), 4.39 (dd, J=16.6, 6.0 Hz, 1H), 4.33 (dd, J=16.6, 5.9 Hz, 1H), 4.07 (dq, J=7.9, 7.1 Hz, 1H), 1.24 (d, J=7.1 Hz, 3H).

Example 181 described in Table 25 was synthesized by using the compounds described in Reference Examples and corresponding commercially available reagents and by an operation similar to that in Example 180.

TABLE 25

| Example No. | structure | compound name |
|---|---|---|
| 180 | 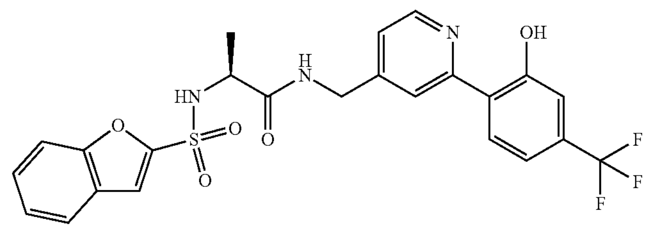 [SMILES: C[C@H](NS(=O)(=O)c1cc2ccccc2o1)C(=O)NCc1ccnc(-c2ccc(C(F)(F)F)cc2O)c1] | (2S)-2-(benzofuran-2-ylsulfonylamino)-N-[[2-[2-hydroxy-4-(trifluoromethyl)phenyl]-4-pyridyl]methyl]propanamide |
| 181 | 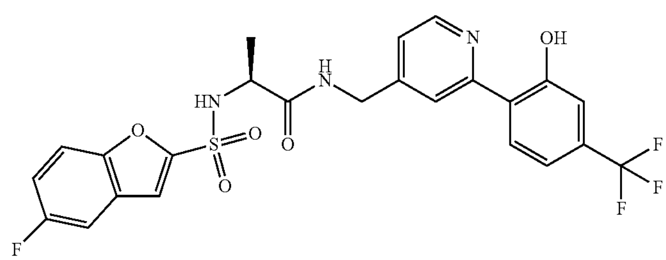 [SMILES: C[C@H](NS(=O)(=O)c1cc2cc(F)ccc2o1)C(=O)NCc1ccnc(-c2ccc(C(F)(F)F)cc2O)c1] | (2S)-2-[(5-fluorobenzofuran-2-yl)sulfonylamino)-N-[[2-[2-hydroxy-4-(trifluoromethyl)phenyl]-4-pyridyl]methyl]propanamide |

Example 182

Synthesis of (2S)-2-(benzofuran-2-ylsulfonylamino)-N-[[3-[(4-cyanophenyl)methoxy]phenyl]methyl]propanamide (182)

To a solution of tert-butyl N-[(3-hydroxyphenyl)methyl]carbamate (50 mg, 0.22 mmol), 4-hydroxybenzonitrile (45 mg, 0.34 mmol) in dichloromethane (2 mL) were added triphenylphosphine (117 mg, 0.44 mmol) and diisopropyl azodicarboxylate (0.088 mL, 0.44 mmol), and the mixture was stirred at room temperature overnight. To the reaction mixture was added trifluoroacetic acid (2 mL) and the mixture was stirred at room temperature overnight, and neutralized with 2 mol/L aqueous sodium hydroxide solution. The mixture was extracted with dichloromethane. The organic layer was dried over sodium sulfate. The desiccant was filtered off, and the solvent was evaporated to give 4-[[3-(aminomethyl)phenoxy]methyl]benzonitrile as a crude product (0.22 g).

To the obtained 4-[[3-(aminomethyl)phenoxy]methyl]benzonitrile as a crude product (0.11 g), B-15 (27 mg, 0.10 mmol), WSC hydrochloride (23 mg, 0.12 mmol) and 1-hydroxy-7-azabenzotriazole (14 mg, 0.10 mmol) were added dichloromethane (2 mL) and triethylamine (0.021 mL, 0.15 mmol) and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (49 mg, 0.10 mmol, 100%).

MS (ESI) m/z 490 (M+H)⁺

$^1$H NMR (400 MHz, DMSO-$d_6$) δ 8.74 (d, J=8.3 Hz, 1H), 8.44 (t, J=5.9 Hz, 1H), 7.86 (d, J=8.2 Hz, 2H), 7.77 (ddd, J=7.9, 1.3, 0.9 Hz, 1H), 7.66 (dd, J=8.4, 0.9 Hz, 1H), 7.62 (d, J=8.2 Hz, 2H), 7.51 (ddd, J=8.4, 7.3, 1.3 Hz, 1H), 7.49 (d, J=0.9 Hz, 1H), 7.38 (ddd, J=7.9, 7.3, 0.9 Hz, 1H), 7.19 (ddd, J=7.4, 7.3, 1.3 Hz, 1H), 6.90-6.83 (m, 2H), 6.77-6.71 (m, 1H), 5.19 (s, 2H), 4.11 (d, J=5.9 Hz, 2H), 4.02 (dq, J=8.3, 7.0 Hz 1H), 1.18 (d, J=7.0 Hz, 3H).

Example 183 to Example 185 described in Table 26 were synthesized by using the compounds described in Reference Examples and corresponding commercially available reagents and by an operation similar to that in Example 182.

Example 186

Synthesis of (2S)-1-(benzofuran-2-ylsulfonyl)-N-[[2-[[4-(trifluoromethyl)phenyl]methylamino]-4-pyridyl]methyl]pyrrolidine-2-carboxamide (186)

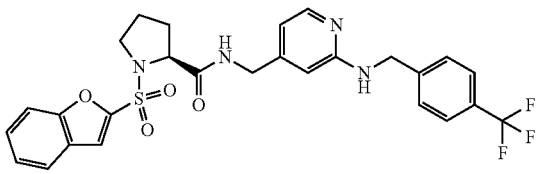

To tris(dibenzylideneacetone)dipalladium(0) (5.5 mg, 0.0060 mmol) and (±)-2,2'-bis(diphenylphosphino)-1,1'-binaphthyl (7.4 mg, 0.012 mmol) was added toluene (2 mL), and argon gas was blown against the mixture for 20 min. C-4 (50 mg, 0.12 mmol), 4-(trifluoromethyl)benzylamine (0.034 mL, 0.24 mmol) and sodium tert-butoxide (22 mg, 0.23

TABLE 26

| Example No. | structure | compound name |
| --- | --- | --- |
| 182 | 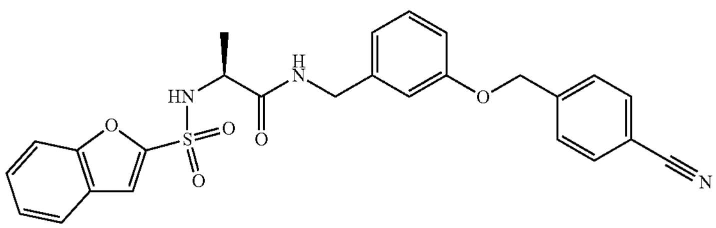 [SMILES: C[C@H](NS(=O)(=O)c1cc2ccccc2o1)C(=O)NCc1cccc(OCc2ccc(C#N)cc2)c1] | (2S)-2-(benzofuran-2-ylsulfonylamino)-N-[[3-[(4-cyanophenyl)methoxy]phenyl]methyl]propanamide |
| 183 | 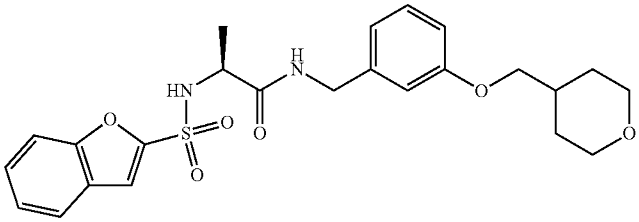 [SMILES: C[C@H](NS(=O)(=O)c1cc2ccccc2o1)C(=O)NCc1cccc(OCC2CCOCC2)c1] | (2S)-2-(benzofuran-2-ylsulfonylamino)-N-[[3-(tetrahydropyran-4-ylmethoxy)phenyl]methyl]propanamide |
| 184 | 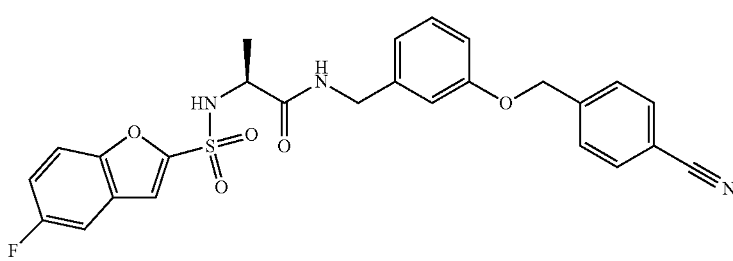 [SMILES: C[C@H](NS(=O)(=O)c1cc2cc(F)ccc2o1)C(=O)NCc1cccc(OCc2ccc(C#N)cc2)c1] | (2S)-N-[[3-[(4-cyanophenyl)methoxy]phenyl]methyl]-2-[(5-fluorobenzofuran-2-yl)sulfonylamino]propanamide |
| 185 | | (2S)-2-[(5-fluorobenzofuran-2-yl)sulfonylamino]-N-[[3-(tetrahydropyran-4-ylmethoxy)phenyl]methyl]propanamide | mmol) were added and sealed tube, and the mixture was stirred at 90° C. overnight. To the reaction mixture was added ethyl acetate, and the mixture was washed with water. The organic layer was dried over sodium sulfate. The desiccant was filtered off, and the solvent was evaporated and the obtained residue was purified by high performance liquid chromatography (water-acetonitrile, each containing 0.1% trifluoroacetic acid) to give trifluoroacetate of the title compound (2.6 mg, 0.0039 mmol, 3%).

MS (ESI) m/z 559 (M+H)$^+$

Example 187

Synthesis of (2S)-1-(benzofuran-2-ylsulfonyl)-N-[[3-[[4-(trifluoromethyl)phenyl]methoxy]phenyl]methyl]-3,6-dihydro-2H-pyridine-2-carboxamide (187)

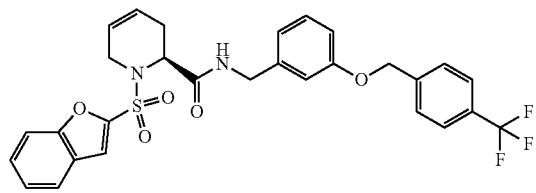 [SMILES: O=C(NCc1cccc(OCc2ccc(C(F)(F)F)cc2)c1)[C@@H]1CC=CCN1S(=O)(=O)c1cc2ccccc2o1]

(step 1) Synthesis of (2S)—N-[(3-{[4-(trifluoromethyl)phenyl]methoxy}phenyl)methyl]-1,2,3,6-tetrahydropyridine-2-carboxamide hydrochloride Dichloromethane (2 mL) was added to suspend (S)—N-Boc-1,2,3,6-tetrahydro-2-pyridinecarboxylic acid (0.10 g, 0.44 mmol), D-2 (0.15 g, 0.46 mmol), WSC hydrochloride (0.10 g, 0.53 mmol) and 1-hydroxy-7-azabenzotriazole (60 mg, 0.44 mmol), triethylamine (0.092 mL, 0.66 mmol) was added, and the mixture was stirred at room temperature overnight. To the reaction mixture was added ethyl acetate, and the mixture was washed successively with 0.5 mol/L aqueous hydrochloric acid solution, saturated aqueous sodium hydrogen carbonate and saturated brine. The organic layer was dried over sodium sulfate. The desiccant was filtered off, and the solvent was evaporated. To the obtained residue was added 4 mol/L hydrochloric acid/1,4-dioxane solution (3 mL) and the mixture was stirred at room temperature for 5 hr. The solvent was evaporated to give the title compound (0.19 g, 0.44 mmol, 99%).

MS (ESI) m/z 391 (M+H)$^+$ (step 2) Synthesis of (2S)-1-(benzofuran-2-ylsulfonyl)-N-[[3-[[4-(trifluoromethyl)phenyl]methoxy]phenyl]methyl]-3,6-dihydro-2H-pyridine-2-carboxamide (187)

To the compound (40 mg, 0.094 mmol) obtained in step 1 and benzofuran-2-ylsulfonylchloride (22 mg, 0.11 mmol) were added acetonitrile (1 mL) and triethylamine (0.033 mL, 0.23 mmol) and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (27 mg, 0.047 mmol, 50%).

MS (ESI) m/z 571 (M+H)$^+$ $^1$H NMR (400 MHz, DMSO-d$_6$) δ 8.52 (t, J=6.0 Hz, 1H), 7.82-7.72 (m, 3H), 7.70-7.57 (m, 4H), 7.50 (ddd, J=8.5, 7.2, 1.4 Hz, 1H), 7.42-7.33 (m, 1H), 7.24 (dd, J=7.9, 7.9 Hz, 1H), 6.94-6.82 (m, 2H), 6.77 (d, J=7.6 Hz, 1H), 5.74-5.61 (m, 2H), 5.20 (s, 2H), 4.75 (dd, J=6.8, 1.6 Hz, 1H), 4.23-3.98 (m, 4H), 2.47-2.29 (m, 2H).

Example 188

Synthesis of (2S)-1-(benzofuran-2-ylsulfonyl)-N-[(3-benzylsulfinylphenyl)methyl]pyrrolidine-2-carboxamide (188)

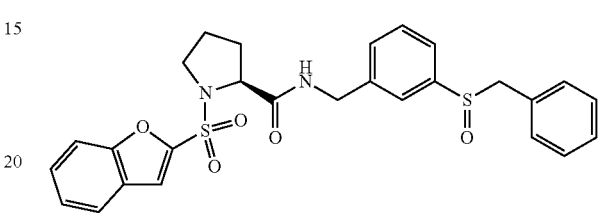

To a solution of (2S)-1-(benzofuran-2-ylsulfonyl)-N-[(3-benzylsulfanylphenyl)methyl]pyrrolidine-2-carboxamide (57) (16 mg, 0.032 mmol) in dichloromethane (1 mL) was added 3-chloroperbenzoic acid (7.6 mg, 0.044 mmol) and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (9.6 mg, 0.018 mmol, 57%).

MS (ESI) m/z 523 (M+H)$^+$ $^1$H NMR (400 MHz, DMSO-d$_6$) δ 8.77 (ddd, J=6.2, 6.0, 1.8 Hz, 1H), 7.84 (d, J=7.9 Hz, 1H), 7.79-7.71 (m, 2H), 7.61-7.33 (m, 6H), 7.33-7.23 (m, 3H), 7.16-7.08 (m, 2H), 4.41-4.34 (m, 2H), 4.31 (ddd, J=8.2, 3.8, 2.2 Hz, 1H), 4.23 (dd, J=12.7, 1.6 Hz, 1H), 4.02 (dd, J=12.7, 5.0 Hz, 1H), 3.61 (ddd, J=10.1, 7.0, 5.3 Hz, 1H), 3.45-3.39 (m, 1H), 2.01-1.82 (m, 3H), 1.71-1.58 (m, 1H).

Example 189

Synthesis of (2S)-3-tert-butoxy-2-[(5-fluorobenzofuran-2-yl) sulfonylamino]-N-[[3-[6-trifluoromethyl-3-pyridyl]phenyl]methyl]propanamide (189)

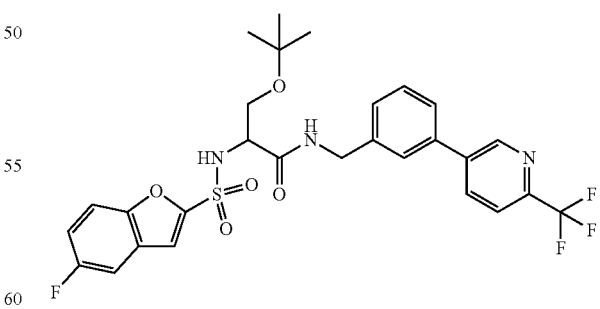

(step 1) Synthesis of (2S)-3-tert-butoxy-2-[(5-fluorobenzofuran-2-yl)sulfonylamino]propanoic acid To A-3 (0.23 g, 1.0 mmol) and O-tert-butyl-L-serine methyl ester hydrochloride (0.21 g, 1.0 mmol) were added acetonitrile (5 mL) and triethylamine (0.30 mL, 2.2 mmol) and the mixture was stirred at room temperature overnight. The reaction mixture was concentrated under reduced pressure. To the obtained residue was added ethyl acetate, and the mixture was washed with water. The organic layer was dried over sodium sulfate, and the desiccant was filtered off. The solvent was evaporated. To the obtained residue were added tetrahydrofuran (5 mL), methanol (0.5 mL) and 1 mol/L aqueous sodium hydroxide solution (1.2 mL, 1.2 mmol), and the mixture was stirred at room temperature for 2 hr. To the reaction mixture was added 2 mol/L aqueous sodium hydroxide solution (0.5 mL) and the mixture was further stirred at room temperature overnight. To the reaction mixture was added 1 mol/L aqueous hydrochloric acid solution (4 mL), and the mixture was extracted with dichloromethane. The organic layer was dried over sodium sulfate, and the desiccant was filtered off. The solvent was evaporated to give the title compound (0.30 g, 0.84 mmol, 84%).

MS (ESI) m/z 360 (M+H)$^+$ (step 2) Synthesis of (2S)-3-tert-butoxy-2-[(5-fluorobenzofuran-2-yl)sulfonylamino]-N-[[3-[6-trifluoromethyl-3-pyridyl]phenyl]methyl]propanamide (189)

Using the compound obtained in step 1 and D-9 instead of B-1 and D-1, and by an operation similar to that in Example 37, the title compound was obtained (yield 31%).

MS (ESI) m/z 594 (M+H)$^+$

Example 190

Synthesis of (2S)-2-[(5-fluorobenzofuran-2-yl) sulfonylamino]-N-[[6-[4-(trifluoromethoxy)phenyl]pyrimidin-4-yl]methyl]propanamide (190)

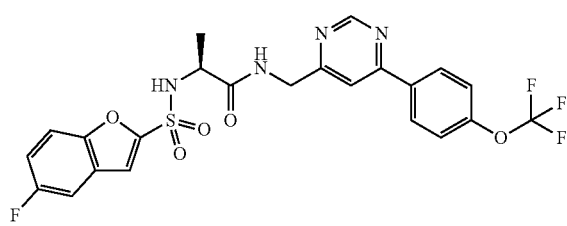 [SMILES: C[C@H](NS(=O)(=O)c1cc2cc(F)ccc2o1)C(=O)NCc1cc(-c2ccc(OC(F)(F)F)cc2)ncn1]

To B-16 (29 mg, 0.10 mmol), D-38 (31 mg, 0.10 mmol), WSC hydrochloride (38 mg, 0.20 mmol) and 1-hydroxy-7-azabenzotriazole (27 mg, 0.20 mmol) were added triethylamine (42 L, 0.30 mmol) and dichloromethane (1 mL), and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (45 mg, 0.084 mmol, 84%).

MS (ESI) m/z 539 (M+H)$^+$ $^1$H NMR (400 MHz, DMSO-d$_6$) δ 9.16 (d, J=1.3 Hz, 1H), 8.94 (brs, 1H), 8.73 (t, J=5.9 Hz, 1H), 8.31-8.24 (m, 2H), 7.87 (d, J=1.3 Hz, 1H), 7.70 (dd, J=9.0, 4.2 Hz, 1H), 7.58-7.48 (m, 4H), 7.34 (td, J=9.2, 2.8 Hz, 1H), 4.42-4.26 (m, 2H), 4.16-4.05 (m, 1H), 1.26 (d, J=7.1 Hz, 3H).

Example 191

Synthesis of (2S)-2-[(5-fluorobenzofuran-2-yl)sulfonylamino]-N-[[6-[6-(trifluoromethyl)-3-pyridyl]pyrimidin-4-yl]methyl]propanamide (191)

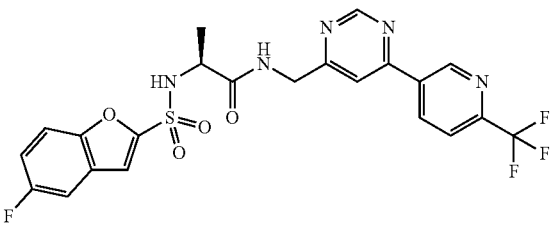 [SMILES: C[C@H](NS(=O)(=O)c1cc2cc(F)ccc2o1)C(=O)NCc1cc(-c2ccc(C(F)(F)F)nc2)ncn1]

To B-16 (29 mg, 0.10 mmol), D-40 (29 mg, 0.10 mmol), WSC hydrochloride (38 mg, 0.20 mmol) and 1-hydroxy-7-azabenzotriazole (27 mg, 0.20 mmol) were added triethylamine (42 µL, 0.30 mmol) and dichloromethane (1 mL), and the mixture was stirred at room temperature for 2 hr. The reaction mixture was concentrated under reduced pressure and the obtained residue was purified by high performance liquid chromatography (water-acetonitrile, each containing 0.1% trifluoroacetic acid) to give the title compound (22 mg, 0.042 mmol, 42%).

MS (ESI) m/z 524 (M+H)$^+$ $^1$H NMR (400 MHz, DMSO-d$_6$) δ 9.45 (d, J=2.1 Hz, 1H), 9.26 (d, J=1.3 Hz, 1H), 8.97 (d, J=7.8 Hz, 1H), 8.83-8.73 (m, 2H), 8.12 (d, J=8.2 Hz, 1H), 8.04 (s, 1H), 7.70 (dd, J=9.1, 4.0 Hz, 1H), 7.56-7.48 (m, 2H), 7.34 (td, J=9.2, 2.8 Hz, 1H), 4.46-4.30 (m, 2H), 4.17-4.06 (m, 1H), 1.27 (d, J=7.1 Hz, 3H).

Example 192

Synthesis of (2S)-1-(benzofuran-2-ylsulfonyl)-N-[[4-[5-(trifluoromethyl)pyrimidin-2-yl]-2-pyridyl]methyl]pyrrolidine-2-carboxamide (192)

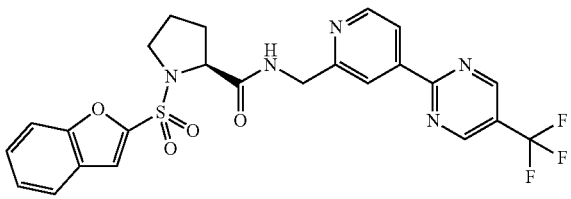 [SMILES: O=C(NCc1cc(-c2ncc(C(F)(F)F)cn2)ccn1)[C@@H]1CCCN1S(=O)(=O)c1cc2ccccc2o1]

To B-1 (30 mg, 0.10 mmol), D-33 (29 mg, 0.10 mmol), WSC hydrochloride (27 mg, 0.12 mmol) and 1-hydroxy-7-azabenzotriazole (14 mg, 0.10 mmol) were added triethylamine (21 µL, 0.15 mmol) and dichloromethane (1 mL), and the mixture was stirred at room temperature for 2 hr. The reaction mixture was concentrated under reduced pressure and the obtained residue was purified by high performance liquid chromatography (water-acetonitrile, each containing 0.1% trifluoroacetic acid) to give trifluoroacetate of the title compound (36 mg, 0.056 mmol, 56%).

MS (ESI) m/z 532 (M+H)$^+$

¹H NMR (400 MHz, DMSO-d₆) δ 9.44 (d, J=0.9 Hz, 2H), 8.89 (t, J=6.0 Hz, 1H), 8.77 (dd, J=5.1, 0.8 Hz, 1H), 8.27 (brs, 1H), 8.20 (dd, J=5.2, 1.6 Hz, 1H), 7.82 (ddd, J=7.8, 1.3, 0.7 Hz, 1H), 7.76 (ddd, J=8.5, 1.3, 0.9 Hz, 1H), 7.73 (d, J=0.9 Hz, 1H), 7.56 (ddd, J=8.5, 7.3, 1.3 Hz, 1H), 7.44-7.39 (m, 1H), 4.53 (d, J=6.0 Hz, 2H), 4.42-4.36 (m, 1H), 3.63-3.58 (m, 1H), 3.46-3.37 (m, 1H), 2.00-1.91 (m, 3H), 1.76-1.63 (m, 1H).

Example 193

Synthesis of (2S)-1-(benzofuran-2-ylsulfonyl)-N-[[4-hydroxy-3-[5-(trifluoromethyl)-2-pyridyl]phenyl]methyl]pyrrolidine-2-carboxamide (193)

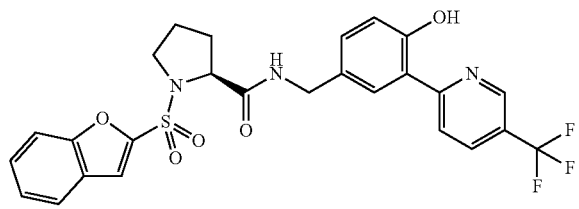 [SMILES: O=C(NCc1ccc(O)c(-c2ccc(C(F)(F)F)cn2)c1)[C@@H]1CCCN1S(=O)(=O)c1cc2ccccc2o1]

To B-1 (30 mg, 0.10 mmol), D-48 (31 mg, 0.10 mmol), WSC hydrochloride (27 mg, 0.12 mmol) and 1-hydroxy-7-azabenzotriazole (14 mg, 0.10 mmol) were added triethylamine (21 μL, 0.15 mmol) and dichloromethane (1 mL), and the mixture was stirred at room temperature for 2 hr. The reaction mixture was concentrated under reduced pressure and the obtained residue was purified by high performance liquid chromatography (water-acetonitrile, each containing 0.1% trifluoroacetic acid) to give the title compound (37 mg, 0.068 mmol, 68%).

MS (ESI) m/z 546 (M+H)⁺

¹H NMR (400 MHz, DMSO-d₆) δ 9.06 (s, 1H), 8.66 (t, J=6.0 Hz, 1H), 8.38-8.35 (m, 2H), 7.96 (d, J=2.1 Hz, 1H), 7.86-7.80 (m, 1H), 7.77-7.71 (m, 2H), 7.55 (ddd, J=8.5, 7.2, 1.3 Hz, 1H), 7.44-7.39 (m, 1H), 7.30 (dd, J=8.4, 2.1 Hz, 1H), 6.96 (d, J=8.4 Hz, 1H), 4.41-4.24 (m, 3H), 3.64-3.56 (m, 1H), 3.47-3.41 (m, 1H), 1.97-1.83 (m, 3H), 1.69-1.59 (m, 1H).

Example 194 to Example 276 described in Table 27 were synthesized by using the compounds described in Reference Examples and corresponding commercially available reagents and by an operation similar to that in Example 37.

TABLE 27

| Example No. | structural formula | compound name |
|---|---|---|
| 194 | | (2S)-1-(benzofuran-2-ylsulfonyl)-N-[[3-[5-(trifluoromethyl)pyrimidin-2-yl]phenyl]methyl]pyrrolidine-2-carboxamide |
| 195 | | (2S)-1-(benzofuran-2-ylsulfonyl)-N-[[3-[2-(trifluoromethyl)pyrimidin-5-yl]phenyl]methyl]pyrrolidine-2-carboxamide |
| 196 | | (2S)-1-(benzofuran-2-ylsulfonyl)-N-[[3-[5-(trifluoromethyl)pyrazin-2-yl]phenyl]methyl]pyrrolidine-2-carboxamide |
| 197 | | (2S)-1-(benzofuran-2-ylsulfonyl)-N-[[3-[6-(trifluoromethyl)pyridazin-3-yl]phenyl]methyl]pyrrolidine-2-carboxamide |

TABLE 27-continued

| Example No. | structural formula | compound name |
|---|---|---|
| 198 | | (2S)-1-(benzofuran-2-ylsulfonyl)-N-[[2-(4-chlorophenyl)-4-pyridyl]methyl]pyrrolidine-2-carboxamide |
| 199 | | (2S)-1-(benzofuran-2-ylsulfonyl)-N-[[2-[2-(trifluoromethyl)pyrimidin-5-yl]-4-pyridyl]methyl]pyrrolidine-2-carboxamide |
| 200 | | (2S)-1-(benzofuran-2-ylsulfonyl)-N-[[4-[2-(trifluoromethyl)pyrimidin-5-yl]-2-pyridyl]methyl]pyrrolidine-2-carboxamide |
| 201 | | (2S)-1-(benzofuran-2-ylsulfonyl)-N-[[4-[5-(trifluoromethyl)pyrazin-2-yl]-2-pyridyl]methyl]pyrrolidine-2-carboxamide |
| 202 | | (2S)-1-(benzofuran-2-ylsulfonyl)-N-[[4-[6-(trifluoromethyl)pyridazin-3-yl]-2-pyridyl]methyl]pyrrolidine-2-carboxamide |
| 203 | | (2S)-1-(benzofuran-2-ylsulfonyl)-N-[[6-[4-(trifluoromethoxy)phenyl]-pyrimidin-4-yl]methyl]pyrrolidine-2-carboxamide |
| 204 | | (2S)-1-(benzofuran-2-ylsulfonyl)-N-[[2-[4-(2,2,2-trifluoroethoxy)phenyl]-4-pyridyl]methyl]pyrrolidine-2-carboxamide |

TABLE 27-continued

| Example No. | structural formula | compound name |
|---|---|---|
| 205 | | (2S)-1-(benzofuran-2-ylsulfonyl)-N-[[6-[6-(trifluoromethyl)-3-pyridyl]pyrimidin-4-yl]methyl]pyrrolidine-2-carboxamide |
| 206 | | (2S)-1-(benzofuran-2-ylsulfonyl)-N-[[6-[5-(trifluoromethyl)-2-pyridyl]pyrimidin-4-yl]methyl]pyrrolidine-2-carboxamide |
| 207 | | (2S)-1-(benzofuran-2-ylsulfonyl)-N-[[6-[2-(trifluoromethyl)pyrimidin-5-yl]pyrimidin-4-yl]methyl]pyrrolidine-2-carboxamide |
| 208 | | (2S)-1-(benzofuran-2-ylsulfonyl)-N-[[6-[4-(trifluoromethyl)phenyl]-pyridazin-4-yl]methyl]pyrrolidine-2-carboxamide |
| 209 | | (2S)-1-(benzofuran-2-ylsulfonyl)-N-[[6-[6-(trifluoromethyl)-3-pyridyl]pyridazin-4-yl]methyl]pyrrolidine-2-carboxamide |
| 210 | | (2S)-1-(benzofuran-2-ylsulfonyl)-N-[[5-[4-(trifluoromethyl)phenyl]-pyridazin-3-yl]methyl]pyrrolidine-2-carboxamide |
| 211 | | (2S)-1-(benzofuran-2-ylsulfonyl)-N-[[5-[6-(trifluoromethyl)-3-pyridyl]pyridazin-3-yl]methyl]pyrrolidine-2-carboxamide |

TABLE 27-continued

| Example No. | structural formula | compound name |
|---|---|---|
| 212 | | (2S)-1-(benzofuran-2-ylsulfonyl)-N-[[5-[5-(trifluoromethyl)-2-pyridyl]pyridazin-3-yl]methyl]pyrrolidine-2-carboxamide |
| 213 | | (2S)-1-(benzofuran-2-ylsulfonyl)-N-[[4-hydroxy-3-[5-(trifluoromethyl)-pyrimidin-2-yl]phenyl]-methyl]pyrrolidine-2-carboxamide |
| 214 | | (2S)-1-(benzofuran-2-ylsulfonyl)-N-[[4-hydroxy-3-[5-(trifluoromethyl)-pyrazin-2-yl]phenyl]-methyl]pyrrolidine-2-carboxamide |
| 215 | | (2S)-1-(benzofuran-2-ylsulfonyl)-N-[[5-hydroxy-4-[5-(trifluoromethyl)-2-pyridyl]-2-pyridyl]methyl]pyrrolidine-2-carboxamide |
| 216 | | (2S)-1-(benzofuran-2-ylsulfonyl)-N-[1-[3-chloro-5-[6-(trifluoromethyl)-3-pyridyl]phenyl]cyclopropyl]-pyrrolidine-2-carboxamide |
| 217 | | (2S)-1-(benzofuran-2-ylsulfonyl)-N-[1-[2-[4-(trifluoromethyl)phenyl]-4-pyridyl]cyclopropyl]-pyrrolidine-2-carboxamide |

TABLE 27-continued

| Example No. | structural formula | compound name |
|---|---|---|
| 218 | | (2S)-1-(benzofuran-2-ylsulfonyl)-N-[1-[2-[6-(trifluoromethyl)-3-pyridyl]-4-pyridyl]cyclopropyl]-pyrrolidine-2-carboxamide |
| 219 | | (2S)-1-(7-fluorobenzofuran-2-yl)sulfonyl-N-[[2-[4-(trifluoromethyl)phenyl]-4-pyridyl]methyl]pyrrolidine-2-carboxamide |
| 220 | | (2S)-1-(6-fluorobenzofuran-2-yl)sulfonyl-N-[[2-[4-(trifluoromethyl)phenyl]-4-pyridyl]methyl]pyrrolidine-2-carboxamide |
| 221 | | (2S)-1-(5-fluorobenzofuran-2-yl)sulfonyl-N-[[2-[5-(trifluoromethyl)-2-pyridyl]-4-pyridyl]methyl]pyrrolidine-2-carboxamide |
| 222 | | (2S)-1-(5-fluorobenzofuran-2-yl)sulfonyl-N-[[4-[4-(trifluoromethoxy)phenyl]-2-pyridyl]methyl]pyrrolidine-2-carboxamide |
| 223 | | (2S)-1-(5-fluorobenzofuran-2-yl)sulfonyl-N-[[4-[5-(trifluoromethyl)-2-pyridyl]-2-pyridyl]methyl]pyrrolidine-2-carboxamide |

TABLE 27-continued

| Example No. | structural formula | compound name |
|---|---|---|
| 224 | | (2S)-1-(5-fluorobenzofuran-2-yl)sulfonyl-N-[[6-[6-(trifluoromethyl)-3-pyridyl]pyrimidin-4-yl]methyl]pyrrolidine-2-carboxamide |
| 225 | | (2S)-1-(5-fluorobenzofuran-2-yl)sulfonyl-N-[[4-[5-(trifluoromethyl)-2-pyridyl]-2-pyridyl]methyl]-2,5-dihydropyrrole-2-carboxamide |
| 226 | | (2S,3S)-1-(benzofuran-2-ylsulfonyl)-3-hydroxy-N-[[6-[4-(trifluoromethyl)phenyl]pyrimidin-4-yl]methyl]pyrrolidine-2-carboxamide |
| 227 | | (2S,3S)-1-(benzofuran-2-ylsulfonyl)-3-hydroxy-N-[[4-[5-(trifluoromethyl)-2-pyridyl]-2-pyridyl]methyl]pyrrolidine-2-carboxamide |
| 228 | | (2S,3S)-1-(5-fluorobenzofuran-2-yl)sulfonyl-3-hydroxy-N-[[4-[5-(trifluoromethyl)-2-pyridyl]-2-pyridyl]methyl]pyrrolidine-2-carboxamide |
| 229 | | (2S)-4,4-difluoro-1-(5-fluorobenzofuran-2-yl)sulfonyl-N-[[4-[5-(trifluoromethyl)-2-pyridyl]-2-pyridyl]methyl]pyrrolidine-2-carboxamide |

TABLE 27-continued

| Example No. | structural formula | compound name |
|---|---|---|
| 230 | | (2S)-1-(5-fluorobenzofuran-2-yl)sulfonyl-N-[[4-[5-(trifluoromethyl)-2-pyridyl]-2-pyridyl]methyl]azetidine-2-carboxamide |
| 231 | | (2S)-2-(benzofuran-2-ylsulfonylamino)-N-[[6-[4-(trifluoromethoxy)phenyl]-pyrimidin-4-yl]methyl]propanamide |
| 232 | | (2S)-2-[(5-fluorobenzofuran-2-yl)sulfonylamino]-N-[[3-[5-(trifluoromethyl)pyrimidin-2-yl]phenyl]methyl]propanamide |
| 233 | | (2S)-2-[(5-fluorobenzofuran-2-yl)sulfonylamino]-N-[[3-[2-(trifluoromethyl)pyrimidin-5-yl]phenyl]methyl]propanamide |
| 234 | | (2S)-2-[(5-fluorobenzofuran-2-yl)sulfonylamino]-N-[[3-[5-(trifluoromethyl)pyrazin-2-yl]phenyl]methyl]propanamide |
| 235 | | (2S)-2-[(5-fluorobenzofuran-2-yl)sulfonylamino]-N-[[3-[6-(trifluoromethyl)pyridazin-3-yl]phenyl]methyl]propanamide |

TABLE 27-continued

| Example No. | structural formula | compound name |
| --- | --- | --- |
| 236 | | (2S)-2-[(5-fluorobenzofuran-2-yl)sulfonylamino]-N-[[2-[6-(trifluoromethyl)-3-pyridyl]-4-pyridyl]methyl]propanamide |
| 237 | | (2S)-2-[(5-fluorobenzofuran-2-yl)sulfonylamino]-N-[[2-[5-(trifluoromethyl)-2-pyridyl]-4-pyridyl]methyl]propanamide |
| 238 | | (2S)-2-[(5-fluorobenzofuran-2-yl)sulfonylamino]-N-[[2-[2-(trifluoromethyl)pyrimidin-5-yl]-4-pyridyl]methyl]propanamide |
| 239 | | (2S)-2-[(5-fluorobenzofuran-2-yl)sulfonylamino]-N-[[4-[4-(trifluoromethoxy)phenyl]-2-pyridyl]methyl]propanamide |
| 240 | | (2S)-2-[(5-fluorobenzofuran-2-yl)sulfonylamino]-N-[[4-[5-(trifluoromethyl)-2-pyridyl]-2-pyridyl]methyl]propanamide |
| 241 | | (2S)-2-[(5-fluorobenzofuran-2-yl)sulfonylamino]-N-[[4-[2-(trifluoromethyl)pyrimidin-5-yl]-2-pyridyl]methyl]propanamide |

TABLE 27-continued

| Example No. | structural formula | compound name |
|---|---|---|
| 242 | | (2S)-2-[(5-fluorobenzofuran-2-yl)sulfonylamino]-N-[[4-[5-(trifluoromethyl)pyrimidin-2-yl]-2-pyridyl]methyl]propanamide |
| 243 | | (2S)-2-[(5-fluorobenzofuran-2-yl)sulfonylamino]-N-[[4-[5-(trifluoromethyl)pyrazin-2-yl]-2-pyridyl]methyl]propanamide |
| 244 | | (2S)-2-[(5-fluorobenzofuran-2-yl)sulfonylamino]-N-[[4-[6-(trifluoromethyl)pyridazin-3-yl]-2-pyridyl]methyl]propanamide |
| 245 | | (2S)-2-[(5-fluorobenzofuran-2-yl)sulfonylamino]-N-[[5-[6-(trifluoromethyl)-3-pyridyl]-3-pyridyl]methyl]propanamide |
| 246 | | (2S)-2-[(5-fluorobenzofuran-2-yl)sulfonylamino]-N-[[5-[5-(trifluoromethyl)-2-pyridyl]-3-pyridyl]methyl]propanamide |
| 247 | | (2S)-2-[(5-fluorobenzofuran-2-yl)sulfonylamino]-N-[[6-[5-(trifluoromethyl)-2-pyridyl]pyrimidin-4-yl]methyl]propanamide |

TABLE 27-continued

| Example No. | structural formula | compound name |
|---|---|---|
| 248 | | (2S)-2-[(5-fluorobenzofuran-2-yl)sulfonylamino]-N-[[6-[2-(trifluoromethyl)pyrimidin-5-yl]pyrimidin-4-yl]methyl]propanamide |
| 249 | | (2S)-2-[(5-fluorobenzofuran-2-yl)sulfonylamino]-N-[[6-[4-(trifluoromethyl)phenyl]-pyridazin-4-yl]methyl]propanamide |
| 250 | | (2S)-2-[(5-fluorobenzofuran-2-yl)sulfonylamino]-N-[[5-[4-(trifluoromethyl)phenyl]-pyridazin-3-yl]methyl]propanamide |
| 251 | | (2S)-2-[(5-fluorobenzofuran-2-yl)sulfonylamino]-N-[[5-[5-(trifluoromethyl)-2-pyridyl]pyridazin-3-yl]methyl]propanamide |
| 252 | | (2S)-2-[(5-fluorobenzofuran-2-yl)sulfonylamino]-N-[[4-hydroxy-3-[5-(trifluoromethyl)-2-pyridyl]-phenyl]methyl]propanamide |
| 253 | | (2S)-2-[(5-fluorobenzofuran-2-yl)sulfonylamino]-N-[[4-hydroxy-3-[5-(trifluoromethyl)pyrimidin-2-yl]phenyl]methyl]propanamide |

TABLE 27-continued

| Example No. | structural formula | compound name |
|---|---|---|
| 254 | | (2S)-2-[(5-fluorobenzofuran-2-yl)sulfonylamino]-N-[[4-hydroxy-3-[5-(trifluoromethyl)pyrazin-2-yl]phenyl]methyl]propanamide |
| 255 | | (2S)-2-[(5-fluorobenzofuran-2-yl)sulfonylamino]-N-[[5-hydroxy-4-[5-(trifluoromethyl)-2-pyridyl]-2-pyridyl]methyl]propanamide |
| 256 | | (2S,4R)-1-(5-fluorobenzofuran-2-yl)sulfonyl-4-hydroxy-N-[[4-[5-(trifluoromethyl)-2-pyridyl]-2-pyridyl]methyl]pyrrolidine-2-carboxamide |
| 257 | | (1R,4S,5S)-3-(5-fluorobenzofuran-2-yl)sulfonyl-N-[[4-[5-(trifluoromethyl)-2-pyridyl]-2-pyridyl]methyl]-3-azabicyclo[3.1.0]hexane-4-carboxamide |
| 258 | | (1R,3S,5R)-4-(5-fluorobenzofuran-2-yl)sulfonyl-N-[[4-[5-(trifluoromethyl)-2-pyridyl]-2-pyridyl]methyl]-4-azabicyclo[3.1.0]hexane-3-carboxamide |
| 259 | | (1S,3S,5S)-4-(5-fluorobenzofuran-2-yl)sulfonyl-N-[[4-[5-(trifluoromethyl)-2-pyridyl]-2-pyridyl]methyl]-4-azabicyclo[3.1.0]hexane-3-carboxamide |

TABLE 27-continued

| Example No. | structural formula | compound name |
|---|---|---|
| 260 | | (2S,4S)-1-(5-fluorobenzofuran-2-yl)sulfonyl-4-phenyl-N-[[4-[5-(trifluoromethyl)-2-pyridyl]-2-pyridyl]methyl]pyrrolidine-2-carboxamide |
| 261 | | (2S)-1-(5-fluorobenzofuran-2-yl)sulfonyl-N-[[4-[5-(trifluoromethyl)-2-pyridyl]-2-pyridyl]methyl]piperidine-2-carboxamide |
| 262 | | (1S,2S,4R)-3-(5-fluorobenzofuran-2-yl)sulfonyl-N-[[4-[5-(trifluoromethyl)-2-pyridyl]-2-pyridyl]methyl]-3-azabicyclo[2.2.1]heptane-2-carboxamide |
| 263 | | (2S)-1-(5-fluorobenzofuran-2-yl)sulfonyl-N-[[4-[5-(trifluoromethyl)-2-pyridyl]-2-pyridyl]methyl]-3,6-dihydro-2H-pyridine-2-carboxamide |
| 264 | | (rac)-2-(5-fluorobenzofuran-2-yl)sulfonyl-N-[[4-[5-(trifluoromethyl)-2-pyridyl]-2-pyridyl]methyl]isoindoline-1-carboxamide |

TABLE 27-continued

| Example No. | structural formula | compound name |
|---|---|---|
| 265 | | (2S)-1-(4-chlorofuro[3,2-c]pyridin-2-yl)sulfonyl-N-[[4-[5-(trifluoromethyl)-2-pyridyl]-2-pyridyl]methyl]pyrrolidine-2-carboxamide |
| 266 | | (2S)-N-[[2-chloro-5-(trifluoromethyl)phenyl]methyl]-1-furo[3,2-c]pyridin-2-ylsulfonyl-pyrrolidine-2-carboxamide |
| 267 | | (2S)-N-[(3-benzyloxyphenyl)methyl]-1-furo[3,2-c]pyridin-2-ylsulfonyl-pyrrolidine-2-carboxamide |
| 268 | | (2S)-1-furo[3,2-c]pyridin-2-ylsulfonyl-N-[[4-[3-(trifluoromethyl)phenoxy]-phenyl]methyl]pyrrolidine-2-carboxamide |
| 269 | | (2S)-1-furo[3,2-c]pyridin-2-ylsulfonyl-N-[[3-[4-(trifluoromethyl)phenoxy]-phenyl]methyl]pyrrolidine-2-carboxamide |
| 270 | | (2S)-1-furo[3,2-c]pyridin-2-ylsulfonyl-N-[[6-[4-(trifluoromethyl)phenyl]-pyrimidin-4-yl]methyl]pyrrolidine-2-carboxamide |

TABLE 27-continued

| Example No. | structural formula | compound name |
|---|---|---|
| 271 | | (2S)-1-furo[3,2-c]pyridin-2-ylsulfonyl-N-[[2-[2-hydroxy-4-(trifluoromethyl)phenyl]-4-pyridyl]methyl]pyrrolidine-2-carboxamide |
| 272 | | (2S)-1-furo[3,2-c]pyridin-2-ylsulfonyl-N-[[4-[5-(trifluoromethyl)-2-pyridyl]-2-pyridyl]methyl]pyrrolidine-2-carboxamide |
| 273 | | (2S)-1-furo[3,2-c]pyridin-2-ylsulfonyl-N-[[4-hydroxy-3-[5-(trifluoromethyl)-2-pyridyl]phenyl]methyl]-pyrrolidine-2-carboxamide |
| 274 | | (2S)-1-furo[3,2-c]pyridin-2-ylsulfonyl-N-[[3-[[2-(trifluoromethyl)-4-pyridyl]methoxy]phenyl]-methyl]pyrrolidine-2-carboxamide |
| 275 | | (2S)-2-[(5-fluorobenzofuran-2-yl)sulfonyl-2-propynylamino]-N-[[2-[2-hydroxy-4-(trifluoromethyl)phenyl]-4-pyridyl]methyl]propanamide |
| 276 | | N-[2-[4-[[[(2S)-1-(benzofuran-2-ylsulfonyl)pyrrolidine-2-carbonyl]amino]methyl]-2-pyridyl]phenyl]carbamic acid tert-butyl |

Example 277 to Example 286 described in Table 28 were synthesized by using the compounds described in Reference Examples and by an operation similar to that in Example 112.

TABLE 28

| Example No. | structural formula | compound name |
|---|---|---|
| 277 | | (2S)-1-(benzofuran-2-ylsulfonyl)-N-[[2-(4-chloro-2-thienyl)-4-pyridyl]methyl]pyrrolidine-2-carboxamide |
| 278 | | (2S)-1-(benzofuran-2-ylsulfonyl)-N-[[2-(4-methylsulfanylphenyl)-4-pyridyl]methyl]pyrrolidine-2-carboxamide |
| 279 | | (2S)-1-(5-fluorobenzofuran-2-yl)sulfonyl-N-[[5-[4-(trifluoromethoxy)phenyl]-3-pyridyl]methyl]pyrrolidine-2-carboxamide |
| 280 | | (2S)-1-(5-fluorobenzofuran-2-yl)sulfonyl-N-[[4-[2-hydroxy-4-(trifluoromethyl)phenyl]-2-pyridyl]methyl]pyrrolidine-2-carboxamide |
| 281 | | (2S)-1-(benzofuran-2-ylsulfonyl)-N-[[4-(4-cyanophenyl)-2-pyridyl]methyl]pyrrolidine-2-carboxamide |
| 282 | | (2S)-1-(benzofuran-2-ylsulfonyl)-N-[[4-[(E)-2-cyclopropylvinyl]-2-pyridyl]methyl]pyrrolidine-2-carboxamide |

TABLE 28-continued

| Example No. | structural formula | compound name |
| --- | --- | --- |
| 283 | | (2S)-1-(benzofuran-2-ylsulfonyl)-N-[[4-(cyclohexen-1-yl)-2-pyridyl]methyl]pyrrolidine-2-carboxamide |
| 284 | | (2S)-1-(benzofuran-2-ylsulfonyl)-N-[[4-(p-tolyl)-2-pyridyl]methyl]pyrrolidine-2-carboxamide |
| 285 | | (2S)-1-(benzofuran-2-ylsulfonyl)-N-[[4-(4-tert-butylphenyl)-2-pyridyl]methyl]pyrrolidine-2-carboxamide |
| 286 | | (2S)-1-(benzofuran-2-ylsulfonyl)-N-[[4-(4-chloro-2-thienyl)-2-pyridyl]methyl]pyrrolidine-2-carboxamide |

Example 287

Synthesis of (2S)-1-(benzofuran-2-ylsulfonyl)-N-[(1S)-1-[3-[6-(trifluoromethyl)-3-pyridyl]phenyl]ethyl]pyrrolidine-2-carboxamide (287)

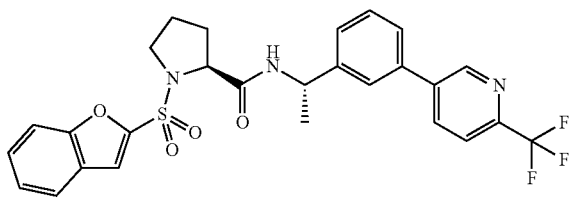 [SMILES: C[C@H](NC(=O)[C@@H]1CCCN1S(=O)(=O)c1cc2ccccc2o1)c1cccc(-c2ccc(C(F)(F)F)nc2)c1]

(step 1) Synthesis of (2S)-1-(benzofuran-2-ylsulfonyl)-N-[(1S)-1-(3-bromophenyl)ethyl]pyrrolidine-2-carboxamide To B-1 (30 mg, 0.10 mmol), (1S)-1-(3-bromophenyl)ethylamine (0.015 mL, 0.10 mmol), WSC hydrochloride (27 mg, 0.12 mmol) and 1-hydroxy-7-azabenzotriazole (14 mg, 0.15 mmol) was added dichloromethane (1 mL), and the mixture was stirred at room temperature for 30 min. The reaction mixture was partitioned by adding saturated aqueous sodium hydrogen carbonate. The organic layer was dried over sodium sulfate. The desiccant was filtered off, and the solvent was evaporated to give the title compound (42 mg, 0.088 mmol, 88%).

MS (ESI) m/z 477 (M+H)$^+$ (step 2) Synthesis of (2S)-1-(benzofuran-2-ylsulfonyl)-N-[(1S)-1-[3-[6-(trifluoromethyl)-3-pyridyl]phenyl]ethyl]pyrrolidine-2-carboxamide(287)

Using the compound obtained in step 1 and [6-(trifluoromethyl)-3-pyridyl]boronic acid instead of C-4 and phenylboronic acid, and by an operation similar to that in Example 112, the title compound was obtained (yield 57%).

MS (ESI) m/z 544 (M+H)$^+$ $^1$H NMR (400 MHz, DMSO-d$_6$) δ 9.10 (d, J=2.2 Hz, 1H), 8.57 (d, J=8.2 Hz, 1H), 8.37 (dd, J=8.2, 2.2 Hz, 1H), 7.99 (d, J=8.2 Hz, 1H), 7.84 (ddd, J=7.8, 1.4, 0.9 Hz, 1H), 7.78 (dd, J=1.8, 1.8 Hz, 1H), 7.75 (dd, J=8.5, 0.9 Hz, 1H), 7.73 (d, J=0.9 Hz, 1H), 7.69 (ddd, J=7.6, 1.8, 1.8 Hz, 1H), 7.56 (ddd, J=8.5, 7.2, 1.4 Hz, 1H), 7.51 (dd, J=7.6, 7.6 Hz, 1H), 7.47-7.40 (m, 2H), 5.04 (dq, J=8.2, 7.0 Hz, 1H), 4.32 (dd, J=8.3, 3.8 Hz, 1H), 3.65-3.56 (m, 1H), 3.41-3.35 (m, 1H), 1.98-1.76 (m, 3H), 1.67-1.58 (m, 1H), 1.46 (d, J=7.0 Hz, 3H).

Example 288

Synthesis of (2S)-1-(benzofuran-2-ylsulfonyl)-N-[[6-[2-hydroxy-4-(trifluoromethyl)phenyl]pyrimidin-4-yl]methyl]pyrrolidine-2-carboxamide (288)

(step 1) Synthesis of 4-[2-benzyloxy-4-(trifluoromethyl)phenyl]-6-cyanopyrimidine To 2-benzyloxy-4-trifluoromethylphenylboronic acid (0.25 g, 0.84 mmol), 4,6-dichloropyrimidine (0.13 g, 0.84 mmol) and 1,1'-bis(diphenylphosphino)ferrocenedichloropalladium(II) (62 mg, 0.084 mmol) were added 1,4-dioxane (5 mL) and 1 mol/L aqueous sodium carbonate solution (5 mL) and the mixture was stirred with heating by using a microwave reactor at 100° C. for 20 min. To the reaction mixture was added water, and the mixture was extracted with ethyl acetate. The organic layer was dried over sodium sulfate. The desiccant was filtered off, and the solvent was evaporated. To the obtained residue were added dimethyl sulfoxide (2 mL), water (0.6 mL), sodium cyanide (0.12 g, 2.5 mmol) and 1,8-diazabicyclo[2.2.2]octane (19 mg, 0.17 mmol) and the mixture was stirred at 60° C. for 1 hr. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (0.18 g, 0.52 mmol, 61%).

MS (ESI) m/z 356 (M+H)$^+$ (step 2) Synthesis of (2S)-1-(benzofuran-2-ylsulfonyl)-N-[{6-[2-hydroxy-4-(trifluoromethyl)phenyl]pyrimidin-4-yl}methyl]pyrrolidine-2-carboxamide (288)

The compound (50 mg, 0.14 mmol) obtained in step 1 was dissolved by adding ethanol (2 mL) and tetrahydrofuran (1 mL). 10% Palladium/carbon (15 mg) was added, and the mixture was stirred at normal pressure under a hydrogen atmosphere at room temperature for 3 hr. The catalyst was filtered off and the filtrate was concentrated under reduced pressure. To the obtained residue were added B-1 (47 mg, 0.16 mmol), WSC hydrochloride (37 mg, 0.19 mmol), 1-hydroxy-7-azabenzotriazole (22 mg, 0.16 mmol) and dichloromethane (2 mL), and the mixture was stirred at room temperature for 10 min. The reaction mixture was concentrated under reduced pressure and the obtained residue was purified by high performance liquid chromatography (water-acetonitrile, each containing 0.1% trifluoroacetic acid) to give the title compound (41 mg, 0.075 mmol, 53%).

MS (ESI) m/z 547 (M+H)$^+$ $^1$H NMR (400 MHz, DMSO-d$_6$) δ 12.90 (s, 1H), 9.24 (d, J=1.3 Hz, 1H), 8.96 (dd, J=6.1, 5.8 Hz, 1H), 8.25 (d, J=8.3 Hz, 1H), 8.14 (d, J=1.3 Hz, 1H), 7.84 (ddd, J=7.9, 1.3, 0.9 Hz, 1H), 7.80-7.72 (m, 2H), 7.57 (ddd, J=8.5, 7.2, 1.3 Hz, 1H), 7.43 (ddd, J=7.9, 7.2, 0.9 Hz, 1H), 7.32 (d, J=1.9 Hz, 1H), 7.28 (dd, J=8.3, 1.9 Hz, 1H), 4.53 (dd, J=17.3, 6.1 Hz, 1H), 4.46 (dd, J=17.3, 5.8 Hz, 1H), 4.37 (dd, J=8.0, 3.9 Hz, 1H), 3.67-3.59 (m, 1H), 3.45-3.41 (m, 1H), 2.05-1.90 (m, 3H), 1.73-1.63 (m, 1H).

Example 289 to Example 290 described in Table 29 were synthesized by using the compounds described in Reference Examples and by an operation similar to that in Example 288.

TABLE 29

| Example No. | structural formula | compound name |
|---|---|---|
| 288 | | (2S)-1-(benzofuran-2-ylsulfonyl)-N-[[6-[2-hydroxy-4-(trifluoromethyl)phenyl]pyrimidin-4-yl]methyl]pyrrolidine-2-carboxamide |
| 289 | | (2S)-1-(5-fluorobenzofuran-2-yl)sulfonyl-N-[[6-[2-hydroxy-4-(trifluoromethyl)phenyl]pyrimidin-4-yl]methyl]pyrrolidine-2-carboxamide |

| Example No. | structural formula | compound name |
|---|---|---|
| 290 | | (2S)-2-[(5-fluorobenzofuran-2-yl)sulfonylamino]-N-[[6-[2-hydroxy-4-(trifluoromethyl)phenyl]pyrimidin-4-yl]methyl]propanamide |

Example 291

Synthesis of (2S)-1-(benzofuran-2-ylsulfonyl)-N-[[3-[[5-(trifluoromethyl)-2-pyridyl]methoxy]phenyl]methyl]pyrrolidine-2-carboxamide (291)

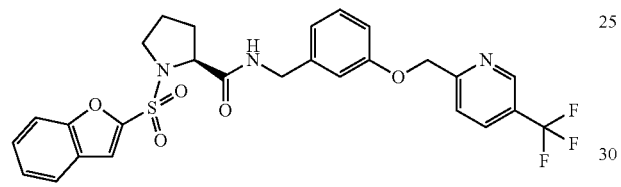

(step 1) Synthesis of [5-(trifluoromethyl)-2-pyridyl]methanol

A solution of 5-(trifluoromethyl)pyridine-2-carboxylic acid (0.19 g, 1.0 mmol) in tetrahydrofuran (10 mL) was cooled to 0° C., triethylamine (0.18 mL, 1.3 mmol) and ethyl chloroformate (0.11 mL, 1.1 mmol) were added and the mixture was stirred for 10 min. The reaction mixture was filtered, to the filtrate were added sodium tetrahydroborate (49 mg, 1.3 mmol) and one piece of ice, and the mixture was stirred at 0° C. for 1 hr. To the reaction mixture was added aqueous sodium hydroxide solution and the mixture was stirred for 30 min, and extracted with dichloromethane. The organic layer was washed with water, dried over sodium sulfate, and the desiccant was filtered off. The solvent was evaporated to give the title compound as a crudely purified product (0.12 g).

MS (ESI) m/z 178 (M+H)+

(step 2) Synthesis of (2S)-1-(benzofuran-2-ylsulfonyl)-N-[[3-[[5-(trifluoromethyl)-2-pyridyl]methoxy]phenyl]methyl]pyrrolidine-2-carboxamide(291)

The crudely purified product (20 mg) obtained in step 1 and C-1 (40 mg, 0.10 mmol) was dissolved by adding dichloromethane (2 mL). Triphenylphosphine (39 mg, 0.15 mmol) and diisopropyl azodicarboxylate (0.032 mL, 0.15 mmol) were added and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (11 mg, 0.019 mmol, 19%).

MS (ESI) m/z 560 (M+H)+

$^1$H NMR (400 MHz, DMSO-d$_6$) δ 8.97 (brs, 1H), 8.65 (t, J=6.1 Hz, 1H), 8.25 (dd, J=8.4, 2.4 Hz, 1H), 7.83 (d, J=7.8 Hz, 1H), 7.77-7.70 (m, 3H), 7.56 (ddd, J=8.5, 7.2, 1.4 Hz, 1H), 7.45-7.39 (m, 1H), 7.26 (t, J=7.9 Hz, 1H), 6.99 (brs, 1H), 6.93-6.88 (m, 2H), 5.30 (s, 2H), 4.37-4.22 (m, 3H), 3.62-3.55 (m, 1H), 3.42-3.35 (m, 1H), 1.94-1.80 (m, 3H), 1.68-1.59 (m, 1H).

Example 292

Synthesis of (2S)-1-(benzofuran-2-ylsulfonyl)-N-[[2-[2-(methylamino)phenyl]-4-pyridyl]methyl]pyrrolidine-2-carboxamide (292)

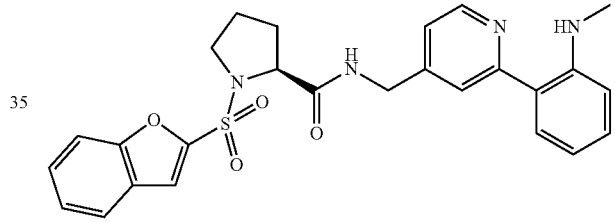

(step 1) Synthesis of (2S)—N-[[2-(2-aminophenyl)-4-pyridyl]methyl]-1-(benzofuran-2-ylsulfonyl)pyrrolidine-2-carboxamide To C-4 (84 mg, 0.20 mmol), [2-(tert-butoxycarbonylamino)phenyl]boronic acid (47 mg, 0.20 mmol), and 1,1'-bis(diphenylphosphino)ferrocenedichloropalladium(II) (15 mg, 0.020 mmol) were added 1,4-dioxane (1.4 mL) and 1 mol/L aqueous sodium carbonate solution (1.4 mL) and the mixture was stirred with heating by using a microwave reactor at 100° C. for 10 min. The reaction mixture was neutralized with trifluoroacetic acid, purified by high performance liquid chromatography (water-acetonitrile, each containing 0.1% trifluoroacetic acid). The obtained compound was dissolved in dichloromethane (1 mL), trifluoroacetic acid (1 mL) was added and the mixture was stirred at room temperature for 30 min, and concentrated under reduced pressure to give 2 trifluoroacetate of the title compound (42 mg, 0.088 mmol, 44%).

MS (ESI) m/z 477 (M+H)+

(step 2) Synthesis of (2S)-1-(benzofuran-2-ylsulfonyl)-N-[[2-[2-(methylamino)phenyl]-4-pyridyl]methyl]pyrrolidine-2-carboxamide (292)

To a solution of the compound (15 mg, 0.031 mmol) obtained in step 1 in acetonitrile (1 mL) were added potassium carbonate (4.3 mg, 0.031 mmol) and methyl iodide (0.014 mL, 0.031 mmol), and the mixture was stirred at room temperature overnight. The insoluble material was filtered off, and the filtrate was concentrated under reduced pressure and the obtained residue was purified by high performance liquid chromatography (water-acetonitrile, each containing 0.1% trifluoroacetic acid) to give 2 trifluoroacetate of the title compound (2.5 mg, 0.0041 mmol, 13%).

MS (ESI) m/z 491 (M+H)$^+$

Example 293

Synthesis of (2S)-1-(benzofuran-2-ylsulfonyl)-N-[[2-(4-cyanophenyl)-4-pyridyl]methyl]pyrrolidine-2-carbothioamide (293)

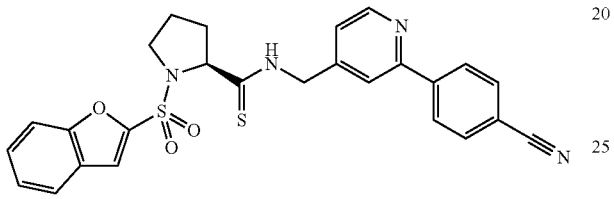

To (2S)-1-(benzofuran-2-ylsulfonyl)-N-[[2-(4-cyanophenyl)-4-pyridyl]methyl]pyrrolidine-2-carboxamide(117) (50 mg, 0.10 mmol) and Lawesson reagent (50 mg, 0.12 mmol) was added tetrahydrofuran (2 mL) and the mixture was stirred 50° C. overnight. The reaction mixture was concentrated under reduced pressure and the obtained residue was purified by high performance liquid chromatography (water-acetonitrile, each containing 0.1% trifluoroacetic acid) to give trifluoroacetate of the title compound (4.3 mg, 0.0070 mmol, 7.0%).

MS (ESI) m/z 503 (M+H)$^+$ $^1$H NMR (400 MHz, DMSO-d$_6$) δ 10.75 (dd, J=6.5, 5.9 Hz, 1H), 8.68 (d, J=5.1 Hz, 1H), 8.31-8.24 (m, 2H), 8.03-7.94 (m, 3H), 7.86 (d, J=7.8 Hz, 1H), 7.82 (s, 1H), 7.80 (d, J=8.5 Hz, 1H), 7.61-7.55 (m, 1H), 7.44 (t, J=7.5 Hz, 1H), 7.37 (dd, J=5.1, 1.5 Hz, 1H), 5.15 (dd, J=16.0, 6.5 Hz, 1H), 4.89-4.78 (m, 2H), 3.95-3.83 (m, 1H), 3.76-3.69 (m, 1H), 1.93-1.51 (m, 4H).

Example 294

Synthesis of (2S)-1-(benzofuran-2-ylsulfonyl)-N-[[2-[3-(trifluoromethyl)-1H-pyrazol-5-yl]-4-pyridyl]methyl]pyrrolidine-2-carboxamide (294)

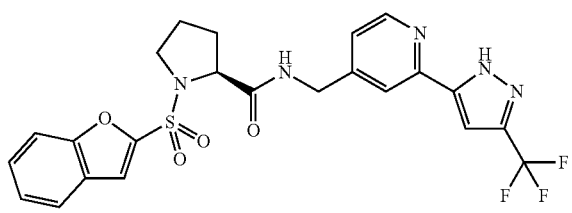 [SMILES: O=C(NCc1ccnc(-c2cc(C(F)(F)F)n[nH]2)c1)[C@@H]1CCCN1S(=O)(=O)c1cc2ccccc2o1]

To C-4 (42 mg, 0.10 mmol), [2-tetrahydropyran-2-yl-5-(trifluoromethyl)pyrazol-3-yl]boronic acid (53 mg, 0.20 mmol), potassium phosphate (64 mg, 0.30 mmol) and tetrakis(triphenylphosphine)palladium(0) (5.7 mg, 0.005 mmol) was added toluene (3 mL). The mixture was successively stirred with heating by using a microwave reactor at 100° C. for 20 min, 130° C. for 10 min, and 130° C. for 30 min, and the reaction mixture was purified by silica gel column chromatography (ethyl acetate/dichloromethane). To the obtained compound were added dichloromethane (2 mL) and trifluoroacetic acid (0.10 mL) and the mixture was stirred at room temperature for 30 min. Water and acetonitrile were added and the mixture was freeze-dried to give trifluoroacetate of the title compound (5.0 mg, 0.0078 mmol, 8%).

MS (ESI) m/z 520 (M+H)$^+$

Example 295

Synthesis of 5-fluorobenzofuran-2-sulfonic acid [3-[[[(2S)-1-(5-fluorobenzofuran-2-yl)sulfonylpyrrolidine-2-carbonyl]amino]methyl]phenyl]ester (295)

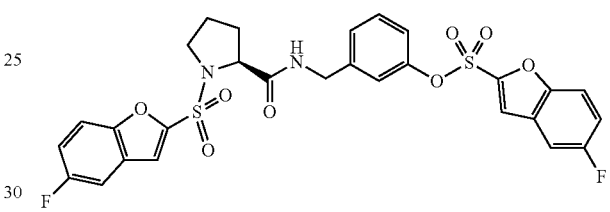

To a solution of C-2 (21 mg, 0.050 mmol) in acetonitrile (1 mL) were added A-3 (14 mg, 0.060 mmol) and triethylamine (0.010 mL, 0.075 mmol), and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (28 mg, 0.045 mmol, 90%).

MS (ESI) m/z 617 (M+H)$^+$ $^1$H NMR (400 MHz, DMSO-d$_6$) δ 8.71 (dd, J=6.2, 5.9 Hz, 1H), 7.92 (dd, J=9.2, 4.1 Hz, 1H), 7.89 (d, J=0.9 Hz, 1H), 7.81 (dd, J=9.1, 4.2 Hz, 1H), 7.67 (d, J=0.9 Hz, 1H), 7.66-7.60 (m, 2H), 7.52 (ddd, J=9.2, 9.2, 2.7 Hz, 1H), 7.43 (ddd, J=9.3, 9.1, 2.8 Hz, 1H), 7.36 (dd, J=8.2, 7.8 Hz, 1H), 7.27 (ddd, J=7.8, 1.4, 1.2 Hz, 1H), 7.14 (dd, J=2.6, 1.4 Hz, 1H), 6.95 (ddd, J=8.2, 2.6, 1.2 Hz, 1H), 4.31 (dd, J=15.7, 6.2 Hz, 1H), 4.28-4.20 (m, 2H), 3.57 (ddd, J=9.5, 6.8, 4.8 Hz, 1H), 3.41-3.35 (m, 1H), 1.95-1.75 (m, 3H), 1.69-1.57 (m, 1H).

Example 296

Synthesis of (2S)-1-(5-fluorobenzofuran-2-yl) sulfonyl-N-[[3-[4-(trifluoromethyl)anilino]phenyl]methyl]pyrrolidine-2-carboxamide (296)

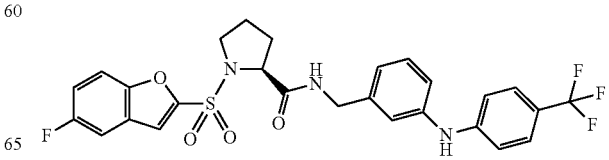

To C-10 (47 mg, 0.089 mmol) was added 4-aminobenzotrifluoride (0.017 mL, 0.13 mmol), tris(dibenzylideneacetone)dipalladium(0) (2.0 mg, 0.0022 mmol), dicyclohexylphosphino-2',4',6'-triisopropylbiphenyl (4.2 mg, 0.0089 mmol) and sodium tert-butoxide (0.17 g, 0.18 mmol) was added toluene (1.0 mL) and the mixture was stirred at 100° C. for 24 hr. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (26 mg, 0.047 mmol, 53%).

MS (ESI) m/z 562 (M+H)$^+$ $^1$H NMR (400 MHz, DMSO-$d_6$) δ 8.68 (s, 1H), 8.65 (dd, J=6.1, 6.1 Hz, 1H), 7.79 (dd, J=9.0, 4.0 Hz, 1H), 7.66 (d, J=0.9 Hz, 1H), 7.63 (dd, J=8.5, 2.8 Hz, 1H), 7.50 (d, J=8.5 Hz, 2H), 7.49-7.36 (m, 1H), 7.26 (t, J=7.8 Hz, 1H), 7.14 (d, J=8.5 Hz, 2H), 7.11 (s, 1H), 7.04-6.99 (m, 1H), 6.88 (d, J=7.6 Hz, 1H), 4.36-4.19 (m, 3H), 3.67-3.54 (m, 1H), 3.45-3.35 (m, 1H), 2.00-1.78 (m, 3H), 1.71-1.58 (m, 1H).

Example 297

Synthesis of (2S)-1-(5-fluorobenzofuran-2-yl)sulfonyl-N-[[3-[(E)-2-[4-(trifluoromethyl)phenyl]vinyl]phenyl]methyl]pyrrolidine-2-carboxamide (297)

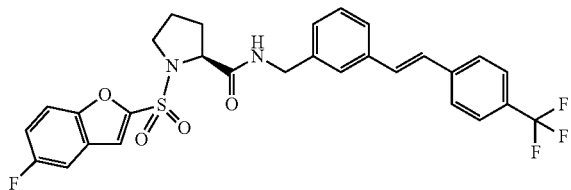 [SMILES: O=C(NCc1cccc(/C=C/c2ccc(C(F)(F)F)cc2)c1)[C@@H]1CCCN1S(=O)(=O)c1cc2cc(F)ccc2o1]

To C-10 (86 mg, 0.16 mmol) and 4-(trifluoromethyl)styrene (56 mg, 0.33 mmol), palladium(II) acetate (3.7 mg, 0.016 mmol), triphenylphosphine (8.6 mg, 0.033 mmol) and triethylamine (0.11 mL, 0.82 mmol) was added N,N-dimethylformamide (1.6 mL) and the mixture was stirred 100° C. for 24 hr. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (18 mg, 0.031 mmol, 19%).

MS (ESI) m/z 573 (M+H)$^+$ $^1$H NMR (400 MHz, DMSO-$d_6$) δ 8.72 (dd, J=6.2, 6.1 Hz, 1H), 7.84-7.77 (m, 3H), 7.74-7.70 (m, 3H), 7.64 (dd, J=8.5, 2.7 Hz, 1H), 7.60 (s, 1H), 7.50 (d, J=7.7 Hz, 1H), 7.44 (dd, J=9.3, 2.6 Hz, 1H), 7.41-7.33 (m, 3H), 7.23 (d, J=7.7 Hz, 1H), 4.40 (dd, J=15.5, 6.2 Hz, 1H), 4.36-4.29 (m, 2H), 3.66-3.58 (m, 1H), 3.46-3.37 (m, 1H), 2.05-1.83 (m, 3H), 1.74-1.60 (m, 1H).

Example 298

Synthesis of (2S)-1-(benzofuran-2-ylsulfonyl)-N-[[3-[[4-(trifluoromethyl)phenoxy]methyl]phenyl]methyl]pyrrolidine-2-carboxamide (298)

(step 1) Synthesis of 3-[[4-(trifluoromethyl)phenoxy]methyl]benzonitrile

To 3-cyanobenzylalcohol (0.050 mL, 0.45 mmol), diisopropyl azodicarboxylate (0.13 mL, 0.68 mmol), triphenylphosphine (0.18 g, 0.68 mmol), 4-hydroxybenzotrifluoride (0.088 g, 0.54 mmol) was added tetrahydrofuran (4.5 mL), and the mixture was stirred at room temperature for 24 hr. The reaction mixture was concentrated under reduced pressure and the obtained residue was purified by high performance liquid chromatography (water-acetonitrile, each containing 0.1% trifluoroacetic acid) to give the title compound (53 mg, 0.19 mmol, 42%).

MS (ESI) m/z 278 (M+H)$^+$ (step 2) Synthesis of (2S)-1-(benzofuran-2-ylsulfonyl)-N-[[3-[[4-(trifluoromethyl)phenoxy]methyl]phenyl]methyl]pyrrolidine-2-carboxamide (298)

The compound (53 mg, 0.19 mmol) obtained in step 1 was dissolved by adding tetrahydrofuran (1.9 mL), 0.95 mol/L borane (tetrahydrofuran solution, 0.30 mL, 0.29 mmol) was added, and the mixture was stirred at room temperature for 4 hr. To the reaction mixture was added 1 mol/L hydrochloric acid until the mixture reached pH1 and the mixture was stirred for 10 min. 1 mol/L Aqueous sodium hydroxide solution was added and the mixture was extracted with ethyl acetate. The organic layer was dried over sodium sulfate, the desiccant was filtered off, and the solvent was evaporated. To the obtained residue, B-1 (56 mg, 0.19 mmol), triethylamine (0.040 mL, 0.29 mmol), WSC hydrochloride (55 mg, 0.29 mmol) and 1-hydroxy-7-azabenzotriazole (13 mg, 0.095 mmol) was added dichloromethane (1.9 mL) and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (34 mg, 0.060 mmol, 32%).

MS (ESI) m/z 559 (M+H)$^+$ $^1$H NMR (400 MHz, DMSO-$d_6$) δ 8.69 (dd, J=6.1, 6.1 Hz, 1H), 7.83 (ddd, J=7.7, 1.3, 0.9 Hz, 1H), 7.74 (dd, J=8.4, 0.9 Hz, 1H), 7.71 (d, J=0.9 Hz, 1H), 7.65 (d, J=8.6 Hz, 2H), 7.55 (ddd, J=8.4, 7.3, 1.3 Hz, 1H), 7.44-7.39 (m, 1H), 7.38 (s, 1H), 7.37-7.31 (m, 2H), 7.29-7.23 (m, 1H), 7.19 (d, J=8.6 Hz, 2H), 5.18 (s, 2H), 4.37 (dd, J=15.4, 6.1 Hz, 1H), 4.33-4.25 (m, 2H), 3.68-3.50 (m, 1H), 3.43-3.34 (m, 1H), 1.94-1.80 (m, 3H), 1.69-1.55 (m, 1H).

Example 299 described in Table 30 was synthesized by using the compounds described in Reference Examples and corresponding commercially available reagent and by an operation similar to that in Example 298.

TABLE 30

| Example No. | structural formula | compound name |
|---|---|---|
| 298 | | (2S)-1-(benzofuran-2-ylsulfonyl)-N-[[3-[[4-(trifluoromethyl)phenoxy]methyl]phenyl]methyl]pyrrolidine-2-carboxamide |
| 299 | | (2S)-1-(benzofuran-2-ylsulfonyl)-N-[[3-[[4-(trifluoromethyl)phenyl]sulfanylmethyl]phenyl]methyl]pyrrolidine-2-carboxamide |

Example 300

Synthesis of (2S)-1-(benzofuran-2-ylsulfonyl)-N-[[3-[[4-(trifluoromethyl)benzoyl]amino]phenyl]methyl]pyrrolidine-2-carboxamide (300)

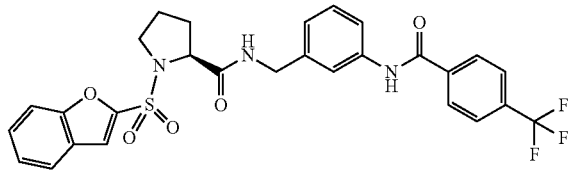 [SMILES: O=C(Nc1cccc(CNC(=O)[C@@H]2CCCN2S(=O)(=O)c2cc3ccccc3o2)c1)c1ccc(C(F)(F)F)cc1]

To 3-aminobenzonitrile (0.050 g, 0.42 mmol) and 4-trifluoromethylbenzoylchloride (0.075 g, 0.51 mmol) and triethylamine (0.088 mL, 0.64 mmol) was added dichloromethane (4.2 mL) and the mixture was stirred at room temperature for 5 hr. To the reaction mixture was added water, and the mixture was extracted with dichloromethane. The organic layer was dried over sodium sulfate. The desiccant was filtered off, and the solvent was evaporated. The obtained residue was dissolved by adding acetic acid (2.1 mL) and methanol (2.1 mL), 10% palladium/carbon (25 mg) was added, and the mixture was stirred at normal pressure under a hydrogen atmosphere at room temperature for 5 hr. The catalyst was filtered off and the filtrate was concentrated under reduced pressure. To the obtained residue (0.34 g) and B-1 (76 mg, 0.26 mmol), triethylamine (0.054 mL, 0.39 mmol), WSC hydrochloride (74 mg, 0.39 mmol) and 1-hydroxy-7-azabenzotriazole (18 mg, 0.13 mmol) was added N,N-dimethylformamide (2.6 mL), and the mixture was stirred at room temperature for 3 hr. To the reaction mixture was added water, and the mixture was extracted with ethyl acetate. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (0.13 g, 0.23 mmol, 55%).

MS (ESI) m/z 572 (M+H)$^+$ $^1$H NMR (400 MHz, DMSO-d$_6$) δ 10.47 (s, 1H), 8.68 (dd, J=6.0, 6.0 Hz, 1H), 8.14 (d, J=8.1 Hz, 2H), 7.92 (d, J=8.1 Hz, 2H), 7.83 (ddd, J=8.0, 1.3, 0.9 Hz, 1H), 7.75 (dd, J=8.4, 0.9 Hz, 1H), 7.73-7.72 (m, 1H), 7.71 (d, J=0.9 Hz, 1H), 7.64-7.60 (m, 1H), 7.56 (ddd, J=8.4, 7.2, 1.3 Hz, 1H), 7.42 (ddd, J=8.0, 7.2, 0.9 Hz, 1H), 7.33 (t, J=7.9 Hz, 1H), 7.06 (d, J=7.8 Hz, 1H), 4.39-4.24 (m, 3H), 3.65-3.57 (m, 1H), 3.45-3.35 (m, 1H), 1.99-1.84 (m, 3H), 1.72-1.60 (m, 1H).

Example 301 to Example 306 described in Table 31 were synthesized by using the compounds described in Reference Examples and corresponding commercially available reagents and by an operation similar to that in Example 37.

TABLE 31

| Example No. | structural formula | compound name |
|---|---|---|
| 301 | | (2S)-2-(furo[3,2-c]pyridin-2-ylsulfonylamino)-N-[[6-[4-(trifluoromethyl)phenyl]pyrimidin-4-yl]methyl]propanamide |

TABLE 31-continued

| Example No. | structural formula | compound name |
|---|---|---|
| 302 | | (2S)-2-(furo[3,2-c]pyridin-2-ylsulfonylamino)-N-[[2-[6-(trifluoromethyl)-3-pyridyl]-4-pyridyl]methyl]propanamide |
| 303 | | (2S)-2-(furo[3,2-c]pyridin-2-ylsulfonylamino)-N-[[2-[2-hydroxy-4-(trifluoromethyl)phenyl]-4-pyridyl]methyl]propanamide |
| 304 | | (2S)-2-(furo[3,2-c]pyridin-2-ylsulfonylamino)-N-[[4-[5-(trifluoromethyl)-2-pyridyl]-2-pyridyl]methyl]propanamide |
| 305 | | (2S)-2-(furo[3,2-c]pyridin-2-ylsulfonylamino)-N-[[6-[4-(trifluoromethoxy)phenyl]pyrimidin-4-yl]methyl]propanamide |
| 306 | | (2S)-1-furo[3,2-c]pyridin-2-ylsulfonyl-N-[[6-[4-(trifluoromethoxy)phenyl]pyrimidin-4-yl]methyl]pyrrolidine-2-carboxamide |

Example 307

Synthesis of (2S)-1-(benzofuran-2-ylsulfonyl)-N-[[4-fluoro-3-[4-(trifluoromethyl)phenyl]phenyl]methyl]pyrrolidine-2-carboxamide (307)

(step 1) Synthesis of (2S)-1-(benzofuran-2-ylsulfonyl)-N-[(3-bromo-4-fluoro-phenyl)methyl]pyrrolidine-2-carboxamide To B-1 (0.30 g, 1.0 mmol), 3-bromo-4-fluorobenzylamine (0.24 g, 1.0 mmol), WSC hydrochloride (0.38 g, 2.0 mmol) and 1-hydroxy-7-azabenzotriazole (0.27 g, 2.0 mmol) were added dichloromethane (10 mL) and triethylamine (0.54 mL, 3.0 mmol), and the mixture was stirred at room temperature for 30 min. The reaction mixture was partitioned by adding dichloromethane and saturated aqueous sodium hydrogen carbonate. The organic layer was dried over sodium sulfate. The desiccant was filtered off, and the solvent was evaporated to give the title compound as a crudely purified product (0.54 g).

MS (ESI) m/z 481 (M+H)$^+$ (step 2) Synthesis of (2S)-1-(benzofuran-2-ylsulfonyl)-N-[[4-fluoro-3-[4-(trifluoromethyl)phenyl]phenyl]methyl]pyrrolidine-2-carboxamide (307)

To the crudely purified product (48 mg) obtained in step 1, 4-(trifluoromethyl)phenylboronic acid (19 mg, 0.10 mmol), and 1,1'-bis(diphenylphosphino)ferrocenedichloropalladium(II) (7.3 mg, 0.010 mmol) were added 1,4-dioxane (0.7 mL) and 1 mol/L aqueous sodium carbonate solution (0.7 mL) and the mixture was stirred with heating by using a microwave reactor at 100° C. for 10 min. The reaction mixture was neutralized with trifluoroacetic acid, and purified by high performance liquid chromatography (water-acetonitrile, each containing 0.1% trifluoroacetic acid) to give the title compound (21 mg, 0.039 mmol, 39%).

MS (ESI) m/z 547 (M+H)$^+$ $^1$H NMR (400 MHz, DMSO-d$_6$) δ 8.75 (t, J=6.1 Hz, 1H), 7.87-7.81 (m, 3H), 7.78 (d, J=8.1 Hz, 2H), 7.74 (dd, J=8.5, 1.0 Hz, 1H), 7.72 (d, J=0.9 Hz, 1H), 7.56 (ddd, J=8.5, 7.2, 1.3 Hz, 1H), 7.52 (dd, J=7.7, 2.2 Hz, 1H), 7.44-7.40 (m, 1H), 7.40-7.29 (m, 2H), 4.41 (dd, J=15.4, 6.2 Hz, 1H), 4.35 (dd, J=15.4, 6.0 Hz, 1H), 4.30 (dd, J=8.2, 3.7 Hz, 1H), 3.64-3.56 (m, 1H), 3.42-3.35 (m, 1H), 1.98-1.82 (m, 3H), 1.68-1.59 (m, 1H).

Example 308 described in Table 32 was synthesized by using the compounds described in Reference Examples and corresponding commercially available reagents and by an operation similar to that in Example 307.

Example 310

Synthesis of (2S)-1-(benzofuran-2-ylsulfonyl)-N-[[3-methoxy-5-[6-(trifluoromethyl)-3-pyridyl]phenyl]methyl]pyrrolidine-2-carboxamide (310)

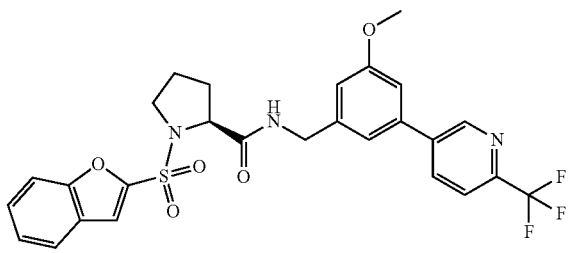

(step 1) Synthesis of 3-methoxy-5-[6-(trifluoromethyl)-3-pyridyl]benzonitrile

To 3-bromo-5-methoxybenzonitrile (0.11 g, 0.50 mmol), [6-(trifluoromethyl)-3-pyridyl]boronic acid (95 mg, 0.50

TABLE 32

| Example No. | structural formula | compound name |
| --- | --- | --- |
| 307 | | (2S)-1-(benzofuran-2-ylsulfonyl)-N-[[4-fluoro-3-[4-(trifluoromethyl)phenyl]phenyl]methyl]pyrrolidine-2-carboxamide |
| 308 | | (2S)-1-(benzofuran-2-ylsulfonyl)-N-[[4-fluoro-3-[2-hydroxy-4-(trifluoromethyl)phenyl]phenylmethyl]pyrrolidine-2-carboxamide |

Example 309

Synthesis of (2S)-1-(benzofuran-2-ylsulfonyl)-N-[[4-fluoro-3-[5-(trifluoromethyl)-2-pyridyl]phenyl]methyl]pyrrolidine-2-carboxamide (309)

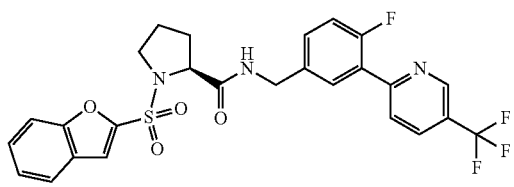 [SMILES: O=C(NCc1ccc(F)c(-c2ccc(C(F)(F)F)cn2)c1)[C@@H]1CCCN1S(=O)(=O)c1cc2ccccc2o1]

Using the compound obtained in Example 307, step 1, instead of C-5, and by an operation similar to that in Example 178, the title compound was obtained (yield 3%).

MS (ESI) m/z 548 (M+H)$^+$ mmol), and 1,1'-bis(diphenylphosphino)ferrocenedichloropalladium(II) (37 mg, 0.050 mmol) were added 1,4-dioxane (5 mL) and 1 mol/L aqueous sodium carbonate solution (5 mL) and the mixture was stirred with heating by using a microwave reactor at 100° C. for 20 min. To the reaction mixture was added water and the mixture was extracted with ethyl acetate. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (84 mg, 0.030 mmol, 61%).

MS (ESI) m/z 279 (M+H)$^+$ (step 2) Synthesis of [3-methoxy-5-[6-(trifluoromethyl)-3-pyridyl]phenyl]methylamine To a solution of the compound (0.28 g, 1.0 mmol) obtained in step 1 in acetic acid (5 mL) was added 10% palladium/carbon (240 mg), and the mixture was stirred under a hydrogen atmosphere at room temperature for 3 hr. The catalyst was filtered off, and the filtrate was concentrated under reduced pressure and the obtained residue was purified by high performance liquid chromatography (water-acetonitrile, each containing 0.1% trifluoroacetic acid) to give trifluoroacetate of the title compound (0.10 g, 0.26 mmol, 26%).

MS (ESI) m/z 283 (M+H)+

(step 3) Synthesis of (2S)-1-(benzofuran-2-ylsulfonyl)-N-[[3-methoxy-5-[6-(trifluoromethyl)-3-pyridyl]phenyl]methyl]pyrrolidine-2-carboxamide (310)

Using the compound obtained in step 2 instead of D-1, and by an operation similar to that in Example 37, the title compound was obtained (yield 16%).

MS (ESI) m/z 560 (M+H)+
1H NMR (400 MHz, DMSO-d6) δ 9.09 (d, J=2.0 Hz, 1H), 8.77 (dd, J=6.3, 5.8 Hz, 1H), 8.36 (dd, J=8.2, 2.0 Hz, 1H), 7.98 (d, J=8.2 Hz, 1H), 7.83 (dd, J=8.3, 0.8 Hz, 1H), 7.79-7.71 (m, 2H), 7.56 (ddd, J=8.3, 7.2, 1.3 Hz, 1H), 7.42 (ddd, J=7.5, 7.2, 0.8 Hz, 1H), 7.31 (dd, J=1.7, 1.4 Hz, 1H), 7.26 (dd, J=2.2, 1.7 Hz, 1H), 7.00 (dd, J=2.2, 1.4 Hz, 1H), 4.45 (dd, J=15.7, 6.3 Hz, 1H), 4.41-4.28 (m, 2H), 3.85 (s, 3H), 3.67-3.56 (m, 1H), 3.42-3.36 (m, 1H), 2.01-1.83 (m, 3H), 1.70-1.58 (m, 1H).

Example 311

Synthesis of (2S)-1-(benzofuran-2-ylsulfonyl)-N-[[2-isobutoxy-6-[4-(trifluoromethyl)phenyl]pyrimidin-4-yl]methyl]pyrrolidine-2-carboxamide (311)

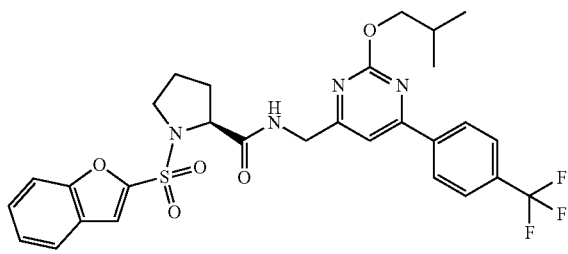 [SMILES: CC(C)COc1nc(CNC(=O)[C@@H]2CCCN2S(=O)(=O)c2cc3ccccc3o2)cc(-c2ccc(C(F)(F)F)cc2)n1]

(step 1) Synthesis of tert-butyl N-[[2-benzylsulfanyl-6-[4-(trifluoromethyl)phenyl]pyrimidin-4-yl]methyl]carbamate To a solution of tert-butyl N-prop-2-ynyl carbamate (5.0 g, 32 mmol) in tetrahydrofuran (100 mL) were added 4-trifluoromethylbenzoylchloride (4.3 mL, 29 mmol), dichlorobis(triphenylphosphine)palladium(II) (0.25 g, 0.36 mmol) and copper(I) iodide (0.25 g, 1.3 mmol) and the mixture was stirred at room temperature for 5 min. Triethylamine (5.5 mL, 39 mmol) was added and the mixture was stirred for 30 min. Using a small amount of silica gel, the insoluble material was filtered off, and the filtrate was concentrated under reduced pressure. The obtained residue was dissolved in acetonitrile (300 mL), and S-benzylisothiourea hydrochloride (7.5 g, 37 mmol) and potassium carbonate (6.0 g, 43 mmol) were added. The reaction mixture was stirred at 70° C. overnight, dichloromethane was added and the mixture was washed with water. The organic layer was dried over sodium sulfate, and the desiccant was filtered off. The solvent was evaporated and the obtained residue was purified by silica gel column chromatography (hexane/ethyl acetate) to give the title compound (4.0 g, 8.4 mmol, 26%)

MS (ESI) m/z 476 (M+H)+

(step 2) Synthesis of (2S)-1-(benzofuran-2-ylsulfonyl)-N-[[2-benzylsulfanyl-6-[4-(trifluoromethyl)phenyl]pyrimidin-4-yl]methyl]pyrrolidine-2-carboxamide To the compound (0.48 g, 1.0 mmol) obtained in step 1 was added 4 mol/L hydrochloric acid (1,4-dioxane solution, 5 mL, 20 mmol), and the mixture was stirred at room temperature for 1.5 hr. The reaction mixture was concentrated under reduced pressure. To the obtained residue were added B-1 (0.30 g, 1.0 mmol), WSC hydrochloride (0.29 g, 1.5 mmol) and 1-hydroxy-7-azabenzotriazole (0.14 g, 1.0 mmol), dichloromethane (5 mL) and triethylamine (0.20 mL, 1.4 mmol), and the mixture was stirred at room temperature for 1.5 hr. The reaction mixture was concentrated under reduced pressure and the obtained residue was purified by high performance liquid chromatography (water-acetonitrile, each containing 0.1% trifluoroacetic acid) to give the title compound (0.13 g, 0.20 mmol, 20%).

MS (ESI) m/z 653 (M+H)+

(step 3) (2S)-1-(benzofuran-2-ylsulfonyl)-N-[[2-benzylsulfonyl-6-[4-(trifluoromethyl)phenyl]pyrimidin-4-yl]methyl]pyrrolidine-2-carboxamide To a solution of the compound (0.16 g, 0.25 mmol) obtained in step 2 in dichloromethane (2 mL) was added 3-chloroperbenzoic acid (0.42 g, 2.5 mmol) at 0° C., and the mixture was stirred at room temperature for 3 hr. To the reaction mixture was added 1 mol/L aqueous sodium hydroxide solution, and the mixture was extracted with dichloromethane. The organic layer was dried over sodium sulfate. The desiccant was filtered off, and the solvent was evaporated to give the title compound (0.15 g, 0.23 mmol, 92%).

MS (ESI) m/z 685 (M+H)+

(step 4) Synthesis of (2S)-1-(benzofuran-2-ylsulfonyl)-N-[[2-isobutoxy-6-[4-(trifluoromethyl)phenyl]pyrimidin-4-yl]methyl]pyrrolidine-2-carboxamide (311)

To 2-methyl-1-propanol (0.20 mL) was added sodium hydride (60% in oil, 4.8 mg, 0.12 mmol) and the mixture was stirred for 5 min. A solution of the compound (50 mg, 0.073 mmol) obtained in step 3 in N,N-dimethylformamide (1 mL) was added, and the mixture was stirred with heating by using a microwave reactor at 100° C. for 10 min. The reaction mixture was concentrated under reduced pressure and the obtained residue was purified by high performance liquid chromatography (water-acetonitrile, each containing 0.1% trifluoroacetic acid) to give the title compound (4.8 mg, 0.0080 mmol, 11%).

MS (ESI) m/z 603 (M+H)+
1H NMR (400 MHz, DMSO-d6) δ 8.92 (dd, J=6.2, 5.7 Hz, 1H), 8.36 (d, J=8.1 Hz, 2H), 7.91 (d, J=8.1 Hz, 2H), 7.84 (ddd, J=7.7, 1.3, 0.9 Hz, 1H), 7.79 (d, J=0.9 Hz, 1H), 7.76 (dd, J=8.4, 0.9 Hz, 1H), 7.69 (s, 1H), 7.57 (ddd, J=8.4, 7.3, 1.3 Hz, 1H), 7.43 (ddd, J=7.7, 7.3, 0.9 Hz, 1H), 4.46 (dd, J=17.3, 6.2 Hz, 1H), 4.40-4.31 (m, 2H), 4.21 (d, J=6.6 Hz, 2H), 3.67-3.59 (m, 1H), 3.49-3.40 (m, 1H), 2.18-2.03 (m, 1H), 2.05-1.88 (m, 3H), 1.73-1.62 (m, 1H), 1.02 (d, J=6.7 Hz, 6H).

Example 312

Synthesis of (2S)-1-(benzofuran-2-ylsulfonyl)-N-[[2-(dimethylamino)-6-[4-(trifluoromethyl)phenyl]pyrimidin-4-yl]methyl]pyrrolidine-2-carboxamide (312)

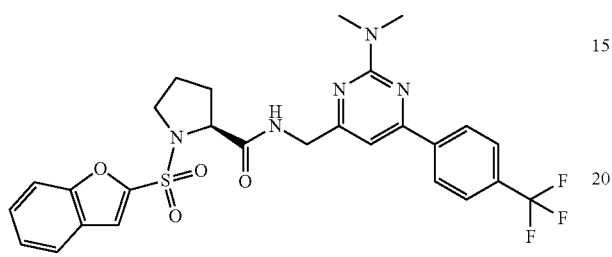

To a solution of the compound (68 mg, 0.10 mmol) obtained in Example 311, step 3 in N,N-dimethylformamide (1 mL) was added 2 mol/L dimethylamine (tetrahydrofuran solution, 0.30 mL, 0.60 mmol), and the mixture was stirred with heating by using a microwave reactor at 100° C. for 10 min. The reaction mixture was concentrated under reduced pressure and the obtained residue was purified by high performance liquid chromatography (water-acetonitrile, each containing 0.1% trifluoroacetic acid) to give trifluoroacetate of the title compound (10 mg, 0.015 mmol, 15%).

MS (ESI) m/z 574 (M+H)$^+$ $^1$H NMR (400 MHz, DMSO-d$_6$) δ 8.80 (dd, J=6.1, 5.7 Hz, 1H), 8.32 (d, J=8.1 Hz, 2H), 7.90-7.81 (m, 3H), 7.78 (d, J=0.9 Hz, 1H), 7.76 (dd, J=8.4, 0.8 Hz, H), 7.57 (ddd, J=8.4, 7.3, 1.3 Hz, 1H), 7.47-7.38 (m, 1H), 7.20 (s, 1H), 4.42-4.31 (m, 2H), 4.25 (dd, J=17.1, 5.7 Hz, 1H), 3.68-3.57 (m, 1H), 3.42-3.36 (m, 1H), 3.23 (s, 6H), 2.03-1.85 (m, 3H), 1.72-1.60 (m, 1H).

Example 313

Synthesis of (2S)-2-[but-2-ynyl-(5-fluorobenzofuran-2-yl)sulfonyl-amino]-N-[[2-[6-(trifluoromethyl)-3-pyridyl]-4-pyridyl]methyl]propanamide (313)

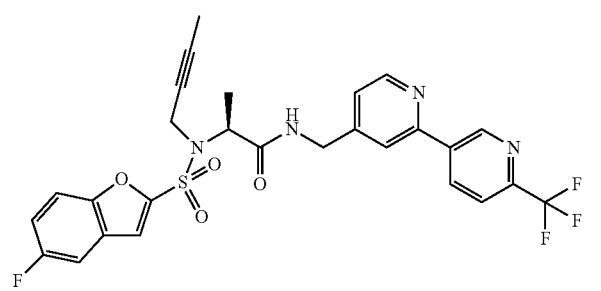 [SMILES: CC#CCN([C@@H](C)C(=O)NCc1ccnc(-c2ccc(C(F)(F)F)nc2)c1)S(=O)(=O)c1cc2cc(F)ccc2o1]

To a solution of (2S)-2-[(5-fluorobenzofuran-2-yl)sulfonylamino]-N-[[2-[6-(trifluoromethyl)-3-pyridyl]-4-pyridyl]methyl]propanamide (236) (30 mg, 0.058 mmol), potassium carbonate (24 mg, 0.17 mmol) in N,N-dimethylformamide (0.6 mL) was added 1-bromo-2-butyne (7.6 L, 0.086 mmol), and the mixture was stirred at room temperature for 3 hr. Using acetonitrile, the insoluble material was filtered and purified by high performance liquid chromatography (water-acetonitrile, each containing 0.1% trifluoroacetic acid) to give trifluoroacetate of the title compound (33 mg, 0.048 mmol, 83%).

MS (ESI) m/z 575 (M+H)$^+$ $^1$H NMR (400 MHz, DMSO-d$_6$) δ 9.41 (s, 1H), 8.76 (t, J=5.9 Hz, 1H), 8.71-8.65 (m, 2H), 8.05 (d, J=8.3 Hz, 1H), 8.01 (s, 1H), 7.74 (dd, J=9.1, 4.1 Hz, 1H), 7.66 (s, 1H), 7.61 (dd, J=8.5, 2.7 Hz, 1H), 7.44-7.34 (m, 1H), 7.31 (dd, J=5.1, 1.5 Hz, 1H), 4.74 (q, J=7.2 Hz, 1H), 4.43-4.33 (m, 2H), 4.33-4.24 (m, 2H), 1.51 (d, J=7.2 Hz, 3H), 1.48-1.40 (m, 3H).

Example 314

Synthesis of (2S)-2-[(5-fluorobenzofuran-2-yl)sulfonyl-prop-2-ynyl-amino]-N-[[2-[6-(trifluoromethyl)-3-pyridyl]-4-pyridyl]methyl]propanamide (314)

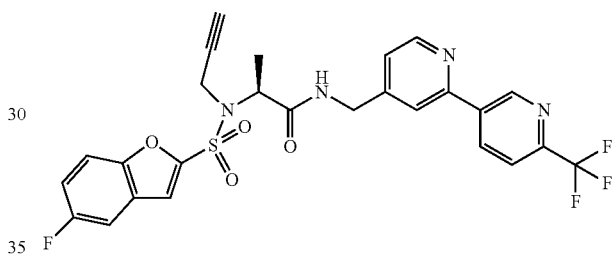

Using propargylbromide instead of 1-bromo-2-butyne, and by an operation similar to that in Example 313, trifluoroacetate of the title compound (yield 50%) was obtained.

MS (ESI) m/z 561 (M+H)$^+$ $^1$H NMR (400 MHz, DMSO-d$_6$) δ 9.40 (s, 1H), 8.78 (t, J=5.9 Hz, 1H), 8.71-8.64 (m, 2H), 8.05 (d, J=8.2 Hz, 1H), 7.99 (s, 1H), 7.70 (dd, J=9.1, 4.1 Hz, 1H), 7.65 (s, 1H), 7.58 (dd, J=8.5, 2.7 Hz, 1H), 7.38 (td, J=9.2, 2.8 Hz, 1H), 7.29 (dd, J=5.1, 1.5 Hz, 1H), 4.75 (q, J=7.2 Hz, 1H), 4.44-4.29 (m, 4H), 3.18-3.12 (m, 1H), 1.53 (d, J=7.2 Hz, 3H).

Example 315

Synthesis of (2S)-1-(benzofuran-2-ylsulfonyl)-N-[[3-[[4-(trifluoromethyl)phenyl]methylsulfanyl]phenyl]methyl]pyrrolidine-2-carboxamide (315)

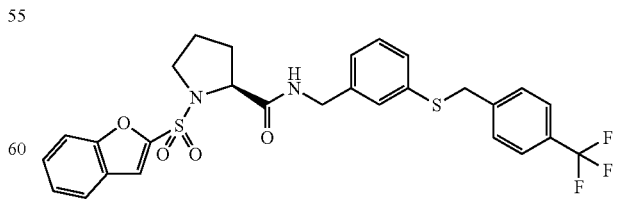

To 3-fluorobenzonitrile (73 mg, 0.19 mmol) and [4-(trifluoromethyl)phenyl]methanethiol (0.15 g, 0.79 mmol) and potassium tert-butoxide (0.21 g, 1.8 mmol) was added N,N-dimethylformamide (1.6 mL) and the mixture was stirred with heating by using a microwave reactor at 100° C. for 10 min. To the reaction mixture was added water, and the mixture was extracted with ethyl acetate. The organic layer was dried over sodium sulfate, the desiccant was filtered off, and the solvent was evaporated. The obtained residue was dissolved by adding tetrahydrofuran (3.0 mL), 0.95 mol/L borane-tetrahydrofuran solution (3.2 mL, 3.0 mmol) was added, and the mixture was stirred at room temperature for 5.5 hr. To the reaction mixture was added 1 mol/L hydrochloric acid until pH1 and the mixture was stirred for 10 min. 1 mol/L Aqueous sodium hydroxide solution was added and the mixture was extracted with ethyl acetate. The organic layer was dried over sodium sulfate, the desiccant was filtered off, and the solvent was evaporated. To the obtained residue, B-1 (59 mg, 0.20 mmol), triethylamine (0.17 mL, 1.2 mmol), WSC hydrochloride (58 mg, 0.30 mmol) and 1-hydroxy-7-azabenzotriazole (14 mg, 0.10 mmol) was added so acetonitrile (2.0 mL), and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (48 mg, 0.083 mmol, 14%).

MS (ESI) m/z 575 (M+H)$^+$ $^1$H NMR (400 MHz, DMSO-d$_6$) δ 8.66 (dd, J=6.0, 5.9 Hz, 1H), 7.83 (d, J=7.8 Hz, 1H), 7.74 (d, J=8.9 Hz, 1H), 7.71 (d, J=1.0 Hz, 1H), 7.64 (d, J=8.1 Hz, 2H), 7.57 (d, J=8.1 Hz, 2H), 7.57-7.53 (m, 1H), 7.46-7.39 (m, 1H), 7.30 (dd, J=1.6, 1.6 Hz, 1H), 7.28-7.17 (m, 2H), 7.09 (d, J=7.4 Hz, 1H), 4.34 (s, 2H), 4.32-4.28 (m, 2H), 4.24 (dd, J=15.5, 5.9 Hz, 1H), 3.63-3.55 (m, 1H), 3.48-3.37 (m, 1H), 1.96-1.80 (m, 3H), 1.68-1.59 (m, 1H).

Example 316

Synthesis of (2S)-1-(benzofuran-2-ylsulfonyl)-N-[[3-[[4-(trifluoromethyl)phenyl]methylsulfinyl]phenyl]methyl]pyrrolidine-2-carboxamide (316)

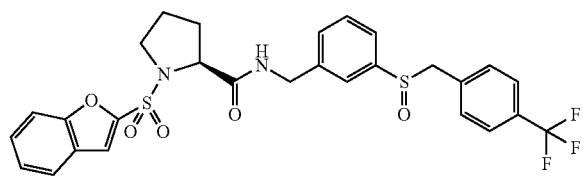 [SMILES: O=C(NCc1cccc(S(=O)Cc2ccc(C(F)(F)F)cc2)c1)[C@@H]1CCCN1S(=O)(=O)c1cc2ccccc2o1]

To (2S)-1-(benzofuran-2-ylsulfonyl)-N-[[3-[[4-(trifluoromethyl)phenyl]methylsulfanyl]phenyl]methyl]pyrrolidine-2-carboxamide(315) (43 mg, 0.075 mmol) and 3-chloroperbenzoic acid (30 mg, 0.11 mmol) was added dichloromethane (1.5 mL) and the mixture was stirred 0° C. for 5 hr. To the reaction mixture were added saturated aqueous sodium hydrogen carbonate and saturated aqueous sodium thiosulfate solution, and the mixture was extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (2.3 mg, 0.0040 mmol, 5%).

MS (ESI) m/z 591 (M+H)$^+$ $^1$H NMR (400 MHz, DMSO-d$_6$) δ 8.77 (dd, J=6.0, 6.0 Hz, 1H), 7.85-7.82 (m, 1H), 7.77-7.73 (m, 2H), 7.63 (d, J=7.8 Hz, 2H), 7.56 (ddd, J=8.2, 7.2, 1.1 Hz, 1H), 7.53-7.48 (m, 1H), 7.48-7.40 (m, 3H), 7.35 (dt, J=7.4, 1.7 Hz, 1H), 7.30 (d, J=7.4 Hz, 2H), 4.44-4.33 (m, 3H), 4.33-4.28 (m, 1H), 4.13 (dd, J=12.7, 3.8 Hz, 1H), 3.66-3.55 (m, 1H), 3.49-3.36 (m, 1H), 1.99-1.81 (m, 3H), 1.71-1.57 (m, 1H).

Example 317

Synthesis of (2S)-1-(benzofuran-2-ylsulfonyl)-N-[[3-[(E)-2-[4-(trifluoromethyl)phenyl]vinyl]phenyl]methyl]pyrrolidine-2-carboxamide (317)

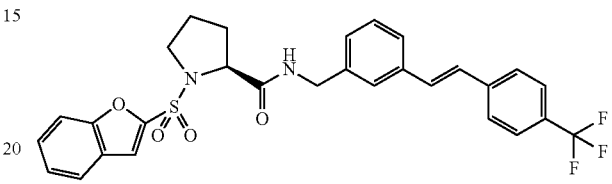

(step 1) Synthesis of (2S)-1-(benzofuran-2-ylsulfonyl)-N-[(3-iodophenyl)methyl]pyrrolidine-2-carboxamide To B-1 (0.30 g, 1.0 mmol), 3-iodobenzylamine hydrochloride (0.33 mg, 1.2 mmol), triethylamine (0.43 mL, 3.1 mmol), WSC hydrochloride (0.29 g, 1.5 mmol) and 1-hydroxy-7-azabenzotriazole (69 mg, 0.51 mmol) was added dichloromethane (10 mL), and the mixture was stirred at room temperature for 24 hr. To the reaction mixture was added water, and the mixture was extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (0.29 g, 0.56 mmol, 55%).

MS (ESI) m/z 511 (M+H)$^+$ (step 2) Synthesis of (2S)-1-(benzofuran-2-ylsulfonyl)-N-[[3-[(E)-2-[4-(trifluoromethyl)phenyl]vinyl]phenyl]methyl]pyrrolidine-2-carboxamide (317)

To the compound (96 mg, 0.19 mmol) obtained in step 1, 4-(trifluoromethyl)styrene (65 mg, 0.38 mmol), palladium (II) acetate (4.2 mg, 0.019 mmol), triphenylphosphine (9.9 mg, 0.038 mmol) and triethylamine (0.13 mL, 0.94 mmol) was added N,N-dimethylformamide (1.9 mL) and the mixture was stirred at 100° C. for 22 hr. To the reaction mixture was added water, and the mixture was extracted with ethyl acetate. The organic layer was dried over sodium sulfate. The desiccant was filtered off, and the solvent was evaporated. The obtained residue was purified by silica gel column chromatography (hexane/ethyl acetate) to give the title compound (30 mg, 0.055 mmol, 29%).

MS (ESI) m/z 555 (M+H)$^+$ $^1$H NMR (400 MHz, DMSO-d$_6$) δ 8.72 (dd, J=6.1, 6.0 Hz, 1H), 7.86-7.82 (m, 1H), 7.80 (d, J=8.2 Hz, 2H), 7.77-7.70 (m, 4H), 7.61 (t, J=1.7 Hz, 1H), 7.56 (ddd, J=8.6, 7.3, 1.3 Hz, 1H), 7.50 (d, J=7.7 Hz, 1H), 7.46-7.33 (m, 4H), 7.23 (d, J=7.7 Hz, 1H), 4.41 (dd, J=15.5, 6.1 Hz, 1H), 4.36-4.29 (m, 2H), 3.68-3.57 (m, 1H), 3.47-3.35 (m, 1H), 1.99-1.85 (m, 3H), 1.71-1.60 (m, 1H).

Example 318

Synthesis of (2S)-1-(benzofuran-2-ylsulfonyl)-N-[[3-[2-[4-(trifluoromethyl)phenyl]ethyl]phenyl]methyl]pyrrolidine-2-carboxamide (318)

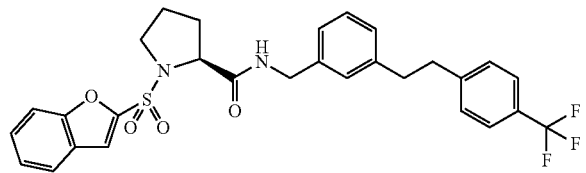 [SMILES: O=C(NCc1cccc(CCc2ccc(C(F)(F)F)cc2)c1)[C@@H]1CCCN1S(=O)(=O)c1cc2ccccc2o1]

(2S)-1-(benzofuran-2-ylsulfonyl)-N-[[3-[(E)-2-[4-(trifluoromethyl)phenyl]vinyl]phenyl]methyl]pyrrolidine-2-carboxamide (317) (28 mg, 0.050 mmol) was dissolved by adding methanol (1.0 mL), 10% palladium/carbon (15 mg) was added, and the mixture was stirred at normal pressure under a hydrogen atmosphere at room temperature for 5 hr. The catalyst was filtered off and the filtrate was concentrated under reduced pressure and the obtained residue was purified by high performance liquid chromatography (water-acetonitrile, each containing 0.1% trifluoroacetic acid) to give the title compound (20 mg, 0.036 mmol, 72%).

MS (ESI) m/z 557 (M+H)$^+$ $^1$H NMR (400 MHz, DMSO-d$_6$) δ 8.64 (dd, J=6.0, 5.9 Hz, 1H), 7.83 (ddd, J=8.0, 1.0, 1.2 Hz, 1H), 7.74 (ddd, J=8.4, 1.0, 0.9 Hz, 1H), 7.72 (d, J=1.0 Hz, 1H), 7.62 (d, J=8.0 Hz, 2H), 7.56 (ddd, J=8.4, 7.3, 1.2 Hz, 1H), 7.46 (d, J=8.0 Hz, 2H), 7.42 (ddd, J=8.0, 7.3, 1.0 Hz, 1H), 7.27-7.20 (m, 2H), 7.10 (dd, J=7.7, 1.7 Hz, 2H), 4.38-4.29 (m, 2H), 4.25 (dd, J=15.4, 5.9 Hz, 1H), 3.64-3.54 (m, 1H), 3.43-3.34 (m, 1H), 3.01-2.93 (m, 2H), 2.93-2.85 (m, 2H), 1.93-1.76 (m, 3H), 1.69-1.54 (m, 1H).

Example 319

Synthesis of (2S)—N-[(3-benzylphenyl)methyl]-1-(5-fluorobenzofuran-2-yl)sulfonyl-pyrrolidine-2-carboxamide (319)

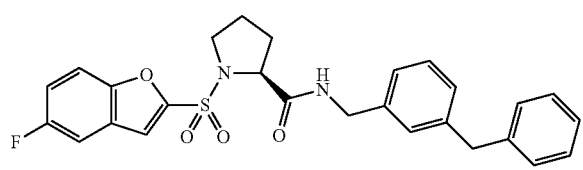 [SMILES: O=C(NCc1cccc(Cc2ccccc2)c1)[C@@H]1CCCN1S(=O)(=O)c1cc2cc(F)ccc2o1]

To C-10 (37 mg, 0.071 mmol) and 2-benzyl-4,4,5,5-tetramethyl-1,3,2-dioxaborolane (0.22 mL, 0.099 mmol), tetrakis(triphenylphosphine)palladium(0) (8.2 mg, 0.0071 mmol), triphenylphosphine (8.0 mg, 0.0304 mmol), silver oxide(I) (26 mg, 0.11 mmol) and potassium carbonate (15 mg, 0.11 mmol) was added 1,2-dimethoxyethane (1.0 mL) and the mixture was stirred 80° C. for 20 hr. The catalyst was filtered off and the mixture was concentrated under reduced pressure, the obtained residue was purified by silica gel column chromatography (hexane/ethyl acetate) to give the title compound (8.8 mg, 0.018 mmol, 25%)

MS (ESI) m/z 493 (M+H)$^+$

Example 320

Synthesis of (2S)-1-(benzofuran-2-ylsulfonyl)-N-[[3-[[[5-(trifluoromethyl)-2-pyridyl]amino]methyl]phenyl]methyl]pyrrolidine-2-carboxamide (320)

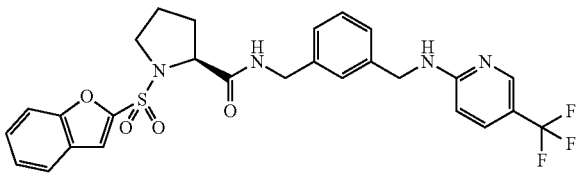 [SMILES: O=C(NCc1cccc(CNc2ccc(C(F)(F)F)cn2)c1)[C@@H]1CCCN1S(=O)(=O)c1cc2ccccc2o1]

(step 1) Synthesis of 3-[[[5-(trifluoromethyl)-2-pyridyl]amino]methyl]benzonitrile To 3-cyanobenzylalcohol (0.13 g, 0.95 mmol) and methanesulfonylchloride (0.088 mL, 1.1 mmol), pyridine (0.12 mL, 1.4 mmol) was added dichloromethane (4.5 mL), and the mixture was stirred at room temperature for 6 hr. To the reaction mixture was added water, and the mixture was extracted with dichloromethane. The organic layer was dried over sodium sulfate. The desiccant was filtered off, and the solvent was evaporated. To the obtained residue, 2-amino-5-(trifluoromethyl)pyridine (0.18 g, 1.1 mmol), tetra-n-butylammonium iodide (0.21 g, 0.56 mmol) and potassium carbonate (0.23 g, 1.7 mmol) was added acetonitrile (5.5 mL), and the mixture was stirred at 80° C. for 21 hr. The insoluble material was filtered off, concentrated under reduced pressure, and the obtained residue was purified by silica gel column chromatography (hexane/ethyl acetate) to give the title compound (38 mg, 0.014 mmol, 15%).

MS (ESI) m/z 278 (M+H)$^+$ (step 2) Synthesis of (2S)-1-(benzofuran-2-ylsulfonyl)-N-[[3-[[[5-(trifluoromethyl)-2-pyridyl]amino]methyl]phenyl]methyl]pyrrolidine-2-carboxamide (320)

To lithium aluminum hydride (12 mg, 0.28 mmol) were added tetrahydrofuran (1.4 mL) and the compound (38 mg, 0.14 mmol) obtained in step 1, and the mixture was stirred at room temperature for 1.5 hr. To the reaction mixture was added 1.0 mol/L aqueous sodium hydroxide solution, and the insoluble material was filtered off, and concentrated under reduced pressure. To the obtained residue, B-1 (41 mg, 0.14 mmol), triethylamine (0.058 mL, 0.41 mmol), WSC hydrochloride (40 mg, 0.21 mmol) and 1-hydroxy-7-azabenzotriazole (9.4 mg, 0.069 mmol) was added dichloromethane (1.4 mL), and the mixture was stirred at room temperature for 1 hr. The reaction mixture was concentrated under reduced pressure and the obtained residue was purified by high performance liquid chromatography (water-acetonitrile, each containing 0.1% trifluoroacetic acid) to give the title compound (12 mg, 0.021 mmol, 15%).

MS (ESI) m/z 559 (M+H)$^+$ $^1$H NMR (400 MHz, DMSO-d$_6$) δ 8.63 (dd, J=6.1, 6.1 Hz, 1H), 8.28-8.26 (m, 1H), 7.87-7.80 (m, 2H), 7.74 (dd, J=8.4, 0.9 Hz, 1H), 7.70 (d, J=0.9 Hz, 1H), 7.63 (dd, J=8.9, 2.6 Hz, 1H), 7.55 (ddd, J=8.4, 7.3, 1.3 Hz, 1H), 7.42 (ddd, J=8.0, 7.3, 0.9 Hz, 1H), 7.27 (t, J=7.5 Hz, 1H), 7.22 (s, 1H), 7.20-7.13 (m, 2H), 6.62 (d, J=8.9 Hz, 1H), 4.52 (d, J=5.9 Hz, 2H), 4.37-4.20 (m, 3H), 3.60-3.53 (m, 1H), 3.41-3.34 (m, 1H), 1.91-1.75 (m, 3H), 1.65-1.56 (m, 1H).

Example 321

Synthesis of (2S)-1-(benzofuran-2-ylsulfonyl)-N-[[3-[4-(trifluoromethyl)phenyl]sulfanylphenyl]methyl]pyrrolidine-2-carboxamide (321)

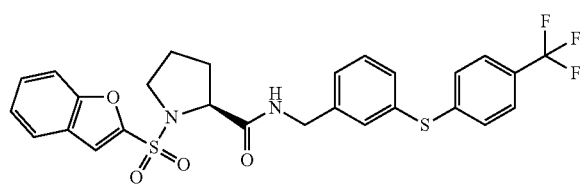 [SMILES: O=C(NCc1cccc(Sc2ccc(C(F)(F)F)cc2)c1)[C@@H]1CCCN1S(=O)(=O)c1cc2ccccc2o1]

To the compound (0.19 g, 0.37 mmol) obtained in Example 317, step 1, 4-(trifluoromethyl)thiophenol (0.054 mL, 0.41 mmol), tris(dibenzylideneacetone)dipalladium(0) (8.5 mg, 0.0093 mmol), 4,5-bis(diphenylphosphino)-9,9-dimethylxanthene (11 mg, 0.019 mmol) and N,N-diisopropylethylamine (0.13 mL, 0.74 mmol) was added 1,4-dioxane (3.7 mL) and the mixture was stirred with heating at 80° C. for 12 hr. To the reaction mixture was added water, and the mixture was extracted with ethyl acetate. The organic layer was dried over sodium sulfate, the desiccant was filtered off, and the solvent was evaporated. The obtained residue was purified by high performance liquid chromatography (water-acetonitrile, each containing 0.1% trifluoroacetic acid) to give the title compound (0.13 g, 0.24 mmol, 64%).

MS (ESI) m/z 561 (M+H)+

$^1$H NMR (400 MHz, DMSO-$d_6$) δ 8.71 (dd, J=6.2, 6.1 Hz, 1H), 7.82 (ddd, J=7.8, 1.3, 0.9 Hz, 1H), 7.74 (dd, J=8.5, 0.9 Hz, 1H), 7.70 (d, J=0.9 Hz, 1H), 7.65 (d, J=8.3 Hz, 2H), 7.56 (ddd, J=8.5, 7.2, 1.3 Hz, 1H), 7.47-7.41 (m, 3H), 7.41-7.39 (m, 1H), 7.39-7.33 (m, 3H), 4.37 (dd, J=15.6, 6.2 Hz, 1H), 4.31 (dd, J=15.6, 6.1 Hz, 1H), 4.27 (dd, J=8.3, 3.4 Hz, 1H), 3.61-3.51 (m, 1H), 3.41-3.35 (m, 1H), 1.95-1.72 (m, 3H), 1.66-1.53 (m, 1H).

Example 322

Synthesis of (2S)-1-(benzofuran-2-ylsulfonyl)-N-[[3-[4-(trifluoromethyl)phenyl]sulfonylphenyl]methyl]pyrrolidine-2-carboxamide (322)

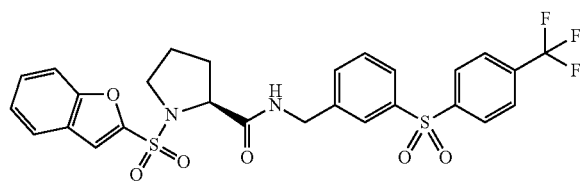 [SMILES: O=C(NCc1cccc(S(=O)(=O)c2ccc(C(F)(F)F)cc2)c1)[C@@H]1CCCN1S(=O)(=O)c1cc2ccccc2o1]

To (2S)-1-(benzofuran-2-ylsulfonyl)-N-[[3-[4-(trifluoromethyl)phenyl]sulfanylphenyl]methyl]pyrrolidine-2-carboxamide(321) (0.13 g, 0.24 mmol) and 3-chloroperbenzoic acid (94 mg, 0.35 mmol) was added dichloromethane (2.4 mL) and the mixture was stirred 0° C. for 5 hr. To the reaction mixture were added saturated aqueous sodium hydrogen carbonate and saturated aqueous sodium thiosulfate solution, and the mixture was extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (70 mg, 0.12 mmol, 50%).

MS (ESI) m/z 593 (M+H)+

$^1$H NMR (400 MHz, DMSO-$d_6$) δ 8.80 (dd, J=6.1, 6.1 Hz, 1H), 8.17 (d, J=8.3 Hz, 2H), 7.98 (d, J=8.3 Hz, 2H), 7.93-7.89 (m, 2H), 7.83 (ddd, J=8.0, 1.3, 0.7 Hz, 1H), 7.76-7.71 (m, 2H), 7.64-7.60 (m, 2H), 7.56 (ddd, J=8.6, 7.3, 1.3 Hz, 1H), 7.42 (ddd, J=8.0, 7.3, 0.9 Hz, 1H), 4.46-4.33 (m, 2H), 4.27 (dd, J=8.4, 3.5 Hz, 1H), 3.62-3.53 (m, 1H), 3.44-3.34 (m, 1H), 1.96-1.74 (m, 3H), 1.70-1.56 (m, 1H).

Example 323

Synthesis of (2S)-1-(benzofuran-2-ylsulfonyl)-N-[[3-[4-(trifluoromethyl)phenyl]sulfinylphenyl]methyl]pyrrolidine-2-carboxamide (323)

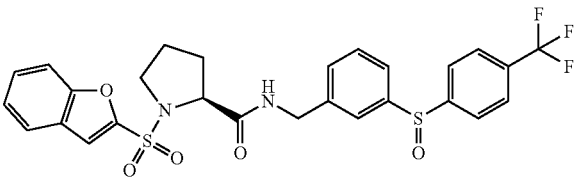 [SMILES: O=C(NCc1cccc(S(=O)c2ccc(C(F)(F)F)cc2)c1)[C@@H]1CCCN1S(=O)(=O)c1cc2ccccc2o1]

To (2S)-1-(benzofuran-2-ylsulfonyl)-N-[[3-[4-(trifluoromethyl)phenyl]sulfanylphenyl]methyl]pyrrolidine-2-carboxamide(321) (0.13 g, 0.24 mmol) and 3-chloroperbenzoic acid (94 mg, 0.35 mmol) was added dichloromethane (2.4 mL) and the mixture was stirred 0° C. for 5 hr. To the reaction mixture were added saturated aqueous sodium hydrogen carbonate and saturated aqueous sodium thiosulfate solution, and the mixture was stirred at extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (1.7 mg, 0.0030 mmol, 1%).

MS (ESI) m/z 577 (M+H)+

Example 324

Synthesis of (2S)-1-(benzofuran-2-ylsulfonyl)-N-[[3-[[4-(trifluoromethyl)phenyl]methylsulfonyl]phenyl]methyl]pyrrolidine-2-carboxamide (324)

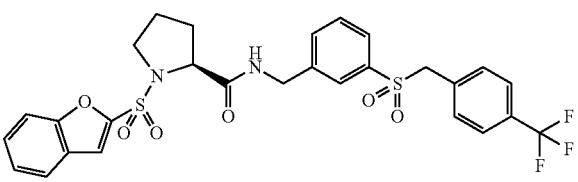 [SMILES: O=C(NCc1cccc(S(=O)(=O)Cc2ccc(C(F)(F)F)cc2)c1)[C@@H]1CCCN1S(=O)(=O)c1cc2ccccc2o1]

To ((2S)-1-(benzofuran-2-ylsulfonyl)-N-[[3-[[4-(trifluoromethyl)phenyl]methylsulfanyl]phenyl]methyl]pyrrolidine-2-carboxamide (315) (43 mg, 0.075 mmol) and 3-chloroperbenzoic acid (30 mg, 0.11 mmol) was added dichloromethane (1.5 mL) and the mixture was stirred 00° C. for 5 hr. To the reaction mixture were added saturated aqueous sodium hydrogen carbonate and saturated aqueous sodium thiosulfate solution, and the mixture was extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (24 mg, 0.040 mmol, 53%).

MS (ESI) m/z 607 (M+H)+

Example 325

Synthesis of (2S)-1-(benzofuran-2-ylsulfonyl)-N-[[3-[[4-(trifluoromethyl)phenyl]sulfinylmethyl]phenyl]methyl]pyrrolidine-2-carboxamide (325)

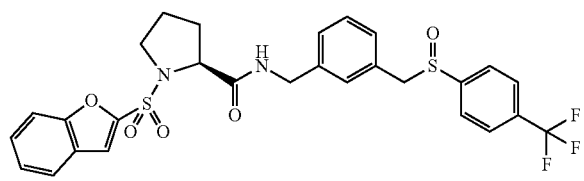 [SMILES: O=C(NCc1cccc(CS(=O)c2ccc(C(F)(F)F)cc2)c1)[C@@H]1CCCN1S(=O)(=O)c1cc2ccccc2o1]

To (2S)-1-(benzofuran-2-ylsulfonyl)-N-[[3-[[4-(trifluoromethyl)phenyl]sulfanylmethyl]phenyl]methyl]pyrrolidine-2-carboxamide (299) (0.10 g, 0.18 mmol) and 3-chloroperbenzoic acid (46 mg, 0.27 mmol) was added dichloromethane (1.8 mL), and the mixture was stirred at room temperature for 5 hr. To the reaction mixture were added saturated aqueous sodium hydrogen carbonate and saturated aqueous sodium thiosulfate solution, and the mixture was extracted with dichloromethane. The organic layer was dried over sodium sulfate. The desiccant was filtered off, and the solvent was evaporated. The obtained residue was purified by high performance liquid chromatography (water-acetonitrile, each containing 0.1% trifluoroacetic acid) to give the title compound (17 mg, 0.028 mmol, 16%).

MS (ESI) m/z 591 (M+H)+

$^1$H NMR (400 MHz, DMSO-de) δ 8.65 (dd, J=6.1, 6.1 Hz, 1H), 7.91 (d, J=8.1 Hz, 2H), 7.83 (d, J=7.9 Hz, 1H), 7.79-7.70 (m, 4H), 7.59-7.53 (m, 1H), 7.42 (t, J=7.5 Hz, 1H), 7.28-7.19 (m, 2H), 7.08 (s, 1H), 6.97 (ddt, J=6.1, 4.1, 2.1 Hz, 1H), 4.38-4.17 (m, 4H), 4.09 (dd, J=12.8, 2.9 Hz, 1H), 3.66-3.55 (m, 1H), 3.46-3.37 (m, 1H), 1.95-1.82 (m, 3H), 1.70-1.58 (m, 1H).

Example 326, and Example 328 to Example 330 described in Table 33 were synthesized by using the compound obtained in Example 311, step 3 and corresponding commercially available reagents and by an operation similar to that in Example 312.

TABLE 33

| Example No. | structural formula | compound name |
|---|---|---|
| 326 | | (2S)-1-(benzofuran-2-ylsulfonyl)-N-[[2-(methylamino)-6-[4-(trifluoromethyl)phenyl]pyrimidin-4-yl]methyl]pyrrolidine-2-carboxamide |
| 328 | | (2S)-N-[[2-(azetidin-1-yl)-6-[4-(trifluoromethyl)phenyl]pyrimidin-4-yl]methyl]-1-(benzofuran-2-ylsulfonyl)pyrrolidine-2-carboxamide |

TABLE 33-continued

| Example No. | structural formula | compound name |
|---|---|---|
| 329 | | (2S)-1-(benzofuran-2-ylsulfonyl)-N-[[2-pyrrolidin-1-yl-6-[4-(trifluoromethyl)phenyl]pyrimidin-4-yl]methyl]pyrrolidine-2-carboxamide |
| 330 | | (2S)-1-(benzofuran-2-ylsulfonyl)-N-[[2-morpholino-6-[4-(trifluoromethyl)phenyl]pyrimidin-4-yl]methyl]pyrrolidine-2-carboxamide |

Example 327

Synthesis of (2S)-1-(benzofuran-2-ylsulfonyl)-N-[[2-benzyloxy-6-[4-(trifluoromethyl)phenyl]pyrimidin-4-yl]methyl]pyrrolidine-2-carboxamide (327)

Using benzylalcohol instead of 2-methyl-1-propanol, and by an operation similar to that in Example 311, step 4, the title compound (9.9 mg, 0.016 mmol, yield 16%) was obtained.

MS (ESI) m/z 637 (M+H)$^+$

Example 331

Synthesis of (2S)-1-(benzofuran-2-ylsulfonyl)-N-[[2-[6-(2,2,2-trifluoroethoxymethyl)-3-pyridyl]-4-pyridyl]methyl]pyrrolidine-2-carboxamide (331)

(step 1) Synthesis of (2S)-1-(benzofuran-2-ylsulfonyl)-N-[[2-[6-(hydroxymethyl)-3-pyridyl]-4-pyridyl]methyl]pyrrolidine-2-carboxamide To C-4 (82 mg, 0.20 mmol), [6-(hydroxymethyl)-3-pyridyl]boronic acid (30.6 mg, 0.20 mmol) and 1,1'-bis(diphenylphosphino)ferrocenedichloropalladium(II) (14 mg, 0.019 mmol) were added 1,4-dioxane (0.7 mL) and 1 mol/L aqueous sodium carbonate solution (0.7 mL) and the mixture was stirred with heating by using a microwave reactor at 100° C. for 10 min. The reaction mixture was neutralized with trifluoroacetic acid, and purified by high performance liquid chromatography (water-acetonitrile, each containing 0.1% trifluoroacetic acid). Saturated aqueous sodium hydrogen carbonate was added and the mixture was extracted with dichloromethane. The organic layer was dried over sodium sulfate. The desiccant was filtered off, and the solvent was evaporated to give the title compound (42 mg, 0.085 mmol, 43%).
MS (ESI) m/z 493 (M+H)+

(step 2) Synthesis of (2S)-1-(benzofuran-2-ylsulfonyl)-N-[[2-[6-(2,2,2-trifluoroethoxymethyl)-3-pyridyl]-4-pyridyl]methyl]pyrrolidine-2-carboxamide (331)

To the compound (38 mg, 0.077 mmol) obtained in step 1 in tetrahydrofuran solution (13.3 mL) were added sodium hydride (55% oily, 4.0 mg, 0.092 mmol) and 2,2,2-trifluoroethyl trifluoromethanesulfonate (13 μL, 0.092 mmol) at 0° C., and the mixture was stirred at room temperature for a few hours. The reaction mixture was neutralized with water and trifluoroacetic acid, and purified by high performance liquid chromatography (water-acetonitrile, each containing 0.1% trifluoroacetic acid) to give trifluoroacetate of the title compound (2.4 mg, 0.0034 mmol, 4.5%).
MS (ESI) m/z 575 (M+H)+
$^1$H NMR (400 MHz, DMSO-d$_6$) δ 9.23 (d, J=2.2 Hz, 1H), 8.89 (dd, J=6.1, 6.1 Hz, 1H), 8.66 (d, J=5.1 Hz, 1H), 8.50 (dd, J=8.2, 2.2 Hz, 1H), 7.97 (s, 1H), 7.84 (dd, J=7.9, 1.3 Hz, 1H), 7.78-7.74 (m, 2H), 7.60-7.53 (m, 2H), 7.43 (ddd, J=7.9, 7.5, 0.8 Hz, 1H), 7.35 (dd, J=5.1, 1.5 Hz, 1H), 4.82 (s, 2H), 4.50 (dd, J=16.6, 6.1 Hz, 1H), 4.41 (dd, J=16.6, 6.1 Hz, 1H), 4.34 (dd, J=8.3, 3.8 Hz, 1H), 4.25 (q, J=9.3 Hz, 2H), 3.66-3.61 (m, 1H), 3.45-3.38 (m, 1H), 2.06-1.85 (m, 3H), 1.72-1.59 (m, 1H).

Example 332 to Example 333 described in Table 34 were synthesized by using the compounds described in Reference Examples and corresponding commercially available reagents and by an operation similar to that in Example 112.

TABLE 34

| Example No. | structural formula | compound name |
|---|---|---|
| 332 | | (2S)-1-(benzofuran-2-ylsulfonyl)-N-[[2-[4-(difluoromethyl)phenyl]-4-pyridyl]methyl]pyrrolidine-2-carboxamide |
| 333 | | (2S)-1-(benzofuran-2-ylsulfonyl)-N-[[4-[4-(difluoromethyl)phenyl]-2-pyridyl]methyl]pyrrolidine-2-carboxamide |

Example 334 to Example 411 described in Table 35 were synthesized by using the compounds described in Reference Examples and corresponding commercially available reagents and by an operation similar to that in Example 37.

TABLE 35

| Example No. | structural formula | compound name |
|---|---|---|
| 334 | | (2S,4R)-1-(benzofuran-2-ylsulfonyl)-4-(dimethylamino)-N-[[2-[2-hydroxy-4-(trifluoromethyl)phenyl]-4-pyridyl]methyl]pyrrolidine-2-carboxamide |

TABLE 35-continued

| Example No. | structural formula | compound name |
|---|---|---|
| 335 | | (2S)-2-[(5-fluorobenzofuran-2-yl)sulfonylamino]-N-[[4-[5-(trifluoromethyl)-2-pyridyl]-2-pyridyl]methyl]butaneamide |
| 336 | | tert-butyl 4-[[[(2S)-1-(benzofuran-2-ylsulfonyl)pyrrolidine-2-carbonyl]amino]methyl]-2-[4-(trifluoromethyl)phenyl]-benzoate |
| 337 | | (2S)-1-(benzofuran-2-ylsulfonyl)-N-[[4-(dimethylcarbamoyl)-3-[4-(trifluoromethyl)phenyl]-phenyl]methyl]pyrrolidine-2-carboxamide |
| 338 | | tert-butyl 3-[[[(2S)-1-(benzofuran-2-ylsulfonyl)pyrrolidine-2-carbonyl]amino]methyl]-5-[4-(trifluoromethyl)phenyl]-benzoate |
| 339 | | 2-[(5-fluorobenzofuran-2-yl)sulfonyl-methyl-amino]-N-[[4-[5-(trifluoromethyl)-2-pyridyl]-2-pyridyl]methyl]acetamide |

TABLE 35-continued

| Example No. | structural formula | compound name |
| --- | --- | --- |
| 340 | | 2-[(5-fluorobenzofuran-2-yl)sulfonyl-methyl-amino]-2-methyl-N-[[4-[5-(trifluoromethyl)-2-pyridyl]-2-pyridyl]methyl]propanamide |
| 341 | | (2S)-1-(5-fluorobenzofuran-2-yl)sulfonyl-2-methyl-N-[[4-[5-(trifluoromethyl)-2-pyridyl]-2-pyridyl]methyl]pyrrolidine-2-carboxamide |
| 342 | | (2R)-2-[(5-fluorobenzofuran-2-yl)sulfonyl-methyl-amino]-N-[[4-[5-(trifluoromethyl)-2-pyridyl]-2-pyridyl]methyl]propanamide |
| 343 | | 2-[(5-fluorobenzofuran-2-yl)sulfonylamino]-N-[[4-[5-(trifluoromethyl)-2-pyridyl]-2-pyridyl]methyl]acetamide |
| 344 | | 2-[(5-fluorobenzofuran-2-yl)sulfonyl-methyl-amino]-N-[[6-[4-(trifluoromethyl)phenyl]pyrimidin-4-yl]methyl]acetamide |

TABLE 35-continued

| Example No. | structural formula | compound name |
|---|---|---|
| 345 | | 2-[(5-fluorobenzofuran-2-yl)sulfonylamino]-N-[[6-[4-(trifluoromethyl)phenyl]-pyrimidin-4-yl]methyl]acetamide |
| 346 | | (2S)-1-furo[2,3-c]pyridin-2-ylsulfonyl-N-[[4-[5-(trifluoromethyl)-2-pyridyl]-2-pyridyl]methyl]pyrrolidine-2-carboxamide |
| 347 | | (2S)-1-furo[2,3-c]pyridin-2-ylsulfonyl-N-[[6-[4-(trifluoromethyl)phenyl]-pyrimidin-4-yl]methyl]pyrrolidine-2-carboxamide |
| 348 | | 2-[(5-fluorobenzofuran-2-yl)sulfonyl-isopropyl-amino]-N-[[4-[5-(trifluoromethyl)-2-pyridyl]-2-pyridyl]methyl]acetamide |
| 349 | | 2-[cyclopropylmethyl-(5-fluorobenzofuran-2-yl)sulfonyl-amino]-N-[[4-[5-(trifluoromethyl)-2-pyridyl]-2-pyridyl]methyl]acetamide |

TABLE 35-continued

| Example No. | structural formula | compound name |
|---|---|---|
| 350 | | 2-[benzyl-(5-fluorobenzofuran-2-yl)sulfonyl-amino]-N-[[4-[5-(trifluoromethyl)-2-pyridyl]-2-pyridyl]methyl]acetamide |
| 351 | | 2-[(5-fluorobenzofuran-2-yl)sulfonyl-(oxazol-2-ylmethyl)amino]-N-[[4-[5-(trifluoromethyl)-2-pyridyl]-2-pyridyl]methyl]acetamide |
| 352 | | 2-[benzyl-(5-fluorobenzofuran-2-yl)sulfonyl-amino]-N-[[6-[4-(trifluoromethyl)phenyl]-pyrimidin-4-yl]methyl]acetamide |
| 353 | | 2-[(5-fluorobenzofuran-2-yl)sulfonyl-(2-pyridylmethyl)-amino]-N-[[6-[4-(trifluoromethyl)-phenyl]pyrimidin-4-yl]methyl]acetamide |

TABLE 35-continued

| Example No. | structural formula | compound name |
|---|---|---|
| 354 | | 2-[(5-fluorobenzofuran-2-yl)sulfonyl-(oxazol-2-ylmethyl)amino]-N-[[6-[4-(trifluoromethyl)phenyl]-pyrimidin-4-yl]methyl]acetamide |
| 355 | | 2-[(5-fluorobenzofuran-2-yl)sulfonyl-(2-methoxyethyl)amino]-N-[[4-[5-(trifluoromethyl)-2-pyridyl]-2-pyridyl]methyl]acetamide |
| 356 | | 2-[(5-fluorobenzofuran-2-yl)sulfonyl-(2-isopropoxyethyl)amino]-N-[[4-[5-(trifluoromethyl)-2-pyridyl]-2-pyridyl]methyl]acetamide |
| 357 | | 2-[(5-fluorobenzofuran-2-yl)sulfonyl-(2-methoxyethyl)-amino]-N-[[6-[4-(trifluoromethyl)-phenyl]pyrimidin-4-yl]methyl]acetamide |
| 358 | | 2-[(5-fluorobenzofuran-2-yl)sulfonyl-(2-isopropoxyethyl)amino]-N-[[6-[4-(trifluoromethyl)-phenyl]pyrimidin-4-yl]methyl]acetamide |

TABLE 35-continued

| Example No. | structural formula | compound name |
|---|---|---|
| 359 | | 2-[(5-fluorobenzofuran-2-yl)sulfonyl-isopropyl-amino]-N-[[6-[6-(trifluoromethyl)-3-pyridyl]pyrimidin-4-yl]methyl]acetamide |
| 360 | | 2-[(5-fluorobenzofuran-2-yl)sulfonyl-isopropyl-amino]-N-[[6-[2-(trifluoromethyl)pyrimidin-5-yl]pyrimidin-4-yl]methyl]acetamide |
| 361 | | 2-[(5-fluorobenzofuran-2-yl)sulfonyl-(pyrazin-2-ylmethyl)amino]-N-[[6-[4-(trifluoromethyl)phenyl]-pyrimidin-4-yl]methyl]acetamide |
| 362 | | 2-[(5-fluorobenzofuran-2-yl)sulfonyl-methyl-amino]-N-[[6-[4-(trifluoromethoxy)-phenyl]pyrimidin-4-yl]methyl]acetamide |
| 363 | | 2-[(5-fluorobenzofuran-2-yl)sulfonylamino]-N-[[6-[4-(trifluoromethoxy)phenyl]-pyrimidin-4-yl]methyl]acetamide |

TABLE 35-continued

| Example No. | structural formula | compound name |
|---|---|---|
| 364 | | 2-[(5-fluorobenzofuran-2-yl)sulfonyl-isopropyl-amino]-N-[[6-[4-(trifluoromethoxy)-phenyl]pyrimidin-4-yl]methyl]acetamide |
| 365 | | (2S)-1-furo[3,2-c]pyridin-2-ylsulfonyl-N-[[4-[5-(trifluoromethyl)pyrimidin-2-yl]-2-pyridyl]methyl]pyrrolidine-2-carboxamide |
| 366 | | (2S)-2-(furo[3,2-c]pyridin-2-ylsulfonylamino)-N-[[2-[4-(trifluoromethyl)phenyl]-4-pyridyl]methyl]propanamide |
| 367 | | (2S)-2-(furo[3,2-c]pyridin-2-ylsulfonylamino)-N-[[3-[5-(trifluoromethyl)-2-pyridyl]-phenyl]methyl]propanamide |
| 368 | | 2-[furo[3,2-c]pyridin-2-ylsulfonyl(isopropyl)amino]-N-[[6-[4-(trifluoromethyl)-phenyl]pyrimidin-4-yl]methyl]acetamide |
| 369 | | (2S)-N-[[2-(dimethylamino)-6-[4-(trifluoromethyl)-phenyl]pyrimidin-4-yl]methyl]-2-(furo[3,2-c]pyridin-2-ylsulfonylamino)propanamide |

TABLE 35-continued

| Example No. | structural formula | compound name |
|---|---|---|
| 370 | | (2S)-N-[[2-(dimethylamino)-6-[4-(trifluoromethyl)-phenyl]pyrimidin-4-yl]methyl]-2-[(5-fluorobenzofuran-2-yl)sulfonylamino]propanamide |
| 371 | | (2S)-1-(benzofuran-2-ylsulfonyl)-N-[[2-(dimethylamino)-6-[6-(trifluoromethyl)-3-pyridyl]pyrimidin-4-yl]methyl]pyrrolidine-2-carboxamide |
| 372 | | (2S)-N-[[2-(dimethylamino)-6-[6-(trifluoromethyl)-3-pyridyl]pyrimidin-4-yl]methyl]-2-[(5-fluorobenzofuran-2-yl)sulfonylamino]propanamide |
| 373 | | (2S)-2-(furo[3,2-c]pyridin-2-ylsulfonylamino)-N-[[4-hydroxy-3-[5-(trifluoromethyl)-2-pyridyl]-phenyl]methyl]propanamide |
| 374 | | 2-[furo[3,2-c]pyridin-2-ylsulfonyl(isopropyl)amino]-N-[[4-hydroxy-3-[5-(trifluoromethyl)-2-pyridyl]-phenyl]methyl]acetamide |

TABLE 35-continued

| Example No. | structural formula | compound name |
|---|---|---|
| 375 | | (2S)-N-[[2-(dimethylamino)-6-[4-(trifluoromethyl)phenyl]-pyrimidin-4-yl]methyl]-1-furo[3,2-c]pyridin-2-ylsulfonyl-pyrrolidine-2-carboxamide |
| 376 | | (2S)-1-(benzofuran-2-ylsulfonyl)-N-[[2-(dimethylamino)-6-[2-hydroxy-4-(trifluoromethyl)phenyl]-pyrimidin-4-yl]methyl]pyrrolidine-2-carboxamide |
| 377 | | (2S)-N-[[2-(dimethylamino)-6-[2-hydroxy-4-(trifluoromethyl)phenyl]-pyrimidin-4-yl]methyl]-2-[(5-fluorobenzofuran-2-yl)sulfonylamino]propanamide |
| 378 | | (2S)-N-[[2-(dimethylamino)-6-[4-(trifluoromethyl)phenyl]-pyrimidin-4-yl]methyl]-1-(5-fluorobenzofuran-2-yl)sulfonyl-pyrrolidine-2-carboxamide |
| 379 | | (2S)-N-[[2-(dimethylamino)-6-[4-(trifluoromethyl)phenyl]-pyrimidin-4-yl]methyl]-1-(5-fluorobenzofuran-2-yl)sulfonyl-azetidine-2-carboxamide |

TABLE 35-continued

| Example No. | structural formula | compound name |
|---|---|---|
| 380 | | (2S)-1-(benzofuran-2-ylsulfonyl)-N-[[4-hydroxy-3-[6-(trifluoromethyl)pyridazin-3-yl]phenyl]methyl]pyrrolidine-2-carboxamide |
| 381 | | (2S)-2-[(5-fluorobenzofuran-2-yl)sulfonylamino]-N-[[4-hydroxy-3-[6-trifluoromethyl)pyridazin-3-yl]phenyl]methyl]propanamide |
| 382 | | (2S)-N-[[2-amino-6-[4-(trifluoromethyl)phenyl]-pyrimidin-4-yl]methyl]-1-(5-fluorobenzofuran-2-yl)sulfonyl-pyrrolidine-2-carboxamide |
| 383 | | (2S)-1-(5-fluorobenzofuran-2-yl)sulfonyl-N-[[2-[2-hydroxy-4-(trifluoromethyl)phenyl]-4-pyridyl]methyl]azetidine-2-carboxamide |
| 384 | | (2S)-N-[[2-(dimethylamino)-6-[6-(trifluoromethyl)-3-pyridyl]pyrimidin-4-yl]methyl]-1-(5-fluorobenzofuran-2-yl)sulfonyl-azetidine-2-carboxamide |

TABLE 35-continued

| Example No. | structural formula | compound name |
|---|---|---|
| 385 | | (2S)-1-(benzofuran-2-ylsulfonyl)-N-[[4-[5-(trifluoromethyl)-2-pyridyl]-2-pyridyl]methyl]azetidine-2-carboxamide |
| 386 | | (2S)-1-(benzofuran-2-ylsulfonyl)-N-[[6-[4-(trifluoromethyl)phenyl]-pyrimidin-4-yl]methyl]azetidine-2-carboxamide |
| 387 | | (2S)-1-(5-fluorobenzofuran-2-yl)sulfonyl-N-[[6-[2-(trifluoromethyl)pyrimidin-5-yl]pyrimidin-4-yl]methyl]azetidine-2-carboxamide |
| 388 | | (2S)-1-(5-fluorobenzofuran-2-yl)sulfonyl-N-[[6-[6-(trifluoromethyl)-3-pyridyl]pyrimidin-4-yl]methyl]azetidine-2-carboxamide |
| 389 | | (2S)-1-(5-fluorobenzofuran-2-yl)sulfonyl-N-[[4-[2-(trifluoromethyl)pyrimidin-5-yl]-2-pyridyl]methyl]azetidine-2-carboxamide |
| 390 | | (2S)-1-(5-fluorobenzofuran-2-yl)sulfonyl-N-[[4-hydroxy-3-[5-(trifluoromethyl)pyrazin-2-yl]phenyl]methyl]azetidine-2-carboxamide |

TABLE 35-continued

| Example No. | structural formula | compound name |
|---|---|---|
| 391 | | (2S)-1-(5-fluorobenzofuran-2-yl)sulfonyl-N-[[5-[5-(trifluoromethyl)-2-pyridyl]pyridazin-3-yl]methyl]azetidine-2-carboxamide |
| 392 | | (2S)-1-(5-fluorobenzofuran-2-yl)sulfonyl-N-[[3-[5-(trifluoromethyl)pyrazin-2-yl]phenyl]methyl]azetidine-2-carboxamide |
| 393 | | (2S)-1-(5-fluorobenzofuran-2-yl)sulfonyl-N-[[4-[5-(trifluoromethyl)pyrazin-2-yl]-2-pyridyl]methyl]azetidine-2-carboxamide |
| 394 | | (2S)-1-(5-fluorobenzofuran-2-yl)sulfonyl-N-[[4-[5-(trifluoromethyl)pyrimidin-2-yl]-2-pyridyl]methyl]azetidine-2-carboxamide |
| 395 | | (2S)-1-(5-fluorobenzofuran-2-yl)sulfonyl-N-[[6-]4-(trifluoromethoxy)phenyl]-pyrimidin-4-yl]methyl]azetidine-2-carboxamide |

TABLE 35-continued

| Example No. | structural formula | compound name |
|---|---|---|
| 396 | | (2S)-1-(5-fluorobenzofuran-2-yl)sulfonyl-N-[[5-[5-(trifluoromethyl)-2-pyridyl]pyridazin-3-yl]methyl]pyrrolidine-2-carboxamide |
| 397 | | (2S)-N-[[2-(dimethylamino)-6-[2-hydroxy-4-(trifluoromethyl)phenyl]-pyrimidin-4-yl]methyl]-1-(5-fluorobenzofuran-2-yl)sulfonyl-pyrrolidine-2-carboxamide |
| 398 | | (2S)-N-[[2-(dimethylamino)-6-[2-hydroxy-4-(trifluoromethyl)phenyl]-pyrimidin-4-yl]methyl]-1-(5-fluorobenzofuran-2-yl)sulfonyl-azetidine-2-carboxamide |
| 399 | | (2S)-1-(5-fluorobenzofuran-2-yl)sulfonyl-N-[[3-[5-(trifluoromethyl)pyrazin-2-yl]phenyl]methyl]pyrrolidine-2-carboxamide |
| 400 | | (2S)-1-(5-fluorobenzofuran-2-yl)sulfonyl-N-[[6-[5-(trifluoromethyl)-2-pyridyl]pyrimidin-4-yl]methyl]pyrrolidine-2-carboxamide |

TABLE 35-continued

| Example No. | structural formula | compound name |
|---|---|---|
| 401 | | (2S)-1-(5-fluorobenzofuran-2-yl)sulfonyl-N-[[6-[5-(trifluoromethyl)-2-pyridyl]pyrimidin-4-yl]methyl]azetidine-2-carboxamide |
| 402 | | (2S)-1-(5-fluorobenzofuran-2-yl)sulfonyl-N-[[2-[2-(trifluoromethyl)pyrimidin-5-yl]-4-pyridyl]methyl]pyrrolidine-2-carboxamide |
| 403 | | (2S)-1-(5-fluorobenzofuran-2-yl)sulfonyl-N-[[2-[2-(trifluoromethyl)pyrimidin-5-yl]-4-pyridyl]methyl]azetidine-2-carboxamide |
| 404 | | (2S)-1-(5-fluorobenzofuran-2-yl)sulfonyl-N-[[4-hydroxy-3-[5-(trifluoromethyl)-2-pyridyl]phenyl]methyl]azetidine-2-carboxamide |
| 405 | | (2S)-1-(5-fluorobenzofuran-2-yl)sulfonyl-N-[[4-[5-(trifluoromethyl)pyrazin-2-yl]-2-pyridyl]methyl]pyrrolidine-2-carboxamide |

TABLE 35-continued

| Example No. | structural formula | compound name |
|---|---|---|
| 406 | | (2S)-1-(5-fluorobenzofuran-2-yl)sulfonyl-N-[[6-[4-(trifluoromethoxy)phenyl]-pyrimidin-4-yl]methyl]pyrrolidine-2-carboxamide |
| 407 | | (2S)-1(5-fluorobenzofuran-2-yl)sulfonyl-N-[[4-[5-(trifluoromethyl)pyrimidin-2-yl]-2-pyridyl]methyl]pyrrolidine-2-carboxamide |
| 408 | | (2S)-1-(benzofuran-2-ylsulfonyl)-N-[[6-[6-(trifluonomethyl)-3-pyridyl]pyrimidin-4-yl]methyl]azetidine-2-carboxamide |
| 409 | | (2S)-1-(benzofuran-2-ylsulfonyl)-N-[[6-[2-(trifluoromethyl)pyrimidin-5-yl]pyrimidin-4-yl]methyl]azetidine-2-carboxamide |
| 410 | | (2S)-1-(benzofuran-2-ylsulfonyl)-N-[[2-(dimethylamino)-6-[6-(trifluoromethyl)-3-pyridyl]pyrimidin-4-yl]methyl]azetidine-2-carboxamide |
| 411 | | (2S)-1-(benzofuran-2-ylsulfonyl)-N-[[2-[2-hydroxy-4-(trifluoromethyl)phenyl]-4-pyridyl]methyl]azetidine-2-carboxamide |

Example 412 to Example 414 described in Table 36 were synthesized by using the compounds described in Reference Examples and corresponding commercially available reagents and by an operation similar to that in Example 288.

that in Example 37, the title compound (yield 31%) was obtained.

MS (ESI) m/z 595 (M+H)$^+$

TABLE 36

| Example No. | structural formula | compound name |
|---|---|---|
| 412 |  | (2S)-1-(5-fluorobenzofuran-2-yl)sulfonyl-N-[[6-[2-hydroxy-4-(trifluoromethyl)phenyl]pyrimidin-4-yl]methyl]azetidine-2-carboxamide |
| 413 |  | 2-[(5-fluorobenzofuran-2-yl)sulfonyl-isopropyl-amino]-N-[[6-[2-hydroxy-4-(trifluoromethyl)phenyl]pyrimidin-4-yl]methyl]acetamide |
| 414 |  | (2S)-2-(furo[3,2-c]pyridin-2-ylsulfonylamino)-N-[[6-[2-hydroxy-4-(trifluoromethyl)phenyl]pyrimidin-4-yl]methyl]propanamide |

Example 415

Synthesis of (2S)-3-tert-butoxy-2-[(5-fluorobenzofuran-2-yl)sulfonylamino]-N-[[6-[4-(trifluoromethyl)phenyl]pyrimidin-4-yl]methyl]propanamide (415)

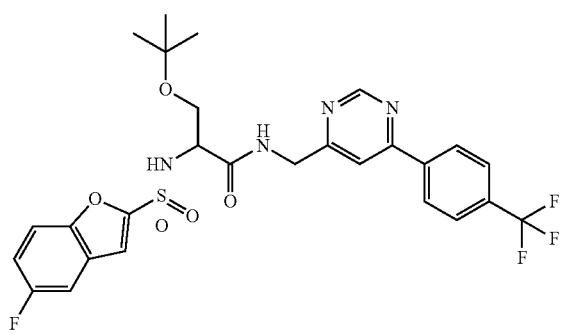

Using the compound obtained in Example 189, step 1 and D-16 instead of B-1 and D-1, and by an operation similar to

Example 416

Synthesis of (2S)-2-[ethyl-(5-fluorobenzofuran-2-yl)sulfonyl-amino]-N-[[4-[5-(trifluoromethyl)-2-pyridyl]-2-pyridyl]methyl]propanamide (416)

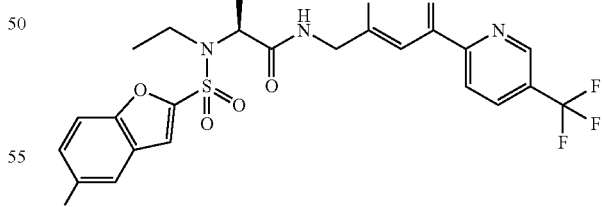

To a solution of (2S)-2-[(5-fluorobenzofuran-2-yl)sulfonylamino]-N-[[4-[5-(trifluoromethyl)-2-pyridyl]-2-pyridyl]methyl]propanamide (240) (52 mg, 0.10 mmol), potassium carbonate (28 mg, 0.20 mmol) in N,N-dimethylformamide (1.0 mL) was added ethyl iodide (16 L, 0.20 mmol), and the mixture was stirred at 60° C. for 3 hr. Using acetonitrile, the insoluble material was filtered and purified by high performance liquid chromatography (water-acetonitrile, each containing 0.1% trifluoroacetic acid) to give trifluoroacetate of the title compound (4.5 mg, 0.0068 mmol, 6.8%).
MS (ESI) m/z 551 (M+H)+
$^1$H NMR (400 MHz, DMSO-d$_6$) δ 9.13-9.10 (m, 1H), 8.73-8.68 (m, 2H), 8.41 (dd, J=8.4, 2.4 Hz, 1H), 8.30 (d, J=8.4 Hz, 1H), 8.04 (dd, J=5.3, 1.7 Hz, 1H), 8.00 (d, J=1.7 Hz, 1H), 7.66 (dd, J=9.1, 4.0 Hz, 1H), 7.55 (d, J=0.9 Hz, 1H), 7.48 (dd, J=8.5, 2.7 Hz, 1H), 7.32 (ddd, J=9.2, 9.1, 2.8 Hz, 1H), 4.67 (q, J=7.2 Hz, 1H), 4.44-4.33 (m, 2H), 3.55-3.40 (m, 2H), 1.38 (d, J=7.2 Hz, 3H), 1.20 (t, J=7.0 Hz, 3H).

Example 417 to Example 422 described in Table 37 were synthesized by using the compounds corresponding Example 240, Example 345 and Example 109 and corresponding commercially available reagents and by an operation similar to that in Example 416.

TABLE 37

| Example No. | structural formula | compound name |
| --- | --- | --- |
| 417 |  | (2S)-2-[allyl-(5-fluorobenzofuran-2-yl)sulfonyl-amino]-N-[[4-[5-(trifluoromethyl)-2-pyridyl]-2-pyridyl]methyl]propanamide |
| 418 |  | (2S)-2-[(5-fluorobenzofuran-2-yl)sulfonyl-prop-2-ynylamino]-N-[[4-[5-(trifluoromethyl)-2-pyridyl]-2-pyridyl]methyl]propanamide |
| 419 |  | 2-[ethyl-(5-fluorobenzofuran-2-yl)sulfonyl-amino]-N-[[6-[4-(trifluoromethyl)phenyl]pyrimidin-4-yl]methyl]acetamide |
| 420 |  | 2-[(5-fluorobenzofuran-2-yl)sulfonyl-isopropyl-amino]-N-[[6-[4-(trifluoromethyl)phenyl]pyrimidin-4-yl]methyl]acetamide |
| 421 |  | (2S)-2-[(5-fluorobenzofuran-2-yl)sulfonyl-methyl-amino]-N-[[6-[4-(trifluoromethyl)phenyl]pyrimidin-4-yl]methyl]propanamide |

TABLE 37-continued

| Example No. | structural formula | compound name |
|---|---|---|
| 422 | | (2S)-2-[ethyl-(5-fluorobenzofuran-2-yl)sulfonyl-amino]-N-[[6-[4-(trifluoromethyl)phenyl]pyrimidin-4-yl]methyl]propanamide |

Example 423

Synthesis of 2-[(5-fluorobenzofuran-2-yl)sulfonyl-(4-piperidylmethyl)amino]-N-[[4-[5-(trifluoromethyl)-2-pyridyl]-2-pyridyl]methyl]acetamide (423)

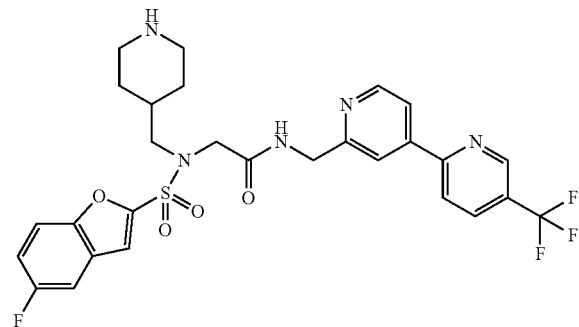 [SMILES: O=C(CN(CC1CCNCC1)S(=O)(=O)c1cc2cc(F)ccc2o1)NCc1cc(-c2ccc(C(F)(F)F)cn2)ccn1]

(step 1) Synthesis of tert-butyl 4-[[[(5-fluorobenzofuran-2-yl)sulfonyl-[2-oxo-2-[[4-[5-(trifluoromethyl)-2-pyridyl]-2-pyridyl]methylamino]ethyl]amino]methyl]piperidine-1-carboxylate Using B-47 instead of B-1, and D-31 instead of D-1, and by an operation similar to that in Example 37, the title compound was obtained (0.043 mmol, yield 20%).
MS (ESI) m/z 706 (M+H)⁺

(step 2) Synthesis of 2-[(5-fluorobenzofuran-2-yl)sulfonyl-(4-piperidylmethyl)amino]-N-[[4-[5-(trifluoromethyl)-2-pyridyl]-2-pyridyl]methyl]acetamide (423)

To a solution (1 mL) of the compound obtained in step 1 in dichloromethane was added trifluoroacetic acid (200 μL), and the mixture was stirred at room temperature for 30 min. The solvent was evaporated to give ditrifluoroacetate of the title compound (34.3 mg, 0.041 mmol, 95%).

MS (ESI) m/z 606 (M+H)⁺

$^1$H NMR (400 MHz, DMSO-$d_6$) δ 9.13 (d, J=2.3 Hz, 1H), 8.75 (t, J=5.8 Hz, 1H), 8.71 (d, J=5.1 Hz, 1H), 8.55-8.45 (m, 1H), 8.42 (dd, J=8.4, 2.3 Hz, 1H), 8.32 (d, J=8.4 Hz, 1H), 8.24-8.12 (m, 1H), 8.05-7.99 (m, 2H), 7.70 (dd, J=9.1, 4.0 Hz, 1H), 7.58 (d, J=0.8 Hz, 1H), 7.52 (dd, J=8.5, 2.7 Hz, 1H), 7.36 (ddd, J=9.2, 9.1, 2.8 Hz, 1H), 4.42 (d, J=5.8 Hz, 2H), 4.09 (s, 2H), 3.33-3.21 (m, 4H), 2.86-2.71 (m, 2H), 2.02-1.82 (m, 3H), 1.36-1.20 (m, 2H).

Example 424 to Example 425 described in Table 38 were synthesized by using the compounds described in Reference Examples and by an operation similar to that in Example 423.

TABLE 38

| Example No. | structural formula | compound name |
|---|---|---|
| 424 | | 2-[(5-fluorobenzofuran-2-yl)sulfonyl-(4-piperidylmethyl)amino]-N-[[6-[4-(trifluoromethyl)phenyl]pyrimidin-4-yl]methyl]acetamide |

TABLE 38-continued

| Example No. | structural formula | compound name |
|---|---|---|
| 425 | | 2-[(5-fluorobenzofuran-2-yl)sulfonyl-(pyrrolidin-3-ylmethyl)amino]-N-[[6-[4-(trifluoromethyl)phenyl]pyrimidin-4-yl]methyl]acetamide |

Example 426

Synthesis of (2S)-2-[(5-fluorobenzofuran-2-yl)sulfonyl-methyl-amino]-N-[[4-[5-(trifluoromethyl)-2-pyridyl]-2-pyridyl]methyl]propanamide (426)

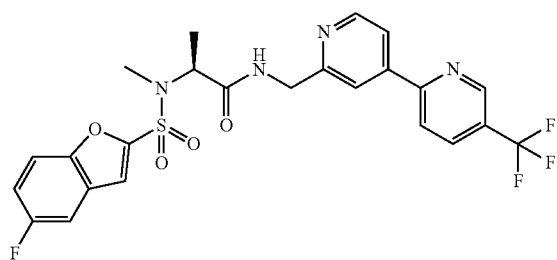 [SMILES: C[C@@H](C(=O)NCc1cc(-c2ccc(C(F)(F)F)cn2)ccn1)N(C)S(=O)(=O)c1cc2cc(F)ccc2o1]

To N-(tert-butoxycarbonyl)-N-methyl-L-alanine (20.3 mg, 0.10 mmol), D-31 (28.9 mg, 0.10 mmol), WSC hydrochloride (38 mg, 0.20 mmol) and 1-hydroxy-7-azabenzotriazole (27 mg, 0.20 mmol) were added dichloromethane (1 mL) and triethylamine (54 μL, 0.40 mmol), and the mixture was stirred at room temperature for 30 min. Water was added to the reaction mixture, and the mixture was extracted with dichloromethane. The organic layer was dried over sodium sulfate, the desiccant was filtered off, and the solvent was evaporated. To the obtained residue was added 4 mol/L hydrochloric acid/1,4-dioxane solution (3 mL), and the mixture was stirred at room temperature for 30 min. The solvent was evaporated, and the residue was dissolved in tetrahydrofuran (2 mL), 2 mol/L aqueous sodium hydroxide solution (20 mL), A-3 (23.4 mg, 0.10 mmol) were added, and the mixture was stirred at room temperature for 2 hr. To the reaction mixture was added water and the mixture was extracted with dichloromethane. The organic layer was dried over sodium sulfate, and the desiccant was filtered off. The solvent was evaporated and the obtained residue was purified by high performance liquid chromatography (water-acetonitrile, each containing 0.1% trifluoroacetic acid) to give trifluoroacetate of the title compound (3.61 mg, 0.0055 mmol, 5.5%).

MS (ESI) m/z 537 (M+H)+

$^1$H NMR (400 MHz, DMSO-d$_6$) δ 9.12 (d, J=2.3 Hz, 1H), 8.77 (dd, J=5.9, 5.8 Hz, 1H), 8.70 (d, J=5.2 Hz, 1H), 8.41 (dd, J=8.5, 2.3 Hz, 1H), 8.30 (d, J=8.5 Hz, 1H), 8.04 (dd, J=5.2, 1.7 Hz, 1H), 8.01 (d, J=1.7 Hz, 1H), 7.69 (dd, J=9.2, 4.1 Hz, 1H), 7.59 (d, J=0.9 Hz, 1H), 7.52 (dd, J=8.5, 2.7 Hz, 1H), 7.35 (ddd, J=9.2, 9.2, 2.7 Hz, 1H), 4.70 (q, J=7.1 Hz, 1H), 4.44 (dd, J=16.3, 5.8 Hz, 1H), 4.39 (dd, J=16.3, 5.9 Hz, 1H), 2.99 (s, 3H), 1.28 (d, J=7.1 Hz, 3H).

Example 427

Synthesis of 3-fluoro-2-[(5-fluorobenzofuran-2-yl)sulfonylamino]-N-[[4-[5-(trifluoromethyl)-2-pyridyl]-2-pyridyl]methyl]propanamide (427)

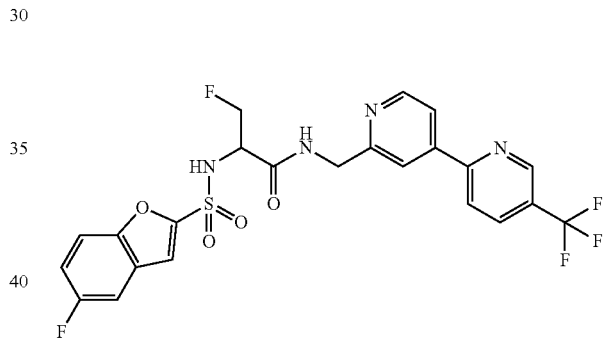

To 3-amino-2-fluoropropanoic acid (21 mg, 0.20 mmol) were added di-tert-butyl dicarbonate (42 mg, 0.20 mmol), triethylamine (40 μL), acetonitrile (2 mL), and the mixture was stirred at room temperature for 2 hr. The solvent was evaporated. To the obtained residue were added D-31 (56 mg, 0.20 mmol), WSC hydrochloride (76 mg, 0.40 mmol) and 1-hydroxy-7-azabenzotriazole (54 mg, 0.40 mmol), dichloromethane (2 mL) and triethylamine (110 μL, 0.80 mmol), and the mixture was stirred at room temperature for 30 min. Water was added to the reaction mixture, and the mixture was extracted with dichloromethane. The organic layer was dried over sodium sulfate, the desiccant was filtered off, and the solvent was evaporated. To the obtained residue were added 4 mol/L hydrochloric acid/1, 4-dioxane solution (2 mL) and 1,4-dioxane (2 mL), and the mixture was stirred at room temperature for 1 hr. The solvent was evaporated and the obtained compound (37 mg, 0.10 mmol) was dissolved in dichloromethane (1 mL), triethylamine (20 μL, 0.15 mmol), A-3 (23 mg, 0.10 mmol) were added, and the mixture was stirred at room temperature for 2 hr. The reaction mixture was neutralized with water and trifluoroacetic acid, and purified by high performance liquid chromatography (water-acetonitrile, each containing 0.1% trifluoroacetic acid) to give trifluoroacetate of the title compound (3.96 mg, 0.0061 mmol, 6.1%).

MS (ESI) m/z 541 (M+H)⁺

¹H NMR (400 MHz, DMSO-d₆) δ 9.27 (d, J=8.6 Hz, 1H), 9.11 (d, J=2.4 Hz, 1H), 8.92 (dd, J=5.8, 5.8 Hz, 1H), 8.68 (d, J=5.2 Hz, 1H), 8.41 (dd, J=8.4, 2.4 Hz, 1H), 8.27 (d, J=8.4 Hz, 1H), 8.03 (dd, J=5.2, 1.7 Hz, 1H), 7.95 (d, J=1.7 Hz, 1H), 7.65 (dd, J=9.1, 4.1 Hz, 1H), 7.51-7.44 (m, 2H), 7.31 (ddd, J=9.2, 9.1, 2.8 Hz, 1H), 4.66-4.58 (m, 1H), 4.53-4.34 (m, 4H).

The property data (MS, NMR) of the Example compounds are shown in Table 39.

TABLE 39

| Example No. | Salt | MS(ESI) m/z (M + H)⁺ | NMR |
|---|---|---|---|
| 1 | — | 516 | ¹H NMR (400 MHz, DMSO-d₆) δ 8.65 (t, J = 6.0 Hz, 1H), 7.89-7.80 (m, 3H), 7.75 (dt, J = 8.5, 0.8, 0.8 Hz, 1H), 7.72 (d, J = 0.9 Hz, 1H), 7.62 (dt, J = 8.2, 1.4, 1.3 Hz, 2H), 7.56 (ddd, J = 8.5, 7.3, 1.3 Hz, 1H), 7.42 (ddd, J = 8.0, 7.2, 0.9 Hz, 1H), 7.24 (dd, J = 7.9, 7.9 Hz, 1H), 6.96 (dd, J = 2.0, 2.0 Hz, 1H), 6.91-6.85 (m, 2H), 5.21 (s, 2H), 4.37-4.20 (m, 3H), 3.64-3.55 (m, 2H), 1.96-1.79 (m, 3H), 1.68-1.58 (m, 1H). |
| 2 | — | 516 | ¹H NMR (400 MHz, DMSO-d₆) δ 8.65 (dd, J = 6.3, 5.8 Hz, 1H), 7.90 (s, 1H), 7.85-7.76 (m, 3H), 7.75 (dd, J = 8.4, 0.9 Hz, 1H), 7.72 (d, J = 1.0 Hz, 1H), 7.61 (dd, J = 7.8, 7.8 Hz, 1H), 7.56 (ddd, J = 8.4, 7.3, 1.3 Hz, 1H), 7.42 (ddd, J = 8.0, 7.3, 0.9 Hz, 1H), 7.25 (dd, J = 7.9, 7.9 Hz, 1H), 6.97 (s, 1H), 6.93-6.86 (m, 2H), 5.16 (s, 2H), 4.38-4.21 (m, 3H), 3.59 (ddd, J = 9.3, 6.6, 4.6 Hz, 1H), 3.42-3.35 (m, 1H), 1.97-1.80 (m, 3H), 1.68-1.58 (m, 1H). |
| 3 | TFA | 492 | ¹H NMR (400 MHz, DMSO-d₆) δ 8.75 (s, 1H), 8.70-8.60 (m, 2H), 8.07 (d, J = 8.2 Hz, 1H), 7.83 (ddd, J = 7.8, 1.3, 1.0 Hz, 1H), 7.75 (dd, J = 8.4, 1.0 Hz, 1H), 7.72 (d, J = 1.0 Hz, 1H), 7.64-7.52 (m, 2H), 7.45-7.39 (m, 1H), 7.26 (dd, J = 7.9, 7.9 Hz, 1H), 7.01-6.96 (m, 1H), 6.94-6.87 (m, 2H), 5.20 (m, 2H), 4.39-4.22 (m, 3H), 3.59 (ddd, J = 9.7, 6.0, 6.0 Hz, 1H), 3.38 (ddd, J = 9.7, 6.7, 6.7 Hz, 1H), 1.98-1.80 (m, 3H), 1.70-1.58 (m, 1H). |
| 4 | — | 481 | ¹H NMR (400 MHz, DMSO-d₆) δ 8.64 (dd, J = 6.2, 5.9 Hz, 1H), 7.83 (ddd, J = 7.9, 1.4, 1.0 Hz, 1H), 7.75 (dd, J = 8.5, 0.9 Hz, 1H), 7.71 (d, J = 1.0 Hz, 1H), 7.68 (dd, J = 1.9, 0.8 Hz, 1H), 7.55 (ddd, J = 8.5, 7.3, 1.4 Hz, 1H), 7.42 (ddd, J = 8.0, 7.3, 0.9 Hz, 1H), 7.24 (dd, J = 7.9, 7.9 Hz, 1H), 6.96-6.93 (m, 1H), 6.91-6.84 (m, 2H), 6.58 (dd, J = 3.2, 0.8 Hz, 1H), 6.46 (dd, J = 3.2, 1.9 Hz, 1H), 5.03 (s, 2H), 4.37-4.21 (m, 3H), 3.64-3.56 (m, 1H), 3.42-3.35 (m, 1H), 1.97-1.81 (m, 3H), 1.68-1.59 (m, 1H). |
| 5 | — | 497 | ¹H NMR (400 MHz, DMSO-d₆) δ 8.64 (dd, J = 6.1, 6.1 Hz, 1H), 7.83 (ddd, J = 7.9, 1.3, 0.9 Hz, 1H), 7.75 (dd, J = 8.4, 0.9 Hz, 1H), 7.71 (d, J = 0.9 Hz, 1H), 7.58-7.52 (m, 2H), 7.42 (ddd, J = 7.9, 7.3, 0.9 Hz, 1H), 7.24 (dd, J = 7.9, 7.9 Hz, 1H), 7.20 (dd, J = 3.4, 1.2 Hz, 1H), 7.03 (dd, J = 5.1, 3.4 Hz, 1H), 6.97-6.94 (m, 1H), 6.93-6.83 (m, 2H), 5.27 (s, 2H), 4.37-4.22 (m, 3H), 3.64-3.56 (m, 1H), 3.42-3.35 (m, 1H), 1.97-1.81 (m, 3H), 1.68-1.58 (m, 1H). |
| 6 | — | 497 | — |
| 7 | — | 560 | ¹H NMR (400 MHz, DMSO-d₆) δ 8.77 (d, J = 5.0 Hz, 1H), 8.66 (t, J = 6.1 Hz, 1H), 7.93 (s, 1H), 7.83 (d, J = 7.6 Hz, 1H), 7.76 (Br-s, 1H), 7.73 (d, J = 7.0 Hz, 2H), 7.56 (ddd, J = 8.4, 7.2, 1.4 Hz, 1H), 7.46-7.38 (m, 1H), 7.27 (t, J = 7.9 Hz, 1H), 7.00 (Br-s, 1H), 6.96-6.88 (m, 2H), 5.31 (s, 2H), 4.39-4.21 (m, 3H), 3.64-3.56 (m, 1H), 3.39 (dt, J = 9.7, 6.6 Hz, 1H), 1.97-1.80 (m, 3H), 1.67-1.58 (m, 1H). |
| 8 | — | 560 | ¹H NMR (400 MHz, DMSO-d₆) δ 8.85 (d, J = 1.9 Hz, 1H), 8.66 (t, J = 6.1 Hz, 1H), 8.16-8.12 (m, 1H), 7.97-7.92 (m, 1H), 7.83 (dq, J = 7.8, 0.7 Hz, 1H), 7.78-7.70 (m, 2H), 7.56 (ddd, J = 8.5, 7.2, 1.3 Hz, 1H), 7.42 (ddd, J = 8.1, 7.3, 0.9 Hz, 1H), 7.31-7.23 (m, 1H), 7.02-6.96 (m, 1H), 6.96-6.86 (m, 2H), 5.29 (s, 2H), 4.39-4.22 (m, 3H), 3.59 (ddd, J = 9.7, 6.8, 5.3 Hz, 1H), 3.38-3.35 (m, 1H), 1.97-1.79 (m, 3H), 1.69-1.59 (m, 1H). |
| 9 | — | 560 | — |
| 10 | — | 526 | — |
| 11 | — | 534 | ¹H NMR (400 MHz, DMSO-d₆) δ 8.66 (t, J = 6.0 Hz, 1H), 7.90-7.83 (m, 2H), 7.80 (dd, J = 9.2, 4.0 Hz, 1H), 7.68 (d, J = 1.0 Hz, 1H), 7.67-7.59 (m, 3H), 7.42 (td, J = 9.2, 2.8 Hz, 1H), 7.25 (t, J = 7.9 Hz, 1H), 6.96 (t, J = 2.0 Hz, 1H), 6.92-6.85 (m, 2H), 5.21 (s, 2H), 4.38-4.20 (m, 3H), 3.60 (ddd, J = 9.5, 6.7, 4.7 Hz, 1H), 3.41-3.33 (m, 1H), 2.00-1.79 (m, 3H), 1.71-1.59 (m, 1H). |
| 12 | TFA | 552 | ¹H NMR (400 MHz, DMSO-d₆) δ 8.65 (t, J = 6.0 Hz, 1H), 7.80 (dd, J = 9.2, 4.1 Hz, 1H), 7.68 (s, 1H), 7.63 (d, J = 8.4, 2.7 Hz, 1H), 7.42 (td, J = 9.2, 2.8 Hz, 1H), 7.22 (q, J = 7.7 Hz, 1H), 6.95 (t, J = 1.9 Hz, 1H), 6.92-6.82 (m, 3H), 6.82-6.72 (m, 2H), 5.02 (s, 2H), 4.38-4.20 (m, 3H), 3.64-3.59 (m, 1H), 3.39 (dt, J = 10.0, 6.8 Hz, 1H), 2.91 (s, 6H), 1.99-1.81 (m, 3H), 1.73-1.60 (m, 1H). |

TABLE 39-continued

| Example No. | Salt | MS(ESI) m/z (M + H)+ | NMR |
|---|---|---|---|
| 13 | TFA | 510 | — |
| 14 | TFA | 510 | — |
| 15 | TFA | 510 | ¹H NMR (400 MHz, DMSO-d₆) δ 8.65 (t, J = 6.1 Hz, 1H), 8.61 (d, J = 4.3 Hz, 1H), 7.91 (t, J = 7.8 Hz, 1H), 7.80 (dd, J = 9.0, 4.2 Hz, 1H), 7.68 (d, J = 0.9 Hz, 1H), 7.64 (dd, J = 8.5, 2.7 Hz, 1H), 7.57 (d, J = 7.9 Hz, 1H), 7.47-7.39 (m, 2H), 7.25 (t, J = 7.9 Hz, 1H), 6.98-6.95 (m, 1H), 6.93-6.85 (m, 2H), 5.20 (s, 2H), 4.39-4.20 (m, 3H), 3.59 (ddd, J = 9.4, 6.6, 4.7 Hz, 1H), 3.39 (dt, J = 10.0, 6.9 Hz, 1H), 2.53-1.78 (m, 3H), 1.71-1.60 (m, 1H). |
| 16 | — | 578 | — |
| 17 | TFA | 553 | — |
| 18 | TFA | 595 | ¹H NMR (400 MHZ, DMSO-d₆) δ 8.67 (t, J = 6.1 Hz, 1H), 8.07 (d, J = 5.7 Hz, 1H), 7.80 (dd, J = 9.2, 4.0 Hz, 1H), 7.69 (s, 1H), 7.64 (dd, J = 8.5, 2.7 Hz, 1H), 7.43 (td, J = 9.2, 2.8 Hz, 1H), 7.26 (t, J = 7.9 Hz, 1H), 7.13 (s, 1H), 6.98 (t, J = 2.0 Hz, 1H), 6.94-6.81 (m, 3H), 5.13 (s, 2H), 4.39-4.23 (m, 3H), 3.73-3.68 (m, 4H), 3.63-3.58 (m, 1H), 3.56-3.50 (m, 4H), 3.39 (dt, J = 10.0, 6.9 Hz, 1H), 2.01-1.80 (m, 3H), 1.72-1.60 (m, 1H). |
| 19 | TFA | 524 | — |
| 20 | — | 578 | ¹H NMR (400 MHz, DMSO-d₆) δ 8.77 (d, J = 5.0 Hz, 1H), 8.67 (t, J = 6.1 Hz, 1H), 7.92 (s, 1H), 7.79 (dd, J = 9.2, 4.1 Hz, 1H), 7.74 (d, J = 4.9 Hz, 1H), 7.68 (d, J = 0.9 Hz, 1H), 7.64 (dd, J = 8.5, 2.7 Hz, 1H), 7.42 (td, J = 9.2, 2.7 Hz, 1H), 7.27 (t, J = 7.9 Hz, 1H), 6.99 (t, J = 2.0 Hz, 1H), 6.95-6.88 (m, 2H), 5.31 (s, 2H), 4.38-4.22 (m, 3H), 3.64-3.54 (m, 1H), 3.35-3.28 (m, 1H), 1.99-1.79 (m, 3H), 1.72-1.60 (m, 1H). |
| 21 | TFA | 553 | — |
| 22 | TFA | 595 | — |
| 23 | TFA | 553 | — |
| 24 | TFA | 581 | — |
| 25 | — | 578 | ¹H NMR (400 MHz, DMSO-d₆) δ 8.65 (t, J = 6.1 Hz, 1H), 8.14 (t, J = 7.9 Hz, 1H), 7.89-7.77 (m, 3H), 7.68 (d, J = 0.9 Hz, 1H), 7.63 (dd, J = 8.5, 2.7 Hz, 1H), 7.42 (td, J = 9.2, 2.7 Hz, 1H), 7.26 (t, J = 7.9 Hz, 1H), 7.00 (t, J = 2.0 Hz, 1H), 6.96-6.87 (m, 2H), 5.27 (s, 2H), 4.39-4.20 (m, 3H), 3.63-3.56 (m, 1H), 3.39 (dt, J = 10.0, 6.9 Hz, 1H), 2.00-1.79 (m, 3H), 1.72-1.59 (m, 1H). |
| 26 | TFA | 553 | — |
| 27 | TFA | 608 | ¹H NMR (400 MHz, DMSO-d₆) δ 10.00 (br-s, 1H), 8.67 (t, J = 6.1 Hz, 1H), 7.80 (dd, J = 9.1, 4.1 Hz, 1H), 7.69 (d, J = 0.8 Hz, 1H), 7.64 (dd, J = 8.4, 2.7 Hz, 1H), 7.58 (Br-s, J = 1.7 Hz, 1H), 7.57-7.39 (m, 4H), 7.25 (t, J = 7.9 Hz, 1H), 6.96 (t, J = 2.0 Hz, 1H), 6.92-6.86 (m, 2H), 5.14 (s, 2H), 4.41-4.22 (m, 5H), 4.01-3.87 (m, 2H), 3.65-3.51 (m, 3H), 3.38 (dt, J = 10.0, 6.9 Hz, 1H), 3.31-3.03 (m, 4H), 1.99-1.79 (m, 3H), 1.73-1.57 (m, 1H). |
| 28 | TFA | 638 | ¹H NMR (400 MHz, DMSO-d₆) δ 10.03 (Br-s, 1H), 8.67 (t, J = 6.1 Hz, 1H), 7.80 (dd, J = 9.2, 4.1 Hz, 1H), 7.68 (d, J = 0.8 Hz, 1H), 7.64 (dd, J = 8.5, 2.7 Hz, 1H), 7.43 (td, J = 9.2, 2.8 Hz, 1H), 7.35 (t, J = 8.1 Hz, 1H), 7.28-7.19 (m, 1H), 7.11-7.04 (m, 2H), 7.01-6.92 (m, 2H), 6.87 (dd, J = 8.1, 2.1 Hz, 2H), 5.08 (s, 2H), 4.41-4.21 (m, 5H), 4.04-3.90 (m, 2H), 3.77-3.64 (m, 2H), 3.66-3.52 (m, 3H), 3.53-3.35 (m, 3H), 3.27-3.13 (m, 2H), 2.03-1.79 (m, 3H), 1.71-1.61 (m, 1H). |
| 29 | — | 567 | — |
| 30 | — | 517 | ¹H NMR (400 MHz, DMSO-d₆) δ 8.64 (t, J = 6.0 Hz, 1H), 7.80 (dd, J = 9.2, 4.1 Hz, 1H), 7.67 (d, J = 0.9 Hz, 1H), 7.64 (dd, J = 8.5, 2.7 Hz, 1H), 7.42 (ddd, J = 9.2, 9.2, 2.8 Hz, 1H), 7.21 (dd, J = 7.9, 7.9 Hz, 1H), 6.90-6.76 (m, 3H), 4.36-4.20 (m, 3H), 3.90-3.79 (m, 4H), 3.64-3.56 (m, 1H), 3.43-3.26 (m, 3H), 2.06-1.80 (m, 4H), 1.71-1.60 (m, 3H), 1.36-1.22 (m, 2H). |
| 31 | — | 517 | — |
| 32 | — | 503 | — |
| 33 | — | 503 | — |
| 34 | — | 527 | ¹H NMR (400 MHz, DMSO-d₆) δ 8.71 (t, J = 6.1 Hz, 1H), 7.80 (dd, J = 9.2, 4.0 Hz, 1H), 7.69 (s, 1H), 7.63 (dd, J = 8.4, 2.8 Hz, 1H), 7.50-7.29 (m, 6H), 6.82 (s, 1H), 6.77 (dt, J = 10.9, 2.4 Hz, 1H), 6.70 (d, J = 9.2 Hz, 1H), 5.11 (s, 2H), 4.39-4.22 (m, 3H), 3.67-3.55 (m, 1H), 3.39 (dt, J = 10.0, 6.8 Hz, 1H), 2.04-1.79 (m, 3H), 1.73-1.58 (m, 1H). |
| 35 | TFA | 528 | — |
| 36 | — | 552 | — |
| 37 | — | 491 | ¹H NMR (400 MHz, DMSO-d₆) δ 8.65 (t, J = 6.1 Hz, 1H), 7.83 (ddd, J = 7.9, 1.4, 0.8 Hz, 1H), 7.75 (dd, J = 8.4, 0.9 Hz, 1H), 7.71 (d, J = 0.9 Hz, 1H), 7.55 (ddd, J = 8.5, 7.2, 1.3 Hz, 1H), 7.47-7.28 (m, 6H), 7.23 (dd, J = 8.2, 7.5 Hz, 1H), 6.99-6.94 (m, |

TABLE 39-continued

| Example No. | Salt | MS(ESI) m/z (M + H)+ | NMR |
|---|---|---|---|
| | | | 1H), 6.91-6.83 (m, 2H), 5.09 (s, 2H), 4.38-4.20 (m, 3H), 3.64-3.55 (m, 1H), 3.44-3.35 (m, 1H), 1.97-1.80 (m, 3H), 1.70-1.57 (m, 1H). |
| 38 | — | 559 | — |
| 39 | — | 577 | ¹H NMR (400 MHz, DMSO-$d_6$) δ 8.67 (dd, J = 6.0, 5.8 Hz, 1H), 7.81 (d, J = 2.7 Hz, 1H), 7.78-7.72 (m, 2H), 7.69-7.62 (m, 3H), 7.49 (ddd, J = 11.1, 8.1, 1.1 Hz, 1H), 7.41 (ddd, J = 8.1, 8.0, 4.5 Hz, 1H), 7.25 (dd, J = 7.9, 7.9 Hz, 1H), 6.96 (dd, J = 2.6, 1.5 Hz, 1H), 6.92-6.85 (m, 2H), 5.22 (s, 2H), 4.37-4.29 (m, 1H), 4.25 (dd, J = 15.5, 5.8 Hz, 1H), 3.61 (ddd, J = 9.8, 7.0, 4.7 Hz, 1H), 3.45-3.36 (m, 1H), 2.04-1.80 (m, 3H), 1.74-1.62 (m, 1H). |
| 40 | — | 577 | ¹H NMR (400 MHz, DMSO-$d_6$) δ 8.65 (t, J = 6.1 Hz, 1H), 7.86 (dd, J = 8.7, 5.6 Hz, 1H), 7.78-7.70 (m, 3H), 7.65 (d, J = 8.1 Hz, 2H), 7.32 (ddd, J = 9.7, 8.7, 2.3 Hz, 1H), 7.25 (t, J = 7.9 Hz, 1H), 6.97 (Br-s, 1H), 6.92-6.84 (m, 2H), 5.22 (s, 2H), 4.38-4.21 (m, 3H), 3.64-3.55 (m, 1H), 3.43-3.37 (m, 1H), 1.99-1.79 (m, 3H), 1.72-1.61 (m, 1H). |
| 41 | — | 577 | — |
| 42 | — | 577 | ¹H NMR (400 MHz, DMSO-$d_6$) δ 8.65 (t, J = 6.0 Hz, 1H), 7.83 (d, J = 0.9 Hz, 1H), 7.75 (d, J = 8.1 Hz, 2H), 7.68-7.55 (m, 4H), 7.31-7.21 (m, 2H), 6.97 (dd, J = 2.6, 1.5 Hz, 1H), 6.92-6.85 (m, 2H), 5.22 (s, 2H), 4.36-4.22 (m, 3H), 3.64-3.56 (m, 1H), 3.45-3.38 (m, 1H), 1.99-1.79 (m, 3H), 1.70-1.61 (m, 1H). |
| 43 | — | 509 | — |
| 44 | — | 557 | ¹H NMR (400 MHz, DMSO-$d_6$) δ 8.76 (t, J = 6.1 Hz, 1H), 7.86-7.80 (m, 1H), 7.80-7.70 (m, 4H), 7.66 (d, J = 8.1 Hz, 2H), 7.55 (ddd, J = 8.5, 7.2, 1.3 Hz, 1H), 7.46-7.37 (m, 1H), 7.25 (t, J = 7.9 Hz, 1H), 7.00-6.95 (m, 1H), 6.93-6.86 (m, 2H), 5.94 (dq, J = 6.2, 2.0 Hz, 1H), 5.75 (dq, J = 6.4, 2.2 Hz, 1H), 5.22 (s, 2H), 5.11-5.05 (m, 1H), 4.44-4.21 (m, 4H). |
| 45 | — | 575 | ¹H NMR (400 MHz, DMSO-$d_6$) δ 8.75 (t, J = 6.1 Hz, 1H), 7.82 (d, J = 7.6 Hz, 1H), 7.76 (d, J = 8.1 Hz, 2H), 7.73-7.64 (m, 4H), 7.53 (ddd, J = 8.4, 7.2, 1.3 Hz, 1H), 7.44-7.35 (m, 1H), 7.25 (t, J = 7.9 Hz, 1H), 6.98 (Br-s, 1H), 6.92-6.85 (m, 2H), 5.22 (s, 2H), 5.19 (s, 1H), 4.37 (dd, J = 15.5, 6.5 Hz, 1H), 4.23 (dd, J = 15.5, 5.7 Hz, 1H), 4.16-4.08 (m, 2H), 3.67 (td, J = 8.5, 1.6 Hz, 1H), 3.50 (ddd, J = 11.2, 8.8, 6.3 Hz, 1H), 2.02-1.88 (m, 1H), 1.73 (dd, J = 13.1, 6.2 Hz, 1H). |
| 46 | — | 575 | — |
| 47 | — | 595 | — |
| 48 | — | 545 | ¹H NMR (400 MHz, DMSO-$d_6$) δ 8.87 (t, J = 6.0 Hz, 1H), 7.88-7.81 (m, 1H), 7.81-7.72 (m, 4H), 7.66 (d, J = 8.1 Hz, 2H), 7.58 (ddd, J = 8.5, 7.2, 1.3 Hz, 1H), 7.47-7.39 (m, 1H), 7.26 (t, J = 7.9 Hz, 1H), 7.00 (t, J = 2.0 Hz, 1H), 6.96-6.84 (m, 2H), 5.22 (s, 2H), 4.56 (dd, J = 8.8, 6.8 Hz, 1H), 4.38-4.24 (m, 2H), 4.09-3.91 (m, 2H), 2.81-2.65 (m, 1H), 2.50-2.34 (m, 1H). |
| 49 | — | 551 | — |
| 50 | — | 545 | — |
| 51 | — | 563 | — |
| 52 | — | 545 | — |
| 53 | — | 563 | ¹H NMR (400 MHz, DMSO-$d_6$) δ 8.70 (t, J = 6.1 Hz, 1H), 7.79 (ddd, J = 9.2, 4.1, 0.9 Hz, 1H), 7.77-7.70 (m, 2H), 7.66 (d, J = 0.9 Hz, 1H), 7.64 (dd, J = 8.5, 2.7 Hz, 1H), 7.47-7.36 (m, 2H), 7.17-7.11 (m, 3H), 7.04-6.99 (m, 2H), 4.40-4.29 (m, 2H), 4.26 (dd, J = 8.4, 3.5 Hz, 1H), 3.60-3.52 (m, 1H), 3.39-3.32 (m, 1H), 1.97-1.72 (m, 3H), 1.69-1.55 (m, 1H). |
| 54 | — | 546 | ¹H NMR (400 MHz, DMSO-$d_6$) δ 8.70 (t, J = 6.1 Hz, 1H), 8.54 (d, J = 2.8 Hz, 1H), 7.89 (d, J = 8.7 Hz, 1H), 7.85-7.80 (m, 2H), 7.78-7.71 (m, 2H), 7.69 (d, J = 0.9 Hz, 1H), 7.59-7.51 (m, 2H), 7.46-7.39 (m, 2H), 7.23-7.16 (m, 1H), 7.12-7.06 (m, 2H), 4.41-4.28 (m, 2H), 4.25 (dd, J = 8.3, 3.6 Hz, 1H), 3.56 (ddd, J = 9.7, 6.7, 4.8 Hz, 2H), 3.36 (dt, J = 9.7, 6.8 Hz, 1H), 1.95-1.75 (m, 3H), 1.65-1.54 (m, 1H). |
| 55 | — | 546 | — |
| 56 | — | 564 | — |
| 57 | — | 507 | ¹H NMR (400 MHz, DMSO-$d_6$) δ 8.66 (t, J = 6.1 Hz, 1H), 7.83 (ddd, J = 7.9, 1.3, 0.9 Hz, 1H), 7.74 (dd, J = 8.5, 1.0 Hz, 1H), 7.71 (d, J = 0.9 Hz, 1H), 7.55 (ddd, J = 8.5, 7.2, 1.3 Hz, 1H), 7.42 (ddd, J = 7.9, 7.2, 1.0 Hz, 1H), 7.38-7.33 (m, 2H), 7.32-7.16 (m, 6H), 7.08 (ddd, J = 7.4, 1.5, 1.5 Hz, 1H), 4.36-4.20 (m, 5H), 3.63-3.55 (m, 1H), 3.42-3.36 (m, 1H), 1.96-1.80 (m, 3H), 1.68-1.57 (m, 1H). |
| 58 | — | 491 | — |
| 59 | — | 403 | — |
| 60 | — | 419 | — |

TABLE 39-continued

| Example No. | Salt | MS(ESI) m/z (M + H)+ | NMR |
|---|---|---|---|
| 61 | — | 453 | ¹H NMR (400 MHz, DMSO-d₆) δ 8.80 (t, J = 6.1 Hz, 1H), 7.86-7.81 (m, 1H), 7.77-7.73 (m, 1H), 7.72 (d, J = 0.9 Hz, 1H), 7.65 (s, 1H), 7.63-7.53 (m, 4H), 7.45-7.40 (m, 1H), 4.44 (dd, J = 15.7, 6.2 Hz, 1H) 4.38 (dd, J = 15.7, 6.0 Hz, 1H), 4.30 (dd, J = 8.3, 3.6 Hz, 1H), 3.63-3.55 (m, 1H), 3.38 (dt, J = 9.8, 6.8 Hz, 1H), 2.01-1.80 (m, 3H), 1.70-1.59 (m, 1H). |
| 62 | — | 469 | — |
| 63 | — | 469 | — |
| 64 | — | 469 | — |
| 65 | — | 487 | — |
| 66 | — | 487 | — |
| 67 | — | 487 | ¹H NMR (400 MHz, DMSO-d₆) δ 8.86 (t, J = 6.0 Hz, 1H), 7.88-7.81 (m, 2H), 7.79-7.65 (m, 5H), 7.57 (ddd, J = 8.5, 7.2, 1.3 Hz, 1H), 7.46-7.39 (m, 1H), 4.49 (dd, J = 16.4, 6.2 Hz, 1H), 4.39 (dd, J = 16.4, 5.7 Hz, 1H), 4.34 (dd, J = 8.4, 3.7 Hz, 1H), 3.39 (dt, J = 9.8, 6.8 Hz, 1H), 2.04-1.81 (m, 3H), 1.72-1.61 (m, 1H). |
| 68 | — | 451 | ¹H NMR (400 MHz, DMSO-d₆) δ 8.66 (t, J = 5.9 Hz, 1H), 7.83 (ddd, J = 8.0, 1.4, 0.8 Hz, 1H), 7.75 (dd, J = 8.4, 0.9 Hz, 1H), 7.72 (d, J = 0.8 Hz, 1H), 7.56 (ddd, J = 8.5, 7.3, 1.4 Hz, 1H), 7.42 (ddd, J = 8.0, 7.3, 0.9 Hz, 1H), 7.17-6.99 (m, 2H), 4.38-4.23 (m, 3H), 3.63-3.54 (m, 1H), 3.44-3.35 (m, 1H), 1.97-1.79 (m, 3H), 1.68-1.57 (m, 1H). |
| 69 | — | 505 | ¹H NMR (400 MHz, DMSO-d₆) δ 8.78 (dd, J = 6.2, 6.0 Hz, 1H), 7.81 (dd, J = 9.0, 4.2 Hz, 1H), 7.70 (d, J = 0.9 Hz, 1H), 7.64 (dd, J = 8.5, 2.7 Hz, 1H), 7.53 (ddd, J = 8.6, 8.3, 1.2 Hz, 1H), 7.43 (ddd, J = 9.3, 9.0, 2.7 Hz, 1H), 7.38 (dd, J = 11.5, 2.1 Hz, 1H), 7.22 (ddd, J = 8.6, 2.1, 1.1 Hz, 1H), 4.38 (dd, J = 15.9, 6.2 Hz, 1H), 4.31 (dd, J = 15.9, 6.0 Hz, 1H), 4.28 (dd, J = 8.4, 3.6 Hz, 1H), 3.60 (ddd, J = 9.9, 7.0, 5.1 Hz, 1H), 3.40 (ddd, J = 9.9, 7.0, 7.0 Hz, 1H), 2.04-1.81 (m, 3H), 1.71-1.60 (m, 1H). |
| 70 | — | 505 | ¹H NMR (400 MHz, DMSO-d₆) δ 8.79 (dd, J = 6.2, 6.1 Hz, 1H), 7.81 (dd, J = 9.1, 4.2 Hz, 1H), 7.69 (d, J = 0.9 Hz, 1H), 7.64 (dd, J = 8.5, 2.7 Hz, 1H), 7.50-7.39 (m, 3H), 7.35 (ddd, J = 8.6, 4.6, 2.2 Hz, 1H), 4.40-4.24 (m, 3H), 3.60 (ddd, J = 9.7, 6.9, 4.9 Hz, 1H), 3.42-3.33 (m, 1H), 2.01-1.78 (m, 3H), 1.71-1.60 (m, 1H). |
| 71 | — | 505 | ¹H NMR (400 MHz, DMSO-d₆) δ 8.78 (dd, J = 6.1, 5.8 Hz, 1H), 7.81 (dd, J = 9.1, 4.1 Hz, 1H), 7.69 (d, J = 0.9 Hz, 1H), 7.64 (dd, J = 8.5, 2.7 Hz, 1H), 7.43 (ddd, J = 9.3, 9.1, 2.7 Hz, 1H), 7.38-7.30 (m, 3H), 4.40 (dd, J = 16.0, 6.1 Hz, 1H), 4.38-4.25 (m, 2H), 3.60 (ddd, J = 9.6, 6.5, 4.6 Hz, 1H), 3.38 (ddd, J = 9.6, 6.7, 6.7 Hz, 1H), 2.04-1.79 (m, 3H), 1.72-1.60 (m, 1H). |
| 72 | — | 461 | ¹H NMR (400 MHz, DMSO-d₆) δ 8.81 (d, J = 8.0 Hz, 1H), 8.63 (t, J = 5.8 Hz, 1H), 7.78 (ddd, J = 7.9, 1.4, 0.9 Hz, 1H), 7.71-7.65 (m, 3H), 7.61 (d, J = 1.0 Hz, 1H), 7.52 (ddd, J = 8.4, 7.3, 1.4 Hz, 1H), 7.50 (d, J = 0.9 Hz, 1H), 7.39 (ddd, J = 7.9, 7.3, 1.0 Hz, 1H), 4.26 (d, J = 5.8 Hz, 2H), 4.04 (dq, J = 8.0, 7.1 Hz, 1H), 1.21 (d, J = 7.1 Hz, 3H). |
| 73 | — | 479 | ¹H NMR (400 MHz, DMSO-d₆) δ 8.86 (d, J = 8.1 Hz, 1H), 8.59 (t, J = 5.9 Hz, 1H), 7.72 (dd, J = 9.2, 4.0 Hz, 1H), 7.58 (dd, J = 8.5, 2.8 Hz, 1H), 7.46 (s, 1H), 7.38 (ddd, J = 9.2, 9.2, 2.7 Hz, 1H), 7.34-7.27 (m, 2H), 7.25-7.17 (m, 1H), 4.20 (d, J = 5.9 Hz, 2H), 4.02 (dq, J = 8.1, 7.0 Hz, 1H), 1.19 (d, J = 7.0 Hz, 3H). |
| 74 | — | 443 | ¹H NMR (400 MHz, DMSO-d₆) δ 8.67 (t, J = 6.0 Hz, 1H), 7.97 (d, J = 2.2 Hz, 1H), 7.80 (dd, J = 9.1, 4.4 Hz, 1H), 7.68 (d, J = 0.9 Hz, 1H), 7.63 (dd, J = 8.5, 2.7 Hz, 1H), 7.55 (s, 1H), 7.53 (d, J = 6.0 Hz, 1H), 7.42 (td, J = 9.2, 2.7 Hz, 1H), 7.23 (dd, J = 8.4, 1.8 Hz, 1H), 6.93 (dd, J = 2.2, 0.9 Hz, 1H), 4.46-4.32 (m, 2H), 4.30 (dd, J = 8.2, 3.5 Hz, 1H), 3.60 (dt, J = 9.8, 6.1 Hz, 1H), 3.39 (dt, J = 9.6, 6.7 Hz, 1H), 1.99-1.80 (m, 3H), 1.71-1.60 (m, 1H). |
| 76 | — | 479 | ¹H NMR (400 MHz, DMSO-d₆) δ 8.69 (dd, J = 6.2, 6.2 Hz, 1H), 7.81 (dd, J = 9.0, 4.0 Hz, 1H), 7.69 (d, J = 0.9 Hz, 1H), 7.68-7.60 (m, 5H), 7.49-7.39 (m, 3H), 7.39-7.32 (m, 3H), 4.42-4.28 (m, 3H), 3.61 (ddd, J = 9.6, 6.8, 5.0 Hz, 1H), 3.43-3.37 (m, 1H), 2.00-1.83 (m, 3H), 1.72-1.61 (m, 1H). |
| 77 | — | 479 | ¹H NMR (400 MHz, DMSO-d₆) δ 8.72 (dd, J = 6.2, 5.8 Hz, 1H), 7.80 (dd, J = 8.9, 4.1 Hz, 1H), 7.70-7.65 (m, 3H), 7.63 (dd, J = 8.5, 2.8 Hz, 1H), 7.60-7.57 (m, 1H), 7.54 (ddd, J = 7.8, 1.4, 1.4 Hz, 1H), 7.49-7.39 (m, 4H), 7.39-7.33 (m, 1H), 7.27 (ddd, J = 7.7, 1.4, 1.4 Hz, 1H), 4.43 (dd, J = 15.4, 6.2 Hz, 1H), 4.35 (dd, J = 15.4, 5.8 Hz, 1H), 4.32 (dd, J = 8.1, 3.4 Hz, 1H), 3.61 (ddd, J = 9.9, 6.8, 5.2 Hz, 1H), 3.39 (ddd, J = 9.9, 6.8, 6.8 Hz, 1H), 2.00-1.83 (m, 3H), 1.72-1.61 (m, 1H). |
| 78 | — | 479 | ¹H NMR (400 MHz, DMSO-d₆) δ 8.53 (dd, J = 6.0, 5.5 Hz, 1H), 7.77 (dd, J = 9.1, 4.0 Hz, 1H), 7.66 (d, J = 0.9 Hz, 1H), 7.62 (dd, |

TABLE 39-continued

| Example No. | Salt | MS(ESI) m/z (M + H)+ | NMR |
|---|---|---|---|
| | | | J = 8.5, 2.7 Hz, 1H), 7.49-7.31 (m, 9H), 7.23 (dd, J = 7.4, 1.5 Hz, 1H), 4.31-4.23 (m, 2H), 4.16 (dd, J = 15.4, 5.5 Hz, 1H), 3.56 (ddd, J = 11.0, 6.8, 4.8 Hz, 1H), 3.40-3.34 (m, 1H), 1.96-1.76 (m, 3H), 1.69-1.59 (m, 1H). |
| 79 | — | 530 | $^1$H NMR (400 MHz, DMSO-d$_6$) δ 9.09 (d, J = 2.4 Hz, 1H), 8.77 (dd, J = 6.3, 5.8 Hz, 1H), 8.36 (dd, J = 8.3, 2.4 Hz, 1H), 7.99 (d, J = 8.3 Hz, 1H), 7.83 (ddd, J = 7.9, 1.6, 0.9 Hz, 1H), 7.77-7.68 (m, 4H), 7.56 (ddd, J = 8.7, 7.3, 1.6 Hz, 1H), 7.52 (dd, J = 7.5, 7.5 Hz, 1H), 7.45-7.38 (m, 2H), 4.47 (dd, J = 15.6, 6.3 Hz, 1H), 4.39 (dd, J = 15.6, 5.8 Hz, 1H), 4.32 (dd, J = 8.1, 3.6 Hz, 1H), 3.66-3.56 (m, 1H), 3.44-3.35 (m, 1H), 2.01-1.81 (m, 3H), 1.70-1.59 (m, 1H). |
| 80 | — | 530 | $^1$H NMR (400 MHz, DMSO-d$_6$) δ 9.04 (d, J = 2.7 Hz, 1H), 8.77 (dd, J = 6.2, 5.9 Hz, 1H), 8.29 (dd, J = 8.6, 2.7 Hz, 1H), 8.19 (d, J = 8.6 Hz, 1H), 8.09 (dd, J = 1.5, 1.5 Hz, 1H), 8.05 (ddd, J = 7.7, 1.5, 1.5 Hz, 1H), 7.83 (ddd, J = 7.9, 1.3, 0.9 Hz, 1H), 7.75 (dd, J = 8.4, 0.9 Hz, 1H), 7.73 (d, J = 0.9 Hz, 1H), 7.56 (ddd, J = 8.4, 7.2, 1.3 Hz, 1H), 7.51 (dd, J = 7.7, 7.7 Hz, 1H), 7.44 (ddd, J = 7.7, 1.5, 1.5 Hz, 1H), 7.42 (ddd, J = 7.9, 7.2, 0.9 Hz, 1H), 4.46 (dd, J = 15.4, 6.2 Hz, 1H), 4.39 (dd, J = 15.4, 5.9 Hz, 1H), 4.33 (dd, J = 7.6, 3.7 Hz, 1H), 3.61 (ddd, J = 9.3, 6.7, 4.6 Hz, 1H), 3.40 (ddd, J = 9.3, 6.6, 6.6 Hz, 1H), 1.98-1.83 (m, 3H), 1.72-1.60 (m, 1H). |
| 84 | TFA | 531 | $^1$H NMR (400 MHz, DMSO-d$_6$) δ 9.25 (d, J = 1.3 Hz, 1H), 8.99 (dd, J = 6.2, 5.7 Hz, 1H), 8.40 (d, J = 8.2 Hz, 2H), 8.06 (d, J = 1.3 Hz, 1H), 7.92 (d, J = 8.2 Hz, 2H), 7.85 (ddd, J = 7.8, 1.3, 1.0 Hz, 1H), 7.80 (d, J = 1.0 Hz, 1H), 7.76 (dd, J = 8.4, 1.0 Hz, 1H), 7.57 (ddd, J = 8.4, 7.4, 1.3 Hz, 1H), 7.43 (ddd, J = 7.8, 7.4 1.0 Hz, 1H), 4.56 (dd, J = 17.3, 6.2 Hz, 1H), 4.45 (dd, J = 17.3, 5.7 Hz, 1H), 4.38 (dd, J = 8.2, 3.8 Hz, 1H), 3.69-3.60 (m, 1H), 3.49-3.39 (m, 1H), 2.10-1.87 (m, 3H), 1.74-1.62 (m, 1H). |
| 86 | TFA | 531 | — |
| 87 | TFA | 531 | — |
| 88 | — | 548 | $^1$H NMR (400 MHz, DMSO-d$_6$) δ 9.09 (d, J = 2.4 Hz, 1H), 8.77 (dd, J = 6.2, 5.8 Hz, 1H), 8.35 (dd, J = 8.3, 2.4 Hz, 1H), 7.99 (d, J = 8.3 Hz, 1H), 7.80 (dd, J = 8.8, 4.0 Hz, 1H), 7.75-7.68 (m, 3H), 7.64 (dd, J = 8.5, 2.7 Hz, 1H), 7.52 (dd, J = 7.6, 7.6 Hz, 1H), 7.46-7.38 (m, 2H), 4.47 (dd, J = 15.6, 6.2 Hz, 1H), 4.38 (dd, J = 15.6, 5.8 Hz, 1H), 4.32 (dd, J = 8.2, 3.5 Hz, 1H), 3.66-3.58 (m, 1H), 3.44-3.35 (m, 1H), 2.04-1.83 (m, 3H), 1.71-1.62 (m, 1H). |
| 89 | — | 548 | $^1$H NMR (400 MHz, DMSO-d$_6$) δ 9.04 (d, J = 2.4 Hz, 1H), 8.77 (dd, J = 6.1, 5.9 Hz, 1H), 8.29 (dd, J = 8.5, 2.4 Hz, 1H), 8.19 (d, J = 8.5 Hz, 1H), 8.08 (dd, J = 1.8, 1.8 Hz, 1H), 8.05 (ddd, J = 7.7, 1.8, 1.5 Hz, 1H), 7.80 (dd, J = 9.1, 4.1 Hz, 1H), 7.69 (d, J = 0.9 Hz, 1H), 7.63 (dd, J = 8.5, 2.7 Hz, 1H), 7.51 (dd, J = 7.7, 7.7 Hz, 1H), 7.46-7.38 (m, 2H), 4.45 (dd, J = 15.4, 6.1 Hz, 1H), 4.39 (dd, J = 15.4, 5.9 Hz, 1H), 4.32 (dd, J = 8.1, 3.4 Hz, 1H), 3.65-3.58 (m, 1H), 3.44-3.36 (m, 1H), 2.01-1.84 (m, 3H), 1.72-1.63 (m, 1H). |
| 90 | TFA | 549 | $^1$H NMR (400 MHz DMSO-d$_6$) δ 9.25 (d, J = 1.3 Hz, 1H), 8.97 (dd, J = 6.2, 5.8 Hz, 1H), 8.39 (d, J = 8.3 Hz, 2H), 8.05 (d, J = 1.3 Hz, 1H), 7.92 (d, J = 8.3 Hz, 2H), 7.81 (dd, J = 9.0, 4.1 Hz, 1H), 7.76 (d, J = 0.9 Hz, 1H), 7.65 (dd, J = 8.5, 2.8 Hz, 1H), 7.43 (ddd, J = 9.2, 9.0, 2.8 Hz, 1H), 4.55 (dd, J = 17.3, 6.2 Hz, 1H), 4.44 (dd, J = 17.3, 5.8 Hz, 1H), 4.37 (dd, J = 8.4, 3.8 Hz, 1H), 3.70-3.57 (m, 1H), 3.48-3.40 (m, 1H), 2.12-1.88 (m, 3H), 1.74-1.62 (m, 1H). |
| 92 | — | 548 | $^1$H NMR (400 MHz, DMSO-d$_6$) δ 9.09 (d, J = 2.2 Hz, 1H), 8.77 (t, J = 6.1 Hz, 1H), 8.35 (dd, J = 8.2, 2.3 Hz, 1H), 7.99 (d, J = 8.2 Hz, 1H), 7.84 (d, J = 0.8 Hz, 1H), 7.75-7.69 (m, 2H), 7.66-7.55 (m, 2H), 7.52 (t, J = 7.6 Hz, 1H), 7.45-7.38 (m, 1H), 7.27 (ddd, J = 9.5, 7.8, 1.0 Hz, 1H), 4.46 (dd, J = 15.6, 6.2 Hz, 1H), 4.39 (dd, J = 15.6, 5.9 Hz, 1H), 4.33 (dd, J = 8.3, 3.5 Hz, 1H), 3.65-3.60 (m, 1H), 3.43 (dt, J = 9.7, 6.8 Hz, 1H), 2.04-1.83 (m, 3H), 1.75-1.63 (m, 1H). |
| 93 | — | 564 | — |
| 94 | — | 564 | — |
| 95 | TFA | 564 | $^1$H NMR (400 MHz, DMSO-d$_6$) δ 9.09 (d, J = 2.2 Hz, 1H), 8.89 (t, J = 6.1 Hz, 1H), 8.36 (dd, J = 8.0, 2.3 Hz, 1H), 7.99 (d, J = 8.2 Hz, 1H), 7.80-7.67 (m, 4H), 7.64 (dd, J = 8.5, 2.7 Hz, 1H), 7.52 (t, J = 7.6 Hz, 1H), 7.44-7.36 (m, 2H), 4.51 (dd, J = 15.5, 6.5 Hz, 1H), 4.36 (dd, J = 15.6, 5.6 Hz, 1H), 4.20-4.10 (m, 2H), 3.74-3.67 (m, 1H), 3.51 (ddd, J = 11.1, 8.9, 6.4 Hz, 1H), 2.05-1.91 (m, 1H), 1.76 (dd, J = 12.9, 6.2 Hz, 1H). |

TABLE 39-continued

| Example No. | Salt | MS(ESI) m/z (M + H)+ | NMR |
|---|---|---|---|
| 96 | TFA | 523 | — |
| 97 | TFA | 548 | — |
| 98 | TFA | 546 | $^1$H NMR (400 MHz, DMSO-$d_6$) δ 8.98 (t, J = 6.1 Hz, 1H), 8.66 (d, J = 5.1 Hz, 1H), 8.30 (d, J = 8.1 Hz, 2H), 7.96 (s, 1H), 7.86 (d, J = 8.3 Hz, 2H), 7.80 (dd, J = 9.2, 4.1 Hz, 1H), 7.77 (d, J = 0.9 Hz, 1H), 7.65 (dd, J = 8.4, 2.8 Hz, 1H), 7.43 (td, J = 9.2, 2.8 Hz, 1H), 7.34 (dd, J = 5.1, 1.5 Hz, 1H), 6.00 (dq, J = 6.2, 2.0 Hz, 1H), 5.82 (dq, J = 6.4, 2.2 Hz, 1H), 5.14-5.08 (m, 1H), 4.51 (dd, J = 16.6, 6.3 Hz, 1H), 4.47-4.36 (m, 2H), 4.32 (dq, J = 14.9, 2.3 Hz, 1H). |
| 99 | TFA | 584 | — |
| 100 | — | 534 | — |
| 101 | — | 504 | $^1$H NMR (400 MHz, DMSO-$d_6$) δ 9.06 (d, J = 2.2 Hz, 1H), 8.78 (d, J = 8.2 Hz, 1H), 8.56 (dd, J = 6.0, 6.0 Hz, 1H), 8.33 (dd, J = 8.3, 2.2 Hz, 1H), 7.99 (d, J = 8.3 Hz, 1H), 7.80-7.72 (m, 1H), 7.72-7.60 (m, 3H), 7.59-7.33 (m, 4H), 7.27 (ddd, J = 7.7, 1.2, 1.2 Hz, 1H), 4.34-4.19 (m, 2H), 4.04 (dq, J = 8.2, 7.0 Hz, 1H), 1.21 (d, J = 7.0 Hz, 3H). |
| 102 | — | 504 | $^1$H NMR (400 MHz, DMSO-$d_6$) δ 9.04 (dq, J = 2.5, 0.9 Hz, 1H), 8.76 (d, J = 8.4 Hz, 1H), 8.57 (t, J = 5.8 Hz, 1H), 8.29 (ddq, J = 8.5, 2.5, 0.8 Hz, 1H), 8.16 (d, J = 8.5 Hz, 1H), 8.06-7.98 (m, 2H), 7.75 (ddd, J = 8.0, 1.3, 1.0 Hz, 1H), 7.66 (dd, J = 8.4, 0.9 Hz, 1H), 7.55-7.45 (m, 2H), 7.45 (ddd, J = 7.7, 7.6, 0.9 Hz, 1H), 7.36 (ddd, J = 8.0, 7.3, 0.9 Hz, 1H), 7.29 (ddd, J = 7.7, 1.4, 1.4 Hz, 1H), 4.25 (d, J = 5.8 Hz, 2H), 4.05 (dq, J = 8.4, 7.0 Hz, 1H), 1.22 (d, J = 7.0 Hz, 3H). |
| 103 | TFA | 504 | $^1$H NMR (400 MHz, DMSO-$d_6$) δ 8.85 (d, J = 8.0 Hz, 1H), 8.69 (dd, J = 6.2, 6.1 Hz, 1H), 8.59 (d, J = 5.0 Hz, 1H), 8.31-8.24 (m, 2H), 7.92-7.82 (m, 3H), 7.76 (ddd, J = 7.9, 1.3, 0.9 Hz, 1H), 7.67 (dd, J = 8.5, 0.9 Hz, 1H), 7.53 (d, J = 0.9 Hz, 1H), 7.51 (ddd, J = 8.5, 7.3, 1.3 Hz, 1H), 7.37 (ddd, J = 7.9, 7.3, 0.9 Hz, 1H), 7.33 (dd, J = 5.0, 1.5 Hz, 1H), 4.35 (dd, J = 16.4, 6.1 Hz, 1H), 4.28 (dd, J = 16.4, 6.2 Hz, 1H), 4.06 (dq, J = 8.0, 7.0 Hz, 1H), 1.24 (d, J = 7.0 Hz, 3H). |
| 104 | TFA | 505 | $^1$H NMR (400 MHz, DMSO-$d_6$) δ 9.21 (d, J = 1.3 Hz, 1H), 8.89 (d, J = 7.8 Hz, 1H), 8.75 (dd, J = 6.0, 5.9 Hz, 1H), 8.36 (d, J = 8.1 Hz, 2H), 7.95 (d, J = 1.3 Hz, 1H), 7.93 (d, J = 8.1 Hz, 2H), 7.73 (ddd, J = 7.9, 1.3, 1.0 Hz, 1H), 7.65 (dd, J = 8.5, 0.9 Hz, 1H), 7.55 (d, J = 1.0 Hz, 1H), 7.49 (ddd, J = 8.5, 7.2, 1.3 Hz, 1H), 7.35 (ddd, J = 7.9, 7.2, 0.9 Hz, 1H), 4.39 (dd, J = 17.2, 5.9 Hz, 1H), 4.33 (dd, J = 17.2, 6.0 Hz, 1H), 4.10 (dq, J = 7.8, 7.1 Hz, 1H), 1.25 (d, J = 7.1 Hz, 3H). |
| 105 | TFA | 505 | $^1$H NMR (400 MHz, DMSO-$d_6$) δ 9.16 (d, J = 1.0 Hz, 1H), 8.83 (d, J = 7.9 Hz, 1H), 8.73-8.60 (m, 2H), 8.45 (dd, J = 8.2, 2.3 Hz, 1H), 8.08 (d, J = 8.2 Hz, 1H), 7.84-7.76 (m, 1H), 7.73 (ddd, J = 7.8, 1.3, 0.9 Hz, 1H), 7.72-7.67 (m, 1H), 7.64 (dd, J = 8.4, 1.0 Hz, 1H), 7.52 (d, J = 0.9 Hz, 1H), 7.49 (ddd, J = 8.4, 7.2, 1.3 Hz, 1H), 7.35 (ddd, J = 7.8, 7.2, 1.0 Hz, 1H), 4.46-4.30 (m, 2H), 4.08 (dq, J = 7.9, 7.0 Hz, 1H), 1.23 (d, J = 7.0 Hz, 3H). |
| 106 | — | 522 | $^1$H NMR (400 MHz, DMSO-$d_6$) δ 9.05 (d, J = 2.2 Hz, 1H), 8.85 (d, J = 8.2 Hz, 1H), 8.57 (dd, J = 5.8, 5.7 Hz, 1H), 8.32 (dd, J = 8.2, 2.2 Hz, 1H), 7.99 (d, J = 8.2 Hz, 1H), 7.73-7.66 (m, 2H), 7.66-7.62 (m, 1H), 7.56 (dd, J = 8.5, 2.7 Hz, 1H), 7.50-7.43 (m, 2H), 7.36 (ddd, J = 9.2, 9.2, 2.7 Hz, 1H), 7.28 (d, J = 7.9 Hz, 1H), 4.29 (dd, J = 15.5, 5.7 Hz, 1H), 4.24 (dd, J = 15.5, 5.8 Hz, 1H), 4.05 (dq, J = 8.2, 7.0 Hz, 1H), 1.22 (d, J = 7.0 Hz, 3H). |
| 107 | — | 522 | $^1$H NMR (400 MHz, DMSO-$d_6$) δ 9.03 (d, J = 2.4 Hz, 1H), 8.84 (d, J = 8.4 Hz, 1H), 8.58 (t, J = 5.9 Hz, 1H), 8.29 (dd, J = 8.5, 2.4 Hz, 1H), 8.16 (d, J = 8.5 Hz, 1H), 8.06-7.97 (m, 2H), 7.69 (dd, J = 9.2, 4.0 Hz, 1H), 7.54 (dd, J = 8.5, 2.7 Hz, 1H), 7.46 (d, J = 0.9 Hz, 1H), 7.46 (dd, J = 7.7, 7.7 Hz, 1H), 7.35 (ddd, J = 9.2, 9.2, 2.7 Hz, 1H), 7.30 (ddd, J = 7.7, 1.4, 1.4 Hz, 1H), 4.25 (d, J = 5.9 Hz, 2H), 4.06 (dq, J = 8.4, 7.0 Hz, 1H), 1.23 (d, J = 7.0 Hz, 3H). |
| 108 | TFA | 522 | $^1$H NMR (400 MHz, DMSO-$d_6$) δ 8.93 (d, J = 8.0 Hz, 1H), 8.71 (dd, J = 6.0, 5.9 Hz, 1H), 8.62 (d, J = 4.9 Hz, 1H), 8.26 (d, J = 8.3 Hz, 2H), 7.90 (s, 1H), 7.87 (d, J = 8.3 Hz, 2H), 7.71 (dd, J = 9.1, 4.1 Hz, 1H), 7.55 (dd, J = 8.5, 2.8 Hz, 1H), 7.51 (d, J = 0.9 Hz, 1H), 7.36 (ddd, J = 9.3, 9.1, 2.8 Hz, 1H), 7.24 (d, J = 4.9 Hz, 1H), 4.36 (dd, J = 16.4, 6.0 Hz, 1H), 4.30 (dd, J = 16.4, 5.9 Hz, 1H), 4.08 (dq, J = 8.0, 7.0 Hz, 1H), 1.25 (d, J = 7.0 Hz, 3H). |
| 109 | TFA | 523 | $^1$H NMR (400 MHz, DMSO-$d_6$) δ 9.21 (d, J = 1.3 Hz, 1H), 8.95 (d, J = 7.8 Hz, 1H), 8.76 (t, J = 5.9 Hz, 1H), 8.35 (d, J = 8.2 Hz, 2H), 7.99-7.89 (m, 3H), 7.70 (dd, J = 9.1, 4.0 Hz, 1H), 7.57-7.48 (m, 2H), 7.34 (ddd, J = 9.3, 9.1, 2.8 Hz, 1H), 4.44-4.28 (m, 2H), 4.11 (dq, J = 7.8, 7.1 Hz, 1H), 1.26 (d, J = 7.1 Hz, 3H), |

TABLE 39-continued

| Example No. | Salt | MS(ESI) m/z (M + H)+ | NMR |
|---|---|---|---|
| 110 | TFA | 523 | $^1$H NMR (400 MHz, DMSO-d$_6$) δ 9.15 (d, J = 2.2 Hz, 1H), 8.90 (d, J = 8.1 Hz, 1H), 8.70-8.61 (m, 2H), 8.44 (dd, J = 8.2, 2.2 Hz, 1H), 8.07 (d, J = 8.2 Hz, 1H), 7.81-7.74 (m, 1H), 7.71-7.65 (m, 2H), 7.52 (dd, J = 8.5, 2.7 Hz, 1H), 7.48 (d, J = 0.9 Hz, 1H), 7.34 (ddd, J = 9.2, 9.2, 2.7 Hz, 1H), 4.39 (dd, J = 16.2, 5.7 Hz, 1H), 4.34 (dd, J = 16.2, 6.2 Hz, 1H), 4.09 (dq, J = 8.1, 7.0 Hz, 1H), 1.24 (d, J = 7.0 Hz, 3H). |
| 111 | — | 544 | |
| 112 | TFA | 462 | $^1$H NMR (400 MHz, DMSO-d$_6$) δ 8.90 (dd, J = 5.9, 5.8 Hz, 1H), 8.66 (d, J = 5.2 Hz, 1H), 8.07 (ddd, J = 8.0, 1.4, 1.4 Hz, 2H), 7.98-7.91 (m, 1H), 7.88-7.81 (m, 1H), 7.79-7.73 (m, 2H), 7.60-7.33 (m, 6H), 4.52 (dd, J = 16.7, 5.9 Hz, 1H), 4.43 (dd, J = 16.7, 5.8 Hz, 1H), 4.34 (dd, J = 8.3, 3.7 Hz, 1H), 3.67-3.59 (m, 1H), 3.47-3.37 (m, 1H), 2.06-1.83 (m, 3H), 1.71-1.60 (m, 1H). |
| 113 | TFA | 480 | — |
| 114 | TFA | 480 | $^1$H NMR (400 MHz, DMSO-d$_6$) δ 8.88 (dd, J = 6.1, 5.7 Hz, 1H), 8.63 (d, J = 5.1 Hz, 1H), 8.17-8.08 (m, 2H), 7.91 (s, 1H), 7.84 (ddd, J = 7.9, 1.3, 0.9 Hz, 1H), 7.79-7.73 (m, 2H), 7.56 (ddd, J = 8.6, 7.3, 1.3 Hz, 1H), 7.43 (ddd, J = 7.9, 7.3, 0.9 Hz, 1H), 7.39-7.28 (m, 3H), 4.50 (dd, J = 16.6, 6.1 Hz, 1H), 4.41 (dd, J = 16.6, 5.7 Hz, 1H), 4.33 (dd, J = 8.2, 3.8 Hz, 1H), 3.67-3.59 (m, 1H), 3.41 (ddd, J = 9.7, 6.8, 6.8 Hz, 1H), 2.06-1.84 (m, 3H), 1.72-1.60 (m, 1H). |
| 115 | TFA | 530 | $^1$H NMR (400 MHz, DMSO-d$_6$) δ 8.89 (t, J = 6.1 Hz, 1H), 8.67 (d, J = 5.0 Hz, 1H), 8.30 (d, J = 8.1 Hz, 2H), 7.99 (s, 1H), 7.89-7.82 (m, 3H), 7.79-7.73 (m, 2H), 7.56 (ddd, J = 8.5, 7.2, 1.3 Hz, 1H), 7.46-7.39 (m, 1H), 7.36 (dd, J = 5.1, 1.5 Hz, 1H), 4.51 (dd, J = 16.5, 6.3 Hz, 1H), 4.41 (dd, J = 16.6, 5.9 Hz, 1H), 4.34 (dd, J = 8.3, 3.8 Hz, 1H), 3.67-3.58 (m, 1H), 3.54-3.49 (m, 1H), 2.05-1.84 (m, 3H), 1.72-1.60 (m, 1H). |
| 116 | TFA | 546 | $^1$H NMR (400 MHz, DMSO-d$_6$) δ 8.92-8.78 (m, 1H), 8.63 (dd, J = 5.2, 1.8 Hz, 1H), 8.20 (d, J = 8.8 Hz, 2H), 7.95-7.89 (m, 1H), 7.84 (ddd, J = 7.8, 1.3, 0.9 Hz, 1H), 7.79-7.71 (m, 2H), 7.56 (ddd, J = 8.5, 7.3, 1.3 Hz, 1H), 7.48 (d, J = 8.8 Hz, 2H), 7.42 (ddd, J = 7.8, 7.3, 0.9 Hz, 1H), 7.36-7.29 (m, 1H), 4.50 (dd, J = 16.5, 6.0 Hz, 1H), 4.40 (dd, J = 16.5, 8.0 Hz, 1H), 4.34 (dd, J = 8.2, 3.4 Hz, 1H), 3.67-3.58 (m, 1H), 3.46-3.37 (m, 1H), 2.05-1.82 (m, 3H), 1.72-1.60 (m, 1H). |
| 117 | TFA | 487 | $^1$H NMR (400 MHz, DMSO-d$_6$) δ 8.89 (dd, J = 6.2, 5.8 Hz, 1H), 8.67 (d, J = 5.2 Hz, 1H), 8.31-8.24 (m, 2H), 8.03-7.93 (m, 3H), 7.88-7.82 (m, 1H), 7.79-7.72 (m, 2H), 7.57 (ddd, J = 8.3, 7.4, 1.4 Hz, 1H), 7.47-7.40 (m, 1H), 7.39-7.33 (m, 1H), 4.50 (dd, J = 16.5, 6.2 Hz, 1H), 4.41 (dd, J = 16.5, 5.8 Hz, 1H), 4.33 (dd, J = 8.3, 3.7 Hz, 1H), 3.67-3.58 (m, 1H), 3.51-3.45 (m, 1H), 2.05-1.84 (m, 3H), 1.73-1.61 (m, 1H). |
| 118 | TFA | 487 | — |
| 119 | TFA | 505 | — |
| 120 | TFA | 478 | $^1$H NMR (400 MHz, DMSO-d$_6$) δ 8.93 (dd, J = 6.1, 5.8 Hz, 1H), 8.61 (d, J = 5.5 Hz, 1H), 8.11 (s, 1H), 8.02-7.93 (m, 1H), 7.84 (ddd, J = 8.0, 1.3, 0.9 Hz, 1H), 7.79-7.73 (m, 2H), 7.56 (ddd, J = 8.7, 7.3, 1.3 Hz, 1H), 7.43 (ddd, J = 8.0, 7.3, 0.9 Hz, 1H), 7.43-7.38 (m, 1H), 7.33 (ddd, J = 7.8, 7.3, 1.7 Hz, 1H), 6.97-6.89 (m, 2H), 4.54 (dd, J = 16.7, 6.1 Hz, 1H), 4.46 (dd, J = 16.7, 5.8 Hz, 1H), 4.34 (dd, J = 8.3, 3.8 Hz, 1H), 3.63 (ddd, J = 9.9, 6.7, 4.8 Hz, 1H), 3.41 (ddd, J = 9.9, 6.9, 6.9 Hz, 1H), 2.06-1.84 (m, 3H), 1.72-1.61 (m, 1H). |
| 121 | TFA | 496 | $^1$H NMR (400 MHz, DMSO-d$_6$) δ 8.92 (dd, J = 6.2, 5.9 Hz, 1H), 8.58 (d, J = 5.2 Hz, 1H), 8.10-7.99 (m, 2H), 7.84 (ddd, J = 7.8, 1.3, 0.8 Hz, 1H), 7.79-7.72 (m, 2H), 7.57 (ddd, J = 8.3, 7.2, 1.3 Hz, 1H), 7.47-7.37 (m, 2H), 6.81-6.73 (m, 2H), 4.53 (dd, J = 16.8, 6.2 Hz, 1H), 4.44 (dd, J = 16.8, 5.9 Hz, 1H), 4.34 (dd, J = 8.3, 3.7 Hz, 1H), 3.63 (ddd, J = 9.9, 6.9, 5.1 Hz, 1H), 3.42 (ddd, J = 9.9, 6.9, 6.9 Hz, 1H), 2.06-1.84 (m, 3H), 1.72-1.61 (m, 1H). |
| 122 | TFA | 514 | $^1$H NMR (400 MHz, DMSO-d$_6$) δ 8.91 (dd, J = 6.2, 5.9 Hz, 1H), 8.58 (d, J = 5.3 Hz, 1H), 8.15-8.03 (m, 2H), 7.84 (dd, J = 8.1, 1.3 Hz, 1H), 7.79-7.73 (m, 2H), 7.56 (ddd, J = 8.4, 7.3, 1.3 Hz, 1H), 7.47-7.38 (m, 1H), 7.38 (dd, J = 5.3, 1.4 Hz, 1H), 7.00 (dd, J = 12.3, 7.3 Hz, 1H), 4.52 (dd, J = 16.8, 6.2 Hz, 1H), 4.43 (dd, J = 16.8, 5.9 Hz, 1H), 4.33 (dd, J = 8.3, 3.8 Hz, 1H), 3.63 (ddd, J = 11.6, 6.1, 6.1 Hz, 1H), 3.45-3.38 (m, 1H), 2.07-1.85 (m, 3H), 1.72-1.60 (m, 1H). |
| 123 | TFA | 546 | $^1$H NMR (400 MHz, DMSO-d$_6$) δ 14.67 (brs, 1H), 8.93 (dd, J = 6.3, 5.9 Hz, 1H), 8.64 (d, J = 5.3 Hz, 1H), 8.24 (d, J = 8.2 Hz, 1H), 8.20 (s, 1H), 7.84 (d, J = 7.9 Hz, 1H), 7.78 (d, J = 0.9 Hz, 1H), 7.76 (dd, J = 8.5, 0.9 Hz, 1H), 7.57 (ddd, J = 8.5, 7.2, 1.3 Hz, 1H), 7.46-7.40 (m, 2H), 7.26-7.21 (m, 2H), 4.54 (dd, J = |

TABLE 39-continued

| Example No. | Salt | MS(ESI) m/z (M + H)+ | NMR |
|---|---|---|---|
| | | | 16.7, 6.3 Hz, 1H), 4.45 (dd, J = 16.7, 5.9 Hz, 1H), 4.34 (dd, J = 8.3, 3.8 Hz, 1H), 3.67-3.59 (m, 1H), 3.45-3.41 (m, 1H), 2.07-1.85 (m, 3H), 1.72-1.61 (m, 1H). |
| 124 | TFA | 531 | ¹H NMR (400 MHz, DMSO-d₆) δ 9.42 (d, J = 2.1 Hz, 1H), 8.90 (d, J = 6.2, 5.9 Hz, 1H), 8.74-8.66 (m, 2H), 8.07 (s, 1H), 8.05 (dd, J = 8.4, 0.8 Hz, 1H), 7.84 (ddd, J = 7.9, 1.3, 0.9 Hz, 1H), 7.77 (d, J = 0.9 Hz, 1H), 7.75 (dd, J = 8.5, 1.0 Hz, 1H), 7.56 (ddd, J = 8.5, 7.3, 1.3 Hz, 1H), 7.45-7.39 (m, 2H), 4.52 (dd, J = 16.6, 6.2 Hz, 1H), 4.42 (dd, J = 16.6, 5.9 Hz, 1H), 4.34 (dd, J = 8.3, 3.8 Hz, 1H), 3.66-3.59 (m, 1H), 3.47-3.40 (m, 1H), 2.04-1.85 (m, 3H), 1.71-1.61 (m, 1H). |
| 125 | 2TFA | 506 | ¹H NMR (400 MHz, DMSO-d₆) δ 8.90 (dd, J = 6.2, 5.9 Hz, 1H), 8.68 (s, 1H), 8.60 (d, J = 5.3 Hz, 1H), 8.36 (d, J = 7.9 Hz, 1H), 7.90 (s, 1H), 7.88-7.81 (m, 1H), 7.79-7.72 (m, 2H), 7.57 (ddd, J = 8.4, 7.3, 1.4 Hz, 1H), 7.49-7.39 (m, 1H), 7.33 (d, J = 5.3 Hz, 1H), 7.05 (brs, 1H), 4.51 (dd, J = 16.7, 6.2 Hz, 1H), 4.40 (dd, J = 16.7, 5.9 Hz, 1H), 4.34 (dd, J = 8.4, 3.8 Hz, 1H), 3.67-3.58 (m, 1H), 3.46-3.34 (m, 1H), 3.18 (s, 6H), 2.08-1.82 (m, 3H), 1.73-1.59 (m, 1H). |
| 126 | TFA | 593 | — |
| 127 | TFA | 534 | |
| 128 | TFA | 548 | ¹H NMR (400 MHz, DMSO-d₆) δ 8.89 (t, J = 6.1 Hz, 1H), 8.67 (d, J = 5.1 Hz, 1H), 8.30 (d, J = 8.2 Hz, 2H), 7.99 (s, 1H), 7.86 (d, J = 8.3 Hz, 2H), 7.81 (dd, J = 9.2, 4.1 Hz, 1H), 7.73 (d, J = 0.7 Hz, 1H), 7.65 (dd, J = 8.5, 2.7 Hz, 1H), 7.43 (td, J = 9.2, 2.8 Hz, 1H), 7.37 (dd, J = 5.1, 1.5 Hz, 1H), 4.50 (dd, J = 16.5, 6.2 Hz, 1H), 4.42 (dd, J = 16.5, 5.9 Hz, 1H), 4.34 (dd, J = 8.4, 3.7 Hz, 1H), 3.68-3.58 (m, 1H), 3.42 (dt, J = 9.8, 6.9 Hz, 1H), 2.08-1.83 (m, 3H), 1.76-1.61 (m, 1H). |
| 129 | TFA | 564 | ¹H NMR (400 MHz, DMSO-d₆) δ 8.90 (t, J = 6.1 Hz, 1H), 8.66 (d, J = 5.1 Hz, 1H), 8.24-8.17 (m, 2H), 7.95 (s, 1H), 7.81 (dd, J = 9.1, 4.0 Hz, 1H), 7.74 (s, 1H), 7.65 (dd, J = 8.5, 2.7 Hz, 1H), 7.50 (d, J = 8.4 Hz, 2H), 7.43 (td, J = 9.2, 2.8 Hz, 1H), 7.37 (dd, J = 5.2, 1.5 Hz, 1H), 4.51 (dd, J = 16.6, 6.3 Hz, 1H), 4.43 (dd, J = 16.5, 6.0 Hz, 1H), 4.34 (dd, J = 8.4, 3.6 Hz, 1H), 3.69-3.59 (m, 1H), 3.42 (dt, J = 9.9, 6.9 Hz, 1H), 2.09-1.85 (m, 3H), 1.76-1.63 (m, 1H). |
| 130 | TFA | 546 | ¹H NMR (400 MHz, DMSO-d₆) δ 8.90 (t, J = 6.1 Hz, 1H), 8.65 (d, J = 5.2 Hz, 1H), 8.16-8.10 (m, 2H), 7.93 (Br-s, 1H), 7.81 (dd, J = 9.1, 4.0 Hz, 1H), 7.73 (d, J = 0.9 Hz, 1H), 7.65 (dd, J = 8.5, 2.7 Hz, 1H), 7.43 (td, J = 9.2, 2.8 Hz, 1H), 7.39-7.28 (m, 3H), 4.51 (dd, J = 16.6, 6.2 Hz, 1H), 4.43 (dd, J = 16.7, 5.9 Hz, 1H), 4.34 (dd, J = 8.4, 3.6 Hz, 1H), 3.68-3.59 (m, 1H), 3.42 (dt, J = 9.9, 6.9 Hz, 1H), 2.09-1.84 (m, 3H), 1.75-1.62 (m, 1H). |
| 131 | TFA | 510 | ¹H NMR (400 MHz, DMSO-d₆) δ 9.01-8.89 (m, 1H), 8.65 (dd, J = 5.5, 2.6 Hz, 1H), 8.03 (d, J = 8.9 Hz, 2H), 8.00-7.93 (m, 1H), 7.81 (dd, J = 9.2, 4.0 Hz, 1H), 7.73 (d, J = 0.9 Hz, 1H), 7.65 (dd, J = 8.4, 2.7 Hz, 1H), 7.49-7.37 (m, 2H), 7.11 (d, J = 8.9 Hz, 2H), 4.54 (dd, J = 16.9, 6.0 Hz, 1H), 4.46 (dd, J = 16.9, 5.8 Hz, 1H), 4.34 (dd, J = 8.5, 3.6 Hz, 1H), 3.84 (s, 3H), 3.63 (ddd, J = 9.9, 7.0, 5.4 Hz, 1H), 3.41 (ddd, J = 9.9, 6.9, 6.9 Hz, 1H), 2.10-1.83 (m, 3H), 1.74-1.61 (m, 1H). |
| 132 | TFA | 505 | ¹H NMR (400 MHz, DMSO-d₆) δ 8.89 (t, J = 6.1 Hz, 1H), 8.68 (d, J = 5.0 Hz, 1H), 8.30-8.23 (m, 2H), 8.02-7.95 (m, 3H), 7.81 (dd, J = 9.2, 4.1 Hz, 1H), 7.73 (d, J = 0.9 Hz, 1H), 7.65 (dd, J = 8.5, 2.7 Hz, 1H), 7.43 (td, J = 9.2, 2.8 Hz, 1H), 7.37 (dd, J = 5.1, 1.5 Hz, 1H), 4.50 (dd, J = 16.5, 6.2 Hz, 1H), 4.41 (dd, J = 16.5, 5.9 Hz, 1H), 4.33 (dd, J = 8.4, 3.6 Hz, 1H), 3.68-3.58 (m, 1H), 3.42 (dt, J = 10.0, 7.0 Hz, 1H), 2.08-1.84 (m, 3H), 1.74-1.63 (m, 1H). |
| 133 | TFA | 549 | ¹H NMR (400 MHz, DMSO-d₆) δ 9.42 (d, J = 2.1 Hz, 1H), 8.91 (t, J = 6.1 Hz, 1H), 8.73-8.67 (m, 2H), 8.10-8.02 (m, 2H), 7.81 (dd, J = 9.1, 4.1 Hz, 1H), 7.74 (d, J = 0.9 Hz, 1H), 7.65 (dd, J = 8.5, 2.7 Hz, 1H), 7.44 (dd, J = 9.2, 2.7 Hz, 1H), 7.42-7.38 (m, 1H), 4.52 (dd, J = 16.6, 6.2 Hz, 1H), 4.42 (dd, J = 16.6, 5.9 Hz, 1H), 4.34 (dd, J = 8.4, 3.7 Hz, 1H), 3.66-3.59 (m, 1H), 3.42 (dt, J = 9.9, 6.9 Hz, 1H), 2.09-1.84 (m, 3H), 1.74-1.62 (m, 1H). |
| 134 | 2TFA | 522 | — |
| 135 | TFA | 496 | ¹H NMR (400 MHz, DMSO-d₆) δ 8.93 (dd, J = 6.1, 5.9 Hz, 1H), 8.61 (d, J = 5.1 Hz, 1H), 8.10 (s, 1H), 7.95 (d, J = 7.8 Hz, 1H), 7.81 (dd, J = 9.0, 4.2 Hz, 1H), 7.73 (d, J = 0.9 Hz, 1H), 7.65 (dd, J = 8.4, 2.7 Hz, 1H), 7.49-7.38 (m, 2H), 7.33 (ddd, J = 8.7, 7.1, 1.8 Hz, 1H), 6.99-6.89 (m, 2H), 4.53 (dd, J = 16.9, 6.1 Hz, 1H), 4.46 (dd, J = 16.9, 5.9 Hz, 1H), 4.34 (dd, J = 8.4, 3.7 Hz, 1H), 3.63 (ddd, J = 9.8, 6.9, 5.2 Hz, 1H), 3.41 (ddd, J = 9.8, 6.9, 6.9 Hz, 1H), 2.09-1.84 (m, 3H), 1.74-1.61 (m, 1H). |

TABLE 39-continued

| Example No. | Salt | MS(ESI) m/z (M + H)+ | NMR |
|---|---|---|---|
| 136 | TFA | 514 | $^1$H NMR (400 MHz, DMSO-d$_6$) δ 8.91 (dd, J = 6.2, 5.9 Hz, 1H), 8.56 (d, J = 5.3 Hz, 1H), 8.09-8.01 (m, 2H), 7.81 (dd, J = 9.1, 4.0 Hz, 1H), 7.73 (d, J = 0.9 Hz, 1H), 7.65 (dd, J = 8.5, 2.7 Hz, 1H), 7.43 (ddd, J = 9.2, 9.1, 2.7 Hz, 1H), 7.35 (d, J = 5.3 Hz, 1H), 6.80-6.72 (m, 2H), 4.51 (dd, J = 16.6, 6.2 Hz, 1H), 4.43 (dd, J = 16.6, 5.9 Hz, 1H), 4.33 (dd, J = 8.4, 3.7 Hz, 1H), 3.68-3.58 (m, 1H), 3.42 (ddd, J = 10.1, 6.8, 6.8 Hz, 1H), 2.09-1.85 (m, 3H), 1.74-1.62 (m, 1H). |
| 137 | TFA | 532 | $^1$H NMR (400 MHz, DMSO-d$_6$) δ 8.91 (dd, J = 6.1, 5.9 Hz, 1H), 8.58 (d, J = 5.3 Hz, 1H), 8.09 (dd, J = 12.3, 9.1 Hz, 1H), 8.07 (s, 1H), 7.81 (dd, J = 9.1, 4.0 Hz, 1H), 7.73 (d, J = 0.9 Hz, 1H), 7.65 (dd, J = 8.5, 2.7 Hz, 1H), 7.43 (ddd, J = 9.2, 9.1, 2.7 Hz, 1H), 7.38 (d, J = 5.3 Hz, 1H), 7.00 (dd, J = 12.3, 7.3 Hz, 1H), 4.51 (dd, J = 16.7, 6.1 Hz, 1H), 4.43 (dd, J = 16.7, 5.9 Hz, 1H), 4.33 (dd, J = 8.5, 3.7 Hz, 1H), 3.63 (ddd, J = 9.9, 6.3, 6.3 Hz, 1H), 3.42 (ddd, J = 9.9, 7.1, 7.1 Hz, 1H), 2.10-1.85 (m, 3H), 1.74-1.62 (m, 1H). |
| 138 | TFA | 564 | $^1$H NMR (400 MHz, DMSO-d$_6$) δ 14.67 (s, 1H), 8.93 (dd, J = 6.2, 5.9 Hz, 1H), 8.64 (d, J = 5.3 Hz, 1H), 8.23 (d, J = 8.2 Hz, 1H), 8.19 (s, 1H), 7.81 (dd, J = 8.9, 4.3 Hz, 1H), 7.74 (d, J = 0.9 Hz, 1H), 7.65 (dd, J = 8.4, 2.7 Hz, 1H), 7.47-7.40 (m, 2H), 7.27-7.20 (m, 2H), 4.53 (dd, J = 16.7, 6.2 Hz, 1H), 4.45 (dd, J = 16.7, 5.9 Hz, 1H), 4.33 (dd, J = 8.4, 3.7 Hz, 1H), 3.68-3.58 (m, 1H), 3.46-3.38 (m, 1H), 2.09-1.84 (m, 3H), 1.74-1.62 (m, 1H). |
| 139 | TFA | 548 | — |
| 140 | TFA | 549 | $^1$H NMR (400 MHz, DMSO-d$_6$) δ 9.17 (d, J = 2.2 Hz, 1H), 9.01 (d, J = 2.2 Hz, 1H), 8.89 (t, J = 6.0 Hz, 1H), 8.67 (d, J = 2.0 Hz, 1H), 8.46 (dd, J = 8.2, 2.2 Hz, 1H), 8.25 (t, J = 2.0 Hz, 1H), 8.07 (d, J = 8.2 Hz, 1H), 7.80 (dd, J = 9.1, 4.0 Hz, 1H), 7.71 (d, J = 0.8 Hz, 1H), 7.64 (dd, J = 8.5, 2.7 Hz, 1H), 7.43 (td, J = 9.2, 2.8 Hz, 1H), 4.53 (dd, J = 15.8, 6.1 Hz, 1H), 4.46 (dd, J = 15.8, 5.8 Hz, 1H), 4.30 (dd, J = 8.4, 3.7 Hz, 1H), 3.61 (ddd, J = 9.8, 6.8, 4.9 Hz, 1H), 3.40 (dt, J = 9.8, 6.9 Hz, 1H), 2.08-1.83 (m, 3H), 1.73-1.61 (m, 1H). |
| 141 | TFA | 549 | $^1$H NMR (400 MHz, DMSO-d$_6$) δ 9.27 (d, J = 2.2 Hz, 1H), 9.13-9.09 (m, 1H), 8.89 (t, J = 6.0 Hz, 1H), 8.67 (d, J = 2.0 Hz, 1H), 8.52 (t, J = 2.1 Hz, 1H), 8.39 (dd, J = 8.4, 2.3 Hz, 1H), 8.30 (d, J = 8.4 Hz, 1H), 7.80 (dd, J = 9.2, 4.0 Hz, 1H), 7.70 (d, J = 0.8 Hz, 1H), 7.63 (dd, J = 8.5, 2.7 Hz, 1H), 7.42 (td, J = 9.2, 2.8 Hz, 1H), 4.56-4.41 (m, 2H), 4.30 (dd, J = 8.3, 3.6 Hz, 1H), 3.64-3.57 (m, 1H), 3.42-3.34 (m, 1H), 2.06-1.83 (m, 3H), 1.74-1.61 (m, 1H). |
| 142 | TFA | 505 | — |
| 143 | TFA | 496 | — |
| 144 | TFA | 548 | — |
| 145 | TFA | 549 | — |
| 146 | TFA | 505 | — |
| 147 | TFA | 564 | — |
| 148 | TFA | 548 | — |
| 149 | TFA | 549 | $^1$H NMR (400 MHz, DMSO-d$_6$) δ 9.18 (d, J = 2.3 Hz, 1H), 8.89 (t, J = 6.0 Hz, 1H), 8.69 (dd, J = 4.9, 1.0 Hz, 1H), 8.47 (dd, J = 8.4, 2.2 Hz, 1H), 8.07 (d, J = 8.2 Hz, 1H), 7.83-7.77 (m, 3H), 7.72 (d, J = 0.9 Hz, 1H), 7.64 (dd, J = 8.5, 2.8 Hz, 1H), 7.43 (td, J = 9.2, 2.7 Hz, 1H), 4.57 (dd, J = 16.3, 6.2 Hz, 1H), 4.46 (dd, J = 16.5, 5.7 Hz, 1H), 4.36 (dd, J = 8.2, 3.7 Hz, 1H), 3.67-3.58 (m, 1H), 3.47-3.40 (m, 1H), 2.05-1.88 (m, 3H), 1.76-1.62 (m, 1H). |
| 150 | TFA | 505 | — |
| 151 | TFA | 531 | $^1$H NMR (400 MHz, DMSO-d$_6$) δ 9.19 (d, J = 2.2 Hz, 1H), 8.89 (t, J = 6.2 Hz, 1H), 8.73-8.67 (m, 1H), 8.47 (dd, J = 8.1, 2.2 Hz, 1H), 8.07 (d, J = 8.2 Hz, 1H), 7.86-7.72 (m, 5H), 7.56 (ddd, J = 8.5, 7.2, 1.4 Hz, 1H), 7.47-7.38 (m, 1H), 4.58 (dd, J = 16.4, 6.2 Hz, 1H), 4.46 (dd, J = 16.5, 5.7 Hz, 1H), 4.36 (dd, J = 8.1, 3.8 Hz, 1H), 3.68-3.58 (m, 1H), 3.50-3.40 (m, 1H), 2.05-1.86 (m, 3H), 1.72-1.61 (m, 1H). |
| 152 | TFA | 488 | — |
| 153 | TFA | 546 | $^1$H NMR (400 MHz, DMSO-d$_6$) δ 8.91 (t, J = 6.0 Hz, 1H), 8.71-8.66 (m, 1H), 8.01-7.95 (m, 2H), 7.86-7.72 (m, 5H), 7.60-7.51 (m, 3H), 7.47-7.38 (m, 1H), 4.59 (dd, J = 16.4, 6.1 Hz, 1H), 4.49 (dd, J = 16.4, 5.7 Hz, 1H), 4.36 (dd, J = 8.1, 3.8 Hz, 1H), 3.66-3.63 (m, 1H), 3.41 (dt, J = 9.8, 6.8 Hz, 1H), 2.06-1.86 (m, 3H), 1.71-1.60 (m, 1H). |
| 154 | TFA | 534 | $^1$H NMR (400 MHz, DMSO-d$_6$) δ 8.85 (dd, J = 6.1, 5.8 Hz, 1H), 8.67 (dd, J = 4.9, 1.1 Hz, 1H), 7.83 (d, J = 7.8 Hz, 1H), 7.78-7.70 (m, 2H), 7.61-7.51 (m, 3H), 7.42 (ddd, J = 7.5, 7.2, 0.9 Hz, 1H), 7.09 (s, 1H), 4.54 (dd, J = 16.4, 6.1 Hz, 1H), 4.45 (dd, J = |

TABLE 39-continued

| Example No. | Salt | MS(ESI) m/z (M + H)+ | NMR |
|---|---|---|---|
| | | | 16.4, 5.8 Hz, 1H), 4.34 (dd, J = 8.0, 3.9 Hz, 1H), 4.02 (s, 3H), 3.61 (m, 2H), 2.02-1.84 (m, 3H), 1.71-1.58 (m, 1H). |
| 155 | — | 497 | — |
| 156 | — | 513 | — |
| 157 | — | 547 | ¹H NMR (400 MHz, DMSO-d₆) δ 8.76 (t, J = 6.0 Hz, 1H), 7.90 (d, J = 8.0 Hz, 1H), 7.84-7.77 (m, 3H), 7.69 (d, J = 0.9 Hz, 1H), 7.68-7.60 (m, 3H), 7.48 (t, J = 7.7 Hz, 1H), 7.42 (td, J = 9.3, 2.7 Hz, 1H), 7.35 (dt, J = 7.7, 1.3 Hz, 1H), 4.45 (dd, J = 15.5, 6.2 Hz, 1H), 4.37 (dd, J = 15.5, 5.9 Hz, 1H), 4.32 (dd, J = 8.2, 3.5 Hz, 1H), 3.61 (ddd, J = 9.3, 6.7, 4.9 Hz, 1H), 3.36-3.30 (m, 1H), 2.03-1.83 (m, 3H), 1.73-1.62 (m, 1H). |
| 158 | — | 563 | — |
| 159 | TFA | 523 | ¹H NMR (400 MHz, DMSO-d₆) δ 8.76 (t, J = 6.0 Hz, 1H), 8.25-8.17 (m, 2H), 7.79 (dd, J = 9.1, 4.0 Hz, 1H), 7.70 (d, J = 0.8 Hz, 2H), 7.64 (dd, J = 8.5, 2.7 Hz, 1H), 7.56 (d, J = 8.8 Hz, 2H), 7.48-7.39 (m, 2H), 7.30 (d, J = 7.6 Hz, 1H), 7.20 (d, J = 9.2 Hz, 1H), 4.44 (dd, J = 15.5, 6.2 Hz, 1H), 4.41-4.28 (m, 2H), 3.80-3.62 (m, 1H), 3.39 (dt, J = 9.6, 6.7 Hz, 1H), 3.21 (s, 6H), 2.01-1.83 (m, 3H), 1.72-1.62 (m, 1H). |
| 160 | TFA | 549 | — |
| 161 | TFA | 565 | — |
| 162 | — | 537 | ¹H NMR (400 MHz, DMSO-d₆) δ 8.93 (d, J = 2.2 Hz, 1H), 8.81-8.74 (m, 2H), 8.26 (dd, J = 8.2, 2.3 Hz, 1H), 8.09 (d, J = 8.1 Hz, 1H), 7.80 (dd, J = 9.1, 4.0 Hz, 1H), 7.73-7.67 (m, 3H), 7.64 (dd, J = 8.5, 2.8 Hz, 1H), 7.50 (t, J = 7.6 Hz, 1H), 7.46-7.36 (m, 2H), 4.46 (dd, J = 15.5, 6.2 Hz, 1H), 4.38 (dd, J = 15.5, 5.8 Hz, 1H), 4.32 (dd, J = 8.2, 3.5 Hz, 1H), 3.67-3.58 (m, 1H), 3.39 (dt, J = 9.7, 6.7 Hz, 1H), 2.84 (d, J = 4.8 Hz, 3H), 2.05-1.82 (m, 3H), 1.72-1.61 (m, 1H). |
| 163 | — | 505 | — |
| 164 | — | 551 | ¹H NMR (400 MHz, DMSO-d₆) δ 8.75 (t, J = 6.0 Hz, 1H), 7.80 (dd, J = 9.1, 4.0 Hz, 1H), 7.68 (d, J = 0.9 Hz, 1H), 7.64 (dd, J = 8.5, 2.7 Hz, 1H), 7.53-7.47 (m, 3H), 7.46-7.38 (m, 2H), 6.88 (s, 1H), 4.43 (dd, J = 15.5, 6.1 Hz, 1H), 4.36 (dd, J = 15.6, 5.9 Hz, 1H), 4.30 (dd, J = 8.3, 3.5 Hz, 1H), 3.94 (s, 3H), 3.63-3.56 (m, 1H), 3.39 (dt, J = 9.6, 6.7 Hz, 1H), 2.02-1.81 (m, 3H), 1.70-1.59 (m, 1H). |
| 165 | — | 529 | ¹H NMR (400 MHz, DMSO-d₆) δ 8.72 (dd, J = 6.1, 6.0 Hz, 1H), 7.90 (d, J = 8.2 Hz, 2H), 7.84 (ddd, J = 7.8, 1.3, 1.0 Hz, 1H), 7.81 (d, J = 8.2 Hz, 2H), 7.76 (dd, J = 8.5, 0.9 Hz, 1H), 7.73 (d, J = 1.0 Hz, 1H), 7.71 (d, J = 8.3 Hz, 2H), 7.56 (ddd, J = 8.5, 7.2, 1.3 Hz, 1H), 7.45-7.39 (m, 3H), 4.41 (dd, J = 15.5, 6.1 Hz, 1H), 4.37-4.29 (m, 2H), 3.65-3.57 (m, 1H), 3.44-3.38 (m, 1H), 1.98-1.84 (m, 3H), 1.71-1.60 (m, 1H). |
| 166 | — | 529 | — |
| 167 | — | 529 | — |
| 168 | — | 479 | — |
| 189 | — | 479 | — |
| 170 | — | 486 | — |
| 171 | — | 486 | — |
| 172 | TFA | 523 | ¹H NMR (400 MHz, DMSO-d₆) δ 8.75 (dd, J = 6.2, 5.7 Hz, 1H), 8.24 (s, 1H), 8.06 (d, J = 8.6 Hz, 1H), 7.83 (dd, J = 7.5, 1.3 Hz, 1H), 7.78-7.70 (m, 2H), 7.64-7.57 (m, 2H), 7.56 (ddd, J = 8.6, 7.2, 1.3 Hz, 1H), 7.42 (ddd, J = 7.5, 7.2, 0.9 Hz, 1H), 7.29 (dd, J = 10.3, 8.1 Hz, 1H), 7.05 (br-s, 1H), 4.47 (dd, J = 15.7, 6.2 Hz, 1H), 4.40-4.30 (m, 2H), 3.65-3.55 (m, 1H), 3.38 (ddd, J = 9.7, 6.8, 6.8 Hz, 1H), 3.15 (s, 6H), 2.03-1.82 (m, 3H), 1.70-1.59 (m, 1H). |
| 173 | TFA | 521 | — |
| 174 | TFA | 524 | — |
| 175 | — | 609 | — |
| 176 | TFA | 501 | ¹H NMR (400 MHz, DMSO-d₆) δ 11.67 (s, 1H), 8.87 (t, J = 6.0 Hz, 1H), 8.57 (dd, J = 5.1, 0.8 Hz, 1H), 7.91 (s, 1H), 7.87-7.82 (m, 1H), 7.80-7.74 (m, 2H), 7.60-7.53 (m, 2H), 7.48-7.40 (m, 2H), 7.26-7.20 (m, 1H), 7.16-7.08 (m, 2H), 6.99 (ddd, J = 8.0, 7.0, 1.0 Hz, 1H), 4.52-4.33 (m, 3H), 3.68-3.60 (m, 1H), 3.47-3.38 (m, 1H), 2.04-1.86 (m, 3H), 1.73-1.62 (m, 1H). |
| 177 | TFA | 509 | — |
| 178 | TFA | 531 | — |
| 179 | TFA | 531 | ¹H NMR (400 MHz, DMSO-d₆) δ 9.12 (d, J = 2.4 Hz, 1H), 8.89 (dd, J = 6.1, 5.9 Hz, 1H), 8.73 (d, J = 5.1 Hz, 1H), 8.41 (dd, J = 8.5, 2.4 Hz, 1H), 8.32 (d, J = 8.5 Hz, 1H), 8.11-8.02 (m, 2H), 7.83 (dd, J = 7.7, 1.1 Hz, 1H), 7.79-7.71 (m, 2H), 7.56 (ddd, J = 8.6, 7.4, 1.4 Hz, 1H), 7.42 (ddd, J = 7.7, 7.4, 0.8 Hz, 1H), 4.57 (dd, J = 16.3, 6.1 Hz, 1H), 4.50 (dd, J = 16.3, 5.9 Hz, 1H), 4.38 |

TABLE 39-continued

| Example No. | Salt | MS(ESI) m/z (M + H)+ | NMR |
|---|---|---|---|
| | | | (dd, J = 7.4, 4.1 Hz, 1H), 3.68-3.58 (m, 1H), 3.43-3.38 (m, 1H), 2.03-1.88 (m, 3H), 1.75-1.62 (m, 1H). |
| 180 | TFA | 520 | $^1$H NMR (400 MHz, DMSO-$d_6$) δ 14.47 (s, 1H), 8.87 (d, J = 7.9 Hz, 1H), 8.73 (dd, J = 6.0, 5.9 Hz, 1H), 8.57 (dd, J = 5.3, 0.7 Hz, 1H), 8.21-8.15 (m, 1H), 8.11 (s, 1H), 7.76 (ddd, J = 7.9, 1.3, 0.9 Hz, 1H), 7.66 (dd, J = 8.5, 0.9 Hz, 1H), 7.54 (d, J = 0.9 Hz, 1H), 7.50 (ddd, J = 8.5, 7.3, 1.3 Hz, 1H), 7.37 (ddd, J = 7.9, 7.3, 0.9 Hz, 1H), 7.30 (dd, J = 5.3, 1.4 Hz, 1H), 7.27-7.21 (m, 2H), 4.39 (dd, J = 16.6, 6.0 Hz, 1H), 4.33 (dd, J = 16.6, 5.9 Hz, 1H), 4.07 (dq, J = 7.9, 7.1 Hz, 1H), 1.24 (d, J = 7.1 Hz, 3H). |
| 181 | TFA | 538 | $^1$H NMR (400 MHz, DMSO-$d_6$) δ 8.94 (d, J = 8.0 Hz, 1H), 8.75 (dd, J = 6.1, 6.1 Hz, 1H), 8.59 (d, J = 5.2 Hz, 1H), 8.17 (d, J = 8.8 Hz, 1H), 8.11 (s, 1H), 7.71 (dd, J = 9.0, 4.2 Hz, 1H), 7.54 (dd, J = 8.5, 2.7 Hz, 1H), 7.50 (d, J = 0.9 Hz, 1H), 7.36 (ddd, J = 9.2, 9.0, 2.7 Hz, 1H), 7.31 (d, J = 5.2 Hz, 1H), 7.26-7.21 (m, 2H), 4.39 (dd, J = 16.7, 6.1 Hz, 1H), 4.33 (dd, J = 16.7, 6.1 Hz, 1H), 4.08 (dq, J = 8.0, 7.1 Hz, 1H), 1.25 (d, J = 7.1 Hz, 3H). |
| 182 | — | 490 | $^1$H NMR (400 MHz, DMSO-$d_6$) δ 8.74 (d, J = 8.3 Hz, 1H), 8.44 (t, J = 5.9 Hz, 1H), 7.86 (d, J = 8.2 Hz, 2H), 7.77 (ddd, J = 7.9, 1.3, 0.9 Hz, 1H), 7.66 (dd, J = 8.4, 0.9 Hz, 1H), 7.62 (d, J = 8.2 Hz, 2H), 7.51 (ddd, J = 8.4, 7.3, 1.3 Hz, 1H), 7.49 (d, J = 0.9 Hz, 1H), 7.38 (ddd, J = 7.9, 7.3, 0.9 Hz, 1H), 7.19 (ddd, J = 7.4, 7.3, 1.3 Hz, 1H), 6.90-6.83 (m, 2H), 6.77-6.71 (m, 1H), 5.19 (s, 2H), 4.11 (d, J = 5.9 Hz, 2H), 4.02 (dq, J = 8.3, 7.0 Hz 1H), 1.18 (d, J = 7.0 Hz, 3H). |
| 183 | — | 473 | — |
| 184 | — | 508 | — |
| 185 | — | 491 | — |
| 186 | TFA | 559 | — |
| 187 | — | 571 | $^1$H NMR (400 MHz, DMSO-$d_6$) δ 8.52 (t, J = 6.0 Hz, 1H), 7.82-7.72 (m, 3H), 7.70-7.57 (m, 4H), 7.50 (ddd, J = 8.5, 7.2, 1.4 Hz, 1H), 7.42-7.33 (m, 1H), 7.24 (dd, J = 7.9, 7.9 Hz, 1H), 6.94-6.82 (m, 2H), 6.77 (d, J = 7.6 Hz, 1H), 5.74-5.61 (m, 2H), 5.20 (s, 2H), 4.75 (dd, J = 6.8, 1.6 Hz, 1H), 4.23-3.98 (m, 4H), 2.47-2.29 (m, 2H). |
| 188 | — | 523 | $^1$H NMR (400 MHz, DMSO-$d_6$) δ 8.77 (ddd, J = 6.2, 6.0, 1.8 Hz, 1H), 7.84 (d, J = 7.9 Hz, 1H), 7.79-7.71 (m, 2H), 7.61-7.33 (m, 6H), 7.33-7.23 (m, 3H), 7.16-7.08 (m, 2H), 4.41-4.34 (m, 1H), 4.31 (ddd, J = 8.2, 3.8, 2.2 Hz, 1H), 4.23 (dd, J = 12.7, 1.6 Hz, 1H), 4.02 (dd, J = 12.7, 5.0 Hz, 1H), 3.61 (ddd, J = 10.1, 7.0, 5.3 Hz, 1H), 3.45-3.39 (m, 1H), 2.01-1.82 (m, 3H), 1.71-1.58 (m, 1H). |
| 189 | — | 594 | — |
| 190 | — | 539 | $^1$H NMR (400 MHz, DMSO-$d_6$) δ 9.16 (d, J = 1.3 Hz, 1H), 8.94 (brs, 1H), 8.73 (t, J = 5.9 Hz, 1H), 8.31-8.24 (m, 2H), 7.87 (d, J = 1.3 Hz, 1H), 7.70 (dd, J = 9.0, 4.2 Hz, 1H), 7.58-7.48 (m, 4H), 7.34 (td, J = 9.2, 2.8 Hz, 1H), 4.42-4.26 (m, 2H), 4.16-4.05 (m, 1H), 1.26 (d, J = 7.1 Hz, 3H). |
| 191 | — | 524 | $^1$H NMR (400 MHz, DMSO-$d_6$) δ 9.45 (d, J = 2.1 Hz, 1H), 9.26 (d, J = 1.3 Hz, 1H), 8.97 (d, J = 7.8 Hz, 1H), 8.83-8.73 (m, 2H), 8.12 (d, J = 8.2 Hz, 1H), 8.04 (s, 1H), 7.70 (dd, J = 9.1, 4.0 Hz, 1H), 7.56-7.48 (m, 2H), 7.34 (td, J = 9.2, 2.8 Hz, 1H), 4.46-4.30 (m, 2H), 4.17-4.06 (m, 1H), 1.27 (d, J = 7.1 Hz, 3H). |
| 192 | TFA | 532 | $^1$H NMR (400 MHz, DMSO-$d_6$) δ 9.44 (d, J = 0.9 Hz, 1H), 8.89 (t, J = 6.0 Hz, 1H), 8.77 (dd, J = 5.1, 0.8 Hz, 1H), 8.27 (brs, 1H), 8.20 (dd, J = 5.2, 1.6 Hz, 1H), 7.82 (ddd, J = 7.8, 1.3, 0.7 Hz, 1H), 7.76 (ddd, J = 8.5, 1.3, 0.9 Hz, 1H), 7.73 (d, J = 0.9 Hz, 1H), 7.56 (ddd, J = 8.5, 7.3, 1.3 Hz, 1H), 7.44-7.39 (m, 1H), 4.53 (d, J = 6.0 Hz, 2H), 4.42-4.36 (m, 1H), 3.63-3.58 (m, 1H), 3.46-3.37 (m, 1H), 2.00-1.91 (m, 3H), 1.76-1.63 (m, 1H). |
| 193 | — | 546 | $^1$H NMR (400 MHz, DMSO-$d_6$) δ 9.06 (s, 1H), 8.66 (t, J = 6.0 Hz, 1H), 8.38-8.35 (m, 2H), 7.96 (d, J = 2.1 Hz, 1H), 7.86-7.80 (m, 1H), 7.77-7.71 (m, 2H), 7.55 (ddd, J = 8.5, 7.2, 1.3 Hz, 1H), 7.44-7.39 (m, 1H), 7.30 (dd, J = 8.4, 2.1 Hz, 1H), 6.96 (d, J = 8.4 Hz, 1H), 4.41-4.24 (m, 3H), 3.64-3.56 (m, 1H), 3.47-3.41 (m, 1H), 1.97-1.83 (m, 3H), 1.69-1.59 (m, 1H). |
| 194 | — | 531 | $^1$H NMR (400 MHz, DMSO-$d_6$) δ 9.34 (d, J = 1.0 Hz, 2H), 8.79 (t, J = 6.1 Hz, 1H), 8.39 (Br-s, 1H), 8.34 (dt, J = 6.7, 2.3 Hz, 1H), 7.86-7.79 (m, 1H), 7.79-7.72 (m, 1H), 7.72 (d, J = 0.9 Hz, 1H), 7.58-7.52 (m, 3H), 7.42 (ddd, J = 8.1, 7.3, 0.9 Hz, 1H), 4.49-4.37 (m, 2H), 4.35-4.31 (m, 1H), 3.64-3.58 (m, 1H), 3.44-3.35 (m, 1H), 1.95-1.87 (m, 3H), 1.69-1.64 (m, 1H). |
| 195 | — | 531 | $^1$H NMR (400 MHz, DMSO-$d_6$) δ 9.39 (s, 2H), 8.79 (t, J = 6.1 Hz, 1H), 7.86-7.78 (m, 3H), 7.77-7.71 (m, 2H), 7.60-7.52 (m, |

TABLE 39-continued

| Example No. | Salt | MS(ESI) m/z (M + H)+ | NMR |
|---|---|---|---|
| | | | 2H), 7.51-7.38 (m, 2H), 4.49 (dd, J = 15.6, 6.2 Hz, 1H), 4.40 (dd, J = 15.6, 5.8 Hz, 1H), 4.32 (dd, J = 8.1, 3.7 Hz, 1H), 3.61 (ddd, J = 9.8, 6.8, 4.9 Hz, 1H), 3.41-3.35 (m, 1H), 2.03-1.83 (m, 3H), 1.70-1.60 (m, 1H). |
| 196 | — | 531 | $^1$H NMR (400 MHz, DMSO-$d_6$) δ 9.45 (d, J = 1.4 Hz, 1H), 9.23 (d, J = 1.4 Hz, 1H), 8.81 (t, J = 6.0 Hz, 1H), 8.17-8.10 (m, 2H), 7.87-7.80 (m, 1H), 7.77-7.73 (m, 2H), 7.60-7.49 (m, 3H), 7.45-7.39 (m, 1H), 4.48 (dd, J = 15.5, 6.2 Hz, 1H), 4.41 (dd, J = 15.5, 5.9 Hz, 1H), 4.33 (dd, J = 7.9, 3.7 Hz, 1H), 3.67-3.58 (m, 1H), 3.45-3.35 (m, 1H), 2.00-1.82 (m, 3H), 1.72-1.59 (m, 1H). |
| 197 | — | 531 | $^1$H NMR (400 MHz, DMSO-$d_6$) δ 8.80 (t, J = 6.1 Hz, 1H), 8.51 (d, J = 9.0 Hz, 1H), 8.36 (d, J = 9.0 Hz, 1H), 8.18-8.15 (m, 1H), 8.15-8.10 (m, 1H), 7.83 (d, J = 7.8 Hz, 1H), 7.79-7.71 (m, 2H), 7.61-7.49 (m, 3H), 7.42 (t, J = 7.5 Hz, 1H), 4.49 (dd, J = 15.5, 6.2 Hz, 1H), 4.42 (dd, J = 15.5, 5.9 Hz, 1H), 4.33 (dd, J = 7.9, 3.6 Hz, 1H), 3.55-3.49 (m, 1H), 3.40 (dt, J = 9.3, 6.4 Hz, 1H), 2.00-1.83 (m, 3H), 1.71-1.58 (m, 1H). |
| 198 | TFA | 496 | $^1$H NMR (400 MHz, DMSO-$d_6$) δ 8.89 (t, J = 6.0 Hz, 1H), 8.65 (d, J = 5.2 Hz, 1H), 8.13-8.06 (m, 2H), 7.94 (s, 1H), 7.87-7.81 (m, 1H), 7.78-7.73 (m, 2H), 7.60-7.53 (m, 3H), 7.47-7.40 (m, 1H), 7.36 (dd, J = 5.2, 1.5 Hz, 1H), 4.51 (dd, J = 16.6, 6.2 Hz, 1H), 4.42 (dd, J = 16.6, 5.9 Hz, 1H), 4.34 (dd, J = 8.3, 3.7 Hz, 1H), 3.63 (ddd, J = 9.8, 6.8, 5.1 Hz, 1H), 3.41 (dt, J = 9.7, 6.8 Hz, 1H), 2.05-1.83 (m, 3H), 1.72-1.59 (m, 1H). |
| 199 | TFA | 532 | $^1$H NMR (400 MHz, DMSO-$d_6$) δ 9.65 (s, 2H), 8.92 (t, J = 6.1 Hz, 1H), 8.74 (dd, J = 5.1, 0.8 Hz, 1H), 8.14 (dd, J = 1.7, 0.9 Hz, 1H), 7.86-7.82 (m, 1H), 7.78 (d, J = 0.9 Hz, 1H), 7.76 (dq, J = 8.4, 0.8 Hz, 1H), 7.59-7.54 (m, 1H), 7.46 (dd, J = 5.1, 1.5 Hz, 1H), 7.45-7.40 (m, 1H), 4.53 (dd, J = 16.6, 6.3 Hz, 1H), 4.43 (dd, J = 16.7, 5.8 Hz, 1H), 4.34 (dd, J = 8.3, 3.8 Hz, 1H), 3.69-3.59 (m, 1H), 3.46-3.37 (m, 1H), 2.08-1.86 (m, 3H), 1.71-1.61 (m, 1H). |
| 200 | TFA | 532 | $^1$H NMR (400 MHz, DMSO-$d_6$) δ 9.48 (s, 2H), 8.91 (t, J = 6.0 Hz, 1H), 8.76 (dd, J = 5.2, 0.8 Hz, 1H), 7.90 (dd, J = 5.2, 1.8 Hz, 1H), 7.86 (brs, J = 1.9, 0.9 Hz, 1H), 7.88-7.80 (m, 1H), 7.77 (d, J = 0.9 Hz, 1H), 7.76-7.73 (m, 1H), 7.56 (ddd, J = 8.5, 7.3, 1.3 Hz, 1H), 7.42 (ddd, J = 8.0, 7.3, 0.9 Hz, 1H), 4.60 (dd, J = 16.5, 6.3 Hz, 1H), 4.48 (dd, J = 16.5, 5.7 Hz, 1H), 4.37 (dd, J = 8.0, 3.9 Hz, 1H), 3.67-3.58 (m, 1H), 3.45-3.36 (m, 1H), 2.03-1.87 (m, 3H), 1.73-1.60 (m, 1H). |
| 201 | TFA | 532 | $^1$H NMR (400 MHz, DMSO-$d_6$) δ 9.52 (d, J = 1.4 Hz, 1H), 9.32 (d, J = 1.4 Hz, 1H), 8.91 (t, J = 6.0 Hz, 1H), 8.77 (dd, J = 5.0, 1.0 Hz, 1H), 8.11-8.07 (m, 2H), 7.83 (dq, J = 7.8, 0.6 Hz, 1H), 7.77-7.73 (m, 2H), 7.56 (ddd, J = 8.6, 7.2, 1.3 Hz, 1H), 7.42 (ddd, J = 8.0, 7.2, 0.9 Hz, 1H), 4.57 (dd, J = 16.3, 6.1 Hz, 1H), 4.50 (dd, J = 16.4, 5.9 Hz, 1H), 4.38 (dd, J = 7.4, 4.3 Hz, 1H), 3.66-3.59 (m, 1H), 3.45-3.36 (m, 1H), 2.02-1.89 (m, 3H), 1.73-1.63 (m, 1H). |
| 202 | TFA | 532 | $^1$H NMR (400 MHz, DMSO-$d_6$) δ 8.91 (t, J = 6.0 Hz, 1H), 8.81-8.78 (m, 1H), 8.61 (d, J = 8.9 Hz, 1H), 8.49 (d, J = 8.9 Hz, 1H), 8.15-8.13 (m, 2H), 7.85-7.81 (m, 1H), 7.77-7.74 (m, 2H), 7.56 (ddd, J = 8.7, 7.2, 1.3 Hz, 1H), 7.44-7.40 (m, 1H), 4.59 (dd, J = 16.3, 6.1 Hz, 1H), 4.52 (dd, J = 16.3, 5.8 Hz, 1H), 4.37 (dd, J = 7.7, 4.1 Hz, 1H), 3.67-3.59 (m, 1H), 3.46-3.36 (m, 1H), 2.02-1.89 (m, 3H), 1.73-1.62 (m, 1H). |
| 203 | TFA | 547 | $^1$H HMR (400 MHz, DMSO-$d_6$) δ 9.20 (d, J = 1.3 Hz, 1H), 8.96 (t, J = 6.0 Hz, 1H), 8.35-8.29 (m, 2H), 7.99 (d, J = 1.3 Hz, 1H), 7.87-7.82 (m, 1H), 7.79 (d, J = 0.8 Hz, 1H), 7.78-7.74 (m, 1H), 7.60-7.51 (m, 3H), 7.46-7.40 (m, 1H), 4.54 (dd, J = 17.2, 6.2 Hz, 1H), 4.46-4.34 (m, 2H), 3.67-3.56 (m, 1H), 3.43 (dt, J = 9.4, 6.7 Hz, 1H), 2.08-1.87 (m, 3H), 1.75-1.61 (m, 1H). |
| 204 | TFA | 560 | $^1$H NMR (400 MHz, DMSO-$d_6$) δ 8.88 (t, J = 6.1 Hz, 1H), 8.61 (d, J = 5.3 Hz, 1H), 8.09-8.06 (m, 2H), 7.91 (brs, 1H), 7.84 (ddd, J = 7.9, 1.4, 0.7 Hz, 1H), 7.78-7.74 (m, 2H), 7.57 (ddd, J = 8.6, 7.3, 1.3 Hz, 1H), 7.43 (ddd, J = 8.0, 7.3, 0.9 Hz, 1H), 7.34-7.30 (m, 1H), 7.23-7.18 (m, 2H), 4.85 (q, J = 8.8 Hz, 2H), 4.50 (dd, J = 16.7, 6.2 Hz, 1H), 4.41 (dd, J = 16.7, 5.9 Hz, 1H), 4.34 (dd, J = 8.3, 3.7 Hz, 1H), 3.64-3.53 (m, 1H), 3.43-3.34 (m, 1H), 2.04-1.86 (m, 3H), 1.73-1.61 (m, 1H). |
| 205 | TFA | 532 | $^1$H NMR (400 MHz, DMSO-$d_6$) δ 9.48 (d, J = 2.1 Hz, 1H), 9.30 (d, J = 1.3 Hz, 1H), 8.99 (t, J = 6.0 Hz, 1H), 8.79 (dd, J = 8.3, 2.4 Hz, 1H), 8.15-8.11 (m, 2H), 7.88-7.82 (m, 1H), 7.80 (d, J = 0.9 Hz, 1H), 7.76 (dq, J = 8.5, 0.8 Hz, 1H), 7.57 (ddd, J = 8.5, 7.2, 1.3 Hz, 1H), 7.43 (ddd, J = 8.1, 7.3, 0.9 Hz, 1H), 4.58 (dd, J = 17.3, 6.2 Hz, 1H), 4.46 (dd, J = 17.3, 5.6 Hz, 1H), 4.38 (dd, J = |

TABLE 39-continued

| Example No. | Salt | MS(ESI) m/z (M + H)+ | NMR |
|---|---|---|---|
| | | | 8.2, 3.9 Hz, 1H), 3.63 (ddd, J = 9.9, 6.6, 5.0 Hz, 1H), 3.42 (dt, J = 9.8, 6.8 Hz, 1H), 2.10-1.89 (m, 3H), 1.73-1.63 (m, 1H). |
| 206 | TFA | 532 | $^1$H NMR (400 MHz, DMSO-d$_6$) δ 9.29 (d, J = 1.3 Hz, 1H), 9.14-9.12 (m, 1H), 8.96 (t, J = 6.0 Hz, 1H), 8.63 (d, J = 8.3 Hz, 1H), 8.46 (dd, J = 8.5, 2.3 Hz, 1H), 8.35 (d, J = 1.3 Hz, 1H), 7.85-7.80 (m, 1H), 7.78-7.73 (m, 2H), 7.56 (ddd, J = 8.4, 7.2, 1.3 Hz, 1H), 7.44-7.39 (m, 1H), 4.51 (d, J = 6.0 Hz, 2H), 4.40 (t, J = 5.7 Hz, 1H), 3.66-3.59 (m, 1H), 3.46-3.36 (m, 1H), 1.99-1.93 (m, 3H), 1.77-1.68 (m, 1H). |
| 207 | — | 533 | $^1$H NMR (400 MHz, DMSO-d$_6$) δ 9.69 (s, 2H), 9.34 (d, J = 1.3 Hz, 1H), 9.01 (t, J = 6.0 Hz, 1H), 8.18 (d, J = 1.3 Hz, 1H), 7.85 (ddd, J = 7.9, 1.4, 0.7 Hz, 1H), 7.81 (d, J = 0.9 Hz, 1H), 7.76 (ddd, J = 8.5, 0.9 Hz, 1H), 7.57 (ddd, J = 8.5, 7.2, 1.3 Hz, 1H), 7.43 (ddd, J = 8.0, 7.2, 0.9 Hz, 1H), 4.58 (dd, J = 17.4, 6.2 Hz, 1H), 4.47 (dd, J = 17.4, 5.7 Hz, 1H), 4.38 (dd, J = 8.2, 3.9 Hz, 1H), 3.71-3.60 (m, 1H), 3.48-3.39 (m, 1H), 2.10-1.89 (m, 3H), 1.73-1.61 (m, 1H). |
| 208 | — | 531 | $^1$H NMR (400 MHz, DMSO-d$_6$) δ 9.23 (d, J = 2.0 Hz, 1H), 8.95 (t, J = 6.0 Hz, 1H), 8.37 (d, J = 8.1 Hz, 2H), 8.17 (d, J = 2.0 Hz, 1H), 7.94 (d, J = 8.2 Hz, 2H), 7.86-7.82 (m, 1H), 7.78 (d, J = 0.9 Hz, 1H), 7.77-7.74 (m, 1H), 7.56 (ddd, J = 8.5, 7.3, 1.3 Hz, 1H), 7.45-7.40 (m, 1H), 4.55 (dd, J = 16.8, 6.1 Hz, 1H), 4.46 (dd, J = 16.7, 5.8 Hz, 1H), 4.32 (dd, J = 8.5, 3.9 Hz, 1H), 3.52-3.48 (m, 1H), 3.46-3.37 (m, 1H), 2.08-1.83 (m, 3H), 1.72-1.61 (m, 1H). |
| 209 | — | 532 | $^1$H NMR (400 MHz, DMSO-d$_6$) δ 9.47 (d, J = 2.1 Hz, 1H), 9.28 (d, J = 2.0 Hz, 1H), 8.97 (t, J = 6.0 Hz, 1H), 8.79 (dd, J = 8.2, 2.2 Hz, 1H), 8.26 (d, J = 2.0 Hz, 1H), 8.13 (d, J = 8.2 Hz, 1H), 7.86-7.82 (m, 1H), 7.78 (d, J = 0.9 Hz, 1H), 7.75 (dd, J = 8.5, 0.8 Hz, 1H), 7.57 (ddd, J = 8.5, 7.2, 1.3 Hz, 1H), 7.45-7.38 (m, 1H), 4.57 (dd, J = 16.8, 6.2 Hz, 1H), 4.47 (dd, J = 16.9, 5.8 Hz, 1H), 4.32 (dd, J = 8.5, 3.9 Hz, 1H), 3.74-3.60 (m, 1H), 3.47-3.38 (m, 1H), 2.10-1.82 (m, 3H), 1.70-1.60 (m, 1H). |
| 210 | — | 531 | $^1$H NMR (400 MHz, DMSO-d$_6$) δ 9.63 (d, J = 2.2 Hz, 1H), 9.00 (t, J = 6.0 Hz, 1H), 8.12 (d, J = 8.2 Hz, 2H), 7.96-7.91 (m, 3H), 7.85-7.81 (m, 1H), 7.77-7.72 (m, 2H), 7.59-7.54 (m, 1H), 7.45-7.40 (m, 1H), 4.76 (dd, J = 16.2, 6.1 Hz, 1H), 4.67 (dd, J = 16.2, 5.8 Hz, 1H), 4.35 (dd, J = 8.2, 4.0 Hz, 1H), 3.66-3.56 (m, 1H), 3.46-3.36 (m, 1H), 2.05-1.87 (m, 3H), 1.72-1.61 (m, 1H). |
| 211 | — | 532 | $^1$H NMR (400 MHz, DMSO-d$_6$) δ 9.70 (d, J = 2.2 Hz, 1H), 9.27 (d, J = 2.2 Hz, 1H), 9.01 (t, J = 6.0 Hz, 1H), 8.59 (dd, J = 8.0, 2.2 Hz, 1H), 8.13 (dd, J = 8.3, 0.8 Hz, 1H), 8.02 (d, J = 2.2 Hz, 1H), 7.85-7.81 (m, 1H), 7.77-7.73 (m, 2H), 7.59-7.53 (m, 1H), 7.45-7.39 (m, 1H), 4.78 (dd, J = 16.2, 6.2 Hz, 1H), 4.68 (dd, J = 16.2, 5.7 Hz, 1H), 4.34 (dd, J = 8.2, 4.0 Hz, 1H), 3.67-3.58 (m, 1H), 3.45-3.36 (m, 1H), 2.05-1.85 (m, 3H), 1.70-1.59 (m, 1H). |
| 212 | — | 532 | $^1$H NMR (400 MHz, DMSO-d$_6$) δ 9.87 (d, J = 2.1 Hz, 1H), 9.19-9.17 (m, 1H), 9.01 (t, J = 6.0 Hz, 1H), 8.49 (dd, J = 8.7, 2.2 Hz, 1H), 8.42 (d, J = 8.4 Hz, 1H), 8.24 (d, J = 2.1 Hz, 1H), 7.84-7.81 (m, 1H), 7.77-7.73 (m, 2H), 7.56 (ddd, J = 8.6, 7.2, 1.3 Hz, 1H), 7.42 (ddd, J = 7.5, 0.9 Hz, 1H), 4.81-4.66 (m, 2H), 4.36 (dd, J = 7.9, 3.9 Hz, 1H), 3.67-3.57 (m, 1H), 3.45-3.36 (m, 1H), 2.02-1.86 (m, 3H), 1.73-1.63 (m, 1H). |
| 213 | — | 547 | $^1$H NMR (400 MHz, DMSO-d$_6$) δ 12.68 (brs, 1H), 9.40 (d, J = 0.8 Hz, 2H), 8.69 (t, J = 6.0 Hz, 1H), 8.35 (d, J = 2.3 Hz, 1H), 7.87-7.79 (m, 1H), 7.75 (dd, J = 8.4, 1.0 Hz, 1H), 7.71 (d, J = 0.9 Hz, 1H), 7.55 (ddd, J = 8.5, 7.3, 1.3 Hz, 1H), 7.48-7.37 (m, 2H), 7.00 (d, J = 8.5 Hz, 1H), 4.39-4.23 (m, 3H), 3.66-3.57 (m, 1H), 3.39 (dt, J = 10.8, 6.7 Hz, 1H), 1.95-1.81 (m, 3H), 1.72-1.60 (m, 1H). |
| 214 | — | 547 | $^1$H NMR (400 MHz, DMSO-d$_6$) δ 11.04 (Br-s, 1H), 9.50 (d, J = 1.4 Hz, 1H), 9.21 (d, J = 1.0 Hz, 1H), 8.65 (t, J = 6.0 Hz, 1H), 7.90 (d, J = 2.2 Hz, 1H), 7.86-7.79 (m, 1H), 7.75 (dd, 1H), 7.71 (s, 1H), 7.55 (ddd, J = 8.5, 7.2, 1.3 Hz, 1H), 7.42 (ddd, J = 7.5 Hz, 1H), 7.32 (dd, J = 8.4, 2.3 Hz, 1H), 7.01 (d, J = 8.4 Hz, 1H), 4.38-4.21 (m, 3H), 3.66-3.56 (m, 1H), 3.41-3.34 (m, 1H), 1.95-1.80 (m, 3H), 1.69-1.59 (m, 1H). |
| 215 | TFA | 547 | $^1$H NMR (400 MHz, DMSO-d$_6$) δ 12.18 (Br-s, 1H), 9.14-9.11 (m, 1H), 8.76 (t, J = 5.9 Hz, 1H), 8.45 (d, J = 1.7 Hz, 2H), 8.35 (s, 1H), 7.91 (s, 1H), 7.84-7.81 (m, 1H), 7.77-7.72 (m, 2H), 7.56 (ddd, J = 8.7, 7.2, 1.3 Hz, 1H), 7.44-7.39 (m, 1H), 4.45 (dd, J = 15.7, 6.1 Hz, 1H), 4.40-4.32 (m, 2H), 3.66-3.51 (m, 1H), 3.44-3.36 (m, 1H), 1.98-1.87 (m, 3H), 1.71-1.63, (m, 1H). |

TABLE 39-continued

| Example No. | Salt | MS(ESI) m/z (M + H)+ | NMR |
|---|---|---|---|
| 216 | — | 590 | $^1$H NMR (400 MHz, DMSO-d$_6$) δ 9.11 (d, J = 2.2 Hz, 1H), 8.97 (s, 1H), 8.40 (dd, J = 8.3, 2.2 Hz, 1H), 7.98 (d, J = 8.3 Hz, 1H), 7.83 (dd, J = 7.9, 1.3 Hz, 1H), 7.78-7.68 (m, 3H), 7.56 (ddd, J = 8.8, 7.2, 1.3 Hz, 1H), 7.48-7.38 (m, 2H), 7.36 (dd, J = 1.8, 1.8 Hz, 1H), 4.25 (dd, J = 8.5, 4.3 Hz, 1H), 3.66-3.57 (m, 1H), 3.39 (ddd, J = 9.9, 6.9, 6.9 Hz, 1H), 2.06-1.77 (m, 3H), 1.70-1.58 (m, 1H), 1.48-1.37 (m, 2H), 1.30-1.12 (m, 2H). |
| 217 | — | 556 | $^1$H NMR (400 MHz, DMSO-d$_6$) δ 9.02 (s, 1H), 8.57 (d, J = 5.3 Hz, 1H), 8.31 (d, J = 8.1 Hz, 2H), 7.90-7.69 (m, 6H), 7.61-7.52 (m, 1H), 7.43 (t, J = 7.6 Hz, 1H), 7.15 (dd, J = 5.3, 1.8 Hz, 1H), 4.32-4.25 (m, 1H), 3.67-3.59 (m, 1H), 3.45-3.27 (m, 1H), 2.10-1.83 (m, 3H), 1.71-1.60 (m, 1H), 1.53-1.23 (m, 4H). |
| 218 | TFA | 557 | $^1$H NMR (400 MHz, DMSO-d$_6$) δ 9.43 (s, 1H), 9.04 (s, 1H), 8.72 (d, J = 7.7 Hz, 1H), 8.62 (d, J = 5.3 Hz, 1H), 8.02 (d, J = 8.3 Hz, 1H), 7.91-7.67 (m, 4H), 7.57 (t, J = 7.8 Hz, 1H), 7.50-7.38 (m, 1H), 7.24 (d, J = 5.3 Hz, 1H), 4.32-4.23 (m, 1H), 3.65-3.35 (m, 2H), 2.11-1.81 (m, 3H), 1.72-1.45 (m, 3H), 1.45-1.23 (m, 2H). |
| 219 | TFA | 548 | $^1$H NMR (400 MHz, DMSO-d$_6$) δ 8.90 (t, J = 6.0 Hz, 1H), 8.66 (d, J = 5.0 Hz, 1H), 8.30 (d, J = 8.4 Hz, 2H), 7.98 (s, 1H), 7.88-7.83 (m, 3H), 7.66 (dd, J = 7.8, 1.1 Hz, 1H), 7.49 (ddd, J = 11.1, 8.2, 1.1 Hz, 1H), 7.44-7.39 (m, 1H), 7.35 (dd, J = 5.1, 1.5 Hz, 1H), 4.49 (dd, J = 16.5, 6.2 Hz, 1H), 4.42 (dd, J = 16.5, 5.9 Hz, 1H), 4.34 (dd, J = 8.6, 3.5 Hz, 1H), 3.69-3.63 (m, 1H), 3.48-3.37 (m, 1H), 2.10-2.00 (m, 1H), 1.98-1.86 (m, 2H), 1.78-1.66 (m, 1H). |
| 220 | TFA | 548 | $^1$H NMR (400 MHz, DMSO-d$_6$) δ 8.88 (t, J = 6.1 Hz, 1H), 8.67 (dd, J = 5.1, 0.8 Hz, 1H), 8.30 (d, J = 8.0 Hz, 2H), 7.98 ( Br-s, J = 1.7, 0.9 Hz, 1H), 7.91-7.83 (m, 3H), 7.78 (d, J = 0.9 Hz, 1H), 7.75 (dd, J = 9.0, 2.4 Hz, 1H), 7.38-7.29 (m, 2H), 4.50 (dd, J = 16.5, 6.2 Hz, 1H), 4.41 (dd, J = 16.5, 5.9 Hz, 1H), 4.32 (dd, J = 8.4, 3.7 Hz, 1H), 3.67-3.58 (m, 1H), 3.40 (dt, J = 9.9, 6.9 Hz, 1H), 2.06-1.84 (m, 3H), 1.74-1.61 (m, 1H). |
| 221 | TFA | 549 | $^1$H NMR (400 MHz, DMSO-d$_6$) δ 9.08-9.05 (m, 1H), 8.89 (t, J = 6.1 Hz, 1H), 8.72-8.66 (m, 1H), 8.59 (d, J = 8.4 Hz, 1H), 8.40-8.33 (m, 2H), 7.81 (dd, J = 9.2, 4.0 Hz, 1H), 7.71 (d, J = 0.9 Hz, 1H), 7.63 (dd, J = 8.5, 2.7 Hz, 1H), 7.46-7.39 (m, 2H), 4.46 (d, J = 6.3 Hz, 2H), 4.33 (dd, J = 8.1, 3.5 Hz, 1H), 3.68-3.57 (m, 1H), 3.54-3.47 (m, 1H), 2.04-1.87 (m, 3H), 1.77-1.65 (m, 1H). |
| 222 | TFA | 564 | $^1$H NMR (400 MHz, DMSO-d$_6$) δ 8.91 (t, J = 6.0 Hz, 1H), 8.69 (dd, J = 5.3, 0.9 Hz, 1H), 8.00-7.95 (m, 2H), 7.82-7.77 (m, 3H), 7.72 (d, J = 0.9 Hz, 1H), 7.64 (dd, J = 8.4, 2.7 Hz, 1H), 7.55-7.51 (m, 2H), 7.43 (td, J = 9.2, 2.8 Hz, 1H), 4.58 (dd, J = 16.4, 6.1 Hz, 1H), 4.49 (dd, J = 16.4, 5.7 Hz, 1H), 4.36 (dd, J = 8.2, 3.7 Hz, 1H), 3.65-3.59 (m, 1H), 3.45-3.37 (m, 1H), 2.05-1.87 (m, 3H), 1.73-1.62 (m, 1H). |
| 223 | TFA | 549 | $^1$H NMR (400 MHz, DMSO-d$_6$) δ 9.15-9.10 (m, 1H), 8.89 (t, J = 6.0 Hz, 1H), 8.71 (dd, J = 5.0, 0.9 Hz, 1H), 8.41 (dd, J = 8.5, 2.4 Hz, 1H), 8.31 (d, J = 8.4 Hz, 1H), 8.07-8.02 (m, 2H), 7.80 (dd, J = 9.1, 4.0 Hz, 1H), 7.71 (d, J = 0.9 Hz, 1H), 7.63 (dd, J = 8.5, 2.7 Hz, 1H), 7.42 (td, J = 9.2, 2.7 Hz, 1H), 4.55 (dd, J = 16.3, 6.2 Hz, 1H), 4.48 (dd, J = 16.3, 5.8 Hz, 1H), 4.37 (dd, J = 7.8, 3.6 Hz, 1H), 3.68-3.58 (m, 1H), 3.33-3.24 (m, 1H), 2.05-1.87 (m, 3H), 1.76-1.65 (m, 1H). |
| 224 | TFA | 550 | $^1$H NMR (400 MHz, DMSO-d$_6$) δ 9.47 (d, J = 2.2 Hz, 1H), 9.30 (d, J = 1.3 Hz, 1H), 9.00 (t, J = 6.0 Hz, 1H), 8.78 (dd, J = 8.3, 2.2 Hz, 1H), 8.16-8.10 (m, 2H), 7.81 (dd, J = 9.1, 4.1 Hz, 1H), 7.77 (d, J = 0.9 Hz, 1H), 7.65 (dd, J = 8.5, 2.8 Hz, 1H), 7.43 (td, J = 9.2, 2.7 Hz, 1H), 4.57 (dd, J = 17.3, 6.2 Hz, 1H), 4.46 (dd, J = 17.3, 5.7 Hz, 1H), 4.38 (dd, J = 8.4, 3.8 Hz, 1H), 3.65-3.59 (m, 1H), 3.43 (dt, J = 9.9, 6.9 Hz, 1H), 2.11-1.90 (m, 3H), 1.76-1.65 (m, 1H). |
| 225 | TFA | 547 | $^1$H NMR (400 MHz, DMSO-d$_6$) δ 9.16-9.12 (m, 1H), 9.01 (t, J = 6.0 Hz, 1H), 8.74 (dd, J = 5.2, 0.9 Hz, 1H), 8.42 (dd, J = 8.5, 2.4 Hz, 1H), 8.30 (d, J = 8.4 Hz, 1H), 8.07 (dd, J = 5.1, 1.8 Hz, 1H), 8.05 (brs, J = 1.1 Hz, 1H), 7.79 (dd, J = 9.3, 4.2 Hz, 1H), 7.74 (d, J = 0.9 Hz, 1H), 7.63 (dd, J = 8.4, 2.7 Hz, 1H), 7.43 (td, J = 9.2, 2.7 Hz, 1H), 6.00 (dq, J = 6.2, 2.0 Hz, 1H), 5.81 (dq, J = 6.5, 2.2 Hz, 1H), 5.15 (dq, J = 4.8, 2.2 Hz, 1H), 4.58 (dd, J = 16.3, 6.1 Hz, 1H), 4.48 (dd, J = 16.3, 5.8 Hz, 1H), 4.45-4.37 (m, 1H), 4.35-4.28 (m, 1H). |
| 226 | TFA | 547 | $^1$H NMR (400 MHz, DMSO-d$_6$) δ 9.25 (d, J = 1.3 Hz, 1H), 9.05 (t, J = 6.1 Hz, 1H), 8.40 (d, J = 8.2 Hz, 2H), 8.04 (d, J = 1.3 Hz, 1H), 7.93 (d, J = 8.3 Hz, 2H), 7.86-7.81 (m, 1H), 7.76 (d, J = 0.9 Hz, 1H), 7.74-7.70 (m, 1H), 7.55 (ddd, J = 8.5, 7.2, 1.3 Hz, |

TABLE 39-continued

| Example No. | Salt | MS(ESI) m/z (M + H)+ | NMR |
|---|---|---|---|
| | | | 1H), 7.44-7.38 (m, 1H), 5.22 (Br-s, 1H), 4.57 (dd, J = 17.3, 6.4 Hz, 1H), 4.42 (dd, J = 17.3, 5.6 Hz, 1H), 4.24-4.20 (m, 1H), 4.16 (s, 1H), 3.71 (td, J = 8.4, 1.7 Hz, 1H), 3.60-3.50 (m, 1H), 2.11-1.98 (m, 1H), 1.82-1.74 (m, 1H). |
| 227 | TFA | 547 | 1H NMR (400 MHz, DMSO-d6) δ 9.15-9.10 (m, 1H), 8.96 (t, J = 6.0 Hz, 1H), 8.73-8.69 (m, 1H), 8.41 (dd, J = 8.5, 2.4 Hz, 1H), 8.31 (d, J = 8.4 Hz, 1H), 8.07-8.01 (m, 2H), 7.86-7.79 (m, 1H), 7.74-7.68 (m, 2H), 7.54 (ddd, J = 8.6, 7.2, 1.3 Hz, 1H), 7.44-7.36 (m, 1H), 5.17 (Br-s, 1H), 4.57 (dd, J = 16.3, 6.2 Hz, 1H), 4.48 (dd, J = 16.3, 5.9 Hz, 1H), 4.24-4.19 (m, 1H), 4.16 (s, 1H), 3.73-3.67 (m, 1H), 3.59-3.50 (m, 1H), 2.12-2.00 (m, 1H), 1.78 (dd, J = 13.1, 6.2 Hz, 1H). |
| 228 | TFA | 565 | 1H NMR (400 MHz, DMSO-d6) δ 9.13-9.12 (m, 1H), 8.98 (t, J = 6.0 Hz, 1H), 8.72 (dd, J = 4.9, 1.3 Hz, 1H), 8.42 (dd, J = 8.5, 2.3 Hz, 1H), 8.32 (d, J = 8.3 Hz, 1H), 8.06 (d, J = 4.8 Hz, 2H), 7.77 (dd, J = 9.1, 4.1 Hz, 1H), 7.68 (d, J = 0.9 Hz, 1H), 7.63 (dd, J = 8.5, 2.7 Hz, 1H), 7.40 (td, J = 9.3, 2.8 Hz, 1H), 4.57 (dd, J = 16.3, 6.2 Hz, 1H), 4.49 (dd, J = 16.3, 5.9 Hz, 1H), 4.21 (d, J = 3.6 Hz, 1H), 4.16 (s, 1H), 3.73-3.67 (m, 2H), 3.56-3.48 (m, 1H), 2.12-1.99 (m, 1H), 1.79 (dd, J = 12.9, 6.3 Hz, 1H). |
| 229 | TFA | 585 | $^1$H NMR (400 MHz, DMSO-d$_6$) δ 9.13-9.11 (m, 1H), 9.09 (t, J = 5.9 Hz, 1H), 8.74 (dd, J = 5.2, 0.9 Hz, 1H), 8.44-8.39 (m, 1H), 8.32 (d, J = 8.7 Hz, 2H), 8.11-8.06 (m, 2H), 7.82-7.77 (m, 2H), 7.65 (dd, J = 8.4, 2.7 Hz, 1H), 7.44 (ddd, J = 9.2, 2.8 Hz, 1H), 4.63 (dd, J = 8.8, 6.6 Hz, 1H), 4.57-4.52 (m, 2H), 4.08-3.93 (m, 2H), 2.89-2.74 (m, 1H), 2.60-2.53 (m, 1H). |
| 230 | — | 535 | $^1$H NMR (400 MHz, DMSO-d$_6$) δ 9.15-9.10 (m, 1H), 8.90 (dd, J = 6.4, 5.8 Hz, 1H), 8.71 (dd, J = 5.1, 0.8 Hz, 1H), 8.40 (dd, J = 8.5, 2.1 Hz, 1H), 8.31 (d, J = 8.5 Hz, 1H), 8.06 (brs, 1H), 8.02 (dd, J = 5.1, 1.7 Hz, 1H), 7.86 (dd, J = 9.3, 4.2 Hz, 1H), 7.83 (d, J = 0.9 Hz, 1H), 7.68 (dd, J = 8.5, 2.8 Hz, 1H), 7.46 (ddd, J = 9.3, 9.2, 2.8 Hz, 1H), 4.69 (dd, J = 9.1, 7.5 Hz, 1H), 4.59 (dd, J = 16.3, 6.4 Hz, 1H), 4.51 (dd, J = 16.3, 5.8 Hz, 1H), 3.99-3.88 (m, 2H), 2.76 (d, J = 4.9 Hz, 1H), 2.39-2.23 (m, 1H). |
| 231 | TFA | 521 | $^1$H NMR (400 MHz, DMSO-d$_6$) δ 9.17 (d, J = 1.3 Hz, 1H), 8.89 (d, J = 7.8 Hz, 1H), 8.74 (t, J = 5.9 Hz, 1H), 8.33-8.25 (m, 2H), 7.88 (d, J = 1.3 Hz, 1H), 7.77-7.71 (m, 1H), 7.65 (dd, J = 8.5, 1.0 Hz, 1H), 7.59-7.53 (m, 3H), 7.49 (ddd, J = 8.5, 7.2, 1.3 Hz, 1H), 7.39-7.32 (m, 1H), 4.43-4.27 (m, 2H), 4.16-4.04 (m, 1H), 1.25 (d, J = 7.1 Hz, 3H). |
| 232 | — | 523 | $^1$H NMR (400 MHz, DMSO-d$_6$) δ 9.35-9.33 (m, 2H), 8.84 (d, J = 8.5 Hz, 1H), 8.62 (t, J = 5.9 Hz, 1H), 8.34-8.31 (m, 1H), 8.31-8.29 (m, 1H), 7.69 (dd, J = 8.9, 4.2 Hz, 1H), 7.54-7.47 (m, 2H), 7.45 (d, J = 0.9 Hz, 1H), 7.41-7.38 (m, 1H), 7.34 (ddd, J = 9.2, 2.7 Hz, 1H), 4.25 (d, J = 5.8 Hz, 2H), 4.06 (dq, J = 8.5, 7.0 Hz, 1H), 1.24 (d, J = 7.0 Hz, 3H). |
| 233 | — | 523 | $^1$H NMR (400 MHz, DMSO-d$_6$) δ 9.35 (s, 2H), 8.86 (d, J = 8.2 Hz, 1H), 8.58 (t, J = 5.9 Hz, 1H), 7.80-7.75 (m, 1H), 7.73-7.66 (m, 2H), 7.56 (dd, J = 8.6, 2.7 Hz, 1H), 7.50 (t, J = 7.7 Hz, 1H), 7.47 (d, J = 0.9 Hz, 1H), 7.37 (dd, J = 9.2, 2.7 Hz, 1H), 7.34-7.30 (m, 1H), 4.34-4.21 (m, 2H), 4.10-4.00 (m, 1H), 1.23 (d, J = 7.1 Hz, 3H). |
| 234 | — | 523 | $^1$H NMR (400 MHz, DMSO-d$_6$) δ 9.42 (d, J = 1.4 Hz, 1H), 9.22 (d, J = 1.4 Hz, 1H), 8.85 (d, J = 8.3 Hz, 1H), 8.61 (t, J = 5.9 Hz, 1H), 8.13-8.09 (m, 1H), 8.08-8.05 (m, 1H), 7.69 (dd, J = 9.1, 4.0 Hz, 1H), 7.54 (dd, J = 8.7, 2.6 Hz, 1H), 7.50 (t, J = 7.7 Hz, 1H), 7.46 (d, J = 0.9 Hz, 1H), 7.39-7.35 (m, 1H), 7.34 (dd, J = 9.2, 2.7 Hz, 1H), 4.33-4.21 (m, 2H), 4.11-4.01 (m, 1H), 1.23 (d, J = 7.0 Hz, 3H). |
| 235 | — | 523 | $^1$H NMR (400 MHz, DMSO-d$_6$) δ 8.85 (d, J = 8.4 Hz, 1H), 8.61 (t, J = 5.9 Hz, 1H), 8.49 (d, J = 8.9 Hz, 1H), 8.35 (d, J = 9.0 Hz, 1H), 8.13-8.08 (m, 2H), 7.70 (dd, J = 9.0, 4.0 Hz, 1H), 7.57-7.49 (m, 2H), 7.47 (d, J = 0.9 Hz, 1H), 7.42-7.31 (m, 2H), 4.28 (d, J = 5.9 Hz, 2H), 4.12-4.00 (m, 1H), 1.23 (d, J = 7.0 Hz, 3H). |
| 236 | TFA | 523 | $^1$H NMR (400 MHz, DMSO-d$_6$) δ 9.39 (d, J = 2.1 Hz, 1H), 8.93 (d, J = 7.9 Hz, 1H), 8.72 (t, J = 6.0 Hz, 1H), 8.70-8.62 (m, 2H), 8.04 (d, J = 8.2 Hz, 1H), 7.98 (s, 1H), 7.71 (dd, J = 9.1, 4.0 Hz, 1H), 7.55 (dd, J = 8.5, 2.7 Hz, 1H), 7.51 (d, J = 0.9 Hz, 1H), 7.36 (td, J = 9.2, 2.8 Hz, 1H), 7.27 (dd, J = 5.1, 1.5 Hz, 1H), 4.40-4.27 (m, 2H), 4.12-4.03 (m, 1H), 1.26 (d, J = 7.1 Hz, 3H). |
| 237 | TFA | 523 | $^1$H NMR (400 MHz, DMSO-d$_6$) δ 9.06-9.04 (m, 1H), 8.89 (d, J = 8.3 Hz, 1H), 8.73 (t, J = 6.0 Hz, 1H), 8.63 (d, J = 5.0 Hz, 1H), 8.58 (d, J = 8.4 Hz, 1H), 8.37 (dd, J = 8.4, 2.4 Hz, 1H), 8.30 (d, |

TABLE 39-continued

| Example No. | Salt | MS(ESI) m/z (M + H)+ | NMR |
|---|---|---|---|
| | | | J = 1.6 Hz, 1H), 7.70 (dd, J = 9.1, 4.1 Hz, 1H), 7.50 (dd, J = 8.5, 2.8 Hz, 1H), 7.47 (d, J = 0.9 Hz, 1H), 7.34 (ddd, J = 9.2, 2.8 Hz, 1H), 7.30 (dd, J = 5.0, 1.7 Hz, 1H), 4.37-4.25 (m, 2H), 4.11-4.06 (m, 1H), 1.26 (d, J = 7.1 Hz, 3H), |
| 238 | TFA | 524 | 1H NMR (400 MHz, DMSO-d6) δ 9.62 (s, 2H), 8.93 (d, J = 8.0 Hz, 1H), 8.72 (t, J = 6.0 Hz, 1H), 8.68 (dd, J = 5.0, 0.8 Hz, 1H), 8.05 (brs, 1H), 7.71 (dd, J = 8.9, 4.2 Hz, 1H), 7.55 (dd, J = 8.5, 2.7 Hz, 1H), 7.51 (d, J = 0.9 Hz, 1H), 7.36 (ddd, J = 9.2, 2.7 Hz, 1H), 7.31 (dd, J = 5.1, 1.5 Hz, 1H), 4.41-4.26 (m, 2H), 4.12-4.03 (m, 1H), 1.25 (d, J = 7.1 Hz, 3H). |
| 239 | TFA | 538 | 1H NMR (400 MHz, DMSO-d6) δ 8.91 (d, J = 8.0 Hz, 1H), 8.70 (t, J = 5.8 Hz, 1H), 8.67 (d, J = 5.4 Hz, 1H), 7.96-7.92 (m, 2H), 7.79 (dd, J = 5.4, 1.8 Hz, 1H), 7.71-7.66 (m, 2H), 7.57-7.51 (m, 3H), 7.49 (d, J = 0.9 Hz, 1H), 7.35 (td, J = 9.2, 2.8 Hz, 1H), 4.46-4.34 (m, 2H), 4.14-4.04 (m, 1H), 1.24 (d, J = 7.0 Hz, 3H). |
| 240 | TFA | 523 | 1H NMR (400 MHz, DMSO-d6) δ 9.05 (d, J = 2.3 Hz, 1H), 8.82 (d, J = 8.3 Hz, 1H), 8.67-8.60 (m, 2H), 8.34 (dd, J = 8.5, 2.3 Hz, 1H), 8.22 (d, J = 8.4 Hz, 1H), 7.97 (dd, J = 5.2, 1.7 Hz, 1H), 7.91 (Br-s, J = 1.5 Hz, 1H), 7.61 (dd, J = 9.1, 4.0 Hz, 1H), 7.45-7.38 (m, 2H), 7.25 (td, J = 9.2, 2.7 Hz, 1H), 4.29 (d, J = 5.7 Hz, 2H), 4.10-4.00 (m, 1H), 1.19 (d, J = 7.2 Hz, 3H). |
| 241 | TFA | 524 | 1H NMR (400 MHz, DMSO-d6) δ 9.45 (s, 2H), 8.90 (d, J = 8.0 Hz, 1H), 8.71 (dd, J = 5.2, 0.8 Hz, 1H), 8.66 (t, J = 5.8 Hz, 1H), 7.85 (dd, J = 5.2, 1.8 Hz, 1H), 7.76-7.73 (m, 1H), 7.69 (dd, J = 9.1, 4.0 Hz, 1H), 7.53 (dd, J = 8.5, 2.7 Hz, 1H), 7.49 (d, J = 0.9 Hz, 1H), 7.34 (ddd, J = 9.2, 2.8 Hz, 1H), 4.44-4.30 (m, 2H), 4.14-4.05 (m, 1H), 1.24 (d, J = 7.1 Hz, 3H). |
| 242 | TFA | 524 | 1H NMR (400 MHz, DMSO-d6) δ 9.45-9.43 (m, 2H), 8.87 (d, J = 8.6 Hz, 1H), 8.77-8.72 (m, 2H), 8.19 (dd, J = 5.1, 1.6 Hz, 1H), 8.16 (Br-s, 1H), 7.66 (dd, J = 8.9, 4.1 Hz, 1H), 7.47-7.42 (m, 2H), 7.30 (ddd, J = 9.2, 2.8 Hz, 1H), 4.34 (d, J = 5.8 Hz, 2H), 4.13 (dq, J = 8.6, 7.1 Hz, 1H), 1.27 (d, J = 7.1 Hz, 3H). |
| 243 | TFA | 524 | 1H NMR (400 MHz, DMSO-d6) δ 9.51 (d, J = 1.4 Hz, 1H), 9.32 (d, J = 1.3 Hz, 1H), 8.89 (d, J = 8.3 Hz, 1H), 8.75-8.70 (m, 2H), 8.08 (dd, J = 5.2, 1.7 Hz, 1H), 8.00-7.99 (m, 1H), 7.67 (dd, J = 9.0, 4.2 Hz, 1H), 7.49 (dd, J = 8.6, 2.7 Hz, 1H), 7.46 (d, J = 0.9 Hz, 1H), 7.32 (ddd, J = 9.2, 2.7 Hz, 1H), 4.44-4.30 (m, 2H), 4.16-4.07 (m, 1H), 1.25 (d, J = 7.1 Hz, 3H). |
| 244 | TFA | 524 | 1H NMR (400 MHz, DMSO-d6) δ 8.88 (d, J = 8.3 Hz, 1H), 8.75 (dd, J = 5.2, 0.6 Hz, 1H), 8.72 (t, J = 5.9 Hz, 1H), 8.61 (d, J = 8.9 Hz, 1H), 8.48 (d, J = 8.9 Hz, 1H), 8.10 (dd, J = 5.2, 1.7 Hz, 1H), 8.06-8.04 (m, 1H), 7.68 (dd, J = 9.1, 4.0 Hz, 1H), 7.51-7.46 (m, 2H), 7.32 (ddd, J = 9.2, 2.8 Hz, 1H), 4.38 (d, J = 5.8 Hz, 2H), 4.16-4.06 (m, 1H), 1.26 (d, J = 7.1 Hz, 3H). |
| 245 | TFA | 523 | 1H NMR (400 MHz, DMSO-d6) δ 9.13 (d, J = 2.2 Hz, 1H), 8.96 (d, J = 2.2 Hz, 1H), 8.89 (d, J = 8.0 Hz, 1H), 8.67 (t, J = 5.9 Hz, 1H), 8.56 (d, J = 2.0 Hz, 1H), 8.42 (dd, J = 7.9, 2.1 Hz, 1H), 8.12 (t, J = 2.1 Hz, 1H), 8.06 (dd, J = 8.2, 0.8 Hz, 1H), 7.71 (dd, J = 9.1, 4.1 Hz, 1H), 7.56 (dd, J = 8.5, 2.7 Hz, 1H), 7.48 (d, J = 0.9 Hz, 1H), 7.35 (ddd, J = 9.2, 2.8 Hz, 1H), 4.39-4.27 (m, 2H), 4.08-3.98 (m, 1H), 1.21 (d, J = 7.0 Hz, 3H). |
| 246 | TFA | 523 | 1H NMR (400 MHz, DMSO-d6) δ 9.23 (d, J = 2.1 Hz, 1H), 9.10-9.09 (m, 1H), 8.87 (d, J = 8.2 Hz, 1H), 8.69 (t, J = 5.9 Hz, 1H), 8.57 (d, J = 2.1 Hz, 1H), 8.40 (t, J = 2.2 Hz, 1H), 8.39-8.36 (m, 1H), 8.27 (d, J = 8.2 Hz, 1H), 7.69 (dd, J = 9.0, 4.2 Hz, 1H), 7.53 (dd, J = 8.5, 2.7 Hz, 1H), 7.46 (d, J = 0.9 Hz, 1H), 7.34 (ddd, J = 9.2, 2.8 Hz, 1H), 4.37-4.27 (m, 2H), 4.07-4.01 (m, 1H), 1.22 (d, J = 7.1 Hz, 3H). |
| 247 | TFA | 524 | 1H NMR (400 MHz, DMSO-d6) δ 9.25 (d, J = 1.3 Hz, 1H), 9.12-9.10 (m, 1H), 8.91 (d, J = 8.5 Hz, 1H), 8.82 (t, J = 5.9 Hz, 1H), 8.63 (d, J = 8.3 Hz, 1H), 8.50-8.42 (m, 1H), 8.23 (d, J = 1.3 Hz, 1H), 7.67 (dd, J = 9.0, 4.2 Hz, 1H), 7.45 (d, J = 0.9 Hz, 1H), 7.43 (dd, J = 8.6, 2.7 Hz, 1H), 7.30 (ddd, J = 9.2, 2.8 Hz, 1H), 4.41-4.28 (m, 2H), 4.19-4.10 (m, 1H), 1.28 (d, J = 7.1 Hz, 3H). |
| 248 | — | 525 | 1H NMR (400 MHz, DMSO-d6) δ 9.68 (s, 2H), 9.30 (d, J = 1.3 Hz, 1H), 8.96 (d, J = 7.8 Hz, 1H), 8.78 (t, J = 5.9 Hz, 1H), 8.09 (d, J = 1.3 Hz, 1H), 7.70 (dd, J = 9.1, 4.3 Hz, 1H), 7.55-7.51 (m, 2H), 7.34 (td, J = 9.2, 2.8 Hz, 1H), 4.47-4.32 (m, 2H), 4.16-4.07 (m, 1H), 1.26 (d, J = 7.1 Hz, 3H). |
| 249 | — | 523 | 1H NMR (400 MHz, DMSO-d6) δ 9.13 (d, J = 2.0 Hz, 1H), 8.95 (d, J = 7.8 Hz, 1H), 8.76 (t, J = 5.9 Hz, 1H), 8.33 (d, J = 8.1 Hz, 2H), 8.09 (d, J = 1.8 Hz, 1H), 7.94 (d, J = 8.2 Hz, 2H), 7.71 (dd, J = 9.1, 4.0 Hz, 1H), 7.55 (dd, J = 8.5, 2.7 Hz, 1H), 7.51 (d, J = |

TABLE 39-continued

| Example No. | Salt | MS(ESI) m/z (M + H)+ | NMR |
|---|---|---|---|
| | | | 0.9 Hz, 1H), 7.35 (td, J = 9.2, 2.7 Hz, 1H), 4.45-4.31 (m, 2H), 4.10-4.01 (m, 1H), 1.24 (d, J = 7.1 Hz, 3H). |
| 250 | — | 523 | ¹H NMR (400 MHz, DMSO-d₆) δ 9.61 (d, J = 2.2 Hz, 1H), 8.92 (d, J = 8.0 Hz, 1H), 8.81 (t, J = 5.8 Hz, 1H), 8.09 (d, J = 8.0 Hz, 2H), 7.94 (d, J = 8.3 Hz, 2H), 7.85 (d, J = 2.3 Hz, 1H), 7.68 (dd, J = 8.9, 4.1 Hz, 1H), 7.52 (dd, J = 8.5, 2.7 Hz, 1H), 7.48 (d, J = 0.9 Hz, 1H), 7.34 (td, J = 9.2, 2.8 Hz, 1H), 4.63-4.49 (m, 2H), 4.14-4.03 (m, 1H), 1.24 (d, J = 7.0 Hz, 3H). |
| 251 | — | 524 | ¹H NMR (400 MHz, DMSO-d₆) δ 9.85 (d, J = 2.1 Hz, 1H), 9.18-9.16 (m, 1H), 8.90 (d, J = 8.2 Hz, 1H), 8.85 (t, J = 5.9 Hz, 1H), 8.48 (dd, J = 8.4, 2.5 Hz, 1H), 8.43-8.39 (m, 1H), 8.15 (d, J = 2.1 Hz, 1H), 7.67 (dd, J = 9.0, 4.2 Hz, 1H), 7.48 (dd, J = 8.6, 2.7 Hz, 1H), 7.46 (d, J = 0.9 Hz, 1H), 7.31 (td, J = 9.2, 2.7 Hz, 1H), 4.64-4.49 (m, 2H), 4.15-4.06 (m, 1H), 1.25 (d, J = 7.1 Hz, 3H). |
| 252 | — | 538 | ¹H NMR (400 MHz, DMSO-d₆) δ 9.07-9.04 (m, 1H), 8.82 (d, J = 8.4 Hz, 1H), 8.46 (t, J = 5.8 Hz, 1H), 8.36 (dd, J = 8.7, 2.4 Hz, 1H), 8.31 (d, J = 8.7 Hz, 1H), 7.87 (d, J = 1.9 Hz, 1H), 7.69 (dd, J = 9.1, 4.0 Hz, 1H), 7.54 (dd, J = 8.5, 2.7 Hz, 1H), 7.45 (d, J = 0.9 Hz, 1H), 7.34 (td, J = 9.2, 2.8 Hz, 1H), 7.15 (dd, J = 8.5, 2.1 Hz, 1H), 6.91 (d, J = 8.4 Hz, 1H), 4.19-4.08 (m, 2H), 4.08-3.99 (m, 1H), 1.21 (d, J = 7.0 Hz, 3H). |
| 253 | — | 539 | ¹H NMR (400 MHz, DMSO-d₆) δ 12.68 (s, 1H), 9.39 (d, J = 0.9 Hz, 2H), 8.81 (d, J = 8.6 Hz, 1H), 8.51 (t, J = 5.9 Hz, 1H), 8.26 (d, J = 2.3 Hz, 1H), 7.68 (dd, J = 9.0, 4.2 Hz, 1H), 7.52 (dd, J = 8.6, 2.7 Hz, 1H), 7.43 (d, J = 0.9 Hz, 1H), 7.33 (td, J = 9.3, 2.8 Hz, 1H), 7.28 (dd, J = 8.5, 2.4 Hz, 1H), 6.94 (d, J = 8.5 Hz, 1H), 4.12 (d, J = 5.8 Hz, 2H), 4.07-3.99 (m, 1H), 1.22 (d, J = 7.1 Hz, 3H). |
| 254 | — | 539 | ¹H NMR (400 MHz, DMSO-d₆) δ 11.00 (s, 1H), 9.47 (d, J = 1.5 Hz, 1H), 9.20 (d, J = 1.4 Hz, 1H), 8.80 (d, J = 8.5 Hz, 1H), 8.46 (t, J = 5.8 Hz, 1H), 7.81 (d, J = 2.3 Hz, 1H), 7.69 (dd, J = 9.2, 4.1 Hz, 1H), 7.54 (dd, J = 8.5, 2.7 Hz, 1H), 7.45 (d, J = 0.9 Hz, 1H), 7.35 (td, J = 9.2, 2.8 Hz, 1H), 7.18 (dd, J = 8.4, 2.3 Hz, 1H), 6.97 (d, J = 8.4 Hz, 1H), 4.11 (d, J = 5.8 Hz, 2H), 4.06-3.97 (m, 1H), 1.20 (d, J = 7.1 Hz, 3H). |
| 255 | TFA | 539 | ¹H NMR (400 MHz, DMSO-d₆) δ 12.04 (Br-s, 1H), 9.13-9.11 (m, 1H), 8.84 (d, J = 8.4 Hz, 1H), 8.56 (t, J = 5.7 Hz, 1H), 8.44 (dd, J = 8.6, 2.3 Hz, 1H), 8.40 (d, J = 8.6 Hz, 1H), 8.31 (s, 1H), 7.81 (s, 1H), 7.67 (dd, J = 9.1, 4.1 Hz, 1H), 7.48 (dd, J = 8.5, 2.7 Hz, 1H), 7.45 (d, J = 0.9 Hz, 1H), 7.31 (td, J = 9.2, 2.7 Hz, 1H), 4.22 (d, J = 5.6 Hz, 2H), 4.13-4.03 (m, 1H), 1.23 (d, J = 7.0 Hz, 3H). |
| 256 | TFA | 565 | ¹H NMR (400 MHz, DMSO-d₆) δ 9.15-9.10 (m, 1H), 8.96 (dd, J = 6.1, 5.8 Hz, 1H), 8.73 (d, J = 5.3 Hz, 1H), 8.40 (dd, J = 8.4, 2.4 Hz, 1H), 8.32 (d, J = 8.4 Hz, 1H), 8.11 (brs, 1H), 8.08 (dd, J = 5.3, 1.7 Hz, 1H), 7.76 (dd, J = 9.1, 4.0 Hz, 1H), 7.65 (d, J = 0.7 Hz, 1H), 7.62 (dd, J = 8.5, 2.7 Hz, 1H), 7.39 (ddd, J = 9.2, 9.1, 2.7 Hz, 1H), 4.56 (dd, J = 16.4, 6.1 Hz, 1H), 4.50 (dd, J = 16.4, 5.8 Hz, 1H), 4.43 (dd, J = 8.1, 8.1 Hz, 1H), 4.24 (brs, 1H), 3.65 (dd, J = 11.3, 3.6 Hz, 1H), 3.44-3.37 (m, 1H), 2.14-2.05 (m, 1H), 2.02-1.94 (m, 1H). |
| 257 | — | 561 | ¹H NMR (400 MHz, DMSO-d₆) δ 9.13-9.09 (m, 1H), 8.79 (t, J = 6.0 Hz, 1H), 8.70 (dd, J = 5.2, 0.8 Hz, 1H), 8.38 (dd, J = 8.5, 2.4 Hz, 1H), 8.27 (d, J = 8.5 Hz, 1H), 8.08 (brs, 1H), 8.01 (dd, J = 5.2, 1.7 Hz, 1H), 7.83 (dd, J = 9.1, 4.1 Hz, 1H), 7.72 (d, J = 0.9 Hz, 1H), 7.66 (dd, J = 8.5, 2.7 Hz, 1H), 7.45 (ddd, J = 9.3, 9.1, 2.7 Hz, 1H), 4.55-4.52 (m, 2H), 4.42 (d, J = 5.2 Hz, 1H), 3.60 (d, J = 9.5 Hz, 1H), 3.53 (dd, J = 9.5, 4.9 Hz, 1H), 2.02-1.94 (m, 1H), 1.74-1.63 (m, 1H), 1.01-0.95 (m, 1H), 0.70-0.63 (m, 1H). |
| 258 | TFA | 561 | ¹H NMR (400 MHz, DMSO-d₆) δ 9.14-9.11 (m, 1H), 8.85 (dd, J = 6.1, 5.8 Hz, 1H), 8.73 (dd, J = 5.3, 0.8 Hz, 1H), 8.40 (dd, J = 8.3, 2.4 Hz, 1H), 8.31 (d, J = 8.3 Hz, 1H), 8.12 (brs, 1H), 8.07 (dd, J = 5.3, 1.8 Hz, 1H), 7.84 (dd, J = 9.0, 4.2 Hz, 1H), 7.77 (d, J = 0.9 Hz, 1H), 7.68 (dd, J = 8.5, 2.7 Hz, 1H), 7.46 (ddd, J = 9.2, 9.0, 2.7 Hz, 1H), 4.61-4.45 (m, 2H), 3.98 (t, J = 8.1 Hz, 1H), 3.50-3.42 (m, 1H), 2.36 (dd, J = 13.1, 8.8 Hz, 1H), 2.25-2.17 (m, 1H), 1.78-1.69 (m, 1H), 0.54-0.47 (m, 1H), −0.16-−0.20 (m, 1H). |
| 259 | TFA | 561 | ¹H NMR (400 MHz, DMSO-d₆) δ 9.17-9.10 (m, 1H), 8.81-8.73 (m, 2H), 8.44 (dd, J = 8.4, 2.6 Hz, 1H), 8.34 (d, J = 8.4 Hz, 1H), 8.13-8.08 (m, 2H), 7.80 (dd, J = 9.0, 4.2 Hz, 1H), 7.72 (d, J = 0.9 Hz, 1H), 7.63 (dd, J = 8.5, 2.7 Hz, 1H), 7.43 (ddd, J = 9.2, 9.0, 2.7 Hz, 1H), 4.71 (dd, J = 10.0, 3.4 Hz, 1H), 4.56 (dd, J = 16.1, 6.0 Hz, 1H), 4.49 (dd, J = 16.1, 5.8 Hz, 1H), 3.67 (ddd, J = |

TABLE 39-continued

| Example No. | Salt | MS(ESI) m/z (M + H)+ | NMR |
|---|---|---|---|
| | | | 6.8, 6.7, 2.5 Hz, 1H), 2.10-1.94 (m, 2H), 1.52-1.41 (m, 1H), 0.92-0.84 (m, 1H), 0.82-0.74 (m, 1H). |
| 260 | TFA | 625 | $^1$H NMR (400 MHz, DMSO-$d_6$) δ 9.03 (t, J = 6.0 Hz, 1H), 8.91-8.85 (m, 1H), 8.72 (d, J = 5.3 Hz, 1H), 8.36 (dd, J = 8.4, 2.3 Hz, 1H), 8.30 (d, J = 8.4 Hz, 1H), 8.07 (brs, 1H), 8.03 (dd, J = 5.3, 1.7 Hz, 1H), 7.79 (dd, J = 9.1, 4.0 Hz, 1H), 7.72 (d, J = 0.9 Hz, 1H), 7.62 (dd, J = 8.5, 2.8 Hz, 1H), 7.42 (ddd, J = 9.3, 9.1, 2.8 Hz, 1H), 7.24-7.12 (m, 5H), 4.59 (dd, J = 9.1, 2.0 Hz, 1H), 4.56 (d, J = 6.0 Hz, 2H), 4.09 (dd, J = 9.1, 7.4 Hz, 1H), 3.77-3.69 (m, 1H), 3.32 (t, J = 9.5 Hz, 1H), 2.39-2.31 (m, 1H), 2.24-2.14 (m, 1H). |
| 261 | TFA | 563 | $^1$H NMR (400 MHz, DMSO-$d_6$) δ 9.13-9.10 (m, 1H), 8.78 (t, J = 5.8 Hz, 1H), 8.71 (dd, J = 5.2, 0.8 Hz, 1H), 8.42 (dd, J = 8.5, 2.4 Hz, 1H), 8.31 (d, J = 8.5 Hz, 1H), 8.05 (dd, J = 5.2, 1.7 Hz, 1H), 8.01 (brs, 1H), 7.70 (dd, J = 9.1, 4.0 Hz, 1H), 7.52 (d, J = 0.9 Hz, 1H), 7.49 (dd, J = 8.5, 2.7 Hz, 1H), 7.35 (ddd, J = 9.2, 9.1, 2.7 Hz, 1H), 4.70-4.66 (m, 1H), 4.40 (d, J = 5.8 Hz, 2H), 3.90-3.72 (m, 1H), 3.68-3.58 (m, 1H), 2.15-2.08 (m, 1H), 1.70-1.53 (m, 3H), 1.41-1.21 (m, 2H). |
| 262 | TFA | 575 | $^1$H NMR (400 MHz, DMSO-$d_6$) δ 9.13-9.11 (m, 1H), 8.80 (dd, J = 6.1, 5.7 Hz, 1H), 8.73 (dd, J = 5.0, 1.1 Hz, 1H), 8.40 (dd, J = 8.5, 2.4 Hz, 1H), 8.30 (d, J = 8.5 Hz, 1H), 8.09-8.05 (m, 2H), 7.80 (dd, J = 9.1, 4.0 Hz, 1H), 7.66 (d, J = 0.9 Hz, 1H), 7.61 (dd, J = 8.4, 2.7 Hz, 1H), 7.41 (ddd, J = 9.2, 9.1, 2.7 Hz, 1H), 4.53 (dd, J = 16.2, 6.1 Hz, 1H), 4.47 (dd, J = 16.2, 5.7 Hz, 1H), 4.28 (brs, 1H), 4.06 (s, 1H), 2.72-2.67 (m, 1H), 2.15 (d, J = 10.1 Hz, 1H), 1.75-1.61 (m, 1H), 1.52-1.29 (m, 3H), 1.20-1.11 (m, 1H). |
| 263 | TFA | 561 | $^1$H NMR (400 MHz, DMSO-$d_6$) δ 9.15-9.14 (m, 1H), 8.75 (dd, J = 5.8, 5.8 Hz, 1H), 8.70 (dd, J = 5.3, 0.8 Hz, 1H), 8.43 (dd, J = 8.5, 2.4 Hz, 1H), 8.29 (d, J = 8.5 Hz, 1H), 8.04 (dd, J = 5.3, 1.7 Hz, 1H), 7.94-7.93 (m, 1H), 7.67 (dd, J = 9.1, 4.1 Hz, 1H), 7.57 (d, J = 0.9 Hz, 1H), 7.50 (dd, J = 8.5, 2.7 Hz, 1H), 7.34 (ddd, J = 9.3, 9.1, 2.7 Hz, 1H), 5.73-5.68 (m, 2H), 4.84 (d, J = 6.2 Hz, 1H), 4.40 (dd, J = 16.2, 5.8 Hz, 1H), 4.35 (dd, J = 16.2, 5.8 Hz, 1H), 4.18 (d, J = 17.8 Hz, 1H), 4.07 (d, J = 17.8 Hz, 1H), 2.57 (d, J = 17.1 Hz, 1H), 2.46-2.37 (m, 1H). |
| 264 | TFA | 597 | $^1$H NMR (400 MHz, DMSO-$d_6$) δ 9.24 (dd, J = 6.2, 5.7 Hz, 1H), 9.11 (dd, J = 2.4, 1.1 Hz, 1H), 8.72 (dd, J = 5.2, 1H), 8.41 (dd, J = 8.4, 2.4 Hz, 1H), 8.16 (d, J = 8.4 Hz, 1H), 8.03 (dd, J = 5.2, 1.7 Hz, 1H), 7.91-7.90 (m, 1H), 7.75-7.69 (m, 2H), 7.59 (dd, J = 8.4, 2.7 Hz, 1H), 7.41-7.34 (m, 3H), 7.34-7.28 (m, 1H), 7.25 (ddd, J = 7.4, 7.4, 1.4 Hz, 1H), 5.65 (d, J = 2.6 Hz, 1H), 4.99 (dd, J = 14.1, 2.6 Hz, 1H), 4.85 (d, J = 14.1 Hz, 1H), 4.58 (dd, J = 16.3, 6.2 Hz, 1H), 4.47 (dd, J = 16.3, 5.7 Hz, 1H). |
| 265 | TFA | 566 | $^1$H NMR (400 MHz, DMSO-$d_6$) δ 9.15-9.09 (m, 1H), 8.92 (dd, J = 5.9, 5.9 Hz, 1H), 8.73 (dd, J = 5.2, 0.7 Hz, 1H), 8.48 (d, J = 5.9 Hz, 1H), 8.42 (dd, J = 8.4, 2.4 Hz, 1H), 8.32 (d, J = 8.4 Hz, 1H), 8.09-8.06 (m, 2H), 7.90 (dd, J = 5.9, 1.0 Hz, 1H), 7.83 (d, J = 1.0 Hz, 1H), 4.55 (dd, J = 16.2, 5.9 Hz, 1H), 4.50 (dd, J = 16.2, 5.9 Hz, 1H), 4.40 (dd, J = 8.4, 3.3 Hz, 1H), 3.67-3.62 (m, 1H), 3.52-3.43 (m, 1H), 2.14-1.89 (m, 3H), 1.82-1.72 (m, 1H). |
| 266 | TFA | 488 | $^1$H NMR (400 MHz, DMSO-$d_6$) δ 9.22 (d, J = 1.0 Hz, 1H), 8.87 (dd, J = 6.1, 5.7 Hz, 1H), 8.73 (d, J = 6.1 Hz, 1H), 7.96 (d, J = 6.1 Hz, 1H), 7.89 (d, J = 1.0 Hz, 1H), 7.76-7.64 (m, 3H), 4.47 (dd, J = 16.3, 6.1 Hz, 1H), 4.38 (dd, J = 16.3, 5.7 Hz, 1H), 4.35 (dd, J = 8.6, 3.5 Hz, 1H), 3.69-3.59 (m, 1H), 3.46-3.38 (m, 1H), 2.12-1.97 (m, 1H), 1.96-1.80 (m, 2H), 1.78-1.66 (m, 1H). |
| 267 | TFA | 492 | $^1$H NMR (400 MHz, DMSO-$d_6$) δ 9.23 (d, J = 0.9 Hz, 1H), 8.74 (d, J = 6.1 Hz, 1H), 8.67 (dd, J = 6.3, 5.8 Hz, 1H), 8.00 (d, J = 6.1 Hz, 1H), 7.88 (d, J = 1.0 Hz, 1H), 7.46-7.29 (m, 5H), 7.23 (dd, J = 7.9, 7.9 Hz, 1H), 6.96-6.94 (m, 1H), 6.90-6.83 (m, 2H), 5.09 (s, 2H), 4.37-4.21 (m, 2H), 4.24 (dd, J = 15.5, 5.9 Hz, 1H), 3.68-3.59 (m, 1H), 3.47-3.38 (m, 1H), 2.06-1.95 (m, 1H), 1.93-1.81 (m, 2H), 1.76-1.64 (m, 1H). |
| 268 | TFA | 546 | $^1$H NMR (400 MHz, DMSO-$d_6$), δ 9.21 (d, J = 1.0 Hz, 1H), 8.72 (d, J = 6.1 Hz, 1H), 8.69 (dd, J = 6.1, 6.1 Hz, 1H), 7.96 (d, J = 6.1 Hz, 1H), 7.87 (d, J = 1.0 Hz, 1H), 7.61 (ddd, J = 8.7, 7.7, 0.8 Hz, 1H), 7.48 (dd, J = 7.4, 1.7 Hz, 1H), 7.33 (d, J = 8.6 Hz, 2H), 7.30-7.23 (m, 2H), 7.07 (d, J = 8.6 Hz, 2H), 4.39-4.23 (m, 3H), 3.66-3.59 (m, 1H), 3.48-3.37 (m, 1H), 2.00 (ddd, J = 10.9, 9.9, 5.8 Hz, 1H), 1.95-1.81 (m, 2H), 1.75-1.66 (m, 1H). |
| 269 | TFA | 546 | $^1$H NMR (400 MHz, DMSO-$d_6$) δ 9.19 (d, J = 0.9 Hz, 1H), 8.72 (m, 2H), 7.94 (ddd, J = 6.1, 1.0, 0.9 Hz, 1H), 7.84 (d, J = 1.0 Hz, 1H), 7.73 (d, J = 8.2 Hz, 2H), 7.41 (dd, J = 8.9, 7.6 Hz, 1H), 7.18-7.10 (m, 3H), 7.05-6.98 (m, 2H), 4.39-4.24 (m, 3H), 3.64- |

TABLE 39-continued

| Example No. | Salt | MS(ESI) m/z (M + H)+ | NMR |
|---|---|---|---|
| | | | 3.53 (m, 1H), 3.39 (ddd, J = 9.9, 7.1, 7.1 Hz, 1H), 2.01-1.89 (m, 1H), 1.88-1.73 (m, 2H), 1.71-1.61 (m, 1H). |
| 270 | TFA | 532 | ¹H NMR (400 MHz, DMSO-d₆) δ 9.26 (s, 1H), 9.25 (d, J = 1.3 Hz, 1H), 8.99 (dd, J = 6.2, 5.7 Hz, 1H), 8.76 (d, J = 6.2 Hz, 1H), 8.38 (d, J = 8.2 Hz, 2H), 8.04 (d, J = 1.3 Hz, 1H), 8.02 (d, J = 6.2 Hz, 1H), 7.98 (s, 1H), 7.93 (d, J = 8.2 Hz, 2H), 4.54 (dd, J = 17.2, 6.2 Hz, 1H), 4.44 (dd, J = 17.2, 5.7 Hz, 1H), 4.40 (dd, J = 8.6, 3.5 Hz, 1H), 3.71-3.61 (m, 1H), 3.50-3.42 (m, 1H), 2.14-2.04 (m, 1H), 2.03-1.90 (m, 2H), 1.79-1.68 (m, 1H), |
| 271 | TFA | 547 | ¹H NMR (400 MHz, DMSO-d₆) δ 9.28 (d, J = 0.9 Hz, 1H), 8.97 (dd, J = 6.2, 6.0 Hz, 1H), 8.77 (d, J = 6.1 Hz, 1H), 8.66 (d, J = 5.4 Hz, 1H), 8.24-8.17 (m, 2H), 8.04 (d, J = 6.1 Hz, 1H), 7.97 (d, J = 1.0 Hz, 1H), 7.46 (dd, J = 5.4, 1.4 Hz, 1H), 7.28-7.22 (m, 2H), 4.54 (dd, J = 16.7, 6.2 Hz, 2H), 4.46 (dd, J = 16.7, 6.0 Hz, 1H), 4.37 (dd, J = 8.6, 3.5 Hz, 1H), 3.71-3.63 (m, 1H), 3.51-3.42 (m, 1H), 2.14-2.02 (m, 1H), 1.99-1.87 (m, 2H), 1.81-1.69 (m, 1H). |
| 272 | 2TFA | 532 | ¹H NMR (400 MHz, DMSO-d₆) δ 9.16 (d, J = 0.8 Hz, 1H), 9.15-9.09 (m, 1H), 8.89 (dd, J = 6.1, 5.9 Hz, 1H), 8.74-8.66 (m, 2H), 8.41 (dd, J = 8.5, 2.4 Hz, 1H), 8.30 (d, J = 8.5 Hz, 1H), 8.07-8.00 (m, 2H), 7.94-7.86 (m, 2H), 4.54 (dd, J = 16.2, 6.1 Hz, 1H), 4.47 (dd, J = 16.2, 5.9 Hz, 1H), 4.39 (dd, J = 8.2, 3.3 Hz, 1H), 3.70-3.59 (m, 1H), 3.58-3.45 (m, 1H), 2.09-1.89 (m, 3H), 1.78-1.70 (m, 1H). |
| 273 | TFA | 547 | ¹H NMR (400 MHz, DMSO-d₆) δ9.19 (d, J = 1.0 Hz, 1H), 9.07-9.04 (m, 2H), 8.71 (d, J = 6.1 Hz, 1H), 8.66 (dd, J = 6.0, 6.0 Hz, 1H), 8.38-8.35 (m, 2H), 7.95 (d, J = 2.1 Hz, 1H), 7.93 (d, J = 6.1 Hz, 1H), 7.87 (d, J = 1.0 Hz, 1H), 7.28 (dd, J = 8.4, 2.1 Hz, 1H), 6.96 (d, J = 8.4 Hz, 1H), 4.39-4.21 (m, 3H), 3.81-3.52 (m, 1H), 3.47-3.39 (m, 1H), 2.05-1.83 (m, 3H), 1.77-1.64 (m, 1H). |
| 274 | TFA | 561 | ¹H NMR (400 MHz, DMSO-d₆) δ 9.22 (d, J = 0.9 Hz, 1H), 8.77 (d, J = 5.0 Hz, 1H), 8.73 (d, J = 6.1 Hz, 1H), 8.68 (dd J = 6.0, 5.9 Hz, 1H), 7.96 (ddd, J = 6.1, 1.0, 0.9 Hz, 1H), 7.92 (brs, 1H), 7.88 (d, J = 1.0 Hz, 1H), 7.74 (d, J = 5.0 Hz, 1H), 7.27 (dd, J = 7.9, 7.9 Hz, 1H), 7.00-6.97 (m, 1H), 6.94-6.88 (m, 2H), 5.31 (s, 2H), 4.36-4.29 (m, 2H), 4.25 (dd, J = 15.5, 5.9 Hz, 1H), 3.64-3.56 (m, 1H), 3.42 (ddd, J = 9.8, 7.0, 7.0 Hz, 1H), 2.06-1.79 (m, 3H), 1.77-1.65 (m, 1H). |
| 275 | TFA | 576 | ¹H NMR (400 MHz, DMSO-d₆) δ 8.81 (t, J = 6.0 Hz, 1H), 8.61 (d, J = 5.3 Hz, 1H), 8.17 (d, J = 8.7 Hz, 1H), 8.13, (s, 1H), 7.70 (dd, J = 9.2, 4.0 Hz, 1H), 7.65 (s, 1H), 7.58 (d, J = 8.5, 2.8 Hz, 1H), 7.42-7.31 (m, 2H), 7.29-7.22 (m, 2H), 4.82-4.70 (m, 1H), 4.47-4.32 (m, 4H), 3.18-3.12 (m, 1H), 1.53 (d, J = 7.2 Hz, 3H). |
| 276 | TFA | 577 | — |
| 277 | TFA | 502 | ¹H NMR (400 MHz, DMSO-d₆) δ 8.86 (dd, J = 6.3, 5.9 Hz, 1H), 8.48 (dd, J = 5.1, 0.8 Hz, 1H), 7.87-7.81 (m, 2H), 7.77-7.74 (m, 3H), 7.66 (d, J = 1.5 Hz, 1H), 7.57 (ddd, J = 8.4, 7.2, 1.4 Hz, 1H), 7.47-7.38 (m, 1H), 7.24 (dd, J = 5.1, 1.5 Hz, 1H), 4.45 (dd, J = 16.6, 6.3 Hz, 1H), 4.39-4.31 (m, 2H), 3.68-3.57 (m, 1H), 3.47-3.36 (m, 1H), 2.06-1.85 (m, 3H), 1.71-1.60 (m, 1H). |
| 278 | TFA | 508 | ¹H NMR (400 MHz, DMSO-d₆) δ 8.90 (dd, J = 6.2, 5.9 Hz, 1H), 8.63 (d, J = 5.1 Hz, 1H), 8.02 (d, J = 8.5 Hz, 2H), 7.94 (d, J = 1.6 Hz, 1H), 7.84 (ddd, J = 7.8, 1.3, 0.7 Hz, 1H), 7.77-7.74 (m, 2H), 7.57 (ddd, J = 8.6, 7.3, 1.3 Hz, 1H), 7.43 (ddd, J = 7.8, 7.3, 0.9 Hz, 1H), 7.41-7.35 (m, 3H), 4.52 (dd, J = 16.7, 6.2 Hz, 1H), 4.43 (dd, J = 16.7, 5.9 Hz, 1H), 4.34 (dd, J = 8.3, 3.8 Hz, 1H), 3.67-3.60 (m, 1H), 3.41 (ddd, J = 9.8, 6.8, 6.8 Hz, 1H), 2.53 (s, 3H), 2.03-1.86 (m, 3H), 1.71-1.61 (m, 1H). |
| 279 | TFA | 564 | ¹H NMR (400 MHz, DMSO-d₆) δ 8.89 (d, J = 2.2 Hz, 1H), 8.86 (dd, J = 6.1, 5.9 Hz, 1H), 8.58 (d, J = 1.9 Hz, 1H), 8.15 (dd, J = 2.2, 1.9 Hz, 1H), 7.89 (d, J = 8.5 Hz, 2H), 7.80 (dd, J = 9.1, 4.0 Hz, 1H), 7.64 (s, 1H), 7.64 (d, J = 8.5, 2.7 Hz, 1H), 7.53 (d, J = 8.5 Hz, 2H), 7.43 (ddd, J = 9.2, 9.1, 2.7 Hz, 1H), 4.50 (dd, J = 15.7, 6.1 Hz, 1H), 4.43 (dd, J = 15.7, 5.9 Hz, 1H), 4.29 (dd, J = 8.4, 3.7 Hz, 1H), 3.64-3.56 (m, 1H), 3.44-3.35 (m, 1H), 2.05-1.82 (m, 3H), 1.72-1.61 (m, 1H). |
| 280 | TFA | 564 | ¹H NMR (400 MHz, DMSO-d₆) δ 10.74 (s, 1H), 8.86 (dd, J = 6.0, 5.8 Hz, 1H), 8.63 (d, J = 5.4 Hz, 1H), 7.80 (dd, J = 9.2, 4.0 Hz, 1H), 7.72-7.57 (m, 5H), 7.42 (ddd, J = 9.3, 9.2, 2.8 Hz, 1H), 7.31-7.22 (m, 2H), 4.59-4.39 (m, 2H), 4.34 (dd, J = 7.8, 3.7 Hz, 1H), 3.66-3.55 (m, 1H), 3.45-3.34 (m, 1H), 2.03-1.85 (m, 3H), 1.73-1.61 (m, 1H). |
| 281 | TFA | 487 | ¹H NMR (400 MHz, DMSO-d₆) δ 8.83 (t, J = 6.0 Hz, 1H), 8.65-8.60 (m, 1H), 7.94 (s, 4H), 7.80-7.75 (m, 1H), 7.74-7.66 (m, 4H), 7.50 (ddd, J = 8.6, 7.3, 1.4 Hz, 1H), 7.39-7.33 (m, 1H), |

TABLE 39-continued

| Example No. | Salt | MS(ESI) m/z (M + H)+ | NMR |
|---|---|---|---|
| | | | 4.51 (dd, J = 16.5, 6.2 Hz, 1H), 4.41 (dd, J = 16.4, 5.7 Hz, 1H), 4.29 (dd, J = 8.1, 3.8 Hz, 1H), 3.59-3.49 (m, 1H), 3.40-3.30 (m, 1H), 1.99-1.78 (m, 3H), 1.67-1.54 (m, 1H). |
| 282 | TFA | 452 | $^1$H NMR (400 MHz, DMSO-d$_6$) δ 8.93 (dd, J = 6.2, 5.7 Hz, 1H), 8.58 (d, J = 5.8 Hz, 1H), 7.85 (d, J = 8.1 Hz, 1H), 7.79-7.72 (m, 2H), 7.62-7.52 (m, 3H), 7.48-7.39 (m, 1H), 6.61 (d, J = 15.8 Hz, 1H), 6.46 (dd, J = 15.8, 9.6 Hz, 1H), 4.54 (dd, J = 16.8, 6.2 Hz, 1H), 4.45 (dd, J = 16.8, 5.7 Hz, 1H), 4.32 (dd, J = 8.4, 3.8 Hz, 1H), 3.64-3.57 (m, 1H), 3.41 (ddd, J = 9.7, 6.8, 6.8 Hz, 1H), 2.06-1.84 (m, 3H), 1.79-1.58 (m, 2H), 0.99-0.89 (m, 2H), 0.67-0.59 (m, 2H). |
| 283 | — | 466 | $^1$H NMR (400 MHz, DMSO-d$_6$) δ 8.97 (t, J = 5.9 Hz, 1H), 8.65, (d, J = 6.0 Hz, 1H), 7.86-7.82 (m, 1H), 7.78-7.72 (m, 3H), 7.68 (Br-s, 1H), 7.57 (ddd, J = 8.6, 7.2, 1.3 Hz, 1H), 7.43 (td, J = 7.5, 0.9 Hz, 1H), 6.85-6.81 (m, 1H), 4.60 (dd, J = 16.6, 6.0 Hz, 1H), 4.52 (dd, J = 16.6, 5.8 Hz, 1H), 4.33 (dd, J = 8.3, 3.8 Hz, 1H), 3.60 (ddd, J = 9.9, 6.9, 5.1 Hz, 1H), 3.39 (dt, J = 10.0, 6.9 Hz, 1H), 2.43-2.36 (m, 2H), 2.30-2.23 (m, 2H), 2.04-1.82 (m, 3H), 1.77-1.56 (m, 5H). |
| 284 | TFA | 476 | $^1$H NMR (400 MHz, DMSO-d$_6$) δ 8.92 (t, J = 6.2 Hz, 1H), 8.67-8.63 (m, 1H), 7.87-7.74 (m, 7H), 7.56 (ddd, J = 8.6, 7.2, 1.3 Hz, 1H), 7.45-7.40 (m, 1H), 7.35 (d, J = 8.0 Hz, 2H), 4.58 (dd, J = 16.4, 6.2 Hz, 1H), 4.49 (dd, J = 16.6, 5.7 Hz, 1H), 4.36 (dd, J = 8.1, 3.7 Hz, 1H), 3.65-3.58 (m, 1H), 3.35-3.24 (m, 1H), 2.36 (s, 3H), 2.03-1.85 (m, 3H), 1.71-1.60 (m, 1H). |
| 285 | TFA | 518 | $^1$H NMR (400 MHz, DMSO-d$_6$) δ 8.91 (t, J = 6.0 Hz, 1H), 8.67-8.64 (m, 1H), 7.85-7.82 (m, 1H), 7.82-7.78 (m, 3H), 7.77-7.73 (m, 2H), 7.73-7.69 (m, 1H), 7.59-7.52 (m, 2H), 7.43 (ddd, 1H), 7.37-7.32 (m, 1H), 4.58 (dd, J = 16.4, 6.1 Hz, 1H), 4.49 (dd, J = 16.4, 5.7 Hz, 1H), 4.37 (dd, J = 8.0, 3.8 Hz, 1H), 3.44-3.36 (m, 2H), 2.04-1.86 (m, 3H), 1.71-1.61 (m, 1H), 1.31 (s, 6H), 1.27 (s, 3H). |
| 286 | TFA | 502 | $^1$H NMR (400 MHz, DMSO-d$_6$) δ 8.88 (dd, J = 6.2, 6.0 Hz, 1H), 8.58 (d, J = 5.4 Hz, 1H), 7.88-7.79 (m, 3H), 7.78-7.73 (m, 2H), 7.67 (dd, J = 5.4, 1.8 Hz, 1H), 7.61 (brs, 1H), 7.56 (ddd, J = 8.6, 7.3, 1.3 Hz, 1H), 7.45-7.40 (m, 1H), 4.51 (dd, J = 16.4, 6.2 Hz, 1H), 4.42 (dd, J = 16.4, 6.0 Hz, 1H), 4.36 (dd, J = 8.2, 3.7 Hz, 1H), 3.67-3.60 (m, 1H), 3.46-3.35 (m, 1H), 2.04-1.86 (m, 3H), 1.72-1.63 (m, 1H). |
| 287 | TFA | 544 | $^1$H NMR (400 MHz, DMSO-d$_6$) δ 9.10 (d, J = 2.2 Hz, 1H), 8.57 (d, J = 8.2 Hz, 1H), 8.37 (dd, J = 8.2, 2.2 Hz, 1H), 7.99 (d, J = 8.2 Hz, 1H), 7.84 (ddd, J = 7.8, 1.4, 0.9 Hz, 1H), 7.78 (dd, J = 1.8, 1.8 Hz, 1H), 7.75 (dd, J = 8.5, 0.9 Hz, 1H), 7.73 (d, J = 0.9 Hz, 1H), 7.69 (ddd, J = 7.6, 1.8, 1.8 Hz, 1H), 7.56 (ddd, J = 8.5, 7.2, 1.4 Hz, 1H), 7.51 (dd, J = 7.6, 7.6 Hz, 1H), 7.47-7.40 (m, 2H), 5.04 (dq, J = 8.2, 7.0 Hz, 1H), 4.32 (dd, J = 8.3, 3.8 Hz, 1H), 3.65-3.56 (m, 1H), 3.41-3.35 (m, 1H), 1.98-1.76 (m, 3H), 1.67-1.58 (m, 1H), 1.46 (d, J = 7.0 Hz, 3H). |
| 288 | — | 547 | $^1$H NMR (400 MHz, DMSO-d$_6$) δ 12.90 (s, 1H), 9.24 (d, J = 1.3 Hz, 1H), 8.96 (dd, J = 6.1, 5.8 Hz, 1H), 8.25 (d, J = 8.3 Hz, 1H), 8.14 (d, J = 1.3 Hz, 1H), 7.84 (ddd, J = 7.9, 1.3, 0.9 Hz, 1H), 7.80-7.72 (m, 2H), 7.57 (ddd, J = 8.5, 7.2, 1.3 Hz, 1H), 7.43 (ddd, J = 7.9, 7.2, 0.9 Hz, 1H), 7.32 (d, J = 1.9 Hz, 1H), 7.28 (dd, J = 8.3, 1.9 Hz, 1H), 4.53 (dd, J = 17.3, 6.1 Hz, 1H), 4.46 (dd, J = 17.3, 5.8 Hz, 1H), 4.37 (dd, J = 8.0, 3.9 Hz, 1H), 3.67-3.59 (m, 1H), 3.45-3.41 (m, 1H), 2.05-1.90 (m, 3H), 1.73-1.63 (m, 1H). |
| 289 | — | 565 | $^1$H NMR (400 MHz, DMSO-d$_6$) δ 12.88 (s, 1H), 9.24 (d, J = 1.3 Hz, 1H), 8.96 (dd, J = 6.1, 5.8 Hz, 1H), 8.24 (d, J = 8.3 Hz, 1H), 8.13 (d, J = 1.3 Hz, 1H), 7.81 (dd, J = 8.9, 4.1 Hz, 1H), 7.74 (d, J = 0.9 Hz, 1H), 7.64 (dd, J = 8.4, 2.7 Hz, 1H), 7.43 (ddd, J = 9.3, 8.9, 2.7 Hz, 1H), 7.32 (d, J = 1.2 Hz, 1H), 7.28 (dd, J = 8.3, 1.2 Hz, 1H), 4.52 (dd, J = 17.2, 6.1 Hz, 1H), 4.45 (dd, J = 17.2, 5.8 Hz, 1H), 4.37 (dd, J = 8.1, 3.7 Hz, 1H), 3.68-3.58 (m, 1H), 3.47-3.40 (m, 1H), 2.08-1.88 (m, 3H), 1.76-1.65 (m, 1H). |
| 290 | — | 539 | $^1$H NMR (400 MHz, DMSO-d$_6$) δ 12.70 (s, 1H), 9.20 (d, J = 1.3 Hz, 1H), 8.93 (d, J = 8.2 Hz, 1H), 8.77 (t, J = 5.8 Hz, 1H), 8.21 (d, J = 8.2 Hz, 1H), 8.05 (d, J = 1.3 Hz, 1H), 7.70 (dd, J = 9.1, 4.0 Hz, 1H), 7.51 (dd, J = 8.5, 2.7 Hz, 1H), 7.49 (d, J = 0.9 Hz, 1H), 7.37-7.27 (m, 3H), 4.33 (d, J = 5.8 Hz, 2H), 4.11 (dq, J = 8.2, 7.1 Hz, 1H), 1.27 (d, J = 7.1 Hz, 3H). |
| 291 | — | 560 | $^1$H NMR (400 MHz, DMSO-d$_6$) δ 8.97 (Br-s, 1H), 8.65 (t, J = 6.1 Hz, 1H), 8.25 (dd, J = 8.4, 2.4 Hz, 1H), 7.83 (d, J = 7.8 Hz, 1H), 7.77-7.70 (m, 3H), 7.56 (ddd, J = 8.5, 7.2, 1.4 Hz, 1H), 7.45-7.39 (m, 1H), 7.26 (t, J = 7.9 Hz, 1H), 6.99 (brs, 1H), 6.93-6.88 (m, 2H), 5.30 (s, 2H), 4.37-4.22 (m, 3H), 3.62-3.55 (m, |

TABLE 39-continued

| Example No. | Salt | MS(ESI) m/z (M + H)+ | NMR |
|---|---|---|---|
| | | | 1H), 3.42-3.35 (m, 1H), 1.94-1.80 (m, 3H), 1.68-1.59 (m, 1H). |
| 292 | 2TFA | 491 | — |
| 293 | TFA | 503 | ¹H NMR (400 MHz, DMSO-d₆) δ 10.75 (dd, J = 6.5, 5.9 Hz, 1H), 8.68 (d, J = 5.1 Hz, 1H), 8.31-8.24 (m, 2H), 8.03-7.94 (m, 3H), 7.86 (d, J = 7.8 Hz, 1H), 7.82 (s, 1H), 7.80 (d, J = 8.5 Hz, 1H), 7.61-7.55 (m, 1H), 7.44 (t, J = 7.5 Hz, 1H), 7.37 (dd, J = 5.1, 1.5 Hz, 1H), 5.15 (dd, J = 16.0, 6.5 Hz, 1H), 4.89-4.78 (m, 2H), 3.95-3.83 (m, 1H), 3.76-3.69 (m, 1H), 1.93-1.51 (m, 4H). |
| 294 | TFA | 520 | — |
| 295 | — | 617 | ¹H NMR (400 MHz, DMSO-d₆) δ 8.71 (dd, J = 6.2, 5.9 Hz, 1H), 7.92 (dd, J = 9.2, 4.1 Hz, 1H), 7.89 (d, J = 0.9 Hz, 1H), 7.81 (dd, J = 9.1, 4.2 Hz, 1H), 7.67 (d, J = 0.9 Hz, 1H), 7.66-7.60 (m, 2H), 7.52 (ddd, J = 9.2, 9.2, 2.7 Hz, 1H), 7.43 (ddd, J = 9.3, 9.1, 2.8 Hz, 1H), 7.36 (dd, J = 8.2, 7.8 Hz, 1H), 7.27 (ddd, J = 7.8, 1.4, 1.2 Hz, 1H), 7.14 (dd, J = 2.6, 1.4 Hz, 1H), 6.95 (ddd, J = 8.2, 2.6, 1.2 Hz, 1H), 4.31 (dd, J = 15.7, 6.2 Hz, 1H), 4.28-4.20 (m, 2H), 3.57 (ddd, J = 9.5, 6.8, 4.8 Hz, 1H), 3.41-3.35 (m, 1H), 1.95-1.75 (m, 3H), 1.69-1.57 (m, 1H). |
| 296 | — | 562 | ¹H NMR (400 MHz, DMSO-d₆) δ 8.68 (s, 1H), 8.65 (dd, J = 6.1, 6.1 Hz, 1H), 7.79 (dd, J = 9.0, 4.0 Hz, 1H), 7.66 (d, J = 0.9 Hz, 1H), 7.63 (dd, J = 8.5, 2.8 Hz, 1H), 7.50 (d, J = 8.5 Hz, 2H), 7.49-7.36 (m, 1H), 7.26 (t, J = 7.8 Hz, 1H), 7.14 (d, J = 8.5 Hz, 2H), 7.11 (s, 1H), 7.04-6.99 (m, 1H), 6.88 (d, J = 7.6 Hz, 1H), 4.36-4.19 (m, 3H), 3.67-3.54 (m, 1H), 3.45-3.35 (m, 1H), 2.00-1.78 (m, 3H), 1.71-1.58 (m, 1H). |
| 297 | — | 573 | ¹H NMR (400 MHz, DMSO-d₆) δ 8.72 (dd, J = 6.2, 6.1 Hz, 1H), 7.84-7.77 (m, 3H), 7.74-7.70 (m, 3H), 7.64 (dd, J = 8.5, 2.7 Hz, 1H), 7.60 (s, 1H), 7.50 (d, J = 7.7 Hz, 1H), 7.44 (dd, J = 9.3, 2.6 Hz, 1H), 7.41-7.33 (m, 3H), 7.23 (d, J = 7.7 Hz, 1H), 4.40 (dd, J = 15.5, 6.2 Hz, 1H), 4.36-4.29 (m, 2H), 3.66-3.58 (m, 1H), 3.46-3.37 (m, 1H), 2.05-1.83 (m, 3H), 1.74-1.60 (m, 1H). |
| 298 | — | 559 | 1H NMR (400 MHz, DMSO-d6) δ 8.69 (dd, J = 6.1, 6.1 Hz, 1H), 7.83 (ddd, J = 7.7, 1.3, 0.9 Hz, 1H), 7.74 (dd, J = 8.4, 0.9 Hz, 1H), 7.71 (d, J = 0.9 Hz, 1H), 7.65 (d, J = 8.6 Hz, 2H), 7.55 (ddd, J = 8.4, 7.3, 1.3 Hz, 1H), 7.44-7.39 (m Hz, 1H), 7.38 (s, 1H), 7.37-7.31 (m, 2H), 7.29-7.23 (m, 1H), 7.19 (d, J = 8.6 Hz, 2H), 5.18 (s, 2H), 4.37 (dd, J = 15.4, 6.1 Hz, 1H), 4.33-4.25 (m, 2H), 3.68-3.50 (m, 1H), 3.43-3.34 (m, 1H), 1.94-1.80 (m, 3H), 1.69-1.55 (m, 1H). |
| 299 | — | 575 | 1H NMR (400 MHz, DMSO-d6) δ 8.66 (dd, J = 6.1, 6.1 Hz, 1H), 7.83 (ddd, J = 7.9, 1.3, 0.9 Hz, 1H), 7.74 (dd, J = 8.4, 0.9 Hz, 1H), 7.71 (d, J = 0.9 Hz, 1H), 7.61 (d, J = 8.26 Hz, 2H), 7.55 (ddd, J = 8.5, 7.2, 1.3 Hz, 1H), 7.50 (d, J = 8.26 Hz, 2H), 7.42 (ddd, J = 7.9, 7.2, 1.3 Hz, 1H), 7.34 (s, 1H), 7.32-7.25 (m, 2H), 7.20-7.15 (m, 1H), 4.40-4.20 (m, 5H), 3.62-3.55 (m, 1H), 3.46-3.33 (m, 1H), 1.97-1.80 (m, 3H), 1.68-1.58 (m, 1H). |
| 300 | — | 572 | 1H NMR (400 MHz, DMSO-d6) δ 10.47 (s, 1H), 8.68 (dd, J = 6.0, 6.0 Hz, 1H), 8.14 (d, J = 8.1 Hz, 2H), 7.92 (d, J = 8.1 Hz, 2H), 7.83 (ddd, J = 8.0, 1.3, 0.9 Hz, 1H), 7.75 (dd, J = 8.4, 0.9 Hz, 1H), 7.73-7.72 (m, 1H), 7.71 (d, J = 0.9 Hz, 1H), 7.64-7.60 (m, 1H), 7.56 (ddd, J = 8.4, 7.2, 1.3 Hz, 1H), 7.42 (ddd, J = 8.0, 7.2, 0.9 Hz, 1H), 7.33 (t, J = 7.9 Hz, 1H), 7.06 (d, J = 7.8 Hz, 1H), 4.39-4.24 (m, 3H), 3.65-3.57 (m, 1H), 3.45-3.35 (m, 1H), 1.99-1.84 (m, 3H), 1.72-1.60 (m, 1H). |
| 301 | TFA | 506 | ¹H NMR (400 MHz, DMSO-d₆) δ 9.21 (d, J = 1.3 Hz, 1H), 9.19-9.15 (m, 2H), 8.79 (dd, J = 5.9, 5.9 Hz, 1H), 8.72 (d, J = 6.1 Hz, 1H), 8.35 (d, J = 8.1 Hz, 2H), 7.98 (d, J = 6.1, 1.1 Hz, 1H), 7.96-7.91 (m, 3H), 7.75 (d, J = 1.0 Hz, 1H), 4.41-4.29 (m, 2H), 4.16 (dq, J = 7.1, 6.1 Hz, 1H), 1.29 (d, J = 7.1 Hz, 3H). |
| 302 | 2TFA | 506 | ¹H NMR (400 MHz, DMSO-d₆) δ 9.39 (d, J = 2.1 Hz, 1H), 9.29 (d, J = 0.9 Hz, 1H), 9.22 (d, J = 8.2 Hz, 1H), 8.82-8.76 (m, 2H), 8.69-8.65 (m, 2H), 8.11 (dd, J = 6.3, 1.0 Hz, 1H), 8.05 (d, J = 8.2 Hz, 1H), 7.98 (d, J = 1.6 Hz, 1H), 7.80 (d, J = 1.0 Hz, 1H), 7.27 (dd, J = 5.1, 1.6 Hz, 1H), 4.39-4.25 (m, 2H), 4.14 (dq, J = 8.0, 7.1 Hz, 1H), 1.30 (d, J = 7.1 Hz, 3H). |
| 303 | 2TFA | 521 | ¹H NMR (400 MHz, DMSO-d₆) δ 9.16 (d, J = 0.9 Hz, 1H), 9.14 (d, J = 8.0 Hz, 1H), 8.78 (dd, J = 6.0, 6.0 Hz, 1H), 8.70 (d, J = 6.1 Hz, 1H), 8.59 (d, J = 5.3 Hz, 1H), 8.16 (d, J = 8.7 Hz, 1H), 8.10 (s, 1H), 7.94 (d, J = 6.1 Hz, 1H), 7.73 (d, J = 1.0 Hz, 1H), 7.30 (dd, J = 5.3, 1.5 Hz, 1H), 7.27-7.23 (m, 2H), 4.41-4.28 (m, 2H), 4.12 (dq, J = 8.0, 7.1 Hz, 1H), 1.28 (d, J = 7.1 Hz, 3H). |
| 304 | 2TFA | 506 | ¹H NMR (400 MHz, DMSO-d₆) δ 9.20 (d, J = 0.9 Hz, 1H), 9.16 (d, J = 8.4 Hz, 1H), 9.13 (d, J = 2.3 Hz, 1H), 8.80-8.74 (m, 2H), 8.70 (dd, J = 5.3, 0.8 Hz, 1H), 8.42 (dd, J = 8.5, 2.3 Hz, 1H), |

TABLE 39-continued

| Example No. | Salt | MS(ESI) m/z (M + H)+ | NMR |
|---|---|---|---|
| | | | 8.31 (d, J = 8.5 Hz, 1H), 8.07-8.03 (m, 2H), 8.00 (brs, 1H), 7.74 (d, J = 1.0 Hz, 1H), 4.35 (d, J = 5.7 Hz, 2H), 4.21-4.12 (m, 1H), 1.30 (d, J = 7.0 Hz, 3H). |
| 305 | TFA | 522 | $^1$H NMR (400 MHz, DMSO-d$_6$) δ 9.22-9.15 (m, 3H), 8.78 (dd, J = 5.9, 5.8 Hz, 1H), 8.74 (d, J = 6.2 Hz, 1H), 8.27 (d, J = 8.9 Hz, 2H), 8.00 (dd, J = 6.2, 1.0 Hz, 1H), 7.88 (d, J = 1.4 Hz, 1H), 7.76 (d, J = 1.0 Hz, 1H), 7.56 (d, J = 8.9 Hz, 2H), 4.35 (dd, J = 17.1, 5.8 Hz, 1H), 4.30 (dd, J = 17.1, 5.9 Hz, 1H), 4.20-4.14 (m, 1H), 1.30 (d, J = 7.1 Hz, 3H). |
| 306 | TFA | 548 | — |
| 307 | — | 547 | $^1$H NMR (400 MHz, DMSO-d$_6$) δ 8.75 (t, J = 6.1 Hz, 1H), 7.87-7.81 (m, 3H), 7.78 (d, J = 8.1 Hz, 2H), 7.74 (dd, J = 8.5, 1.0 Hz, 1H), 7.72 (d, J = 0.9 Hz, 1H), 7.56 (ddd, J = 8.5, 7.2, 1.3 Hz, 1H), 7.52 (dd, J = 7.7, 2.2 Hz, 1H), 7.44-7.40 (m, 1H), 7.40-7.29 (m, 2H), 4.41 (dd, J = 15.4, 6.2 Hz, 1H), 4.35 (dd, J = 15.4, 6.0 Hz, 1H), 4.30 (dd, J = 8.2, 3.7 Hz, 1H), 3.64-3.56 (m, 1H), 3.42-3.35 (m, 1H), 1.98-1.82 (m, 3H), 1.68-1.59 (m, 1H). |
| 308 | — | 563 | $^1$H NMR (400 MHz, DMSO-d$_6$) δ 10.33 (s, 1H), 8.71 (t, J = 6.0 Hz, 1H), 7.84-7.81 (m, 1H), 7.74 (dd, J = 8.3, 1.0 Hz, 1H), 7.70 (d, J = 0.9 Hz, 1H), 7.55 (ddd, J = 8.5, 7.3, 1.3 Hz, 1H), 7.43 (ddd, J = 8.3, 1H), 7.38 (d, J = 8.3 Hz, 1H), 7.35-7.28 (m, 2H), 7.26-7.19 (m, 3H), 4.40-4.26 (m, 3H), 3.63-3.55 (m, 1H), 3.42-3.36 (m, 1H), 1.97-1.80 (m, 3H), 1.69-1.59 (m, 1H). |
| 309 | — | 548 | — |
| 310 | — | 560 | $^1$H NMR (400 MHz, DMSO-d$_6$) δ 9.09 (d, J = 2.0 Hz, 1H), 8.77 (dd, J = 6.3, 5.8 Hz, 1H), 8.36 (dd, J = 8.2, 2.0 Hz, 1H), 7.98 (d, J = 8.2 Hz, 1H), 7.83 (dd, J = 8.3, 0.8 Hz, 1H), 7.79-7.71 (m, 2H), 7.56 (ddd, J = 8.3, 7.2, 1.3 Hz, 1H), 7.42 (ddd, J = 7.5, 7.2, 0.8 Hz, 1H), 7.31 (dd, J = 1.7, 1.4 Hz, 1H), 7.26 (d, J = 2.2, 1.7 Hz, 1H), 7.00 (dd, J = 2.2, 1.4 Hz, 1H), 4.45 (dd, J = 15.7, 6.3 Hz, 1H), 4.41-4.28 (m, 2H), 3.85 (s, 3H), 3.67-3.56 (m, 1H), 3.42-3.36 (m, 1H), 2.01-1.83 (m, 3H), 1.70-1.58 (m, 1H). |
| 311 | — | 603 | $^1$H NMR (400 MHz, DMSO-d$_6$) δ 8.92 (dd, J = 6.2, 5.7 Hz, 1H), 8.36 (d, J = 8.1 Hz, 2H), 7.91 (d, J = 8.1 Hz, 2H), 7.84 (ddd, J = 7.7, 1.3, 0.9 Hz, 1H), 7.79 (d, J = 0.9 Hz, 1H), 7.76 (dd, J = 8.4, 0.9 Hz, 1H), 7.69 (s, 1H), 7.57 (ddd, J = 8.4, 7.3, 1.3 Hz, 1H), 7.43 (ddd, J = 7.7, 7.3, 0.9 Hz, 1H), 4.46 (dd, J = 17.3, 6.2 Hz, 1H), 4.40-4.31 (m, 2H), 4.21 (d, J = 6.6 Hz, 2H), 3.67-3.59 (m, 1H), 3.49-3.40 (m, 1H), 2.18-2.03 (m, 1H), 2.05-1.88 (m, 3H), 1.73-1.62 (m, 1H), 1.02 (d, J = 6.7 Hz, 6H). |
| 312 | TFA | 574 | $^1$H NHR (400 MHz, DMSO-d$_6$) δ 8.80 (dd, J = 6.1, 5.7 Hz, 1H), 8.32 (d, J = 8.1 Hz, 2H), 7.90-7.81 (m, 3H), 7.78 (d, J = 0.9 Hz, 1H), 7.76 (dd, J = 8.4, 0.8 Hz, 1H), 7.57 (ddd, J = 8.4, 7.3, 1.3 Hz, 1H), 7.47-7.38 (m, 1H), 7.20 (s, 1H), 4.42-4.31 (m, 2H), 4.25 (dd, J = 17.1, 5.7 Hz, 1H), 3.68-3.57 (m, 1H), 3.42-3.36 (m, 1H), 3.23 (s, 6H), 2.03-1.85 (m, 3H), 1.72-1.60 (m, 1H). |
| 313 | TFA | 575 | $^1$H NMR (400 MHz, DMSO-d$_6$) δ 9.41 (s, 1H), 8.76 (t, J = 5.9 Hz, 1H), 8.71-8.65 (m, 2H), 8.05 (d, J = 8.3 Hz, 1H), 8.01 (s, 1H), 7.74 (dd, J = 9.1, 4.1 Hz, 1H), 7.66 (s, 1H), 7.61 (dd, J = 8.5, 2.7 Hz, 1H), 7.44-7.34 (m, 1H), 7.31 (dd, J = 5.1, 1.5 Hz, 1H), 4.74 (q, J = 7.2 Hz, 1H), 4.43-4.33 (m, 2H), 4.33-4.24 (m, 2H), 1.51 (d, J = 7.2 Hz, 3H), 1.48-1.40 (m, 3H). |
| 314 | TFA | 561 | $^1$H NMR (400 MHz, DMSO-d$_6$) δ 9.40 (s, 1H), 8.78 (t, J = 5.9 Hz, 1H), 8.71-8.64 (m, 2H), 8.05 (d, J = 8.2 Hz, 1H), 7.99 (s, 1H), 7.70 (dd, J = 9.1, 4.1 Hz, 1H), 7.65 (s, 1H), 7.58 (dd, J = 8.5, 2.7 Hz, 1H), 7.38 (td, J = 9.2, 2.8 Hz, 1H), 7.29 (dd, J = 5.1, 1.5 Hz, 1H), 4.75 (q, J = 7.2 Hz, 1H), 4.44-4.29 (m, 4H), 3.18-3.12 (m, 1H), 1.53 (d, J = 7.2 Hz, 3H). |
| 315 | — | 575 | $^1$H NMR (400 MHz, DMSO-d$_6$) δ 8.66 (dd, J = 6.0, 5.9 Hz, 1H), 7.83 (d, J = 7.8 Hz, 1H), 7.74 (d, J = 8.9 Hz, 1H), 7.71 (d, J = 1.0 Hz, 1H), 7.64 (d, J = 8.1 Hz, 2H), 7.57 (d, J = 8.1 Hz, 2H), 7.57-7.53 (m, 1H), 7.46-7.39 (m, 1H), 7.30 (dd, J = 1.6, 1.6 Hz, 1H), 7.28-7.17 (m, 2H), 7.09 (d, J = 7.4 Hz, 1H), 4.34 (s, 2H), 4.32-4.28 (m, 2H), 4.24 (dd, J = 15.5, 5.9 Hz, 1H), 3.63-3.55 (m, 1H), 3.48-3.37 (m, 1H), 1.96-1.80 (m, 3H), 1.68-1.59 (m, 1H). |
| 316 | — | 591 | $^1$H NMR (400 MHz, DMSO-d$_6$) δ 8.77 (dd, J = 6.0, 6.0 Hz, 1H), 7.85-7.82 (m, 1H), 7.77-7.73 (m, 2H), 7.63 (d, J = 7.8 Hz, 2H), 7.56 (ddd, J = 8.2, 7.2, 1.1 Hz, 1H), 7.53-7.48 (m, 1H), 7.48-7.40 (m, 3H), 7.35 (dt, J = 7.4, 1.7 Hz, 1H), 7.30 (d, J = 7.4 Hz, 2H), 4.44-4.33 (m, 3H), 4.33-4.28 (m, 3H), 4.13 (dd, J = 12.7, 3.8 Hz, 1H), 3.66-3.55 (m, 1H), 3.49-3.36 (m, 1H), 1.99-1.81 (m, 3H), 1.71-1.57 (m, 1H). |
| 317 | — | 555 | $^1$H NMR (400 MHz, DMSO-d$_6$) δ 8.72 (dd, J = 6.1, 6.0 Hz, 1H), 7.86-7.82 (m, 1H), 7.80 (d, J = 8.2 Hz, 2H), 7.77-7.70 (m, 4H), 7.61 (t, J = 1.7 Hz, 1H), 7.56 (ddd, J = 8.6, 7.3, 1.3 Hz, 1H), |

TABLE 39-continued

| Example No. | Salt | MS(ESI) m/z (M + H)+ | NMR |
|---|---|---|---|
| | | | 7.50 (d, J = 7.7 Hz, 1H), 7.46-7.33 (m, 4H), 7.23 (d, J = 7.7 Hz, 1H), 4.41 (dd, J = 15.5, 6.1 Hz, 1H), 4.36-4.29 (m, 2H), 3.68-3.57 (m, 1H), 3.47-3.35 (m, 1H), 1.99-1.85 (m, 3H), 1.71-1.60 (m, 1H). |
| 318 | — | 557 | $^1$H NMR (400 MHz, DMSO-$d_6$) δ 8.64 (dd, J = 6.0, 5.9 Hz, 1H), 7.83 (ddd, J = 8.0, 1.0, 1.2 Hz, 1H), 7.74 (ddd, J = 8.4 1.0, 0.9 Hz, 1H), 7.72 (d, J = 1.0 Hz, 1H), 7.62 (d, J = 8.0 Hz, 2H), 7.56 (ddd, J = 8.4, 7.3, 1.2 Hz, 1H), 7.46 (d, J = 8.0 Hz, 2H), 7.42 (ddd, J = 8.0, 7.3, 1.0 Hz, 1H), 7.27-7.20 (m, 2H), 7.10 (d, J = 7.7, 1.7 Hz, 2H), 4.38-4.29 (m, 2H), 4.25 (dd, J = 15.4, 5.9 Hz, 1H), 3.64-3.54 (m, 1H), 3.43-3.34 (m, 1H), 3.01-2.93 (m, 2H), 2.93-2.85 (m, 2H), 1.93-1.76 (m, 3H), 1.69-1.54 (m, 1H). |
| 319 | — | 493 | — |
| 320 | — | 559 | $^1$H NMR (400 MHz, DMSO-$d_6$) δ 8.63 (dd, J = 6.1, 6.1 Hz, 1H), 8.28-8.26 (m, 1H), 7.87-7.80 (m, 2H), 7.74 (dd, J = 8.4, 0.9 Hz, 1H), 7.70 (d, J = 0.9 Hz, 1H), 7.63 (dd, J = 8.9, 2.6 Hz, 1H), 7.55 (ddd, J = 8.4, 7.3, 1.3 Hz, 1H), 7.42 (ddd, J = 8.0, 7.3, 0.9 Hz, 1H), 7.27 (t, J = 7.5 Hz, 1H), 7.22 (s, 1H), 7.20-7.13 (m, 2H), 6.62 (d, J = 8.9 Hz, 1H), 4.52 (d, J = 5.9 Hz, 2H), 4.37-4.20 (m, 3H), 3.60-3.53 (m, 1H), 3.41-3.34 (m, 1H), 1.91-1.75 (m, 3H), 1.65-1.56 (m, 1H). |
| 321 | — | 561 | $^1$H NMR (400 MHz, DMSO-$d_6$) δ 8.71 (dd, J = 6.2, 6.1 Hz, 1H), 7.82 (ddd, J = 7.8, 1.3, 0.9 Hz, 1H), 7.74 (dd, J = 8.5, 0.9 Hz, 1H), 7.70 (d, J = 0.9 Hz, 1H), 7.65 (d, J = 8.3 Hz, 2H), 7.56 (ddd, J = 8.5, 7.2, 1.3 Hz, 1H), 7.47-7.41 (m, 3H), 7.41-7.39 (m, 1H), 7.39-7.33 (m, 3H), 4.37 (dd, J = 15.6, 6.2 Hz, 1H), 4.31 (dd, J = 15.6, 6.1 Hz, 1H), 4.27 (dd, J = 8.3, 3.4 Hz, 1H), 3.61-3.51 (m, 1H), 3.41-3.35 (m, 1H), 1.95-1.72 (m, 3H), 1.66-1.53 (m, 1H). |
| 322 | — | 593 | $^1$H NMR (400 MHz, DMSO-$d_6$) δ 8.80 (dd, J = 6.1, 6.1 Hz, 1H), 8.17 (d, J = 8.3 Hz, 2H), 7.98 (d, J = 8.3 Hz, 2H), 7.93-7.89 (m, 2H), 7.83 (ddd, J = 8.0, 1.3, 0.7 Hz, 1H), 7.76-7.71 (m, 2H), 7.64-7.60 (m, 2H), 7.56 (ddd, J = 8.6, 7.3, 1.3 Hz, 1H), 7.42 (ddd, J = 8.0, 7.3, 0.9 Hz, 1H), 4.46-4.33 (m, 2H), 4.27 (dd, J = 8.4, 3.5 Hz, 1H), 3.62-3.53 (m, 1H), 3.44-3.34 (m, 1H), 1.96-1.74 (m, 3H), 1.70-1.56 (m, 1H). |
| 323 | — | 577 | — |
| 324 | — | 607 | — |
| 325 | — | 591 | $^1$H NMR (400 MHz, DMSO-$d_6$) δ 8.65 (dd, J = 6.1, 6.1 Hz, 1H), 7.91 (d, J = 8.1 Hz, 2H), 7.83 (d, J = 7.9 Hz, 1H), 7.79-7.70 (m, 4H), 7.59-7.53 (m, 1H), 7.42 (t, J = 7.5 Hz, 1H), 7.28-7.19 (m, 2H), 7.08 (s, 1H), 6.97 (ddt, J = 6.1, 4.1, 2.1 Hz, 1H), 4.38-4.17 (m, 4H), 4.09 (dd, J = 12.8, 2.9 Hz, 1H), 3.66-3.55 (m, 1H), 3.46-3.37 (m, 1H), 1.95-1.82 (m, 3H), 1.70-1.58 (m, 1H). |
| 326 | TFA | 560 | $^1$H NMR (400 MHz, DMSO-$d_6$) δ 8.82 (t, J = 6.1 Hz, 1H), 8.29 (d, J = 7.9 Hz, 2H), 7.90-7.83 (m, 3H), 7.79 (d, J = 0.9 Hz, 1H), 7.76 (dd, J = 8.4, 0.8 Hz, 1H), 7.57 (ddd, J = 8.5, 7.2, 1.3 Hz, 1H), 7.46-7.40 (m, 1H), 7.26 (brs, 1H), 7.18 (s, 1H), 4.39-4.29 (m, 2H), 4.21 (dd, J = 16.9, 5.2 Hz, 1H), 3.67-3.59 (m, 1H), 3.51-3.42 (m, 1H), 2.91 (s, 3H), 2.04-1.87 (m, 3H), 1.72-1.63 (m, 1H). |
| 327 | — | 637 | — |
| 328 | — | 586 | $^1$H NMR (400 MHz, DMSO-$d_6$) δ 8.81 (dd, J = 5.9, 5.9 Hz, 1H), 8.29 (d, J = 8.2 Hz, 2H), 7.89-7.83 (m, 3H), 7.79 (d, J = 0.9 Hz, 1H), 7.76 (dd, J = 8.5, 0.8 Hz, 1H), 7.57 (ddd, J = 8.5, 7.2, 1.3 Hz, 1H), 7.43 (ddd, J = 8.1, 7.2, 0.8 Hz, 1H), 7.25 (s, 1H), 4.38-4.31 (m, 2H), 4.24 (dd, J = 17.2, 5.7 Hz, 1H), 4.14 (t, J = 7.5 Hz, 4H), 3.71-3.59 (m, 1H), 3.45-3.35 (m, 1H), 2.41-2.31 (m, 2H), 2.03-1.87 (m, 3H), 1.71-1.61 (m, 1H). |
| 329 | — | 600 | $^1$H NMR (400 MHz, DMSO-$d_6$) δ 8.80 (dd, J = 5.8, 5.8 Hz, 1H), 8.32 (d, J = 8.1 Hz, 2H), 7.89-7.83 (m, 3H), 7.79 (d, J = 0.9 Hz, 1H), 7.76 (dd, J = 8.5, 0.8 Hz, 1H), 7.57 (ddd, J = 8.5, 7.3, 1.3 Hz, 1H), 7.43 (ddd, J = 7.5, 7.3, 0.8 Hz, 1H), 7.21 (s, 1H), 4.40-4.32 (m, 2H), 4.25 (dd, J = 17.1, 5.8 Hz, 1H), 3.69-3.62 (m, 5H), 3.47-3.37 (m, 1H), 2.03-1.85 (m, 7H), 1.73-1.63 (m, 1H). |
| 330 | — | 616 | $^1$H NMR (400 MHz, DMSO-$d_6$) δ 8.82 (dd, J = 5.9, 5.9 Hz, 1H), 8.32 (d, J = 8.1 Hz, 2H), 7.88-7.83 (m, 3H), 7.79 (d, J = 0.9 Hz, 1H), 7.76 (dd, J = 8.5, 0.8 Hz, 1H), 7.57 (ddd, J = 8.5, 7.4, 1.3 Hz, 1H), 7.43 (ddd, J = 7.8, 7.4, 0.8 Hz, 1H), 7.28 (s, 1H), 4.42-4.32 (m, 2H), 4.26 (dd, J = 17.1, 5.9 Hz, 1H), 3.88-3.79 (m, 4H), 3.74-3.67 (m, 4H), 3.65-3.63 (m, 1H), 3.45-3.36 (m, 1H), 2.04-1.84 (m, 3H), 1.72-1.61 (m, 1H), |
| 331 | TFA | 575 | $^1$H NMR (400 MHz, DMSO-$d_6$) δ 9.23 (d, J = 2.2 Hz, 1H), 8.89 (dd, J = 6.1, 6.1 Hz, 1H), 8.66 (d, J = 5.1 Hz, 1H), 8.50 (dd, J = 8.2, 2.2 Hz, 1H), 7.97 (s, 1H), 7.84 (dd, J = 7.9, 1.3 Hz, 1H), 7.78-7.74 (m, 2H), 7.60-7.53 (m, 2H), 7.43 (ddd, J = 7.9, 7.5, 0.8 Hz, 1H), 7.35 (dd, J = 5.1, 1.5 Hz, 1H), 4.82 (s, 2H), 4.50 (dd, J = 16.6, 6.1 Hz, |

TABLE 39-continued

| Example No. | Salt | MS(ESI) m/z (M + H)+ | NMR |
|---|---|---|---|
| | | | 1H), 4.41 (dd, J = 16.6, 6.1 Hz, 1H), 4.34 (dd, J = 8.3, 3.8 Hz, 1H), 4.25 (q, J = 9.3 Hz, 2H), 3.66-3.61 (m, 1H), 3.45-3.38 (m, 1H), 2.06-1.85 (m, 3H), 1.72-1.59 (m, 1H). |
| 332 | TFA | 512 | 1H NMR (400 MHz, DMSO-d6) δ 8.90 (dd, J = 6.1, 6.1 Hz, 1H), 8.66 (d, J = 5.1 Hz, 1H), 8.22 (d, J = 8.1 Hz, 2H), 7.97 (s, 1H), 7.84 (dd, J = 7.9, 1.3 Hz, 1H), 7.78-7.74 (m, 2H), 7.73-7.69 (m, 2H), 7.57 (ddd, J = 8.3, 7.3, 1.4 Hz, 1H), 7.46-7.40 (m, 1H), 7.37 (dd, J = 5.1, 1.5 Hz, 1H), 7.10 (t, J = 55.9 Hz, 1H), 4.51 (dd, J = 16.6, 6.1 Hz, 1H), 4.42 (dd, J = 16.6, 6.1 Hz, 1H), 4.34 (dd, J = 8.2, 3.7 Hz, 1H), 3.67-3.59 (m, 1H), 3.46-3.38 (m, 1H), 2.04-1.85 (m, 3H), 1.71-1.60 (m, 1H). |
| 333 | TFA | 512 | 1H NMR (400 MHz, DMSO-d6) δ 8.90 (dd, J = 6.0, 6.0 Hz, 1H), 8.66 (d, J = 5.3 Hz, 1H), 7.97 (d, J = 8.0 Hz, 2H), 7.84 (d, J = 7.8 Hz, 1H), 7.80-7.69 (m, 6H), 7.56 (dd, J = 7.8, 7.8 Hz, 1H), 7.42 (dd, J = 7.5, 7.5 Hz, 1H), 7.10 (t, J = 55.8 Hz, 1H), 4.57 (dd, J = 16.4, 6.0 Hz, 1H), 4.47 (dd, J = 16.4, 6.0 Hz, 1H), 4.36 (dd, J = 8.1, 3.7 Hz, 1H), 3.65-3.58 (m, 1H), 3.43-3.35 (m, 1H), 2.03-1.86 (m, 3H), 1.72-1.61 (m, 1H). |
| 334 | 2TFA | 589 | 1H NMR (400 MHz, DMSO-d6) δ 9.83 (brs, 1H), 9.11 (t, J = 6.0 Hz, 1H), 8.66 (d, J = 5.3 Hz, 1H), 8.28-8.15 (m, 2H), 7.86 (dd, J = 7.9, 1.2 Hz, 1H), 7.79 (s, 1H), 7.72 (d, J = 8.5 Hz, 2H), 7.63-7.54 (m, 1H), 7.49-7.39 (m, 2H), 7.27-7.18 (m, 2H), 4.69 (d, J = 9.3 Hz, 1H), 4.50 (d, J = 5.9 Hz, 2H), 4.23-4.10 (m, 1H), 4.06 (t, J = 8.5 Hz, 1H), 3.66-3.16 (m, 1H), 2.90-2.68 (m, 6H), 2.48-2.39 (m, 1H), 2.27-2.13 (m, 1H). |
| 335 | TFA | 537 | 1H NMR (400 MHz, DMSO-d6) δ 9.13-9.09 (m, 1H), 8.82 (d, J = 8.5 Hz, 1H), 8.74 (t, J = 5.7 Hz, 1H), 8.69 (d, J = 5.2 Hz, 1H), 8.41 (dd, J = 8.5, 2.3 Hz, 1H), 8.29 (d, J = 8.4 Hz, 1H), 8.04 (dd, J = 5.3, 1.7 Hz, 1H), 7.99 (d, J = 1.6 Hz, 1H), 7.65 (dd, J = 9.2, 4.0 Hz, 1H), 7.47 (dd, J = 8.5, 2.7 Hz, 1H), 7.44 (d, J = 0.9 Hz, 1H), 7.30 (ddd, J = 9.2, 9.2, 2.7 Hz, 1H), 4.34 (d, J = 5.7 Hz, 2H), 3.96-3.89 (m, 1H), 1.75-1.63 (m, 1H), 1.63-1.50 (m, 1H), 0.80 (dd, J = 7.3, 7.3 Hz, 3H). |
| 336 | — | 629 | — |
| 337 | — | 600 | — |
| 338 | — | 629 | — |
| 339 | TFA | 523 | 1H NMR (400 MHz, DMSO-d6) δ 9.15-9.12 (m, 1H), 8.78 (t, J = 5.8 Hz, 1H), 8.73-8.70 (m, 1H), 8.42 (dd, J = 8.5, 2.4 Hz, 1H), 8.33 (d, J = 8.3 Hz, 1H), 8.06-8.03 (m, 2H), 7.74 (dd, J = 9.2, 4.1 Hz, 1H), 7.61 (d, J = 0.8 Hz, 1H), 7.57 (dd, J = 8.5, 2.7 Hz, 1H), 7.38 (ddd, J = 9.2, 9.2, 2.7 Hz, 1H), 4.47 (d, J = 5.8 Hz, 2H), 4.04 (s, 2H), 3.00 (s, 3H). |
| 340 | TFA | 551 | 1H NMR (400 MHz, DMSO-d6) δ 9.12-9.07 (m, 1H), 8.72-8.69 (m, 1H), 8.57 (t, J = 5.9 Hz, 1H), 8.38 (dd, J = 8.5, 2.4 Hz, 1H), 8.26 (d, J = 8.4 Hz, 1H), 8.13-8.11 (m, 1H), 8.04 (dd, J = 5.3, 1.8 Hz, 1H), 7.72 (dd, J = 9.2, 4.0 Hz, 1H), 7.66 (d, J = 0.9 Hz, 1H), 7.60 (dd, J = 8.5, 2.7 Hz, 1H), 7.38 (ddd, J = 9.2, 9.2, 2.7 Hz, 1H), 4.54 (d, J = 5.9 Hz, 2H), 2.95 (s, 3H), 1.48 (s, 6H). |
| 341 | TFA | 563 | 1H NMR (400 MHz, DMSO-d6) δ 9.15-9.10 (m, 1H), 8.72 (d, J = 5.2 Hz, 1H), 8.61 (d, J = 5.9, 5.9 Hz, 1H), 8.42 (dd, J = 8.6, 2.4 Hz, 1H), 8.31 (d, J = 8.4 Hz, 1H), 8.09 (brs, 1H), 8.05 (dd, J = 5.2, 1.7 Hz, 1H), 7.77 (dd, J = 9.2, 4.1 Hz, 1H), 7.62-7.57 (m, 2H), 7.39 (ddd, J = 9.2, 9.2, 2.7 Hz, 1H), 4.58 (dd, J = 16.3, 5.9 Hz, 1H), 4.48 (dd, J = 16.3, 5.9 Hz, 1H), 3.86-3.75 (m, 1H), 3.64-3.55 (m, 1H), 2.29-2.18 (m, 1H), 2.05-1.86 (m, 3H), 1.59 (s, 3H). |
| 342 | TFA | 537 | 1H NMR (400 MHz, DMSO-d6) δ 9.13-9.10 (m, 1H), 8.76 (t, J = 5.8 Hz, 1H), 8.70 (dd, J = 5.7, 0.5 Hz, 1H), 8.41 (dd, J = 8.5, 2.4 Hz, 1H), 8.29 (d, J = 8.4 Hz, 1H), 8.02 (dd, J = 5.2, 1.7 Hz, 1H), 7.99 (brs, 1H), 7.69 (dd, J = 9.2, 4.1 Hz, 1H), 7.59 (d, J = 0.9 Hz, 1H), 7.52 (dd, J = 8.5, 2.7 Hz, 1H), 7.35 (td, J = 9.2, 2.8 Hz, 1H), 4.70 (q, J = 7.1 Hz, 1H), 4.47-4.36 (m, 2H), 2.99 (s, 3H), 1.28 (d, J = 7.1 Hz, 3H). |
| 343 | TFA | 509 | 1H NMR (400 MHz, DMSO-d6) δ 9.15-9.12 (m, 1H), 8.84 (t, J = 6.1 Hz, 1H), 8.71 (dd, J = 5.2, 0.7 Hz, 1H), 8.67 (t, J = 5.9 Hz, 1H), 8.42 (dd, J = 8.4, 2.4 Hz, 1H), 8.32 (d, J = 8.4 Hz, 1H), 8.05 (dd, J = 5.2, 1.7 Hz, 1H), 8.02 (brs, J = 1.5 Hz, 1H), 7.71 (dd, J = 9.1, 4.1 Hz, 1H), 7.55-7.50 (m, 2H), 7.34 (t, J = 9.2, 2.7 Hz, 1H), 4.43 (d, J = 5.8 Hz, 2H), 3.80 (d, J = 6.0 Hz, 2H), |
| 344 | — | 523 | 1H NMR (400 MHz, DMSO-d6) δ 9.24 (d, J = 1.3 Hz, 1H), 8.81 (t, J = 5.8 Hz, 1H), 8.38 (d, J = 7.7 Hz, 2H), 8.02 (d, J = 1.3 Hz, 1H), 7.94 (d, J = 7.8 Hz, 2H), 7.74 (dd, J = 9.2, 4.3 Hz, 1H), 7.63 (d, J = 0.9 Hz, 1H), 7.58 (dd, J = 8.5, 2.8 Hz, 1H), 7.38 (ddd, J = 9.2, 9.2, 2.8 Hz, 1H), 4.45 (d, J = 5.8 Hz, 2H), 4.08 (s, 2H), 3.01 (s, 3H). |
| 345 | — | 509 | 1H NMR (400 MHz, DMSO-d6) δ 9.22 (d, J = 1.3 Hz, 1H), 8.90 (t, J = 6.0 Hz, 1H), 8.73 (t, J = 5.9 Hz, 1H), 8.38 (d, J = 8.0 Hz, 2H), 7.99 (d, J = 1.3 Hz, 1H), 7.93 (d, J = 8.3 Hz, 2H), 7.72 (dd, J = |

TABLE 39-continued

| Example No. | Salt | MS(ESI) m/z (M + H)+ | NMR |
|---|---|---|---|
| | | | 9.0, 4.1 Hz, 1H), 7.57-7.53 (m, 2H), 7.36 (td, J = 9.2, 2.7 Hz, 1H), 4.41 (d, J = 5.8 Hz, 2H), 3.83 (d, J = 6.0 Hz, 2H). |
| 346 | 2TFA | 532 | $^1$H NMR (400 MHz, DMSO-$d_6$) δ 9.22 (s, 1H), 9.15-9.12 (m, 1H), 8.94 (t, J = 6.0 Hz, 1H), 8.77-8.74 (m, 1H), 8.59 (d, J = 5.4 Hz, 1H), 8.43 (dd, J = 8.4, 2.4 Hz, 1H), 8.33 (d, J = 8.4 Hz, 1H), 8.12-8.08 (m, 2H), 7.94 (dd, J = 5.4, 1.0 Hz, 1H), 7.84 (d, J = 0.8 Hz, 1H), 4.60-4.47 (m, 2H), 4.42 (dd, J = 8.3, 3.3 Hz, 1H), 3.70-3.63 (m, 1H), 3.51-3.42 (m, 1H), 2.11-1.90 (m, 3H), 1.80-1.71 (m, 1H). |
| 347 | TFA | 532 | $^1$H NMR (400 MHz, DMSO-$d_6$) δ 9.27-9.22 (m, 2H), 9.01 (dd, J = 6.1, 6.0 Hz, 1H), 8.61 (d, J = 5.4 Hz, 1H), 8.39 (d, J = 8.2 Hz, 2H), 8.04 (d, J = 1.3 Hz, 1H), 7.97 (dd, J = 5.4, 1.1 Hz, 1H), 7.93 (d, J = 8.2 Hz, 2H), 7.90 (d, J = 0.8 Hz, 1H), 4.55 (dd, J = 17.2, 6.1 Hz, 1H), 4.49-4.40 (m, 2H), 3.72-3.64 (m, 1H), 3.52-3.44 (m, 1H), 2.17-2.05 (m, 1H), 2.03-1.90 (m, 2H), 1.80-1.71 (m, 1H). |
| 348 | TFA | 551 | $^1$H NMR (400 MHz, DMSO-$d_6$) δ 9.13-9.10 (m, 1H), 8.71 (d, J = 5.2 Hz, 1H), 8.67 (t, J = 5.8 Hz, 1H), 8.41 (dd, J = 8.5, 2.4 Hz, 1H), 8.31 (d, J = 8.4 Hz, 1H), 8.07 (brs, 1H), 8.04 (dd, J = 5.2, 1.7 Hz, 1H), 7.77 (dd, J = 9.1, 4.1 Hz, 1H), 7.63 (d, J = 0.9 Hz, 1H), 7.60 (dd, J = 8.5, 2.7 Hz, 1H), 7.39 (ddd, J = 9.1, 9.1, 2.7 Hz, 1H), 4.52 (d, J = 5.8 Hz, 2H), 4.16 (p, J = 6.7 Hz, 1H), 4.01 (s, 2H), 1.06 (d, J = 6.7 Hz, 6H). |
| 349 | TFA | 563 | $^1$H NMR (400 MHz, DMSO-$d_6$) δ 9.14-9.11 (m, 1H), 8.76 (t, J = 5.8 Hz, 1H), 8.73-8.70 (m, 1H), 8.43 (dd, J = 8.5, 2.4 Hz, 1H), 8.32 (d, J = 8.4 Hz, 1H), 8.06-8.03 (m, 2H), 7.72 (dd, J = 9.2, 4.0 Hz, 1H), 7.59 (d, J = 0.8 Hz, 1H), 7.54 (dd, J = 8.5, 2.7 Hz, 1H), 7.36 (ddd, J = 9.2, 9.2, 2.7 Hz, 1H), 4.47 (d, J = 5.8 Hz, 2H), 4.19 (s, 2H), 3.27 (d, J = 7.0 Hz, 2H), 1.03-0.93 (m, 1H), 0.45-0.37 (m, 2H), 0.20-0.14 (m, 2H). |
| 350 | TFA | 599 | $^1$H NMR (400 MHz, DMSO-$d_6$) δ 9.13-9.09 (m, 1H), 8.74-8.68 (m, 1H), 8.67 (t, J = 5.9 Hz, 1H), 8.45-8.40 (m, 1H), 8.32 (d, J = 8.4 Hz, 1H), 8.05 (dd, J = 5.3, 1.7 Hz, 1H), 8.00 (brs, J = 1.6 Hz, 1H), 7.70 (dd, J = 9.1, 4.0 Hz, 1H), 7.59 (d, J = 0.8 Hz, 1H), 7.52 (dd, J = 8.5, 2.7 Hz, 1H), 7.35 (td, J = 9.2, 2.7 Hz, 1H), 7.32-7.25 (m, 5H), 4.61 (s, 2H), 4.39 (d, J = 5.8 Hz, 2H), 4.00 (s, 2H). |
| 351 | TFA | 590 | $^1$H NMR (400 MHz, DMSO-$d_6$) δ 9.14-9.10 (m, 1H), 8.86 (t, J = 5.9 Hz, 1H), 8.72-8.69 (m, 1H), 8.43-8.39 (m, 1H), 8.32 (d, J = 8.4 Hz, 1H), 8.04-8.00 (m, 2H), 7.96 (d, J = 0.9 Hz, 1H), 7.67 (dd, J = 9.0, 4.1 Hz, 1H), 7.58 (d, J = 0.9 Hz, 1H), 7.53 (dd, J = 8.5, 2.7 Hz, 1H), 7.37 (td, J = 9.2, 2.7 Hz, 1H), 7.04 (d, J = 0.9 Hz, 1H), 4.80 (s, 2H), 4.46 (d, J = 5.8 Hz, 2H), 4.22 (s, 2H). |
| 352 | — | 599 | $^1$H NMR (400 MHz, DMSO-$d_6$) δ 9.23 (d, J = 1.3 Hz, 1H), 8.69 (t, J = 5.9 Hz, 1H), 8.36 (d, J = 7.6 Hz, 2H), 7.97 (d, J = 1.3 Hz, 1H), 7.94 (d, J = 8.4 Hz, 2H), 7.69 (dd, J = 9.1, 4.3 Hz, 1H), 7.60 (d, J = 0.9 Hz, 1H), 7.52 (dd, J = 8.5, 2.7 Hz, 1H), 7.35 (td, J = 9.3, 2.8 Hz, 1H), 7.32-7.24 (m, 5H), 4.61 (s, 2H), 4.37 (d, J = 5.8 Hz, 2H), 4.04 (s, 2H). |
| 353 | TFA | 600 | $^1$H NMR (400 MHz, DMSO-$d_6$) δ 9.23 (d, J = 1.3 Hz, 1H), 9.16 (t, J = 6.0 Hz, 1H), 8.36 (d, J = 8.1 Hz, 2H), 8.30-8.27 (m, 1H), 8.01 (d, J = 1.3 Hz, 1H), 7.91 (d, J = 8.3 Hz, 2H), 7.74 (td, J = 7.7, 1.8 Hz, 1H), 7.68 (dd, J = 9.2, 4.0 Hz, 1H), 7.58 (d, J = 0.9 Hz, 1H), 7.54 (dd, J = 8.5, 2.7 Hz, 1H), 7.42 (d, J = 7.8 Hz, 1H), 7.37 (td, J = 9.2, 2.8 Hz, 1H), 7.25-7.19 (m, 1H), 4.74 (s, 2H), 4.46 (d, J = 5.8 Hz, 2H), 4.25 (s, 2H). |
| 354 | — | 590 | $^1$H NMR (400 MHz, DMSO-$d_6$) δ 9.24 (d, J = 1.3 Hz, 1H), 8.92 (t, J = 5.8 Hz, 1H), 8.39 (d, J = 8.2 Hz, 2H), 8.02 (d, J = 1.3 Hz, 1H), 7.97 (d, J = 0.9 Hz, 1H), 7.93 (d, J = 8.2 Hz, 2H), 7.67 (dd, J = 9.1, 4.1 Hz, 1H), 7.60 (d, J = 0.9 Hz, 1H), 7.54 (dd, J = 8.5, 2.7 Hz, 1H), 7.37 (ddd, J = 9.2, 9.1, 2.7 Hz, 1H), 7.05 (d, J = 0.9 Hz, 1H), 4.80 (s, 2H), 4.44 (d, J = 5.8 Hz, 2H), 4.25 (s, 2H). |
| 355 | TFA | 567 | $^1$H NMR (400 MHz, DMSO-$d_6$) δ 9.13 (d, J = 2.6 Hz, 1H), 8.71-8.66 (m, 2H), 8.41 (dd, J = 8.4, 2.6 Hz, 1H), 8.30 (d, J = 8.4 Hz, 1H), 8.03-7.99 (m, 2H), 7.73 (dd, J = 9.1, 4.1 Hz, 1H), 7.58 (d, J = 0.9 Hz, 1H), 7.54 (dd, J = 8.5, 2.7 Hz, 1H), 7.36 (ddd, J = 9.2, 9.1, 2.7 Hz, 1H), 4.45 (d, J = 5.9 Hz, 2H), 4.14 (s, 2H), 3.58-3.48 (m, 2H), 3.44-3.37 (m, 2H), 3.11 (s, 3H). |
| 356 | TFA | 595 | $^1$H NMR (400 MHz, DMSO-$d_6$) δ 9.15-9.10 (m, 1H), 8.75-8.67 (m, 2H), 8.42 (dd, J = 8.4, 2.4 Hz, 1H), 8.31 (d, J = 8.4 Hz, 1H), 8.03 (d, J = 4.2 Hz, 2H), 7.73 (dd, J = 9.1, 4.0 Hz, 1H), 7.59 (d, J = 0.9 Hz, 1H), 7.55 (dd, J = 8.5, 2.7 Hz, 1H), 7.37 (ddd, J = 9.3, 9.1, 2.7 Hz, 1H), 4.47 (d, J = 5.8 Hz, 2H), 4.17 (s, 2H), 3.53 (s, 4H), 3.46-3.35 (m, 1H), 0.88 (d, J = 6.1 Hz, 6H). |
| 357 | — | 567 | $^1$H NMR (400 MHz, DMSO-$d_6$) δ 9.24 (d, J = 1.3 Hz, 1H), 8.73 (t, J = 5.9 Hz, 1H), 8.38 (d, J = 7.9 Hz, 2H), 8.02 (d, J = 1.3 Hz, |

TABLE 39-continued

| Example No. | Salt | MS(ESI) m/z (M + H)+ | NMR |
|---|---|---|---|
| | | | 1H), 7.94 (d, J = 8.3 Hz, 2H), 7.73 (dd, J = 8.9, 4.1 Hz, 1H), 7.62 (d, J = 0.9 Hz, 1H), 7.56 (dd, J = 8.5, 2.7 Hz, 1H), 7.37 (td, J = 9.2, 2.8 Hz, 1H), 4.45 (d, J = 5.8 Hz, 2H), 4.17 (s, 2H), 3.61-3.48 (m, 4H), 3.13 (s, 3H). |
| 358 | — | 595 | $^1$H NMR (400 MHz, DMSO-$d_6$) δ 9.24 (d, J = 1.3 Hz, 1H), 8.75 (t, J = 5.9 Hz, 1H), 8.38 (d, J = 7.9 Hz, 2H), 8.02 (d, J = 1.3 Hz, 1H), 7.93 (d, J = 8.3 Hz, 2H), 7.73 (dd, J = 9.1, 4.1 Hz, 1H), 7.62 (d, J = 0.9 Hz, 1H), 7.57 (dd, J = 8.5, 2.7 Hz, 1H), 7.38 (td, J = 9.3, 2.8 Hz, 1H), 4.46 (d, J = 5.8 Hz, 2H), 4.19 (s, 2H), 3.56-3.53 (m, 4H), 3.47-3.39 (m, 1H), 0.90 (d, J = 6.1 Hz, 6H). |
| 359 | — | 552 | $^1$H NMR (400 MHz, DMSO-$d_6$) δ 9.47 (d, J = 2.1 Hz, 1H), 9.29 (d, J = 1.3 Hz, 1H), 8.80-8.74 (m, 2H), 8.15-8.09 (m, 2H), 7.78 (dd, J = 9.2, 4.0 Hz, 1H), 7.68 (d, J = 0.9 Hz, 1H), 7.62 (dd, J = 8.5, 2.7 Hz, 1H), 7.40 (td, J = 9.2, 2.8 Hz, 1H), 4.51 (d, J = 5.8 Hz, 2H), 4.22-4.12 (m, 1H), 4.06 (s, 2H), 1.07 (d, J = 6.7 Hz, 6H). |
| 360 | — | 553 | $^1$H NMR (400 MHz, DMSO-$d_6$) δ 9.69 (s, 2H), 9.33 (d, J = 1.3 Hz, 1H), 8.78 (t, J = 5.9 Hz, 1H), 8.17 (d, J = 1.3 Hz, 1H), 7.78 (dd, J = 9.2, 4.0 Hz, 1H), 7.71-7.59 (m, 2H), 7.40 (td, J = 9.2, 2.8 Hz, 1H), 4.52 (d, J = 5.8 Hz, 2H), 4.17 (p, J = 6.6 Hz, 1H), 4.06 (s, 2H), 1.06 (d, J = 6.7 Hz, 6H). |
| 361 | — | 601 | $^1$H NMR (400 MHz, DMSO-$d_6$) δ 9.23 (d, J = 1.3 Hz, 1H), 8.93 (t, J = 5.9 Hz, 1H), 8.71 (d, J = 1.5 Hz, 1H), 8.49 (d, J = 2.6 Hz, 1H), 8.39-8.34 (m, 3H), 8.01 (d, J = 1.3 Hz, 1H), 7.92 (d, J = 8.3 Hz, 2H), 7.66 (dd, J = 9.0, 4.1 Hz, 1H), 7.60 (d, J = 0.9 Hz, 1H), 7.55 (dd, J = 8.5, 2.7 Hz, 1H), 7.38 (td, J = 9.2, 2.7 Hz, 1H), 4.82 (s, 2H), 4.44 (d, J = 5.8 Hz, 2H), 4.30 (s, 2H). |
| 362 | — | 539 | $^1$H NMR (400 MHz, DMSO-$d_6$) δ 9.19 (d, J = 1.3 Hz, 1H), 8.80 (t, J = 5.9 Hz, 1H), 8.33-8.28 (m, 2H), 7.95 (d, J = 1.3 Hz, 1H), 7.74 (dd, J = 8.9, 4.2 Hz, 1H), 7.63 (d, J = 0.9 Hz, 1H), 7.60-7.53 (m, 3H), 7.38 (dt, J = 9.2, 2.8 Hz, 1H), 4.43 (d, J = 5.8 Hz, 2H), 4.08 (s, 2H), 3.01 (s, 3H). |
| 363 | — | 525 | $^1$H NMR (400 MHz, DMSO-$d_6$) δ 9.17 (d, J = 1.3 Hz, 1H), 8.92-8.86 (m, 1H), 8.70 (t, J = 5.9 Hz, 1H), 8.33-8.27 (m, 2H), 7.91 (d, J = 1.4 Hz, 1H), 7.72 (dd, J = 9.1, 4.1 Hz, 1H), 7.58-7.53 (m, 4H), 7.36 (td, J = 9.2, 2.7 Hz, 1H), 4.39 (d, J = 5.8 Hz, 2H), 3.82 (d, J = 5.4 Hz, 2H). |
| 364 | — | 567 | $^1$H NMR (400 MHz, DMSO-$d_6$) δ 9.19 (d, J = 1.3 Hz, 1H), 8.72 (t, J = 5.9 Hz, 1H), 8.33-8.27 (m, 2H), 7.98 (d, J = 1.3 Hz, 1H), 7.78 (dd, J = 9.0, 4.2 Hz, 1H), 7.67 (d, J = 0.9 Hz, 1H), 7.62 (dd, J = 8.5, 2.7 Hz, 1H), 7.57-7.51 (m, 2H), 7.40 (td, J = 9.2, 2.8 Hz, 1H), 4.48 (d, J = 5.8 Hz, 2H), 4.22-4.12 (m, 1H), 4.05 (s, 2H), 1.07 (d, J = 6.7 Hz, 6H), |
| 365 | 2TFA | 533 | $^1$H NMR (400 MHz, DMSO-$d_6$) δ 9.45 (s, 2H), 9.24 (d, J = 1.0 Hz, 1H), 8.92 (t, J = 6.0 Hz, 1H), 8.77 (d, J = 5.5 Hz, 1H), 8.75 (d, J = 6.1 Hz, 1H), 8.27 (s, 1H), 8.21 (dd, J = 5.2, 1.6 Hz, 1H), 8.03 (d, J = 6.1 Hz, 1H), 7.90 (d, J = 1.0 Hz, 1H), 4.52 (d, J = 6.0 Hz, 2H), 4.41 (dd, J = 8.1, 3.1 Hz, 1H), 3.71-3.61 (m, 1H), 3.51-3.38 (m, 1H), 2.12-1.89 (m, 3H), 1.84-1.72 (m, 1H). |
| 366 | 2TFA | 505 | $^1$H NMR (400 MHz, DMSO-$d_6$) δ 9.21 (d, J = 0.9 Hz, 1H), 9.16 (d, J = 8.1 Hz, 1H), 8.77-8.72 (m, 2H), 8.61 (d, J = 4.9 Hz, 1H), 8.26 (d, J = 8.1 Hz, 2H), 8.00 (d, J = 6.1 Hz, 1H), 7.90-7.84 (m, 3H), 7.75 (d, J = 1.0 Hz, 1H), 7.21 (dd, J = 5.1, 1.5 Hz, 1H), 4.36-4.24 (m, 2H), 4.17-4.07 (m, 1H), 1.28 (d, J = 7.0 Hz, 3H). |
| 367 | TFA | 505 | $^1$H NMR (400 MHz, DMSO-$d_6$) δ 9.16 (d, J = 0.9 Hz, 1H), 9.09-9.01 (m, 2H), 8.70 (d, J = 6.1 Hz, 1H), 8.63 (t, J = 5.9 Hz, 1H), 8.30 (dd, J = 8.5, 2.4 Hz, 1H), 8.16 (d, J = 8.4 Hz, 1H), 8.04-7.98 (m, 2H), 7.94 (d, J = 6.1 Hz, 1H), 7.69 (d, J = 1.0 Hz, 1H), 7.45 (t, J = 7.6 Hz, 1H), 7.28 (d, J = 7.8 Hz, 1H), 4.23 (d, J = 5.8 Hz, 2H), 4.15-4.05 (m, 1H), 1.26 (d, J = 7.1 Hz, 3H). |
| 368 | TFA | 534 | $^1$H NMR (400 MHz, DMSO-$d_6$) δ 9.24 (d, J = 1.3 Hz, 1H), 9.20 (d, J = 0.8 Hz, 1H), 8.76 (t, J = 5.9 Hz, 1H), 8.72 (d, J = 6.0 Hz, 1H), 8.38 (d, J = 8.1 Hz, 2H), 8.04 (d, J = 1.3 Hz, 1H), 7.96 (d, J = 6.2 Hz, 1H), 7.93 (d, J = 8.3 Hz, 2H), 7.87 (d, J = 0.9 Hz, 1H), 4.49 (d, J = 5.9 Hz, 2H), 4.28-4.14 (m, 1H), 4.10 (s, 2H), 1.10 (d, J = 6.7 Hz, 6H). |
| 369 | TFA | 549 | $^1$H NMR (400 MHz, DMSO-$d_6$) δ 9.13-9.08 (m, 2H), 8.67 (d, J = 6.0 Hz, 1H), 8.61 (t, J = 5.8 Hz, 1H), 8.27 (d, J = 8.2 Hz, 2H), 7.91-7.85 (m, 3H), 7.69 (d, J = 1.0 Hz, 1H), 7.06 (s, 1H), 4.18-4.10 (m, 3H), 3.20 (s, 6H), 1.28 (d, J = 7.1 Hz, 3H). |
| 370 | — | 566 | $^1$H NMR (400 MHz, DMSO-$d_6$) δ 8.93 (d, J = 8.1 Hz, 1H), 8.57 (t, J = 5.8 Hz, 1H), 8.27 (d, J = 8.1 Hz, 2H), 7.87 (d, J = 8.3 Hz, 2H), 7.70 (dd, J = 9.1, 4.1 Hz, 1H), 7.51 (dd, J = 8.5, 2.7 Hz, 1H), 7.49 (d, J = 0.9 Hz, 1H), 7.34 (td, J = 9.3, 2.8 Hz, 1H), 7.07 (s, |

TABLE 39-continued

| Example No. | Salt | MS(ESI) m/z (M + H)+ | NMR |
|---|---|---|---|
| | | | 1H), 4.17 (d, J = 5.8 Hz, 2H), 4.14-4.06 (m, 1H), 3.21 (s, 6H), 1.25 (d, J = 7.1 Hz, 3H). |
| 371 | — | 575 | ¹H NMR (400 MHz, DMSO-d₆) δ 9.42 (d, J = 2.1 Hz, 1H), 8.82 (t, J = 6.0 Hz, 1H), 8.72 (dd, J = 8.2, 2.1 Hz, 1H), 8.06 (dd, J = 8.2, 0.8 Hz, 1H), 7.86-7.83 (m, 1H), 7.79 (d, J = 0.9 Hz, 1H), 7.76 (dd, J = 8.5, 0.9 Hz, 1H), 7.57 (ddd, J = 8.5, 7.2, 1.3 Hz, 1H), 7.46-7.40 (m, 1H), 7.28 (s, 1H), 4.42-4.34 (m, 2H), 4.26 (dd, J = 17.1, 5.6 Hz, 1H), 3.65-3.58 (m, 1H), 3.46-3.37 (m, 1H), 3.24 (s, 6H), 2.05-1.86 (m, 3H), 1.72-1.61 (m, 1H). |
| 372 | — | 567 | ¹H NMR (400 MHz, DMSO-d₆) δ 9.38 (d, J = 2.1 Hz, 1H), 8.94 (d, J = 8.0 Hz, 1H), 8.68 (dd, J = 8.1, 2.1 Hz, 1H), 8.58 (t, J = 5.9 Hz, 1H), 8.06 (dd, J = 8.3, 0.8 Hz, 1H), 7.69 (dd, J = 9.1, 4.1 Hz, 1H), 7.55-7.47 (m, 2H), 7.34 (td, J = 9.2, 2.7 Hz, 1H), 7.14 (s, 1H), 4.19 (d, J = 5.8 Hz, 2H), 4.14-4.06 (m, 1H), 3.21 (s, 6H), 1.26 (d, J = 7.1 Hz, 3H). |
| 373 | TFA | 521 | ¹H NMR (400 MHz, DMSO-d₆) δ 9.17 (d, J = 0.9 Hz, 1H), 9.08-9.02 (m, 2H), 8.71 (d, J = 6.1 Hz, 1H), 8.50 (t, J = 5.8 Hz, 1H), 8.37 (dd, J = 8.8, 2.4 Hz, 1H), 8.31 (d, J = 8.7 Hz, 1H), 7.94 (d, J = 6.1 Hz, 1H), 7.87 (d, J = 2.2 Hz, 1H), 7.68 (d, J = 1.0 Hz, 1H), 7.13 (dd, J = 8.4, 2.1 Hz, 1H), 6.91 (d, J = 8.4 Hz, 1H), 4.14-4.03 (m, 3H), 1.24 (d, J = 7.0 Hz, 3H). |
| 374 | TFA | 549 | ¹H NMR (400 MHz, DMSO-d₆) δ 9.23 (d, J = 0.9 Hz, 1H), 9.06-9.04 (m, 1H), 8.74 (d, J = 6.1 Hz, 1H), 8.47 (t, J = 5.9 Hz, 1H), 8.37 (dd, J = 8.7, 2.3 Hz, 1H), 8.34 (d, J = 9.0 Hz, 1H), 8.03-7.99 (m, 1H), 7.95 (d, J = 2.2 Hz, 1H), 7.84 (d, J = 1.0 Hz, 1H), 7.27 (dd, J = 8.4, 2.1 Hz, 1H), 6.96 (d, J = 8.4 Hz, 1H), 4.27 (d, J = 5.8 Hz, 2H), 4.23-4.15 (m, 1H), 3.99 (s, 2H), 1.08 (d, J = 6.7 Hz, 6H). |
| 375 | TFA | 575 | ¹H NMR (400 MHz, DMSO-d₆) δ 9.29 (d, J = 0.9 Hz, 1H), 8.83 (t, J = 6.0 Hz, 1H), 8.78 (d, J = 6.2 Hz, 1H), 8.31 (d, J = 8.2 Hz, 2H), 8.07 (d, J = 6.1 Hz, 1H), 7.98 (d, J = 1.0 Hz, 1H), 7.87 (d, J = 8.2 Hz, 2H), 7.19 (s, 1H), 4.43-4.22 (m, 3H), 3.71-3.61 (m, 1H), 3.50-3.40 (m, 1H), 3.23 (s, 6H), 2.14-2.01 (m, 1H), 2.01-1.87 (m, 2H), 1.81-1.68 (m, 1H). |
| 376 | — | 590 | — |
| 377 | — | 582 | — |
| 378 | — | 592 | ¹H NMR (400 MHz, DMSO-d₆) δ 8.80 (t, J = 6.0 Hz, 1H), 8.32 (d, J = 8.1 Hz, 2H), 7.86 (d, J = 8.3 Hz, 2H), 7.81 (dd, J = 9.2, 4.1 Hz, 1H), 7.75 (d, J = 0.8 Hz, 1H), 7.65 (dd, J = 8.5, 2.7 Hz, 1H), 7.43 (td, J = 9.2, 2.8 Hz, 1H), 7.20 (s, 1H), 4.39-4.32 (m, 2H), 4.25 (dd, J = 17.0, 5.7 Hz, 1H), 3.67-3.59 (m, 1H), 3.40-3.33 (m, 1H), 3.23 (s, 6H), 2.03-1.86 (m, 3H), 1.76-1.62 (m, 1H). |
| 379 | — | 578 | ¹H NMR (400 MHz, DMSO-d₆) δ 8.85 (t, J = 5.9 Hz, 1H), 8.32 (d, J = 8.1 Hz, 2H), 7.90-7.83 (m, 4H), 7.69 (dd, J = 8.4, 2.7 Hz, 1H), 7.47 (td, J = 9.2, 2.7 Hz, 1H), 7.19 (s, 1H), 4.69 (dd, J = 9.3, 7.5 Hz, 1H), 4.41 (dd, J = 17.1, 6.1 Hz, 1H), 4.31 (dd, J = 17.1, 5.7 Hz, 1H), 4.00-3.86 (m, 2H), 3.23 (s, 6H), 2.41-2.23 (m, 2H). |
| 380 | — | 547 | ¹H NMR (400 MHz, DMSO-d₆) δ 11.24 (brs, 1H), 8.66 (t, J = 6.0 Hz, 1H), 8.59 (d, J = 9.0 Hz, 1H), 8.33 (d, J = 9.1 Hz, 1H), 7.93 (d, J = 2.2 Hz, 1H), 7.84-7.81 (m, 1H), 7.77-7.73 (m, 1H), 7.72 (d, J = 0.9 Hz, 1H), 7.55 (ddd, J = 8.5, 7.2, 1.3 Hz, 1H), 7.42 (ddd, J = 8.0, 7.5, 0.9 Hz, 1H), 7.34 (dd, J = 8.4, 2.3 Hz, 1H), 7.03 (d, J = 8.4 Hz, 1H), 4.39-4.25 (m, 3H), 3.63-3.56 (m, 1H), 3.42-3.34 (m, 1H), 1.96-1.82 (m, 3H), 1.70-1.60 (m, 1H). |
| 381 | — | 539 | ¹H NMR (400 MHz, DMSO-d₆) δ 11.08 (brs, 1H), 8.81 (d, J = 8.5 Hz, 1H), 8.56 (d, J = 9.0 Hz, 1H), 8.47 (t, J = 5.8 Hz, 1H), 8.32 (d, J = 9.1 Hz, 1H), 7.84 (d, J = 2.2 Hz, 1H), 7.70 (dd, J = 9.1, 4.1 Hz, 1H), 7.54 (dd, J = 8.5, 2.7 Hz, 1H), 7.46 (d, J = 0.9 Hz, 1H), 7.35 (td, J = 9.2, 2.8 Hz, 1H), 7.20 (dd, J = 8.4, 2.2 Hz, 1H), 6.98 (d, J = 8.4 Hz, 1H), 4.13 (d, J = 5.7 Hz, 2H), 4.08-3.98 (m, 1H), 1.21 (d, J = 7.0 Hz, 3H). |
| 382 | TFA | 564 | ¹H NMR (400 MHz, DMSO-d₆) δ 8.84 (t, J = 6.1 Hz, 1H), 8.25 (d, J = 8.2 Hz, 2H), 7.86 (d, J = 8.3 Hz, 2H), 7.81 (dd, J = 9.2, 4.0 Hz, 1H), 7.75 (d, J = 0.9 Hz, 1H), 7.65 (dd, J = 8.5, 2.8 Hz, 1H), 7.43 (td, J = 9.2, 2.7 Hz, 1H), 7.17 (s, 1H), 7.03-6.66 (m, 2H), 4.40-4.26 (m, 2H), 4.19 (dd, J = 16.9, 5.7 Hz, 1H), 3.89-3.79 (m, 1H), 3.48-3.34 (m, 1H), 2.09-1.85 (m, 3H), 1.75-1.64 (m, 1H). |
| 383 | — | 550 | ¹H NMR (400 MHz, DMSO-d₆) δ 9.02 (t, J = 6.1 Hz, 1H), 8.65 (d, J = 5.3 Hz, 1H), 8.23 (d, J = 8.2 Hz, 1H), 8.20 (s, 1H), 7.89-7.84 (m, 2H), 7.70 (dd, J = 8.5, 2.7 Hz, 1H), 7.48 (dd, J = 9.2, 2.7 Hz, 1H), 7.47-7.44 (m, 1H), 7.26-7.20 (m, 1H), 4.66 (dd, J = 9.2, 7.5 Hz, 1H), 4.58 (dd, J = 16.6, 6.3 Hz, 1H), 4.49 (dd, J = 16.7, 5.8 Hz, 1H), 4.01-3.87 (m, 2H), 2.42-2.22 (m, 2H). |
| 384 | — | 579 | ¹H NMR (400 MHz, DMSO-d₆) δ 9.42 (d, J = 2.1 Hz, 1H), 8.87 (t, |

TABLE 39-continued

| Example No. | Salt | MS(ESI) m/z (M + H)+ | NMR |
|---|---|---|---|
| | | | J = 5.9 Hz, 1H), 8.72 (dd, J = 8.2, 2.1 Hz, 1H), 8.06 (d, J = 8.2 Hz, 1H), 7.89-7.84 (m, 2H), 7.69 (dd, J = 8.4, 2.7 Hz, 1H), 7.47 (td, J = 9.3, 2.8 Hz, 1H), 7.26 (s, 1H), 4.69 (dd, J = 9.2, 7.5 Hz, 1H), 4.43 (dd, J = 17.2, 6.2 Hz, 1H), 4.32 (dd, J = 17.2, 5.6 Hz, 1H), 4.00-3.87 (m, 2H), 3.24 (s, 6H), 2.42-2.25 (m, 2H). |
| 385 | — | 517 | ¹H NMR (400 MHz, DMSO-d₆) δ 9.14-9.11 (m, 1H), 8.90 (t, J = 5.9 Hz, 1H), 8.71 (dd, J = 5.1, 0.8 Hz, 1H), 8.40 (dd, J = 8.7, 2.1 Hz, 1H), 8.31 (d, J = 8.3 Hz, 1H), 8.05 (s, 1H), 8.02 (dd, J = 5.2, 1.7 Hz, 1H), 7.89-7.86 (m, 2H), 7.82-7.78 (m, 1H), 7.60 (ddd, J = 8.5, 7.3, 1.3 Hz, 1H), 7.45 (ddd, J = 8.0, 7.2, 0.9 Hz, 1H), 4.68 (dd, J = 9.3, 7.5 Hz, 1H), 4.60 (dd, J = 16.1, 6.1 Hz, 1H), 4.52 (dd, J = 16.2, 5.8 Hz, 1H), 3.99-3.86 (m, 2H), 2.39-2.22 (m, 2H). |
| 386 | — | 517 | ¹H NMR (400 MHz, DMSO-d₆) δ 9.25 (d, J = 1.3 Hz, 1H), 9.04 (t, J = 6.0 Hz, 1H), 8.40 (d, J = 7.8 Hz, 2H), 8.05 (d, J = 1.3 Hz, 1H), 7.94-7.88 (m, 4H), 7.83-7.78 (m, 1H), 7.60 (ddd, J = 8.5, 7.3, 1.3 Hz, 1H), 7.46 (ddd, J = 8.1, 7.3, 0.9 Hz, 1H), 4.69 (dd, J = 9.0, 7.7 Hz, 1H), 4.61 (dd, J = 17.2, 6.3 Hz, 1H), 4.49 (dd, J = 17.2, 5.6 Hz, 1H), 3.99-3.88 (m, 2H), 2.39-2.28 (m, 2H). |
| 387 | — | 537 | ¹H NMR (400 MHz, DMSO-d₆) δ 9.70 (s, 2H), 9.35 (d, J = 1.3 Hz, 1H), 9.07 (dd, J = 6.3, 5.6 Hz, 1H), 8.17 (d, J = 1.3 Hz, 1H), 7.91-7.83 (m, 2H), 7.70 (dd, J = 8.5, 2.7 Hz, 1H), 7.47 (ddd, J = 9.2, 9.2, 2.7 Hz, 1H), 4.70 (dd, J = 8.4, 8.4 Hz, 1H), 4.63 (dd, J = 17.3, 6.3 Hz, 1H), 4.51 (dd, J = 17.3, 5.6 Hz, 1H), 4.00-3.87 (m, 2H), 2.40-2.29 (m, 2H). |
| 388 | — | 536 | ¹H NMR (400 MHz, DMSO-d₆) δ 9.48 (d, J = 2.2 Hz, 1H), 9.30 (d, J = 1.3 Hz, 1H), 9.06 (dd, J = 6.3, 5.6 Hz, 1H), 8.79 (dd, J = 8.4, 2.2 Hz, 1H), 8.16-8.08 (m, 2H), 7.91-7.82 (m, 2H), 7.70 (dd, J = 8.4, 2.7 Hz, 1H), 7.47 (ddd, J = 9.3, 9.2, 2.7 Hz, 1H), 4.70 (dd, J = 9.0, 7.7 Hz, 1H), 4.62 (dd, J = 17.3, 6.3 Hz, 1H), 4.50 (dd, J = 17.3, 5.6 Hz, 1H), 4.00-3.87 (m, 2H), 2.43-2.27 (m, 2H). |
| 389 | — | 536 | ¹H NMR (400 MHz, DMSO-d₆) δ 9.47 (s, 2H), 8.94 (dd, J = 6.2, 5.6 Hz, 1H), 8.73 (dd, J = 5.2, 0.8 Hz, 1H), 7.89-7.79 (m, 4H), 7.69 (dd, J = 8.5, 2.7 Hz, 1H), 7.47 (ddd, J = 9.3, 9.3, 2.7 Hz, 1H), 4.68 (dd, J = 9.0, 7.7 Hz, 1H), 4.61 (dd, J = 16.4, 6.2 Hz, 1H), 4.51 (dd, J = 16.4, 5.6 Hz, 1H), 3.99-3.83 (m, 2H), 2.41-2.24 (m, 2H). |
| 390 | — | 551 | ¹H NMR (400 MHz, DMSO-d₆) δ 11.01 (s, 1H), 9.50 (d, J = 1.4 Hz, 1H), 9.25-9.17 (m, 1H), 8.68 (dd, J = 6.1, 5.8 Hz, 1H), 7.92 (d, J = 2.2 Hz, 1H), 7.85 (dd, J = 9.1, 4.0 Hz, 1H), 7.79 (d, J = 0.9 Hz, 1H), 7.67 (dd, J = 8.4, 2.7 Hz, 1H), 7.46 (ddd, J = 9.3, 9.1, 2.7 Hz, 1H), 7.33 (dd, J = 8.4, 2.3 Hz, 1H), 7.01 (d, J = 8.4 Hz, 1H), 4.60 (dd, J = 9.2, 7.3 Hz, 1H), 4.36 (dd, J = 14.9, 6.1 Hz, 1H), 4.29 (dd, J = 14.9, 5.8 Hz, 1H), 3.98-3.82 (m, 2H), 2.38-2.15 (m, 2H). |
| 391 | TFA | 536 | ¹H NMR (400 MHz, DMSO-d₆) δ 9.88 (d, J = 2.1 Hz, 1H), 9.21-9.18 (m, 1H), 9.07 (t, J = 5.9 Hz, 1H), 8.49 (dd, J = 8.5, 2.3 Hz, 1H), 8.44 (d, J = 8.4 Hz, 1H), 8.27 (d, J = 2.2 Hz, 1H), 7.86 (dd, J = 9.2, 4.1 Hz, 1H), 7.83 (d, J = 0.8 Hz, 1H), 7.68 (dd, J = 8.5, 2.7 Hz, 1H), 7.47 (td, J = 9.2, 2.8 Hz, 1H), 4.81 (dd, J = 16.0, 6.1 Hz, 1H), 4.74 (dd, J = 16.1, 5.8 Hz, 1H), 4.68 (dd, J = 9.2, 7.4 Hz, 1H), 3.99-3.87 (m, 2H), 2.43-2.22 (m, 2H). |
| 392 | — | 535 | ¹H NMR (400 MHz, DMSO-d₆) δ 9.45 (s, 1H), 9.24 (s, 1H), 8.86 (t, J = 6.1 Hz, 1H), 8.17 (s, 1H), 8.14 (d, J = 7.7 Hz, 1H), 7.86 (dd, J = 9.2, 4.1 Hz, 1H), 7.82 (s, 1H), 7.69 (dd, J = 8.4, 2.7 Hz, 1H), 7.58 (d, J = 7.6 Hz, 1H), 7.52 (d, J = 7.7 Hz, 1H), 7.47 (td, J = 9.3, 2.8 Hz, 1H), 4.64 (dd, J = 9.3, 7.3 Hz, 1H), 4.52 (dd, J = 15.5, 6.2 Hz, 1H), 4.44 (dd, J = 15.4, 5.8 Hz, 1H), 3.99-3.86 (m, 2H), 2.41-2.20 (m, 2H). |
| 393 | TFA | 536 | ¹H NMR (400 MHz, DMSO-d₆) δ 9.53 (d, J = 1.4 Hz, 1H), 9.33 (d, J = 1.4 Hz, 1H), 8.95 (t, J = 6.0 Hz, 1H), 8.78 (dd, J = 5.1, 0.7 Hz, 1H), 8.14-8.09 (m, 2H), 7.89-7.82 (m, 2H), 7.68 (dd, J = 8.4, 2.7 Hz, 1H), 7.47 (td, J = 9.2, 2.7 Hz, 1H), 4.69 (dd, J = 9.2, 7.4 Hz, 1H), 4.63 (dd, J = 16.3, 6.1 Hz, 1H), 4.55 (dd, J = 16.3, 5.8 Hz, 1H), 3.99-3.87 (m, 2H), 2.42-2.23 (m, 2H). |
| 394 | TFA | 536 | ¹H NMR (400 MHz, DMSO-d₆) δ 9.46-9.43 (m, 2H), 8.89 (t, J = 6.3 Hz, 1H), 8.77 (dd, J = 5.1, 0.8 Hz, 1H), 8.28 (brs, 1H), 8.20 (dd, J = 5.2, 1.6 Hz, 1H), 7.86 (dd, J = 9.2, 4.2 Hz, 1H), 7.81 (d, J = 0.9 Hz, 1H), 7.67 (dd, J = 8.5, 2.7 Hz, 1H), 7.46 (td, J = 9.2, 2.7 Hz, 1H), 4.73-4.65 (m, 1H), 4.59-4.54 (m, 2H), 3.99-3.88 (m, 2H), 2.42-2.20 (m, 2H). |
| 395 | — | 551 | ¹H NMR (400 MHz, DMSO-d₆) δ 9.21 (d, J = 1.2 Hz, 1H), 9.02 (t, J = 6.0 Hz, 1H), 8.34-8.29 (m, 2H), 7.98 (s, 1H), 7.89-7.84 (m, 2H), 7.70 (dd, J = 8.5, 2.7 Hz, 1H), 7.54 (d, J = 8.4 Hz, 2H), 7.47 (td, J = |

TABLE 39-continued

| Example No. | Salt | MS(ESI) m/z (M + H)+ | NMR |
|---|---|---|---|
| | | | 9.3, 2.7 Hz, 1H), 4.73-4.66 (m, 1H), 4.58 (dd, J = 17.2, 6.3 Hz, 1H), 4.46 (dd, J = 17.2, 5.6 Hz, 1H), 4.00-3.88 (m, 2H), 2.41-2.26 (m, 2H). |
| 396 | TFA | 550 | $^1$H NMR (400 MHz, DMSO-$d_6$) δ 9.87 (d, J = 2.2 Hz, 1H), 9.20-9.16 (m, 1H), 9.01 (t, J = 6.0 Hz, 1H), 8.49 (dd, J = 8.5, 2.3 Hz, 1H), 8.42 (d, J = 8.4 Hz, 1H), 8.24 (d, J = 2.1 Hz, 1H), 7.80 (dd, J = 9.0, 4.2 Hz, 1H), 7.71 (d, J = 0.9 Hz, 1H), 7.63 (dd, J = 8.4, 2.7 Hz, 1H), 7.42 (td, J = 9.2, 2.8 Hz, 1H), 4.80-4.67 (m, 2H), 4.36 (dd, J = 8.0, 3.6 Hz, 1H), 3.66-3.59 (m, 1H), 3.45-3.38 (m, 1H), 2.05-1.87 (m, 3H), 1.74-1.65 (m, 1H). |
| 397 | — | 608 | $^1$H NMR (400 MHz, DMSO-$d_6$) δ 14.38 (brs, 1H), 8.83 (t, J = 6.0 Hz, 1H), 8.17 (d, J = 8.3 Hz, 1H), 7.82 (dd, J = 9.2, 4.0 Hz, 1H), 7.75 (d, J = 0.9 Hz, 1H), 7.65 (dd, J = 8.5, 2.7 Hz, 1H), 7.43 (td, J = 9.2, 2.8 Hz, 1H), 7.30 (s, 1H), 7.24 (s, 1H), 7.21 (dd, J = 8.4, 1.9 Hz, 1H), 4.42-4.33 (m, 2H), 4.27 (dd, J = 17.2, 5.7 Hz, 1H), 3.68-3.59 (m, 1H), 3.46-3.37 (m, 1H), 3.20 (s, 6H), 2.04-1.87 (m, 3H), 1.73-1.64 (m, 1H). |
| 398 | — | 594 | $^1$H NMR (400 MHz, DMSO-$d_6$) δ 14.36 (s, 1H), 8.88 (dd, J = 6.2, 5.7 Hz, 1H), 8.17 (d, J = 8.3 Hz, 1H), 7.91-7.83 (m, 2H), 7.69 (dd, J = 8.5, 2.7 Hz, 1H), 7.47 (ddd, J = 9.3, 9.2, 2.7 Hz, 1H), 7.31 (s, 1H), 7.27-7.16 (m, 2H), 4.69 (dd, J = 9.3, 7.5 Hz, 1H), 4.42 (dd, J = 17.2, 6.2 Hz, 1H), 4.33 (dd, J = 17.2, 5.7 Hz, 1H), 4.01-3.86 (m, 2H), 3.20 (s, 6H), 2.41-2.25 (m, 2H). |
| 399 | — | 549 | $^1$H NMR (400 MHz, DMSO-$d_6$) δ 9.44 (d, J = 1.4 Hz, 1H), 9.23 (d, J = 1.4 Hz, 1H), 8.80 (dd, J = 6.2, 5.9 Hz, 1H), 8.17-8.10 (m, 1H), 7.80 (dd, J = 9.2, 4.0 Hz, 1H), 7.70 (d, J = 0.9 Hz, 1H), 7.63 (dd, J = 8.5, 2.7 Hz, 1H), 7.57 (dd, J = 7.6, 7.6 Hz, 1H), 7.53-7.49 (m, 1H), 7.42 (ddd, J = 9.2, 9.2, 2.7 Hz, 1H), 4.47 (dd, J = 15.5, 6.2 Hz, 1H), 4.40 (dd, J = 15.5, 5.9 Hz, 1H), 4.32 (dd, J = 8.1, 3.5 Hz, 1H), 3.66-3.57 (m, 1H), 3.44-3.37 (m, 1H), 2.01-1.85 (m, 3H), 1.72-1.63 (m, 1H). |
| 400 | — | 550 | $^1$H NMR (400 MHz, DMSO-$d_6$) δ 9.29 (d, J = 1.3 Hz, 1H), 9.14-9.11 (m, 1H), 8.96 (t, J = 6.0 Hz, 1H), 8.63 (d, J = 8.4 Hz, 1H), 8.46 (dd, J = 8.4, 2.4 Hz, 1H), 8.35 (d, J = 1.3 Hz, 1H), 7.81 (dd, J = 9.2, 4.1 Hz, 1H), 7.71 (d, J = 0.9 Hz, 1H), 7.62 (dd, J = 8.5, 2.7 Hz, 1H), 7.42 (ddd, J = 9.3, 9.2, 2.7 Hz, 1H), 4.51 (d, J = 6.0 Hz, 2H), 4.39 (dd, J = 7.5, 3.7 Hz, 1H), 3.67-3.60 (m, 1H), 3.46-3.39 (m, 1H), 2.03-1.92 (m, 3H), 1.79-1.70 (m, 1H). |
| 401 | — | 536 | $^1$H NMR (400 MHz, DMSO-$d_6$) δ 9.30 (d, J = 1.3 Hz, 1H), 9.17-9.11 (m, 1H), 8.98 (dd, J = 6.0, 6.0 Hz, 1H), 8.64 (d, J = 8.2 Hz, 1H), 8.46 (dd, J = 8.2, 2.4 Hz, 1H), 8.37 (d, J = 1.3 Hz, 1H), 7.87 (dd, J = 9.2, 4.1 Hz, 1H), 7.83 (d, J = 0.9 Hz, 1H), 7.67 (dd, J = 8.5, 2.7 Hz, 1H), 7.46 (ddd, J = 9.3, 9.2, 2.8 Hz, 1H), 4.70 (dd, J = 9.3, 7.3 Hz, 1H), 4.64-4.48 (m, 2H), 4.02-3.87 (m, 2H), 2.48-2.34 (m, 1H), 2.32-2.22 (m, 1H). |
| 402 | TFA | 550 | $^1$H NMR (400 MHz, DMSO-$d_6$) δ 9.65 (s, 2H), 8.92 (dd, J = 6.3, 5.9 Hz, 1H), 8.75 (d, J = 5.1 Hz, 1H), 8.13 (s, 1H), 7.81 (dd, J = 9.1, 4.1 Hz, 1H), 7.75 (d, J = 0.9 Hz, 1H), 7.65 (dd, J = 8.5, 2.8 Hz, 1H), 7.47-7.44 (m, 1H), 7.42 (dd, J = 9.2, 2.8 Hz, 1H), 4.52 (dd, J = 16.7, 6.3 Hz, 1H), 4.43 (dd, J = 16.7, 5.9 Hz, 1H), 4.34 (dd, J = 8.4, 3.7 Hz, 1H), 3.68-3.60 (m, 1H), 3.46-3.37 (m, 1H), 2.07-1.98 (m, 1H), 1.98-1.86 (m, 2H), 1.73-1.63 (m, 1H). |
| 403 | TFA | 536 | $^1$H NMR (400 MHz, DMSO-$d_6$) δ 9.65 (s, 2H), 9.01 (dd, J = 6.4, 5.9 Hz, 1H), 8.74 (d, J = 4.7 Hz, 1H), 8.14 (s, 1H), 7.89-7.84 (m, 2H), 7.69 (dd, J = 8.4, 2.7 Hz, 1H), 7.51-7.44 (m, 2H), 4.66 (dd, J = 9.2, 7.5 Hz, 1H), 4.57 (dd, J = 16.6, 6.4 Hz, 1H), 4.46 (dd, J = 16.6, 5.9 Hz, 1H), 4.03-3.91 (m, 2H), 2.42-2.23 (m, 2H). |
| 404 | — | 550 | $^1$H NMR (400 MHz, DMSO-$d_6$) δ 12.74 (s, 1H), 9.06 (s, 1H), 8.68 (dd, J = 6.0, 5.8 Hz, 1H), 8.38-8.35 (m, 2H), 7.98 (d, J = 2.2 Hz, 1H), 7.85 (dd, J = 9.1, 4.0 Hz, 1H), 7.80 (d, J = 0.9 Hz, 1H), 7.67 (dd, J = 8.5, 2.7 Hz, 1H), 7.46 (ddd, J = 9.3, 9.1, 2.7 Hz, 1H), 7.30 (dd, J = 8.4, 2.2 Hz, 1H), 6.96 (d, J = 8.4 Hz, 1H), 4.65-4.58 (m, 1H), 4.38 (dd, J = 15.0, 5.8 Hz, 1H), 4.31 (dd, J = 15.0, 6.0 Hz, 1H), 3.96-3.85 (m, 2H), 2.27-2.17 (m, 2H). |
| 405 | — | 550 | $^1$H NMR (400 MHz, DMSO-$d_6$) δ 9.51 (d, J = 0.8 Hz, 1H), 9.32 (d, J = 0.8 Hz, 1H), 8.90 (dd, J = 6.1, 5.9 Hz, 1H), 8.78-8.73 (m, 1H), 8.10-8.05 (m, 2H), 7.80 (dd, J = 9.1, 4.1 Hz, 1H), 7.72 (d, J = 0.9 Hz, 1H), 7.63 (dd, J = 8.4, 2.8 Hz, 1H), 7.43 (ddd, J = 9.3, 9.1, 2.8 Hz, 1H), 4.56 (dd, J = 16.3, 6.1 Hz, 1H), 4.49 (dd, J = 16.3, 5.9 Hz, 1H), 4.38 (dd, J = 7.9, 3.6 Hz, 1H), 3.68-3.58 (m, 1H), 3.46-3.37 (m, 1H), 2.06-1.87 (m, 3H), 1.78-1.62 (m, 1H). |
| 406 | — | 565 | $^1$H NMR (400 MHz, DMSO-$d_6$) δ 9.20 (d, J = 1.3 Hz, 1H), 8.96 (dd, J = 6.2, 5.7 Hz, 1H), 8.35-8.27 (m, 2H), 7.98 (d, J = 1.3 Hz, 1H), 7.84-7.78 (m, 1H), 7.76 (d, J = 0.9 Hz, 1H), 7.65 (dd, J = 8.4, 2.7 Hz, 1H), 7.58-7.51 (m, 2H), 7.43 (ddd, J = 9.2, 9.2, 2.7 Hz, 1H), |

TABLE 39-continued

| Example No. | Salt | MS(ESI) m/z (M + H)+ | NMR |
|---|---|---|---|
| 407 | — | 550 | 4.53 (dd, J = 17.2, 6.2 Hz, 1H), 4.46-4.33 (m, 2H), 3.68-3.59 (m, 1H), 3.47-3.39 (m, 1H), 2.10-1.87 (m, 3H), 1.74-1.63 (m, 1H).<br>$^1$H NMR (400 MHz, DMSO-d$_6$) δ 9.44 (q, J = 0.8 Hz, 2H), 8.88 (t, J = 5.9 Hz, 1H), 8.76 (dd, J = 5.1, 0.8 Hz, 1H), 8.25 (d, J = 1.6, 0.8 Hz, 1H), 8.19 (dd, J = 5.1, 1.6 Hz, 1H), 7.81 (dd, J = 9.0, 4.2 Hz, 1H), 7.68 (d, J = 0.9 Hz, 1H), 7.62 (dd, J = 8.4, 2.7 Hz, 1H), 7.42 (ddd, J = 9.2, 9.0, 2.7 Hz, 1H), 4.52 (d, J = 5.9 Hz, 2H), 4.39 (dd, J = 6.6, 4.7 Hz, 1H), 3.67-3.58 (m, 1H), 3.46-3.37 (m, 1H), 2.03-1.90 (m, 3H), 1.80-1.66 (m, 1H). |
| 408 | — | 518 | $^1$H NMR (400 MHz, DMSO-d$_6$) δ 9.48 (d, J = 2.2 Hz, 1H), 9.30 (d, J = 1.3 Hz, 1H), 9.06 (dd, J = 6.3, 5.6 Hz, 1H), 8.79 (dd, J = 8.1, 2.2 Hz, 1H), 8.16-8.09 (m, 2H), 7.94-7.86 (m, 2H), 7.81 (dd, J = 8.5, 1.1 Hz, 1H), 7.60 (ddd, J = 8.5, 7.2, 1.4 Hz, 1H), 7.46 (ddd, J = 8.0, 7.2, 0.9 Hz, 1H), 4.69 (dd, J = 8.4, 8.4 Hz, 1H), 4.63 (dd, J = 17.3, 6.3 Hz, 1H), 4.50 (dd, J = 17.3, 5.6 Hz, 1H), 4.00-3.86 (m, 2H), 2.40-2.28 (m, 2H). |
| 409 | — | 519 | $^1$H NMR (400 MHz, DMSO-d$_6$) δ 9.70 (s, 2H), 9.35 (d, J = 1.3 Hz, 1H), 9.07 (dd, J = 6.3, 5.7 Hz, 1H), 8.18 (d, J = 1.3 Hz, 1H), 7.95-7.86 (m, 2H), 7.81 (dd, J = 8.5, 0.9 Hz, 1H), 7.60 (ddd, J = 8.5, 7.2, 1.3 Hz, 1H), 7.46 (ddd, J = 8.0, 7.2, 0.9 Hz, 1H), 4.69 (dd, J = 8.4, 8.4 Hz, 1H), 4.63 (dd, J = 17.4, 6.3 Hz, 1H), 4.51 (dd, J = 17.4, 5.7 Hz, 1H), 4.01-3.86 (m, 2H), 2.41-2.30 (m, 2H). |
| 410 | — | 561 | $^1$H NMR (400 MHz, DMSO-d$_6$) δ 9.42 (d, J = 2.2 Hz, 1H), 8.87 (dd, J = 6.1, 5.6 Hz, 1H), 8.73 (dd, J = 8.3, 2.2 Hz, 1H), 8.06 (d, J = 8.3 Hz, 1H), 7.92-7.86 (m, 2H), 7.81 (dd, J = 8.5, 0.9 Hz, 1H), 7.60 (ddd, J = 8.5, 7.2, 1.3 Hz, 1H), 7.46 (ddd, J = 8.0, 7.2, 0.9 Hz, 1H), 7.27 (s, 1H), 4.67 (dd, J = 9.2, 7.6 Hz, 1H), 4.43 (dd, J = 17.2, 6.1 Hz, 1H), 4.32 (dd, J = 17.2, 5.6 Hz, 1H), 3.99-3.85 (m, 2H), 3.24 (s, 6H), 2.42-2.23 (m, 2H). |
| 411 | — | 532 | $^1$H NMR (400 MHz, DMSO-d$_6$) δ 14.65 (s, 1H), 9.01 (dd, J = 6.3, 5.8 Hz, 1H), 8.64 (dd, J = 5.3, 0.8 Hz, 1H), 8.25 (d, J = 8.2 Hz, 1H), 8.21 (d, J = 1.6 Hz, 1H), 7.92-7.88 (m, 2H, 7.84-7.79 (m, 1H), 7.60 (ddd, J = 8.5, 7.2, 1.3 Hz, 1H), 7.49-7.42 (m, 2H), 7.27-7.19 (m, 2H), 4.65 (dd, J = 9.2, 7.5 Hz, 1H), 4.59 (dd, J = 16.6, 6.3 Hz, 1H), 4.49 (dd, J = 16.6, 5.8 Hz, 1H), 4.00-3.85 (m, 2H), 2.41-2.22 (m, 2H). |
| 412 | — | 551 | $^1$H NMR (400 MHz, DMSO-d$_6$) δ 12.87 (s, 1H), 9.25 (d, J = 1.1 Hz, 1H), 9.02 (dd, J = 6.1, 5.8 Hz, 1H), 8.25 (d, J = 7.9 Hz, 1H), 8.16 (d, J = 1.1 Hz, 1H), 7.91-7.82 (m, 2H), 7.69 (dd, J = 8.5, 2.7 Hz, 1H), 7.47 (ddd, J = 9.2, 9.2, 2.8 Hz, 1H), 7.34-7.30 (m, 1H), 7.30-7.24 (m, 1H), 4.69 (dd, J = 9.2, 7.5 Hz, 1H), 4.57 (dd, J = 17.2, 6.1 Hz, 1H), 4.50 (dd, J = 17.2, 5.8 Hz, 1H), 4.01-3.86 (m, 2H), 2.44-2.24 (m, 2H). |
| 413 | — | 567 | $^1$H NMR (400 MHz, DMSO-d$_6$) δ 12.99 (s, 1H), 9.24 (d, J = 1.3 Hz, 1H), 8.74 (t, J = 5.8 Hz, 1H), 8.22 (d, J = 8.3 Hz, 1H), 8.14 (d, J = 1.3 Hz, 1H), 7.78 (dd, J = 9.1, 4.1 Hz, 1H), 7.66 (s, 1H), 7.61 (dd, J = 8.5, 2.7 Hz, 1H), 7.40 (ddd, J = 9.2, 9.1, 2.7 Hz, 1H), 7.31 (d, J = 1.8 Hz, 1H), 7.27 (dd, J = 8.3, 1.8 Hz, 1H), 4.50 (d, J = 5.8 Hz, 2H), 4.24-4.09 (m, 1H), 4.03 (s, 2H), 1.06 (d, J = 6.7 Hz, 6H). |
| 414 | TFA | 522 | $^1$H NMR (400 MHz, DMSO-d$_6$) δ 12.63 (s, 1H), 9.19 (d, J = 1.3 Hz, 1H), 9.16-9.09 (m, 2H), 8.81 (t, J = 5.8 Hz, 1H), 8.70 (d, J = 6.1 Hz, 1H), 8.21 (d, J = 8.1 Hz, 1H), 8.06 (d, J = 1.3 Hz, 1H), 7.94 (dd, J = 6.1, 1.0 Hz, 1H), 7.71 (d, J = 1.0 Hz, 1H), 7.34-7.26 (m, 2H), 4.31 (d, J = 5.8 Hz, 2H), 4.22-4.09 (m, 1H), 1.30 (d, J = 7.0 Hz, 3H). |
| 415 | — | 595 | — |
| 416 | TFA | 551 | $^1$H NMR (400 MHz, DMSO-d$_6$) δ 9.13-9.10 (m, 1H), 8.73-8.68 (m, 2H), 8.41 (dd, J = 8.4, 2.4 Hz, 1H), 8.30 (d, J = 8.4 Hz, 1H), 8.04 (dd, J = 5.3, 1.7 Hz, 1H), 8.00 (d, J = 1.7 Hz, 1H), 7.66 (dd, J = 9.1, 4.0 Hz, 1H), 7.55 (d, J = 0.9 Hz, 1H), 7.48 (dd, J = 8.5, 2.7 Hz, 1H), 7.32 (ddd, J = 9.2, 9.1, 2.8 Hz, 1H), 4.67 (q, J = 7.2 Hz, 1H), 4.44-4.33 (m, 2H), 3.55-3.40 (m, 2H), 1.38 (d, J = 7.2 Hz, 3H), 1.20 (t, J = 7.0 Hz, 3H). |
| 417 | TFA | 563 | $^1$H NMR (400 MHz, DMSO-d$_6$) δ 9.15-9.10 (m, 1H), 8.77-8.71 (m, 2H), 8.43 (dd, J = 8.5, 2.4 Hz, 1H), 8.32 (d, J = 8.5 Hz, 1H), 8.09 (dd, J = 5.4, 1.7 Hz, 1H), 8.04 (brs, 1H), 7.66 (dd, J = 9.1, 4.1 Hz, 1H), 7.55 (d, J = 0.9 Hz, 1H), 7.48 (dd, J = 8.5, 2.7 Hz, 1H), 7.32 (ddd, J = 9.2, 9.1, 2.7 Hz, 1H), 5.93-5.82 (m, 1H), 5.23 (ddd, J = 17.1, 1.5, 1.5 Hz, 1H), 5.06 (dd, J = 10.3, 1.3, 1.3 Hz, 1H), 4.72 (q, J = 7.2 Hz, 1H), 4.38 (d, J = 5.8 Hz, 2H), 4.20-4.05 (m, 2H), 1.38 (d, J = 7.2 Hz, 3H). |
| 418 | TFA | 561 | $^1$H NMR (400 MHz, DMSO-d$_6$) δ 9.13-9.10 (m, 1H), 8.79 (t, J = 5.8 Hz, 1H), 8.69 (dd, J = 5.2, 0.6 Hz, 1H), 8.41 (dd, J = 8.4, 2.4 Hz, 1H), 8.29 (d, J = 8.4 Hz, 1H), 8.02 (dd, J = 5.2, 1.7 Hz, |

TABLE 39-continued

| Example No. | Salt | MS(ESI) m/z (M + H)+ | NMR |
|---|---|---|---|
| | | | 1H), 7.97 (brs, 1H), 7.67 (dd, J = 9.1, 4.1 Hz, 1H), 7.60 (d, J = 0.9 Hz, 1H), 7.51 (dd, J = 8.5, 2.7 Hz, 1H), 7.34 (ddd, J = 9.3, 9.1, 2.7 Hz, 1H), 4.77 (q, J = 7.2 Hz, 1H), 4.46-4.29 (m, 4H), 3.15-3.12 (m, 1H), 1.52 (d, J = 7.2 Hz, 3H). |
| 419 | — | 537 | $^1$H NMR (400 MHz, DMSO-d$_6$) δ 9.24 (d, J = 1.3 Hz, 1H), 8.79 (t, J = 5.8 Hz, 1H), 8.38 (d, J = 8.0 Hz, 2H), 8.02 (d, J = 1.3 Hz, 1H), 7.93 (d, J = 8.0 Hz, 2H), 7.73 (dd, J = 9.0, 4.2 Hz, 1H), 7.63 (d, J = 0.9 Hz, 1H), 7.57 (dd, J = 8.5, 2.7 Hz, 1H), 7.38 (ddd, J = 9.2, 9.0, 2.7 Hz, 1H), 4.45 (d, J = 5.8 Hz, 2H), 4.11 (s, 2H), 3.44 (q, J = 7.2 Hz, 2H), 1.14 (t, J = 7.2 Hz, 3H). |
| 420 | — | 551 | $^1$H NMR (400 MHz, DMSO-d$_6$) δ 9.24 (d, J = 1.3 Hz, 1H), 8.74 (t, J = 5.8 Hz, 1H), 8.37 (d, J = 8.2 Hz, 2H), 8.05 (d, J = 1.3 Hz, 1H), 7.92 (d, J = 8.2 Hz, 2H), 7.78 (dd, J = 9.0, 4.2 Hz, 1H), 7.68 (d, J = 0.9 Hz, 1H), 7.62 (dd, J = 8.5, 2.7 Hz, 1H), 7.40 (ddd, J = 9.2, 9.0, 2.7 Hz, 1H), 4.49 (d, J = 5.8 Hz, 2H), 4.22-4.11 (m, 1H), 4.05 (s, 2H), 1.07 (d, J = 6.7 Hz, 6H). |
| 421 | — | 537 | $^1$H NMR (400 MHz, DMSO-d$_6$) δ 9.22 (d, J = 1.3 Hz, 1H), 8.78 (dd, J = 5.9, 5.9 Hz, 1H), 8.35 (d, J = 8.3 Hz, 2H), 7.96 (d, J = 1.3 Hz, 1H), 7.93 (d, J = 8.3 Hz, 2H), 7.71 (dd, J = 9.1, 4.0 Hz, 1H), 7.62 (d, J = 0.9 Hz, 1H), 7.55 (dd, J = 8.5, 2.7 Hz, 1H), 7.36 (ddd, J = 9.2, 9.1, 2.7 Hz, 1H), 4.72 (q, J = 7.1 Hz, 1H), 4.47-4.33 (m, 2H), 2.99 (s, 3H), 1.29 (d, J = 7.1 Hz, 3H). |
| 422 | — | 551 | $^1$H NMR (400 MHz, DMSO-d$_6$) δ 9.22 (d, J = 1.3 Hz, 1H), 8.72 (dd, J = 5.9, 5.9 Hz, 1H), 8.35 (d, J = 8.2 Hz, 2H), 7.96 (d, J = 1.3 Hz, 1H), 7.93 (d, J = 8.2 Hz, 2H), 7.67 (dd, J = 9.1, 4.0 Hz, 1H), 7.58 (d, J = 0.8 Hz, 1H), 7.51 (dd, J = 8.5, 2.7 Hz, 1H), 7.34 (ddd, J = 9.2, 9.1, 2.7 Hz, 1H), 4.69 (q, J = 7.1 Hz, 1H), 4.46-4.29 (m, 2H), 3.63-3.39 (m, 2H), 1.40 (d, J = 7.2 Hz, 3H), 1.20 (t, J = 7.1 Hz, 3H). |
| 423 | 2TFA | 606 | $^1$H NMR (400 MHz, DMSO-d$_6$) δ 9.13 (d, J = 2.3 Hz, 1H), 8.75 (t, J = 5.8 Hz, 1H), 8.71 (d, J = 5.1 Hz, 1H), 8.55-8.45 (m, 1H), 8.42 (dd, J = 8.4, 2.3 Hz, 1H), 8.32 (d, J = 8.4 Hz, 1H), 8.24-8.12 (m, 1H), 8.05-7.99 (m, 2H), 7.70 (dd, J = 9.1, 4.0 Hz, 1H), 7.58 (d, J = 0.8 Hz, 1H), 7.52 (dd, J = 8.5, 2.7 Hz, 1H), 7.36 (ddd, J = 9.2, 9.1, 2.8 Hz, 1H), 4.42 (d, J = 5.8 Hz, 2H), 4.09 (s, 2H), 3.33-3.21 (m, 4H), 2.86-2.71 (m, 2H), 2.02-1.82 (m, 3H), 1.36-1.20 (m, 2H). |
| 424 | TFA | 606 | $^1$H NMR (400 MHz, DMSO-d$_6$) δ 9.25 (d, J = 1.3 Hz, 1H), 8.82 (t, J = 5.8 Hz, 1H), 8.60-8.49 (m, 1H), 8.39 (d, J = 8.2 Hz, 2H), 8.31-8.17 (m, 1H), 8.03 (d, J = 1.3 Hz, 1H), 7.94 (d, J = 8.2 Hz, 2H), 7.71 (dd, J = 8.8, 4.0 Hz, 1H), 7.62 (d, J = 0.9 Hz, 1H), 7.55 (dd, J = 8.4, 2.7 Hz, 1H), 7.37 (ddd, J = 9.2, 8.8, 2.7 Hz, 1H), 4.42 (d, J = 5.8 Hz, 2H), 4.14 (s, 2H), 3.31-3.24 (m, 4H), 2.87-2.72 (m, 2H), 2.03-1.84 (m, 3H), 1.35-1.20 (m, 2H). |
| 425 | TFA | 592 | $^1$H NMR (400 MHz, DMSO-d$_6$) δ 9.25 (d, J = 1.3 Hz, 1H), 8.85 (t, J = 5.8 Hz, 1H), 8.73 (s, 2H), 8.39 (d, J = 8.0 Hz, 2H), 8.03 (d, J = 1.3 Hz, 1H), 7.94 (d, J = 8.0 Hz, 2H), 7.72 (dd, J = 9.0, 4.1 Hz, 1H), 7.63 (d, J = 0.9 Hz, 1H), 7.58 (dd, J = 8.5, 2.7 Hz, 1H), 7.39 (ddd, J = 9.2, 9.1, 2.7 Hz, 1H), 4.44 (d, J = 5.8 Hz, 2H), 4.20 (d, J = 17.4 Hz, 1H), 4.14 (d, J = 17.4 Hz, 1H), 3.49-3.41 (m, 2H), 3.40-3.37 (m, 1H), 3.27-3.18 (m, 1H), 3.16-3.05 (m, 1H), 3.02-2.91 (m, 1H), 2.75-2.62 (m, 1H), 2.10-1.96 (m, 1H), 1.74-1.59 (m, 1H). |
| 426 | TFA | 537 | $^1$H NMR (400 MHz, DMSO-d$_6$) δ 9.12 (d, J = 2.3 Hz, 1H), 8.77 (dd, J = 5.9, 5.8 Hz, 1H), 8.70 (d, J = 5.2 Hz, 1H), 8.41 (dd, J = 8.5, 2.3 Hz, 1H), 8.30 (d, J = 8.5 Hz, 1H), 8.04 (dd, J = 5.2, 1.7 Hz, 1H), 8.01 (d, J = 1.7 Hz, 1H), 7.69 (dd, J = 9.2, 4.1 Hz, 1H), 7.59 (d, J = 0.9 Hz, 1H), 7.52 (dd, J = 8.5, 2.7 Hz, 1H), 7.35 (ddd, J = 9.2, 9.2, 2.7 Hz, 1H), 4.70 (q, J = 7.1 Hz, 1H), 4.44 (dd, J = 16.3, 5.8 Hz, 1H), 4.39 (dd, J = 16.3, 5.9 Hz, 1H), 2.99 (s, 3H), 1.28 (d, J = 7.1 Hz, 3H). |
| 427 | TFA | 541 | $^1$H NMR (400 MHz, DMSO-d$_6$) δ 9.27 (d, J = 8.6 Hz, 1H), 9.11 (d, J = 2.4 Hz, 1H), 8.92 (dd, J = 5.8, 5.8 Hz, 1H), 8.68 (d, J = 5.2 Hz, 1H), 8.41 (dd, J = 8.4, 2.4 Hz, 1H), 8.27 (d, J = 8.4 Hz, 1H), 8.03 (dd, J = 5.2, 1.7 Hz, 1H), 7.95 (d, J = 1.7 Hz, 1H), 7.65 (dd, J = 9.1, 4.1 Hz, 1H), 7.51-7.44 (m, 2H), 7.31 (ddd, J = 9.2, 9.1, 2.8 Hz, 1H), 4.66-4.58 (m, 1H), 4.53-4.34 (m, 4H). |

Experimental Example 1-1

Measurement of TRPA1 Antagonist Activity (1)

Human TRPA1 Expression Plasmid

As cDNA encoding human TRPA1 (GenBank accession No. NM_0078332), a commercially available product was purchased (manufactured by Kazusa DNA Research Institute, clone No.: pFN21AB7348, item No.: FHC07217). Using this as a template, full-length human TRPA1 gene was amplified using the primer sequences shown below, by reaction using DNA polymerase (manufactured by Stratagene, trade name: PfuUltra High-Fidelity DNA Polymerase).

```
primer 1:
                                            (SEQ ID NO: 1)
5'-AACTTTAGTAAGCTTCGATCGCCATGAAG-3' primer 2:
                                            (SEQ ID NO: 2)
5'-GTACCGATCTAGATTTCGTTTACTAAGGCTCAAG-3'
```

A recognition site (underlined) of restriction enzyme HindIII was added to the 5' side, and XbaI site (underlined) was added to the 3' side, and GTT of the template sequence was changed to termination codon TAG (bold). The obtained double stranded DNA was enzyme-digested with HindIII and XbaI, and introduced into the multicloning site of expression plasmid pcDNA3.1/zeo(+) (manufactured by Invitrogen) to construct a human TRPA1 expression plasmid.

Cell Preparation

Human embryonic kidney-derived 293T cells were cultured in Dulbecco's Modified Eagle Medium containing 10% fetal bovine serum, 10 unit penicillin, and 10 µg streptomycin, plated on a petri dish having a diameter of 10 cm at $3 \times 10^6$ cells, and cultured for 24 hr in a $CO_2$ incubator. A reduced serum medium (manufactured by Invitrogen, trade name: OPTI-MEM, 600 µL), a gene transfer reagent (manufactured by Mirus Bio, trade name: Mirus TransIT-293, 18 µL), and human TRPA1 expression plasmid (6 µg) were mixed, the total amount of the mixture was added to the cells on the petri dish to allow for gene transfer. The cells were recovered about for 8 hr later, plated on a poly-D-lysine coated 384 well black/clear bottom plate at 12,000 cells/well, and cultured overnight.

Measurement of Intracellular Calcium Increase

The 384 well plate was recovered, and the medium was removed. A calcium-bonded fluorescent indicator (manufactured by Molecular Device, trade name: Calcium4 Assay Kit, 38 µL) dissolved in assay buffer (1×HBSS, 20 mM HEPES, pH 7.2) was added, and the cells were stained in a $CO_2$ incubator for 1 hr. The cells were taken out at room temperature, stood for not less than 15 min, a test substance (10 µL) was added by a platereader FDSS7000 (Hamamatsu Photonics K.K.) equipped with a 384ch dispenser. After 10 min, allylisothiocyanate (12 µL) was further added at a final concentration of 20 µM, and changes in the relative fluorescence intensity after addition of allylisothiocyanate were measured for 5 min.

Test Substance Preparation

The test substance was dissolved in dimethyl sulfoxide and serially diluted with an assay buffer containing 0.1% bovine serum albumin (1×HBSS, 20 mM HEPES, pH 7.2) to a 4.8-fold concentration of the evaluation concentration. Allylisothiocyanate, which is a known TRPA1 activator, was dissolved in dimethyl sulfoxide to 100 mM, and further diluted 5-fold (100 µM) of the final concentration, like the test substance.

Calculation of Antagonist Activity

Under the test substance-free conditions, the maximum variation range of the fluorescence intensity before and after allylisothiocyanate stimulation was defined to be 100% activity rate, and the variation range before and after buffer stimulation was defined as 0% activity rate. The activity rate on addition of the test substance was determined, and the numerical value obtained by subtracting the activity rate from 100 was defined to be an inhibitory rate. IC50, which is the concentration of the test substance necessary for reaching the 50% inhibitory rate, was calculated from the sigmoid approximate curve by a spreadsheet software Excel-Fit.

The results are shown in Table 40. As shown, the compound of the present invention exhibited a superior TRPA1 antagonist activity.

TABLE 40

| Example No. | hTRPA1 $IC_{50}$ (uM) |
|---|---|
| 1 | 0.0030 |
| 2 | 0.0079 |
| 3 | 0.072 |
| 4 | 0.023 |
| 5 | 0.012 |
| 6 | 0.0075 |
| 7 | 0.0054 |
| 8 | 0.0062 |
| 9 | 0.0076 |
| 10 | 0.010 |
| 11 | 0.0010 |
| 12 | 0.0081 |
| 13 | 0.019 |
| 14 | 0.020 |
| 15 | 0.10 |
| 16 | 0.0028 |
| 17 | 0.015 |
| 18 | 0.012 |
| 19 | 0.014 |
| 20 | 0.0014 |
| 21 | 0.034 |
| 22 | 0.11 |
| 23 | 0.11 |
| 24 | 0.41 |
| 25 | 0.011 |
| 26 | 0.023 |
| 27 | 0.0082 |
| 28 | 0.056 |
| 29 | 0.34 |
| 30 | 0.0083 |
| 31 | 0.0043 |
| 32 | 0.031 |
| 33 | 0.16 |
| 34 | 0.0016 |
| 35 | 0.0080 |
| 36 | 0.0015 |
| 37 | 0.014 |
| 38 | 0.0091 |
| 39 | 0.19 |
| 40 | 0.096 |
| 41 | 0.0013 |
| 42 | 0.0071 |
| 43 | 0.0016 |
| 44 | 0.0017 |
| 45 | 0.035 |
| 46 | 0.13 |
| 47 | 0.024 |
| 48 | 0.0069 |
| 49 | 0.018 |
| 50 | 0.16 |
| 51 | 0.019 |
| 52 | 0.032 |
| 53 | 0.0027 |
| 54 | 0.0090 |
| 55 | 0.088 |
| 56 | 0.021 |
| 57 | 0.016 |
| 58 | 0.43 |
| 59 | 0.54 |
| 60 | 0.20 |
| 61 | 0.055 |
| 62 | 0.060 |
| 63 | 0.060 |
| 64 | 0.10 |
| 65 | 0.015 |
| 66 | 0.021 |
| 67 | 0.0097 |
| 68 | 0.39 |

TABLE 40-continued

| Example No. | hTRPA1 IC$_{50}$ (uM) |
|---|---|
| 69 | 0.012 |
| 70 | 0.011 |
| 71 | 0.0032 |
| 72 | 0.35 |
| 73 | 0.16 |
| 74 | 0.11 |
| 76 | 0.047 |
| 77 | 0.015 |
| 78 | 0.13 |
| 79 | 0.0016 |
| 80 | 0.0012 |
| 84 | 0.0012 |
| 86 | 0.020 |
| 87 | 0.026 |
| 88 | 0.00041 |
| 89 | 0.00038 |
| 90 | 0.00084 |
| 92 | 0.0022 |
| 93 | 0.023 |
| 94 | 0.011 |
| 95 | 0.0054 |
| 96 | 0.25 |
| 97 | 0.0040 |
| 98 | 0.00076 |
| 99 | 0.013 |
| 100 | 0.0016 |
| 101 | 0.027 |
| 102 | 0.028 |
| 103 | 0.056 |
| 104 | 0.014 |
| 105 | 0.068 |
| 106 | 0.010 |
| 107 | 0.0069 |
| 108 | 0.013 |
| 109 | 0.0047 |
| 110 | 0.017 |
| 111 | 0.13 |
| 112 | 0.27 |
| 113 | 0.12 |
| 114 | 0.032 |
| 115 | 0.0024 |
| 116 | 0.0029 |
| 117 | 0.014 |
| 118 | 0.26 |
| 119 | 0.012 |
| 120 | 0.18 |
| 121 | 0.032 |
| 122 | 0.17 |
| 123 | 0.0026 |
| 124 | 0.0034 |
| 125 | 0.24 |
| 126 | 0.078 |
| 127 | 0.025 |
| 128 | 0.00061 |
| 129 | 0.00061 |
| 130 | 0.0020 |
| 131 | 0.032 |
| 132 | 0.0076 |
| 133 | 0.00083 |
| 134 | 0.042 |
| 135 | 0.030 |
| 136 | 0.013 |
| 137 | 0.029 |
| 138 | 0.00097 |
| 139 | 0.0030 |
| 140 | 0.0022 |
| 141 | 0.0033 |
| 142 | 0.024 |
| 143 | 0.26 |
| 144 | 0.047 |
| 145 | 0.029 |
| 146 | 0.31 |
| 147 | 0.18 |
| 148 | 0.0022 |
| 149 | 0.0015 |
| 150 | 0.013 |
| 151 | 0.0019 |
| 152 | 0.16 |
| 153 | 0.0056 |
| 154 | 0.042 |
| 155 | 0.0040 |
| 156 | 0.0021 |
| 157 | 0.00048 |
| 158 | 0.00083 |
| 159 | 0.0062 |
| 160 | 0.019 |
| 161 | 0.027 |
| 162 | 0.051 |
| 163 | 0.031 |
| 164 | 0.0071 |
| 165 | 0.19 |
| 166 | 0.26 |
| 167 | 0.14 |
| 168 | 0.18 |
| 169 | 0.15 |
| 170 | 0.23 |
| 171 | 0.51 |
| 172 | 0.011 |
| 173 | 0.017 |
| 174 | 0.029 |
| 175 | 0.013 |
| 176 | 0.32 |
| 177 | 0.30 |
| 178 | 0.046 |
| 179 | 0.0013 |
| 180 | 0.069 |
| 181 | 0.021 |
| 182 | 0.094 |
| 183 | 0.57 |
| 184 | 0.041 |
| 185 | 0.25 |
| 186 | 0.086 |
| 187 | 0.071 |
| 188 | 0.89 |
| 189 | 0.84 |
| 190 | 0.0052 |
| 191 | 0.012 |
| 192 | 0.022 |
| 193 | 0.0022 |
| 194 | 0.010 |
| 195 | 0.0025 |
| 196 | 0.0029 |
| 197 | 0.0030 |
| 198 | 0.013 |
| 199 | 0.0050 |
| 200 | 0.016 |
| 201 | 0.0086 |
| 202 | 0.0043 |
| 203 | 0.0032 |
| 204 | 0.035 |
| 205 | 0.0040 |
| 206 | 0.012 |
| 207 | 0.0040 |
| 208 | 0.034 |
| 209 | 0.11 |
| 210 | 0.019 |
| 211 | 0.072 |
| 212 | 0.027 |
| 213 | 0.047 |
| 214 | 0.013 |
| 215 | 0.0021 |
| 216 | 0.013 |
| 217 | 0.064 |
| 218 | 0.096 |
| 219 | 0.39 |
| 220 | 0.054 |
| 221 | 0.0066 |
| 222 | 0.0024 |
| 223 | 0.00088 |
| 224 | 0.00066 |
| 225 | 0.0013 |
| 226 | 0.025 |
| 227 | 0.042 |
| 228 | 0.032 |

TABLE 40-continued

| Example No. | hTRPA1 IC$_{50}$ (uM) |
|---|---|
| 229 | 0.012 |
| 230 | 0.0044 |
| 231 | 0.014 |
| 232 | 0.077 |
| 233 | 0.010 |
| 234 | 0.034 |
| 235 | 0.020 |
| 236 | 0.031 |
| 237 | 0.27 |
| 238 | 0.042 |
| 239 | 0.017 |
| 240 | 0.014 |
| 241 | 0.075 |
| 242 | 0.16 |
| 243 | 0.055 |
| 244 | 0.044 |
| 245 | 0.12 |
| 246 | 0.11 |
| 247 | 0.064 |
| 248 | 0.020 |
| 249 | 0.17 |
| 250 | 0.072 |
| 251 | 0.33 |
| 252 | 0.014 |
| 253 | 0.16 |
| 254 | 0.080 |
| 255 | 0.017 |
| 256 | 0.091 |
| 257 | 0.064 |
| 258 | 0.0019 |
| 259 | 0.0012 |
| 260 | 0.051 |
| 261 | 0.037 |
| 262 | 0.0023 |
| 263 | 0.021 |
| 264 | 0.012 |
| 265 | 0.012 |
| 266 | 0.038 |
| 267 | 0.0064 |
| 268 | 0.029 |
| 269 | 0.0043 |
| 270 | 0.0038 |
| 271 | 0.0044 |
| 272 | 0.012 |
| 273 | 0.0016 |
| 274 | 0.0098 |
| 275 | 0.0038 |
| 276 | 0.15 |
| 277 | 0.089 |
| 278 | 0.016 |
| 279 | 0.0028 |
| 280 | 0.52 |
| 281 | 0.022 |
| 282 | 0.25 |
| 283 | 0.25 |
| 284 | 0.076 |
| 285 | 0.030 |
| 286 | 0.18 |
| 287 | 0.0079 |
| 288 | 0.0025 |
| 289 | 0.0014 |
| 290 | 0.0057 |
| 291 | 0.028 |
| 292 | 0.58 |
| 293 | 0.0031 |
| 294 | 0.17 |
| 295 | 0.069 |
| 296 | 0.0079 |
| 297 | 0.0075 |
| 298 | 0.011 |
| 299 | 0.024 |
| 300 | 0.31 |
| 301 | 0.030 |
| 303 | 0.042 |
| 304 | 0.35 |
| 305 | 0.026 |
| 306 | 0.0028 |
| 307 | 0.0017 |
| 308 | 0.36 |
| 309 | 0.010 |
| 310 | 0.0025 |
| 311 | 0.0037 |
| 312 | 0.0053 |
| 313 | 0.037 |
| 314 | 0.0046 |
| 315 | 0.022 |
| 316 | 0.23 |
| 317 | 0.031 |
| 318 | 0.014 |
| 319 | 0.027 |
| 320 | 0.92 |
| 321 | 0.033 |
| 322 | 0.31 |
| 323 | 0.20 |
| 324 | 0.49 |
| 325 | 0.56 |
| 326 | 0.029 |
| 327 | 0.0043 |
| 331 | 0.17 |
| 334 | 0.63 |
| 335 | 0.054 |
| 336 | 0.0058 |
| 337 | 0.022 |

Experimental Example 1-2

Measurement of TRPA1 Antagonist Activity (2)

By a method similar to that in Experimental Example 1-1 except that the lot of human TRAP1 expression plasmid is different, the TRPA1 antagonist activity of the test substance was measured.

The results are shown in Table 41. As shown therein, the compound of the present invention exhibited a superior TRPA1 antagonist activity.

TABLE 41

| Example No. | hTRPA1 IC50 (uM) |
|---|---|
| 87 | 0.052 |
| 179 | 0.0041 |
| 191 | 0.035 |
| 328 | 0.016 |
| 329 | 0.014 |
| 330 | 0.015 |
| 332 | 0.016 |
| 333 | 0.021 |
| 338 | 0.012 |
| 339 | 0.011 |
| 340 | 0.38 |
| 341 | 0.014 |
| 342 | 0.18 |
| 343 | 0.28 |
| 344 | 0.0033 |
| 345 | 0.27 |
| 346 | 0.70 |
| 347 | 0.074 |
| 348 | 0.016 |
| 349 | 0.043 |
| 350 | 0.63 |
| 351 | 0.99 |
| 352 | 0.41 |
| 353 | 0.30 |
| 354 | 0.38 |
| 355 | 0.10 |
| 356 | 0.19 |
| 357 | 0.044 |

TABLE 41-continued

| Example No. | hTRPA1 IC50 (uM) |
|---|---|
| 358 | 0.11 |
| 359 | 0.0079 |
| 360 | 0.010 |
| 361 | 0.47 |
| 362 | 0.0070 |
| 363 | 0.92 |
| 364 | 0.010 |
| 365 | 0.22 |
| 366 | 0.19 |
| 367 | 0.17 |
| 368 | 0.013 |
| 369 | 0.044 |
| 370 | 0.073 |
| 371 | 0.010 |
| 372 | 0.027 |
| 373 | 0.079 |
| 374 | 0.015 |
| 375 | 0.013 |
| 376 | 0.021 |
| 377 | 0.11 |
| 378 | 0.0052 |
| 379 | 0.019 |
| 380 | 0.0031 |
| 381 | 0.020 |
| 382 | 0.027 |
| 383 | 0.0097 |
| 384 | 0.013 |
| 385 | 0.013 |
| 386 | 0.0066 |
| 387 | 0.055 |
| 388 | 0.0027 |
| 389 | 0.011 |
| 390 | 0.0093 |
| 391 | 0.026 |
| 392 | 0.0046 |
| 393 | 0.0091 |
| 394 | 0.011 |
| 395 | 0.0032 |
| 396 | 0.0076 |
| 397 | 0.0068 |
| 398 | 0.021 |
| 399 | 0.0025 |
| 400 | 0.0052 |
| 401 | 0.012 |
| 402 | 0.0035 |
| 403 | 0.013 |
| 404 | 0.0097 |
| 405 | 0.0035 |
| 406 | 0.0027 |
| 407 | 0.0070 |
| 408 | 0.016 |
| 409 | 0.029 |
| 410 | 0.038 |
| 411 | 0.025 |
| 412 | 0.0027 |
| 413 | 0.012 |
| 414 | 0.034 |
| 415 | 0.41 |
| 416 | 0.0042 |
| 417 | 0.014 |
| 418 | 0.011 |
| 419 | 0.0041 |
| 420 | 0.01 |
| 421 | 0.0029 |
| 422 | 0.0030 |
| 423 | 0.033 |
| 424 | 0.021 |
| 425 | 0.19 |
| 426 | 0.0077 |
| 427 | 0.17 |

Experimental Example 2

AITC-Induced Pain Behavior Evaluation Test

To evaluate the effectiveness of the test substance in vivo, allylisothiocyanate (AITC)-induced pain behavior evaluation test was performed using mice.

AITC is a selective agonist of the TRPA1 channel, and causes a pain behavior through TRPA1 activation when administered to animal. Therefore, the intensity of the TRPA1 antagonist action of the test substance in the living body can be evaluated by measuring the pain behavior after AITC administration.

1. Administration of Test Substance to Animal

As the animal, male ICR mice (6- to 8-week-old) are used. The mice are fasted on the day before test. The test substance is intraperitoneally or orally administered for evaluation. In the case of intraperitoneal administration, the substance is administered for 30 min before the AITC administration. In the case of oral administration, the substance is administered for 60 min before the AITC administration.

2. AITC-Induced Pain Behavior Evaluation

AITC (0.1%) is subcutaneously injected into the plantar surface of the left hindpaw of the mouse, and the time when the mouse shows a behavior of licking plantar of the leg (Licking time) for 5 min immediately after the AITC injection is measured.

3. Calculation of Inhibitory Rate

The licking time of the vehicle administration group in each test is taken as 100%, and the activity rate by administration of each test substance (Licking time on test substance administration/Licking time of vehicle administration group×100) is determined, and the numerical value obtained by subtracting the activity rate from 100 is calculated as an inhibitory rate.

By the above-mentioned method, it can be confirmed that the compound of the present invention has a superior TRPA1 antagonist activity, is superior in vivo kinetics, and shows superior efficacy in animal model.

The effectiveness of the compound of the present invention was confirmed by the above-mentioned evaluation test.

SEQUENCE LISTING FREE TEXT

SEQ ID NO: 1: primer
SEQ ID NO: 2: primer

INDUSTRIAL APPLICABILITY

The compound of the present invention has a superior TRPA1 antagonist activity, and therefore, is useful for the prophylaxis/or treatment of diseases involving TRPA1 (e.g., pain associated diseases, digestive tract diseases, lung diseases, bladder diseases, inflammatory diseases, dermatic diseases, and neurological diseases).

In view of this object, the compound of the present invention shows high blood concentration by oral administration or bioavailability, is superior in sustainability of the blood concentration, and is useful as an oral preparation.

In addition, the compound of the present invention is superior in the stability in acidic or alkaline solutions and is useful and can be applied to, for example, various dosage forms.

Furthermore, the compound of the present invention specifically inhibits TPRA1. That is, the compound of the present invention has high selectivity to a molecular target, is superior in safety and useful since interaction between drugs does not need to be feared.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

is any of the groups of the following formulas:

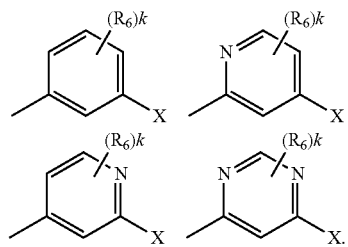

The invention claimed is:

1. A compound represented by formula (I):

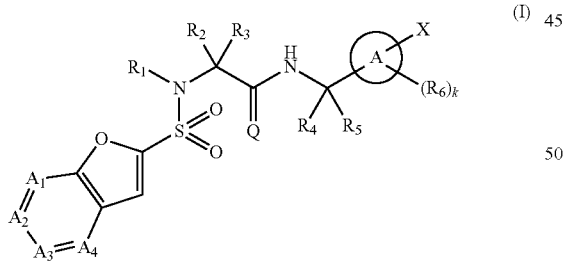

wherein

Q is =O;

partial structure (b) containing ring A

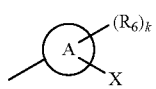

(b)

wherein k is 0 or 1, $R_6$ is a cyclic $C_{3-6}$ alkyl group optionally containing a hetero atom, a halogeno group, a $C_{1-6}$ alkoxy group, a $C_{1-6}$ alkoxycarbonyl group, an amino group, an amino group mono- or di-substituted by a $C_{1-6}$ alkyl group or a hydroxy group;

X is -Cy;

Cy is any of the groups of the following formulas

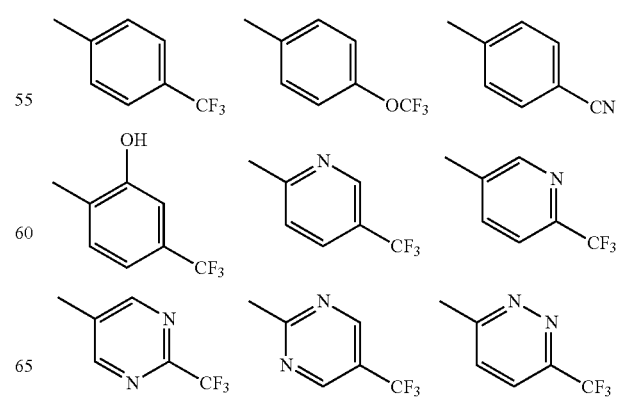

-continued

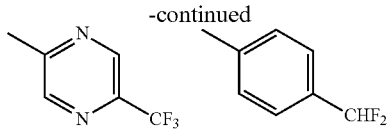

partial structure (c)

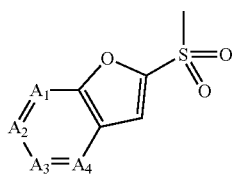

is any of the groups of the following formulas

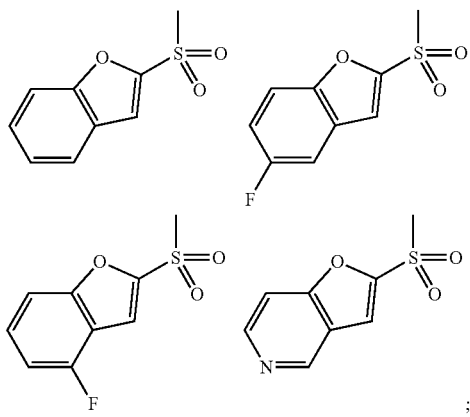

partial structure (a)

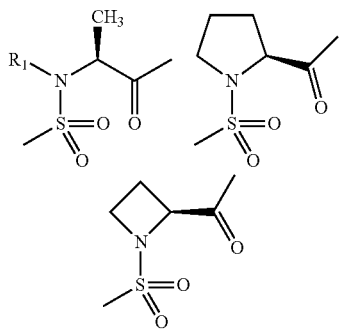

is any of the groups of the following formulas wherein R$_1$ is hydrogen;
R$_4$ is hydrogen; and
R$_5$ is hydrogen,
or a pharmaceutically acceptable salt thereof.

2. The compound or pharmaceutically acceptable salt according to claim 1, wherein the partial structure (b) containing ring A

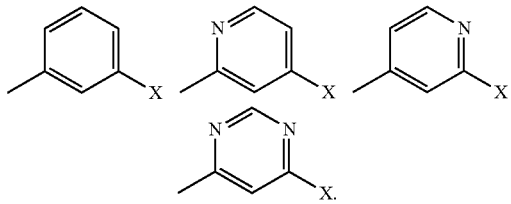

is a group of the following formula

3. The compound or pharmaceutically acceptable salt according to claim 1, wherein the partial structure (b) containing ring A

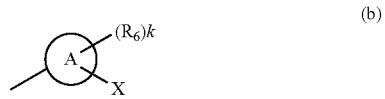

is a group of the following formula

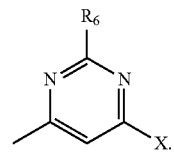

4. The compound according to claim 1, which is represented by any of the following structural formulas:

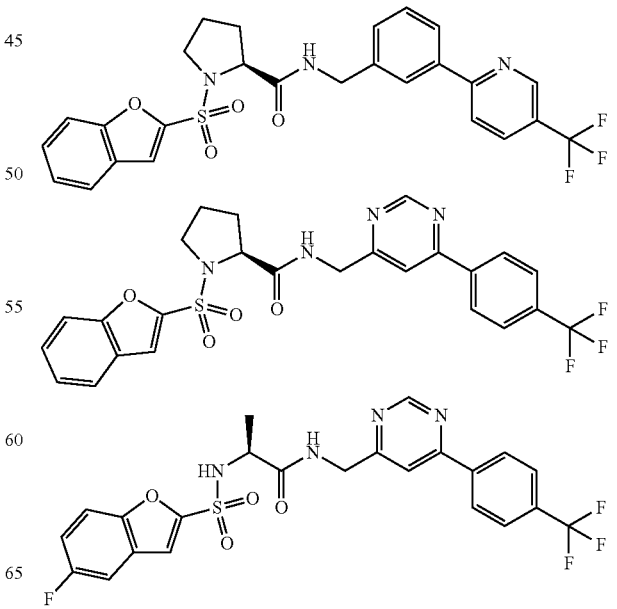

531
-continued
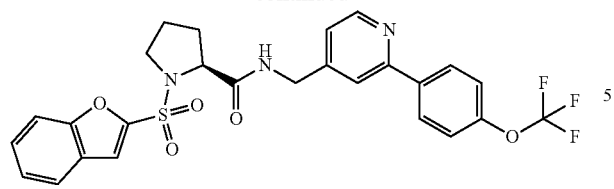
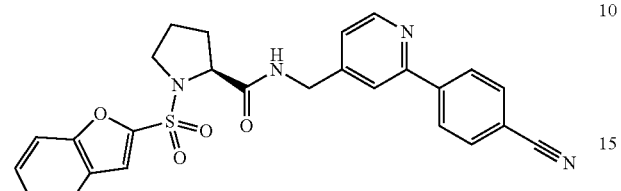
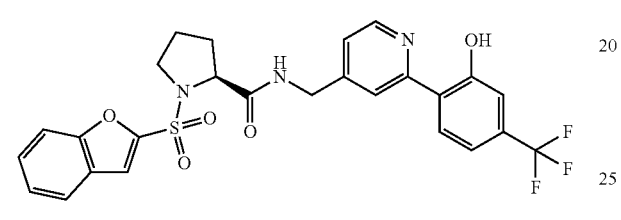
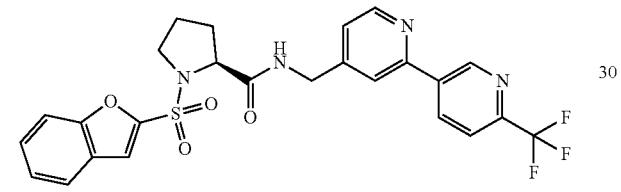
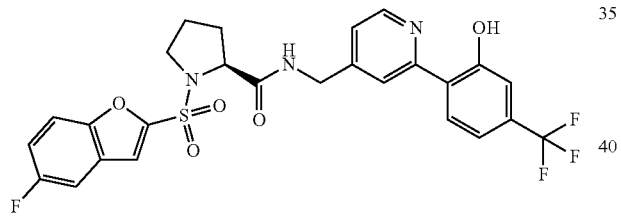
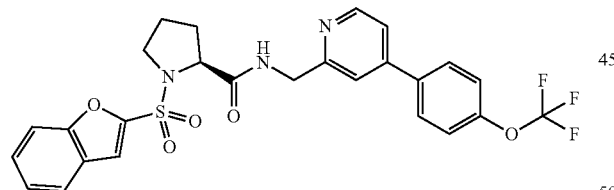
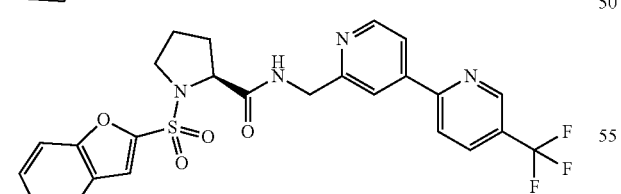
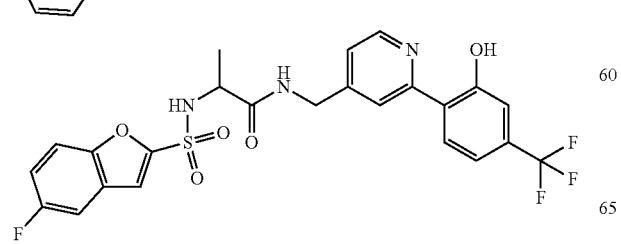
532
-continued
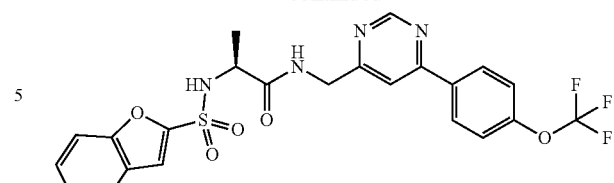
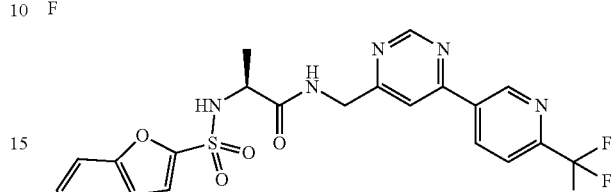
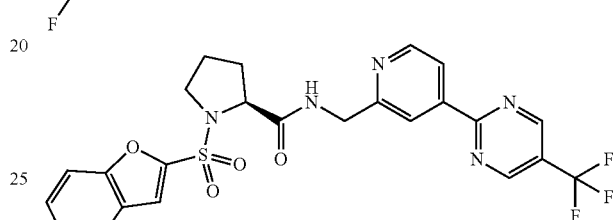
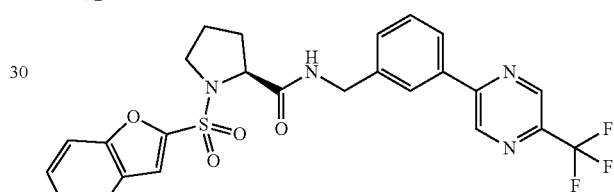
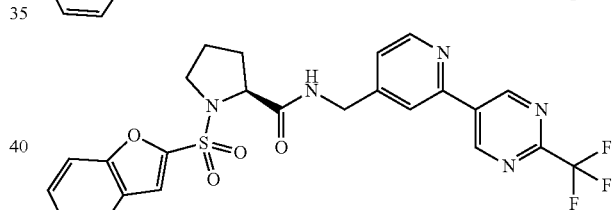
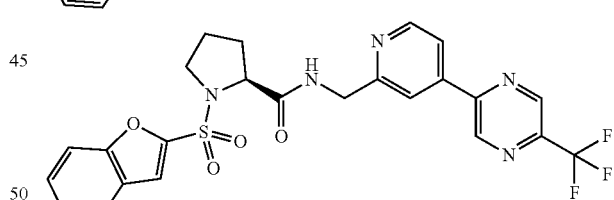
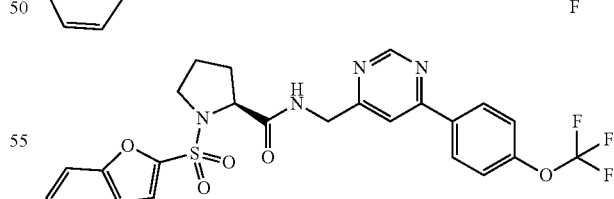
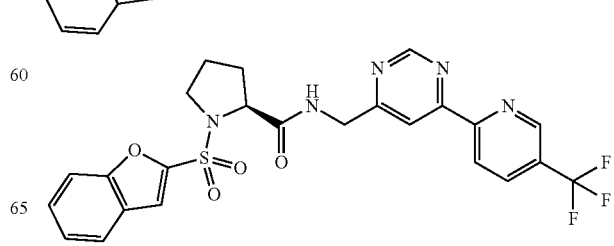

533
-continued
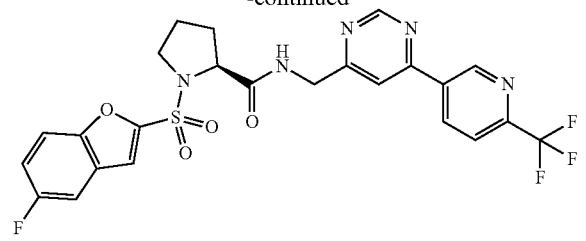
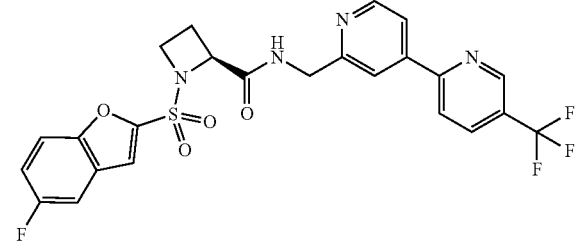
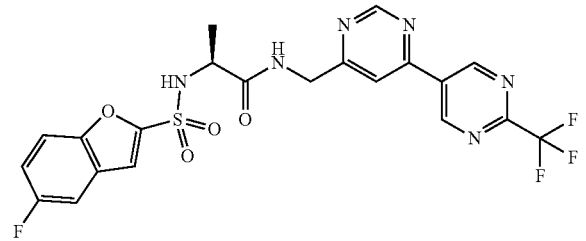
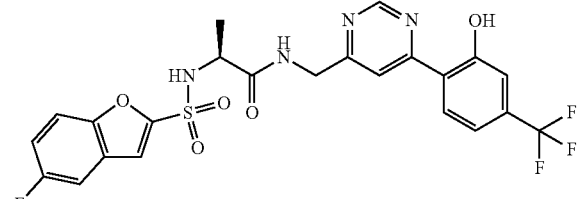
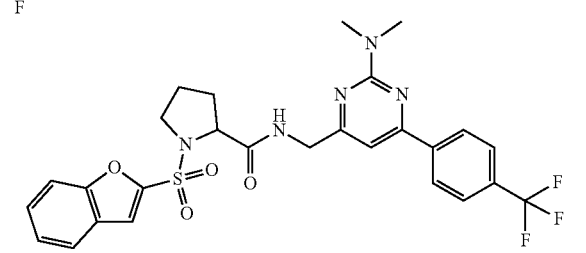
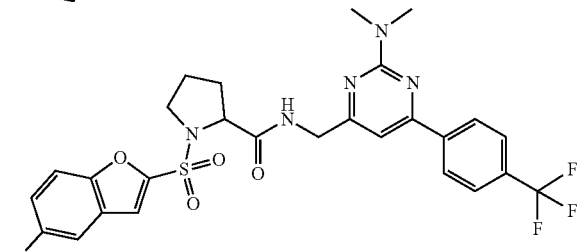
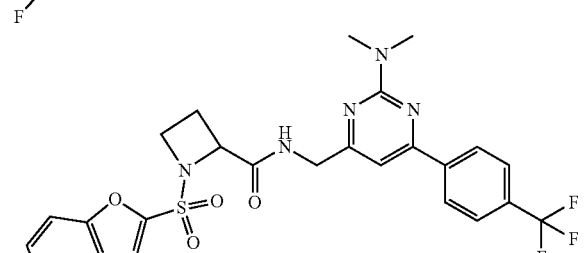
534
-continued
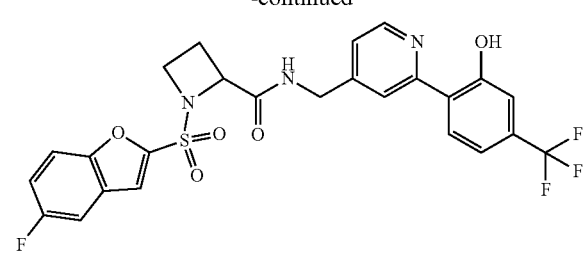
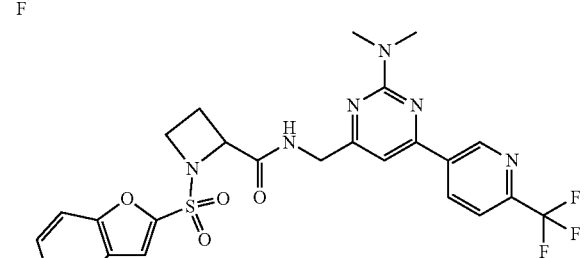
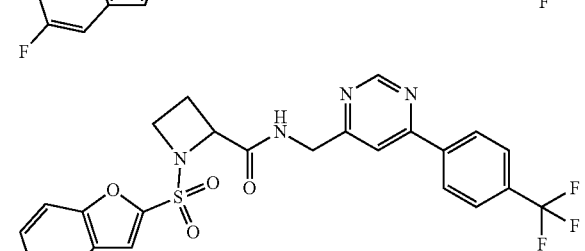
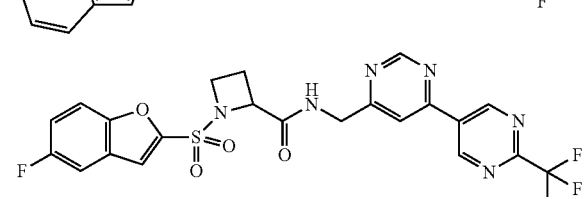
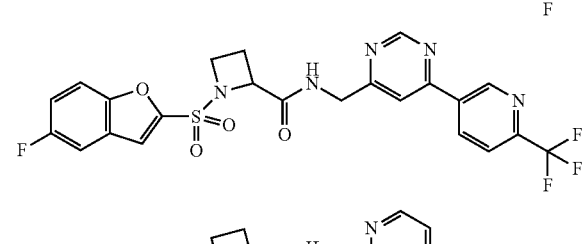
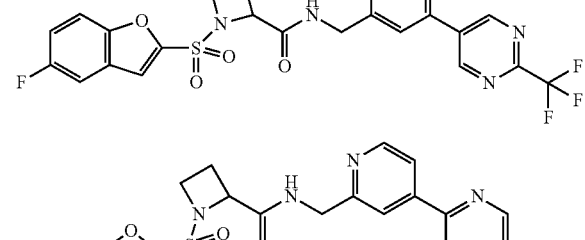
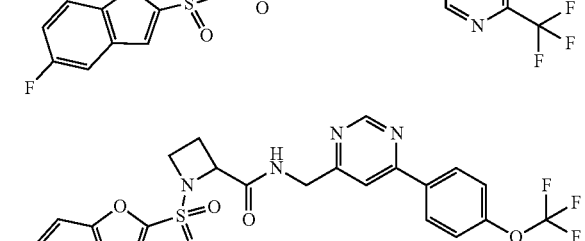

-continued

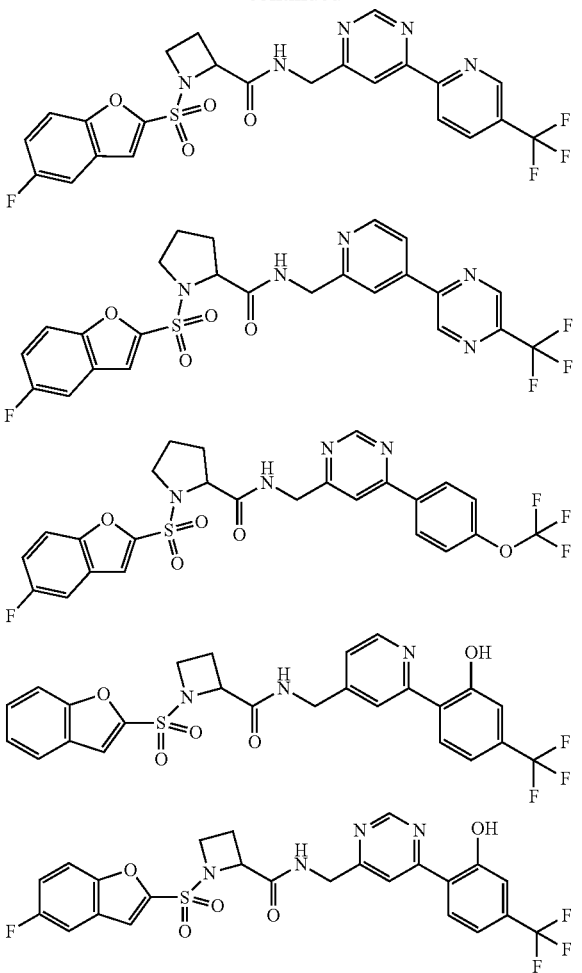

or a pharmaceutically acceptable salt of said compound.

5. A pharmaceutical composition, comprising a compound or pharmaceutically acceptable salt according to claim 4 and one or more pharmaceutically acceptable carriers.

6. A method for the treatment of a disease involving TRPA1, comprising administering an effective amount of a compound or pharmaceutically acceptable salt according to claim 4 to a subject in need thereof,
wherein said disease involving TRPA1 is chronic pain, acute pain, diabetic neuropathy, osteoarthritis, asthma, chronic coughing, chronic obstructive pulmonary disease, functional gastrointestinal disorder, reflux esophagitis, irritable bowel syndrome, inflammatory bowel disease, pancreatitis, anticancer agent-induced neuropathy, pruritus, or allergic dermatitis.

7. The method according to claim 6, wherein said disease involving TRPA1 is chronic pain, acute pain, asthma, chronic obstructive pulmonary disease, functional gastrointestinal disorder, reflux esophagitis, inflammatory bowel disease, anticancer agent-induced neuropathy, or pruritus.

8. A pharmaceutical composition, comprising a compound or pharmaceutically acceptable salt according to claim 1 and one or more pharmaceutically acceptable carriers.

9. A method for the treatment of a disease involving TRPA1, comprising administering an effective amount of a compound or pharmaceutically acceptable salt according to claim 1 to a subject in need thereof,
wherein said disease involving TRPA1 is chronic pain, acute pain, diabetic neuropathy, osteoarthritis, asthma, chronic coughing, chronic obstructive pulmonary disease, functional gastrointestinal disorder, reflux esophagitis, irritable bowel syndrome, inflammatory bowel disease, pancreatitis, anticancer agent-induced neuropathy, pruritus, or allergic dermatitis.

10. The method according to claim 9, wherein said disease involving TRPA1 is chronic pain, acute pain, asthma, chronic obstructive pulmonary disease, functional gastrointestinal disorder, reflux esophagitis, inflammatory bowel disease, anticancer agent-induced neuropathy, or pruritus.

* * * * *